United States Patent [19]

Ohno et al.

[11] Patent Number: 4,775,692
[45] Date of Patent: Oct. 4, 1988

[54] 2,5,6,7-TETRANOR-4,8-INTER-M-PHENYLENE PGI$_2$ DERIVATIVES

[75] Inventors: Kiyotaka Ohno, Fujisawa; Atsushi Ohtake; Hiroshi Nagase, both of Kamakura; Shintaro Nishio, Ebina; Toshiya Takahashi, Kamakura; Hisanori Wakita, Kamakura, all of Japan

[73] Assignee: Toray Industries, Inc., Tokyo, Japan

[21] Appl. No.: 7,291

[22] Filed: Jan. 23, 1987

[30] Foreign Application Priority Data

Jan. 24, 1986 [JP] Japan ................................. 61-13417
Jan. 24, 1986 [JP] Japan ................................. 61-13418

[51] Int. Cl.$^4$ .................. A61K 31/335; C07D 307/93
[52] U.S. Cl. .................... 514/468; 514/337; 514/444; 546/269; 549/60; 549/458
[58] Field of Search ................ 546/269; 549/60, 458; 514/337, 444, 468

[56] References Cited

U.S. PATENT DOCUMENTS 4,301,164 11/1981 Ohno et al. ...................... 424/263
4,474,802 10/1984 Ohno et al. ...................... 549/458
4,564,620 1/1986 Ohno et al. ...................... 514/337

Primary Examiner—Mary Lee
Assistant Examiner—Bernard I. Dentz
Attorney, Agent, or Firm—Austin R. Miller

[57] ABSTRACT

Disclosed herein are novel prostaglandin I$_2$ (PGI$_2$) derivatives exhibiting excellent in vivo duration and activities, said derivatives being represented by the general formula:

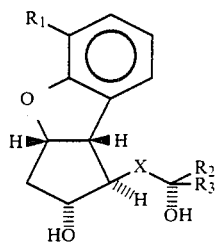

wherein R$_1$, X, R$_2$ and R$_3$ are as defined herein.

1 Claim, No Drawings

2,5,6,7-TETRANOR-4,8-INTER-M-PHENYLENE PGI₂ DERIVATIVES

BACKGROUND OF THE INVENTION

1. Field of the Invention

The present invention relates to novel prostaglandin I₂ (PGI₂) derivatives exhibiting excellent in vivo duration and activities.

2. Description of the Prior Art

Prostaglandin I₂ (PGI₂, prostacyclin) represented by the formula:

PGI₂ was first found by J. R. Vane et al. in 1976. PGI₂ is biosynthesized from arachidonic acid via endoperoxide (PGH₂ or PGG₂) in the vascular wall. It should be noted that PGI₂ shows potent platelet aggregation-inhibiting and gastric acid secretion-inhibiting activities and a potent peripheral blood vessel-dilating activity: refer to C & EN, Dec. 20, 1976, page 17; and S. Moncada, R. Gryglewski, S. Bunting, and J. R. Vane, Nature, 263, 633 (1976).

PGI₂ is extremely unstable even in neutral aqueous solutions due to the unstable exo-enol structure thereof and readily converted to 6-oxo PGF$_{1\alpha}$ which is substantially physiologically inactive. Such instability of PGI₂ is a great obstacle to its use as a drug. Furthermore, PGI₂ is unstable in vivo as well and disadvantageously shows only short duration of physiological activities in vivo.

Many studies have been made on various derivatives for the purpose of improving the chemical stability and duration of activities in vivo of PGI₂.

The present inventors have also studied and solved this problem of chemical instability of PGI₂ by providing novel derivatives of PGI₂ having a cyclopenta[b]benzofuran ring in which the exo-enol structure contributing to the instability is incorporated into the phenyl ring. Thus, the present inventors have attained a series of inventions and filed a number of patent applications: refer to Ohno et al., Japanese Patent Application Laying-Open Nos. 56-36477, 57-32277, 57-144276, 58-124778 and 59-134787.

However, the derivatives of PGI₂ provided by these prior inventions are still unsatisfactory with respect to the in vivo duration and potency of activities. In particular, one of the serious disadvantages concerning the drug duration is the tendency to be converted into carboxylic acids in which the number of carbon atoms is reduced by 2 through β-oxidation, one mode of the metabolism of fatty acids in vivo.

On the basis of this fact, the present inventors have made great efforts and finally achieved the present invention by devising a new structure capable of essentially inhibiting the metabolism through β-oxidation.

The compounds provided according to the present invention are more excellent with respect to the duration as compared to those of the prior inventions by the present inventors. Moreover, they have more potent activities.

It is a primary object of the present invention to solve such a problem in the prior art.

Thus, an object of this invention is to provide novel PGI₂ derivatives which show excellent duration of activities in vivo.

Other objects and advantages of this invention will be apparent from the description hereinbelow.

SUMMARY OF THE INVENTION

According to the present invention there is provided a 2,5,6,7-tetranor-4,8-inter-m-phenylene PGI₂ derivative represented by the following general formula:

wherein:
$R_1$ is
(i) —OCH₂COOR₄,
(ii) —C≡C—COOR₄,
(iii) —O—CH₂—CH₂—OH,
(iv) —(C≡C—CH₂—OH,
(v)

$$-O-CH_2-CON\begin{matrix}R_5,\\ \diagdown\\ R_6\end{matrix}$$

or
(vi)

$$-C\equiv C-CON\begin{matrix}R_5,\\ \diagdown\\ R_6\end{matrix}$$

in which $R_4$ is hydrogen, a pharmacologically acceptable cation, or an ester residue, and $R_5$ and $R_6$ may be same or different and are independently selected from the class consisting of hydrogen, normal alkyl groups having 1 to 12 carbon atoms, branched alkyl groups having 3 to 12 carbon atoms, cycloalkyl groups having 3 to 12 carbon atoms, cycloalkylalkylene groups having 4 to 13 carbon atoms, and phenyl group;
X is
(i) —CH₂—CH₂—, or
(ii) —CH=CH—;
$R_2$ is hydrogen, methyl, ethyl or propyl group; and
$R_3$ is
(i) a normal alkyl group having 1 to 12 carbon atoms or a branched alkyl group having 3 to 14 carbon atoms, (ii) —Z—Ar in which Z is a valence bond or a normal or branched alkylene group represented by the formula $C_tH_{2t}$ (t being an integer of 1 to 6), and Ar is a phenyl group unsubstituted or substituted by 1 to 4 substituents selected from the class consisting of alkyls, methoxy, chloro, bromo, fluoro, iodo, trifluoromethyl, nitro, cyano, and phenyl, (iii) —Z—$R_7$ in which Z is as defined above, and $R_7$ is a cycloalkyl group having 3 to 12 ring carbon atoms, said cycloalkyl group being optionally substituted by 1 to 4 normal alkyl substituents containing 1 to 4 carbon atoms, (iv) —$C_tH_{2t}$—C≡C—$R_8$ in which t is as defined above, and $R_8$ is a normal alkyl group having 1 to 6 carbon atoms, or (v) —$C_tH_{2t}$—O—$R_9$ in which t is as defined above, and $R_9$ is (1) a normal alkyl group having 1 to 6 carbon atoms or a branched alkyl group having 3 to 6 carbon atoms, (2) a cyclopentyl or cyclohexyl group unsubstituted or substituted by 1 to 4 normal alkyl substituents containing 1 to 4 carbon atoms, or (3) Ar as defined above.

DETAILED DESCRIPTION OF THE INVENTION

In the general formula, when $R_4$ represents an ester residue, the residue $R_4$ is selected from the class consisting of the following members:

(i) normal alkyl groups having 1 to 12 carbon atoms and branched alkyl groups having 3 to 14 carbon atoms;

(ii) —Z—$R_7$ wherein Z and $R_7$ are as defined above for $R_3$;

(iii) —Z—Ar wherein Z and Ar are as defined above for $R_3$ (in this case, $R_3$ and $R_4$ represented by the same formula being same or different);

(iv) —(CH$_2$CH$_2$O)$_n$—CH$_3$ wherein n is an integer of 1 to 5;

(V) —Z—$R_{10}$ wherein Z is as defined above for $R_3$ (in this case, when $R_3$ is represented by the formula including Z, the radicals Z for $R_3$ and $R_4$ being same or different), and $R_{10}$ is α-naphthyl, β-naphthyl, 2-pyridyl, 3-pyridyl, 4-pyridyl, α-furyl, β-furyl, α-thienyl, or β-thienyl;

(vi) —$C_tH_{2t}$—COO$R_{11}$ wherein t is as defined above for $R_3$ (in this case, when $R_3$ is represented by the formula including $C_tH_{2t}$, the radicals $C_tH_{2t}$ for $R_3$ and $R_4$ being same or different), and $R_{11}$ is methyl, ethyl or propyl group; and (vii)

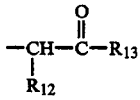

wherein $R_{12}$ is hydrogen or benzoyl group, and $R_{13}$ is phenyl, p-bromophenyl, p-chlorophenyl, p-biphenyl, p-nitrophenyl, p-benzamidophenyl, or 2-naphthyl group.

Pharmacologically acceptable cations represented by $R_4$ include metal cations, ammonium cation, amine cations and quaternary ammonium cations.

Preferred metal cations are derived from alkali metals, for example, lithium, sodium or potassium, or alkaline earth metals, for example, magnesium or calcium. Cations derived from other metals, such as aluminum, zinc and iron, are also included within the scope of this invention.

The pharmacologically acceptable amine cations are those derived from primary, secondary, or tertiary amines. Illustrative examples of suitable amines include aliphatic, alicyclic, aromatic amines containing up to about 18 carbon atoms and heterocyclic amines, such as methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, 1-methylpiperidine, 4-ethylmorpholine, 1-isopropylpyrrolidine, 2-methylpyrrolidine, 1,4-dimethylpiperazine, 2-methylpiperidine, etc.; water-soluble amines and hydrophilic group-containing amines, such as mono-, di-, and triethanolamines, ethyldiethanolamine, N-butylethanolamine, 2-amino-1-butanol, 2-amino-2-ethyl-1,3-propanediol, tris(hydroxymethyl)aminomethane, N-phenylethanolamine, N-(p-tert-amylphenyl)diethanolamine, galactamine, N-methylglutamine, N-methylglucosamine, ephedrine, phenylephrine, epinephrine, procaine, etc; and basic amino acids, such as lysine, arginine, etc.

Illustrative examples of normal alkyl groups having 1 to 12 carbon atoms represented by $R_3$ and $R_4$ may include methyl, ethyl, propyl, butyl, pentyl, hexyl, heptyl, octyl, dodecyl, etc. Examples of branched alkyl groups having 3 to 14 carbon atoms represented by $R_3$ and $R_4$ may include isopropyl, sec-butyl, t-butyl, iso-butyl, 2-methylpentyl, 3-methylpentyl, 4-methylpentyl, 1-methylpentyl, 1-methylhexyl, 2-methylhexyl, 3-methylhexyl, 4-methylhexyl, 5-methylhexyl, 1-methylheptyl, 2-methylheptyl, 3-methylheptyl, 4-methylheptyl, 5-methylheptyl, 6-methylheptyl, 1-methyloctyl, 2-methyloctyl, 3-methyloctyl, 4-methyloctyl, 5-methyloctyl, 6-methyloctyl, 7-methyloctyl, 1-methylnonyl, 1-methyldecanyl, 2-methylnonyl, 2-methyldecanyl, 1,1-dimethylbutyl, 2,2-dimethylbutyl, 1,1-dimethylpentyl, 2,2-dimethylpentyl, 3,3-dimethylpentyl, 4,4-dimethylpentyl, 1,1-dimethylhexyl, 2,2-dimethylhexyl, 3,3-dimethylhexyl, 4,4-dimethylhexyl, 5,5-dimethylhexyl, 6,6-dimethylhexyl, 1,1-dimethylheptyl, 2,2-dimethylheptyl, 3,3-dimethylheptyl, 4,4-dimethylheptyl, 5,5-dimethylheptyl, 6,6-dimethylheptyl, 7,7-dimethylheptyl, 1,1-dimethyloctyl, 2,2-dimethyloctyl, 3,3-dimethyloctyl, 1,1-dimethylnonyl, 2,2-dimethylnonyl, 3,3-dimethylnonyl, 1,1-dimethyldecanyl, 2,2-dimethyldecanyl, 3,3-dimethyldecanyl, 1,1,2,2-tetramethylpentyl, 1,1,3,3-tetramethylpentyl, 1,1,2,2-tetramethylhexyl, 1,1,3,3-tetramethylhexyl, 2,2,3,3-tetramethylhexyl, etc.

Illustrative examples of the radicals —Z—Ar represented by $R_3$ and/or $R_4$ may include phenyl, p-chlorophenyl, p-bromophenyl, p-fluorophenyl, 3,4-dichlorophenyl, m-fluorophenyl, m-trifluoromethylphenyl, p-trifluoromethylphenyl, p-nitrophenyl, p-anisyl, 3,4-dimethoxyphenyl, p-tolyl, m-tolyl, o-tolyl, p-ethylphenyl, p-propylphenyl, p-butylphenyl, 3,4-dimethylphenyl, 2,4-dimethylphenyl, 3-chloro-4-methylphenyl, 3-fluoro-4-methylphenyl, 4-biphenylyl, benzyl, p-chlorobenzyl, m-chlorobenzyl, p-methoxybenzyl, o-methoxybenzyl, p-methylbenzyl, p-ethylbenzyl, p-propylbenzyl, p-nitrobenzyl, 3,4-dichlorobenzyl, α-methylbenzyl, α,α'-dimethylbenzyl, phenethyl, p-chlorophenethyl, p-bromophenethyl, p-fluorophenethyl, m-chlorophenethyl, m-fluorophenethyl, o-chlorophenethyl, p-methylphenethyl, p-methoxyphenethyl, 3,4-dimethoxyphenethyl, p-ethylphenethyl, α-methylphenethyl, β-methylphenethyl, α,α'-dimethylphenethyl, β,β'-dimethylphenethyl, 3-phenylpropyl, 3-(p-chlorophenyl)propyl, 3-(p-fluorophenyl)propyl, 3-(p-bromophenyl)propyl, 3-(m-chlorophenyl)propyl, 3-(3,4-dichlorophenyl)propyl, 3-(p-tolyl)propyl, 3-(p-ethylphenyl)propyl, 4-phenylbutyl, 4-(p-chlorophenyl)butyl, 4-(3,4-dichlorophenyl)butyl, 4-(p-tolyl)butyl, 5-phenylpentyl, α,α'-dimethyl-p-chlorophenethyl, α,α'-dimethyl-p-bromophenethyl, α,α'-dimethyl-p-fluorophenethyl, α,α'-dimethyl-m-chlorophenethyl, α,α'-dimethyl-m-bromophenethyl, α,α'-dimethyl-m-fluorophenetyl, α,α'-dimethyl-p-trifluoromethylphenethyl, α,α'-dimethyl-m-trifluoromethylphenethyl, α,α'-dimethyl-p-methylphenethyl, α,α'-dimethyl-p-methoxyphenethyl, α,α'-dimethyl-p-cyanophenethyl, 1,1-dimethyl-3-phenylpropyl, 1,1-dimethyl-4-phenylbutyl, etc.

Illustrative examples of the radicals —Z—$R_7$ represented by $R_3$ and/or $R_4$ may include, for example, cyclopentyl, cyclohexyl, cycloheptyl, cyclooctyl, cyclododecyl, cyclopentylmethyl, cyclohexylmethyl, cycloheptylmethyl, cyclododecylmethyl, cyclopentylethyl, cyclohexylethyl, cycloheptylethyl, cyclopentylpropyl, cyclohexylpropyl, cyclopentylbutyl, cyclohexylbutyl, cyclohexylpentyl, 2-methylcyclopentyl, 3-methylcyclopentyl, 2-methylcyclohexyl, 3-methylcyclohexyl, 4-methylcyclohexyl, 2-methylcycloheptyl, 3-methylcycloheptyl, 4-methylcycloheptyl, 4-methylcyclooctyl, 2-ethylcyclopentyl, 3-ethylcyclopentyl, 2-ethylcyclohexyl, 3-ethylcyclohexyl, 4-ethylcyclohexyl, 2-ethylcycloheptyl, 2-ethylcyclooctyl, 3-ethylcyclooctyl, 2-methylcyclopentylmethyl, 3-methylcyclopentylmethyl, 2-methylcyclohexylmethyl, 3-methylcyclohexylmethyl, 4-methylcyclohexylmethyl, 2-methylcycloheptylmethyl, 3-methylcycloheptylmethyl, 2-methylcyclooctylmethyl, 2-(2-methylcyclopentyl)ethyl, 2-(3-methylcyclopentyl)ethyl, 2-(2-methylcyclohexyl)ethyl, 2-(3-methylcyclohexyl)ethyl, 2-(4-methylcyclohexyl)ethyl, 2-(2-methylcycloheptyl)ethyl, 2-(2-methylcyclooctyl)ethyl, 3-(2-methylcyclopentyl)propyl, 3-(3-methylcyclopentyl)propyl, 3-(2-methylcyclohexyl)propyl, 3-(3-methylcyclohexyl)propyl, 3-(4-methylcyclohexyl)propyl, 5-(2-methylcyclopentyl)pentyl, 2-ethylcyclopentylmethyl, 3-ethylcyclopentylmethyl, 2-ethylcyclohexylmethyl, 3-ethylcyclohexylmethyl, 4-ethylcyclohexylmethyl, 2-ethylcycloheptylmethyl, 3-methylcycloheptylmethyl, 2-ethylcyclooctylmethyl, 2-(2-ethylcyclopentyl)ethyl, 2-(3-ethylcyclopentyl)ethyl, 2-(4-ethylcyclohexyl)ethyl, 2-(2-ethylcycloheptyl)ethyl, 2-(2-ethylcyclooctyl)ethyl, 3-(2-ethylcyclopentyl)propyl, 3-(3-ethylcyclopentyl)propyl, 3-(2-ethylcyclohexyl)propyl, 3-(3-ethylcyclohexyl)propyl, 3-(4-ethylcyclohexyl)propyl, 5-(2-ethylcyclopentyl)pentyl, 5-(2-ethylcyclopentyl)pentyl, cyclopropyl, cyclobutyl, 2,3-dimethylcyclopropyl, 2,4-dimethylcyclobutyl, 3,3-dimethylcyclobutyl, cyclopentyldimethylmethyl, cyclohexyldimethylmethyl, cyclooctyldimethylmethyl, 2-cyclopentyl-1,1-dimethylethyl, 2-cyclohexyl-1,1-dimethylethyl, 2-cyclooctyl-1,1-dimethylethyl, 2-cyclododecyl-1,1-dimethylethyl, 3-cyclopentyl-1,1-dimethylpropyl, 3-cyclohexyl-1,1-dimethylpropyl, 3-cyclooctyl-1,1-dimethylpropyl, 4-cyclopentyl-1,1-dimethylbutyl, 4-cyclohexyl-1,1-dimethylbutyl, 4-cyclooctyl-1,1-dimethylbutyl, 2-cyclopentyl-2,2-dimethylethyl, 2-cyclohexyl-2,2-dimethylethyl, 2-cyclooctyl-2,2-dimethylethyl, etc.

Illustrative examples of the radical —$C_rH_{2r}$—C≡C—$R_8$ represented by $R_3$ may include 2-pentynyl, 3-pentynyl, 2-hexynyl, 3-hexynyl, 4-hexynyl, 2-heptynyl, 3-heptynyl, 4-heptynyl, 5-heptynyl, 2-octynyl, 3-octynyl, 4-octynyl, 5-octynyl, 6-octynyl, 2-nonynyl, 3-nonynyl, 4-nonynyl, 5-nonynyl, 6-nonynyl, 7-nonynyl, 1-methyl-2-pentynyl, 1-methyl-3-pentynyl, 1-methyl-2-hexynyl, 1-methyl-3-hexynyl, 1-methyl-4-hexynyl, 1-methyl-2-heptynyl, 1-methyl-3-heptynyl, 1-methyl-4-heptynyl, 1-methyl-5-heptynyl, 1-methyl-2-octynyl, 1-methyl-3-octynyl, 1-methyl-4-octynyl, 1-methyl-5-octynyl, 1-methyl-6-octynyl, 1-methyl-2-nonynyl, 1-methyl-3-nonynyl, 1-methyl-4-nonyl, 1-methyl-5-nonynyl, 1-methyl-6-nonynyl, 1,1-dimethyl-2-pentynyl, 1,1-dimethyl-3-pentynyl, 1,1-dimethyl-2-hexynyl, 1,1-dimethyl-3-hexynyl, 1,1-dimethyl-4-hexynyl, 1,1-dimethyl-2-heptynyl, 1,1-dimethyl-3-heptynyl, 1,1-dimethyl-4-heptynyl, 1,1-dimethyl-5-heptynyl, 1,1-dimethyl-2-octynyl, 1,1-dimethyl-3-octynyl, 1,1-dimethyl-4-octynyl, 1,1-dimethyl-5-octynyl, 1,1-dimethyl-6-octynyl, 1,1-dimethyl-2-nonynyl, 1,1-dimethyl-3-nonynyl, 1,1-dimethyl-4-nonynyl, 1,1-dimethyl-5-nonynyl, 2,2-dimethyl-3-pentynyl, 2,2-dimethyl-3-hexynyl, 2,2-dimethyl-4-hexynyl, 2,2-dimethyl-3-heptynyl, 2,2-dimethyl-4-heptynyl, etc.

Illustrative examples of the radicals —$C_rH_{2r}$—O—$R_9$ represented by $R_3$ may include methoxymethyl, ethoxymethyl, propoxymethyl, butoxymethyl, n-pentyloxymethyl, n-hexyloxymethyl, dimethylmethoxymethyl, dimethylethoxymethyl, dimethylpropoxymethyl, dimethylbutoxymethyl, dimethyl-n-pentyloxymethyl, dimethyl-n-hexyloxymethyl, isopropoxymethyl, sec-butoxymethyl, iso-butoxymethyl, t-butoxymethyl, (1,1-dimethylbutoxy)methyl, 2-methoxyethyl, 2-ethoxyethyl, 2-propoxyethyl, 2-butoxyethyl, 2-n-pentyloxyethyl, 2-n-hexyloxyethyl, 1,1-dimethyl-2-methoxyethyl, 1,1-dimethyl-2-propoxyethyl, 1,1-dimethyl-2-butoxyethyl, 1,1-dimethyl-2-n-pentyloxyethyl, 1,1-dimethyl-2-n-hexyloxyethyl, 3-methoxypropyl, 3-ethoxypropyl, 3-propoxypropyl, 3-butoxypropyl, 3-pentyloxypropyl, 3-n-hexyloxypropyl, 1,1-dimethyl-3-methoxypropyl, 1,1-dimethyl-3-ethoxypropyl, 1,1-dimethyl-3-propoxypropyl, 1,1-dimethyl-3-butoxypropyl, 1,1-dimethyl-3-n-pentyloxypropyl, 2-isopropoxyethyl, 2-sec-butoxyethyl, 2-t-butoxyethyl, 1methyl-2-methoxyethyl, 1-methyl-2-ethoxyethyl, 1-methyl-2-propoxyethyl, 1-methyl-2-butoxyethyl, cyclopentyloxymethyl, cyclohexyloxymethyl, cyclopentyloxydimethylmethyl, cyclohexyloxydimethylmethyl, (2,5-dimethylcyclopentyloxy)methyl, (3,4-dimethylcyclopentyloxy)methyl, (4-methylcyclohexyloxy)methyl, (2,6-dimethylcyclohexyloxy)methyl, (2,2,6,6-tetramethylcyclohexyloxy)methyl, dimethyl(3,4-dimethylcyclopentyloxy)methyl, dimethyl(4-methylcyclohexyloxy)methyl, 2-(cyclopentyloxy)ethyl, 2-(cyclohexyloxy)ethyl, 1,1-dimethyl-2-(cyclopentyloxy)ethyl, 1,1-dimethyl-2-(cyclohexyloxy)ethyl, 3-cyclopentyloxypropyl, 3-cyclohexyloxypropyl, 1,1-dimethyl-3-cyclopentyloxypropyl, 1,1-dimethyl-3-cyclohexyloxypropyl, phenoxymethyl, p-chlorophenoxymethyl, m-chlorophenoxymethyl, 2,4-dichlorophenoxymethyl, 3,4-dichlorophenoxymethyl, p-bromophenoxymethyl, m-bromophenoxymethyl, 2,4-dibromophenoxymethyl, 3,4-dibromophenoxymethyl, p-fluorophenoxymethyl, m-fluorophenoxymethyl, o-fluorophenoxymethyl, p-trifluoromethylphenoxymethyl, m-trifluoromethylphenoxymethyl, o-trifluoromethylphenoxymethyl, p-nitrophenoxymethyl, p-cyanophenoxymethyl, p- phenylphenoxymethyl, p-methylphenoxymethyl, m-methylphenoxymethyl, o-methylphenoxymethyl, p-methoxyphenoxymethyl, m-methoxyphenoxymethyl, o-methoxyphenoxymethyl, dimethylphenoxymethyl, dimethyl(p-chlorophenoxy)methyl, dimethyl(m-chlorophenoxy)methyl, dimethyl(2,4-dichlorophenoxy)methyl, dimethyl(3,4-dichlorophenoxy)methyl, dimethyl(p-bromophenoxy)methyl, dimethyl(m-bromophenoxy)methyl, dimethyl(2,4-dibromophenoxy)methyl, dimethyl(3,4-dibromophenoxy)methyl, dimethyl(p-fluorophenoxy)methyl, dimethyl(m-fluorophenoxy)methyl, dimethyl(o-fluorophenoxy)methyl, dimethyl(p-trifluoromethylphenoxy)methyl, dimethyl(m-trifluoromethylphenoxy)methyl, dimethyl(o-trifluoromethylphenoxy)methyl, dimethyl(p-nitrophenoxy)methyl, dimethyl(p-cyanophenoxy)methyl, dimethyl(p-phenylphenoxy)methyl, dimethyl(p-methylphenoxy)methyl, dimethyl(m-methylphenoxy)methyl, dimethyl(o-methylphenoxy)methyl, dimethyl(p-methoxyphenoxy)methyl, dimethyl(m-methoxyphenoxy)methyl, dimethyl(o-methoxyphenoxy)methyl, 2-phenoxyethyl, 2-(p-chlorophenoxy)ethyl, 2-(m-chlorophenoxy)ethyl, 2-(2,4-dichlorophenoxy)ethyl, 2-(3,4-dichlorophenoxy)ethyl, 2-(p-bromophenoxy)ethyl, 2-(m-bromophenoxy)ethyl, 2-(2,4-dibromophenoxy)ethyl, 2-(3,4-dibromophenoxy)ethyl, 2-(p-fluorophenoxy)ethyl, 2-(m-fluorophenoxy)ethyl, 2-(o-fluorophenoxy)ethyl, 2-(p-trifluoromethylphenoxy)ethyl, 2-(m-trifluoromethylphenoxy)ethyl, 2-(o-trifluoromethylphenoxy)ethyl, 2-(p-nitrophenoxy)ethyl, 2-(p-cyanophenoxy)ethyl, 2-(p-phenylphenoxy)ethyl, 2-(p-methylphenoxy)ethyl, 2-(m-methylphenoxy)ethyl, 2-(o-methylphenoxy)ethyl, 2-(p-methoxyphenoxy)ethyl, 2-(m-methoxyphenoxy)ethyl, 2-(o-methoxyphenoxy)ethyl, 3-phenoxypropyl, 1,1-dimethyl-3-phenoxypropyl, methylphenoxymethyl, 1-methyl-2-phenoxyethyl, 1-methyl-3-phenoxypropyl, etc.

Illustrative examples of the radical $-(CH_2CH_2O)_n-CH_3$ represented by $R_4$ may include $-CH_2CH_2OCH_3$, $-CH_2CH_2OCH_2CH_2OCH_3$, $-(CH_2CH_2O)_3CH_3$, $-(CH_2CH_2O)_4CH_3$, $-(CH_2CH_2O)_5CH_3$, etc.

Illustrative examples of the radical $-Z-R_{10}$ represented by $R_4$ may include α-naphthyl, β-naphthyl, 2-pyridyl, 3-pyridyl, 4-pyridyl, α-furyl, β-furyl, α-thienyl, β-thienyl, α-naphthylmethyl, β-naphthylmethyl, 2-pyridylmethyl, 3-pyridylmethyl, 4-pyridylmethyl, α-furylmethyl, β-furylmethyl, α-thienylmethyl, β-thienylmethyl, 2-(α-naphthyl)ethyl, 2-(β-naphthyl)ethyl, 2-(2-pyridyl)ethyl, 2-(3-pyridyl)ethyl, 2-(4-pyridyl)ethyl, 2-(α-furyl)ethyl, 2-(β-furyl)ethyl, 2-(α-thienyl)ethyl, 2-(β-thienyl)ethyl, 3-(α-naphthyl)propyl, 3-(β-naphthyl)propyl, 3-(2-ppyridyl)propyl, 3-(3-pyridyl)propyl, 3-(4-pyridyl)propyl, 3-(α-furyl)propyl, 3-(β-furyl)propyl, 3-(α-thienyl)propyl, 3-(β-thienyl)propyl, etc.

Illustrative examples of the radical $-C_tH_{2t}COOR_{11}$ represented by $R_4$ may include methoxycarbonylmethyl, ethoxycarbonylmethyl, propoxycarbonylmethyl, 1-methoxycarbonylethyl, 1-ethoxycarbonylethyl, 1-propoxycarbonylethyl, 2-methoxycarbonylethyl, 2-ethoxycarbonylethyl, 2-propoxycarbonylethyl, 3-methoxycarbonylpropyl, 3-ethoxycarbonylpropyl, etc.

Illustrative examples of the radical

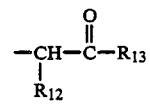

represented by $R_4$ may include phenacyl, p-bromophenacyl, p-nitrophenacyl, p-phenylphenacyl, p-benzamidophenacyl, 2-naphthoylmethyl, α-benzoylphenacyl, etc.

The compounds of the general formula provided according to the present invention are named after the nomenclature for prostaglandins and prostacycline analogs proposed by N. A. Nelson et al.: N. A. Nelson, J. Med. Chem., 17, 911 (1974); and R. A. Johnson, D. R. Morton and N. A. Nelson, Prostaglandins, 15, 737 (1978).

The most fundamental compound, which falls outside the scope of the present invention, is represented by the following formula:

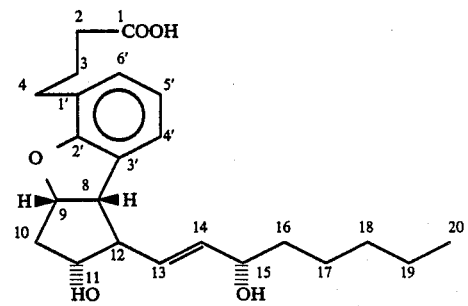

and the compound may be named as 5,6,7-trinor-4,8-inter-m-phenylene $PGI_2$ after numbering each carbon atom as shown above.

Although this naming does not reasonably accord with the nomenclature given in the aforementioned references, the $PGI_2$ derivatives according to the present invention which have the specific structure involving a cyclopenta[b]benzofuran skeleton will be named according to the informal naming to avoid complexity. According to the nomenclature of the aforementiond references, the fundamental compound will be named as 9-deoxy-2′,9α-epoxy-5,6,7-trinor-4,8-inter-m-phenylene $PGF_{1α}$.

In this specification, the fundamental compound is informally called 5,6,7-trinor-4,8-inter-m-phenylene $PGI_2$ as above mentioned, but other rules for naming will follow those given in the aforementioned references.

Incidentally, the nomenclature of the references is also informal, and the fundamental compound is named as having a cyclopenta[b]benzofuran ring as a substituent according to the IUPAC formal nomenclature. The 1H-cyclopenta[b]benzofuran is represented by the formula:

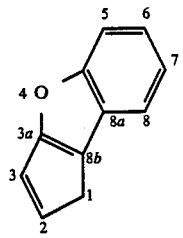

Thus, the fundamental compound is formally named as 4-[1β-(3-hydroxy-1-octenyl)-2α-hydroxy-3aβH,8b,βH-2,3,3a,8b-tetrahydro-1-H-cyclopenta[b]benzofuran-5-yl]butanoic acid.

The naming of the compounds according to the present invention will be hereinbelow illustrated together with the structures thereof.

2,5,6,7-Tetranor-4-oxa-4,8-inter-m-phenylene PGI₂:

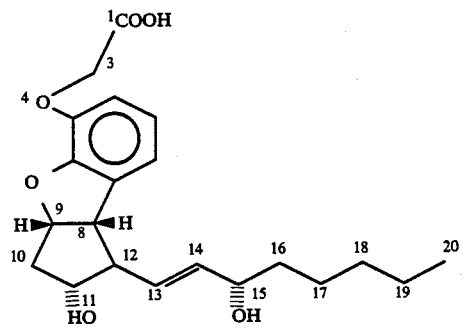

15-Cyclohexyl-2,5,6,7,16,17,18,19,20-nonanor-4-oxa-4,8-inter-m-phenylene PGI₂:

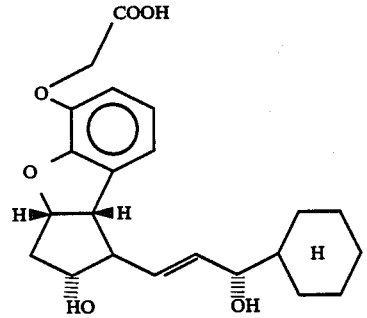

16,16-Dimethyl-20a,20b-dihomo-2,5,6,7-tetranor-4-oxa-4,8-inter-m-phenylene PGI₂ methyl ester:

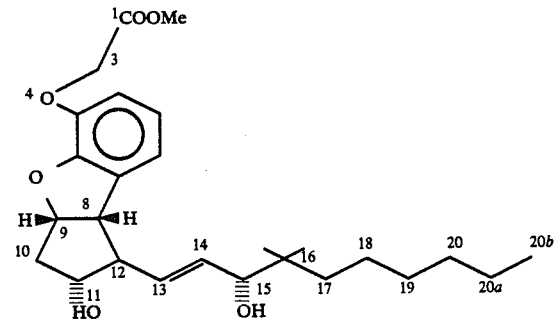

16-Cyclohexyl-16-methyl-15-oxo-2,5,6,7,18,19,20-heptanor-3,3,4,4-tetradehydro-4,8-inter-m-phenylene PGI₂, 11-acetate:

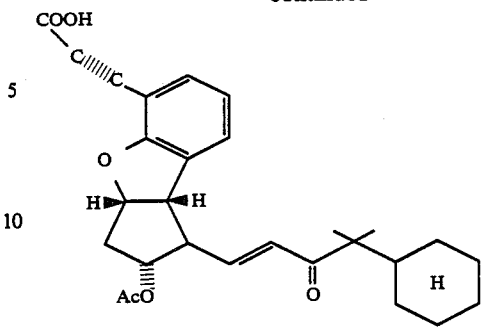

15-Epi-3-decarboxy-3-hydroxymethyl-16-methyl-20a,20b-dihomo-2,5,6,7-tetranor-4-oxa-18,18,19,19-tetradehydro-4,8-inter-m-phenylene PGI₂, 11-acetate:

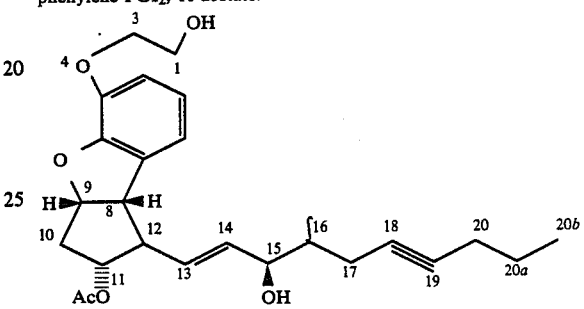

Illustrative examples of the compounds according to the present invention wherein R₃ is a normal or branched alkyl group will be given hereinbelow:
2,5,6,7,17,18,19,20-octanor-4-oxa-4,8-inter-m-phenylene PGI₂;
2,5,6,7,18,19,20-heptanor-4-oxa-4,8-inter-m-phenylene PGI₂;
2,5,6,7,19,20-hexanor-4-oxa-4,8-inter-m-phenylene PGI₂;
2,5,6,7,20-pentanor-4-oxa-4,8-inter-m-phenylene PGI₂;
2,5,6,7-tetranor-4-oxa-4,8-inter-m-phenylene PGI₂;
20a-homo-2,5,6,7-tetranor-4-oxa-4,8-inter-m-phenylene PGI₂;
20a,20b-dihomo-2,5,6,7-tetranor-4-oxa-4,8-inter-m-phenylene PGI₂;
20a,20b,20c-trihomo-2,5,6,7-tetranor-4-oxa-4,8-inter-m-phenylene PGI₂;
20a,20b,20c,20d-tetrahomo-2,5,6,7-tetranor-4-oxa-4,8-inter-m-phenylene PGI₂;
20a,20b,20c,20d,20e-pentahomo-2,5,6,7-tetranor-4-oxa-4,8-inter-m-phenylene PGI₂;
20a,20b,20c,20d,20e,20f-hexahomo-2,5,6,7-tetranor-4-oxa-4,8-inter-m-phenylene PGI₂;
20a,20b,20c,20d,20e,20f,20g-heptahomo-2,5,6,7-tetranor-4-oxa-4,8-inter-m-phenylene PGI₂;
16-methyl-2,5,6,7,18,19,20-heptanor-4-oxa-4,8-inter-m-phenylene PGI₂;
16-methyl-2,5,6,7,19,20-hexanor-4-oxa-4,8-inter-m-phenylene PGI₂;
16-methyl-2,5,6,7,20-pentanor-4-oxa-4,8-inter-m-phenylene PGI₂;
16-methyl-2,5,6,7-tetranor-4-oxa-4,8-inter-m-phenylene PGI₂;
16-methyl-20a-homo-2,5,6,7-tetranor-4-oxa-4,8-inter-m-phenylene PGI₂;
16-methyl-20a,20b-dihomo-2,5,6,7-tetranor-4-oxa-4,8-inter-m-phenylene PGI₂;

16-methyl-20a,20b,20c-trihomo-2,5,6,7-tetranor-4-oxa-4,8-inter-m-phenylene PGI$_2$;
16-methyl-20a,20b,20c,20d-tetrahomo-2,5,6,7-tetranor-4-oxa-4,8-inter-m-phenylene PGI$_2$;
16-methyl-20a,20b,20c,20d,20e-pentahomo-2,5,6,7-tetranor-4-oxa-4,8-inter-m-phenylene PGI$_2$;
16-methyl-20a,20b,20c,20d,20e,20f-hexahomo-2,5,6,7-tetranor-4-oxa-4,8-inter-m-phenylene PGI$_2$;
16-methyl-20a,20b,20c,20d,20e,20f,20g-heptahomo-2,5,6,7-tetranor-4-oxa-4,8-inter-m-phenylene PGI$_2$;
17-methyl-2,5,6,7,19,20-hexanor-4-oxa-4,8-inter-m-phenylene PGI$_2$;
17-methyl-2,5,6,7,20-pentanor-4-oxa-4,8-inter-m-phenylene PGI$_2$;
17-methyl2,5,6,7-tetranor-4-oxa-4,8-inter-m-phenylene PGI$_2$;
17-methyl-20a-homo-2,5,6,7-tetranor-4-oxa-4,8-inter-m-phenylene PGI$_2$;
17-methyl-20a,20b-dihomo-2,5,6,7-tetranor-4-oxa-4,8-inter-m-phenylene PGI$_2$;
17-methyl-20a,20b,20c-trihomo-2,5,6,7-tetranor-4-oxa-4,8-inter-m-phenylene PGI$_2$;
17-methyl-20a,20b,20c,20d-tetrahomo-2,5,6,7-tetranor-4-oxa-4,8-inter-m-phenylene PGI$_2$;
17-methyl-20a,20b,20c,20d,20e-pentahomo-2,5,6,7-tetranor-4-oxa-4,8-inter-m-phenylene PGI$_2$;
17-methyl-20a,20b,20c,20d,20e,20f-hexahomo-2,5,6,7-tetranor-4-oxa-4,8-inter-m-phenylene PGI$_2$;
17-methyl-20a,20b,20c,20d,20e,20f,20g-heptahomo-2,5,6,7-tetranor-4-oxa-4,8-inter-m-phenylene PGI$_2$;
18-methyl-2,5,6,7,20-pentanor-4-oxa-4,8-inter-m-phenylene PGI$_2$;
18-methyl-2,5,6,7-tetranor-4-oxa-4,8-inter-m-phenylene PGI$_2$;
18-methyl-20a-homo-2,5,6,7-tetranor-4-oxa-4,8-inter-m-phenylene PGI$_2$;
18-methyl-20a,20b-dihomo-2,5,6,7-tetranor-4-oxa-4,8-inter-m-phenylene PGI$_2$;
18-methyl-20a,20b,20c-trihomo-2,5,6,7-tetranor-4-oxa-4,8-inter-m-phenylene PGI$_2$;
18-methyl-20a,20b,20c20d-tetrahomo-2,5,6,7-tetranor-4-oxa-4,8-inter-m-phenylene PGI$_2$;
18-methyl-20a,20b,20c,20d,20e-pentahomo-2,5,6,7-tetranor-4-oxa-4,8-inter-m-phenylene PGI$_2$;
18-methyl-20a,20b,20c,20e,20f-hexahomo-2,5,6,7-tetranor-4-oxa-4,8-inter-m-phenylene PGI$_2$;
18-methyl-20a,20b,20c,20d20e,20f20g-heptahomo-2,5,6,7-tetranor-4-oxa-4,8-inter-m-phenylene PGI$_2$;
19-methyl-2,5,6,7-tetranor-4-oxa-4,8-inter-m-phenylene PGI$_2$;
19-methyl-20a-homo-2,5,6,7-tetranor-4-oxa-4,8-inter-m-phenylene PGI$_2$;
19-methyl-20a,20b-dihomo-2,5,6,7-tetranor-4-oxa-4,8-inter-m-phenylene PGI$_2$;
19-methyl-20a20b,20c-trihomo-2,5,6,7-tetranor-4-oxa-4,8-inter-m-phenylene PGI$_2$;
19-methyl-20a,20b,20c,20d-tetrahomo-2,5,6,7-tetranor-4-oxa-4,8-inter-m-phenylene PGI$_2$;
19-methyl-20a,20b,20c,20d,20e-pentahomo-2,5,6,7-tetranor-4-oxa-4,8-inter-m-phenylene PGI$_2$;
19-methyl-20a,20b,20c,20d,20e,20f-hexahomo-2,5,6,7-tetranor-4-oxa-4,8-inter-m-phenylene PGI$_2$;
19-methyl-20a,20b,20c,20d,20e,20f,20g-heptahomo-2,5,6,7-tetranor-4-oxa-4,8-inter-m-phenylene PGI$_2$;
20-methyl-20a-homo-2,5,6,7-tetranor-4-oxa-4,8-inter-m-phenylene PGI$_2$;
20-methyl-20a,20b-dihomo-2,5,6,7-tetranor-4-oxa-4,8-inter-m-phenylene PGI$_2$;
20-methyl-20a,20b,20c-trihomo-2,5,6,7-tetranor-4-oxa-4,8-inter-m-phenylene PGI$_2$;
20-methyl-20a,20b,20c,20d-tetrahomo-2,5,6,7-tetranor-4-oxa-4,8-inter-m-phenylene PGI$_2$;
20-methyl-20a,20b,20c,20d,20e-pentahomo-2,5,6,7-tetranor-4-oxa-4,8-inter-m-phenylene PGI$_2$;
20-methyl-20a,20b,20c,20d,20e,20f-hexahomo-2,5,6,7-tetranor-4-oxa-4,8-inter-m-phenylene PGI$_2$;
20-methyl-20a,20b,20c,20d,20e,20f,20g -heptahomo-2,5,6,7-tetranor-4-oxa-4,8-inter-m-phenylene PGI$_2$;
20a-methyl-20a,20b-dihomo-2,5,6,7-tetranor-4-oxa-4,8-inter-m-phenylene PGI$_2$;
20a-methyl-20a,20b,20c-trihomo-2,5,6,7-tetranor-4-oxa-4,8-inter-m-phenylene PGI$_2$;
20a-methyl-20a,20b,20c,20d-tetrahomo-2,5,6,7-tetranor-4-oxa-4,8-inter-m-phenylene PGI$_2$;
20a-methyl-20a,20b,20c,20d,20e-pentahomo-2,5,6,7-tetranor-4-oxa-4,8-inter-m-phenylene PGI$_2$;
20a-methyl-20a,20b,20c,20d,20e,20f-hexahomo-2,5,6,7-tetranor-4-oxa-4,8-inter-m-phenylene PGI$_2$;
20a-methyl-20a,20b,20c,20d,20e,20f,20g-heptahomo-2,5,6,7-tetranor-4-oxa-4,8-inter-m-phenylene PGI$_2$;
20b-methyl-20a,20b,20c-trihomo-2,5,6,7-tetranor-4-oxa-4,8-inter-m-phenylene PGI$_2$;
20b-methyl-20a,20b,20c,20d-tetrahomo-2,5,6,7-tetranor-4-oxa-4,8-inter-m-phenylene PGI$_2$;
20b-methyl-20a,20b, 20c,20d,20e-pentahomo-2,5,6,7-tetranor-4-oxa-4,8-inter-m-phenylene PGI$_2$;
20b-methyl-20a,20b,20c,20d,20e,20e,20f-hexahomo-2,5,6,7-tetranor-4-oxa-4,8-inter-m-phenylene PGI$_2$;
20b-methyl-20a,20b,20c,20d,20e,20f,20g-heptahomo-2,5,6,7-tetranor-4-oxa-4,8-inter-m-phenylene PGI$_2$;
20c-methyl-20a,20b,20c,20d-tetrahomo-2,5,6,7-tetranor-4-oxa-4,8-inter-m-phenylene PGI$_2$
20c-methyl-20a,20b,20c,20d,20e-pentahomo-2,5,6,7-tetranor-4-oxa-4,8-inter-m-phenylene PGI$_2$;
20c-methyl-20a,20b,20c,20d,20e,20f-hexahomo-2,5,6,7-tetranor-4-oxa-4,8-inter-m-phenylene PGI$_2$;
20c-methyl-20a,20b,20c,20d,20e,20f,20g-heptahomo-2,5,6,7-tetranor-4oxa-4,8-inter-m-phenylene PGI$_2$;
20d-methyl-20a,20b,20c,20d,20e-pentahomo-2,5,6,7-tetranor-4-oxa-4,8-inter-m-phenylene PGI$_2$;
20d-methyl-20a,20b,20c,20d,20e,20f-hexahomo-2,5,6,7-tetranor-4-oxa-4,8-inter-m-phenylene PGI$_2$;
20d-methyl-20a,20b,20c,20d,20e,20f,20g-heptahomo-2,5,6,7-tetranor-4-oxa-4,8-inter-m-phenylene PGI$_2$;
20e-methyl-20a,20b,20c,20d,20 e,20f-hexahomo-2,5,6,7-tetranor-4-oxa-4,8-inter-m-phenylene PGI$_2$;
20e-methyl-20a,20b,20c,20d,20e,20f20g-heptahomo-2,5,6,7-tetranor-4-oxa-4,8-inter-m-phenylene PGI$_2$;
20f-methyl-20a,20b,20c,20d,20e,20f,20g-heptahomo-2,5,6,7-tetranor-4-oxa-4,8-inter-m-phenylene PGI$_2$;
16,16-dimethyl-2,5,6,7,18,19,20-heptanor-4-oxa-4,8-inter-m-phenylene PGI$_2$;
16,16-dimethyl-2,5,6,7,19,20-hexanor-4-oxa-4,8-inter-m-phenylene PGI$_2$;
16,16-dimethyl-2,5,6,7,20-pentanor-4-oxa-4,8-inter-m-phenylene PGI$_2$;
16,16-dimethyl-2,5,6,7-tetranor-4-oxa-4,8-inter-m-phenylene PGI$_2$;
16,16-dimethyl-20a-homo-2,5,6,7-tetranor-4-oxa-4,8-inter-m-phenylene PGI$_2$;
16,16-dimethyl-20a,20b-dihomo-2,5,6,7-tetranor-4-oxa-4,8-inter-m-phenylene PGI$_2$;
16,16-dimethyl-20a,20b,20c-trihomo-2,5,6,7-tetranor-4-oxa-4,8-inter-m-phenylene PGI$_2$;
16,16-dimethyl-20a,20b,20c,20d-tetrahomo-2,5,6,7-tetranor-4-oxa-4,8-inter-m-phenylene PGI$_2$;

16,16-dimethyl-20a,20b,20c,20d,20e-pentahomo-2,5,6,7-tetranor-4-oxa-4,8-inter-m-phenylene PGI₂;
16,16-dimethyl-20a,20b,20c,20d,20e,20f-hexahomo-2,5,6,7-tetranor-4-oxa-4,8-inter-m-phenylene PGI₂;
16,16-dimethyl-20a,20b,20c,20d,20e,20f,20g-heptahomo-2,5,6,7-tetranor-4-oxa-4,8-inter-m-phenylene PGI₂;
17,17-dimethyl-2,5,6,7,19,20-hexanor-4-oxa-4,8-inter-m-phenylene PGI₂;
17,17-dimethyl-2,5,6,7,20-pentanor-4-oxa-4,8-inter-m-phenylene PGI₂;
17,17-dimethyl-2,5,6,7-tetranor-4-oxa-4,8-inter-m-phenylene PGI₂;
17,17-dimethyl-20a-homo-2,5,6,7-tetranor-4-oxa-4,8-inter-m-phenylene PGI₂;
17,17-dimethyl-20a,20b-dihomo-2,5,6,7-tetranor-4-oxa-4,8-inter-m-phenylene PGI₂;
17,17-dimethyl-20a,20b,20c-trihomo-2,5,6,7-tetranor-4-oxa-4,8-inter-m-phenylene PGI₂
17,17-dimethyl-20a,20b,20c,20d-tetrahomo-2,5,6,7-tetranor-4-oxa-4,8-inter-m-phenylene PGI₂;
17,17-dimethyl-20a,20b,20c,20d,20e-pentahomo-2,5,6,7-tetranor-4-oxa-4,8-inter-m-phenylene PGI₂;
17,17-dimethyl-20a,20b,20c,20d,20e,20f-hexahomo-2,5,6,7-tetranor-4-oxa-4,8-inter-m-phenylene PGI₂;
17,17-dimethyl-20a,20b,20c,20d,20e,20f,20g-heptahomo-2,5,6,7-tetranor-4-oxa-4,8-inter-m-phenylene PGI₂;
18,18-dimethyl-2,5,6,7,20-pentanor-4-oxa-4,8-inter-m-phenylene PGI₂;
18,18-dimethyl-2,5,6,7-tetranor-4-oxa-4,8-inter-m-phenylene PGI₂;
18,18-dimethyl-20a-homo-2,5,6,7-tetranor-4-oxa-4,8-inter-m-phenylene PGI₂;
18,18-dimethyl-20a,20b-dihomo-2,5,6,7-tetranor-4-oxa-4,8-inter-m-phenylene PGI₂;
18,18-dimethyl-20a,20b,20c-trihomo-2,5,6,7-tetranor-4-oxa-4,8-inter-m-phenylene PGI₂;
18,18-dimethyl-20a,20b,20c,20d-tetrahomo-2,5,6,7-tetranor-4-oxa-4,8-inter-m-phenylene PGI₂;
18,18-dimethyl-20a,20b,20c,20d,20e-pentahomo-2,5,6,7-tetranor-4-oxa-4,8-inter-m-phenylene PGI₂;
18,18-dimethyl-20a,20b,20c,20d,20e,20f-hexahomo-2,5,6,7-tetranor-4-oxa-4,8-inter-m-phenylene PGI₂;
18,18-dimethyl-20a,20b,20c,20d,20e,20f,20g-heptahomo-2,5,6,7-tetranor-4-oxa-4,8-inter-m-phenylene PGI₂;
19,19-dimethyl-2,5,6,7-tetranor-4-oxa-4,8-inter-m-phenylene PGI₂;
19,19-dimethyl-20a-homo-2,5,6,7-tetranor-4-oxa-4,8-inter-m-phenylene PGI₂;
19,19-dimethyl-20a,20b-dihomo-2,5,6,7-tetranor-4-oxa-4,8-inter-m-phenylene PGI₂;
19,19-dimethyl-20a,20b,20c-trihomo-2,5,6,7-tetranor-4-oxa-4,8-inter-m-phenylene PGI₂;
19,19-dimethyl-20a,20b,20c,20d-tetrahomo-2,5,6,7-tetranor-4-oxa-4,8-inter-m-phenylene PGI₂;
19,19-dimethyl-20a,20b,20c,20d,20e-pentahomo-2,5,6,7-tetranor-4-oxa-4,8-inter-m-phenylene PGI₂;
19,19-dimethyl-20a,20b,20c,20d,20e,20f-hexahomo-2,5,6,7-tetranor-4-oxa-4,8-inter-m-phenylene PGI₂;
19,19-dimethyl-20a,20b,20c,20d,20e,20f,20g-heptahomo-2,5,6,7-tetranor-4-oxa-4,8-inter-m-phenylene PGI₂;
20,20-dimethyl-20a-homo-2,5,6,7-tetranor-4-oxa-4,8-inter-m-phenylene PGI₂;
20,20-dimethyl-20a,20b-dihomo-2,5,6,7-tetranor-4-oxa-4,8-inter-m-phenylene PGI₂;
20,20-dimethyl-20a,20b,20c-trihomo-2,5,6,7-tetranor-4-oxa-4,8-inter-m-phenylene PGI₂;
20,20-dimethyl-20a,20b,20c,20d-tetrahomo-2,5,6,7-tetranor-4-oxa-4,8-inter-m-phenyl PGI₂;
20,20-dimethyl-20a,20b,20c,20d,20e-pentahomo-2,5,6,7-tetranor-4-oxa-4,8-inter-m-phenylene PGI₂;
20,20-dimethyl-20a,20b,20c,20d,20e,20f-hexahomo-2,5,6,7-tetranor-4-oxa-4,8-inter-m-phenylene PGI₂;
20,20-dimethyl-20a,20b,20c,20d,20e,20f,20g-heptahomo-2,5,6,7-tetranor-4-oxa-4,8-inter-m-phenylene PGI₂;
20a,20a-dimethyl-20a,20b-dihomo-2,5,6,7-tetranor-4-oxa-4,8-inter-m-phenylene PGI₂;
20a,20a-dimethyl-20a,20b,20c-trihomo-2,5,6,7-tetranor-4-oxa-4,8-inter-m-phenylene PGI₂;
20a,20a-dimethyl-20a,20b,20c,20d-tetrahomo-2,5,6,7-tetranor-4-oxa-4,8-inter-m-phenylene PGI₂;
20a,20a-dimethyl-20a,20b,20c,20d,20e-pentahomo-2,5,6,7-tetranor-4-oxa-4,8-inter-m-phenylene PGI₂;
20a,20a-dimethyl-20a,20b,20c,20d,20e,20f-hexahomo-2,5,6,7-tetranor-4-oxa-4,8-inter-m-phenylene PGI₂;
20a,20a-dimethyl-20a,20b,20c,20d,20e,20f,20g-heptahomo-2,5,6,7-tetranor-4-oxa-4,8-inter-m-phenylene PGI₂;
20b,20b-dimethyl-20a,20b,20c-trihomo-2,5,6,7-tetranor-4-oxa-4,8-inter-m-phenylene PGI₂;
20b,20b-dimethyl-20a,20b,20c,20d-tetrahomo-2,5,6,7-tetranor-4-oxa-4,8-inter-m-phenylene PGI₂;
20b,20b-dimethyl-20a,20b,20c,20d,20e-pentahomo-2,5,6,7-tetranor-4-oxa-4,8-inter-m-phenylene PGI₂;
20b,20b-dimethyl-20a,20b,20c,20d,20e,20f-hexahomo-2,5,6,7-tetranor-4-oxa-4,8-inter-m-phenylene PGI₂;
20b,20b-dimethyl-20a,20b,20c,20d,20e,20f,20g-heptahomo-2,5,6,7-tetranor-4-oxa-4,8-inter-m-phenylene PGI₂;
20c,20c-dimethyl-20a,20b,20c,20d-tetrahomo-2,5,6,7-tetranor-4-oxa-4,8-inter-m-phenylene PGI₂;
20c,20c-dimethyl-20a,20b,20c,20d,20e-pentahomo-2,5,6,7-tetranor-4-oxa-4,8-inter-m-phenylene PGI₂;
20c,20c-dimethyl-20a,20b,20c,20d,20e,20f-hexahomo-2,5,6,7-tetranor-4-oxa-4,8-inter-m-phenylene PGI₂;
20c,20c-dimethyl-20a,20b,20c,20d,20e,20f,20g-heptahomo-2,5,6,7-tetranor-4-oxa-4,8-inter-m-phenylene PGI₂;
20d,20d-dimethyl-20a,20b,20c,20d,20e-pentahomo-2,5,6,7-tetranor-4-oxa-4,8-inter-m-phenylene PGI₂;
20d,20d-dimethyl-20a,20b,20c,20d,20e,20f-hexahomo-2,5,6,7-tetranor-4-oxa-4,8-inter-m-phenylene PGI₂;
20d,20d-dimethyl-20a,20b, 20c,20d,20e,20f,20g-heptahomo-2,5,6,7-tetranor-4-oxa-4,8-inter-m-phenylene PGI₂;
20e,20e-dimethyl-20a,20b,20c,20d,20e,20 f-hexahomo-2,5,6,7-tetranor-4-oxa-4,8-inter-m-phenylene PGI₂;
20e,20e-dimethyl-20a,20b,20c,20d,20e,20f,20g-heptahomo-2,5,6,7-tetranor-4-oxa-4,8-inter-m-phenylene PGI₂;
20f,20f-dimethyl-20a,20b,20c,20d,20e,20f,20g-heptahomo-2,5,6,7-tetranor-4-oxa-4,8-inter-m-phenylene PGI₂;
16,16,17-trimethyl-2,5,6,7,19,20-hexanor-4-oxa-4,8-inter-m-phenylene PGI₂;
16,16,17-trimethyl-2,5,6,7,20-pentanor-4-oxa-4,8-inter-m-phenylene PGI₂;
16,16,17-trimethyl-2,5,6,7-tetranor-4-oxa-4,8-inter-m-phenylene PGI₂;
16,16,17-trimethyl-20a-homo-2,5,6,7-tetranor-4-oxa-4,8-inter-m-phenylene PGI₂;

16,16,17-trimethyl-20a,20b-dihomo-2,5,6,7-tetranor-4-oxa-4,8-inter-m-phenylene PGI₂;
16,16,17-trimethyl-20a,20b,20c-trihomo-2,5,6,7-tetranor-4-oxa-4,8-inter-m-phenylene PGI₂;
16,16,17-trimethyl-20a,20b,20c,20d-tetrahomo-2,5,6,7-tetranor-4-oxa-4,8-inter-m-phenylene PGI₂;
16,16,17-trimethyl-20a,20b,20c,20d,20e-pentahomo-2,5,6,7-tetra-nor-4-oxa-4,8-inter-m-phenylene PGI₂;
16,16,17-trimethyl-20a,20b,20c,20d,20e,20f-hexahomo-2,5,6,7-tetranor-4-oxa-4,8-inter-m-phenylene PGI₂;
16,16,17-trimethyl-20a,20b,20c,20d,20e,20f,20g-heptahomo-2,5,6,7-tetranor-4-oxa-4,8-inter-m-phenylene PGI₂;
15-methyl-2,5,6,7,17,18,19,20-octanor-4-oxa-4,8-inter-m-phenylene PGI₂;
15-methyl-2,5,6,7,18,19,20-heptanor-4-oxa-4,8-inter-m-phenylene PGI₂;
15-methyl-2,5,6,7,19,20-hexanor-4-oxa-4,8-inter-m-phenylene PGI₂;
15-methyl-2,5,6,7,20-pentanor-4-oxa-4,8-inter-m-phenylene PGI₂;
15-methyl-2,5,6,7-tetranor-4-oxa-4,8-inter-m-phenylene PGI₂;
15-methyl-20a-homo-2,5,6,7-tetranor-4-oxa-4,8-inter-m-phenylene PGI₂;
15-methyl-20a,20b-dihomo-2,5,6,7-tetranor-4-oxa-4,8-inter-m-phenylene PGI₂;
15-methyl-20a,20b,20c-trihomo-2,5,6,7-tetranor-4-oxa-4,8-inter-m-phenylene PGI₂;
15-methyl-20a,20b,20c,20d-tetrahomo-2,5,6,7-tetranor-4-oxa-4,8-inter-m-phenylene PGI₂;
15-methyl-20a,20b,20c,20d,20e-pentahomo-2,5,6,7-tetranor-4-oxa-4,8-inter-m-phenylene PGI₂;
15-methyl-20a,20b,20c,20d,20e,20f-hexahomo-2,5,6,7-tetranor-4-oxa-4,8-inter-m-phenylene PGI₂;
15-methyl-20a,20b,20c,20d,20e,20f,20g-heptahomo-2,5,6,7-tetranor-4-oxa-4,8-inter-m-phenylene PGI₂;
15-ethyl-2,5,6,7,18,19,20-heptanor-4-oxa-4,8-inter-m-phenylene PGI₂;
15-ethyl-2,5,6,7,19,20-hexanor-4-oxa-4,8-inter-m-phenylene PGI₂;
15-ethyl-2,5,6,7,20-pentanor-4-oxa-4,8-inter-m-phenylene PGI₂;
15-ethyl-2,5,6,7-tetranor-4-oxa-4,8-inter-m-phenylene PGI₂;
15-ethyl-20a-homo-2,5,6,7-tetranor-4-oxa-4,8-inter-m-phenylene PGI₂;
15-ethyl-20a,20b-dihomo-2,5,6,7-tetranor-4-oxa-4,8-inter-m-phenylene PGI₂;
15-ethyl-20a,20b,20c-trihomo-2,5,6,7-tetranor-4-oxa-4,8-inter-m-phenylene PGI₂;
15-ethyl-20a,20b,20c,20d-tetrahomo-2,5,6,7-tetranor-4-oxa-4,8-inter-m-phenylene PGI₂;
15-ethyl-20a,20b,20c,20d,20e-pentahomo-2,5,6,7-tetranor-4-oxa-4,8-inter-m-phenylene PGI₂;
15-ethyl-20a,20b,20c,20d,20e,20f-hexahomo-2,5,6,7-tetranor-4-oxa-4,8-inter-m-phenylene PGI₂;
15-ethyl-20a,20b,20c,20d,20e,20f,20g-heptahomo-2,5,6,7-tetranor-4-oxa-4,8-inter-m-phenylene PGI₂; and
methyl, ethyl, butyl, isobutyl, phenyl, benzyl, phenethyl, cyclopentyl, cyclohexyl, cyclohexylmethyl, furylmethyl, 1-carbomethoxy, phenacyl and p-bromophenacyl esters thereof.

Illustrative examples of the compounds represented by the general formula wherein $R_3$ is —Z—Ar will be given hereinbelow:

15-phenyl-2,5,6,7,16,17,18,19,20-nonanor-4-oxa-4,8-inter-m-phenylene PGI₂;
15-(2-chlorophenyl)-2,5,6,7,16,17,18,19,20-nonanor-4-oxa-4,8-inter-m-phenylene PGI₂;
15-(3-chlorophenyl)-2,5,6,7,16,17,18,19,20-nonanor-4-oxa-4,8-inter-,-phenylene PGI₂;
15-(4-chlorophenyl)-2,5,6,7,16,17,18,19,20-nonanor-4-oxa-4,8-inter-m-phenylene PGI₂;
15-(2-bromophenyl)-2,5,6,7,16,17,18,19,20-nonanor-4-oxa-4,8-inter-m-phenylene PGI₂;
15-(3-bromophenyl)-2,5,6,7,16,17,18,19,20-nonanor-4-oxa-4,8-inter-m-phenylene PGI₂;
15-(4-bromophenyl)-2,5,6,7,16,17,18,19,20-nonanor-4-oxa-4,8-inter-m-phenylene PGI₂;
15-(2-fluorophenyl)-2,5,6,7,16,17,18,19,20-nonanor-4-oxa-4,8-inter-m-phenylene PGI₂;
15-(3-fluorophenyl)-2,5,6,7,16,17,18,19,20-nonanor-4-oxa-4,8-inter-m-phenylene PGI₂;
15-(4-fluorophenyl)-2,5,6,7,16,17,18,19,20-nonanor-4-oxa-4,8-inter-m-phenylene PGI₂;
15-(2-methylphenyl)-2,5,6,7,16,17,18,19,20-nonanor-4-oxa-4,8-inter-m-phenylene PGI₂;
15-(3-methylphenyl)-2,5,6,7,16,17,18,19,20-nonanor-4-oxa-4,8-inter-m-phenylene PGI₂;
15-(4-methylphenyl)-2,5,6,7,16,17,18,19,20-nonanor-4-oxa-4,8-inter-m-phenylene PGI₂;
15-(2-methoxyphenyl)-2,5,6,7,16,17,18,19,20-nonanor-4-oxa-4,8-inter-m-phenylene PGI₂;
15-(4-methoxyphenyl)-2,5,6,7,16,17,18,19,20-nonanor-4-oxa-4,8-inter-m-phenylene PGI₂;
15-(4-nitrophenyl)-2,5,6,7,16,17,18,19,20-nonanor-4-oxa-4,8-inter-m-phenylene PGI₂;
15-(4-cyanophenyl)-2,5,6,7,16,17,18,19,20-nonanor-4-oxa-4,8-inter-m-phenylene PGI₂;
15-(3-trifluoromethylphenyl)-2,5,6,7,16,17,18,19,20-nonanor-4-oxa-4,8-inter-m-phenylene PGI₂;
15-(4-trifluoromethylphenyl)-2,5,6,7,16,17,18,19,20-nonanor-4-oxa-4,8-inter-m-phenylene PGI₂;
15-(2,4-dichlorophenyl)-2,5,6,7,16,17,18,19,20-nonanor-4-oxa-4,48-inter-m-phenylene PGI₂;
15-(3,4-dichlorophenyl)-2,5,6,7,16,17,18,19,20-nonanor-4-oxa-4,8-inter-m-phenylene PGI₂;
15-(3,4-dimethylphenyl)-2,5,6,7,16,17,18,19,20-nonanor-4-oxa-4,8-inter-m-phenylene PGI₂;
16-phenyl-2,5,6,7,17,18,19,20-octanor-4-oxa-4,8-inter-m-phenylene PGI₂;
16-(2-chlorophenyl)-2,5,6,7,17,18,19,20-octanor-4-oxa-4,8-inter-m-phenylene PGI₂;
16-(3-chlorophenyl)-2,5,6,7,17,18,19,20-octanor-4-oxa-4,8-inter-m-phenylene PGI₂;
16-(4-chlorophenyl)-2,5,6,7,17,18,19,20-octanor-4-oxa-4,8-inter-m-phenylene PGI₂;
16-(2-bromophenyl)-2,5,6,7,17,18,19,20-octanor-4-oxa-4,8-inter-m-phenylene PGI₂;
16-(3-bromophenyl)-2,5,6,7,17,18,19,20-octanor-4-oxa-4,8-inter-m-phenylene PGI₂;
16-(4-bromophenyl)-2,5,6,7,17,18,19,20-octanor-4-oxa-4,8-inter-m-phenylene PGI₂;
16-(2-fluorophenyl)-2,5,6,7,17,18,19,20-octanor-4-oxa-4,8-inter-m-phenylene PGI₂;
16-(3-fluorophenyl)-2,5,6,7,17,18,19,20-octanor-4-oxa-4,8-inter-m-phenylene PGI₂;
16-(4-fluorophenyl)-2,5,6,7,17,18,19,20-octanor-4-oxa-4,8-inter-m-phenylene PGI₂;
16-(2-methylphenyl)-2,5,6,7,17,18,19,20-octanor-4-oxa-4,8-inter-m-phenylene PGI₂;
16-(3-methylphenyl)-2,5,6,7,17,18,19,20-octanor-4-oxa-4,8-inter-m-phenylene PGI₂;

16-(4-methylphenyl)-2,5,6,7,17,18,19,20-octanor-4-oxa-4,8-inter-m-phenylene PGI$_2$;
16-(2-methoxyphenyl)-2,5,6,7,17,18,19,20-octanor-4-oxa-4,8-inter-m-phenylene PGI$_2$;
16-(4-methoxyphenyl)-2,5,6,7,17,18,19,20-octanor-4-oxa-4,8-inter-m-phenylene PGI$_2$;
16-(4-nitrophenyl)-2,5,6,7,17,18,19,20-octanor-4-oxa-4,8-inter-m-phenylene PGI$_2$;
16-(4-cyanophenyl)-2,5,6,7,17,18,19,20-octanor-4-oxa-4,8-inter-m-phenylene PGI$_2$;
16-(3-trifluoromethylphenyl)-2,5,6,7,17,18,19,20-octanor-4-oxa-4,8-inter-m-phenylene PGI$_2$;
16-(4-trifluoromethylphenyl)-2,5,6,7,17,18,19,20-octanor-4-oxa-4,8-inter-m-phenylene PGI$_2$;
16-(2,4-dichlorophenyl)-2,5,6,7,17,18,19,20-octanor-4-oxa-4,8-inter-m-phenylene PGI$_2$;
16-(3,4-dichlorophenyl)-2,5,6,7,17,18,19,20-octanor-4-oxa-4,8-inter-m-phenylene PGI$_2$;
16-(3,4-dimethylphenyl)-2,5,6,7,17,18,19,20-octanor-4-oxa-4,8-inter-m-phenylene PGI$_2$;
17-phenyl-2,5,6,7,18,19,20-heptanor-4-oxa-4,8-inter-m-phenylene PGI$_2$;
17-(2-chlorophenyl)-2,5,6,7,18,19,20-heptanor-4-oxa-4,8-inter-m-phenylene PGI$_2$;
17-(3-chlorophenyl)-2,5,6,7,18,19,20-heptanor-4-oxa-4,8-inter-m-phenylene PGI$_2$;
17-(4-chlorophenyl)-2,5,6,7,18,19,20-heptanor-4-oxa-4,8-inter-m-phenylene PGI$_2$;
17-(2-bromophenyl)-2,5,6,7,18,19,20-heptanor-4-oxa-4,8-inter-m-phenylene PGI$_2$;
17-(3-bromophenyl)-2,5,6,7,18,19,20-heptanor-4-oxa-4,8-inter-m-phenylene PGI$_2$;
17-(4-bromophenyl)-2,5,6,7,18,19,20-heptanor-4-oxa-4,8-inter-m-phenylene PGI$_2$;
17-(2-fluorophenyl)-2,5,6,7,18,19,20-heptanor-4-oxa-4,8-inter-m-phenylene PGI$_2$;
17-(3-fluorophenyl)-2,5,6,7,18,19,20-heptanor-4-oxa-4,8-inter-m-phenylene PGI$_2$;
17-(4-fluorophenyl)-2,5,6,7,18,19,20-heptanor-4-oxa-4,8-inter-m-phenylene PGI$_2$;
17-(2-methylphenyl)-2,5,6,7,18,19,20-heptanor-4-oxa-4,8-inter-m-phenylene PGI$_2$;
17-(3-methylphenyl)-2,5,6,7,18,19,20-heptanor-4-oxa-4,8-inter-m-phenylene PGI$_2$;
17-(4-methylphenyl)-2,5,6,7,18,19,20-heptanor-4-oxa-4,8-inter-m-phenylene PGI$_2$;
17-(2-methoxyphenyl)-2,5,6,7,18,19,20-heptanor-4-oxa-4,8-inter-m-phenylene PGI$_2$;
17-(4-methoxyphenyl)-2,5,6,7,18,19,20-heptanor-4-oxa-4,8-inter-m-phenylene PGI$_2$;
17-(4-nitrophenyl)-2,5,6,7,18,19,20-heptanor-4-oxa-4,8-inter-m-phenylene PGI$_2$;
17-(4-cyanophenyl)-2,5,6,7,18,19,20-heptanor-4-oxa-4,8-inter-m-phenylene PGI$_2$;
17-(3-trifluoromethylphenyl)-2,5,6,7,18,19,20-hetanor-4-oxa-4,8-inter-m-phenylene PGI$_2$;
17-(4-trifluoromethylphenyl)-2,5,6,7,18,19,20-heptanor-4-oxa-4,8-inter-m-phenylene PGI$_2$;
17-(2,4-dichlorophenyl)-2,5,6,7,18,19,20-heptanor-4-oxa-4,8-inter-m-phenylene PGI$_2$;
17-(3,4-dichlorophenyl)-2,5,6,7,18,19,20-heptanor-4-oxa-4,8-inter-m-phenylene PGI$_2$;
17-(3,4-dimethylphenyl)-2,5,6,7,18,19,20-heptanor-4-oxa-4,8-inter-m-phenylene PGI$_2$;
16,16-dimethyl-17-phenyl-2,5,6,7,18,19,20-heptanor-4-oxa-4,8-inter-m-phenylene PGI$_2$;
17-(2-chlorophenyl)-16,16-dimethyl-2,5,6,7,18,19,20-heptanor-4-oxa-4,8-inter-m-phenylene PGI$_2$;
17-(3-chlorophenyl)-16,16-dimethyl-2,5,6,7,18,19,20-heptanor-4-oxa-4,8-inter-m-phenylene PGI$_2$;
17-(4-chlorophenyl)-16,16-dimethyl-2,5,6,7,18,19,20-heptanor-4-oxa-4,8-inter-m-phenylene PGI$_2$;
17-(2-bromophenyl)-16,16-dimethyl-2,5,6,7,18,19,20-heptanor-4-oxa-4,8-inter-m-phenylene PGI$_2$;
17-(3-bromophenyl)-16,16-dimethyl-2,5,6,7,18,19,20-heptanor-4-oxa-4,8-inter-m-phenylene PGI$_2$;
17-(4-bromophenyl)-16,16-dimethyl-2,5,6,7,18,19,20-heptanor-4-oxa-4,8-inter-m-phenylene PGI$_2$;
17-(2-fluorophenyl)-16,16-dimethyl-2,5,6,7,18,19,20-heptanor-4-oxa-4,8-inter-m-phenylene PGI$_2$;
17-(3-fluorophenyl)-16,16-dimethyl-2,5,6,7,18,19,20-heptanor-4-oxa-4,8-inter-m-phenylene PGI$_2$;
17-(4-fluorophenyl)-16,16-dimethyl-2,5,6,7,18,19,20-heptanor-4-oxa-4,8-inter-m-phenylene PGI$_2$;
16,16-dimethyl-17-(2-methylphenyl)-2,5,6,7,18,19,20-heptanor-4-oxa-4,8-inter-m-phenylene PGI$_2$;
16,16-diemthyl-17-(3-methylphenyl)-2,5,6,7,18,19,20-heptanor-4-oxa-4,8-inter-m-phenylene PGI$_2$;
16,16-dimethyl-17-(4-methylphenyl)-2,5,6,7,18,19,20-heptanor-4-oxa-4,8-inter-m-phenylene PGI$_2$;
16,16-dimethyl-17-(2-methoxyphenyl)-2,5,6,7,18,19,20-heptanor-4-oxa-4,8-inter-m-phenylene PGI$_2$;
16,16-dimethyl-17-(4-methoxyphenyl)-2,5,6,7,18,19,20-heptanor-4-oxa-4,8-inter-m-phenylene PGI$_2$;
16,16-dimethyl-17-(4-nitrophenyl)-2,5,6,7,18,19,20-heptanor-4-oxa-4,8-inter-m-phenylene PGI$_2$;
17-(4-cyanophenyl)-16,16-dimethyl-2,5,6,7,18,19,20-heptanor-4-oxa-4,8-inter-m-phenylene PGI$_2$;
17-(3-trifluoromethylphenyl)-16,16-dimethyl-2,5,6,7,18,19,20-heptanor-4-oxa-4,8-inter-m-phenylene PGI$_2$;
17-(4-trifluoromethylphenyl)-16,16-dimethyl-2,5,6,7,18,19,20-heptanor-4-oxa-4,8-inter-m-phenylene PGI$_2$;
17-(2,4-dichlorophenyl)-16,16-dimethyl-2,5,6,7,18,19,20-heptanor-4-oxa-4,8-inter-m-phenylene PGI$_2$;
17-(3,4-dichlorophenyl)-16,16-dimethyl-2,5,6,7,18,19,20-heptanor-4-oxa-4,8-inter-m-phenylene PGI$_2$;
16,16-dimethyl-17-(3,4-dimethylphenyl)-2,5,6,7,18,19,20-heptanor-4-oxa-4,8-inter-m-phenylene PGI$_2$;
18-phenyl-2,5,6,7,19,20-hexanor-4-oxa-4,8-inter-m-phenylene PGI$_2$;
16,16-dimethyl-18-phenyl-2,5,6,7,19,20-hexanor-4-oxa-4,8-inter-m-phenylene PGI$_2$;
19-phenyl-2,5,6,7,20-pentanor-4-oxa-4,8-inter-m-phenylene PGI$_2$;
16,16-dimethyl-19-phenyl-2,5,6,7,20-pentanor-4-oxa-4,8-inter-m-phenylene PGI$_2$;
20-phenyl-2,5,6,7-tetranor-4-oxa-4,8-inter-m-phenylene PGI$_2$;

and methyl, ethyl, butyl, isobutyl, phenyl, benzyl, phenethyl, cyclopentyl, cyclohexyl, cyclohexylmethyl, furylmethyl, 1-carbomethoxy, phenacyl and p-bromophenacyl esters thereof.

Illustrative examples of the compounds represented by the general formula wherein $R_3$ is -Z-$R_7$ may include the following:

15-cyclopropyl-2,5,6,7,16,17,18,19,20-nonanor-4-oxa-4,8-inter-m-phenylene PGI$_2$;
15-cyclobutyl-2,5,6,7,16,17,18,19,20-nonanor-4-oxa-4,8-inter-m-phenylene PGI$_2$;
15-cyclopentyl-2,5,6,7,16,17,18,19,20-nonanor-4-oxa-4,8-inter-m-phenylene PGI$_2$;

15-(2-methylcyclopentyl)-2,5,6,7,16,17,18,19,20-nonanor-4-oxa-4,8-inter-m-phenylene PGI₂;
15-(3-methylcyclopentyl)-2,5,6,7,16,17,18,19,20-nonanor-4-oxa-4,8-inter-m-phenylene PGI₂;
15-(2,5-dimethylcyclopentyl)-2,5,6,7,16,17,18,19,20-nonanor-4-oxa-4,8-inter-m-phenylene PGI₂;
15-(3,4-dimethylcyclopentyl)-2,5,6,7,16,17,18,19,20-nonanor-4-oxa-4,8-inter-m-phenylene PGI₂;
15-cyclohexyl-2,5,6,7,16,17,18,19,20-nonanor-4-oxa-4,8-inter-m-phenylene PGI₂;
15-(3-methylcyclohexyl)-2,5,6,7,16,17,18,19,20-nonanor-4-oxa-4,8-inter-m-phenylene PGI₂;
15-(3-ethylcyclohexyl)-2,5,6,7,16,17,18,19,20-nonanor-4-oxa-4,8-inter-m-phenylene PGI₂;
15-(3-propylcyclohexyl)-2,5,6,7,16,17,18,19,20-nonanor-4-oxa-4,8-inter-m-phenylene PGI₂;
15-(3-butylcyclohexyl)-2,5,6,7,16,17,18,19,20-nonanor-4-oxa-4,8-inter-m-phenylene PGI₂;
15-(3,3-dimethylcyclohexyl)-2,5,6,7,16,17,18,19,20-nonanor-4-oxa-4,8-inter-m-phenylene PGI₂;
15-(2,6-dimethylcyclohexyl)-2,5,6,7,16,17,18,19,20-nonanor-4-oxa-4,8-inter-m-phenylene PGI₂;
15-(2,4,6-trimethylcyclohexyl)-2,5,6,7,16,17,18,19,20-nonanor-4-oxa-4,8-inter-m-phenylene PGI₂;
15-cyclooctyl-2,5,6,7,16,17,18,19,20-nonanor-4-oxa-4,8-inter-m-phenylene PGI₂;
15-cyclododecyl-2,5,6,7,16,17,18,19,20-nonanor-4-oxa-4,8-inter-m-phenylene PGI₂;
16-cyclopropyl-2,5,6,7,17,18,19,20-octanor-4-oxa-4,8-inter-m-phenylene PGI₂;
16-cyclobutyl-2,5,6,7,17,18,19,20-octanor-4-oxa-4,8-inter-m-phenylene PGI₂;
16-cyclopentyl-2,5,6,7,17,18,19,20-octanor-4-oxa-4,8-inter-m-phenylene PGI₂;
16-(2-methylcyclopentyl)-2,5,6,7,17,18,19,20-octanor-4-oxa-4,8-inter-m-phenylene PGI₂;
16-(3-methylcyclopentyl)-2,5,6,7,17,18,19,20-octanor-4-oxa-4,8-inter-m-phenylene PGI₂;
16-(2,5-dimethylcyclopentyl)-2,5,6,7,17,18,19,20-octanor-4-oxa-4,8-inter-m-phenylene PGI₂;
16-(3,4-dimethylcyclopentyl)-2,5,6,7,17,18,19,20-octanor-4-oxa-4,8-inter-m-phenylene PGI₂;
16-cyclopentyl-16-methyl-2,5,6,7,18,19,20-heptanor-4-oxa-4,8-inter-m-phenylene PGI₂;
16-methyl-16-(2-methylcyclopentyl)-2,5,6,7,18,19,20-heptanor-4-oxa-4,8-inter-m-phenylene PGI₂;
16-methyl-16-(3-methylcyclopentyl)-2,5,6,7,18,19,20-heptanor-4-oxa-4,8-inter-m-phenylene PGI₂;
16-(2,5-dimethylcyclopentyl)-2,5,6,7,18,19,20-heptanor-4-oxa-4,8-inter-m-phenylene PGI₂;
16-methyl-16-(3,4-dimethylcyclopentyl)-2,5,6,7,18,19,20-heptanor-4-oxo-4,8-inter-m-phenylene PGI₂;
16-cyclohexyl-2,5,6,7,17,18,19,20-octanor-4-oxa-4,8-inter-m-phenylene PGI₂;
16-(3-methylcyclohexyl)-2,5,6,7,17,18,19,20-octanor-4-oxa-4,8-inter-m-phenylene PGI₂;
16-(3-ethylcyclohexyl)-2,5,6,7,17,18,19,20-octanor-4-oxa-4,8-inter-m-phenylene PGI₂;
16-(3-propylcyclohexyl)-2,5,6,7,17,18,19,20-octanor-4-oxa-4,8-inter-m-phenylene PGI₂;
16-(3-butylcyclohexyl)-2,5,6,7,17,18,19,20-octanor-4-oxa-4,8-inter-m-phenylene PGI₂;
16-(3,3-dimethylcyclohexyl)-2,5,6,7,17,18,19,20-octanor-4-oxa-4,8-inter-m-phenylene PGI₂;
16-(2,6-dimethylcyclohexyl)-2,5,6,7,17,18,19,20-octanor-4-oxa-4,8-inter-m-phenylene PGI₂;
16-(2,4,6-trimethylcyclohexyl)-2,5,6,7,17,18,19,20-octanor-4-oxa-4,8-inter-m-phenylene PGI₂;
16-cyclohexyl-16-methyl-2,5,6,7,18,19,20-heptanor-4-oxa-4,8-inter-m-phenylene PGI₂;
16-methyl-16-(3-methylcyclohexyl)-2,5,6,7,18,19,20-heptanor-4-oxa-4,8-inter-m-phenylene PGI₂;
16-methyl-16-(3-ethylcyclohexyl)-2,5,6,7,18,19,20-heptanor-4-oxa-4,8-inter-m-phenylene PGI₂;
16-methyl-16-(3-propylcyclohexyl)-2,5,6,7,18,19,20-heptanor-4-oxa-4,8-inter-m-phenylene PGI₂;
16-methyl-16-(3-butylcyclohexyl)-2,5,6,7,18,19,20-heptanor-4-oxa-4,8-inter-m-phenylene PGI₂;
16-methyl-16-(3,3-dimethylcyclohexy)-2,5,6,7,18,19,20-heptanor-4-oxa-4,8-inter-m-phenylene PGI₂;
16-methyl-16-(2,6-dimethylcyclohexyl)-2,5,6,7,18,19,20-heptanor-4-oxa-4,8-inter-m-phenylene PGI₂;
16-methyl-16-(2,4,6-trimethylcyclohexyl)-2,5,6,7,18,19,20-heptanor-4-oxa-4,8-inter-m-phenylene PGI₂;
16-cycloheptyl-2,5,6,7,17,18,19,20-octanor-4-oxa-4,8-inter-m-phenylene PGI₂;
16-cyclooctyl-2,5,6,7,17,18,19,20-octanor-4-oxa-4,8-inter-m-phenylene PGI₂;
16-cyclododecyl-2,5,6,7,17,18,19,20-octanor-4-oxa-4,8-inter-m-phenylene PGI₂;
17-cyclopropyl-2,5,6,7,18,19,20-heptanor-4-oxa-4,8-inter-m-phenylene PGI₂;
17-cyclobutyl-2,5,6,7,18,19,20-heptanor-4-oxa-4,8-inter-m-phenylene PGI₂;
17-cyclopentyl-2,5,6,7,18,19,20-heptanor-4-oxa-4,8-inter-m-phenylene PGI₂;
17-(2-methylcyclopentyl)-2,5,6,7,18,19,20-heptanor-4-oxa-4,8-inter-m-phenylene PGI₂;
17-(3-methylcyclopentyl)-2,5,6,7,18,19,20-heptanor-4-oxa-4,8-inter-m-phenylene PGI₂;
17-(2,5-dimethylcyclopentyl)-2,5,6,7,18,19,20-heptanor-4-oxa-4,8-inter-m-phenylene PGI₂;
17-(3,4-dimethylcyclopentyl)-2,5,6,7,18,19,20-heptanor-4-oxa-4,8-inter-m-phenylene PGI₂;
17-cyclopentyl-16-methyl-2,5,6,7,18,19,20-heptanor-4-oxa-4,8-inter-m-phenylene PGI₂;
16-methyl-17-(2-methylcyclopentyl)-2,5,6,7,18,19,20-heptanor-4-oxa-4,8-inter-m-phenylene PGI₂;
16-methyl-17-(3-methylcyclopentyl)-2,5,6,7,18,19,20-heptanor-4-oxa-4,8-inter-m-phenylene PGI₂;
16-methyl-17-(2,5-dimethylcyclopentyl)-2,5,6,7,18,19,20-heptanor-4-oxa-4,8-inter-m-phenylene PGI₂;
16-methyl-17-(3,4-dimethylcyclopentyl)-2,5,6,7,18,19,20-heptanor-4-oxa-4,8-inter-m-phenylene PGI₂;
17-cyclopentyl-16,16-dimethyl-2,5,6,7,18,19,20-heptanor-4-oxa-4,8-inter-m-phenylene PGI₂;
16,16-dimethyl-17-(2-methylcyclopentyl)-2,5,6,7,18,19,20-heptanor-4-oxa-4,8-inter-m-phenylene PGI₂;
16,16-dimethyl-17-(3-methylcyclopentyl)-2,5,6,7,18,19,20-heptanor-4-oxa-4,8-inter-m-phenylene PGI₂;
16,16-dimethyl-17-(2,5-dimethylcyclopentyl)-2,5,6,7,18,19,20-heptanor-4-oxa-4,8-inter-m-phenylene PGI₂;
16,16-dimethyl-17-(3,4-dimethylcyclopentyl)-2,5,6,7,18,19,20-heptanor-4-oxa-4,8-inter-m-phenylene PGI₂;
17-cyclopentyl-17-methyl-2,5,6,7,19,20-hexanor-4-oxa-4,8-inter-m-phenylene PGI₂;

17-methyl-17-(2-methylcyclopentyl)-2,5,6,7,19,20-hexanor-4-oxa-4,8-inter-m-phenylene PGI₂;
17-methyl-17-(3-methylcyclopentyl)-2,5,6,7,19,20-hexanor-4-oxa-4,8-inter-m-phenylene PGI₂;
17-methyl-17-(2,5-dimethylcyclopentyl)-2,5,6,7,19,20-hexanor-4-oxa-4,8-inter-m-phenylene PGI₂;
17-methyl-17-(3,4-dimethylcyclopentyl)-2,5,6,7,19,20-hexanor-4-oxa-4,8-inter-m-phenylene PGI₂;
17-cyclohexyl-2,5,6,7,18,19,20-heptanor-4-oxa-4,8-inter-m-phenylene PGI₂;
17-(3-methylcyclohexyl)-2,5,6,7,18,19,20-heptanor-4-oxa-4,8-inter-m-phenylene PGI₂;
17-(3-ethylcyclohexyl)-2,5,6,7,18,19,20-heptanor-4-oxa-4,8-inter-m-phenylene PGI₂;
17-(3-propylcyclohexyl)-2,5,6,7,18,19,20-heptanor-4-oxa-4,8-inter-m-phenylene PGI₂;
17-(3-butylcyclohexyl)-2,5,6,7,18,19,20-heptanor-4-oxa-4,8-inter-m-phenylene PGI₂;
17-(3,3-dimethylcyclohexyl)-2,5,6,7,18,19,20-heptanor-4-oxa-4,8-inter-m-phenylene PGI₂;
17-(2,6-dimethylcyclohexyl)-2,5,6,7,18,19,20-heptanor-4-oxa-4,8-inter-m-phenylene PGI₂;
17-(2,4,6-trimethylcyclohexyl)-2,5,6,7,18,19,20-heptanor-4-oxa-4,8-inter-m-phenylene PGI₂;
17-cyclohexyl-16-methyl-2,5,6,7,18,19,20-heptanor-4-oxa-4,8-inter-m-phenylene PGI₂;
16-methyl-17-(3-methylcyclohexyl)-2,5,6,7,18,19,20-heptanor-4-oxa-4,8-inter-m-phenylene PGI₂;
17-(3-ethylcyclohexyl)-16-methyl-2,5,6,7,18,19,20-heptanor-4-oxa-4,8-inter-m-phenylene PGI₂;
16-methyl-17-(3-propylcyclohexyl)-2,5,6,7,18,19,20-heptanor-4-oxa-4,8-inter-m-phenylene PGI₂;
17-(3-butylcyclohexyl)-16-methyl-2,5,6,7,18,19,20-heptanor-4-oxa-4,8-inter-m-phenylene PGI₂;
16-methyl-17-(3,3-dimethylcyclohexyl)-2,5,6,7,18,19,20-heptanor-4-oxa-4,8-inter-m-phenylene PGI₂;
16-methyl-17-(2,6-dimethylcyclohexyl)-2,5,6,7,18,19,20-heptanor-4-oxa-4,8-inter-m-phenylene PGI₂;
16-methyl-17-(2,4,6-trimethylcyclohexyl)-2,5,6,7,18,19,20-heptanor-4-oxa-4,8-inter-m-phenylene PGI₂;
17-cyclohexyl-16,16-dimethyl-2,5,6,7,18,19,20-heptanor-4-oxa-4,8-inter-m-phenylene PGI₂;
16,16-dimethyl-17-(3-methylcyclohexyl)-2,5,6,7,18,19,20-heptanor-4-oxa-4,8-inter-m-phenylene PGI₂;
17-(3-ethylcyclohexyl)-16,16-dimethyl-2,5,6,7,18,19,20-heptanor-4-oxa-4,8-inter-m-phenylene PGI₂;
16,16-dimethyl-17-(3-propylcyclohexyl)-2,5,6,7,18,19,20-heptanor-4-oxa-4,8-inter-m-phenylene PGI₂;
17-(3-butylcyclohexyl)-16,16-dimethyl-2,5,6,7,18,19,20-heptanor-4-oxa-4,8-inter-m-phenylene PGI₂;
16,16-dimethyl-17-(3,3-dimethylcyclohexyl)-2,5,6,7,18,19,20-heptanor-4-oxa-4,8-inter-m-phenylene PGI₂;
16,16-dimethyl-17-(2,6-dimethylcyclohexyl)-2,5,6,7,18,19,20-heptanor-4-oxa-4,8-inter-m-phenylene PGI₂;
16,16-dimethyl-17-(2,4,6-trimethylcyclohexyl)-2,5,6,7,18,19,20-heptanor-4-oxa-4,8-inter-m-phenylene PGI₂;
17-cyclohexyl-17-methyl-2,5,6,7,19,20-hexanor-4-oxa-4,8-inter-m-phenylene PGI₂;
17-methyl-17-(3-methylcyclohexyl)-2,5,6,7,19,20-hexanor-4-oxa-4,8-inter-m-phenylene PGI₂;
17-(3-ethylcyclohexyl)-17-methyl-2,5,6,7,19,20-hexanor-4-oxa-4,8-inter-m-phenylene PGI₂;
17-methyl-(3-propylcyclohexyl)-2,5,6,7,19,20-hexanor-4-oxa-4,8-inter-m-phenylene PGI₂;
17-(3-butylcyclohexyl)-17-methyl-2,5,6,7,19,20-hexanor-4-oxa-4,8-inter-m-phenylene PGI₂;
17-methyl-17-(3,3-dimethylcyclohexyl)-2,5,6,7,19,20-hexanor-4-oxa-4,8-inter-m-phenylene PGI₂;
17-methyl-17-(2,6-dimethylcyclohexyl)-2,5,6,7,19,20-hexanor-4-oxa-4,8-inter-m-phenylene PGI₂;
17-methyl-17-(2,4,6-trimethylcyclohexyl)-2,5,6,7,19,20-hexanor-4-oxa-4,8-inter-m-phenylene PGI₂;
17-cycloheptyl-2,5,6,7,18,19,20-heptanor-4-oxa-4,8-inter-m-phenylene PGI₂;
17-cyclooctyl-2,5,6,7,18,19,20-heptanor-4-oxa-4,8-inter-m-phenylene PGI₂;
17-cyclododecyl-2,5,6,7,18,19,20-heptanor-4-oxa-4,8-inter-m-phenylene PGI₂;
18-cyclopentyl-2,5,6,7,19,20-hexanor-4-oxa-4,8-inter-m-phenylene PGI₂;
18-(2-methylcyclopentyl)-2,5,6,7,19,20-hexanor-4-oxa-4,8-inter-m-phenylene PGI₂;
18-(3-methylcyclopentyl)-2,5,6,7,19,20-hexanor-4-oxa-4,8-inter-m-phenylene PGI₂;
18-(2,5-dimethylcyclopentyl)-2,5,6,7,19,20-hexanor-4-oxa-4,8-inter-m-phenylene PGI₂;
18-(3,4-dimethylcyclopentyl)-2,5,6,7,19,20-hexanor-4-oxa-4,8-inter-m-phenylene PGI₂;
18-cyclopentyl-16-methyl-2,5,6,7,19,20-hexanor-4-oxa-4,8-inter-m-phenylene PGI₂;
16-methyl-18-(2-methylcyclopentyl)-2,5,6,7,19,20-hexanor-4-oxa-4,8-inter-m-phenylene PGI₂;
16-methyl-18-(3-methylcyclopentyl)-2,5,6,7,19,20-hexanor-4-oxa-4,8-inter-m-phenylene PGI₂;
16-methyl-18-(2,5-dimethylcyclopentyl)-2,5,6,7,19,20-hexanor-4-oxa-4,8-inter-m-phenylene PGI₂;
16-methyl-18-(3,5-dimethylcyclopentyl)-2,5,6,7,19,20-hexanor-4-oxa-4,8-inter-m-phenylene PGI₂;
18-cyclopentyl-16,16-dimethyl-2,5,6,7,19,20-hexanor-4-oxa-4,8-inter-m-phenylene PGI₂;
16,16-dimethyl-18-(2-methylcyclopentyl)-2,5,6,7,19,20-hexanor-4-oxa-4,8-inter-m-phenylene PGI₂;
16,16-dimethyl-18-(3-methylcyclopentyl)-2,5,6,7,19,20-hexanor-4-oxa-4,8-inter-m-phenylene PGI₂;
16,16-dimethyl-18-(2,5-dimethylcyclopentyl)-2,5,6,7,19,20-hexanor-4-oxa-4,8-inter-m-phenylene PGI₂;
16,16-dimethyl-18-(3,4-dimethylcyclopentyl)-2,5,6,7,19,20-hexanor-4-oxa-4,8-inter-m-phenylene PGI₂;
18-cyclopentyl-17,17-dimethyl-2,5,6,7,19,20-hexanor-4-oxa-4,8-inter-m-phenylene PGI₂;
17,17-dimethyl-18-(2-methylcyclopentyl)-2,5,6,7,19,20-hexanor-4-oxa-4,8-inter-m-phenylene PGI₂;
17,17-dimethyl-18-(3-methylcyclopentyl)-2,5,6,7,19,20-hexanor-4-oxa-4,8-inter-m-phenylene PGI₂
17,17-dimethyl-18-(2,5-dimethylcyclopentyl)-2,5,6,7,19,20-hexanor-4-oxa-4,8-inter-m-phenylene PGI₂;
17,17-dimethyl-18-(3,4-dimethylcyclopentyl)-2,5,6,7,19,20-hexanor-4-oxa-4,8-inter-m-phenylene PGI₂;
18-cyclohexyl-2,5,6,7,19,20-hexanor-4-oxa-4,8-inter-m-phenylene PGI₂;
18-(3-methylcyclohexyl)-2,5,6,7,19,20-hexanor-4-oxa-4,8-inter-m-phenylene PGI₂;
18-(3-ethylcyclohexyl)-2,5,6,7,19,20-hexanor-4-oxa-4,8-inter-m-phenylene PGI₂;

18-(3-propylcyclohexyl)-2,5,6,7,19,20-hexanor-4-oxa-4,8-inter-m-phenylene PGI₂;
18-(3-butylcyclohexyl)-2,5,6,7,19,20-hexanor-4,8-inter-m-phenylene PGI₂;
18-(3,3-dimethylcyclohexyl)-2,5,6,7,19,20-hexanor-4-oxa-4,8-inter-m-phenylene PGI₂;
18-(2,6-dimethylcyclohexyl)-2,5,6,7,19,20-hexanor-4-oxa-4,8-inter-m-phenylene PGI₂;
18-(2,4,6-trimethylcyclohexyl)-2,5,6,7,19,20-hexanor-4-oxa-4,8-inter-m-phenylene PGI₂;
18-cyclohexyl-16-methyl-2,5,6,7,19,20-hexanor-4-oxa-4,8-inter-m-phenylene PGI₂;
16-methyl-18-(3-methylcyclohexyl)-2,5,6,7,19,20-hexanor-4-oxa-4,8-inter-m-phenylene PGI₂;
18-(3-ethylcyclohexyl)-16-methyl-2,5,6,7,19,20-hexanor-4-oxa-4,8-inter-m-phenylene PGI₂;
16-methyl-18-(3-propylcyclohexyl)-2,5,6,7,19,20-hexanor-4-oxa-4,8-inter-m-phenylene PGI₂;
18-(3-butylcyclohexyl)-16-methyl-2,5,6,7,19,20-hexanor-4-oxa-4,8-inter-m-phenylene PGI₂;
16-methyl-18-(3,3-dimethylcyclohexyl)-2,5,6,7,19,20-hexanor-4-oxa-4,8-inter-m-phenylene PGI₂;
16-methyl-18-(2,6-dimethylcyclohexyl)-2,5,6,7,19,20-hexanor-4-oxa-4,8-inter-m-phenylene PGI₂;
16-methyl-18-(2,4,6-trimethylcyclohexyl)-2,5,6,7,19,20-hexanor-4-4,8-inter-m-phenylene PGI₂;
18-cyclohexyl-16,16-dimethyl-2,5,6,7,19,20-hexanor-4-oxa-4,8-inter-m-phenylene PGI₂;
16,16-dimethyl-18-(3-methylcyclohexyl)-2,5,6,7,19,20-hexanor-4-oxa-4,8-inter-m-phenylene PGI₂;
18-(3-ethylcyclohexyl)-16,16-dimethyl-2,5,6,7,19,20-hexanor-4-oxa-4,8-inter-m-phenylene PGI₂;
16,16-dimethyl-18-(3-propylcyclohexyl)-2,5,6,7,19,20-hexanor-4-oxa-4,8-inter-m-phenylene PGI₂;
18-(3-butylcyclohexyl)-16,16-dimethyl-2,5,6,7,19,20-hexanor-4-oxa-4,8-inter-m-phenylene PGI₂;
16,16-dimethyl-18-(3,3-dimethylcyclohexyl)-2,5,6,7,19,20-hexanor-4-oxa-4,8-inter-m-phenylene PGI₂;
16,16-dimethyl-18-(2,6-dimethylcyclohexyl)-2,5,6,7,19,20-hexanor-4-oxa-4,8-inter-m-phenylene PGI₂;
16,16-dimethyl-18-(2,4,6-trimethylcyclohexyl)-2,5,6,7,19,20-hexanor-4-oxa-4,8-inter-m-phenylene PGI₂;
18-cyclohexyl-17,17-dimethyl-2,5,6,7,19,20-hexanor-4-oxa-4,8-inter-m-phenylene PGI₂;
17,17-dimethyl-18-(3-methylcyclohexyl)-2,5,6,7,19,20-hexanor-4-oxa-4,8-inter-m-phenylene PGI₂;
18-(3-ethylcyclohexyl)-17,17-dimethyl-2,5,6,7,19,20-hexanor-4-oxa-4,8-inter-m-phenylene PGI₂;
17,17-dimethyl-18-(3-propylcyclohexyl)-2,5,6,7,19,20-hexanor-4-oxa-4,8-inter-m-phenylene PGI₂;
18-(3-butylcyclohexyl)-17,17-dimethyl-2,5,6,7,19,20-hexanor-4-oxa-4,8-inter-m-phenylene PGI₂;
17,17-dimethyl-18-(3,3-dimethylcyclohexyl)-2,5,6,7,19,20-hexanor-4-oxa-4,8-inter-m-phenylene PGI₂;
17,17-dimethyl-18-(2,6-dimethylcyclohexyl)-2,5,6,7,19,20-hexanor-4-oxa-4,8-inter-m-phenylene PGI₂;
17,17-dimethyl-18-(2,4,6-trimethylcyclohexyl)-2,5,6,7,19,20-hexanor-4-oxa-4,8-inter-m-phenylene PGI₂;
19-cyclopentyl-2,5,6,7,20-pentanor-4-oxa-4,8-inter-m-phenylene PGI₂;
19-(2-methylcyclopentyl)-2,5,6,7,20-pentanor-4-oxa-4,8-inter-m-phenylene PGI₂;
19-(3-methylcyclopentyl)-2,5,6,7,20-pentanor-4-oxa-4,8-inter-m-phenylene PGI₂;
19-(2,5-dimethylcyclopentyl)-2,5,6,7,20-pentanor-4-oxa-4,8-inter-m-phenylene PGI₂;
19-(3,4-dimethylcyclopentyl)-2,5,6,7,20-pentanor-4-oxa-4,8-inter-m-phenylene PGI₂;
19-cyclopentyl-16-methyl-2,5,6,7,20-pentanor-4-oxa-4,8-inter-m-phenylene PGI₂;
16-methyl-19-(2-methylcyclopentyl)-2,5,6,7,20-pentanor-4-oxa-4,8-inter-m-phenylene PGI₂;
16-methyl-19-(3-methylcyclopentyl)-2,5,6,7,20-pentanor-4-oxa-4,8-inter-m-phenylene PGI₂;
16-methyl-19-(2,5-dimethylcyclopentyl)-2,5,6,7,20-pentanor-4-oxa-4,8-inter-m-phenylene PGI₂;
16-methyl-19-(3,4-dimethylcyclopentyl)-2,5,6,7,20-pentanor-4-oxa-4,8-inter-m-phenylene PGI₂;
19-cyclopentyl-16,16-dimethyl-2,5,6,7,20-pentanor-4-oxa-4,8-inter-m-phenylene PGI₂;
16,16-dimethyl-19-(2-methylcyclopentyl)-2,5,6,7,20-pentanor-4-oxa-4,8-inter-m-phenylene PGI₂;
16,16-dimethyl-19-(3-methylcyclopentyl)-2,5,6,7,20-pentanor-4-oxa-4,8-inter-m-phenylene PGI₂;
16,16-dimethyl-19-(2,5-dimethylcyclopentyl)-2,5,6,7,20-pentanor-4-oxa-4,8-inter-m-phenylene PGI₂;
16,16-dimethyl-19-(3,4-dimethylcyclopentyl)-2,5,6,7,20-pentanor-4-oxa-4,8-inter-m-phenylene PGI₂;
19-cyclopentyl-17,17-dimethyl-2,5,6,7,20-pentanor-4-oxa-4,8-inter-m-phenylene PGI₂;
17,17-dimethyl-19-(2-methylcyclopentyl)-2,5,6,7,20-pentanor-4-oxa-4,8-inter-m-phenylene PGI₂;
17,17-dimethyl-19-(3-methylcyclopentyl)-2,5,6,7,20-pentanor-4-oxa-4,8-inter-m-phenylene PGI₂;
17,17-dimethyl-19-(2,5-dimethylcylcopentyl)-2,5,6,7,20-pentanor-4-oxa-4,8-inter-m-phenylene PGI₂;
17,17-dimethyl-19-(3,4-dimethylcyclopentyl)-2,5,6,7,20-pentanor-4-oxa-4,8-inter-m-phenylene PGI₂;
19-cyclohexyl-2,5,6,7,20-pentanor-4-oxa-4,8-inter-m-phenylene PGI₂;
19-(3-methylcyclohexyl)-2,5,6,7,20-pentanor-4-oxa-4,8-inter-m-phenylene PGI₂;
19-(3-ethylcyclohexyl)-2,5,6,7,20-pentanor-4-oxa-4,8-inter-m-phenylene PGI₂;
19-(3-propylcyclohexyl)-2,5,6,7,20-pentanor-4-oxa-4,8-inter-m-phenylene PGI₂;
19-(3-butylcyclohexyl)-2,5,6,7,20-pentanor-4-oxa-4,8-inter-m-phenylene PGI₂;
19-(3,3-dimethylcyclohexyl)-2,5,6,7,20-pentanor-4-oxa-4,8-inter-m-phenylene PGI₂;
19-(2,6-dimethylcyclohexyl)-2,5,6,7,20-pentanor-4-oxa-4,8-inter-m-phenylene PGI₂;
19-(2,4,6-trimethylcyclohexyl)-2,5,6,7,20-pentanor-4-oxa-4,8-inter-m-phenylene PGI₂;
19-cyclohexyl-16-methyl-2,5,6,7,20-pentanor-4-oxa-4,8-inter-m-phenylene PGI₂;
16-methyl-19-(3-methylcyclohexyl)-2,5,6,7,20-pentanor-4-oxa-4,8-inter-m-phenylene PGI₂;
19-(3-ethylcyclohexyl)-16-methyl-2,5,6,7,20-pentanor-4-oxa-4,8-inter-m-phenylene PGI₂;
16-methyl-19-(3-propylcyclohexyl)-2,5,6,7,20-pentanor-4-oxa-4,8-inter-m-phenylene PGI₂;
19-(3-butylcyclohexyl)-16-methyl-2,5,6,7,20-pentanor-4-oxa-4,8-inter-m-phenylene PGI₂;
16-methyl-19-(3,3-dimethylcyclohexyl)-2,5,6,7,20-pentanor-4-oxa-4,8-inter-m-phenylene PGI₂;
16-methyl-19-(2,6-dimethylcyclohexyl)-2,5,6,7,20-pentanor-4-oxa-4,8-inter-m-phenylene PGI₂;
16-methyl-19-(2,4,6-trimethylcyclohexyl)-2,5,6,7,20-pentanor-4-oxa-4,8-inter-m-phenylene PGI₂;

19-cyclohexyl-16,16-dimethyl-2,5,6,7,20-pentanor-4-oxa-4,8-inter-m-phenylene PGI$_2$;
16,16-dimethyl-19-(3-methylcyclohexyl)-2,5,6,7,20-pentanor-4-oxa-4,8-inter-m-phenylene PGI$_2$;
19-(3-ethylcyclohexyl)-16,16-dimethyl-2,5,6,7,20-pentanor-4-oxa-4,8-inter-m-phenylene PGI$_2$;
16,16-dimethyl-19-(3-propylcyclohexyl)-2,5,6,7,20-pentanor-4-oxa-4,8-inter-m-phenylene PGI$_2$;
19-(3-butylcyclohexyl)-16,16-dimethyl-2,5,6,7,20-pentanor-4-oxa-4,8-inter-m-phenylene PGI$_2$;
16,16-dimethyl-19-(3,3-dimethylcyclohexyl)-2,5,6,7,20-pentanor-4-oxa-4,8-inter-m-phenylene PGI$_2$;
16,16-dimethyl-19-(2,6-dimethylcyclohexyl)-2,5,6,7,20-pentanor-4-oxa-4,8-inter-m-phenylene PGI$_2$;
16,16-dimethyl-19-(2,4,6-trimethylcyclohexyl)-2,5,6,7,20-pentanor-4-oxa-4,8-inter-m-phenylene PGI$_2$;
19-cyclohexyl-17,17-dimethyl-2,5,6,7,20-pentanor-4-oxa-4,8-inter-m-phenylene PGI$_2$;
17,17-dimethyl-19-(3-methylcyclohexyl)-2,5,6,7,20-pentanor-4-oxa-4,8-inter-m-phenylene PGI$_2$;
19-(3-ethylcyclohexyl)-17,17-dimethyl-2,5,6,7,20-pentanor-4-oxa-4,8-inter-m-phenylene PGI$_2$;
17,17-dimethyl-19-(3-propylcyclohexyl)-2,5,6,7,20-pentanor-4-oxa-4,8-inter-m-phenylene PGI$_2$;
19-(3-butylcyclohexyl)-17,17-dimethyl-2,5,6,7,20-pentanor-4-oxa-4,8-inter-m-phenylene PGI$_2$;
17,17-dimethyl-19-(3,3-dimethylcyclohexyl)-2,5,6,7,20-pentanor-4-oxa-4,8-inter-m-phenylene PGI$_2$;
17,17-dimethyl-19-(2,6-dimethylcyclohexyl)-2,5,6,7,20-pentanor-4-oxa-4,8-inter-m-phenylene PGI$_2$;
17,17-dimethyl-19-(2,4,6-trimethylcyclohexyl)-2,5,6,7,20-pentanor-4-oxa-4,8-inter-m-phenylene PGI$_2$; and
methyl, ethyl, butyl, isobutyl, phenyl, benzyl, phenethyl, cyclopentyl, cyclohexyl, cyclohexylmethyl, furylmethyl, 1-carbomethoxy, phenacyl and p-bromophenacyl esters thereof.

Illustrative examples of the compounds represented by the general formula wherein R$_3$ is C$_t$H$_{2t}$—O—R$_9$ will also be given hereinbelow:
2,5,6,7,19,20-hexanor-4,17-dioxa-4,8-inter-m-phenylene PGI$_2$;
2,5,6,7,20-pentanor-4,17-dioxa-4,8-inter-m-phenylene PGI$_2$;
2,5,6,7-tetranor-4,17-dioxa-4,8-inter-m-phenylene PGI$_2$;
20a-homo-2,5,6,7-tetranor-4,17-dioxa-4,8-inter-m-phenylene PGI$_2$;
20a,20b-dihomo-2,5,6,7-tetranor-4,17-dioxa-4,8-inter-m-phenylene PGI$_2$;
20a,20b,20c-trihomo-2,5,6,7-tetranor-4,17-dioxa-4,8-inter-m-phenylene PGI$_2$;
16,16-dimethyl-2,5,6,7,19,20-hexanor-4,17-dioxa-4,8-inter-m-phenylene PGI$_2$;
16,16-dimethyl-2,5,6,7,20-pentanor-4,17-dioxa-4,8-inter-m-phenylene PGI$_2$;
16,16-dimethyl-2,5,6,7-tetranor-4,17-dioxa-4,8-inter-m-phenylene PGI$_2$;
16,16-dimethyl-20a-homo-2,5,6,7-tetranor-4,17-dioxa-4,8-inter-m-phenylene PGI$_2$;
16,16-dimethyl-20a,20b-dihomo-2,5,6,7-tetranor-4,17-dioxa-4,8-inter-m-phenylene PGI$_2$;
16,16-dimethyl-20a,20b,20c-trihomo-2,5,6,7-tetranor-4,17-dioxa-4,8-inter-m-phenylene PGI$_2$;
18-methyl-2,5,6,7,20-pentanor-4,17-dioxa-4,8-inter-m-phenylene PGI$_2$;
18-methyl-2,5,6,7-tetranor-4,17-dioxa-4,8-inter-m-phenylene PGI$_2$;
18,18-dimethyl-2,5,6,7,20-pentanor-4,17-dioxa-4,8-inter-m-phenylene PGI$_2$;
16,16,18-trimethyl-2,5,6,7,20-pentanor-4,17-dioxa-4,8-inter-m-phenylene PGI$_2$;
16,16,18-trimethyl-2,5,6,7-tetranor-4,17-dioxa-4,8-inter-m-phenylene PGI$_2$;
16,16,18,18-tetramethyl-2,5,6,7,20-pentanor-4,17-dioxa-4,8-inter-m-phenylene PGI$_2$;
2,5,6,7,20-pentanor-4,18-dioxa-4,8-inter-m-phenylene PGI$_2$;
2,5,6,7-tetranor-4,18-dioxa-4,8-inter-m-phenylene PGI$_2$;
20a-homo-2,5,6,7-tetranor-4,18-dioxa-4,8-inter-m-phenylene PGI$_2$;
20a,20b-dihomo-2,5,6,7-tetranor-4,18-dioxa-4,8-inter-m-phenylene PGI$_2$;
20a,20b,20c-trihomo-2,5,6,7-tetranor-4,18-dioxa-4,8-inter-m-phenylene PGI$_2$;
20a,20b,20c,20d-tetrahomo-2,5,6,7-tetranor-4,18-dioxa-4,8-inter-m-phenylene PGI$_2$;
16,16-dimethyl-2,5,6,7,20-pentanor-4,18-dioxa-4,8-inter-m-phenylene PGI$_2$;
16,16-dimethyl-2,5,6,7-tetranor-4,18-dioxa-4,8-inter-m-phenylene PGI$_2$;
16,16-dimethyl-20a-homo-2,5,6,7-tetranor-4,18-dioxa-4,8-inter-m-phenylene PGI$_2$;
16,16-dimethyl-20a,20b-dihomo-2,5,6,7-tetranor-4,18-dioxa-4,8-inter-m-phenylene PGI$_2$;
16,16-dimethyl-20a,20b,20c-trihomo-2,5,6,7-tetranor-4,18-dioxa-4,8-inter-m-phenylene PGI$_2$;
16,16-dimethyl-20a,20b,20c,20d-tetrahomo-2,5,6,7-tetranor-4,18-dioxa-4,8-inter-m-phenylene PGI$_2$;
2,5,6,7-tetranor-4,19-dioxa-4,8-inter-m-phenylene PGI$_2$;
20a-homo-2,5,6,7-tetranor-4,19-dioxa-4,8-inter-m-phenylene PGI$_2$;
20a,20b-dihomo-2,5,6,7-tetranor-4,19-dioxa-4,8-inter-m-phenylene PGI$_2$;
16,16-dimethyl-2,5,6,7-tetranor-4,19-dioxa-4,8-inter-m-phenylene PGI$_2$;
16,16-dimethyl-20a-homo-2,5,6,7-tetranor-4,19-dioxa-4,8-inter-m-phenylene PGI$_2$;
16,16-dimethyl-20a,20b-dihomo-2,5,6,7-tetranor-4,19-dioxa-4,8-inter-m-phenylene PGI$_2$;
20a-homo-2,5,6,7-tetranor-4,20-dioxa-4,8-inter-m-phenylene PGI$_2$;
20a,20b-dihomo-2,5,6,7-tetranor-4,20-dioxa-4,8-inter-m-phenylene PGI$_2$;
16,16-dimethyl-20a-homo-2,5,6,7-tetranor-4,20-dioza-4,8-inter-m-phenylene PGI$_2$;
16,16-dimethyl-20a,20b-dinhomo-2,5,6,7-tetranor-4,20-dioxa-4,8-inter-m-phenylene PGI$_2$;
17-cyclopentyl-2,5,6,7,18,19,20-heptanor-4,17-dioxa-4,8-inter-m-phenylene PGI$_2$;
17-(2-methylcyclopentyl)-2,5,6,7,18,19,20-heptanor-4,17-dioxa-4,8-inter-m-phenylene PGI$_2$;
17-(3-methylcyclopentyl)-2,5,6,7,18,19,20-heptanor-4,17-dioxa-4,8-inter-m-phenylene PGI$_2$;
17-(2,5-dimethylcyclopentyl)-2,5,6,7,18,19,20-heptanor-4,17-dioxa-4,8-inter-m-phenylene PGI$_2$;
17-(3,4-dimethylcyclopentyl)-2,5,6,7,18,19,20-heptanor-4,17-dioxa-4,8-inter-m-phenylene PGI$_2$;
17-cyclohexyl-2,5,6,7,18,19,20-heptanor-4,17-dioxa-4,8-inter-m-phenylene PGI$_2$;
17-(4-methylcyclohexyl)-2,5,6,7,18,19,20-heptanor-4,17-dioxa-4,8-inter-m-phenylene PGI$_2$;
17-(4-ethylcyclohexyl)-2,5,6,7,18,19,20-heptanor-4,17-dioxa-4,8-inter-m-phenylene PGI$_2$;
17-(4-propylcyclohexyl)-2,5,6,7,18,19,20-heptanor-4,17-dioxa-4,8-inter-m-phenylene PGI$_2$;

17-(4-butylcyclohexyl)-2,5,6,7,18,19,20-heptanor-4,17-dioxa-4,8-inter-m-phenylene PGI₂;
17-(4,4-dimethylcyclohexyl)-2,5,6,7,18,19,20-heptanor-4,17-dioxa-4,8-inter-m-phenylene PGI₂;
17-(2,6-dimethylcyclohexyl)-2,5,6,7,18,19,20-heptanor-4,17-dioxa-4,8-inter-m-phenylene PGI₂;
17-(2,4,6-trimethylcyclohexyl)-2,5,6,7,18,19,20-heptanor-4,17-dioxa-4,8-inter-m-phenylene PGI₂;
17-cyclopentyl-16,16-dimethyl-2,5,6,7,18,19,20-heptanor-4,17-dioxa-4,8-inter-m-phenylene PGI₂;
17-(2-methylcyclopentyl)-16,16-dimethyl-2,5,6,7,18,19,20-heptanor-4,17-dioxa-4,8-inter-m-phenylene PGI₂;
17-(3-methylcyclopentyl)-16,16-dimethyl-2,5,6,7,18,19,20-heptanor-4,17-dioxa-4,8-inter-m-phenylene PGI₂;
17-(2,5-dimethylcyclopentyl)-16,16-dimethyl-2,5,6,7,18,19,20-heptanor-4,17-dioxa-4,8-inter-m-phenylene PGI₂;
17-(3,4-dimethylcyclopentyl)-16,16-dimethyl-2,5,6,7,18,19,20-heptanor-4,17-dioxa-4,8-inter-m-phenylene PGI₂;
17-cyclohexyl-16,16-dimethyl-2,5,6,7,18,19,20-heptanor-4,17-dioxa-4,8-inter-m-phenylene PGI₂;
17-(4-methylcyclohexyl)-16,16-dimethyl-2,5,6,7,18,19,20-heptanor-4,17-dioxa-4,8-inter-m-phenylene PGI₂;
17-(4-ethylcyclohexyl)-16,16-dimethyl-2,5,6,7,18,19,20-heptanor-4,17-dioxa-4,8-inter-m-phenylene PGI₂;
17-(4-propylcyclohexyl)-16,16-dimethyl-2,5,6,7,18,19,20-heptanor-4,17-dioxa-4,8-inter-m-phenylene PGI₂;
17-(4-butylcyclohexyl)-16,16-dimethyl-2,5,6,7,18,19,20-heptanor-4,17-dioxa-4,8-inter-m-phenylene PGI₂;
17-(4,4-dimethylcyclohexyl)-16,16-dimethyl-2,5,6,7,18,19,20-heptanor-4,17-dioxa-4,8-inter-m-phenylene PGI₂;
17-(2,6-dimethylcyclohexyl)-16,16-dimethyl-2,5,6,7,18,19,20-heptanor-4,17-dioxa-4,8-inter-m-phenylene PGI₂;
17-(2,4,6-trimethylcyclohexyl)-16,16-dimethyl-2,5,6,7,18,19,20-heptanor-4,17-dioxa-4,8-inter-m-phenylene PGI₂;
17-phenyl-2,5,6,7,18,19,20-heptanor-4,17-dioxa-4,8-inter-m-phenylene PGI₂;
17-(2-chlorophenyl)-2,5,6,7,18,19,20-heptanor-4,17-dioxa-4,8-inter-m-phenylene PGI₂;
17-(3-chlorophenyl)-2,5,6,7,18,19,20-heptanor-4,17-dioxa-4,8-inter-m-phenylene PGI₂;
17-(4-chlorophenyl)-2,5,6,7,18,19,20-heptanor-4,17-dioxa-4,8-inter-m-phenylene PGI₂;
17-(2-bromophenyl)-2,5,6,7,18,19,20-heptanor-4,17-dioxa-4,8-inter-m-phenylene PGI₂;
17-(3-bromophenyl)-2,5,6,7,18,19,20-heptanor-4,17-dioxa-4,8-inter-m-phenylene PGI₂;
17-(4-bromophenyl)-2,5,6,7,18,19,20-heptanor-4,17-dioxa-4,8-inter-m-phenylene PGI₂;
17-(2-fluorophenyl)-2,5,6,7,18,19,20-heptanor-4,17-dioxa-4,8-inter-m-phenylene PGI₂;
17-(3-fluorophenyl)-2,5,6,7,18,19,20-heptanor-4,17-dioxa-4,8-inter-m-phenylene PGI₂;
17-(4-fluorophenyl)-2,5,6,7,18,19,20-heptanor-4,17-dioxa-4,8-inter-m-phenylene PGI₂;
17-(2-methylphenyl)-2,5,6,7,18,19,20-heptanor-4,17-dioxa-4,8-inter-m-phenylene PGI₂;
17-(3-methylphenyl)-2,5,6,7,18,19,20-heptanor-4,17-dioxa-4,8-inter-m-phenylene PGI₂;
17-(4-methylphenyl)-2,5,6,7,18,19,20-heptanor-4,17-dioxa-4,8-inter-m-phenylene PGI₂;
17-(2-methoxyphenyl)-2,5,6,7,18,19,20-heptanor-4,17-dioxa-4,8-inter-m-phenylene PGI₂;
17-(4-methoxyphenyl)-2,5,6,7,18,19,20-heptanor-4,17-dioxa-4,8-inter-m-phenylene PGI₂;
17-(3-trifluoromethylphenyl)-2,5,6,7,18,19,20-heptanor-4,17-dioxa-4,8-inter-m-phenylene PGI₂;
17-(4-trifluoromethylphenyl)-2,5,6,7,18,19,20-heptanor-4,17-dioxa-4,8-inter-m-phenylene PGI₂;
18-phenyl-2,5,6,7,19,20-hexanor-4,18-dioxa-4,8-inter-m-phenylene PGI₂;
18-(2-chlorophenyl)-2,5,6,7,19,20-hexanor-4,18-dioxa-4,8-inter-m-phenylene PGI₂;
18-(3-chlorophenyl)-2,5,6,7,19,20-hexanor-4,18-dioxa-4,8-inter-m-phenylene PGI₂;
18-(4-chlorophenyl)-2,5,6,7,19,20-hexanor-4,18-dioxa-4,8-inter-m-phenylene PGI₂;
18-(2-bromophenyl)-2,5,6,7,19,20-hexanor-4,18-dioxa-4,8-inter-m-phenylene PGI₂;
18-(3-bromophenyl)-2,5,6,7,19,20-hexanor-4,18-dioxa-4,8-inter-m-phenylene PGI₂;
18-(4-bromophenyl)-2,5,6,7,19,20-hexanor-4,18-dioxa-4,8-inter-m-phenylene PGI₂;
18-(2-fluorophenyl)-2,5,6,7,19,20-hexanor-4,18-dioxa-4,8-inter-m-phenylene PGI₂;
18-(3-fluorophenyl)-2,5,6,7,19,20-hexanor-4,18-dioxa-4,8-inter-m-phenylene PGI₂;
18-(4-fluorophenyl)-2,5,6,7,19,20-hexanor-4,18-dioxa-4,8-inter-m-phenylene PGI₂;
18-(2-methylphenyl)-2,5,6,7,19,20-hexanor-4,18-dioxa-4,8-inter-m-phenylene PGI₂;
18-(3-methylphenyl)-2,5,6,7,19,20-hexanor-4,18-dioxa-4,8-inter-m-phenylene PGI₂;
18-(4-methylphenyl)-2,5,6,7,19,20-hexanor-4,18-dioxa-4,8-inter-m-phenylene PGI₂;
18-(2-methoxyphenyl)-2,5,6,7,19,20-hexanor-4,18-dioxa-4,8-inter-m-phenylene PGI₂;
18-(4-methoxyphenyl)-2,5,6,7,19,20-hexanor-4,18-dioxa-4,8-inter-m-phenylene PGI₂;
18-(3-trifluoromethylphenyl)-2,5,6,7,19,20-hexanor-4,18-dioxa-4,8-inter-m-phenylene PGI₂;
18-(4-trifluoromethylphenyl)-2,5,6,7,19,20-hexanor-4,18-dioxa-4,8-inter-m-phenylene PGI₂;
19-phenyl-2,5,6,7,20-pentanor-4,19-dioxa-4,8-inter-m-phenylene PGI₂;
20-phenyl-2,5,6,7-tetranor-4,20-dioxa-4,8-inter-m-phenylene PGI₂;
16,16-dimethyl-17-phenyl-2,5,6,7,18,19,20-heptanor-4,17-dioxa-4,8-inter-m-phenylene PGI₂;
17-(2-chlorophenyl)-16,16-dimethyl-2,5,6,7,18,19,20-heptanor-4,17-dioxa-4,8-inter-m-phenylene PGI₂;
17-(3-chlorophenyl)-16,16-dimethyl-2,5,6,7,18,19,20-heptanor-4,17-dioxa-4,8-inter-m-phenylene PGI₂;
17-(4-chlorophenyl)-16,16-dimethyl-2,5,6,7,18,19,20-heptanor-4,17-dioxa-4,8-inter-m-phenylene PGI₂;
17-(2-bromophenyl)-16,16-dimethyl-2,5,6,7,18,19,20-heptanor-4,17-dioxa-4,8-inter-m-phenylene PGI₂;
17-(3-bromophenyl)-16,16-dimethyl-2,5,6,7,18,19,20-heptanor-4,17-dioxa-4,8-inter-m-phenylene PGI₂;
17-(4-bromophenyl)-16,16-dimethyl-2,5,6,7,18,19,20-heptanor-4,17-dioxa-4,8-inter-m-phenylene PGI₂;
17-(2-fluorophenyl)-16,16-dimethyl-2,5,6,7,18,19,20-heptanor-4,17-dioxa-4,8-inter-m-phenylene PGI₂;
17-(3-fluorophenyl)-16,16-dimethyl-2,5,6,7,18,19,20-heptanor-4,17-dioxa-4,8-inter-m-phenylene PGI₂;
17-(4-fluorophenyl)-16,16-dimethyl-2,5,6,7,18,19,20-heptanor-4,17-dioxa-4,8-inter-m-phenylene PGI₂;

16,16-dimethyl-17-(2-methylphenyl)-2,5,6,7,18,19,20-heptanor-4,17-dioxa-4,8-inter-m-phenylene PGI$_2$;
16,16-dimethyl-17-(3-methylphenyl)-2,5,6,7,18,19,20-heptanor-4,17-dioxa-4,8-inter-m-phenylene PGI$_2$;
16,16-dimethyl-17-(4-methylphenyl)-2,5,6,7,18,19,20-heptanor-4,17-dioxa-4,8-inter-m-phenylene PGI$_2$;
16,16-dimethyl-17-(2-methoxyphenyl)-2,5,6,7,18,19,20-heptanor-4,17-dioxa-4,8-inter-m-phenylene PGI$_2$;
16,16-dimethyl-17-(4-methoxyphenyl)-2,5,6,7,18,19,20-heptanor-4,17-dioxa-4,8-inter-m-phenylene PGI$_2$;
17-(3-trifluoromethylphenyl)-16,16-dimethyl-2,5,6,7,18,19,20-heptanor-4,17-dioxa-4,8-inter-m-phenylene PGI$_2$;
17-(4-trifluoromethylphenyl)-16,16-dimethyl-2,5,6,7,18,19,20-heptanor-4,17-dioxa-4,8-inter-m-phenylene PGI$_2$;
16,16-dimethyl-18-phenyl-2,5,6,7,19,20-hexanor-4,18-dioxa-4,8-inter-m-phenylene PGI$_2$;
18-(2-chlorophenyl)-16,16-dimethyl-2,5,6,7,19,20-hexanor-4,18-dioxa-4,8-inter-m-phenylene PGI$_2$;
18-(3-chlorophenyl)-16,16-dimethyl-2,5,6,7,19,20-hexanor-4,18-dioxa-4,8-inter-m-phenylene PGI$_2$;
18-(4-chlorophenyl)-16,16-dimethyl-2,5,6,7,19,20-hexanor-4,18-dioxa-4,8-inter-m-phenylene PGI$_2$
18-(2-bromophenyl)-16,16-dimethyl-2,5,6,7,19,20-hexanor-4,18-dioxa-4,8-inter-m-phenylene PGI$_2$;
18-(3-bromophenyl)-16,16-dimethyl-2,5,6,7,19,20-hexanor-4,18-dioxa-4,8-inter-m-phenylene PGI$_2$;
18-(4-bromophenyl)-16,16-dimethyl-2,5,6,7,19,20-hexanor-4,18-dioxa-4,8-inter-m-phenylene PGI$_2$;
18-(2-fluorophenyl)-16,16-dimethyl-2,5,6,7,19,20-hexanor-4,18-dioxa-4,8-inter-m-phenylene PGI$_2$;
18-(3-fluorophenyl)-16,16-dimethyl-2,5,6,7,19,20-hexanor-4,18-dioxa-4,8-inter-m-phenylene PGI$_2$;
18-(4-fluorophenyl)-16,16-dimethyl-2,5,6,7,19,20-hexanor-4,18-dioxa-4,8-inter-m-phenylene PGI$_2$;
16,16-dimethyl-18-(2-methylphenyl)-2,5,6,7,19,20-hexanor-4,18-dioxa-4,8-inter-m-phenylene PGI$_2$;
16,16-dimethyl-18-(3-methylphenyl)-2,5,6,7,19,20-hexanor-4,18-dioxa-4,8-inter-m-phenylene PGI$_2$;
16,16-dimethyl-18-(4-methylphenyl)-2,5,6,7,19,20-hexanor-4,18-dioxa-4,8-inter-m-phenylene PGI$_2$;
16,16-dimethyl-18-(2-methoxyphenyl)-2,5,6,7,19,20-hexanor-4,18-dioxa-4,8-inter-m-phenylene PGI$_2$;
16,16-dimethyl-18-(4-methoxyphenyl)-2,5,6,7,19,20-hexanor-4,18-dioxa-4,8-inter-m-phenylene PGI$_2$;
18-(3-trifluoromethylphenyl)-16,16-dimethyl-2,5,6,7,19,20-hexanor-4,18-dioxa-4,8-inter-m-phenylene PGI$_2$;
18-(4-trifluoromethylphenyl)-16,16-dimethyl-2,5,6,7,19,20-hexanor-4,18-dioxa-4,8-inter-m-phenylene PGI$_2$;
16,16-dimethyl-19-phenyl-2,5,6,7,20-pentanor-4,19-dioxa-4,8-inter-m-phenylene PGI$_2$;
16,16-dimethyl-20-phenyl-2,5,6,7-tetranor-4,20-dioxa-4,8-inter-m-phenyl PGI$_2$; and
methyl, ethyl, butyl, isobutyl, phenyl, benzyl, phenethyl, cyclopentyl, cyclohexyl, cyclohexylmethyl, furylmethyl, l-carbomethoxy, phenacyl, and p-bromophenacyl esters thereof.

Illustrative examples of the compounds according to the present invention wherein R$_3$ is —C$_t$H$_{2t}$—C≡C—R$_8$ will be given hereinbelow:
2,5,6,7-tetranor-18,18,19,19-tetradehydro-4-oxa-4,8-inter-m-phenylene PGI$_2$;
20a-homo-2,5,6,7-tetranor-18,18,19,19-tetradehydro-4-oxa-4,8-inter-m-phenylene PGI$_2$;
20a,20b-dihomo-2,5,6,7-tetranor-18,18,19,19-tetradehydro-4-oxa-4,8-inter-m-phenylene PGI$_2$;
20a,20b,20c-trihomo-2,5,6,7-tetranor-18,18,19,19-tetradehydro-4-oxa-4,8-inter-m-phenylene PGI$_2$;
20a,20b,20c,20d-tetrahomo-2,5,6,7-tetranor-18,18,19,19-tetradehydro-4-oxa-4,8-inter-m-phenylene PGI$_2$;
20a,20b,20c,20d,20e-pentahomo-2,5,6,7-tetranor-18,18,19,19-tetradehydro-4-oxa-4,8-inter-m-phenylene PGI$_2$;
16-methyl-2,5,6,7-tetranor-18,18,19,19-tetradehydro-4-oxa-4,8-inter-m-phenylene PGI$_2$;
16-methyl-20a-homo-2,5,6,7-tetranor-18,18,19,19-tetradehydro-4-oxa-4,8-inter-m-phenylene PGI$_2$;
16-methyl-20a,20b-dihomo-2,5,6,7-tetranor-18,18,19,19-tetradehydro-4-oxa-4,8-inter-m-phenylene PGI$_2$;
16-methyl-20a,20b,20c-trihomo-2,5,6,7-tetranor-18,18,19,19-tetradehydro-4-oxa-4,8-inter-m-phenylene PGI$_2$;
16-methyl-20a,20b,20c,20d-tetrahomo-2,5,6,7-tetranor-18,18,19,19-tetradehydro-4-oxa-4,8-inter-m-phenylene PGI$_2$;
16-methyl-20a,20b,20c,20d,20e-pentahomo-2,5,6,7-tetranor-18,18,19,19-tetradehydro-4-oxa-4,8-inter-m-phenylene PGI$_2$;
16,16-dimethyl-2,5,6,7-tetranor-18,18,19,19-tetradehydro-4-oxa-4,8-inter-m-phenylene PGI$_2$;
16,16-dimethyl-20a-homo-2,5,6,7-tetranor-18,18,19,19-tetradehydro-4-oxa-4,8-inter-m-phenylene PGI$_2$;
16,16-dimethyl-20a,20b-dihomo-2,5,6,7-tetranor-18,18,19,19-tetrahydro-4-oxa-4,8-inter-m-phenylene PGI$_2$;
16,16-dimethyl-20a,20b,20c-trihomo-2,5,6,7-tetranor-18,18,19,19-tetrahydro-4-oxa-4,8-inter-m-phenylene PGI$_2$;
16,16-dimethyl-20a,20b,20c,20d-tetrahomo-2,5,6,7-tetranor-18,18,19,19-tetradehydro-4-oxa-4,8-inter-m-phenylene PGI$_2$;
16,16-dimethyl-20a,20b,20c,20d,20e-pentahomo-2,5,6,7-tetranor-18,18,19,19-tetradehyro-4-oxa-4,8-inter-m-phenylene PGI$_2$;
20a-homo-2,5,6,7-tetranor-19,19,20,20-tetradehydro-4-oxa-4,8-inter-m-phenylene PGI$_2$;
20a,20b-dihomo-2,5,6,7-tetranor-19,19,20,20-tetradehydro-4-oxa-4,8-inter-m-phenylene PGI$_2$;
20a,20b,20c-trihomo-2,5,6,7-tetranor-19,19,20,20-tetradehydro-4-oxa-4,8-inter-m-phenylene PGI$_2$;
20a,20b,20c,20d-tetrahomo-2,5,6,7-tetranor-19,19,20,20-tetradehydro-4-oxa-4,8-inter-m-phenylene PGI$_2$;
20a,20b,20c,20d,20e-pentahomo-2,5,6,7-tetranor-19,19,20,20-tetradehydro-4-oxa-4,8-inter-m-phenylene PGI$_2$;
16-methyl-20a-homo-2,5,6,7-tetranor-19,19,20,20-tetradehydro-4-oxa-4,8-inter-m-phenylene PGI$_2$;
16-methyl-20a,20b-dihomo-2,5,6,7-tetranor-19,19,20,20-tetradehydro-4-oxa-4,8-inter-m-phenylene PGI$_2$;
16-methyl-20a,20b,20c-trihomo-2,5,6,7-tetranor-19,19,20,20-tetradehydro-4-oxa-4,8-inter-m-phenylene PGI$_2$;
16-methyl-20a,20b,20c,20d-tetrahomo-2,5,6,7-tetranor-19,19,20,20-tetradehydro-4-oxa-4,8-inter-m-phenylene PGI$_2$;
16-methyl-20a,20b,20c,20d,20e-pentahomo-2,5,6,7-tetranor-19,19,20,20-tetradehydro-4-oxa-4,8-inter-m-phenylene PGI$_2$;
16,16-dimethyl-20a-homo-2,5,6,7-tetranor-19,19,20,20-tetradehydro-4-oxa-4,8-inter-m-phenylene PGI$_2$;

16,16-dimethyl-20a,20b-dihomo-2,5,6,7-tetranor-19,19,20,20-tetradehydro-4-oxa-4,8-inter-m-phenylene PGI$_2$;

16,16-dimethyl-20a,20b,20c-trihomo-2,5,6,7-tetranor-19,19,20,20-tetradehydro-4-oxa-4,8-inter-m-phenylene PGI$_2$;

16,16-dimethyl-20a,20b,20c,20d-tetrahomo-2,5,6,7-tetranor-19,19,20,20-tetradehydro-4-oxa-4,8-inter-m-phenylene PGI$_2$;

16,16-dimethyl-20a,20b,20c,20d,20e-pentahomo-2,5,6,7-tetranor-19,19,20,20-tetradehydro-4-oxa-4,8-inter-m-phenylene PGI$_2$; and methyl, ethyl, butyl, isobutyl, phenyl, benzyl, phenethyl, cyclopentyl, cyclohexyl, cyclohexylmethyl, furylmethyl, l-carbomethoxy, phenacyl, and p-bromophenacyl esters thereof.

Illustrative examples of the compounds according to the present invention wherein X is —CH$_2$—CH$_2$— will also be given hereinbelow:

2,5,6,7-tetranor-4-oxa-13,14-dihydro-4,8-inter-m-phenylene PGI$_2$;

20a-homo-2,5,6,7-tetranor-4-oxa-13,14-dihydro-4,8-inter-m-phenylene PGI$_2$;

16-methyl-2,5,6,7,18,19,20-heptanor-4-oxa-13,14-dehydro-4,8-inter-m-phenylene PGI$_2$;

16,16-dimethyl-2,5,6,7,18,19,20-heptanor-4-oxa-13,14-dihydro-4,8-inter-m-phenylene PGI$_2$;

16,16-dimethyl-2,5,6,7,19,20-hexanor-4-oxa-13,14-dihydro-4,8-inter-m-phenylene PGI$_2$;

16,16-dimethyl-2,5,6,7,20-pentanor-4-oxa-13,14-dihydro-4,8-inter-m-phenylene PGI$_2$;

16,16-dimethyl-2,5,6,7-tetranor-4-oxa-13,14-dihydro-4,8-inter-m-phenylene PGI$_2$;

16,16-dimethyl-20a-homo-2,5,6,7-tetranor-4-oxa-13,14-dihydro-4,8-inter-m-phenylene PGI$_2$;

16,16-dimethyl-20a,20b-dihomo-2,5,6,7-tetranor-4-oxa-13,14-dihydro-4,8-inter-m-phenylene PGI$_2$;

16,16-dimethyl-20a,20b,20c-trihomo-2,5,6,7-tetranor-4-oxa-13,14-dihydro-4,8-inter-m-phenylene PGI$_2$;

16,16,17-trimethyl-2,5,6,7,19,20-hexanor-4-oxa-13,14-dihydro-4,8-inter-m-phenylene PGI$_2$;

17,17-dimethyl-2,5,6,7-tetranor-4-oxa-13,14-dihydro-4,8-inter-m-phenylene PGI$_2$;

18,18-dimethyl-2,5,6,7-tetranor-4-oxa-13,14-dihydro-4,8-inter-m-phenylene PGI$_2$;

15-methyl-2,5,6,7-tetranor-4-oxa-13,14-dihydro-4,8-inter-m-phenylene PGI$_2$;

16-methyl-2,5,6,7-tetranor-4-oxa-13,14-dihydro-4,8-inter-m-phenylene PGI$_2$;

17-methyl-2,5,6,7-tetranor-4-oxa-13,14-dihydro-4,8-inter-m-phenylene PGI$_2$;

17-methyl-20a-homo-2,5,6,7-tetranor-4-oxa-13,14-dihydro-4,8-inter-m-phenylene PGI$_2$;

16,16-dimethyl-2,5,6,7,20-pentanor-4,18-dioxa-13,14-dihydro-4,8-inter-m-phenylene PGI$_2$;

16,16-dimethyl-2,5,6,7-tetranor-4,18-dioxa-13,14-dihydro-4,8-inter-m-phenylene PGI$_2$;

16,16-dimethyl-20a-homo-2,5,6,7-tetranor-4,18-dioxa-13,14-dihydro-4,8-inter-m-phenylene PGI$_2$;

16-phenoxy-2,5,6,7,17,18,19,20-octanor-4-oxa-13,14-dihydro-4,8-inter-m-phenylene PGI$_2$;

16,16-dimethyl-16-phenoxy-2,5,6,7,17,18,19,20-octanor-4-oxa-13,14-dihydro-4,8-inter-m-phenylene PGI$_2$;

15-phenyl-2,5,6,7,16,17,18,19,20-nonanor-4-oxa-13,14-dihydro-4,8-inter-m-phenylene PGI$_2$;

16-phenyl-2,5,6,7,17,18,19,20-octanor-4-oxa-13,14-dihydro-4,8-inter-m-phenylene PGI$_2$;

17-phenyl-2,5,6,7,18,19,20-heptanor-4-oxa-13,14-dihydro-4,8-inter-m-phenylene PGI$_2$;

15-(2-methylphenyl)-2,5,6,7,16,17,18,19,20-nonanor-4-oxa-13,14-dihydro-4,8-inter-m-phenylene PGI$_2$;

15-(4-methylphenyl)-2,5,6,7,16,17,18,19,20-nonanor-4-oxa-13,14-dihydro-4,8-inter-m-phenylene PGI$_2$;

15-(3-fluorophenyl)-2,5,6,7,16,17,18,19,20-nonanor-4-oxa-13,14-dihydro-4,8-inter-m-phenylene PGI$_2$;

15-(4-trifluoromethylphenyl)-2,5,6,7,16,17,18,19,20-nonanor-4-oxa-13,14-dihydro-4,8-inter-m-phenylene PGI$_2$;

15-(2-chlorophenyl)-2,5,6,7,16,17,18,19,20-nonanor-4-oxa-13,14-dihydro-4,8-inter-m-phenylene PGI$_2$;

15-(3-chlorophenyl)-2,5,6,7,16,17,18,19,20-nonanor-4-oxa-13,14-dihydro-4,8-inter-m-phenylene PGI$_2$;

15-(4-chlorophenyl)-2,5,6,7,16,17,18,19,20-nonanor-4-oxa-13,14-dihydro-4,8-inter-m-phenylene PGI$_2$;

16-methyl-16-phenyl-2,5,6,7,18,19,20-heptanor-4-oxa-13,14-dihydro-4,8-inter-m-phenylene PGI$_2$;

16,16-dimethyl-17-phenyl-2,5,6,7,18,19,20-heptanor-4-oxa-13,14-dihydro-4,8-inter-m-phenylene PGI$_2$;

15-cyclopentyl-2,5,6,7,16,17,18,19,20-nonanor-4-oxa-13,14-dihydro-4,8-inter-m-phenylene PGI$_2$;

15-cyclohexyl-2,5,6,7,16,17,18,19,20-nonanor-4-oxa-13,14-dihydro-4,8-inter-m-phenylene PGI$_2$;

16-cyclopentyl-2,5,6,7,17,18,19,20-octanor-4-oxa-13,14-dihydro-4,8-inter-m-phenylene PGI$_2$;

16-cyclohexyl-2,5,6,7,17,18,19,20-octanor-4-oxa-13,14-dihydro-4,8-inter-m-phenylene PGI$_2$;

17-cyclohexyl-2,5,6,7,18,19,20-heptanor-4-oxa-13,14-dihydro-4,8-inter-m-phenylene PGI$_2$;

16-cyclohexyl-16-methyl-2,5,6,7,18,19,20-heptanor-4-oxa-13,14-dihydro-4,8-inter-m-phenylene PGI$_2$;

17-cyclohexyl-16,16-dimethyl-2,5,6,7,18,19,20-heptanor-4-oxa-13,14-dihydro-4,8-inter-m-phenylene PGI$_2$; and methyl, ethyl, butyl, isobutyl, phenyl, benzyl, phenethyl, cyclopentyl, cyclohexyl, cyclohexylmethyl, furylmethyl, l-carbomethoxy, phenacyl, and p-bromophenacyl esters thereof.

Illustrative examples of the compounds according to the present invention wherein R$_1$ is —C≡C—COOR$_4$ will be given hereinbelow:

2,5,6,7,19,20-hexanor-3,3,4,4-tetradehydro-4,8-inter-m-phenylene PGI$_2$;

2,4,6,7,20-pentanor-3,3,4,4-tetradehydro-4,8-inter-m-phenylene PGI$_2$;

2,5,6,7-tetranor-3,3,4,4-tetradehydro-4,8-inter-m-phenylene PGI$_2$;

20a-homo-2,5,6,7-tetranor-3,3,4,4-tetradehydro-4,8-inter-m-phenylene PGI$_2$;

20a,20b-dihomo-2,5,6,7-tetranor-3,3,4,4-tetradehydro-4,8-inter-m-phenylene PGI$_2$;

16-methyl-2,5,6,7,19,20-hexanor-3,3,4,4-tetradehydro-4,8-inter-m-phenylene PGI$_2$;

16-methyl-2,5,6,7,20-pentanor-3,3,4,4-tetradehydro-4,8-inter-m-phenylene PGI$_2$;

16-methyl-2,5,6,7-tetranor-3,3,4,4-tetradehydro-4,8-inter-m-phenylene PGI$_2$;

16-methyl-20a-homo-2,5,6,7-tetranor-3,3,4,4-tetradehydro-4,8-inter-m-phenylene PGI$_2$;

16-methyl-20a,20b-dihomo-2,5,6,7-tetranor-3,3,4,4-tetradehydro-4,8-inter-m-phenylene PGI$_2$;

16,16-dimethyl-2,5,6,7,19,20-hexanor-3,3,4,4-tetradehydro-4,8-inter-m-phenylene PGI$_2$;

16,16-dimethyl-2,5,6,7,20-pentanor-3,3,4,4-tetradehydro-4,8-inter-m-phenylene PGI$_2$;

16,16-dimethyl-2,5,6,7-tetranor-3,3,4,4-tetradehydro-4,8-inter-m-phenylene PGI₂;
16,16-dimethyl-20a-homo-2,5,6,7-tetranor-3,3,4,4-tetradehydro-4,8-inter-m-phenylene PGI₂;
16,16-dimethyl-20a,20b-dihomo-2,5,6,7-tetranor-3,3,4,4-tetradehydro-4,8-inter-m-phenylene PGI₂;
17,17-dimethyl-2,5,6,7-tetranor-3,3,4,4-tetradehydro-4,8-inter-m-phenylene PGI₂;
18,18-dimethyl-2,5,6,7-tetranor-3,3,4,4-tetradehydro-4,8-inter-m-phenylene PGI₂;
15-methyl-2,5,6,7,20-pentanor-3,3,4,4-tetradehydro-4,8-inter-m-phenylene PGI₂;
15-methyl-2,5,6,7-tetranor-3,3,4,4-tetradehydro-4,8-inter-m-phenylene PGI₂;
15-methyl-20a-homo-2,5,6,7-tetranor-3,3,4,4-tetradehydro-4,8-inter-m-phenylene PGI₂;
17-methyl-2,5,6,7,20-pentanor-3,3,4,4-tetradehydro-4,8-inter-m-phenylene PGI₂;
17-methyl-2,5,6,7-tetranor-3,3,4,4-tetradehydro-4,8-inter-m-phenylene PGI₂;
17-methyl-20a-homo-2,5,6,7-tetranor-3,3,4,4-tetradehydro-4,8-inter-m-phenylene PGI₂;
2,5,6,7,20-pentanor-3,3,4,4-tetradehydro-18-oxa-4,8-inter-m-phenylene PGI₂;
2,5,6,7-tetranor-3,3,4,4-tetradehydro-18-oxa-4,8-inter-m-phenylene PGI₂;
20a-homo-2,5,6,7-tetranor-3,3,4,4-tetradehydro-18-oxa-4,8-inter-m-phenylene PGI₂;
16,16-dimethyl-2,5,6,7,20-pentanor-3,3,4,4-tetradehydro-18-oxa-4,8-inter-m-phenylene PGI₂;
16,16-dimethyl-2,5,6,7-tetranor-3,3,4,4-tetradehydro-18-oxa-4,8-inter-m-phenylene PGI₂;
16,16-dimethyl-20a-homo-2,5,6,7-tetranor-3,3,4,4-tetradehydro-18-oxa-4,8-inter-m-phenylene PGI₂;
16-phenoxy-2,5,6,7,17,18,19,20-octanor-3,3,4,4-tetradehydro-4,8-inter-m-phenylene PGI₂;
16-methyl-16-phenoxy-2,5,6,7,17,18,19,20-octanor-3,3,4,4-tetradehydro-4,8-inter-m-phenylene PGI₂;
16,16-dimethyl-16-phenoxy-2,5,6,7,17,18,19,20-octanor-3,3,4,4-tetradehydro-4,8-inter-m-phenylene PGI₂;
15-phenyl-2,5,6,7,16,17,18,19,20-nononar-3,3,4,4-tetradehydro-4,8-inter-m-phenylene PGI₂;
16-phenylene-2,5,6,7,17,18,19,20-octanor-3,3,4,4-tetradehydro-4,8-inter-m-phenylene PGI₂;
17-phenyl-2,5,6,7,18,19,20-heptanor-3,3,4,4-tetradehydro-4,8-inter-m-phenylene PGI₂;
18-phenyl-2,5,6,7,19,20-hexanor-3,3,4,4-tetradehydro-4,8-inter-m-phenylene PGI₂;
15-(2-methylphenyl)-2,5,6,7,16,17,18,19,20-nonanor-3,3,4,4-tetradehydro-4,8-inter-m-phenylene PGI₂;
15-(3-methylphenyl)-2,5,6,7,16,17,18,19,20-nonanor-3,3,4,4-tetradehydro-4,8-inter-m-phenylene PGI₂;
15-(4-methylphenyl)-2,5,6,7,16,17,18,19,20-nonanor-3,3,4,4-tetradehydro-4,8-inter-m-phenylene PGI₂;
15-(2-fluorophenyl)-2,5,6,7,16,17,18,19,20-nonanor-3,3,4,4-tetradehydro-4,8-inter-m-phenylene PGI₂;
15-(3-fluorophenyl)-2,5,6,7,16,17,18,19,20-nonanor-3,3,4,4-tetradehydro-4,8-inter-m-phenylene PGI₂;
15-(4-fluorophenyl)-2,5,6,7,16,17,18,19,20-nonanor-3,3,4,4-tetradehydro-4,8-inter-m-phenylene PGI₂;
15-(2-chlorophenyl)-2,5,6,7,16,17,18,19,20-nonanor-3,3,4,4-tetradehydro-4,8-inter-m-phenylene PGI₂;
15-(3-chlorophenyl)-2,5,6,7,16,17,18,19,20-nonanor-3,3,4,4-tetradehydro-4,8-inter-m-phenylene PGI₂;
15-(4-chlorophenyl)-2,5,6,7,16,17,18,19,20-nonanor-3,3,4,4-tetradehydro-4,8-inter-m-phenylene PGI₂;
15-(2-trifluoromethylphenyl)-2,5,6,7,16,17,18,19,20-nonanor-3,3,4,4-tetradehydro-4,8-inter-m-phenylene PGI₂;
15-(3-trifluoromethylphenyl)-2,5,6,7,16,17,18,19,20-nonanor-3,3,4,4-tetradehydro-4,8-inter-m-phenylene PGI₂;
15-(4-trifluoromethylphenyl)-2,5,6,7,16,17,18,19,20-nonanor-3,3,4,4-tetradehydro-4,8-inter-m-phenylene PGI₂;
16-phenyl-2,5,6,7,18,19,20-heptanor-3,3,4,4-tetradehydro-4,8-inter-m-phenylene PGI₂;
16-methyl-17-phenyl-2,5,6,7,18,19,20-heptanor-3,3,4,4-tetradehydro-4,8-inter-m-phenylene PGI₂;
16-methyl-18-phenyl-2,5,6,7,19,20-hexanor-3,3,4,4-tetradehydro-4,8-inter-m-phenylene PGI₂;
16-methyl-16-phenyl-2,5,6,7,18,19,20-heptanor-3,3,4,4-tetradehydro-4,8-inter-m-phenylene PGI₂;
16,16-dimethyl-17-phenyl-2,5,6,7,18,19,20-heptanor-3,3,4,4-tetradehydro-4,8-inter-m-phenylene PGI₂;
16,16-dimethyl-18-phenyl-2,5,6,7,19,20-hexanor-3,3,4,4-tetradehydro-4,8-inter-m-phenylene PGI₂;
15-cyclopentyl-2,5,6,7,16,17,18,19,20-nonanor-3,3,4,4-tetradehydro-4,8-inter-m-phenylene PGI₂;
16-cyclopentyl-2,5,6,7,17,18,19,20-octanor-3,3,4,4-tetradehydro-4,8-inter-m-phenylene PGI₂;
17-cyclopentyl-2,5,6,7,18,19,20-heptanor-3,3,4,4-tetradehydro-4,8-inter-m-phenylene PGI₂;
18-cyclopentyl-2,5,6,7,19,20-hexanor-3,3,4,4-tetradehydro-4,8-inter-m-phenylene PGI₂;
15-cyclohexyl-2,5,6,7,16,17,18,19,20-nonanor-3,3,4,4-tetradehydro-4,8-inter-m-phenylene PGI₂;
16-cyclohexyl-2,5,6,7,17,18,19,20-octanor-3,3,4,4-tetradehydro-4,8-inter-m-phenylene PGI₂;
17-cyclohexyl-2,5,6,7,18,19,20-heptanor-3,3,4,4-tetradehydro-4,8-inter-m-phenylene PGI₂;
18-cyclohexyl-2,5,6,7,19,20-hexanor-3,3,4,4-tetradehydro-4,8-inter-m-phenylene PGI₂;
16-methyl-16-cyclopentyl-2,5,6,7,18,19,20-heptanor-3,3,4,4-tetradehydro-4,8-inter-m-phenylene PGI₂;
16,16-dimethyl-17-cyclopentyl-2,5,6,7,19,20-hexanor-3,3,4,4-tetradehydro-4,8-inter-m-phenylene PGI₂;
16-methyl-16-cyclohexyl-2,5,6,7,18,19,20-heptanor-3,3,4,4-tetradehydro-4,8-inter-m-phenylene PGI₂;
16,16-dimethyl-7-cyclohexyl-2,5,6,7,19,20-hexanor-3,3,4,4-tetradehydro-4,8-inter-m-phenylene PGI₂;
2,5,6,7-tetranor-3,3,4,4,18,18,19,19-octadehydro-4,8-inter-m-phenylene PGI₂;
20a-homo-2,5,6,7-tetranor-3,3,4,4,18,18,19,19-octadehydro-4,8-inter-m-phenylene PGI₂;
20a,20b-dihomo-2,5,6,7-tetranor-3,3,4,4,18,18,19,19-octadehydro-4,8-inter-m-phenylene PGI₂;
20a,20b,20c-trihomo-2,5,6,7-tetranor-3,3,4,4,18,18,19,19-octadehydro-4,8-inter-m-phenylene PGI₂;
20a,20b,20c,20d-tetrahomo-2,5,6,7-tetranor-3,3,4,4,18,18,19,19-octadehydro-4,8-inter-m-phenylene PGI₂;
16-methyl-2,5,6,7-tetranor-3,3,4,4,18,18,19,19-octadehydro-4,8-inter-m-phenylene PGI₂;
16-methyl-20a-homo-2,5,6,7-tetranor-3,3,4,4,18,18,19,19-octadehydro-4,8-inter-m-phenylene PGI₂;
16-methyl-20a,20b-dihomo-2,5,6,7-tetranor-3,3,4,4,18,18,19,19-octadehydro-4,8-inter-m-phenylene PGI₂;
16-methyl-20a,20b,20c-trihomo-2,5,6,7-tetranor-3,3,4,4,18,18,19,19-octadehydro-4,8-inter-m-phenylene PGI₂;

16-methyl-2a,20b,20c,20d-tetrahomo-2,5,6,7-tetranor-3,3,4,4,18,18,19,19-octadehydro-4,8-inter-m-phenylene PGI₂;

16,16-dimethyl-2,5,6,7-tetranor-3,3,4,4,18,18,19,19-octadehydro-4,8-inter-m-phenylene PGI₂;

16,16-dimethyl-20a-homo-2,5,6,7-tetranor-3,3,4,4,18,18,19,19-octadehydro-4,8-inter-m-phenylene PGI₂;

16,16-dimethyl-20a,20b-dihomo-2,5,6,7-tetranor-3,3,4,4,18,18,19,19-octadehydro-4,8-inter-m-phenylene PGI₂;

16,16-dimethyl-20a,20b,20c-trihomo-2,5,6,7-tetranor-3,3,4,4,18,18,19,19-octadehydro-4,8-inter-m-phenylene PGI₂;

16,16-dimethyl-20a,20b,20c,20d-tetrahomo-2,5,6,7-tetranor-3,3,4,4,18,18,19,19-octadehydro-4,8-inter-m-phenylene PGI₂;

and methyl, ethyl, butyl, isobutyl, phenyl, benzyl, phenethyl, cyclopentyl, cyclohexyl, cyclohexylmethyl, furylmethyl, l-carbomethoxy, phenacyl, and p-bromophenacyl esters thereof.

Illustrative examples of the compounds according to the present invention wherein $R_1$ is —O—CH₂—CH₂—OH will be given hereinbelow:

3-decarboxy-3-hydroxymethyl-2,5,6,7-tetranor-4-oxa-4,8-inter-m-phenylene PGI₂;

3-decarboxy-3-hydroxymethyl-20a-homo-2,5,6,7-tetranor-4-oxa-4,8-inter-m-phenylene PGI₂;

3-decarboxy-3-hydroxymethyl-16-methyl-2,5,6,7,18,19,20-heptanor-4-oxa-4,8-inter-m-phenylene PGI₂;

16,16-dimethyl-3-decarboxy-3-hydroxymethyl-2,5,6,7,18,19,20-heptanor-4-oxa-4,8-inter-m-phenylene PGI₂;

16,16-dimethyl-3-decarboxy-3-hydroxymethyl-2,5,6,7,19,20-hexanor-4-oxa-4,8-inter-m-phenylene PGI₂;

16,16-dimethyl-3-decarboxy-3-hydroxymethyl-2,5,6,7,20-pentanor-4-oxa-4,8-inter-m-phenylene PGI₂;

16,16-dimethyl-3-decarboxy-3-hydroxymethyl-2,5,6,7-tetranor-4-oxa-4,8-inter-m-phenylene PGI₂;

16,16-dimethyl-3-decarboxy-3-hydroxymethyl-20a-homo-2,5,6,7-tetranor-4-oxa-4,8-inter-m-phenylene PGI₂;

16,16-dimethyl-3-decarboxy-3-hydroxymethyl-20a,20b-dihomo-2,5,6,7-tetranor-4-oxa-4,8-inter-m-phenylene PGI₂;

16,16-dimethyl-3-decarboxy-3-hydroxymethyl-20a,20b,20c-trihomo-2,5,6,7-tetranor-4-oxa-4,8-inter-m-phenylene PGI₂;

3-decarboxy-3-hydroxymethyl-16,16,17-trimethyl-2,5,6,7,19,20-hexanor-4-oxa-4,8-inter-m-phenylene PGI₂;

17,17-dimethyl-3-decarboxy-3-hydroxymethyl-2,5,6,7-tetranor-4-oxa-4,8-inter-m-phenylene PGI₂;

18,18-dimethyl-3-decarboxy-3-hydroxymethyl-2,5,6,7-tetranor-4-oxa-4,8-inter-m-phenylene PGI₂;

3-decarboxy-3-hydroxymethyl-15-methyl-2,5,6,7-tetranor-4-oxa-4,8-inter-m-phenylene PGI₂;

3-decarboxy-3-hydroxymethyl-16-methyl-2,5,6,7-tetranor-4-oxa-4,8-inter-m-phenylene PGI₂;

3-decarboxy-3-hydroxymethyl-17-methyl-2,5,6,7-tetranor-4-oxa-4,8-inter-m-phenylene PGI₂;

3-decarboxy-3-hydroxymethyl-17-methyl-20a-homo-2,5,6,7-tetranor-4-oxa-4,8-inter-m-phenylene PGI₂;

16,16-dimethyl-3-decarboxy-3-hydroxymethyl-2,5,6,7,20-pentanor-4,18-dioxa-4,8-inter-m-phenylene PGI₂;

16,16-dimethyl-3-decarboxy-3-hydroxymethyl-2,5,6,7-tetranor-4,18-dioxa-4,8-inter-m-phenylene PGI₂;

16,16-dimethyl-3-decarboxy-3-hydroxymethyl-20a-homo-2,5,6,7-tetranor-4,18-dioxa-4,8-inter-m-phenylene PGI₂;

3-decarboxy-3-hydroxymethyl-16-phenoxy-2,5,6,7,17,18,19,20-octanor-4-oxa-4,8-inter-m-phenylene PGI₂;

16,16-dimethyl-3-decarboxy-3-hydroxymethyl-16-phenoxy-2,5,6,7,17,18,19,20-octanor-4-oxa-4,8-inter-m-phenylene PGI₂;

3-decarboxy-3-hydroxymethyl-15-phenyl-2,5,6,7,16,17,18,19,20-nonanor-4-oxa-4,8-inter-m-phenylene PGI₂;

3-decarboxy-3-hydroxymethyl-16-phenyl-2,5,6,7,17,18,19,20-octanor-4-oxa-4,8-inter-m-phenylene PGI₂;

3-decarboxy-3-hydroxymethyl-17-phenyl-2,5,6,7,18,19,20-heptanor-4-oxa-4,8-inter-m-phenylene PGI₂;

3-decarboxy-3-hydroxymethyl-15-(2-methylphenyl)-2,5,6,7,16,17,18,19,20-nonanor-4-oxa-4,8-inter-m-phenylene PGI₂;

3-decarboxy-3-hydroxymethyl-15-(4-methylphenyl)-2,5,6,7,16,17,18,19,20-nonanor-4-oxa-4,8-inter-m-phenylene PGI₂;

3-decarboxy-3-hydroxymethyl-15-(3-fluorophenyl)-2,5,6,7,16,17,18,19,20-nonanor-4-oxa-4,8-inter-m-phenylene PGI₂;

3-decarboxy-3-hydroxymethyl-15-(4-trifluoromethylphenyl)-2,5,6,7,16,17,18,19,20-nonanor-4-oxa-4,8-inter-m-phenylene PGI₂;

3-decarboxy-3-hydroxymethyl-15-(2-chlorophenyl)-2,5,6,7,16,17,18,19,20-nonanor-4-oxa-4,8-inter-m-phenylene PGI₂;

3-decarboxy-3-hydroxymethyl-15-(3-chlorophenyl)-2,5,6,7,16,17,18,19,20-nonanor-4-oxa-4,8-inter-m-phenylene PGI₂;

3-decarboxy-3-hydroxymethyl-15-(4-chlorophenyl)-2,5,6,7,16,17,18,19,20-nonanor-4-oxa-4,8-inter-m-phenylene PGI₂;

3-decarboxy-3-hydroxymethyl-16-methyl-16-phenyl-2,5,6,7,18,19,20-heptanor-4-oxa-4,8-inter-m-phenylene PGI₂;

16,16-dimethyl-3-decarboxy-3-hydroxymethyl-17-phenyl-2,5,6,7,18,19,20-heptanor-4-oxa-4,8-inter-m-phenylene PGI₂;

15-cyclopentyl-3-decarboxy-3-hydroxymethyl-2,5,6,7,16,17,18,19,20-nonanor-4-oxa-4,8-inter-m-phenylene PGI₂;

15-cyclohexyl-3-decarboxy-3-hydroxymethyl-2,5,6,7,16,17,18,19,20-nonanor-4-oxa-4,8-inter-m-phenylene PGI₂;

16-cyclopentyl-3-decarboxy-3-hydroxymethyl-2,5,6,7,17,18,19,20-octanor-4-oxa-4,8-inter-m-phenylene PGI₂;

16-cyclohexyl-3-decarboxy-3-hydroxymethyl-2,5,6,7,17,18,19,20-octanor-4-oxa-4,8-inter-m-phenylene PGI₂;

17-cyclohexyl-3-decarboxy-3-hydroxymethyl-2,5,6,7,18,19,20-heptanor-4-oxa-4,8-inter-m-phenylene PGI₂;

16-cyclohexyl-3-decarboxy-3-hydroxymethyl-16-methyl-2,5,6,7,18,19,20-heptanor-4-oxa-4,8-inter-m-phenylene PGI₂;

17-cyclohexyl-16,16-dimethyl-3-decarboxy-3-hydroxymethyl-2,5,6,7,18,19,20-heptanor-4-oxa-4,8-inter-m-phenylene PGI$_2$;

3-decarboxy-3-hydroxymethyl-16-methyl-18,18,19,19-tetradehydro-2,5,6,7-tetranor-4-oxa-4,8-inter-m-phenylene PGI$_2$;

3-decarboxy-3-hydroxymethyl-16-methyl-18,18,19,19-tetradehydro-20a-homo-2,5,6,7-tetranor-4-oxa-4,8-inter-m-phenylene PGI$_2$;

16,16-dimethyl-3-decarboxy-3-hydroxymethyl-18,18,19,19-tetradehydro-2,5,6,7-tetranor-4-oxa-4,8-inter-m-phenylene PGI$_2$;

3-decarboxy-3-hydroxymethyl-18,18,19,19-tetradehydro-20a,20b,20c,20d-tetrahomo-2,5,6,7-tetranor-4-oxa-4,8-inter-m-phenylene PGI$_2$;

3-decarboxy-3-hydroxymethyl-2,5,6,7-tetranor-4-oxa-13,14-dihydro-4,8-inter-m-phenylene PGI$_2$;

3-decarboxy-3-hydroxymethyl-20a-homo-2,5,6,7-tetranor-4-oxa-13,14-dihydro-4,8-inter-m-phenylene PGI$_2$;

3-decarboxy-3-hydroxymethyl-16-methyl-2,5,6,7,18,19,20-heptanor-4-oxa-13,14-dihydro-4,8-inter-m-phenylene PGI$_2$;

16,16-dimethyl-3-decarboxy-3-hydroxymethyl-2,5,6,7,18,19,20-heptanor-4-oxa-13,14-dihydro-4,8-inter-m-phenylene PGI$_2$;

16,16-dimethyl-3-decarboxy-3-hydroxymethyl-2,5,6,7,19,20-hexanor-4-oxa-13,14-dihydro-4,8-inter-m-phenylene PGI$_2$;

16,16-dimethyl-3-decarboxy-3-hydroxymethyl-2,5,6,7,20-pentanor-4-oxa-13,14-dihydro-4,8-inter-m-phenylene PGI$_2$;

16,16-dimethyl-3-decarboxy-3-hydroxymethyl-2,5,6,7-tetranor-4-oxa-13,14-dihydro-4,8-inter-m-phenylene PGI$_2$;

16,16-dimethyl-3-decarboxy-3-hydroxymethyl-20a-homo-2,5,6,7-tetranor-4-oxa-13,14-dihydro-4,8-inter-m-phenylene PGI$_2$;

16,16-dimethyl-3-decarboxy-3-hydroxymethyl-20a,20b-dihomo-2,5,6,7-tetranor-4-oxa-13,14-dihydro-4,8-inter-m-phenylene PGI$_2$;

16,16-dimethyl-3-decarboxy-3-hydroxymethyl-20a,20b,20c-trihomo-2,5,6,7-tetranor-4-oxa-13,14-dihydro-4,8-inter-m-phenylene PGI$_2$;

3-decarboxy-3-hydroxymethyl-16,16,17-trimethyl-2,5,6,7,19,20-hexanor-4-oxa-13,14-dihydro-4,8-inter-m-phenylene PGI$_2$;

17,17-dimethyl-3-decarboxy-3-hydroxymethyl-2,5,6,7-tetranor-4-oxa-13,14-dihydro-4,8-inter-m-phenylene PGI$_2$;

18,18-dimethyl-3-decarboxy-3-hydroxymethyl-2,5,6,7-tetranor-4-oxa-13,14-dihydro-4,8-inter-m-phenylene PGI$_2$;

3-decarboxy-3-hydroxymethyl-15-methyl-2,5,6,7-tetranor-4-oxa-13,14-dihydro-4,8-inter-m-phenylene PGI$_2$;

3-decarboxy-3-hydroxymethyl-16-methyl-2,5,6,7-tetranor-4-oxa-13,14-dihydro-4,8-inter-m-phenylene PGI$_2$;

3-decarboxy-3-hydroxymethyl-17-methyl-2,5,6,7-tetranor-4-oxa-13,14-dihydro-4,8-inter-m-phenylene PGI$_2$;

3-decarboxy-3-hydroxymethyl-17-methyl-20a-homo-2,5,6,7-tetranor-4-oxa-13,14-dihydro-4,8-inter-m-phenylene PGI$_2$;

16,16-dimethyl-3-decarboxy-3-hydroxymethyl-2,5,6,7,20-pentanor-4,18-dioxa-13,14-dihydro-4,8-inter-m-phenylene PGI$_2$;

16,16-dimethyl-3-decarboxy-3-hydroxymethyl-2,5,6,7-tetranor-4,18-dioxa-13,14-dihydro-4,8-inter-m-phenylene PGI$_2$;

16,16-dimethyl-3-decarboxy-3-hydroxymethyl-20a-homo-2,5,6,7-tetranor-4,18-dioxa-13,14-dihydro-4,8-inter-m-phenylene PGI$_2$;

3-decarboxy-3-hydroxymethyl-16-phenoxy-2,5,6,7,17,18,19,20-octanor-4-oxa-13,14-dihydro-4,8-inter-m-phenylene PGI$_2$;

16,16-dimethyl-3-decarboxy-3-hydroxymethyl-16-phenoxy-2,5,6,7,17,18,19,20-octanor-4-oxa-13,14-dihydro-4,8-inter-m-phenylene PGI$_2$;

3-decarboxy-3-hydroxymethyl-15-phenyl-2,5,6,7,16,17,18,19,20-nonanor-4-oxa-13,14-dihydro-4,8-inter-m-phenylene PGI$_2$;

3-decarboxy-3-hydroxymethyl-16-phenyl-2,5,6,7,17,18,19,20-octanor-4-oxa-13,14-dihydro-4,8-inter-m-phenylene PGI$_2$;

3-decarboxy-3-hydroxymethyl-17-phenyl-2,5,6,7,18,19,20-heptanor-4-oxa-13,14-dihydro-4,8-inter-m-phenylene PGI$_2$;

3-decarboxy-3-hydroxymethyl-15-(2-methylphenyl)-2,5,6,7,16,17,18,19,20-nonanor-4-oxa-13,14-dihydro-4,8-inter-m-phenylene PGI$_2$;

3-decarboxy-3-hydroxymethyl-15-(4-methylphenyl)-2,5,6,7,16,17,18,19,20-nonanor-4-oxa-13,14-dihydro-4,8-inter-m-phenylene PGI$_2$;

3-decarboxy-3-hydroxymethyl-15-(3-fluorophenyl)-2,5,6,7,16,17,18,19,20-nonanor-4-oxa-13,14-dihydro-4,8-inter-m-phenylene PGI$_2$;

3-decarboxy-3-hydroxymethyl-15-(4-trifluoromethylphenyl)-2,5,6,7,16,17,18,19,20-nonanor-4-oxa-13,14-dihydro-4,8-inter-m-phenylene PGI$_2$;

3-decarboxy-3-hydroxymethyl-15-(2-chlorophenyl)-2,5,6,7,16,17,18,19,20-nonanor-4-oxa-13,14-dihydro-4,8-inter-m-phenylene PGI$_2$;

3-decarboxy-3-hydroxymethyl-15-(3-chlorophenyl)-2,5,6,7,16,17,18,19,20-nonanor-4-oxa-13,14-dihydro-4,8-inter-m-phenylene PGI$_2$;

3-decarboxy-3-hydroxymethyl-15-(4-chlorophenyl)-2,5,6,7,16,17,18,19,20-nonanor-4-oxa-13,14-dihydro-4,8-inter-m-phenylene PGI$_2$;

3-decarboxy-3-hydroxymethyl-16-methyl-16-phenyl-2,5,6,7,18,19,20-heptanor-4-oxa-13,14-dihydro-4,8-inter-m-phenylene PGI$_2$;

16,16-dimethyl-3-decarboxy-3-hydroxymethyl-17-phenyl-2,5,6,7,18,19,20-heptanor-4-oxa-13,14-dihydro-4,8-inter-m-phenylene PGI$_2$;

15-cyclopentyl-3-decarboxy-3-hydroxymethyl-2,5,6,7,16,17,18,19,20-nonanor-4-oxa-13,14-dihydro-4,8-inter-m-phenylene PGI$_2$;

15-cyclohexyl-3-decarboxy-3-hydroxymethyl-2,5,6,7,16,17,18,19,20-nonanor-4-oxa-13,14-dihydro-4,8-inter-m-phenylene PGI$_2$;

16-cyclopentyl-3-decarboxy-3-hydroxymethyl-2,5,6,7,17,18,19,20-octanor-4-oxa-13,14-dihydro-4,8-inter-m-phenylene PGI$_2$;

16-cyclohexyl-3-decarboxy-3-hydroxymethyl-2,5,6,7,17,18,19,20-octanor-4-oxa-13,14-dihydro-4,8-inter-m-phenylene PGI$_2$;

17-cyclohexyl-3-decarboxy-3-hydroxymethyl-2,5,6,7,18,19,20-heptanor-4-oxa-13,14-dihydro-4,8-inter-m-phenylene PGI$_2$;

16-cyclohexyl-3-decarboxy-3-hydroxymethyl-16-methyl-2,5,6,7,18,19,20-heptanor-4-oxa-13,14-dihydro-4,8-inter-m-phenylene PGI$_2$; and 17-cyclohexyl-16,16-dimethyl-3-decarboxy-3-hydroxymethyl-2,5,6,7,18,19,20-heptanor-4-oxa-13,14-dihydro-4,8-inter-m-phenylene $PGI_2$.

Illustrative examples of the compounds according to the present invention wherein $R_1$ is —C≡C—CH$_2$—OH will be given hereinbelow:

3-decarboxy-3-hydroxymethyl-2,5,6,7,20-heptanor-3,3,4,4-tetradehydro-4,8-inter-m-phenylene $PGI_2$;
3-decarboxy-3-hydroxymethyl-2,5,6,7-tetranor-3,3,4,4-tetradehydro-4,8-inter-m-phenylene $PGI_2$;
3-decarboxy-3-hydroxymethyl-20a-homo-2,5,6,7-tetranor-3,3,4,4-tetradehydro-4,8-inter-m-phenylene $PGI_2$;
3-decarboxy-3-hydroxymethyl-15-methyl-2,5,6,7-tetranor-3,3,4,4-tetradehydro-4,8-inter-m-phenylene $PGI_2$;
3-decarboxy-3-hydroxymethyl-16-methyl-2,5,6,7,20-heptanor-3,3,4,4-tetradehydro-4,8-inter-m-phenylene $PGI_2$;
3-decarboxy-3-hydroxymethyl-16-methyl-2,5,6,7-tetranor-3,3,4,4-tetradehydro-4,8-inter-m-phenylene $PGI_2$;
3-decarboxy-3-hydroxymethyl-16-methyl-20a-homo-2,5,6,7-tetranor-3,3,4,4-tetradehydro-4,8-inter-m-phenylene $PGI_2$;
3-decarboxy-3-hydroxymethyl-17-methyl-2,5,6,7,20-heptanor-3,3,4,4-tetradehydro-4,8-inter-m-phenylene $PGI_2$;
3-decarboxy-3-hydroxymethyl-17-methyl-2,5,6,7-tetranor-3,3,4,4-tetradehydro-4,8-inter-m-phenylene $PGI_2$;
3-decarboxy-3-hydroxymethyl-17-methyl-20a-homo-2,5,6,7-tetranor-3,3,4,4-tetradehydro-4,8-inter-m-phenylene $PGI_2$;
16,16-dimethyl-3-decarboxy-3-hydroxymethyl-2,5,6,7,20-heptanor-3,3,4,4-tetradehydro-4,8-inter-m-phenylene $PGI_2$;
16,16-dimethyl-3-decarboxy-3-hydroxymethyl-2,5,6,7-tetranor-3,3,4,4-tetrahydro-4,8-inter-m-phenylene $PGI_2$;
16,16-dimethyl-3-decarboxy-3-hydroxymethyl-20a-homo-2,5,6,7-tetranor-3,3,4,4-tetradehydro-4,8-inter-m-phenylene $PGI_2$;
3-decarboxy-3-hydroxymethyl-2,5,6,7,20-heptanor-18-oxa-3,3,4,4-tetradehydro-4,8-inter-m-phenylene $PGI_2$;
3-decarboxy-3-hydroxymethyl-2,5,6,7-tetranor-18-oxa-3,3,4,4-tetradehydro-4,8-inter-m-phenylene $PGI_2$;
3-decarboxy-3-hydroxymethyl-20a-homo-2,5,6,7-tetranor-18-oxa-3,3,4,4-tetradehydro-4,8-inter-m-phenylene $PGI_2$;
16,16-dimethyl-3-decarboxy-3-hydroxymethyl-2,5,6,7,20-heptanor-18-oxa-3,3,4,4-tetradehydro-4,8-inter-m-phenylene $PGI_2$;
16,16-dimethyl-3-decarboxy-3-hydroxymethyl-2,5,6,7-tetranor-18-oxa-3,3,4,4-tetradehydro-4,8-inter-m-phenylene $PGI_2$;
16,16-dimethyl-3-decarboxy-3-hydroxymethyl-20a-homo-2,5,6,7-tetranor-18-oxa-3,3,4,4-tetradehydro-4,8-inter-m-phenylene $PGI_2$;
3-decarboxy-3-hydroxymethyl-16-phenoxy-2,5,6,7,18,19,20-pentanor-3,3,4,4-tetradehydro-4,8-inter-m-phenylene $PGI_2$;
16,16-dimethyl-3-decarboxy-3-hydroxymethyl-16-phenoxy-2,5,6,7,18,19,20-pentanor-3,3,4,4-tetradehydro-4,8-inter-m-phenylene $PGI_2$;
3-decarboxy-3-hydroxymethyl-15-phenyl-2,5,6,7,16,17,18,19,20-nonanor-3,3,4,4-tetradehydro-4,8-inter-m-phenylene $PGI_2$;
3-decarboxy-3-hydroxymethyl-16-phenyl-2,5,6,7,17,18,19,20-octanor-3,3,4,4-tetradehydro-4,8-inter-m-phenylene $PGI_2$;
3-decarboxy-3-hydroxymethyl-17-phenyl-2,5,6,7,18,19,20-heptanor-3,3,4,4-tetradehydro-4,8-inter-m-phenylene $PGI_2$;
3-decarboxy-3-hydroxymethyl-15-(2-methylphenyl)-2,5,6,7,16,17,18,19,20-nonanor-3,3,4,4-tetradehydro-4,8-inter-m-phenylene $PGI_2$;
3-decarboxy-3-hydroxymethyl-15-(3-fluorophenyl)-2,5,6,7,16,17,18,19,20-nonanor-3,3,4,4-tetradehydro-4,8-inter-m-phenylene $PGI_2$;
3-decarboxy-3-hydroxymethyl-15-(2-chlorophenyl)-2,5,6,7,16,17,18,19,20-nonanor-3,3,4,4-tetradehydro-4,8-inter-m-phenylene $PGI_2$;
16-methyl-3-decarboxy-3-hydroxymethyl-16-phenyl-2,5,6,7,18,19,20-heptanor-3,3,4,4-tetradehydro-4,8-inter-m-phenylene $PGI_2$;
16,16-dimethyl-3-decarboxy-3-hydroxymethyl-17-phenyl-2,5,6,7,18,19,20-heptanor-3,3,4,4-tetradehydro-4,8-inter-m-phenylene $PGI_2$;
3-decarboxy-3-hydroxymethyl-15-cyclopentyl-2,5,6,7,16,17,18,19,20-nonanor-3,3,4,4-tetradehydro-4,8-inter-m-phenylene $PGI_2$;
3-decarboxy-3-hydroxymethyl-15-cyclohexyl-2,5,6,7,16,17,18,19,20-nonanor-3,3,4,4-tetradehydro-4,8-inter-m-phenylene $PGI_2$;
3-decarboxy-3-hydroxymethyl-16-cyclopentyl-2,5,6,7,17,18,19,20-octanor-3,3,4,4-tetradehydro-4,8-inter-m-phenylene $PGI_2$;
3-decarboxy-3-hydroxymethyl-16-cyclohexyl-2,5,6,7,17,18,19,20-octanor-3,3,4,4-tetradehydro-4,8-inter-m-phenylene $PGI_2$;
3-decarboxy-3-hydroxymethyl-17-cyclohexyl-2,5,6,7,18,19,20-heptanor-3,3,4,4-tetradehydro-4,8-inter-m-phenylene $PGI_2$;
16-methyl-3-decarboxy-3-hydroxymethyl-16-cyclohexyl-2,5,6,7,18,19,20-heptanor-3,3,4,4-tetradehydro-4,8-inter-m-phenylene $PGI_2$;
16,16-dimethyl-3-decarboxy-3-hydroxymethyl-16-cyclohexyl-2,5,6,7,18,19,20-heptanor-3,3,4,4-tetradehydro-4,8-inter-m-phenylene $PGI_2$;
16-methyl-3-decarboxy-3-hydroxymethyl-2,5,6,7-tetranor-3,3,4,4,18,18,19,19-octadehydro-4,8-inter-m-phenylene $PGI_2$;
16-methyl3-decarboxy-3-hydroxymethyl-20a-homo-2,5,6,7-tetranor-3,3,4,4,18,18,19,19-octadehydro-4,8-inter-m-phenylene $PGI_2$;
16,16-dimethyl-3-decarboxy-3-hydroxymethyl-2,5,6,7-tetranor-3,3,4,4,18,18,19,19-octadehydro-4,8-inter-m-phenylene $PGI_2$; and
16,16-dimethyl-3-decarboxy-3-hydroxymethyl-20a,20b,20c,20d-tetrahomo-2,5,6,7-tetranor-3,3,4,4,18,18,19,19-octadehydro-4,8-inter-m-phenylene $PGI_2$.

Among various compounds according to the present invention, those wherein $R_1$ is —OCH$_2$COOH, —OCH$_2$COOMe, —C≡C—COOH or —C≡C—COOMe and $R_2$ is hydrogen may be prepared by the following Reaction Scheme 1. In the Reaction Scheme 1, Y is OCH$_2$ or C≡C and $R_{14}$ is acetyl or benzoyl group.

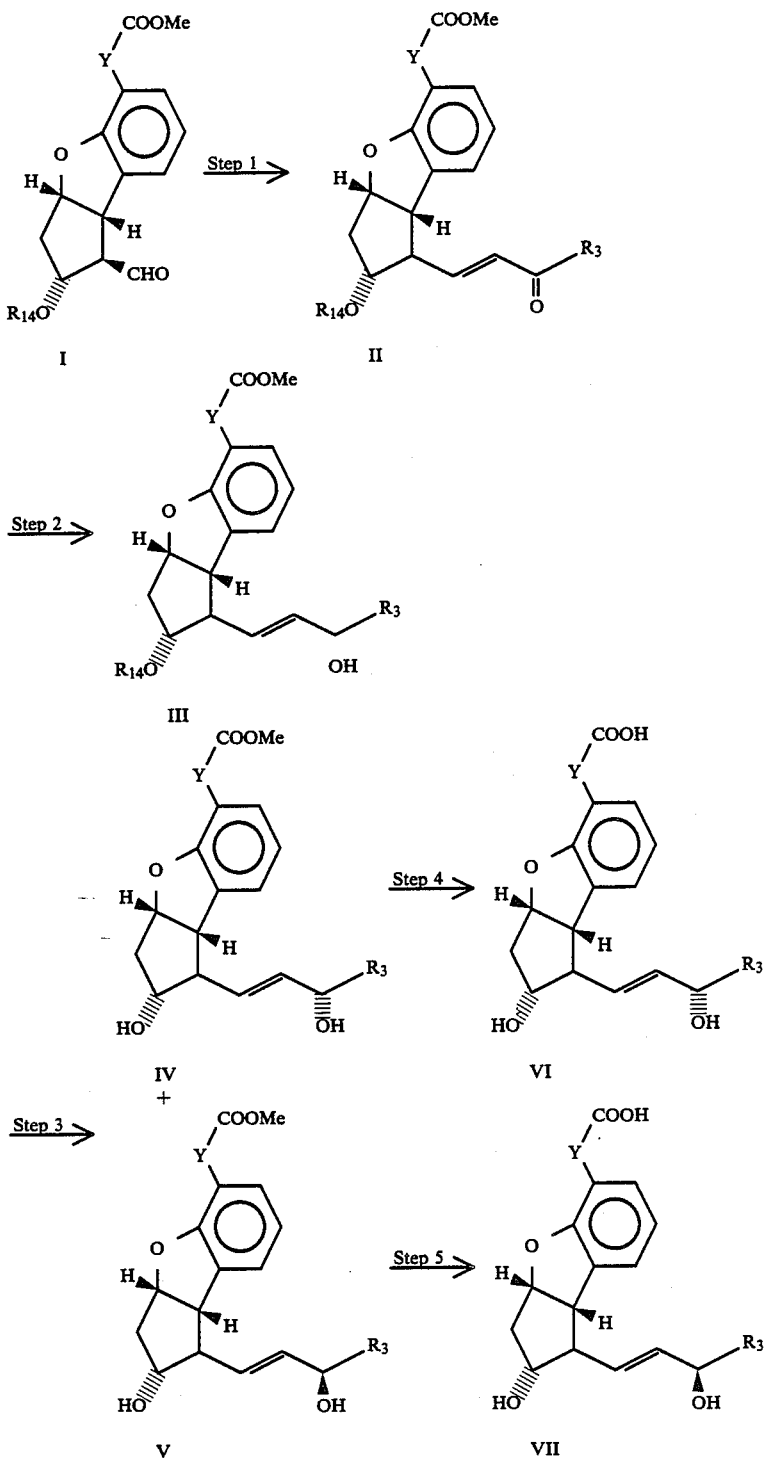

Step 1 of the Reaction Scheme 1 may be easily effected by reacting an aldehyde of the formula I with a sodium or potassium salt of a dimethyl phosphonate represented by the general formula:

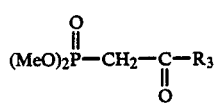

wherein $R_3$ has the same meaning as above. The reaction is generally carried out in an etheric solvent such as dimethoxyethane, tetrahydrofuran (THF), dioxane, or the like. Satisfactory good results can usually be attained by using dimethoxyethane or tetrahydrofuran.

Step 2 is the reduction of an $\alpha,\beta$-unsaturated ketone of the formula II to an allyl alcohol of the formula III. For this purpose, reducing agents which can reduce selectively the ketone moiety alone but cannot reduce the carbon-carbon double bond of the $\alpha,\beta$-unsaturated ketone are utilized. Preferred reducing agents which can be employed in the step may include zinc borohydride ($Zn(BH_4)_2$); aluminum alkoxides such as aluminum isopropoxide; combinations of aluminum lithium hydride and bisphenol; combinations of sodium borohydride and cerium trichloride; diisobutylaluminum 2,6-dimethylphenoxide; and the like. Generally, satisfactory results may be attained by using a combination of sodium borohydride and cerium trichloride. In this case methanol may most preferably be used as a solvent. When zinc borohydride or an organic aluminum reducing agent is employed, an etheric solvent such as ether, tetrahydrofuran, dimethoxyethane or the like may preferably be used.

Step 2 may usually be carried out at a temperature in the range of from −110° C. to 110° C. When the sodium borohydride/cerium trichloride reducing agent system is utilized, a temperature in the range of from −10° C. to room temperature may preferably be employed. In general, approximately 0° C. is especially preferred with this reducing agent system.

After the reaction of Step 2, the resulting compounds of the formula III are generally obtained in the form of a mixture of a 15α isomer and its 15β epimer. These isomeric mixtures may directly be applied to the following Step 3.

Step 3 is the removal of the benzoyl or acetyl group from the compound III. For this purpose the so-called transesterification may be utilized. Generally, the compound III is dissolved in methanol, and a catalytic amount of a base, such as anhydrous sodium carbonate, potassium carbonate, sodium methoxide, or the like, is added to the solution. The reaction temperature may suitably be chosen from the range of −30° C. to 80° C. Satisfactory reaction rates can usually be attained at room temperature.

After Step 3, the resulting product, a mixture of a 15α epimer of the formula IV and a 15β epimer of the formula V, can be separated into each isomer by column chromatography. Generally, the separation may conveniently be effected by developing and eluting the product from a column containing silica gel as a support by means of a mixed solvent of ethyl acetate and cyclohexane.

Steps 4 and 5 are the hydrolyses of the esters represented by the formulae IV and V, respectively. Generally, the ester IV or V may be reacted with a base in an aqueous solvent. Preferred bases may include inorganic bases such as sodium hydroxide, potassium hydroxide, sodium carbonate, potassium carbonate, and the like. The aqueous solvent may include water-containing alcohols and water-containing ethers. Alcohols include methanol and ethanol; and ethers include dioxane and tetrahydrofuran. The reaction temperature may suitably be chosen from the range of −20° C. to 150° C., but satisfactorily high reaction rates can usually be attained at room temperature.

Among the starting compounds of the general formula I in the Reaction Scheme 1, those wherein Y is $OCH_2$ may be prepared by the following Reaction Scheme 2 in which $R_{14}$ has the same meaning as previously defined. Details will be given in Reference Examples hereinbelow.

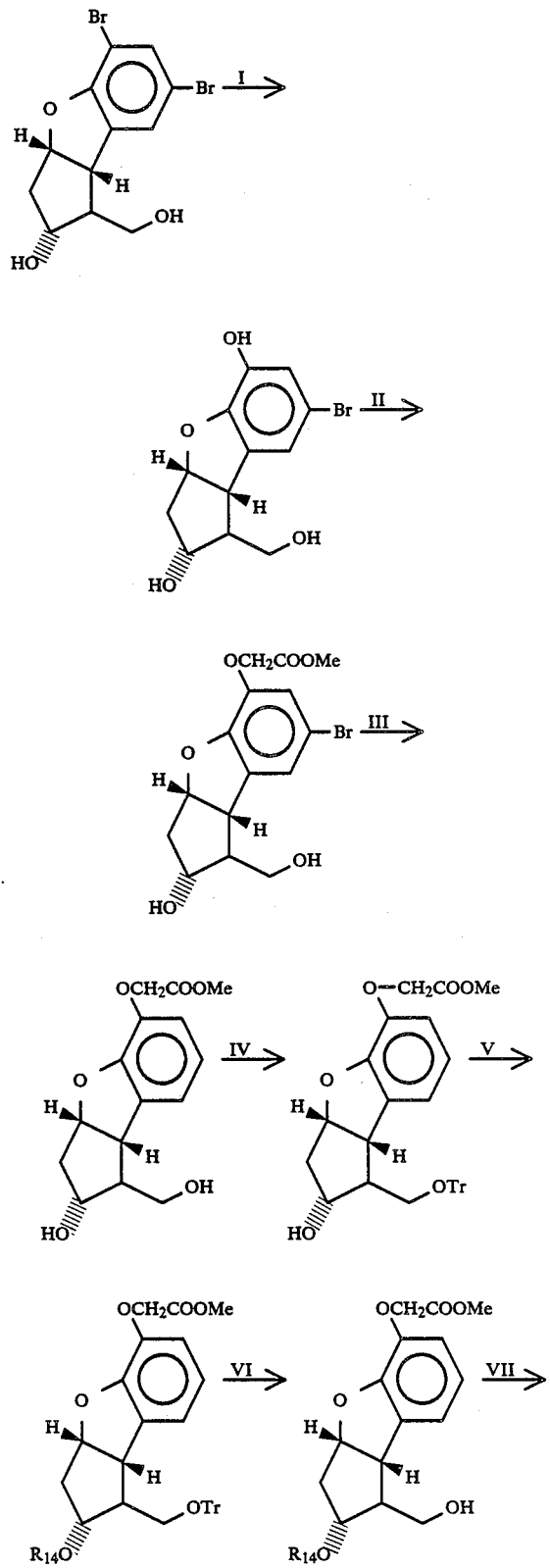

Reaction Scheme 2

-continued
Reaction Scheme 2
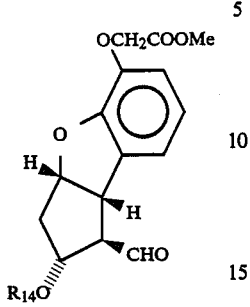
Those compounds of the general formula I in the Reaction Scheme 1 wherein Y is C≡C may be prepared by the following Reaction Schme 3 in which $R_{14}$ is as defined previously. Details will be given in Reference Examples hereinbelow.
Reaction Scheme 3
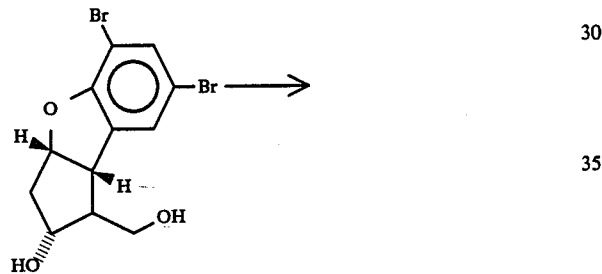
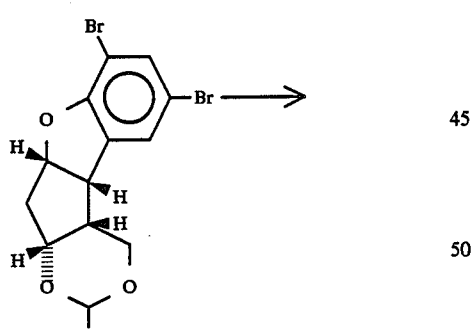
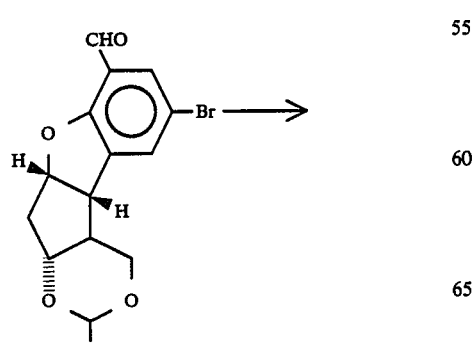
-continued
Reaction Scheme 3
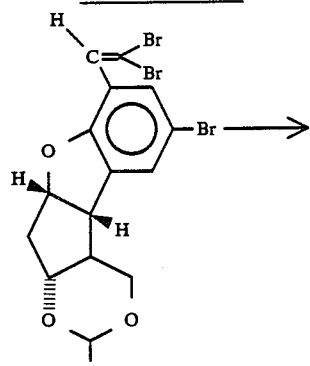
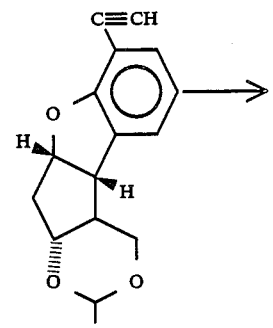
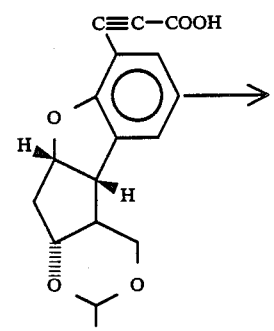
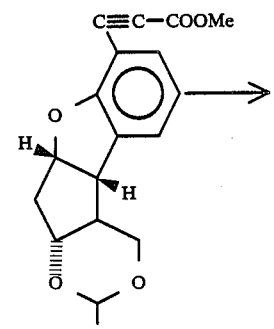
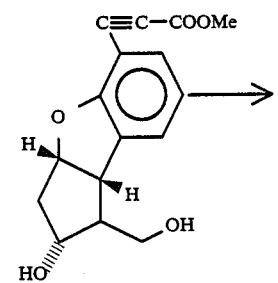

-continued
Reaction Scheme 3

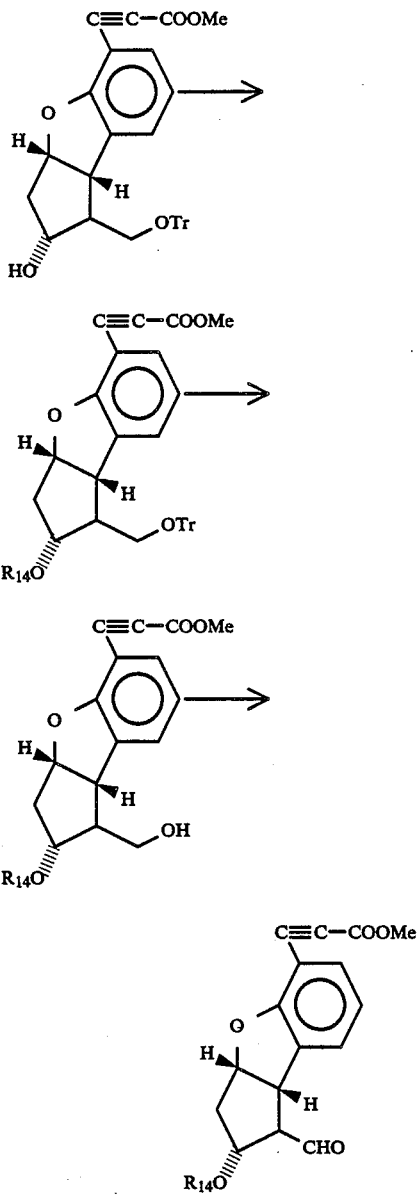

Among the compounds of the present invention, those wherein R₁ is —Y—COOR₄ (Y having the same meaning as above) and R₄ is not hydrogen nor cation, that is, R₄ represents an ester residue, may be prepared by esterification of corresponding carboxylic acids wherein R₄ is hydrogen. There are many known methods of esterification. Methods which may especially be preferred to practice the present invention include the diazoalkane method, the method by utilizing the action of active halides on silver or tertiary amine salts of carboxylic acids, and the mixed acid anhydride method.

In the first method by utilizing the action of diazoalkanes, the reaction may readily be effected by bringing a carboxylic acid into contact with a diazoalkane in a solvent. Diazoalkanes may include, but are not limited to, diazomethane, diazoethane, diazopropane, diazodecane, etc.

The second method may usually be performed by reacting a silver or tertiary amine salt of a carboxylic acid with an active halide in an aprotic polar solvent such as dimethylformamide, acetonitrile, etc. Examples of the active halids may include, but are not limited to, benzyl chloride, benzyl bromide, p-bromobenzyl bromide, p-methoxybenzyl bromide, p-phenylbenzyl bromide, phenacyl bromide, p-bromophenacyl bromide, p-nitrophenacyl bromide, alpha-benzoylphenacyl bromide, etc.

The third, mixed acid anhydride method is widely applied and most of the esterified compounds according to the present invnetion are prepared by this method. First, a carboxylic acid salt is reacted with ethyl chlorocarbonate, pivaloyl chloride, or p-toluenesulfonic acid chloride to produce a mixed acid anhydride. An excess amount of an alcohol represented by the formula R₄OH wherein R₄ is as defined above but does not represent hydrogen nor cation is then added to the mixed anhydride followed by heating. Illustrative examples of the alcohols may include, but are not limited to, methanol, ethanol, propanol, butanol, octanol, decanol, isopropanol, 2-ethylhexanol, benzyl alcohol, p-bromobenzyl alcohol, phenethyl alcohol, cyclopentyl alcohol, cyclopentylmethyl alcohol, cyclohexanol, cyclohexylmethyl alcohol, 2-methoxyethanol, 2-(2-methoxyethoxy)ethanol, hydroxyacetic acid methyl ester, lactic acid ethyl ester, gamma-hydroxybutyric acid methyl ester, 2-butyn-1-ol, 2-pentyn-1-ol, 1,3-di-(O)-methylglycerin, 1,3-diacetylglycerin, phenol, p-bromophenol, p-fluorophenol, m-chlorophenol, m-fluorophenol, 3,4-dichlorophenol, p-(trifluoromethyl)phenol, p-methylphenol, 3,4-dimethylphenol, p-methoxyphenol, 4-phenoxyphenol, p-benzoylaminophenol, etc.

Among the compounds of the present invention, those wherein R₁ is

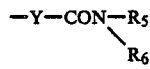

(Y, R₅ and R₆ having the same meanings as defined above) may be prepared by amidizing the compounds wherein R₁ is -Y—COOH (Y having the same meaning as above).

Thus, a compound of the present invention wherein R₁ is —Y—COOH (Y having the same meaning as above) is reacted with a tertiary amine to form a quaternary ammonium salt of a carboxylic acid, which is in turn reacted with ethyl chlorocarbonate or p-toluenesulfonic acid chloride. To the resulting mixed acid anhydride, an amine represented by the formula

is added, and the reaction mixture is then heated to produce the end product. Illustrative examples of the amines which can be used in the present invention may include, but are not limited to, ammonia, N-methylamine, N-ethylamine, N-butylamine, N,N-dimethylamine, N,N-diethylamine, aniline, p-bromoaniline, cyclohexylamine, cyclopentylamine, N-benzylamine, phenethylamine, morpholine, piperidine, etc.

Among the compounds according to the present invention, those wherein R₁ is —Y—CH₂OH (Y having the same meaning as above) may be prepared by reducing the compounds wherein R₁ is —Y—COOCH₃ (Y having the same meaning as above) with metal hydrides. Examples of preferred metal hydrides may include, but are not limited to, lithium aluminum hydride and diisobutylaluminum hydride. When diisobutylaluminum hydride is utilized, the reduction may usually be carried out in a hydrocarbon such as toluene as a solvent at a temperature in the range of from −78° C. to 60° C. When lithium aluminum hydride is used, an etheric solvent such as ether or above) by hydrolyzing as in Step 4 of the Reaction Scheme 1.

Among the compounds of the present invention, those wherein $R_1$ represents —$OCH_2COOR_4$, —$OCH_2CH_2OH$, or

($R_4$, $R_5$ and $R_6$ having the same meaning as above) and X represents —$CH_2CH_2$— may be prepared by hydrogenating the corresponding compounds wherein X is —CH=CH—. Thus, the compounds wherein X is —CH=CH— may be hydrogenated with catalysts such as palladium, palladium/carbon, platinum oxide, Raney nickel, etc. Generally, metallic palladium or palladium on active charcoal is preferably utilized. A solvent which can preferably be employed in the reaction may generally be, but not limited to, methanol, ethanol, ethyl acetate, etc.

The individual compound of the present invention will hererin be shown by the structural formula of one of the optically active isomers thereof. However, it is noticed that the general formula shown herein is intended to encompass d-isomers, l-isomers and dl-isomers. Also, the formulae in the Reaction Schemes are shown by one of the optically active isomers, but the processes can be applied to all other isomers in the same manner as shown.

If the process of the Reaction Scheme 1 is applied to dl isomers, the resulting racemates can be easily resolved into each isomer by the technique of optically active column chromatography.

If optically active compounds wherein Y is —$OCH_2$— in the general formula I are desired, the following Reaction Scheme 5 shown below will be employed. Details of each step of the Reaction Scheme 5 will be given in Reference Examples hereinafter.

Reaction Scheme 4

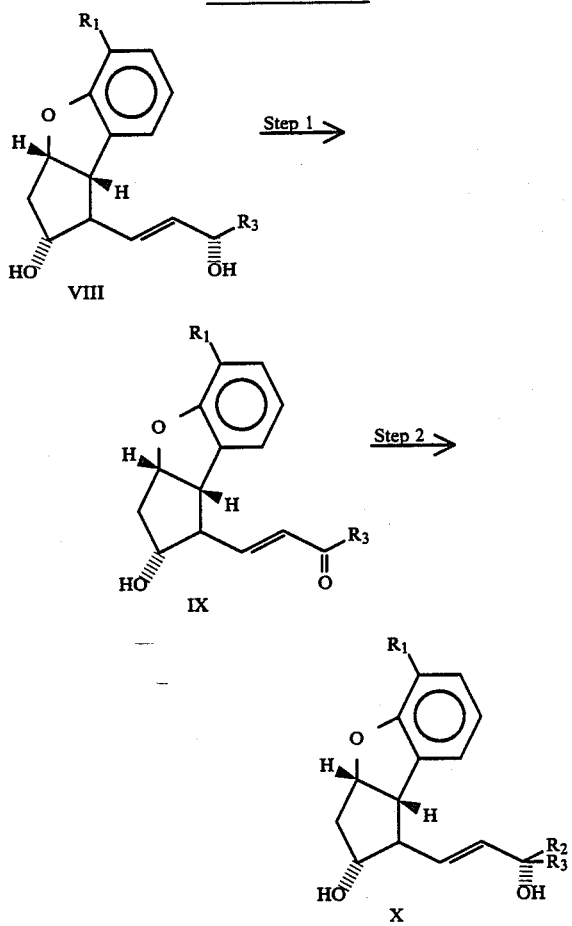

Step 1 of the Reaction Scheme 4 is the oxidation of an allyl alcohol of the formula VIII to a corresponding α,β-unsaturated ketone of the formula IX. For this purpose, the compound of the formula VIII may usually be oxidized with active manganese dioxide in methylene chloride.

Step 2 is the alkylation of the ketone represented by the formula IX, which may suitably be reacted with an excess amount of an alkylating agent. Preferred alkylating agents are generally $R_2MgCl$, $R_2MgBr$ or $RLi$. More preferably, complexes derived from the alkylating agents and anhydrous cerium trichloride may be utilized. The reaction may suitably be carried out at a temperature in the range of from −78° C. to room temperature. Generally, the ketone and the agent are mixed at −78° C. and gradually warmed up to room temperature. When, in the general formula X, $R_1$ represents —Y—$COOR_4$ wherein Y is as defined above and $R_4$ is not cation nor hydrogen, the compounds can be converted into corresponding compounds wherein $R_1$ represents —Y—COOH (Y having the same meaning as

Reaction Scheme 5

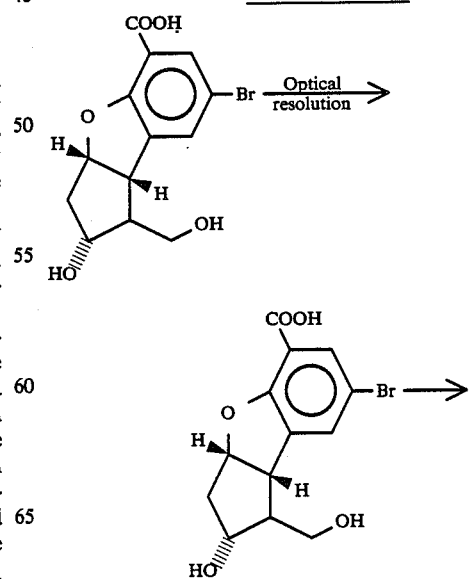

-continued
Reaction Scheme 5
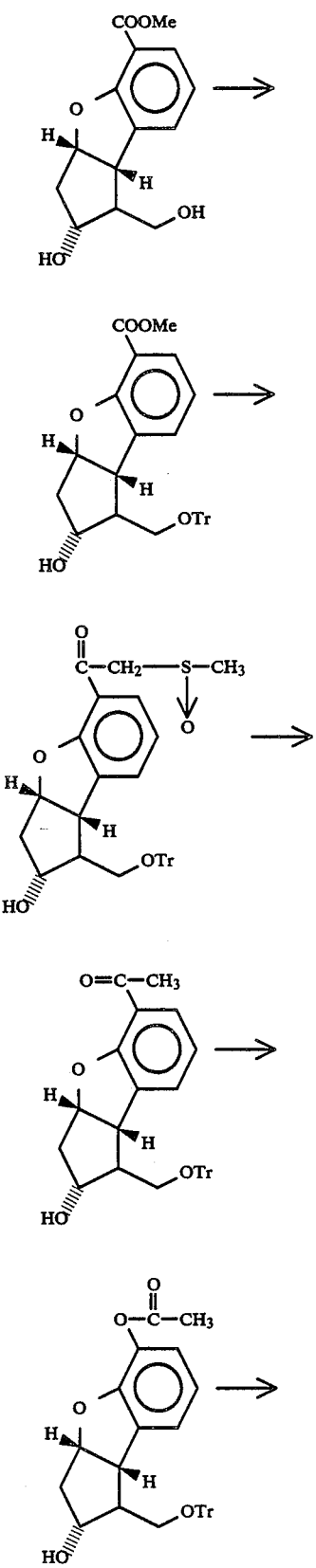
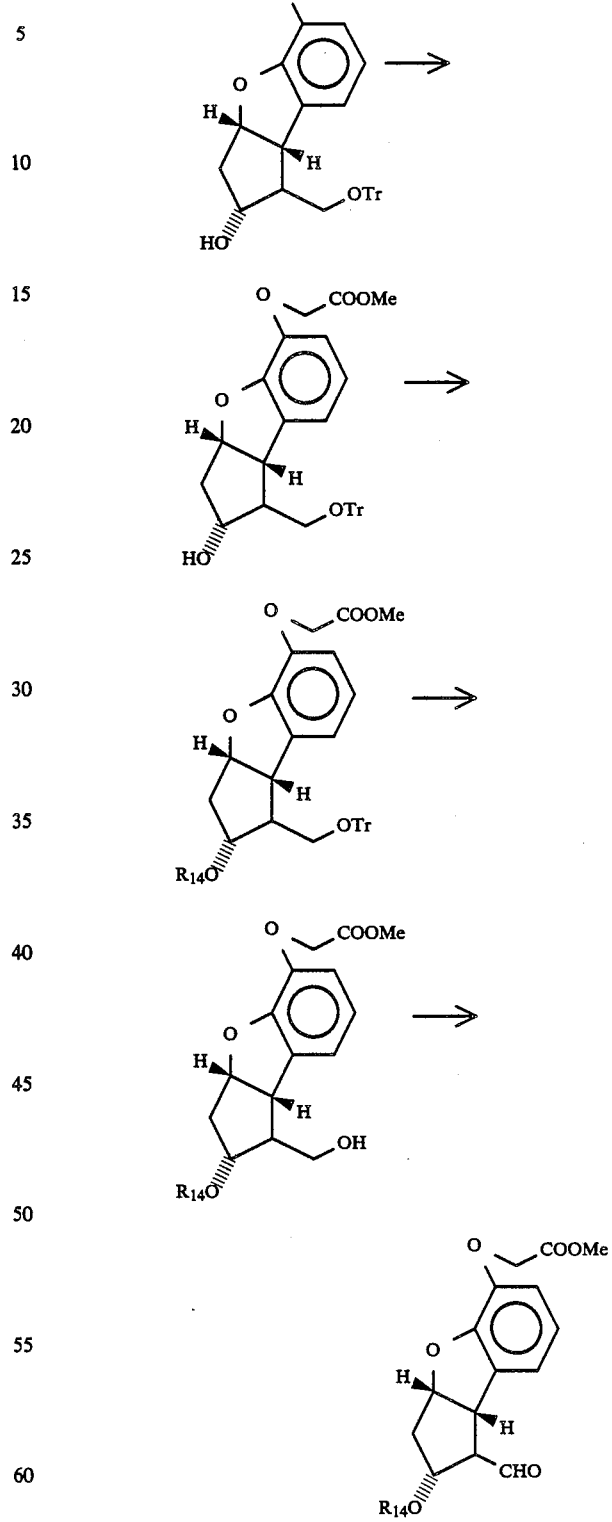
The compounds of the present invention have potent inhibiting effect of platelet aggregation and adhesion and gastric acid secretion, vasodilating effect, gastric cytoprotection effect, bronchodilating effect, luteolytic effect, and uterine constricting effect, etc.

The strong inhibiting effect of platelet aggregation and platelet adhesion, and vasodilating effect can be applied prophylactically and therapeutically to hypertension, myocardinal infarction, angina pectoris, ischemic cerebral disease such as cerebral infarction, TIA, peripheral circulatory disturbance (Burger's disease, Raynaux disease, Behçet disease, purpurea obliterance (thrombocytopenic purpura), arterio-venous fistula, liver diseases, and renal diseases), atherosclerosis, arteriosclerosis, diabetic platelet dysfunctions and retinal vascular obstruction, hyperlipidemia, vibration diseases, etc.

For these applications, drugs containing the compounds of the present invention may usually be applied to patients intravenously, intra-arterially, intramuscularly, intradermally, subcutaneously or orally.

Oral or intrarectal administration needs a usual daily dose in the range of from 0.01 microgram/kg to 10 mg/kg and the drugs are administered at one to four times a day. In the case of intravenous infusion or intra-arterial injection the range of from 0.1 ng/kg/min to 1 microgram/kg/min may cause good therapeutical results. In the case of usual intravenous, intramuscular or subcutaneous injection, a daily dose in the range of from 0.01 microgram/kg to 10 mg/kg may be used at one to four times a day. Individual dose amount of the drugs should be selected from the above specified respective range according to the age, sex, and physical status of patients and the frequency of administration. In the case of intradermal administration dose ranges may vary depending on dosage forms of the drugs, but the dose should be adjusted so that the daily intake of drug may fall within the range of from 0.001 microgram/kg to 10 mg/kg.

The compounds of the present invention may also be used to preserve platelets. For this purpose the compound is added in an amount of the range from 0.01 ng to 1 microgram per ml of concentrated platelet solution.

The compounds of the present invention are effective for the prevention of platelet aggregation and adhesion upon clinical applications of artificial heart and lung, kidney, liver, valve and blood vessel. For this purpose these compounds can be administered orally or by injection. In case of oral administration an effective result may be attained with a dose of the compound of this invention in the range of from 0.01 microgram/kg to 10 mg/kg. It is also effective to infuse the compound into the inlet of the circuit of an artificial organ at a rate in the range of from 0.1 ng/kg to 1 mg/kg per minute.

Further, the compounds of this invention are also effective to prophylactically and therapeutically treat duodenal ulcer, gastric ulcer, chronic gastritis, and digestive organ disorders induced by non-steroidal anti-inflamatory drugs. For this indication drugs containing the compounds may be orally or intravenously administered at a dose in the range of from 0.01 microgram/kg to 1 mg/kg per day. Adequate schedule is one to four times a day.

The compounds of this invention are also effective for the treatment of asthma, bronchitis and respiratory disorders in pneumonia. For this indication, the compounds may be administered orally or by inhalation at a dose in the range of from 0.001 microgram/kg to 1 mg/kg.

The compounds of the present invention are further effective for the induction of labour and the relaxation and softening of uterine cervix. For this indication they may preferably administered orally, intravaginally or by intravenous infusion. In case of oral or intra-vaginal administration doses of the compound may be in the range of from 0.01 microgram/kg to 5 mg/kg. In case of intravenous infusion the compounds may be administered at a rate of from 0.1 ng/kg to 1 microgram/kg per minute.

The compounds of the present invention are also useful for the synchronization of estrus cycle in mammal (e.g., horse, cow, pig, sheep, etc.). For this purpose they may usually be administered orally, intra-vaginally or intra-muscularly at a rate of from 0.01 microgram/kg to 10 mg/kg.

The present compounds are effective for the treatment of congestion of nasal mucosa. For this indication, they may locally be administered in the form of aerosol containing from 10 microgram/ml to 10 mg/ml of the compounds, or in the form of ointment, lotion or liniment containing from 0.1 microgram/ml to 1 mg/ml of the compounds.

The present compounds are also effective for the treatment of hepatitis and nephritis. For this indication, they may be orally or intravenously administered at a dose of from 0.01 microgram/kg to 1 mg/kg.

The compounds of the present invention are useful for the prophylaxis of cancer metastasis. For this purpose, the compounds may be orally or intravenously administered one to four times a day at a daily dose of from 0.01 microgarm/kg to 1 mg/kg. They can also be administered by intravenous infusion. In this case the compounds may be administered at a rate of from 0.1 ng/kg to 100 microgram/kg per minute.

The compounds of this invention are useful as anti-inflammatory and analgesics. For this indication, they may be orally or intravenously administered at a dose of from 0.01 microgram/kg to 1 mg/kg a day.

The compounds of the present invention may be orally administered in the solid form comprising starch, lactose, sucrose, glucose, microcrystal cellulose, clay-like vehicles, coloring agents, lubricants, binders, disintegrators, or coating materials. The compounds can also be parenterally administered in the form of sterilized solutions which may optionally contain an amount of sodium chloride or glucose sufficient to make it iso-osmotic. Because of the chemical stability of the compounds according to the present invention, a wide variety of formulations, such as mentioned above (tablets, powders, and granules), injections, suppositories, ointments, lotions, etc.

The present invention will be illustrated by the following examples and reference examples. These examples should not be construed as limiting the invention.

REFERENCE EXAMPLE 1

7-Bromo-2α,5-dihydroxy-1β-hydroxymethyl-3aβH, 8bβH-2,3,3a,8b-tetrahydro-1H-cyclopenta[b]benzofuran (1)

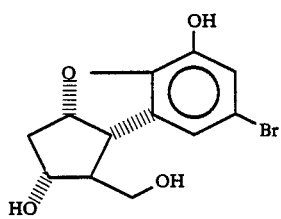

To a stirred solution of 5,7-dibromo-2α-hydroxy-1β-hydroxymethyl-3aβH, 8bβH-2,3,3a,8b-tetrahydro-1H-cyclopenta[b]benzofuran (100 g, 275 mmol) in anhydrous THF (1 liter) was added under argon atmosphere a solution of cyclohexylmagnesium chloride in THF (2.04N, 296 ml, 604 mmol) at 0° C. The reaction mixture was allowed to warm to room temperature and stirred for 30 minutes. To the reaction mixture was added a solution of cyclohexylmagnesium chloride in THF (2.04N, 431 ml, 879 mmol). After being warmed to 40° C. and stirred for 1 hour, the reaction mixture was added dropwise to anhydrous THF (1.5 liters) saturated with oxygen at −78° C. over a period of 2 hours during which a stream of oxygen was passed through the reaction mixture. After being stirred for 2 hours at −78° C., the mixture was warmed to −35° C. and then nitrogen instead of oxygen was bubbled therethrough for 10 minutes. The reaction mixture was warmed up to 0° C. To the reaction mixture were added 3N aqueous hydrogen chloride (800 ml), and then a solution of sodium sulfite (300 g, 2.38 mol) in water (1.2 liters), and the mixture was stirred for 12 hours. Crystals in the mixture were filtered off and washed with ethyl acetate (500 ml×2). The filtrate was combined and the organic layer was separated. The aqueous layer was extracted with ethyl acetate (500 ml×3). The combined ethyl acetate layers were concentrated to 200 ml, and 1 liter portion of 1N aqueous sodium hydroxide and ethyl acetate was added to the residue. The organic layer was separated from the solution and extracted with 1N aqueous sodium hydroxide (200 ml×3). Ethyl acetate (1 l) was added to the combined aqueous layers and the solution was partitioned. To the aqueous layer were added 6N aqueous hydrogen chloride (300 ml) and ethyl acetate (1 l), and the mixture was filtered. The resulting crystals were dried to give 7-bromo-2α,5-dihydroxy-1β-hydroxymethyl-3aβH, 8bβH-2,3,3a, 8b-tetrahydro-1H-cyclopenta[b]benzofuran (49.0 g, 163 mmol). The aqueous layer was separated from the ethyl acetate layer of the filtrate, and extracted further with ethyl acetate (500 ml×3). The combined ethyl acetate extracts were washed once with water (500 ml) and with brine (500 ml), dried over anhydrous magnesium sulfate, and concentrated to give crystalline solid. After washing with ethyl acetate (100 ml×3) and drying, 7.6 g (25.2 mmol) of 7-bromo-2α,5-dihydroxy-1β-hydroxymethyl-3aβH, 8bβH-2,3,3a,8b-tetrahydro-1H-cyclopenta[b]benzofuran was isolated as crystalline solid (68.1% overall yield). The crystalline solid was assigned the structure by the following data. m.p.: 226.5°–227° C. (recrystallized from methanol).

IR (KBr): 3440, 3300, 3150, 2960, 2930, 2880, 1625, 1590, 1495, 1440, 1390, 1360, 1330, 1320, 1310, 1250, 1240, 1220, 1200, 1180, 1160, 1090, 1080, 1050, 1030, 1010, 990, 960, 940, 890, 870, 840, 810, 795, 740, 650, 590, 550, 450, 400 cm$^{-1}$.

NMR (90 MHz, DMSO-d$_6$, δ): 1.5–2.0 (2H, m); 2.2–2.7 (1H, m); 3.1–4.2 (4H, m); 4.5–4.9 (2H, m); 4.9–5.3 (1H, m); 6.72 (1H, d, J=2.0 Hz); 6.86 (1H, dd, J=0.7, 2.0 Hz); 9.3–9.8 (1H, s, broad).

MASS (EI, m/e): 300, 302 (M+).

Elementary Analysis: Calcd. for C$_{12}$H$_{13}$O$_4$Br: C 47.86; H 4.35. Found: C 47.79; H 4.47.

REFERENCE EXAMPLE 2

Methyl 2α-hydroxy-1β-hydroxymethyl-3αβH, 8bβH-2,3,3a,8b-tetrahydro-1H-5-cyclopenta[b]benzofuranyloxy-acetate (2)

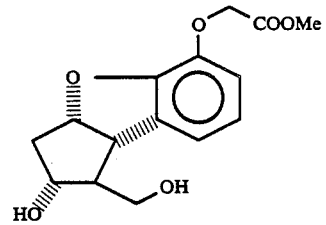

7-Bromo-2α,5-dihyroxy-1β-hydroxymethyl-3aβH, 8bβH-2,3,3a,8b-tetrahydro-1H-cyclopenta[b]benzofuran (56.4 g, 187 mmol) was dissolved in methanol (4 liters) at 50° C. To the solution cooled to room temperature was added a solution of potassium hydroxide in methanol (0.51N, 367 ml, 187 mmol). After stirring for one hour, the reaction mixture was concentrated by a rotary evaporator and dried by a vacuum pump. To the resulting crystals was added DMF (1 liter) to obtain a suspension. A solution of methyl bromoacetate (42.9 g, 280 mmol) in DMF (80 ml) was then added to the suspension and the mixture was stirred at room temperature for 2 hours. DMF (900 ml) in the reaction mixture was distilled off under reduced pressure and water (700 ml) and ethyl acetate (1 liter) were added to the mixture. The resulting crystalline solid was filtered and dried to afford 52.6 g of crude methyl 7-bromo-2α-hydroxy-1β-hydroxymethyl-3aβH,8bβH-2,3,3a,8b-tetrahydro-1H-5-cyclopenta[b]benzofuranyloxy-acetate. The organic layer was separated from the aqueous layer of the filtrate, washed with brine (400 ml) and dried over anhydrous magnesium sulfate, and concentrated to obtain 15.4 g of a residue. A portion of the resulting crude crystals was recrystallized from ethanoL to give pure methyl 7-bromo-2α-hydroxy-1β-hydroxymethyl-3aβH,8bβH-2,3,3a,8b-tetrahydro-1H-5-cyclopenta[b]benzofuranyloxy-acetate. The crystal was assigned the structure by the following data.

m.p.: 174.8°–176.3° C.

IR (KBr): 3270, 3070, 2925, 2875, 1740, 1610, 1580, 1470, 1430, 1390, 1350, 1340, 1320, 1290, 1270, 1240, 1220, 1195, 1150, 1120, 1100, 1070, 1040, 1015, 960, 900, 860, 795, 730, 700, 660, 620, 600, 530, 480, 430 cm$^{-1}$.

NMR (90 MHz, DMSO-d$_6$, δ): 1.5–2.0 (2H, m); 2.2–2.6 (1H, m); 3.2–4.0 (4H, m); 3.70 (3H, s); 4.6–4.9 (2H, m); 4.80 (2H, s); 5.0–5.4 (1H, m); 6.8–7.2 (2H, m).

MASS (EI, m/e): 372, 374 (M+).

Elementary Analysis: Calcd. for C$_{15}$H$_{17}$O$_6$Br: C 48.27; H 4.59. Found: C 48.36; H 4.82.

The above obtained crude methyl 7-bromo-2α-hydroxy-1β-hydroxymethyl-3aβH,8bβH-2,3,3a,8b-tetrahydro-1H-5-cyclopenta[b]benzofuranyloxy-acetate was dissolved in methanol (4 liters), together with the residue. To the resulting solution was added 11 g of 10% palladium on active charcoal, and the mixture was stirred under hydrogen atmosphere at room temperature for one hour. The reaction mixture was filtered and a saturated aqueous solution of sodium hydrogencarbonate (400 ml) was added to the filtrate. The mixture was concentrated to 400 ml and the residue was partitioned between water (200 ml) and ethyl acetate (1 liter). The aqueous layer was further extracted with ethyl acetate (200 ml×6). The combined ethyl acetate extracts were washed with brine (100 ml), dried over anhydrous magnesium sulfate and concentrated to give 48.0 g of crude crystal. Recrystallization from ethyl acetate gave pure, white crystal, methyl 2α-hydroxy-1β-hydroxymethyl-3aβH,8bβH-2,3,3a,8b-tetrahydro-1H-5-cyclopenta[b]benzofuranyloxyl-acetate (37.7 g, 128 mmol). After concentrating the mother liquor, purification of the residue by silica gel column chromatography (acetonitrile/methylene chloride 1:3–1:1) gave 5.50 g (18.7 mmol) of methyl 2α-hydroxy-1β-hydroxymethyl-3aβH,8bβH-2,3,3a,8b-tetrahydro-1H-5-cyclopenta[b]benzofuranyloxy-acetate (78.5% overall yield). This was assigned the structure by the following data.

m.p.: 101.5°–102° C. (recrystallized from ethyl acetate/cyclohexane).

IR (KBr): 3260, 2930, 1750, 1740, 1620, 1590, 1490, 1460, 1440, 1400, 1335, 1300, 1270, 1250, 1220, 1200, 1170, 1110, 1090, 1050, 1030, 1010, 960, 910, 850, 770, 740, 700, 680, 650, 610, 560, 540, 370, 360 cm$^{-1}$.

NMR (400 MHz, CDCl$_3$, δ): 1.95–2.0 (1H, m); 2.10 (1H, ddd, J=4.9, 7.8, 14.0 Hz); 2.17 (1H, dq, J=5.6, 8.0 Hz); 2.3–2.4 (1H, m, alcohol); 2.59 (1H, dt, J=6.8, 14.0 Hz); 3.44 (1H, t, J=8.0 Hz); 3.7–3.8 (1H, m); 3.78 (3H, s); 3.9–4.0 (1H, m); 4.1–4.2 (1H, m); 4.71 (1H, d, J=16.1 Hz); 4.73 (1H, d, J=16.1 Hz); 5.21 (1H, ddd, J=4.9, 6.8, 8.0 Hz); 6.72 (1H, d, J=7.8 Hz); 6.78 (1H, t, J=7.8 Hz); 6.85 (1H, d, J=7.8 Hz).

MASS (EI, m/e): 294 (M+).

Elementary Analysis: Calcd. for C$_{15}$H$_{18}$O$_6$: C 61.21; H 6.17. Found: C 60.99; H 6.11.

REFERENCE EXAMPLE 3

Methyl 2α-benzoyloxy-1β-hydroxymethyl-3aβH,8bβH-2,3,3a,8b-tetrahydro-1H-5-cyclopenta[b]benzofuranyloxy-acetate (3)

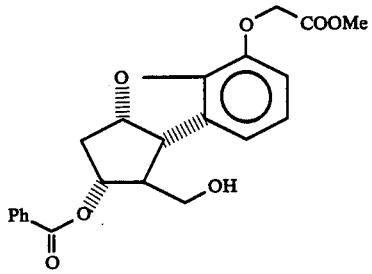

Methyl 2α-hydroxy-1β-hydroxymethyl-3aβH,8bβH-2,3,3a,8b-tetrahydro-1H-5-cyclopenta[b]benzofuranyloxy-acetate (42.4 g, 144 mmol) was dissolved in anhydrous THF (600 ml). To the solution were added anhydrous triethylamine (90.3 ml, 648 mmol) and trityl chloride (90.3 g, 323 mmol). After refluxing for 7 hours, the reaction mixture was cooled to 0° C., and anhydrous triethylamine (80.2 ml, 575 mmol) and benzoyl chloride (50.2 ml, 432 mmol) were added. The reaction mixture was then stirred at room temperature for 14 hours. The mixture was cooled to 0° C. and methanol (200 ml) and 5.24N methanolic hydrogen chloride (100 ml, 524 mmol) were added. The reaction mixture was then stirred at room temperature for 12 hours. Then, the mixture was cooled to 0° C. and the pH was adjusted to 7 by adding 30 g sodium hydrogencarbonate. After concentrating, ethyl acetate (800 ml) was added to the resulting residue. The crystals obtained after filtration was washed with ethyl acetate (400 ml×3). The filtrates were combined and the resulting solution was concentrated to one liter. Aqueous hydrogen chloride (1N, 200 ml) was added to the concentrated liqud and the solution was partitioned. The extracted organic layer was washed with water (200 ml×3) and with brine, and dried over anhydrous magnesium sulfate. After concentration, the residue was purified by silica gel column chromatography (ethyl acetate/cyclohexane 1:10–1:1) to obtain white crystal, methyl 2α-benzoyloxy-1β-hydroxymethyl-3aβH,8bβH-2,3,3a,8b-tetrahydro-1H-5-cyclopenta[b]benzofuranyloxy-acetate (47.2 g, 119 mmol, 82.3%). The structure was identified by the following data.

m.p.: 52°–54° C. (recrystallized from ether).

IR (KBr): 3520, 3400, 3060, 3000, 2950, 2890, 1740, 1710, 1620, 1600, 1490, 1470, 1440, 1390, 1370, 1320, 1300, 1280, 1230, 1190, 1180, 1160, 1110, 1070, 1040, 1020, 1000, 990, 970, 950, 920, 875, 840, 820, 760, 740, 720, 640, 600, 550, 520 cm$^{-1}$.

NMR (400 MHz, CDCl$_3$, δ): 2.1–2.2 (1H, m); 2.45 (1H, dt, J=3.6, 15.1 Hz); 2.50 (1H, m); 2.63 (1H, ddd, J=5.9, 6.8, 15.1 Hz); 3.75 (3H, s); 3.77 (2H, d, J=5.0 Hz); 3.83 (1H, dd, J=5.0, 8.8 Hz); 4.65 (1H, d, J=16.1 Hz); 4.68 (1H, d, J=16.1 Hz); 5.35–5.45 (2H, m); 6.74 (1H, d, J=7.4 Hz); 6.77 (1H, t, J=7.4 Hz); 6.89 (1H, d, J=7.4 Hz); 7.31 (2H, t, J=8.0 Hz); 7.49 (1H, t, J=8.0 Hz); 7.62 (2H, d, J=8.0 Hz).

MASS (EI, m/e): 398 (M+).

Elementary Analysis: Calcd. for C$_{22}$H$_{22}$O$_7$: C 66.32; H 5.57. Found: C 66.10; H 5.59.

REFERENCE EXAMPLE 4

2α-Acetoxy-1β-hydroxymethyl-3aβH,8bβH-2,3,3a,8b-tetrahydro-1H-5-cyclopenta[b]benzofuranyloxyacetic acid methyl ester (4)

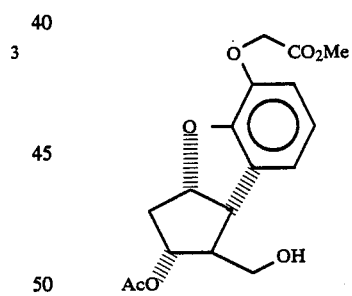

Under argon stream, 2α-hydroxy-1β-hydroxymethyl-3aβH,8bβH-2,3,3a,8b-tetrahydro-1H-5-cyclopenta[b]benzofuranyloxyacetic acid methyl ester (22.00 g, 74.7 mmol) was dissolved in anhydrous THF (400 ml). Anhydrous triethylamine (46.2 ml, 332 mmol) and trityl chloride (46.89 g, 168 mmol) were added to the solution and reflux was conducted for 7 hours. To the reaction mixture were added anhydrous pyridine (100.2 ml, 1.24 mol) and acetic anhydride (49.1 ml, 0.520 mol), and the resulting mixture was stirred at room temperature for 48 hours. The reaction mixture was cooled to 0° C. and methanolic hydrogen chloride (5.24N, 215 ml, 1.13 mol) was added. After stirring the mixture at room temperature for 10 hours, the mixture was cooled to 0° C. and sodium hydrogen-carbonate (120 g, 1.43 mol) was added to adjust pH to 7. The precipitate was filtered and the filtrate was concentrated. To the residue was added water (100 ml) and the mixture was extracted with ethyl acetate (100 ml×5). The ethyl acetate layers were washed with 1N aqueous hydrogen chloride (100 ml), with aqueous solution of sodium hydrogencarbonate (100 ml), with water (200 ml), and with brine (200 ml), dried over anhydrous sodium sulfate, and concentrated. Separation and purification of the obtained residue by silica gel column chromatography (ethyl acetate/cyclohexane=1:1) gave 2α-acetoxy-1β-hydroxymethyl-3aβH,8bβH-2,3,3a,8b-tetrahydro-1H-5-cyclopenta[b]benzofuranyloxyacetic acid methyl ester (17.17 g, 51.0 mmol, 68.3%).

m.p.: 82.5°–83° C. (colorless needle-liike crystals, recrystallized from ethyl acetate and cyclohexane).

IR (KBr): 3510, 2970, 2950, 2925, 2880, 2820, 1724, 1617, 1592, 1491, 1467, 1439, 1429, 1376, 1369, 1332, 1317, 1298, 1245, 1190, 1150, 1110, 1075, 1060, 1013, 980, 962, 927, 894, 841, 822, 784, 769, 732, 706, 654, 637, 609 cm$^{-1}$.

NMR (400 MHz, CDCl$_3$, δ): 1.82 (1H, s, broad); 1.87 (3H, s); 2.24–2.32 (2H, m); 2.53–2.62 (1H, m); 3.67–3.78 (3H, m); 3.79 (3H, s); 4.73 (2H, s); 5.07 (1H, dd, J=12.21, 6.35 Hz); 5.25–5.31 (1H, m); 6.70–6.90 (3H, m).

MASS (EI, m/e): 336 (M$^+$).

Elementary Analysis: Calcd. for C$_{17}$H$_{20}$O$_7$: C 60.71; H 5.99. Found: C 60.91; H 6.03.

REFERENCE EXAMPLE 5 d-7-Bromo-2α-hydroxy-1β-hydroxymethyl-3aβH,8bβH-2,3,3a,8b-tetrahydro-1H-5-cyclopenta[b]benzofurancarboxylic acid (5)

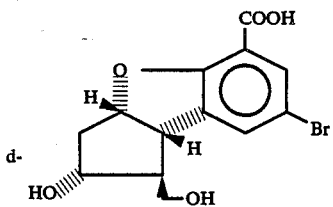

dl-7-Bromo-2α-hydroxy-1β-hydroxymethyl-3aβH,8bβH-2,3,3a,8b-tetrahydro-1H-5-cyclopenta[b]benzofurancarboxylic acid (32.5 g, 99 mmol) and d-cis-N-benzyl-2-hydroxymethylcyclohexylamine (21.7 g, 99 mmol) was dissolved in ethanol (70 ml) under heating. After the solution was cooled to room temperature, a seed crystal of the salt of d-carboxylic acid.d-amine was innoculated in the solution and the solution was allowed to stand for three days. Recrystallization of the resulting crystal from 70 ml of ethanol and then from 10 ml of 50% aqueous methanol solution gave d-7-bromo-2α-hydroxy-1β-hydroxymethyl-3aβH,8bβH-2,3,3a,8b-tetrahydro-1H-5-cyclopenta[b]benzofurancarboxylic acid.d-cis-N-benzyl-2-hydroxymethylcyclohexylamine salt (5.30 g, 9.8%). The recrystallized crystal was dispersed in a distilled water (40 ml). To this was added 6N sulfuric acid (6 ml) and the mixture was stirred for 30 min. to deposit d-carboxylic acid. The deposited crystal was filtered, washed with 10 ml of acetone and dried to afford d-7-bromo-2α-hydroxy-1β-hydroxymethyl-3aβH,8bβH-2,3,3a,8b-tetrahydro-1H-5-cyclopenta[b]benzofurancarboxylic acid (3.00 g, 9.3%). The optical purity was determined by liquid chromatography after conversion of the carboxylic acid into its methyl ester by diazomethane.

Optical purity: more than 99% (column: YHC-pack A-K03, 4.6φ×250 mm; eluate: n-hexane/ethanol/methylene chloride=85/10/5; flow rate: 1 ml/min.; oven temperature: room temp.)

Optical rotation: [α]$_D^{20}$=+15.2° (c=0.92, methanol).

M.p.: 115.5°–116.5° C.

IR (KBr): 3640, 3500, 3400–2500, 3110, 2980, 2850, 1695, 1650, 1605, 1450, 1390, 1370, 1350, 1335, 1305, 1300, 1260, 1240, 1220, 1170, 1120, 1075, 1020, 995, 950, 915, 885, 870, 840, 795, 790, 690, 655, 620, 560, 525 cm$^{-1}$.

NMR (400 MHz, CDCl$_3$-DMSO-d$_6$, δ): 2.02–2.10 (2H, m); 2.50–2.57 (1H, m); 2.80–3.20 (3H, bs); 3.60 (1H, t, J=7.8 Hz); 3.66 (1H, dd, J=5.4, 10.5 Hz); 3.78 (1H, dd, J=5.4, 10.4 Hz); 4.01 (1H, q, J=6.5 Hz); 5.31 (1H, ddd, J=5.4, 7.8, 9.3 Hz); 7.52 (1H, m); 7.81 (1H, d, J=2.4 Hz).

MASS (EI, m/e): 328, 330 (M$^+$).

HR MASS: Calcd. (C$_{13}$H$_{13}$O$_5$Br, M$^+$): 327.9909. Found (M$^+$): 327.9928.

REFERENCE EXAMPLE 6 d-2α-Hydroxy-1β-hydroxymethyl-3aβH,8bβH-2,3,3a,8b-tetrahydro-1H-5-cyclopenta[b]benzofurancarboxylic acid methyl ester (6)

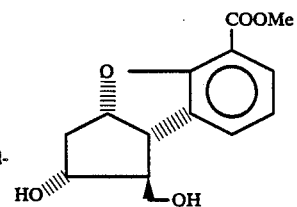

A solution of d-7-bromo-2α-hydroxy-1β-hydroxymethyl-3aβH,8bβH-2,3,3a,8b-tetrahydro-1H-5-cyclopenta[b]benzofurancarboxylic acid (29.18 g, 88.4 mmol) in methanol (1.5 l) was hydrogenated at room temperature for 2 hrs. over 10% palladium on active carbon (3 g). The reaction mixture was refluxed under argon atmosphere for 3 hrs. and then filtered. The filtrate was concentrated. To the residue was added water (200 ml) and the mixture was extracted with chloroform (300 ml×3). The combined chloroform layers were washed with brine (100 ml), dried over anhydrous magnesium sulfate, and concentrated to give a crude crystal (22.3 g). Recrystallization of the crude crystal from ethyl acetate gave d-2α-hydroxy-1β-hydroxymethyl-3aβH,8bβH-2,3,3a,8b-tetrahydro-1H-5-cyclopenta[b]benzofurancarboxylic acid methyl ester as a prism (20.87 g, 79.1 mmol, 89.4%). The compound was assigned the structure by the following data. Optical rotation: [α]$_D^{20}$=+109.6° (c=1.028, methanol)

M.p.: 154°–155° C.

IR (KBr): 3280, 3170, 3030, 2990, 2950, 2900, 1720, 1605, 1445, 1430, 1370, 1355, 1315, 1275, 1250, 1220, 1190, 1170, 1140, 1105, 1075, 1065, 1055, 1040, 1015, 995, 965, 930, 905, 880, 855, 840, 765, 710, 625 cm$^{-1}$.

NMR (400 MHz, CDCl$_3$-DMSO-d$_6$, δ): 2.01–2.08 (2H, m); 2.56–2.63 (1H, m); 3.54 (1H, t, J=8.3 Hz); 3.78 (2H, t, J=5.4 Hz); 3.88 (3H, s); 4.05 (1H, d, J=4.9 Hz); 4.01–4.08 (1H, m); 4.14 (1H, t, J=5.3 Hz); 5.26 (1H, ddd, J=5.3, 8.3, 9.3 Hz); 6.86 (1H, t, J=7.3 Hz); 7.41 (1H, m); 7.70 (1H, dd, J=1.0, 7.3 Hz).

MASS (EI, m/e): 264 (M$^+$).

HR MASS: Calcd. (C$_{14}$H$_{16}$O$_5$, M+): 264.0962. Found (M+): 264.0980.

REFERENCE EXAMPLE 7 d-2α-Hydroxy-1β-trityloxymethyl-3aβH,8bβH-2,3,3a,8b-tetrahydro-1H-5-cyclopenta[b]benzofurancarboxylic acid methyl ester (7)

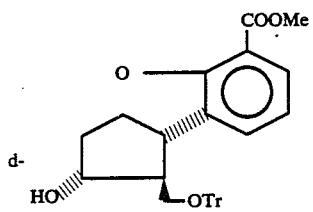

Anhydrous triethylamine (15.45 ml, 111 mmol) and trityl chloride (15.45 g, 55.4 mmol) were added under argon atmosphere to a solution of d-2α-hydroxy-1β-hydroxymethyl-3aβH,8bβH-2,3,3a,8b-tetrahydro-1H-5-cyclopenta[b]benzofurancarboxylic acid methyl ester (9.3 g, 36.9 mmol) in anhydrous THF (200 ml) and the reaction mixture was refluxed for 3 hrs. The solution was cooled, acidified to pH 1 with 6N hydrochloric acid (15 ml) and water (75 ml) was added. The mixture was extracted with ethyl acetate (75 ml×2). The combined ethyl acetate layers were washed with a saturated aqueous solution of sodium bicarbonate (50 ml) and with brine (50 ml), dried over anhydrous magnesium sulfate, and concentrated. The resulting residue was purified by column chromatography (silica gel, ethyl acetate/cyclohexane=1/10 to 1/2) to give d-2α-hydroxy-1β-trityloxymethyl-3aβH,8bβH-2,3,3a,8b-tetrahydro-1H-5-cyclopenta[b]benzofurancarboxylic acid methyl ester (15.3 g, 30.2 mmol, 81.9%). The product was assigned the structure by the following data.

Optical rotation: [α]$_D^{20}$= +94.13° (c=1.176, methanol).

IR (liquid film): 3600–3100, 3090, 3050, 3010, 2930, 1705, 1605, 1485, 1460, 1440, 1430, 1370, 1350, 1330, 1290, 1270, 1210, 1180, 1135, 1060, 1030, 1000, 970, 930, 895, 845, 750, 700 cm$^{-1}$.

NMR (400 MHz, CDCl$_3$, δ): 2.07–2.14 (2H, m); 2.16–2.23 (1H, m); 2.56 (1H, dt, J=6.8, 14.2 Hz); 3.26 (1H, dd, J=6.8, 9.0 Hz); 3.40–3.45 (1H, m); 3.88 (3H, s); 5.29 (1H, ddd, J=4.4, 6.8, 9.0 Hz); 6.83 (1H, t, J=7.3 Hz); 7.15 (1H, m); 7.24–7.34 (9H, m); 7.46 (6H, m); 7.73 (1H, m).

MASS (EI, m/e): 506(M+).

HR MASS: Calcd. (C$_{33}$H$_{30}$O$_5$, M+): 506.2112. Found (M+): 506.2103.

REFERENCE EXAMPLE 8 d-2α-Hydroxy-1β-trityloxymethyl-3aβH,8bβH-2,3,3a,8b-tetrahydro-1H-5-cyclopenta[b]benzofuranyl methyl ketone (8)

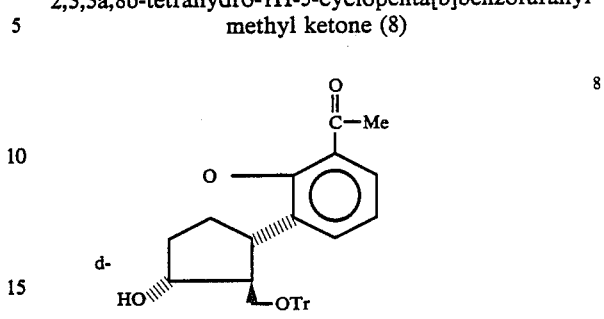

Sodium hydride (60% mineral oil dispersion, 4.5 g, 113 mmol) was washed with n-pentane (10 ml×3) and dried. To this was added under argon atmosphere anhydrous DMSO (100 ml) and the mixture was heated at 70° C. for one hour. After cooling to room temperature, to the mixture was added anhydrous THF (50 ml). To this was dropped under ice-cooling a solution of d-2α-hydroxy-1β-trityloxymethyl-3aβH,8bβH-2,3,3a,8b-tetrahydro-1H-5-cyclopenta[b]benzofurancarboxylic acid methyl ester (14.0 g, 27.7 mmol) in anhydrous THF (50 ml). After stirring for one hour, the mixture was concentrated by a rotary evaporator and then DMSO was distilled out in vacuo at 80° C. To the residue was added water (100 ml) and the mixture was acidified to pH 4 with 1N hydrochloric acid and the resulting mixture was extracted with chloroform (300 ml, 150 ml×2). The combined chloroform layers were washed with brine (100 ml), dried over anhydrous sodium sulfate, and concentrated to give a crude material of d-2α-hydroxy-1β-trityloxymethyl-3aβH,8bβH-2,3,3a,8b-tetrahydro-1H-5-cyclopenta[b]benzofuranyl methylsulfinylmethyl ketone.

Zinc powder (18.2 g, 278 mmol) was added to a mixture of 80 ml of ethanol and 80 ml of acetic acid. To this was dropped under ice-cooling a solution of the above material in ethanol (80 ml). The mixture was stirred for 2 hrs. at room temperature and then concentrated by a vacuum pump. To the residue were added ethyl acetate (100 ml) and sodium bicarbonate (30 g). The mixture was stirred for 10 min. and filtered. To the filtrate was added water (100 ml) and the mixture was partitioned between the organic layer and the aqueous layer. The aqueous layer was further extracted with ethyl acetate (150 ml×3). The combined ethyl acetate layers were washed with brine (50 ml), dried over anhydrous sodium sulfate, and concentrated to give an oily material. Column chromatography (silica gel, cyclohexane/ethyl acetate 10/1 to 3/1) of the material gave the desired product (7.8 g), which was recrystallized from ethyl acetate/cyclohexane (1/1) to give d-2α-hydroxy-1β-trityloxymethyl-3aβH,8bβH-2,3,3a,8b-tetrahydro-1H-5-cyclopenta[b]benzofuranyl methyl ketone (7.5 g, 15.3 mmol, 55.2%) as a white crystal. The product was assigned the structure by the following data.

Optical rotation: [α]$_D^{20}$= +96.03 (c=0.882, methanol).

M.p.: 76.5°–78.0° C.

IR (KBr): 3600–3200, 3090, 3070, 3040, 2930, 2855, 1740, 1660, 1600, 1490, 1465, 1445, 1410, 1365, 1335, 1285, 1250, 1230, 1195, 1155, 1090, 1075, 1025, 1005, 965, 940, 930, 910, 850, 835, 800, 770, 750, 715, 650, 635, 600, 580 cm$^{-1}$.

NMR (400 MHz, CDCl$_3$, δ): 2.03–2.10 (2H, m); 2.17–2.22 (1H, m); 2.56–2.63 (1H, m); 2.61 (3H, s); 3.27 (1H, dd, J=7.3, 9.8 Hz); 3.40–3.49 (2H, m); 4.10–4.12 (1H, m); 5.23 (1H, ddd, J=4.9, 7.3, 8.8 Hz); 6.85 (1H, t, J=7.5 Hz); 7.12–7.14 (1H, m); 7.23–7.35 (9H, m); 7.44–7.46 (6H, m); 7.68–7.71 (1H, m)

MASS (EI, m/e): 490(M+).

HR MASS: Calcd. (C$_{33}$H$_{30}$O$_4$, M+): 490.2108. Found (M+): 490.2126.

REFERENCE EXAMPLE 9 d-5-Acetoxy-2α-hydroxy-1β-trityloxymethyl-3aβH,8bβH-2,3,3a,8b-tetrahydro-1H-cyclopenta[b]benzofuran (9)

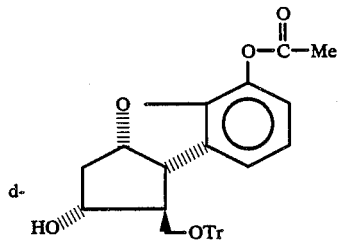

To a solution of d-2α-hydroxy-1β-trityloxymethyl-3aβH,8bβH-2,3,3a,8b-tetrahydro-1H-5-cyclopenta[b]benzofuranyl methyl ketone (7.5 g, 15.3 mmol) in methylene chloride (30 ml) was added sodium bicarbonate (6.4 g, 76.5 mmol). To the mixture was added m-chloroperbenzoic acid (8.3 g, 48.3 mmol) and the mixture was stirred for 10 min. under ice-cooling and then further stirred overnight at room temperature. To the resulting solution was added sodium bisulfite (15 g). The mixture was stirred for 30 min, and filtered and the filtrate was concentrated. To the residue was added ethyl acetate (100 ml) and sodium bicarbonate (15 g). The mixture was stirred for 30 min. and filtered. To the filtrate was added water (100 ml) and the mixture was acidified to pH 4 with 1N hydrochloric acid. The resulting mixture was partitioned between the organic layer and the aqueous layer. The aqueous layer was further extracted with ethyl acetate (150 ml, 50 ml×2). The combined ethyl acetate layers were washed with a saturated aqueous solution of sodium bicarbonate (100 ml), dried over anhydrous sodium sulfate, and concentrated to give an oily material. Column chromatography (silica gel, cyclohexane/ethyl acetate: 8/1 to 3/1) of the material gave d-5-acetoxy-2α-hydroxy-1β-tityloxymethyl-3aβH,8bβH-2,3,3a,8b-tetrahydro-1-H-cyclopenta[b]benzofuran (5.3 g, 10.4 mmol, 68.0%). The product was assigned the structure by the following data.

Optical rotation: [α]$_D^{20}$= +74.19° (c=0.868, methanol).

IR (liquid film): 3600–3200, 3090, 3050, 3020, 2970, 2930, 2860, 1760, 1730, 1615, 1600, 1485, 1460, 1445, 1365, 1260, 1245, 1215, 1180, 1150, 1070, 1045, 995, 955, 940, 910, 895, 845, 775, 760, 745, 700, 635 cm$^{-1}$.

NMR (400 Hz, CDCl$_3$, δ): 2.04–2.10 (1H, m); 2.26–2.28 (2H, m); 2.29 (1H, s); 2.41–2.48 (1H, m); 3.22 (1H, dd, J=7.3, 9.3 Hz); 3.37 (1H, J=5.4, 9.3 Hz); 3.49 (1H, dd, J=6.3, 8.3 Hz); 4.05–4.10 (1H, m); 5.19 (1H, ddd, J=4.4, 6.3, 8.3 Hz); 6.78–6.91 (3H, m); 7.24–7.34 (9H, m); 7.43–7.46 (6H, m).

MASS (EI, m/e): 506(M+).

HR MASS: Calcd. (C$_{33}$H$_{30}$O$_5$, M+): 506.2093. Found (M+): 506.2101.

REFERENCE EXAMPLE 10 d-2α-Hydroxy-1β-trityloxymethyl-3aβH,8bβH-2,3,3a,8b-tetrahydro-1H-5-cyclopenta[b]benzofuranyloxyacetic acid methyl ester (10)

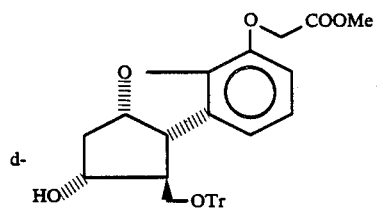

To a solution of d-5-acetoxy-2α-hydroxy-1β-trityloxymethyl-3aβH,8bβH-2,3,3a,8b-tetrahydro-1H-cyclopenta[b]benzofuran (6.2 g, 12.3 mmol) in methanol (50 ml) was dropped under ice-cooling a separately prepared 0.9N solution of potassium hydroxide in methanol. After 30 min., methanol was distilled off. Azeotropic distillation of the residue with benzene gave a dry residue, which was then dissolved in 50 ml of DMF. A solution of methyl bromoacetate (17.4 ml, 18.5 mmol) in DMF (20 ml) was dropped into the above solution and the mixture was stirred for 2 hrs. at room temperature. DMF was distilled out in vacuo. To the residue was added water (50 ml) and the mixture was extracted with ethyl acetate (50 ml×3). The combined ethyl acetate layers were washed with brine (50 ml), dried over anhydrous sodium sulfate, and concentrated to give an oily material. Column chromatography (silica gel, ethyl acetate/cyclohexane: 1/3) followed by recrystallization fom ethyl acetate/cyclohexane (1/1) gave d-2α-hydroxy-1β-trityloxymethyl-3aβH,8bβH-2,3,3a,8b-tetrahydro-1H-5-cyclopenta[b]benzofuranyloxyacetic acid methyl ester (4.9 g, 9.1 mmol, 74.3%) as a white crystal. The product was assigned the structure by the following data.

Optical rotation: [α]$_D^{20}$= +50.37° (c=1.074, methanol).

M.p.: 127.0°–128.0° C.

IR (KBr): 3600–3200, 3060, 3020, 2975, 2950, 2905, 2860, 1760, 1740, 1602, 1598, 1480, 1445, 1435, 1390, 1385, 1370, 1340, 1325, 1305, 1300, 1265, 1240, 1230, 1210, 1185, 1175, 1115, 1090, 1075, 1050, 1035, 1000, 975, 940, 915, 895, 890, 860, 845, 780, 765, 750, 710, 695 cm$^{-1}$.

NMR (400 MHz, CDCl$_3$, δ): 2.04–2.11 (1H, m); 2.21 (1H, d, J=4.4 Hz) 2.24–2.27 (1H, m); 3.23 (1H, dd, J=7.3, 9.3 Hz); 3.40–3.45 (2H, m); 3.78 (3H, s); 4.30–4.10 (1H, m); 4.71 (2H, s); 5.17 (1H, ddd, J=4.9, 7.3, 8.8 Hz); 6.67–6.76 (3H, m); 7.23–7.34 (9H, m); 7.42–7.51 (6H, m).

MASS (EI, m/e): 536(M+).

HR MASS: Calcd. (C$_{34}$H$_{32}$O$_6$, M+): 536.2199. Found (M+): 536.2201.

REFERENCE EXAMPLE 11 d-2α-Acetoxy-1β-hydroxymethyl-3aβH,8bβH-2,3,3a,8b-tetrahydro-1H-5-cyclopenta[b]benzofuranyloxyacetic acid methyl ester (11)

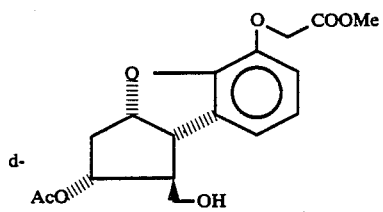

To a solution of d-2α-hydroxy-1β-trityloxymethyl-3aβH,8bβH-2,3,3a,8b-tetrahydro-1H-5-cyclopenta[b]benzofuranyloxyacetic acid methyl ester (4.6 g, 8.6 mmol) in pyridine (10.4 ml) was added under ice-cooling acetic anhydride (8.1 ml, 86 mmol) and the mixture was stirred for 3 hrs. at room temperature. To the solution were added methanol (20 ml) and a 5.3N hydrochloric acid solution in methanol (35 ml), separately prepared, under ice-cooling and then the mixture was stirred for 3 hrs. at room temperature. After being cooled to 0° C., the solution was neutralized to pH 7 with sodium bicarbonate (20 g). The resulting precipitate was filtered off and the filtrate was concentrated. To the residue was added water (15 ml) and the mixture was extracted with ethyl acetate (30 ml, 20 ml×3). The combined ethyl acetate layers were washed with brine (15 ml), dried over anhydrous sodium sulfate, and concentrated to give an oily material. Column chromatography (silica gel, ethyl acetate/cyclohexane: 1/9 to 2/1) followed by recrystallization from ethyl acetate/cyclohexane (2/1) afforded a prism of d-2α-acetoxy-1β-hydroxymethyl-3aβH,8bβH-2,3,3a,8b-tetrahydro-1H-5-cyclopenta[b]benzofuranyloxyacetic acid methyl ester (2.40 g, 7.1 mmol, 83.1%). The product was assigned the structure by the following data.

Optical rotation: $[\alpha]_D^{20} = +26.28°$ (c=1.286, methanol).

M.p.: 80.5°–81.0° C.

IR (KBr): 3550, 3010, 2990, 2955, 2920, 2910, 2820, 1750, 1735, 1615, 1585, 1495, 1465, 1440, 1380, 1360, 1310, 1295, 1255, 1225, 1195, 1185, 1125, 1105, 1075, 1060, 1045, 1020, 1005, 975, 955, 910, 885, 850, 835, 795, 770, 730, 695, 665, 640, 620, 605, 580, 535, 520 cm$^{-1}$.

NMR (400 MHz, CDCl$_3$, δ): 1.87 (3H, s); 2.10 (1H, t, J=5.9 Hz); 2.24–2.31 (2H, m); 2.57 (1H, m); 3.68–3.76 (3H, m); 3.79 (3H, s); 4.71 (1H, d, J=16.3 Hz); 4.74 (1H, J=16.3 Hz); 5.07 (9H, q, J=6.3 Hz); 5.27 (1H, ddd, J×3.9, 8.7, 10.7 Hz); 6.72–6.79 (2H, m); 6.87 (1H, d, J=7.3 Hz).

MASS (EI, m/e): 336(M+).

HR MASS: Calcd. (C$_{17}$H$_{20}$O$_7$, M+): 336.1209. Found (M+): 336.1225.

REFERENCE EXAMPLE 12

6,8-Dibromo-2-methyl-4aαH,4bβH,9aβH,10aβH-4,4a,4b,9a,10,10a-hexahydro-1,3-dioxyno[5',4':3,4]cyclopenta[b]benzofuran (12)

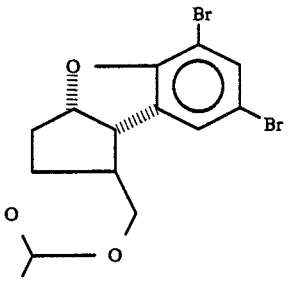

To a solution of 5,7-dibromo-2α-hydroxy-1β-hydroxymethyl-3aβH,8bβH-2,3,3a,8b-tetrahydro-1H-cyclopenta[b]benzofuran (180 mg) in THF (5 ml) was added acetal (2 ml) and 0.3 ml of a solution of p-toluenesulfonic acid (200 mg) in THF (10 ml). The mixture was stirred for 6 hrs. at 60° C. and 1.5 hrs. at 80° C. To the resulting mixture were added water (3 ml) and sodium bicarbonate (280 mg). The mixture was concentrated and the residue was extracted with ethyl acetate (30 ml, 20 ml×2). The combined ethyl acetate layers were washed with water and with brine, dried, and concentrated to give a crude material (200 mg), which was then recrystallized from ethyl acetate/n-hexane (8 ml/10 ml) to give 47 mg of a product. The reaction and post-treatments of the concentrated mother liquor (195 mg) under the same condition as described above gave a crude material (199 mg). Column chromatography (Lobar column, Merck, silica gel, cyclohexane/ethyl acetate: 2/1) of the crude material afforded 75 mg of a final product. The total amount of 6,8-dibromo-2-methyl-4aαH,4bβH,9aβH,10aβH-4,4a,4b,9a,10,10a-hexahydro-1,3-dioxyno[5',4':3,4]cyclopenta[b]benzofuran thus obtained was 122 mg (yield: 63%). The product was assigned the structure by the following data.

IR (KBr): 2850, 1600, 1575, 1160, 750, 730 cm$^{-1}$.

NMR (100 MHz, CDCl$_3$, δ): 1.36 (3H, d, J=5.0 Hz); 1.7–2.2 (2H, m); 2.77 (1H, m); 3.15–3.6(2H, m); 3.70 (1H, t, J=10.5 Hz); 4.40 (1H, dd, J=10.5, 4.0 Hz); 4.72 (1H, q, J=5.0 Hz); 5.24 (1H, m); 7.14 (1H, d, J=2.0 Hz); 7.47 (1H, d, J=2.0 Hz).

MASS (EI, m/e): 398, 390, 392 (M+).

REFERENCE EXAMPLE 13

6-Bromo-2-methyl-4aαH,4bβH,9aβH,10aβH-4,4a,4b,9a,10,10a-hexahydro-1,3-dioxyno[5',4':3,4]cyclopenta[b]benzofuranylaldehyde (13)

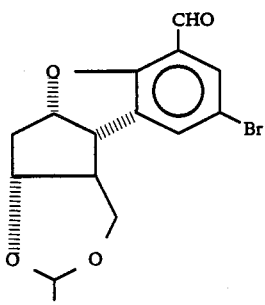

To a solution of 6,8-dibromo-2-methyl-4aαH,4bβH-,9aβH,10aβH-4,4a,4b,9a,10,10a-hexahydro-1,3-dioxyno[5',4':3,4]cyclopenta[b]benzofuran (12.7 g, 32.56 mmol) in anhydrous THF (200 ml) was added under argon atmosphere 21.6 ml of 1.81N cyclohexylmagnesium chloride and the mixture was heated for 3 hrs. at 40° C. The reaction mixture was then cooled to room temperature and anhydrous DMF (63 ml, 814 mmmol) was added. The mixture was stirred for 10 min., a saturated aqueous solution of ammonium chloride (150 ml) was added and the mixture was extracted with ethyl acetate (100 ml×3). The combined ethyl acetate layers were washed with water (300 ml) and with brine (300 ml), dried over anhydrous sodium sulfate (50 g), and concentrated to give a crude material. Recrystallization from chloroform/n-hexane (13/1) of the material gave a colorless and needle-like crystal (8.26 g). On the other hand, the filtrate was concentrated and the residue was purified by column chromatography (silica gel, ethyl acetate/cyclohexane: ½) to give 1.98 g of 6-bromo-2-methyl-4aαH,4bβH,9aβH,10aβH-4,4a,4b,9a,10,10a-hexahydro-1,3-dioxyno[5',4':3,4]cyclopenta[b]benzofuranylaldehyde. The total amount of the product was 10.24 g (30.12 mmol, 93%). The product was assigned the structure by the following data.

M.p.: 212°–213° C.

IR (KBr): 3070, 2980, 2945, 2870, 1669, 1600, 1442, 1381, 1360, 1339, 1313, 1259, 1222, 1203, 1186, 1167, 1143, 1124, 1103, 1065, 1042, 1021, 1003, 989, 960, 928, 882, 865, 825, 750, 724, 702, 675, 642, 601 cm$^{-1}$.

NMR (100 MHz, CDCl$_3$, δ): 1.37 (3H, d, J=5.06 Hz); 1.60–2.25 (2H, m); 2.65–3.57 (3H, m); 3.73 (1H, t, J=10.56 Hz); 4.41 (1H, dd, J=10.56, 4.39 Hz); 4.73 (1H, q, J=5.06 Hz); 5.20–5.42 (1H, m); 7.32–7.41 (1H, m); 7.70–7.80 (1H, m); 10.11 (1H, s).

MASS (EI, m/e): 338 (M+).

REFERENCE EXAMPLE 14

1,1-Dibromo-2-[6-bromo-2-methyl-4aαH,4bβH,9aβH,-10aβH-4,4a,4b,9a,10,10a-hexahydro-1,3-dioxyno[5',4':3,4]cyclopenta[b]benzofuranyl]ethylene (14)

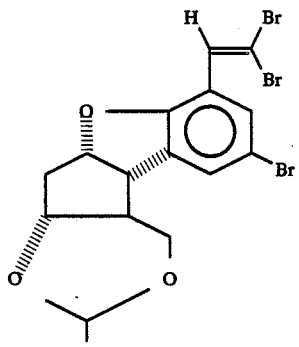

14

Under argon atmosphere, to a solution of triphenylphosphine (16.85 g, 64.24 mmol) in dichloromethane (60 ml) was added carbon tetrabromide (10.65 g, 32.12 mmol), and a solution of 6-bromo-2-methyl-4aαH,4bβH,9aβH,10aβH-4,4a,4b,9a,10,10a-hexahydro-1,3-dioxyno[5',4':3,4]cyclopenta[b]benzofuranylaldehyde (5.46 g, 16.06 mmol) in 50 ml of dichloromethane was added at −78° C. The mixture was stirred for 5 min., water (30 ml) was added and the resulting mixture was extracted with dichloromethane (30 ml×3). The combined organic layers were washed with water (150 ml) and with brine (150 ml), dried over anhydrous sodium sulfate (30 g), and concentrated to give a solid material (31.79 g). Column chromatography (silica gel, dichloromethane) of the material gave 1,1-dibromo-2-[6-bromo-2-methyl-4aαH,4bβH,9aβH,10aβH-4,4a,4b-,9a,10,10a-hexahydro-1,3-dioxyno[5',4':3,4]cyclopenta[b]benzofuranyl]ethylene (4.3156 g, 8.95 mmol, 56%), which was then recrystallized from ethyl acetate/n-hexane (6/15) to afford a colorless and needle-like crystal. The product was assigned the structure by the following data.

M.p.: 128°–130° C.

IR (KBr): 2950, 2910, 2890, 2850, 1600, 1574, 1442, 1422, 1382, 1348, 1304, 1243, 1230, 1203, 1180, 1155, 1135, 1110, 1070, 1041, 1002, 998, 960, 880, 868, 843, 825, 743, 675, 658, 635, 602 cm$^{-1}$.

NMR (100 MHz, CDCl$_3$, δ): 1.36 (3H, d, J=5.06 Hz); 1.60–2.18 (2H, m); 2.55–2.91 (1H, m); 3.01–3.51 (2H, m); 3.70 (1H, t, J=10.56 Hz); 4.34 (1H, dd, J=10.56, 4.62 Hz); 4.71 (1H, q, J=5.06 Hz); 5.02–5.32 (1H, m); 7.16 (1H, d, J=1.98 Hz); 7.43 (1H, s); 7.76 (1H, d, J=1.98 Hz).

MASS (EI, m/e): 492 (M+).

REFERENCE EXAMPLE 15

2-Methyl-4aαH,4bβH,9aβH,10aβH-4,4a,4b,9a,10,10a-hexahydro-1,3-dioxyno[5',4':3,4]cyclopenta[b]benzofuranylacetylene (15)

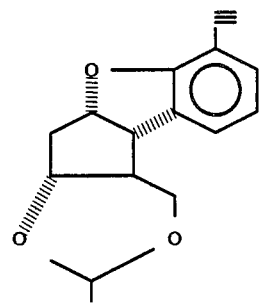

15

Under argon atmosphere, 1,1-dibromo-2-[6-bromo-2-methyl-4aαH,4bβH,9aβH,10aβH-4,4a,4b,9a,10,10a-hexahydro-1,3-dioxyno[5',4':3,4]cyclopenta[b]benzofuranyl]ethylene (4.41 g, 9.15 mmol) was dissolved in anhydrous THF (100 ml) and 1.58N n-butyl lithium (18.5 ml, 29.3 mmol) was added at −110° C. The reaction mixture was stirred for 5 min., a saturated aqueous solution of ammonium chloride was added (50 ml) and the mixture was extracted with ethyl acetate (40 ml×3). The combined ethyl acetate layers were washed with water (100 ml) and with brine (100 ml), dried over anhydrous sodium sulfate (25 g), and concentrated to give a crude crystal (3.109 g). Column chromatography (silica gel, ethyl acetate/cyclohexane: 1/3) of the crude crystal gave 2-methyl-4aαH,4bβH,9aβH,10aβH-4,4a,4b-,9a,10,10a-hexahydro-1,3-dioxyno[5',4':3,4]cyclopenta[b]benzofuranylacetylene (1.975 g, 8.03 mmol, 88%), which was then recrystallized from ethyl acetate/cyclohexane (3/1) to give a colorless and needle-like crystal. The product was assigned the structure by the following data.

M.p.: 148°–148.5° C.

IR (KBr): 3260, 2990, 2950, 2875, 2845, 2800, 2100, 1588, 1442, 1405, 1379, 1345, 1330, 1303, 1255, 1230, 1210, 1199, 1150, 1124, 1108, 1081, 1068, 1057, 1032, 1008, 995, 961, 928, 905, 881, 862, 853, 830, 784, 762, 740, 701, 675, 634, 604 cm$^{-1}$.

NMR (100 MHz, CDCl$_3$, δ): 1.36 (3H, d, J=5.38 Hz); 1.82–1.91 (1H, m); 2.02–2.10 (1H, m); 2.74–2.82 (1H, m); 3.18 (1H, t, J=8.3 Hz); 3.30 (1H, s); 3.40–3.46 (1H, m); 3.73 (1H, q, J=5.38 Hz); 5.17–5.31 (1H, m); 6.82 (1H, t, J=7.33 Hz); 7.08 (1H, d, J=7.33 Hz); 7.28 (1H, d, J=7.33 Hz).

MASS (EI, m/e): 256 (M+).

REFERENCE EXAMPLE 16

2-Methyl-4aαH,4bβH,9aβH,10aβH-4,4a,4b,9a,10,10a-hexahydro-1,3-dioxyno[5',4':3,4]cyclopenta[b]benzofuranylpropynoic acid methyl ester (16)

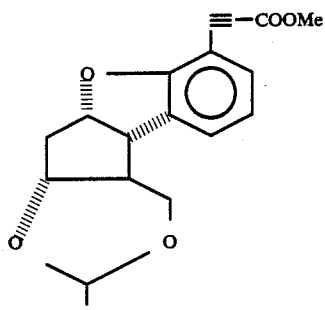

Under argon atmosphere 2-methyl-4aαH,4bβH,9aβH,10aβH-4,4a,4b,9a,10,10a-hexahydro-1,3-dioxyno[5',4':3,4]cyclopenta[b]benzofuranylacetylene (1.6313 g, 6.37 mmol) was dissolved in anhydrous THF (100 ml). To this, 1.58N n-butyl lithium (6.05 ml, 9.56 mmol) was added at −78° C. and carbon dioxide was bubbled through the reaction mixture for 5 minutes. To this were added a saturated aqueous solution of ammonium chloride (10 ml) and 1N hydrochloric acid (15 ml). The resulting solution was extracted with ethyl acetate (20 ml×4). The combined ethyl acetate layers were washed with water (100 ml) and with brine (100 ml), dried over anhydrous sodium sulfate (25 g), and concentrated. The residue was dissolved in 20 ml of methanol and the mixture was treated with diazomethane under ice-cooling. The mixture was concentrated to give a crude crystal (2.576 g), which was then purified by column chromatography (silica gel, ethyl acetate/cyclohexane: 1/2) to give 2-methyl-4aαH,4bβH,9aβH,10aβH-4,4a,4b,9a,10,10a-hexahydro-1,3-dioxyno[5',4':3,4]cyclopenta[b]benzofuranylpropynoic acid methyl ester (1.9504 g, 6.21 mmol, 98%). Recrystallization from ethyl acetate/cyclohexane (10/3) of the material gave a colorless and needle-like crystal. The product was assigned the structure by the following data.

M.p.: 150°–151° C.

IR (KBr): 3001, 2950, 2860, 2800, 2200, 1701, 1590, 1464, 1440, 1410, 1380, 1352, 1325, 1310, 1284, 1258, 1210, 1148, 1124, 1105, 1074, 1058, 1035, 1005, 963, 945, 883, 864, 835, 812, 790, 761, 742, 709, 663, 642, 615 cm$^{-1}$.

NMR (100 MHz, CDCl$_3$, δ): 1.36 (3H, d, J=4.89 Hz); 1.80–1.89 (1H, m); 2.02–2.09 (1H, m); 2.74–2.82 (1H, m); 3.19 (1H, t, J=8.3 Hz); 3.40–3.47 (1H, m); 3.73 (1H, t, J=10.74 Hz); 3.83 (3H, s); 4.39 (1H, dd, J=10.74, 4.39 Hz); 4.73 (1H, q, J=4.89 Hz); 5.22–5.28 (1H, m); 6.84 (1H, t, J=7.33 Hz); 7.17 (1H, d, J=7.33 Hz); 7.33 (1H, d, J=7.33 Hz).

MASS (EI, m/e): 314 (M+).

REFERENCE EXAMPLE 17

2α-Hydroxy-1β-hydroxymethyl-3aβH,8bβH-2,3,3a,8b-tetrahydro-1H-5-cyclopenta[b]benzofuranylpropynoic acid methyl ester (17)

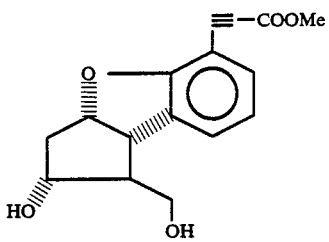

To a solution of 2-methyl-4aαH,4bβH,9aβH,10aβH-4,4a,4b,9a,10,10a-hexahydro-1,3-dioxyno[5',4':3,4]cyclopenta[b]benzofuranylpropynoic acid methyl ester (1.9626 g, 6.25 mmol) in DME (20 ml) was added 1N hydrochloric acid (9 ml) and the mixture was stirred for 9.5 hrs. at room temperature. To the solution was added a saturated aqueous solution of sodium bicarbonate (30 ml) and the mixture was extracted with ethyl acetate (30 ml×4). The combined ethyl acetate layers were washed with water (100 ml) and with brine (100 ml), dried over anhydrous sodium sulfate (25 g), and concentrated to give quantitatively a single product, 2α-hydroxy-1β-hydroxymethyl-3aβH,8bβH-2,3,3a,8b-tetrahydro-1H-5-cyclopenta[b]benzofuranylpropynoic acid methyl ester (1.7988 g, 6.25 mmol), which was then recrystallized from ethyl acetate/cyclohexane (11/1) to give a colorless and needle-like crystal. The product was assigned the structure by the following data.

M.p.: 128°–129° C.

IR (KBr): 3230, 2940, 2910, 2875, 2200, 1702, 1585, 1464, 1434, 1365, 1345, 1330, 1320, 1290, 1255, 1200, 1155, 1101, 1061, 1028, 1009, 943, 894, 866, 847, 820, 783, 739, 664, 630, 604 cm$^{-1}$.

NMR (100 MHz, CDCl$_3$, δ): 1.78 (1H, broad, s); 2.05–2.01 (1H, broad, s); 2.08–2.20 (2H, m); 2.60–2.68 (1H, m); 3.45–3.51 (1H, m); 3.81–3.86 (1H, m); 3.83 (3H, s); 3.91–3.97 (1H, m); 4.12–4.18 (1H, m); 5.23–5.30 (1H, m); 6.84 (1H, t, J=7.33 Hz); 7.26 (1H, d, J=7.33 Hz); 7.32 (1H, d, J=7.33 Hz).

MASS (EI, m/e): 288 (M+).

REFERENCE EXAMPLE 18

2α-Acetoxy-1β-hydroxymethyl-3aβH,8bβH-2,3,3a,8b-tetrahydro-1H-5-cyclopenta[b]benzofuranylpropynoic acid methyl ester (18)

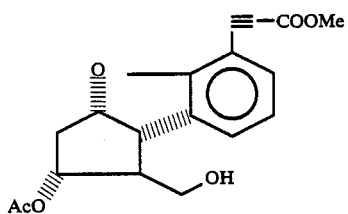

Under argon atmosphere, 2α-hydroxy-1β-hydroxymethyl-3aβH,8bβH-2,3,3a,8b-tetrahydro-1H-5-cyclopenta[b]benzofuranylpropynoic acid methyl ester (1.7682 g, 6.14 mmol) was dissolved in THF (25 ml), and to this were added triethylamine (3 ml, 21.5 mmol)

and trityl chloride (4.15 g, 15.3 mmol). The reaction mixture was refluxed for 4 hrs., cooled to room temperature, pyridine (7.5 ml, 92.1 mmol) and acetic anhydride (5.8 ml, 61.4 mmol) were added, and the mixture was stirred overnight. The resulting solution was cooled in a ice-bath. To this was added 5.24N hydrochloric acid solution in methanol (22 ml) and the mixture was stirred for 2 hrs. and 10 min. at room temperature. To the resulting solution were added sodium bicarbonate (10 g) and water (40 ml) and the mixture was extracted with ethyl acetate (40 ml×3). The combined ethyl acetate layers were washed with water (100 ml) and with brine (100 ml), dried over anhydrous sodium sulfate (25 g), and concentrated to give an oily material (7.51 g), which was then purified by column chromatography (silica gel, ethyl acetate/cyclohexane: 2/1) to give 2α-acetoxy-1β-hydroxymethyl-3aβH,8bβH-2,3,3a,8b-tetrahydro-1H-5-cyclopenta[b]benzofuranylpropynoic acid methyl ester (1.7832 g, 5.40 mmol, 88%). Recrystallization of the product from ethyl acetate/cyclohexane (1/1) gave a colorless and needle-like crystal. The product was assigned by the following data.

M.p.: 82°-83° C.

IR (KBr): 3430, 2998, 2951, 2910, 2875, 2200, 1699, 1590, 1463, 1439, 1365, 1326, 1281, 1244, 1203, 1155, 1124, 1100, 1054, 1019, 966, 958, 943, 915, 901, 875, 850, 825, 789, 770, 744, 667, 644, 632, 603 cm$^{-1}$.

NMR (400 MHz, CDCl$_3$, δ): 1.82 (3H, s); 2.02–2.06 (1H, m); 2.25–2.36 (1H, m); 2.52–2.58 (1H, m); 3.66–3.78 (3H, m); 3.83 (3H, s); 5.04–5.09 (1H, m); 5.32–5.38 (1H, m); 6.83 (1H, t, J=7.33 Hz); 7.26 (1H, d, J=7.33 Hz); 7.32 (1H, d, J=7.33 Hz).

MASS (EI, m/e): 330 (M+).

REFERENCE EXAMPLE 19

Dimethyl 3-methyl-2-oxo-butylphosphonate (19)

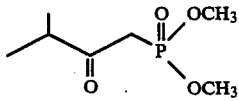

Dimethyl methylphosphonate (8.8 g, 0.071 mol) was dissolved in anhydrous THF (100 ml) under argon atmosphere. To the solution stirred at −78° C. was added dropwise n-butyl lithium (1.58N, 45 ml, 0.071 mol) over 30 minutes and then a solution of methyl isobutyrate (2.9 g, 0.0284 mol) in anhydrous THF (5 ml) was added dropwise over 30 minutes. The reaction mixture was warmed to room temperature. After 30 minutes, acetic acid (4.3 ml) and water (10 ml) were added with ice cooling. After concentration, water (20 ml) was added to the residue and the mixture was extracted with ethyl acetate (50 ml×2). The ethyl acetate layers were washed with water (20 ml×1) and with brine (20 ml×1), dried over anhydrous sodium sulfate, and concentrated. Distillation of the residue gave dimethyl 3-methyl-2-oxo-butylphosphonate (4.8 g, 0.025 mol, yield 88%, b.p.=82°-84° C./0.31 mmHg). The structure was identified by the following data.

IR (liquid film): 3450, 2950, 2870, 1700, 1460, 1380, 1325, 1250, 1180, 1150, 1030, 870, 830, 800, 730, 680 cm$^{-1}$.

NMR (90 MHz, CDCl$_3$, δ): 1.13 (6H, d, J=6.8 Hz); 2.6–3.0 (1H, m); 3.15 (2H, d, J=22.4 Hz); 3.79 (6H, d, J=11.2 Hz).

MASS (EI, m/e: 194 (M+).

REFERENCE EXAMPLE 20

Dimethyl 3,3-dimethyl-2-oxo-butylphosphonate (20)

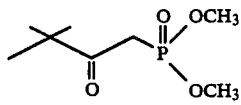

Dimethyl methylphosphonate (13.6 g, 0.11 mol) was dissolved in anhydrous THF (100 ml) under argon atmosphere. To the solution stirred at −78° C. was added dropwise n-butyl lithium (1.61N, 68.3 ml, 0.11 mol) over 30 minutes, and then a solution of commercially available methyl pivalate (5.0 g, 0.043 mol) in anhydrous THF (10 ml) was also added dropwise over 30 minutes. The reaction mixture was warmed to room temperature. Under ice cooling, acetic acid (7 ml) and water (10 ml) were added. After concentrating, water (20 ml) was added to the resulting residue. The mixture was extracted with ethyl acetate (50 ml×2), and the ethyl acetate layers were washed with water (20 ml×1) and with brine (20 ml×1), dried over anhydrous sodium sulfate, concentrated. Distillation of the residue gave dimethyl 3,3-dimethyl-2-oxo-butylphosphonate as a colorless clear oil (6.53 g, 0.031 mol, 72.6%, b.p.=90°-93° C./0.35 mmHg). The structure was identified by the following data.

IR (liquid film): 3470, 2960, 2875, 1700, 1470, 1390, 1360, 1260, 1180, 1040, 940, 870, 840, 800, 775, 720, 635 cm$^{-1}$.

NMR (90 MHz, CDCl$_3$, δ): 1.18 (9H, s); 3.18 (2H, d, J=21.5 Hz); 3.8 (6H, d, J=11.2 Hz).

MASS (EI, m/e): 208 (M+).

REFERENCE EXAMPLE 21

2,2-Dimethyl-butanoic acid methyl ester (21)

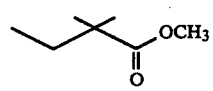

Anhydrous diisopropylamine (11.5 g, 0.114 mol) was dissolved in anhydrous THF (50 ml) under argon atmosphere. To the mixture stirred at −20° C. was added dropwise n-butyl lithium (1.62N, 70 ml, 0.114 mol) over 30 minutes, then a solution of isobutyric acid (5.0 g, 0.057 mol) in anhydrous THF (10 ml) was added dropwise over 30 minutes, and further a solution of ethyl bromide (6.2 g, 0.057 mol) in anhydrous THF (10 ml) was also added dropwise over one hour. Aqueous hydrogen chloride (6N) was added to adjust pH to 2 near 0° C. The reaction mixture was extracted with ethyl acetate (50 ml×2). The ethyl acetate layers were washed with water (20 ml×1) and with brine (20 ml×1), dried over anhydrous sodium sulfate and concentrated. The residue was dissolved in ether (30 ml) and an excess of an ethereal solution of diazomethane was added. Distillation under an atmospheric pressure gave 2,2-dimethyl-butanoic acid methyl ester (5.3 g, 0.046 mol, yield 80.2%, b.p.=115°-120° C.) as a colorless clear liquid. The structure was identified by the following data.

IR (liquid film): 2970, 1725, 1445, 1430, 1380, 1360, 1310, 1240, 1180, 1150, 1060, 1000, 980, 940, 915, 850, 795, 770, 750 cm$^{-1}$.

NMR (90 MHz, CDCl₃, δ): 0.83 (3H, t, J=7.4 Hz); 1.16 (6H, s); 1.4-1.8 (2H, m); 3.66 (3H, s).
MASS (EI, m/e): 130 (M+).

REFERENCE EXAMPLE 22

Dimethyl 3,3-dimethyl-2-oxo-pentylphosphonate (22)

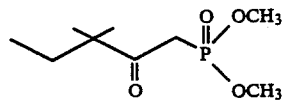

Dimethyl methylphosphonate (9.3 g, 0.075 mol) was dissolved in anhydrous THF (80 ml) under argon atmosphere. To the solution stirred at −78° C. was added dropwise n-butyl lithium (1.61N, 47 ml, 0.075 mol) over 30 minutes, and then a solution of 2,2-dimethylbutanoic acid methyl ester (3.9 g, 0.03 mol) in anhydrous THF (10 ml) was also added dropwise over 30 minutes. The reaction mixture was warmed to room temperature and stirred for 30 minutes. Under ice cooling, acetic acid (4.5 ml) and water (10 ml) were added to the mixture. After concentration, water (20 ml) was added to the residue, and the mixture was then extracted with ethyl acetate (50 ml×2). The ethyl acetate layers were washed with water (20 ml×1) and with brine (20 ml×1), dried over anhydrous sodium sulfate, and concentrated. Distillation of the residue gave dimethyl 3,3-dimethyl-2-oxo-pentylphosphonate (3.36 g, 0.015 mol, yield: 50%, b.p.=115-117/0.5 mmHg). The structure was identified by the following data.

IR (liquid film): 2950, 2870, 1690, 1450, 1380, 1360, 1310, 1250, 1175, 1030, 910, 860, 830, 800, 710 cm⁻¹.
NMR (90 MHz, CDCl₃, δ): 0.82 (3H, t, J=7.5 Hz); 1.13 (6H, s); 2.4-2.7 (2H, m); 3.14 (2H, d, J=21.5 Hz); 3.80 (6H, d, J=11.2 Hz).
MASS (CI, m/e): 223 (M++1).

REFERENCE EXAMPLE 23

Ethyl 2,2-dimethylpentanoate (23)

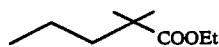

Under argon atmosphere, anhydrous THF (50 ml) and anhydrous diisopropylamine (8.8 mmol) were cooled with ice bath. After 10 minutes, n-butyl lithium (1.42N, 44.4 ml, 63 mmol) was added and the mixture was stirred for 30 minutes. Further, ethyl isobutyrate (7 ml, 52 mmol) dissolved in 15 ml anhydrous THF was added and the resulting mixture was stirred for 30 minutes. Then, HMPA (hexamethylphosphoric triamide: 3.3 ml, 20 mmol) was added to the reaction mixture and the mixture was stirred for 10 minutes. Propyl iodide (6.1 ml, 63 mmol) was also added and the mixture was stirred at room temperature for 30 minutes. Aqueous hydrogen chloride (6N) was added to the reaction mixture to adjust the pH to 7. After adding 100 ml of water, the mixture was extracted with ether (150 ml×3). The organic layers were washed with water (100 ml) and brine and dried over anhydrous sodium sulfate. After removal of ether and THF by distillation with Widmer column, the residue was distilled under reduced pressure to afford ethyl 2,2-dimethylpentanoate (3.81 g, 24.1 mmol, yield: 46%, b.p.=53° C./15 mmHg) as a colorless oil. The structure was identified by the following data.

IR (liquid film): 2975, 2950, 2890, 2745, 1730, 1480, 1460, 1390, 1370, 1330, 1300, 1280, 1260, 1230, 1180, 1150, 1120, 1100, 1070, 1030, 970, 950, 930, 890, 860, 780, 760, 750 cm⁻¹.
NMR (90 MHz, CDCl₃, δ): 0.81-0.97 (3H, m); 1.11-1.58 (13H, m); 4.19 (2H, q, J=7.1 Hz).
MASS (CI, m/e): 159 (M++1).

REFERENCE EXAMPLE 24

Dimethyl 3,3-dimethyl-2-oxo-hexylphosphonate (24)

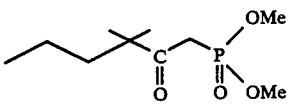

Under argon atmosphere, anhydrous THF (120 ml) and dimethyl methylphosphonate (6.5 ml, 60.3 mmol) were cooled to −78° C. After 20 minutes n-butyl lithium (1.62N, 35.7 ml, 57.8 mmol) was added and the mixture was stirred for 30 minutes. Then, ethyl 2,2-dimethylpentanoate (3.81 g, 24.1 mmol) dissolved in 7 ml anhydrous THF was added, and the reaction mixture was stirred at −78° C. for 30 minutes and then at room temperature for 30 minutes. After acidification with acetic acid, THF was distilled off and the residue was extracted with ethyl acetate (150 ml×3). The combined organic layers were washed with water (100 ml) and with brine (100 ml), dried over anhydrous sodium sulfate, and concentrated to give a colorless oily product. Vacuum distillation of the product gave dimethyl 3,3-dimethyl-2-oxo-heptylphosphonate (4.61 g, 19.5 mmol, 81.1%, b.p.: 127°-130° C./0.7 mmHg). The structure was identified by the following data.

IR (liquid film): 3475, 2960, 2940, 2880, 1720, 1700, 1480, 1460, 1390, 1370, 1320, 1260, 1180, 1030, 990, 960, 860, 840, 810, 740, 720 cm⁻¹.
NMR (90 MHz, CDCl₃, δ): 0.60-0.80 (3H, m); 0.85-1.45 (10H, m); 2.96 (2H, d, J=21.3 Hz); 3.64 (6H, d, J=11.0 Hz).
MASS (CI, m/e): 237 (M++1).

REFERENCE EXAMPLE 25

2,2-Dimethyl-hexanoic acid methyl ester (25)

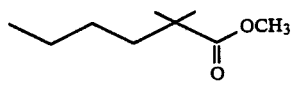

Anhydrous diisopropylamine (14.8 g, 0.146 mol) was dissolved in anhydrous THF (90 ml) under argon atmosphere. To the mixture stirred at −50° C. was added dropwise n-butyl lithium (1.62N, 90 ml, 0.146 mol) over a period of 30 minutes, and then a solution of isobutyric acid (6.4 g, 0.073 mol) in anhydrous THF (10 ml) was added over a period of 30 minutes. After the mixture was warmed to −5° C., n-butyl bromide (15.0 g, 0.11 mol) dissolved in 10 ml anhydrous THF was added dropwise. After 30 minutes, the mixture was acidified to pH2 with 6N aqueous hydrogen chloride. The mixture was extracted with ethyl acetate (60 ml33 2). The ethyl acetate layers were washed with water (30 ml×1) and with brine (20 ml×1), dried over anhydrous sodium sulfate, and concentrated. The residue was dissolved in 50 ml ether, and treated with an excess of ethereal solution of diazomethane. After concentration, distillation of the residue gave 2,2-dimethyl-hexanoic acid methyl ester (8.2 g, 0.052 mol, 71%, b.p.=69°-70° C./25 mmHg) as a colorless clear liquid. The structure of this product was confirmed by the following data.

IR (liquid film): 2940, 2855, 1720, 1460, 1425, 1380, 1360, 1315, 1265, 1200, 1140, 1090, 1070, 980, 940, 910, 860, 800, 760, 725 cm$^{-1}$.

NMR (90 MHz, CDCl$_3$, δ): 0.7-1.0 (3H, m); 1.16 (6H, s); 1.0-1.7 (6H, m); 3.66 (3H, s).

MASS (CI, m/e): 159 (M$^+$+1).

REFERENCE EXAMPLE 26

Dimethyl 3,3-dimethyl-2-oxo-heptylphosphonate (26)

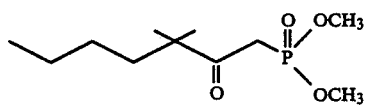

Dimethyl methylphosphonate (9.92 g, 0.08 mol) was dissolved in 60 ml anhydrous THF under argon atmosphere. To the mixture stirred at −78° C. was added drowise n-butyl lithium 1.62N, 49.5 ml, 0.08 mol) over a period of 30 minutes, and then a solution of 2,2-dimethylhexanoic acid methyl ester (5.0 g, 0.032 mol) in 10 ml anhydrous THF was added over a period of 30 minutes. The reaction mixture was warmed to room temperature. Acetic acid (5 ml) and water (10 ml) were added to the reaction mixture cooled with ice bath. After concentration, 20 ml water was added to the residue and the mixture was extracted with ethyl acetate (50 ml×2). The ethyl acetate layers were washed with water (20 ml×1) and with brine (20 ml×1), dried over anhydrous sodium sulfate, and concentrated. Distillation of the residue gave dimethyl 3,3-dimethyl-2-oxoheptylphosphonate (4.74 g, 0.019 mol, yield 59.3%, b.p.=108°-111° C./0.2 mmHg) as a colorless clear oil. The structure of this product was confirmed by the following data.

IR (liquid film): 3380, 2950, 2860, 1700, 1460, 1380, 1365, 1320, 1250, 1180, 1030, 940, 915, 865, 840, 800, 720 cm$^{-1}$.

NMR (90 MHz, CDCl$_3$, δ): 0.89 (3H, t, J=6.4 Hz); 1.14 (6H, s); 1.0-1.7 (6H, m); 3.15 (2H, d, J=21.5 Hz); 3.8 (6H, d, J=11.0 Hz).

MASS (EI, m/e): 250 (M$^+$).

REFERENCE EXAMPLE 27

Methyl 2,2-dimethyl-heptanoate (27)

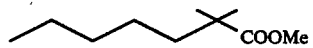

Anhydrous THF (200 ml) and anhydrous diisopropylamine (23.8 ml, 0.17 mol) were cooled with ice bath under argon atmosphere. After 10 minutes, n-butyl lithium (1.44N, 120.7 ml, 0.17 mol) was added and the mixture was stirred for 20 minutes. Then, isobutyric acid (7.37 ml, 0.079 mol) was added and the reaction mixture was stirred for 20 minutes. To the reaction mixture, was added pentyl bromide (10.8 ml, 0.087 mol). After stirring the mixture for 30 minutes, saturated aqueous solution of ammonium chloride (150 ml) was added. Further, 6N aqueous hydrogen chloride (30 ml) was added and the mixture was extracted with ether (150 ml×3). The combined organic layers were washed with 500 ml water and with 500 ml brine, dried over anhydrous sodium sulfate (40 g), and concentrated. A solution of the residue in ethyl acetate (10 ml) was cooled with ice bath, treated with diazomethane and concentrated to give 9.29 g of colorless oily product. Distillation of the product afforded methyl 2,2-dimethylheptanoate (5.9828 g, 45%, b.p.=60° C./2.5 mmHg) as a colorless oil. The structure of this product was confirmed by the following data.

IR (liquid film): 2950, 2860, 1724, 1452, 1382, 1361, 1319, 1283, 1259, 1188, 1142, 1100, 1079, 1042, 1014, 987, 942, 930, 894, 865, 853, 832, 800, 769, 722 cm$^{-1}$.

NMR (100 MHz, CDCl$_3$, δ): 0.69-0.98 (3H, m); 1.16 (6H, s); 1.01-1.60 (8H, m); 3.65 (3H, s).

MASS (CI, m/e): 173 (M$^+$+1).

REFERENCE EXAMPLE 28

Dimethyl 3,3-dimethyl-2-oxo-octylphosphonate (28)

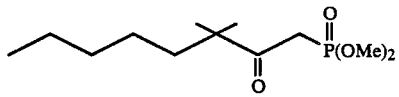

Anhydrous THF (100 ml) and dimethyl methylphosphonate (6.4 ml, 59.0 mmol) were cooled to −78° C. under argon atmosphere. After 20 minutes, n-butyl lithium (1.44N, 41.0 ml, 59.0 mmol) was added and the mixture was stirred for 20 minutes. Methyl 2,2-dimethyl-heptanoate (4.0145 g, 23.6 mmol) was then added. The reaction mixture was stirred at −78° C. for 15 minutes and then at room temperature for further 25 minutes. After adding 100 ml of saturated aqueous ammonium chloride solution, the mixture was extracted with ethyl acetate (80 ml×3). The combined organic layers were washed with 250 ml brine, dried over anhydrous sodium sulfate (40 g), and concentrated to give 5.70 g of colorless oily product. Purification of the product by silica gel column chromatography (ethyl acetate) afforded of dimethyl 3,3-dimethyl-2-oxo-octylphosphonate (2.4856 g, 9.42 mmol, 40%). The structure of this product was confirmed by the following data.

IR (liquid film): 3455, 2950, 2860, 1702, 1442, 1384, 1364, 1323, 1248, 1182, 1023, 928, 866, 839, 803, 711 cm$^{-1}$.

NMR (100 MHz, CDCl$_3$, δ): 0.70-0.96 (3H, m); 0.98-1.61 (8H, m); 1.13 (6H, s); 3.12 (2H, d, J=21.34 Hz); 3.77 (6H, d, J=11.21 Hz).

MASS (CI, m/e): 265 (M$^+$+1).

REFERENCE EXAMPLE 29

2,2-Dimethyl-octanoic acid methyl ester (29)

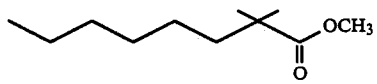

Anhydrous diisopropylamine (19.2 g, 0.19 mol) was dissolved in 150 ml anhydrous THF. To the mixture stirred at −20° C. under argon atmosphere was added dropwise n-butyl lithium (1.61N, 132 ml, 0.19 mol). After stirring the mixture for 30 minutes, methyl octanoate (10.0 g, 0.063 mol) was then added dropwise and the mixture was stirred for 30 minutes. Further, HMPA (10.3 g, 0.057 mol) and methyl iodide (27.0 g, 0.19 mol) were added to the reaction mixture and stirring was continued at −20° C. for additional 2 hours and then at room temperature for an hour. The reaction mixture was cooled with ice bath, and adjusted to pH7 with 6N aqueous hydrogen chloride. The aqueous layer was separated from the organic layer and extracted with ether (30 ml×2). The combined organic layers were washed with water (30 ml×2) and with brine (30 ml×2), dried over anhydrous sodium sulfate, and concentrated. Distillation of the residue gave 6.93 g of a mixture of methyl 2,2-dimethyloctanoate (55%) and methyl 2-methyloctanoate (45%). The mixture was methylated again by the following reaction.

Anhydrous diisopropylamine (8.1 g, 0.08 mol) was dissolved in 80 ml anhydrous THF under argon atmosphere. To the mixture stirred at −20° C. was added dropwise n-butyl lithium (1.44N, 55.6 ml, 0.08 mol). After stirring the mixture for 30 minutes, the mixture of esters (6.93 g) synthesized above was added dropwise and the reaction mixture was further stirred for 30 minutes. To the reaction mixture were added HMPA (4.3 g, 0.024 mol) and methyl iodide (12.7 g, 0.09 mol). After being stirred for one hour the mixture was allowed to warm to room temperature. To the reaction mixture cooled with ice bath, 6N aqueous hydrogen chloride was added to adjust the pH to 7. The aqueous layer was separated from the organic layer and extracted with ether (30 ml×1). The combined organic layers were washed with water (20 ml×1) and with brine (20 ml×1), dried over anhydrous sodium sulfate, and concentrated. Distillation of the residue gave methyl 2,2-dimethyloctanoate (4.54 g, 0.024 mol, 39%, b.p.=110°–112° C./35 mmHg). The structure of this ester was confirmed by the following data.

IR (liquid film): 2925, 2860, 1730, 1450, 1430, 1370, 1315, 1250, 1190, 1140, 1100, 1080, 980, 765, 720 cm⁻¹.

NMR (90 MHz, CDCl₃, δ): 0.6–1.0 (3H, m); 1.15 (6H, s); 1.0–1.8 (10H, m); 3.64 (3H, s).

MASS (CI, m/e): 187 (M⁺+1).

REFERENCE EXAMPLE 30

Dimethyl 3,3-dimethyl-2-oxo-nonanylphosphonate (30)

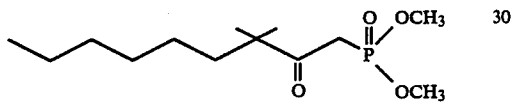

Dimethyl methylphosphonate (7.6 g, 0.061 mol) was dissolved in 70 ml anhydrous THF under argon atmosphere. To the mixture stirred at −78° C. was added dropwise n-butyl lithium (1.44N, 42.4 ml, 0.061 mol). After 30 minutes, methyl 2,2-dimethyloctanoate (4.5 g, 0.024 mol) was further added dropwise. After being stirred for 30 minutes the mixture was warmed to room temperature. To the mixture cooled with ice bath were added 3.8 ml of acetic acid and 10 ml of water. After concentration of the reaction mixture, 20 ml of water was added to the residue and the mixture was extracted with ethyl acetate (50 ml×2). The ethyl acetate layers were washed with water (20 ml×1) and with brine (20 ml×1), dried over anhydrous sodium sulfate, and concentrated. Distillation of the residue gave dimethyl 3,3-dimethyl-2-oxononanylphosphonate (5.34 g, 0.0192 mol, 79%, b.p. 137°–140° C./0.6 mmHg). The structure of this product was confirmed by the following data.

IR (liquid film): 2950, 2930, 2850, 1695, 1455, 1380, 1360, 1250, 1180, 1060, 1030, 860, 830, 800, 720 cm⁻¹.

NMR (90 MHz, CDCl₃, δ): 0.6–1.0 (3H, m); 1.15 (6H, s); 1.0–1.8 (10H, m); 3.64 (3H, s).

MASS (CI, m/e): 279 (M⁺+1).

REFERENCE EXAMPLE 31

Ethyl 2-methylnonanoate (31)

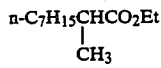

To a solution of diisopropylamine (9.0 ml, 64.4 mmol) in 100 ml anhydrous THF was added dropwise n-butyl lithium (1.61N, 40.0 ml, 64.4 mmol) at −78° C. under argon atmosphere. The mixture was stirred at −78° C. for 30 minutes and ethyl nonanoate (10.00 g, 53.7 mmol) was added dropwise. After stirring the mixture at −78° C. for 30 minutes, a solution of methyl iodide (3.7 ml, 59.1 mmol) in HMPA (2.8 ml, 16.1 mmol) was added dropwise and the mixture was stirred at −78° C. for 3.5 hours. Saturated aqueous solution of ammonium chloride (20 ml) was added to the reaction mixture and the resulting mixture was then extracted with ether (50 ml×4). The ether layers were washed with water (50 ml) and with brine (50 ml), dried over anhydrous sodium sulfate, and concentrated. Distillation gave yellow liquid, ethyl 2-methylnonanoate (9.6892 g, yield: 90.1%, b.p.: 63°–64° C./0.7 mmHg). The structure of this product was confirmed by the following data.

IR (liquid film): 2925, 2855, 1731, 1456, 1371, 1344, 1243, 1168, 1095, 1025, 862, 726 cm⁻¹.

NMR (100 MHz, CDCl₃, δ): 0.70–1.90 (21H, m); 2.19–2.57 (1H, m); 4.12 (2H, q, J=7.11 Hz).

MASS (CI, m/e): 201 (M⁺+1).

REFERENCE EXAMPLE 32

Ethyl 2,2-dimethylnonanoate (32)

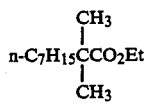

To a solution of diisopropylamine (10.7 ml, 76.6 mmol) in anhydrous THF (100 ml) was added dropwise n-butyl lithium (1.61N, 47.6 ml, 76.6 mmol) at −78° C. under argon stream. After stirring the mixture at −78° C. for 30 minutes, ethyl 2-methylnonanoate (9.6028 g, 47.9 mmol) was added dropwise and the mixture was further stirred at −78° C. for 30 minutes. A solution of methyl iodide (5.5 ml, 88.3 mmol) in HMPA (2.5 ml, 14.4 mmol) was dropwise added and the mixture was stirred at −78° C. for 40 minutes, them at 0° C. for 40 minutes, and further at room temperature for 45 minutes. Saturated aqueous ammonium chloride solution (20 ml) was added and the reaction mixture was extracted with ethyl acetate (50 ml×4). The ethyl acetate layers were washed with water (50 ml) and with brine (50 ml), dried over anhydrous sodium sulfate, and concentrated. Distillation gave ethyl 2,2-dimethylnonanoate (9.6627 g, 94.1% yield, b.p.: 53°–65.5° C./0.22 mmHg) as colorless liquid. The structure of this product was confirmed by the following data.

IR (liquid film): 2930, 2855, 1725, 1460, 1378, 1360, 1315, 1301, 1273, 1243, 1178, 1144, 1110, 1094, 1028, 942, 864, 772, 722 cm⁻¹.

NMR (100 MHz, CDCl₃, δ): 0.70–1.69 (24H, m); 4.11 (2H, q, J=7.11 Hz).

MASS (CI, m/e): 215 (M⁺+1).

REFERENCE EXAMPLE 33

Dimethyl 3,3-dimethyl-2-oxodecylphosphonate (33)

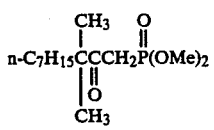

To a solution of dimethyl methylphosphonate (6.1 ml, 56.0 mmol) in 100 ml anhydrous THF was added dropwise n-butyl lithium (1.61N, 34.7 ml, 55.9 mmol) at −78° C. under argon atmosphere. After stirring the mixture for 15 minutes, ethyl 2,2-dimethylnonanoate (5.00 g, 23.3 mmol) was added dropwise and the mixture was stirred at −78° C. for 20 minutes and then at room temperature for 2 hours. To the reaction mixture was added 20 ml of saturated aqueous solution of ammonium chloride. The mixture was extracted with ethyl acetate (50 ml×4). The ethyl acetate layers were washed with water (50 ml) and with brine (50 ml), dried over anhydrous sodium sulfate, and concentrated. Purification by column chromatography on silica gel (ethyl acetate) gave pure dimethyl 3,3-dimethyl-2-oxodecyl-phosphonate (2.3312 g, 7.97 mmol, yield 34%). The structure of this product was confirmed by the following data.

IR (liquid film): 3440, 2930, 2855, 1701, 1461, 1386, 1366, 1251, 1181, 1031, 870, 843, 805, 722 cm$^{-1}$.

NMR (100 MHz, CDCl$_3$, δ): 0.70–1.63 (21H, m); 3.14 (2H, d, J=21.32 Hz); 3.80 (6H, d, J=11.22 Hz).

MASS (CI, m/e): 293 (M$^+$+1).

REFERENCE EXAMPLE 34

Methyl 2,2,3-trimethyl-butyrate (34)

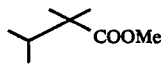

Under argon atmosphere, a solution of anhydrous diisopropylamine (27.1 ml, 194 mmol) in anhydrous THF (250 ml) was cooled to −78° C. After 20 minutes, 1.59N n-butyl lithium (122 ml, 194 mmol) was added and the mixture was stirred for 20 minutes. Then, methyl isovalerate (15 g, 129 mmol) was added and the mixture was stirred for additional 30 minutes. A solution of methyl iodide (9.64 ml, 155 mmol) in HMPA (11.22 ml, 64.5 mmol) was added to the reaction mixture, and the mixture was stirred for one hour at −78° C. Aqueous saturated solution of ammonium chloride (150 ml) was added and the mixture was extracted with ether (150 ml×3). The combined organic layers were washed with water (500 ml) and with brine (500 ml), dried over anhydrous sodium sulfate (60 g), and concentrated. The residue was distilled to give 12.854 g of colorless oily product.

Under argon atmosphere, a solution of anhydrous diisopropylamine (22.32 ml, 159 mmol) in anhydrous THF (250 ml) was cooled to −78° C. After 20 minutes, 1.49N n-butyl lithium (106.9 ml, 159 mmol) was added. Further, after stirring 20 minutes, the colorless oily product (8.2814 g) obtained from the above-mentioned reaction was added and the reaction mixture was further stirred for additional 30 minutes. A solution of methyl iodide (9.91 ml, 159 mmol) in HMPA (11.1 ml, 63.7 mmol) was added to the reaction mixture, and the mixture was stirred at −78° C. for 1.5 hours and then at 0° C. for one hour. After adding aqueous saturated solution of ammonium chloride (200 mL), the mixture was extracted with ether (150 ml×3). The combined organic layers were washed with water (500 ml) and with brine (500 ml), dried over anhydrous sodium sulfate (60 g), and concentrated. The residue was distilled to give colorless oily product, methyl 2,2,3-trimethyl-butyrate (7.2624 g, 50.4 mmol, 39%, b.p.: 140°–144° C./760 mmHg). The structure was identified by the following data.

IR (liquid film): 2970, 2880, 1723, 1400, 1379, 1330, 1261, 1188, 1158, 1132, 1099, 1063, 1004, 984, 944, 893, 840, 779, 739 cm$^{-1}$.

NMR (90 MHz, CDCl$_3$, δ): 0.84 (6H, d, J=6.81 Hz); 1.09 (6H, s); 1.80–2.14 (1H, m); 3.66 (3H, s).

MASS (CI/ m/e): 145 (M$^+$+1).

REFERENCE EXAMPLE 35

Dimethyl 3,3,4-trimethyl-2-oxopentylphosphonate (35)

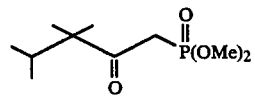

Under argon atmosphere, a solution of dimethyl methylphosphonate (5.18 ml, 47.87 mmol) in anhydrous THF (70 ml) was cooled to −78° C. After 20 minutes, 1.49N n-butyl lithium (32.1 ml, 47.87 mmol) was added and the mixture was stirred for 20 minutes. Then, a solution of methyl 2,2,3-trimethylbutyrate (2.2978 g, 15.96 mmol) in N,N,N',N'-tetramethylethylenediamine (7.22 ml, 47.87 mmol) was added to the reaction mixture, and the mixture was stirred at −78° C. for 30 minutes. After further stirring the resulting mixture at room temperature overnight, aqueous saturated solution of ammonium chloride (70 ml) was added and the mixture was extracted with ethyl acetate (50 ml×3). The combined organic layers were washed with brine (150 ml), dried over anhydrous sodium sulfate (40 g), and concentrated to give 3.48 g of colorless oily product. Purification by silica gel column chromatography (ethyl acetate) gave dimethyl 3,3,4-trimethyl-2-oxopentyl-phosphonate (2.3818 g, 10.09 mmol, 63%). The structure was confirmed by the following data.

IR (liquid film): 3425, 2950, 1699, 1640, 1452, 1381, 1363, 1240, 1179, 1020, 922, 861, 808, 745 cm$^{-1}$.

NMR (90 MHz, CDCl$_3$, δ): 0.77 (6H, d, J=6.61 Hz); 0.99 (6H, s); 1.65–2.08 (1H, m); 3.07 (2H, d, J=21.3 Hz); 3.73 (6H, d, J=11.21 Hz).

MASS (EI, m/e): 236 (M$^+$).

REFERENCE EXAMPLE 36

Diethyl isopropylidenemalonate (36)

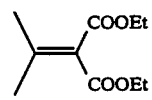

There were placed diethyl malonate (133 g, 0.83 mol), acetone (72 g, 1.24 mol), acetic anhydride (106 g, 1.05 mol) and zinc chloride (17.0 g, 0.125 mmol in a 500 ml three neck flask. After 24 hour reflux, benzene (200 ml) was added and the reaction mixture was washed with water (100 ml×4). The aqueous layer was further extracted with benzene (50 ml×2). The organic layers were combined and concentrated. The residue was distilled under reduced pressure to give oily product, diethyl isopropylidenemalonate (68.0 g, 0.34 mol, 41.0%, b.p.: 112° C./9 mmHg). The structure was confirmed by the following data.

IR (liquid film): 2980, 1730, 1650, 1450, 1380, 1300, 1260, 1220, 1120, 1070, 1030, 930, 870, 800, 740 cm$^{-1}$ NMR (90 MHz, CDCl$_3$, δ): 1.29 (6H, t, J=7.1 Hz); 2.01 (6H, s); 4.23 (4H, q, J=7.1 Hz).

MASS (EI, m/e): 200 (M+).

REFERENCE EXAMPLE 37

Ethyl 2-ethyoxycarbonyl-3,3-dimethylhexanoate (37)

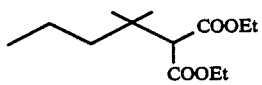

37

To a solution of n-propylmagnesium bromide in THF (1.62N, 149 ml, 242 mmol), anhydrous THF (200 ml) was added and the mixture was cooled to −50° C. After adding hydrated copper acetate (2.42 g, 12.1 mmol), a solution of diethyl isopropylidenemalonate (22 g, 110 mmol) in anhydrous THF (100 ml) was slowly added to the solution at −50° C., and the mixture was stirred at −50° C. for 2 hours. Aqueous hydrogen chloride (1N, 260 ml) was added at room temperature and the mixture was extracted with ethyl acetate (500 ml, 100 ml×3). Aqueous saturated solution of sodium hydrogencarbonate (100 ml) was added to the combined organic layers and filtered. The aqueous layer was separated from the organic layer of the filtrate. The organic layer was washed with brine (300 ml), dried over magnesium sulfate, and concentrated. The residue was distilled under reduced pressure to give ethyl 2-ethoxycarbonyl-3,3-dimethylhexanoate (24.92 g, 102 mmol, 92.7%, b.p.: 85°-87° C./1 mmHg). The structure was identified by the following data.

IR (liquid film): 2960, 1750, 1730, 1460, 1390, 1370, 1310, 1230, 1200, 1120, 1090, 1040 cm$^{-1}$.

NMR (90 MHz, CDCl$_3$, δ): 0.7-1.0 (3H, m); 1.0-1.6 (10H, m); 1.14 (6H, s); 3.31 (1H, s); 4.17 (4H, q, J=7.1 Hz).

MASS (CI, m/e): 245 (M++1).

REFERENCE EXAMPLE 38

Ethyl 3,3-dimethylhexanoate (38)

38

To a solution of ethyl 2-ethoxycarbonyl-3,3-dimethylhexanoate (24.5 g, 100 mmol) in ethanol (150 ml), was added aqueous sodium hydroxide solution (1N, 180 ml, 180 mmol) and the mixture was stirred at room temperature for 24 hours and then at 40° C. for additional 2 hours. Aqueous hydrogen chloride (3N, 60 ml, 180 mmol) was added to the reaction mixture and the resulting mixture was then concentrated to 150 ml. The mixture was extracted with ethyl acetate (200 ml) and the aqueous layer was further extracted with ethyl acetate (50 ml×2). The combined organic layers were washed with water (100 ml) and with brine (100 ml), and dried over anhydrous magnesium sulfate. The resulting solution was concentrated and the residue was stirred at 180° C. for 2.5 hours. Ether (30 ml) was added to the reaction mixture. The resulting mixture was then treated with diazomethane. After removing off ether, the residue was further distilled under reduced pressure to give oily product, ethyl 3,3-dimethylhexanoate (11.07 g, 64.4 mmol), 64.4%, b.p.: 87°-94° C./22 mmHg). The structure was identified by the following data.

IR (liquid film): 3000, 2920, 1740, 1470, 1400, 1380, 1340, 1230, 1140, 1100, 1070, 1040 cm$^{-1}$.

NMR (90 MHz, CDCl$_3$, δ): 0.7-1.5 (10H, m); 0.98 (6H, s); 2.17 (2H, s); 4.11 (2H, q, J=7.1 Hz).

MASS (EI, m/e): 172 (M+).

REFERENCE EXAMPLE 39

Dimethyl 4,4-dimethyl-2-oxoheptyl phosphonate (39)

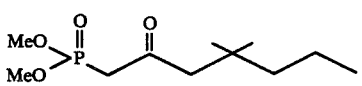

39

Dimethyl methylphosphonate (11.7 g, 102 mmol) was dissolved in anhydrous THF (200 ml) and the resulting solution was cooled to −78° C. under argon atmosphere. A solution of n-butyl lithium in hexane (1.63N, 62.3 ml, 102 mmol) was added and the mixture was stirred for 30 minutes. A solution of ethyl 3,3-dimethylhexanoate (7.00 g, 40.6 mmol) in anhydrous THF (50 ml) was added to the reaction mixture at −78° C. and the mixture was stirred for 30 minutes and then at room temperature for further 2 hours. Acetic acid was added to neutralize the solution. Water (20 ml) was added and then the solution was concentrated. The resulting residue were partitioned between ethyl acetate (200 ml) and water (10 ml). The ethyl acetate layer was separated, washed with water (80 ml) and with brine (100 ml), dried over anhydrous magnesium sulfate, and concentrated. The residue was distilled under reduced pressure to give oily product, dimethyl 4,4-dimethyl-2-oxoheptylphosphonate (8.11 g, 32.4 mmol, 79.8%, b.p.: 101°-104° C./0.03 mmHg). The structure was identified by the following data.

IR (liquid film): 3500, 2970, 2900, 1720, 1460, 1400, 1370, 1270, 1190, 1040, 940, 890, 820, 720 cm$^{-1}$.

NMR (90 MHz, CDCl$_3$, δ): 0.6-1.5 (7H, m); 0.96 (6H, s); 2.48 (2H, s); 3.03 (2H, d, J=22.7 Hz); 3.76 (6H, d, J=11.2 Hz).

MASS (CI, m/e): 251 (M++1).

REFERENCE EXAMPLE 40

Methyl 4,4-dimethylhexanoate (40)

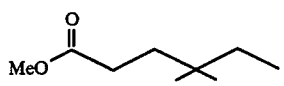

40

In a 100 ml three neck flask, magnesium (2.43 g, 100 mmol) and a small quantity of iodine were placed and heated until iodine vapor was generated. After cooling, 4 ml of a solution of 2-chloro-2-methylbutane (10.7 g, 100 mmol) in anhydrous ether (40 ml) was added. The remainder of the ether solution was then dropwise added in such a rate that ether was slowly refluxed. The mixture was then stirred at room temperature for one hour, and anhydrous THF (50 ml) was added.

To a solution of cuprous chloride (198 mg, 2.00 mmol) in anhydrous THF (150 ml) was slowly added the Grignard reagent prepared above at 0° C. Then, a solution of β-propiolactone (6.00 g, 83.3 mmol) in anhydrous THF (100 ml) was added dropwise to the reaction mixture at 0° C. over 2 hours. After stirring the mixture at 0° C. for 2 hours and then at room temperature for 6 hours, 3N aqueous hydrogen chloride (100 ml) and water (100 ml) were added to the reaction mixture. The mixture was then extracted with ether and the ether layer was concentrated. Aqueous sodium hydroxide solution (1N, 100 ml) and ether were added to the residue. After separating the aqueous layer from the organic layer, 3N aqueous hydrogen chloride was added to the aqueous layer to pH=1. The solution was extracted with ether, and the organic layer was washed with water and with brine, and concentrated. Ether (20 ml) was added to the residue and esterification was effected with diazomethane. After removing off ether, the residue was distilled under reduced pressure to give oily product, methyl 4,4-dimethylhexanoate (3.11 g, 19.7 mmol, 23.6%, b.p.: 80°-83° C./22 mmHg). The structure was confirmed by the following data.

IR (liquid film): 2960, 1740, 1460, 1440, 1390, 1370, 1310, 1280, 1260, 1200, 1170, 1070, 1020, 1000, 900, 870, 860, 790 cm⁻¹.

NMR (90 MHz, CDCl₃, δ): 0.6–1.05 (9H, m); 1.05–1.4 (2H, m); 1.4–1.7 (2H, m); 2.1–2.4 (2H, m); 3.66 (3H, s).

MASS (CI, m/e): 159 (M⁺+1).

REREFENCE EXAMPLE 41

Dimethyl 5,5-dimethyl-2-oxo-heptylphosphonate (41)

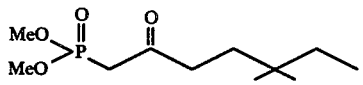

41

Dimethyl methylphosphonate (5.89 g, 47.5 mmol) was dissolved in anhydrous THF (80 ml). To the resulting solution cooled to −78° C. under argon atomosphere, a solution of n-butyl lithium in hexane (1.63N, 29.1 ml, 47.5 mmol) was added and the mixture was stirred for 30 minutes. A solution of methyl 4,4-dimethylhexanoate (3.00 g, 19.0 mmol) in anhydrous THF (15 ml) was then added to the reaction mxiture at −78° C. and the mixture was stirred for 30 minutes. After warming the mixture to room temperature, acetic acid was added to neutralize the solution and a small quantity of water was then added, and concentrated. After ethyl acetate was added to the residue, the ethyl acetate layer was washed with water and with brine, dried over anhydrous magnesium sulfate, and concentrated. The residue was distilled under reduced pressure to give oily product, dimethyl 5,5-dimethyl-2-oxoheptylphosphonate (3.38 g, 13.5 mmol, 71.1%, b.p.: 120°-122° C./0.18 mmHg). The structure was confirmed by the following data.

IR (KBr): 3500, 2970, 1710, 1460, 1390, 1370, 1270, 1190, 1040, 870, 840, 810 cm⁻¹.

NMR (90 NHz, CDCl₃, δ): 0.7–1.0 (9H, m); 1.05–1.7 (4H, m); 2.4–2.8 (2H, m); 3.10 (2H, d, J=22.7 Hz); 3.79 (6H, d, J=11.2 Hz).

MASS (CI, m/e): 251(M⁺+1).

REFERENCE EXAMPLE 42

Dimethyl 3-methyl-2-oxo-heptylphosphonate (42)

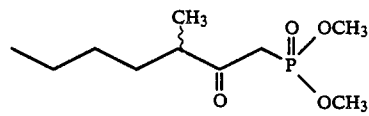

42

To a solution of dimethyl 3-methyl-2-oxo-5-heptynylphosphonate (10.0 g, 0.043 mol) in ethyl acetate (100 ml) was added 10% palladium on active carbon (5.0 g) and the mixture was stirred under hydrogen atmosphere for one hour. The reaction mixture was filtered and the filtrate was concentrated. The residue was distilled under reduced pressure to give colorless oily product dimethyl 3-methyl-2-oxo-heptylphosphonate (8.12 g, 0.034 mol, 80%, b.p. 90°–92° C./0.05 mmHg). The structure was identified by the following data.

IR (liquid film): 3490, 2960, 2930, 2870, 2855, 1715, 1460, 1400, 1380, 1260, 1185, 1030, 880, 840, 810, 725, 680 cm⁻¹.

NMR (90 MHz, CDCl₃, δ): 0.89 (3H, t, J=5.7 Hz); 1.10 (3H, d, J=6.8 Hz); 1.0–2.0 (6H, m); 2.5–2.9 (1H, m); 3.12 (2H, d, J=22.4 Hz); 3.77 (6H, d, J=11.2 Hz).

MASS (EI, m/e): 236 (M⁺).

REFERENCE EXAMPLE 43 l-3-Methylhexanoic acid (43)

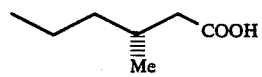

43

Sodium metal (42.0 g, 1.827 mol) was dissolved in absolute ethanol (500 ml) under argon atmosphere. Ethyl malonate (289.3 g, 1.806 mol) was added at a stretch to the solution with stirring. Further, 2-bromopentane (262.6 g, 1.738 mol) was added dropwise at first slowly and, after sodium bromide was precipitated, in such a rate that ethanol was slowly refluxed. After 3 hour reflux, the mixture was cooled to room temperature, and 50% aqueous potassium hydroxide solution (510 g) was added dropwise slowly. The mixture was again warmed slowly and refluxed for 4 hours. After distilling off ethanol, concentrated hydrochloric acid (500 ml) was added and the mixture was refluxed for one hour. The reaction mixture was cooled to room temperature, and extracted with ether (500 ml×3). The combined ether layers were washed with brine (200 ml×2) and dried over anhydrous sodium sulfate. After distilling off ether, the residue was heated at 180° C. until carbon dioxide was no longer generated. The resulting residue was distilled under reduced pressure to give dl-3-methylhexanoic acid (172 g, 1.323 mol, 76%, b.p.: 112°–113° C./15 mmHg).

To a hot solution of dl-3-methylhexanoic acid (110 g, 0.845 mol) in 95% ethanol (500 ml) was added l-cinchonidine (225 g, 0.764 mol). After filtering insolubles, water (200 ml) was added to the filtrate and the mixture was cooled to 0° C. to obtain crystals. Recrystallization of the crystals from 60% ethanol gave 40 g of cinchonidine salt. The salt was decomposed by 10% aqueous hydrogen chloride, and the mixture was extracted with ether (500 ml×4). The combined ether layers were dried over anhydrous sodium sulfate, and concentrated. The residue was distilled under reduced pressure to give l-3-methylhexanoic acid (10.6 g, 0.0815 mol, 19.3%, b.p.: 118°-119° C./17 mmHg) of 98% in optical purity. The structure was confirmed by the following data.

$[\alpha]_D^{27} = -2.20°$ (l=1.0 neat).

IR (liquid film): 3500-2300, 2955, 2920, 2825, 1705, 1460, 1455, 1405, 1375, 1300, 1240, 1200, 1150, 1125, 1100, 930 cm$^{-1}$.

NMR (90 MHz, CDCl$_3$, δ): 0.8-1.1 (6H, m); 1.2-1.5 (4H, m); 1.7-2.5 (3H, m); 11.7 (1H, s)

MASS (EI, m/e) 130 (M$^+$).

REFERENCE EXAMPLE 44

Dimethyl (4S)-4-methyl-2-oxo-heptylphosphonate (44)

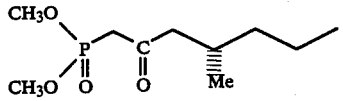

An excess of a solution of diazomethane in ether was added to l-3-methylhexanoic acid (10 g, 76.9 mmol). After concentration, the residue was distilled to give methyl l-3-methylhexanoate (8.7 g, 60.4 mmol, 74%, b.p.: 105°-107° C./105 mmHg).

Under argon atmosphere, 1.63N n-butyl lithium (65 ml, 106 mmol) was added dropwise at -78° C. to a stirred solution of dimethyl methylphosphonate (13.6 g, 110 mmol) in anhydrous THF (200 ml) and stirring was further continued for 20 minutes. A solution of methyl l-3-methylhexanoate (6.92 g, 48 mmol) in anhydrous THF (20 ml) was added dropwise, and the mixture was stirred at room temperature for one hour. Acetic acid (6.7 ml) was added to neutralize the solution and water (70 ml) was then added. After concentration, the residue was extracted with ether (200 ml×2), and the combined organic layers were washed with brine (40 ml×2), and dried over anhydrous sodium sulfate. Concentration and purification by vacuum distillation gave dimethyl 4(S)-methyl-2-oxo-heptylphosphonate (8.18 g, 34.6 mmol, 72%, b.p.: 114°-115° C./0.25 mmHg).

The structure was confirmed by the following data.

NMR (90 MHz, CDCl$_3$, δ): 0.80-1.0 (6H, m); 1.15-1.40 (4H, m); 1.80-2.20 (1H, m); 2.48 (1H, d, J=6.8 Hz); 2.55 (1H, d, J=6.3 Hz); 3.09 (2H, d, J=22.7 Hz); 3.79 (6H, d, J=11.2 Hz).

MASS (EI, m/e): 236 (M$^+$).

REFERENCE EXAMPLE 45

2-Bromohexane (45)

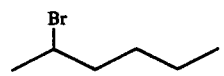

Under argon atmosphere, phosphorus tribromide (657.2 g, 2.43 mol) was added dropwise to 2-hexanol (285.5 g, 2.79 mol) with stirring at 0° C. After the completion of addition, stirring was further continued at 0° C. for 2 hours and at room temperature overnight. Crushed ice (300 g) was carefully added and, after heat was no longer generated, the mixture was further stirred for one hour. The organic layer was separated and the aqueous layer was extracted with ether (500 ml×3). The combined organic layers were washed with brine (300 ml×2) and with 5% aqueous sodium carbonate solution (250 ml×2), dried over anhydrous sodium sulfate, and concentrated. The residue was distilled to give 2-bromohexane (35.5 g, 2.15 mol, 77%, b.p.: 141°-142° C./760 mmHg).

The structure was confirmed by the following data.

IR (liquid film): 2955, 2920, 2860, 1465, 1455, 1375, 1285, 1235, 1190, 1145, 1045, 980, 900, 785, 730 cm$^{-1}$.

NMR (90 MHz, CDCl$_3$, δ): 0.8-1.05 (3H, m); 1.2-1.6 (4H, m); 1.70 (3H, d, J=6.6 Hz); 1.65-2.0 (2H, m); 3.8-4.3 (1H, m).

MASS (EI, m/e): 85 (M$^+$-Br).

REFERENCE EXAMPLE 46 l-3-Methylheptanoic acid (46)

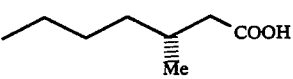

Under argon atmosphere, to a solution of sodium metal (70.6 g, 3.07 mol) in absolute ethanol (900 ml) was added ethyl malonate (510 g, 3.18 mol) with stirring. Further, 2-bromohexane (475 g, 2.88 mol) was added dropwise gradually and, after sodium bromide was precipitated, in such a rate that ethanol was slowly refluxed. After addition reflux was continued for 4 hours. After cooling the mixture to room temperature 50% aqueous potassium hydroxide solution (843 g) was added dropwise and the reaction mixture was refluxed for 5 hours. Ethanol was distilled off and the residue was neutralized with concentrated hydrochloric acid (600 ml). The resulting solution was then extracted with ether (one liter×3) and the extracts were dried over anhydrous sodium sulfate. After concentration, the residue was heated at 130° C. for 2 hours and at 180° C. for 2.5 hours. The distillation of the residue under reduced pressure gave dl-3-methylheptanoic acid (310 g, 2.15 mol, 75%, b.p.: 124°-125° C./25 mmHg).

The dl-3-methylheptanoic acid (163 g, 1.13 mol) obtained from the above-mentioned reaction was reacted with l-cinchonidine (300 g, 1.02 mol) to form salts. These salts were 12 times repeatedly recrystallized from 60% ethanol to obtain 134 g of cinchonidine salt. The salt was decomposed by 10% aqueous hydrogen chloride (230 ml), and the mixture was extracted with ether (500 ml×4). The combined organic layers were dried over anhydrous sodium sulfate, and concentrated. The residue was distilled under reduced pressure to give l-3-methylheptanoic acid (37 g, 0.257 mol, 45.5%, b.p.: 114°-115° C./18 mmHg) of 98% in optical purity. The structure was confirmed by the following data.

$[\alpha]_D^{23} = -3.446°$ (l=1.0 neat).

IR (liquid film): 3500-2200, 2950, 2910, 2860, 1705, 1460, 1455, 1405, 1375, 1300, 1280, 1225, 1190, 1150, 1125, 1100, 940 cm$^{-1}$.

NMR (90 MHz, CDCl$_3$, δ): 0.75-1.1 (6H, m); 1.15-1.5 (6H, m); 1.7-2.6 (3H, m); 11.23 (1H, s).

MASS (EI, m/e): 132 (M$^+$).

REFERENCE EXAMPLE 47

Dimethyl (4S)-4-methyl-2-oxooctylphosphonate (47)

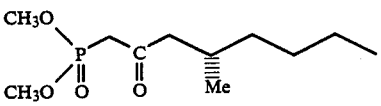

To a solution of l-3-methylheptanoic acid (18.0 g, 0.125 mol) in absolute methanol (100 ml) was added concentrated sulfuric acid (1 ml) and the reaction mixture was refluxed for 3 hours. After removal of methanol by distillation, the mixture was dried over 5% sodium carbonate, and concentrated. The residue was distilled under reduced pressure to give methyl l-3-methylheptanoate (17.1 g, 0.108 mol, 86.5%).

To a solution of dimethyl methylphosphonate (32.5 g, 0.262 mol) in anhydrous THF (480 ml) was dropwise added 1.63N n-butyl lithium (160 ml, 0.261 mol) at −78° C. After stirring for 30 minutes, a solution of methyl l-3-methylheptanoate (16.5 g, 0.104 mol) in anhydrous THF (25 ml) was added dropwise, and the mixture was stirred at −78° C. for one hour and at room temperature for 2 hours. Acetic acid (19 ml) and water (100 ml) were added to the reaction mixture. After distilling off THF, the residue was extracted with ether (500 ml×3). The combined organic layers were washed with brine (250 ml×2), dried over anhydrous sodium sulfate, and concentrated. The residue was distilled under reduced pressure to give dimethyl (4S)-4-methyl-2-oxo-octylphosphonate (23.6 g, 0.094 mol, 90%, b.p.=124°–125° C./0.5 mmHg). The structure was confirmed by the following data.

$[\alpha]_D^{25} = -3.02°$ (c=1.157, methanol).

IR (liquid film): 3480, 2960, 2940, 2890, 2860, 1720, 1715, 1465, 1405, 1380, 1265, 1185, 1060, 1040, 955, 905, 880, 835, 810, 735, 720 cm$^{-1}$.

NMR (90 MHz, CDCl$_3$, δ): 0.80–1.0 (6H, m); 1.15–1.35 (6H, m); 1.80–2.20 (1H, m); 2.45–2.65 (2H, m); 3.08 (2H, d, J=22.6 Hz); 3.79 (2H, d, J=11.2 Hz).

MASS (EI, m/e): 250 (M+).

REFERENCE EXAMPLE 48

Methyl cyclopentanecarboxylate (48)

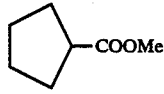

48

To an ice-cooled and stirred solution of cyclopentanecarboxylic acid (8.0 g, 0.070 mol) in 30 ml of ether was slowly added an excess solution of diazomethane in ether. After concentration of ether, the residue was distilled under reduced pressure to give a colorless transparent oil of methyl cyclopentanecarboxylate (7.65 g, 0.053 mol, yield 85.2%, b.p. 82°–83° C./62 mmHg), which was assigned the structure by the following data.

IR(Liquid film method): 2960, 2875, 1730, 1430, 1360, 1305, 1260, 1190, 1080, 1035, 1005, 910, 830, 755 cm$^{-1}$.

NMR(90 MHz, CDCl$_3$, δ): 1.4–2.1(8H, m), 2.5–3.0(1H, m), 3.67(3H, s)

MASS(EI, m/e): 128(M+).

REFERENCE EXAMPLE 49

Dimethyl 2-cyclopentyl-2-oxoethylphosphonate (49)

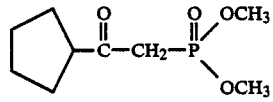

49

To a stirred solution of dimethyl methylphosphonate (11.55 g, 0.093 mol) in 150 ml of anhydrous THF at −78° C. was added dropwise a solution of n-butyl lithium in hexane (1.67N, 56.1 ml, 0.094 mol) under argon atmosphere, and the mixture was stirred for 30 minutes. To this reaction mixture was added a solution of methyl cyclopentanecarboxylate (5.0 g, 0.039 mol) in 10 ml of anhydrous THF. After being stirred for 30 minutes, the reaction mixture was allowed to warm to 0° C. and stirred for 1 hour. The reaction mixture was diluted with 5.4 ml of acetic acid and 10 ml of water, and concentrated. 30 ml of water was added to the residue. The mixture was extracted with ethyl acetate (100 ml×2). The combined organic layers were washed with water (20 ml) and brine (20 ml), dried over anhydrous sodium sulfate, and concentrated. The residue was distilled under reduced pressure to give a colorless transparent oil of dimethyl 2-cyclopentyl-2-oxo-ethylphosphonate (7.65 g, 0.035 mol, yield 89.1%, b.p. 106°–108° C./0.2 mmHg), which was assigned the structure by the following data:

IR(Liquid film method): 3460, 2860, 1700, 1445, 1390, 1355, 1255, 1180, 1015, 910, 865, 800 cm$^{-1}$.

NMR(90 MHz, CDCl$_3$, δ): 1.4–2.0(8H, m), 2.8–3.3(1H, m), 3.14(2H, d, J=22.4 Hz), 3.79(6H, d, J=11.2 Hz).

MASS(EI, m/e): 220(M+).

REFERENCE EXAMPLE 50

Methyl cyclohexanecarboxylate (50)

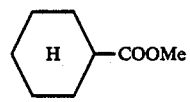

50

To an ice-cooled and stirred solution of cyclohexanecarboxylic acid (7.4 g, 0.058 mol) in 30 ml of ether was slowly added an excess solution of diazomethane in ether. After concentration of ether, the residue was distilled under reduced pressure to give a colorless transparent liquid of methyl cyclohexanecarboxylate (5.6 g, 0.039 mol, yield 67.2%, b.p. 73°–74° C./16 mmHg), which was assigned the structure by the following data:

IR(Liquid film method): 3460, 2930, 2850, 2660, 1740, 1450, 1415, 1380, 1305, 1270, 1190, 1170, 1130, 1070, 1040, 980, 890, 840, 795, 755 cm$^{-1}$.

NMR(90 MHz, CDCl$_3$, δ): 1.0–2.5(11H, m), 3.66(3H, s).

MASS(EI, m/e): 142(M+).

REFERENCE EXAMPLE 51

Dimethyl 2-cyclohexyl-2-oxoethylphosphonate (51)

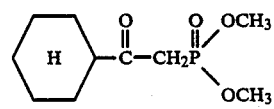

51

To a stirred solution of dimethyl methylphosphonate (11.73 g, 0.095 mol) in 150 ml of anhydrous THF at −78° C. was added dropwise a solution of n-butyl lithium in hexane (1.67N, 56.7 ml, 0.095 mol) under argon atmosphere, and the mixture was stirred for 30 minutes. To this reaction mixture was added dropwise a solution of methyl cyclohexanecarboxylate (5.6 g, 0.0394 mol) in 10 ml of anhydrous THF. After being stirred for 30 minutes, the reaction mixture was allowed to warm to 0° C., diluted with 5.5 ml of acetic acid and 10 ml of water, and concentrated. 30 ml of water was added to the residue, and the mixture was extracted with ethyl acetate (50 ml×2). The combined ethyl acetate layers were washed with water (20 ml×1) and brine (20 ml×1), dried over anhydrous sodium sulfate, and concentrated. The residue was distilled under reduced pressure to give a colorless transparent oil of dimethyl 2-cyclohexyl-2-oxo-ethylphosphonate (8.62 g, 0.037 mol, yield 93.4%, b.p. 114°–115° C./0.25 mmHg), which was assigned the structure by the following data:

IR(Liquid film method): 3450, 2920, 2840, 2660, 1695, 1440, 1390, 1365, 1305, 1250, 1180, 1130, 1025, 990, 915, 890, 855, 830, 795, 730, 680 cm$^{-1}$.

NMR(90 MHz, CDCl$_3$, δ): 0.8–2.1(10H, m), 2.3–2.8(1H, m), 3.13(2H, d, J=22.4 Hz), 5.70(6H, d, J=11.2 Hz).

MASS(EI, m/e): 234(M$^+$).

REFERENCE EXAMPLE 52

Dimethyl 3-cyclopentyl-2-oxopropylphosphonate (52)

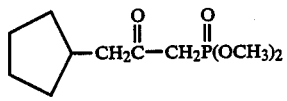

52

To an ice-cooled and stirred solution of cyclopentylacetic acid (7.9 g, 0.062 mol) in 30 ml of ether was added an excess solution of diazomethane in ether. After concentration, the residue was distilled under reduced pressure to give a colorless transparent liquid of methyl cyclopentylacetate (yielded amount 5.5g, 0.039 mol, yield 62.5%, b.p. 64°–65° C./15 mmHg). Then, a solution of n-butyl lithium in hexane (1.58N, 55.7 ml, 0.088 mol) was added dropwise to a stirred solution of dimethyl methylphosphonate (10.9 g, 0.088 mol) in 100 ml of anhydrous THF under argon atmosphere at −78° C. After 30 minutes, the above-mentioned methyl cyclopentylacetate (5.0 g, 0.035 mol) in 10 ml of anhydrous THF was further added dropwise, and the mixture was stirred in situ for 30 minutes. This reaction mixture was allowed to warm to 0° C., diluted with 5.3 ml of acetic acid and 20 ml of water, and concentrated. 30 ml of water was added to the residue. The mixture was extracted with ethyl acetate (50 ml×2), and the combined ethyl acetate layers were washed with water (20 ml×1) and brine (20 ml×1), dried over anhydrous sodium sulfate, and concentrated. The residue was distilled under reduced pressure to give a colorless transparent oil of dimethyl 3-cyclopentyl-2-oxo-propylphosphonate (7.8 g, 0.033 mol, yield 94.7%, b.p. 110°–112° C./0.13 mmHg), which was assigned the structure by the following data:

IR(Liquid film method): 3450, 2950, 2850, 1670, 1600, 1565, 1450, 1405, 1370, 1310, 1250, 1175, 1130, 1110, 1050, 1025, 995, 875, 815, 780, 710, 645 cm$^{-1}$.

NMR(90 MHz, CDCl$_3$, δ): 0.7–1.2(3H, m), 1.2–2.0(6H, m), 2.0–2.4(1H, m), 2.57(2H, d, J=6.8 Hz), 3.01(2H, d, J=22.7 Hz), 3.72(6H, d, J=11.2 Hz).

MASS(EI, m/e): 234(M$^+$).

REFERENCE EXAMPLE 53

Methyl cyclohexylacetate (53)

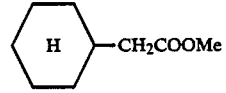

53

To an ice-cooled and stirred solution of cyclohexylacetic acid (9.34 g, 0.066 mol) in 30 ml of ether was slowly added an excess solution of diazomethane in ether. After concentration of ether, the residue was distilled under reduced pressure to give a colorless transparent liquid of methyl cyclohexylacetate (7.45 g, 0.048 mol, yield 72.4%, b.p. 86°–88° C./12 mmHg), which was assigned the structure by the following data:

IR(Liquid film method): 2900, 2830, 2660, 1725, 1435, 1385, 1345, 1275, 1250, 1225, 1180, 1150, 1100, 1070, 1000, 955, 930, 895, 860, 840, 790, 700 cm$^{-1}$.

NMR(90 MHz, CDCl$_3$, δ): 0.7–2.0(11H, m), 2.19(2H, d, J=7.0 Hz), 3.66(3H, s).

MASS(CI, m/e): 157(M$^+$+1).

REFERENCE EXAMPLE 54

Dimethyl 3-cyclohexyl-2-oxopropylphosphonate (54)

54

To a stirred solution of dimethyl methylphosphonate (10.3 g, 0.083 mol) in 150 ml of anhydrous THF at −78° C. was added dropwise a solution of n-butyl lithium in hexane (1.67N, 50 ml, 0.083 mol) under argon atmosphere. After 30 minutes, a solution of methyl cyclohexylacetate (5.0 g, 0.035 mol) in 10 ml of anhydrous THF was further added and the mixture was stirred for 30 minutes. The reaction solution was allowed to warm to 0° C., diluted with 5 ml of acetic acid and 10 ml of water, and concentrated. 30 ml of water was added to the residue, and then the mixture was extracted with ethyl acetate (50 ml×2). The combined ethyl acetate layers were washed with water (20 ml×1) and brine (20 ml×1), dried over anhydrous sodium sulfate, and concentrated. The residue was distilled under reduced pressure to give a colorless transparent oil of dimethyl 3-cyclohexyl-2-oxopropylphosphonate (7.4 g, 0.0298 mol, yield 85.3%, b.p. 118°–122° C./0.23 mmHg), which was assigned the structure by the following data:

IR(Liquid film method): 3450, 2905, 2840, 1705, 1440, 1395, 1375, 1350, 1250, 1030, 960, 930, 910, 895, 840, 820, 710 cm$^{-1}$.

NMR(90 MHz, CDCl$_3$, δ): 0.6–2.1(11H, m), 2.48(2H, d, J=6.6 Hz), 3.06(2H, d, J=22.7 Hz), 3.78(6H, d, J=11.2 Hz).

MASS(EI, m/e): 248(M$^+$).

REFERENCE EXAMPLE 55

Methyl 3-cyclohexylpropionate (55)

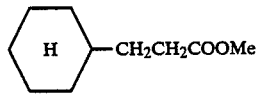

55

To an ice-cooled and stirred solution of 3-cyclohexylpropionic acid (5.0 g, 32.1 mmol) in 30 ml of ether was added an excess solution of diazomethane in ether. After concentration, the residue was distilled under reduced pressure to give a colorless transparent liquid of methyl 3-cyclohexylpropionate (4.8 g, 28.2 mmol, yield 88%, b.p. 95°–99° C./8 mmHg), which was assigned the structure by the following data:

IR(Liquid film method): 2930, 2860, 1740, 1450, 1435, 1370, 1350, 1325, 1310, 1275, 1250, 1195, 1160, 1130, 1080, 1060, 1020, 990, 890, 845, 825, 800, 770 cm$^{-1}$.

NMR(90 MHz, CDCl$_3$, δ): 0.6–1.8(13H, m), 2.32(2H, t, J=7.8 Hz), 3.66(3H, s).

MASS(EI, m/e): 170(M$^+$).

REFERENCE EXAMPLE 56

Dimethyl 4-cyclohexyl-2-oxo-butylphosphonate (56)

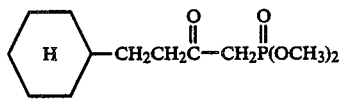

n-Butyl lithium (1.63N, 45.1 ml, 73 mmol) was added dropwise to a stirred solution of dimethyl methylphosphonate (9.05 g, 73 mmol) in 100 ml of anhydrous THF at −78° C. under argon atmosphere. After 30 minutes, a solution of methyl 3-cyclohexylpropionate (5.0 g, 29.4 mmol) in 10 ml of anhydrous THF was further added dropwise and the mixture was stirred for 30 minutes. This reaction solution was allowed to warm to 0° C., diluted with 4.4 ml of acetic acid and 10 ml of water, and concentrated. 30 ml of water was added to the residue and the mixture was extracted with ethyl acetate (50 ml ×2). The combined ethyl acetate layers were washed with water (20 ml×1) and brine (20 ml×1), dried over anhydrous sodium sulfate, and concentrated. The residue was distilled under reduced pressure to give a colorless transparent oil of dimethyl 4-cyclohexyl-2-oxobutylphosphonate (6.3 g, 24 mmol, yield 81.7%, b.p. 138°–142° C./0.05 mmHg), which was assigned the structure by the following data:

IR(Liquid film method): 3500, 2925, 2860, 1710, 1445, 1400, 1365, 1310, 1260, 1180, 1030, 960, 880, 835, 810, 710, 665 cm$^{-1}$.

NMR(90 MHz, CDCl$_3$, δ): 0.6–1.8(13H, m), 2.63(2H, t, J=7.4 Hz), 3.09(2H, d, J=22.7 Hz), 3.78(6H, d, J=11.2 Hz).

MASS(EI, m/e): 262(M$^+$).

REFERENCE EXAMPLE 57

2-cyclohexylpropionic acid (57)

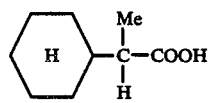

To a solution of anhydrous diisopropylamine (47.04 ml, 335.6 mmol) in anhydrous THF (300 ml) was added 1.63N n-butyl lithium (205.9 ml, 335.6 mmol) under argon atmosphere at 0° C. and the mixture was stirred for 20 minutes. Cyclohexylacetic acid (14.914 g, 104.9 mmol) was further added and the mixture was stirred for 20 minutes. To the reaction mixture was added HMPA (58.39 ml, 335.6 mmol) and stirred for 20 minutes, and then added methyl iodide (19.6 ml, 314.6 mmol) and stirred for 1 hour at room temperature. The reaction mixture was diluted with 40 cc of 6N hydrochloric acid and 400 ml of water, and the mixture was extracted with ether (300 ml, 100 ml×2). The combined organic layers were washed with water (500 ml) and brine (500 ml), dried over anhydrous sodium sulfate (100 g), and concentrated to give 14.42 g of a colorless oil. The oily product was distilled under reduced pressure to give a colorless crystalline product of 2-cyclohexylpropionic acid (12.9017 g, 79%, b.p. 105°–110° C./0.3 mmHg), which was assigned the structure by the following data:

m.p. 63°–64° C.

IR(KBr): 2910(3650–2150), 2850, 2650, 2550, 1700, 1454, 1437, 1411, 1375, 1329, 1284, 1241, 1204, 1182, 1151, 1103, 1049, 1027, 981, 953, 888, 855, 831, 672 cm$^{-1}$.

NMR(100 MHz, CDCl$_3$, δ): 1.13(3H, d, J=7.03 Hz), 0.73–2.00(11H, m), 2.05–2.44 (1H, m), 9.76–10.82(1H, broad s).

MASS(CI, m/e): 157(M$^+$+1).

REFERENCE EXAMPLE 58

Methyl 2-cyclohexyl-2-methylpropionate (58)

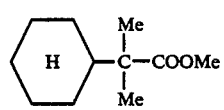

To a solution of anhydrous diisopropylamine (6.03 ml, 43 mmol) in anhydrous THF (50 ml) was added 1.62N n-butyl lithium (26.5 ml, 43 mmol) under argon atmosphere at −78° C. and the mixture was stirred for 20 minutes. Then, methyl 2-cyclohexylpropionate (4.8784 g, 28.7 mmol) was added and the mixture was further stirred for 40 minutes. To the reaction mixture was added a solution of methyl iodide (2.14 ml, 34.4 mmol) in HMPA (2.5 ml, 14.4 mmol) and stirred for 30 minutes. After then, 50 ml of an aqueous saturated solution of ammonium chloride was added and the mixture was extracted with ether (50 ml×3). The combined organic layers were washed with water (150 ml) and brine (150 ml), dried over anhydrous sodium sulfate (35 g), and concentrated to give 5.27 g of a colorless oil. To oily product was distilled under reduced pressure to give a colorless oil of methyl 2-cyclohexyl-2-methylpropionate (3.595 g, 74%, b.p. 137°–138° C./58 mmHg), which was assigned the structure by the following data:

IR(Liquid film method): 2930, 2851, 1727, 1444, 1385, 1363, 1317, 1263, 1242, 1191, 1142, 1103, 1054, 1024, 1005, 984, 945, 901, 863, 842, 819, 778, 760 cm$^{-1}$.

NMR(100 MHz, CDCl$_3$, δ): 0.67–1.95(11H, m), 1.10(6H, s), 3.65(3H, s).

MASS(CI, m/e): 185(M$^+$+1).

REFERENCE EXAMPLE 59

Dimethyl 3-cyclohexyl-3-methyl-2-oxobutylphosphonate (59)

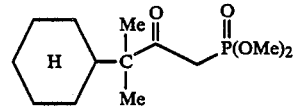

To a solution of dimethyl methylphosphonate (10.6 ml, 97.8 mmol) in anhydrous THF (150 ml) was added 1.61N n-butyl lithium (50.6 ml, 81.5 mmol) under argon atmosphere at −78° C. and the mixture was stirred for 20 minutes. Then, a solution of methyl 2-cyclohexyl-2-methylpropionate (6.001 g, 32.6 mmol) in HMPA (14.2 ml, 81.5 mmol) was added. The reaction mixture was stirred at −78° C. for 30 minutes and then at room temperature for 1 hour. 100 ml of an aqueous saturated solution of ammonium chloride was added and the mixture was extracted with ethyl acetate (50 ml×2). The combined organic layers were washed with water (150 ml) and brine (150 ml), dried over anhydrous sodium sulfate (50 g), and concentrated to give 10.68 g of a colorless oil. The oily product was purified by column chromatography (silica gel; ethyl acetate), to give dimethyl 3-cyclohexyl-3-methyl-2-oxo-butylphosphonate (1.0787 g, 3.9 mmol, 12%). This compound was assigned the structure by the following data:

IR(Liquid film method): 3440, 2910, 2850, 1700, 1443, 1382, 1363, 1243, 1180, 1022, 939, 883, 839, 803, 722 cm$^{-1}$.

NMR(100 MHz, CDCl$_3$, δ): 0.64–1.93(11H, m), 1.06(6H, s), 3.14(2H, d, J=21.10 Hz), 3.80(6H, d, J=11.22 Hz).

MASS(CI, m/e): 277(M$^+$+1).

REFERENCE EXAMPLE 60

Methyl 3-cyclohexyl-2-methylpropionate (60)

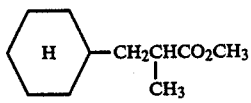

To a solution of diisopropylamine (19.74 ml, 140.8 mmol) in 100 ml of anhydrous THF was added dropwise n-butyl lithium (1.44N, 97.8 ml, 140.8 mmol) at 0° C. under argon atmosphere. The mixture was stirred at 0° C. for 1 hour and a half, and then 3-cyclohexylpropionic acid (10.00 g, 64.0 mmol) was added dropwise. After the mixture was stirred at 0° C. for 10 minutes, HMPA (24.5 ml, 140.8 mmol) was added dropwise and the mixture was stirred for 20 minutes. Methyl iodide (8.4 ml, 134.4 mmol) was further added dropwise at 0° C. and the mixture was stirred at room temperature for 2 hours. The reaction mixture was diluted with an aqueous saturated solution of ammonium chloride, and acidified to pH 2 with concentrated hydrochloric acid. The mixture was extracted with ethyl acetate (50 ml×4), and then, the combined ethyl acetate layers were washed with water (50 ml) and brine (50 ml), dried over anhydrous sodium sulfate, and concentrated. The residue was distilled to give a crude product of 3-cyclohexyl-2-methylpropionic acid (b.p. 90.5°–101° C./0.2 mmHg, 11.8556 g). To a solution of this crude product in 100 ml of ether was added dropwise 110 ml of a solution of diazomethane in ether at 0° C. After concentration, the residue was separated and purified through column chromatography (silica gel, ether), to give a pure product of methyl 3-cyclohexyl-2-methylpropionate (10.8672 g, 59.0 mmol, 92.2%). This compound was assigned the structure by the following data:

IR(Liquid film method): 2930, 2860, 1737, 1447, 1377, 1253, 1190, 1162, 1078, 1045, 1020, 988, 969, 889, 846, 824 cm$^{-1}$.

NMR(100 MHz, CDCl$_3$, δ): 0.60–1.90(16H, m), 0.20–0.85(1H, m), 3.66(3H, s).

MASS(EI, m/e): 184(M$^+$).

REFERENCE EXAMPLE 61

Methyl 3-cyclohexyl-2,2-dimethylpropionate (61)

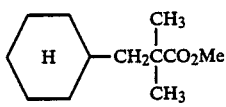

To a solution of diisopropylamine (8.9 ml, 63.3 mmol) in 100 ml of anhydrous THF was added dropwise n-butyl lithium (1.59N, 39.8 ml, 63.3 mmol) at −78° C. under argon atmosphere. After the mixture was stirred at −78° C. for 30 minutes, methyl 3-cyclohexyl-2-methylpropionate (7.7829 g, 42.2 mmol) was added dropwise. After the mixture was stirred at −78° C. for 30 minutes, a solution of methyl iodide (3.9 ml, 63.3 mmol) in HMPA (2.2 ml, 12.7 mmol) was added dropwise. After being stirred at −78° C. for 1 hour, the reaction mixture was diluted with an aqueous saturated solution of ammonium chloride. The aqueous mixture was extracted with ether (50 ml×4). Then, the combined ether layers were washed water (50 ml) and brine (50 ml), dried over anhydrous sodium sulfate, and concentrated. The residue was distilled to give a colorless liquid of methyl 3-cyclohexyl-2,2-dimethylpropionate (5.7294 g, yield 52.2%, b.p. 121.5°–123° C./22 mmHg), which was assigned the structure by the following data:

IR(Liquid film method): 3420, 2910, 2845, 1727, 1444, 1382, 1360, 1300, 1252, 1205, 1190, 1155, 1015, 985, 869, 839, 767 cm$^{-1}$.

NMR(100 MHz, CDCl$_3$, δ): 0.60–2.00(19H, m), 3.64(3H, s).

MASS(EI, m/e): 198(M$^+$).

REFERENCE EXAMPLE 62

Dimethyl 4-cyclohexyl-3,3-dimethyl-2-oxobutylphosphonate (62)

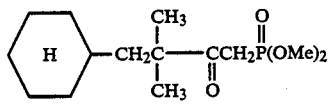

To a solution of dimethyl methylphosphonate (6.6 ml, 60.5 mmol) in 100 ml of anhydrous THF was added dropwise n-butyl lithium (1.59N, 38.1 ml, 60.5 mmol) at −78° C. under argon atmosphere, and the mixture was stirred for 30 minutes. Then, methyl 3-cyclohexyl-2,2-dimethylpropionate (5.00 g, 25.2 mmol) was added dropwise and the mixture was stirred at −78° C. for 20 minutes and then at room temperature for 2 hours. An aqueous saturated solution of ammonium chloride was added to the reaction mixture. The mixture was extracted with ethyl acetate (50 ml×4) and then the combined ethyl acetate layers were washed with water (50 ml) and brine (50 ml), dried over anhydrous sodium sulfate, and concentrated. The residue was purified by column chromatography (silica gel, ethyl acetate) to yield a pure product of dimethyl 4-cyclohexyl-3,3-dimethyl-2-oxobutylphosphonate (3.9491 g, 13.6 mmol, 54.0%). This compound was assigned the structure by the following data:

IR(Liquid film method): 3450, 2920, 2850, 1700, 1639, 1447, 1382, 1367, 1302, 1245, 1180, 1060, 1028, 943, 868, 843, 806, 731 cm$^{-1}$.

NMR(100 MHz, CDCl₃, δ): 0.63–1.80(19H, m), 3.18(2H, d, J=21.32 Hz), 3.80(6H, d, J=11.00 Hz).

MASS(CI, m/e): 291(M⁺+1).

REFERENCE EXAMPLE 63

Methyl 3-phenylpropionate (63)

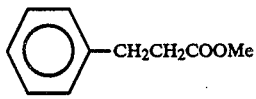
63

To an ice-cooled and stirred solution of 3-phenylpropionic acid (8.0 g, 0.053 mol) in 30 ml of ether was slowly added an excess solution of diazomethane in ether. After concentration of ether, the residue was distilled under reduced pressure to give a colorless transparent oil of methyl 3-phenylpropionate (7.25 g, 0.044 mol, yield 83.1%, b.p. 106°–108° C./10 mmHg), which was assigned the structure by the following data:

IR(Liquid film method): 3030, 2945, 1740, 1600, 1490, 1430, 1360, 1290, 1155, 1075, 1020, 980, 890, 830, 750, 695 cm⁻¹.

NMR(90 MHz, CDCl₃, δ): 2.5–3.2(4H, m), 3.66(3H, s), 7.0–7.5(5H, m).

MASS(EI, m/e): 164(M⁺).

REFERENCE EXAMPLE 64

Dimethyl 2-oxo-4-phenylbutylphosphonate (64)

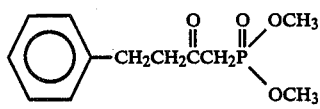
64

To a stirred solution of dimethyl methylphosphonate (8.85 g, 0.071 mol) in 150 ml of anhydrous THF at −78° C. was added dropwise a solution of n-butyl lithium in hexane (1.67N, 43.1 ml, 0.072 mol) under argon atmosphere, and the mixture was stirred for 30 minutes. To this reaction solution was added methyl 3-phenylpropionate (5.0 g, 0.030 mol) in 10 ml of anhydrous THF. After being stirred for 30 minutes, the reaction mixture was allowed to warm to 0° C., diluted with 5.5 ml of acetic acid and 10 ml of water, and concentrated. 30 ml of water was added to the residue and the mixture was extracted with ethyl acetate (100 ml×2). The combined organic layers were washed with water (20 ml) and brine (20 ml), dried over anhydrous sodium sulfate, and concentrated. The residue was distilled under reduced pressure to give a colorless transparent oil of dimethyl 2-oxo-4-phenylbutylphosphonate (7.39 g, 0.029 mol, yield 96%, b.p. 104°–105° C./0.23 mmHg).

IR(Liquid film method): 3050, 3020, 2940, 2840, 1705, 1595, 1485, 1445, 1395, 1360, 1250, 1170, 1025, 885, 840, 810, 740, 690 cm⁻¹.

NMR(90 MHz, CDCl₃): 2.93(4H, broad s), 3.07(2H, d, J=22.9 Hz), 3.74(6H, J=11.2 Hz), 7.0–7.4(5H, m).

MASS(EI, m/e): 256(M⁺).

REFERENCE EXAMPLE 65

Dimethyl 2-o-methylphenyl-2-oxoethylphosphonate (65)

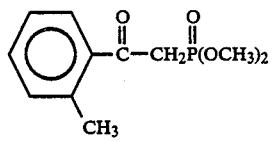
65 n-Butyl lithium (1.58N, 52.5 ml, 83 mmol) was added dropwise to a stirred solution of dimethyl methylphosphonate (10.3 g, 83 mmol) in 100 ml of anhydrous THF at −78° C. under argon atmosphere. After 30 minutes, methyl o-methylbenzoate (5.0 g, 33 mmol) in 10 ml of anhydrous THF was added dropwise. After being stirred for 30 minutes, this reaction mixture was allowed to warm to 0° C., diluted with 5 ml of acetic acid and 10 ml of water, and concentrated. 20 ml of water was added and the mixture was extracted with ethyl acetate (50 ml×2). The combined ethyl acetate layers were washed with water (20 ml×1) and brine (20 ml×1), dried over anhydrous sodium sulfate, and concentrated. The residue was distilled under reduced pressure to give an oil of dimethyl 2-o-methylphenyl-2-oxoethylphosphonate (68 g, 28.1 mmol, yield 85.1%, b.p. 134°–136° C./0.21 mmHg), which was assigned the structure by the following data:

IR(Liquid film method): 3450, 2940, 2840, 1675, 1595, 1560, 1450, 1390, 1370, 1250, 1180, 1110, 1050, 1020, 990, 870, 835, 810, 795, 775, 740 cm⁻¹.

NMR(90 MHz, CDCl₃, δ): 2.52(3H, s), 3.60(2H, d, J=22.4 Hz), 3.76(2H, d, J=11.2Hz), 7.15–7.55(3H, m), 7.65–7.85(1H, m).

MASS(EI, m/e): 242(M⁺).

REFERENCE EXAMPLE 66

Dimethyl 2-p-methylphenyl-2-oxoethylphosphonate (66)

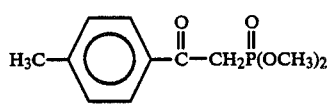
66

To a stirred solution of dimethyl methylphosphonate (10.23 g, 82.5 mmol) in 100 ml of anhydrous THF at −78° C. was added dropwise a solution of n-butyl lithium in hexane (1.58N, 52 ml, 82.5 mmol) under argon atmosphere, and the mixture was stirred for 30 minutes. Subsequently, methyl p-methylphenylcarboxylate (5.0 g, 33 mmol, commercially available product) in 10 ml of anhydrous THF was added dropwise and the mixture was stirred for 30 minutes. This reaction mixture was allowed to warm to 0° C., diluted with 5 ml of acetic acid and 10 ml of water and concentrated. 30 ml of water was added to the residue, and the mixture was extracted with ethyl acetate (50 ml×2). The combined ethyl acetate layers were washed with water (30 ml×1) and brine (30 ml×1), dried over anhydrous sodium sulfate, and concentrated. The residue was distilled under reduced pressure to give a colorless transparent oil of dimethyl 2-p-methylphenyl-2-oxo-ethylphosphonate (7.2 g, 29.8 mmol, yield 90.2%, b.p. 150°–153°

C./0.27 mmHg), which was assigned the structure by the following data:

IR(Liquid film method): 3460, 2940, 2850, 1670, 1600, 1565, 1450, 1405, 1250, 1175, 1130, 1110, 1050, 1020, 995, 875, 820, 760, 710, 695, 645 cm$^{-1}$.

NMR(90 MHz, CDCl$_3$, δ): 2.41(3H, s), 3.61(2H, d, J=22.6 Hz), 3.77(6H, d, J=11.2 Hz), 7.27(2H, d, J=8.0 Hz), 7.90(2H, d, J=8.0 Hz).

MASS(EI, m/e): 242(M$^+$).

REFERENCE EXAMPLE 67

Methyl m-fluorobenzoate (67)

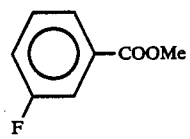

To an ice-cooled and stirred solution of m-fluorobenzoic acid (8.0 g, 57 mmol) in 50 ml of ether was added an excess solution of diazomethane in ether. After concentration, the residue was distilled under reduced pressure to give a colorless transparent oil of methyl m-fluorobenzoate (7.4 g, 48.1 mmol, yield 84.4%, b.p. 80°-82° C./16 mmHg), which was assigned the structure by the following data:

IR(Liquid film method): 2990, 2950, 2840, 1725, 1610, 1590, 1425, 1330, 1295, 1260, 1165, 1130, 1085, 1070, 970, 915, 840, 815, 770, 750, 690, 660 cm$^{-1}$.

NMR(90 MHz, CDCl$_3$, δ): 3.92(3H, s), 7.1-7.9(4H, m).

MASS(EI, m/e): 154(M$^+$).

REFERENCE EXAMPLE 68

Dimethyl 2-m-fluorophenyl-2-oxoethylphosphonate (68)

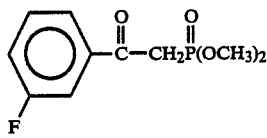

To a stirred solution of dimethyl methylphosphonate (10.1 g, 81.2 mmol) in 100 ml of anhydrous THF was added dropwise n-butyl lithium (1.58N, 51.4 ml, 81.2 mmol) at −78° C. under argon atmosphere. After 30 minutes, methyl m-fluorobenzoate (5.0 g, 32 mmol) was further added dropwise and the mixture was stirred for 30 minutes. The reaction solution was allowed to warm to 0° C., diluted with 4.9 ml of acetic acid and 10 ml of water, and concentrated. 30 ml of water was added to the residue and the mixture was extracted with ethyl acetate (50 ml×2). The combined ethyl acetate layers were washed with water (20 ml×1) and brine (20 ml×1), dried over anhydrous sodium sulfate, and concentrated. The residue was distilled under reduced pressure to give an oil of dimethyl 2-m-fluorophenyl-2-oxoethylphosphonate (6.6 g, 26.8 mmol, yield 83.8%, b.p. 132°-134° C./0.17 mmHg), which was assigned the structure by the following data:

IR(Liquid film method): 3450, 3060, 2940, 2840, 1680, 1580, 1475, 1430, 1400, 1290, 1260, 1190, 1110, 1055, 1030, 870, 825, 790, 760, 710, 665 cm$^{-1}$.

NMR (90 MHz, CDCl$_3$, δ): 3.62(2H, d, J=22.6 Hz), 3.79(6H, d, J=11.4 Hz), 7.15-7.9(4H, m).

MASS(CI, m/e): 247(M$^+$+1)

REFERENCE EXAMPLE 69

Methyl m-trifluoromethylbenzoate (69)

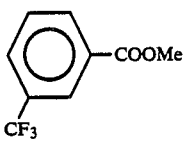

An excess solution of diazomethane in ether was added to an ice-cooled and stirred solution of m-trifluoromethylbenzoic acid (8.0 g, 42.1 mmol) in 50 ml of ether. After concentration, the residue was distilled under reduced pressure to give a colorless transparent oil of methyl m-trifluoromethylbenzoate (8.4 g, 41.2 mmol, yield 97.8%, b.p. 76°-78° C./12 mmHg), which was assigned the structure by the following data:

IR(Liquid film method): 2990, 2950, 2840, 1725, 1610, 1590, 1430, 1330, 1300, 1260, 1165, 1130, 1085, 1070, 970, 915, 840, 810, 770, 750, 690, 660 cm$^{-1}$.

NMR(90 MHz, CDCl$_3$, δ): 3.96(3H, s), 7.45-7.9(2H, m), 8.15-8.4(2H, m).

MASS(EI, m/e): 204(M$^+$).

REFERENCE EXAMPLE 70

Dimethyl 2-m-trifluoromethylphenyl-2-oxoethylphosphonate (70)

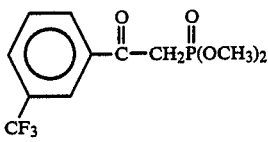

A solution of n-butyl lithium in hexane (1.58N, 38.8 ml, 61.3 mmol) was added dropwise under argon atmosphere to a stirred solution of dimethyl methylphosphonate (7.6 g, 61.3 mmol) in 100 ml of anhydrous THF at −78° C. After 30 minutes, methyl m-trifluoromethylbenzoate (5.0 g, 24.5 mmol) was added dropwise and the mixture was stirred for 30 minutes. The reaction mixture was allowed to warm to 0° C., diluted with 3.7 ml of acetic acid and 10 ml of water, and concentrated. 30 ml of water was added to the residue and the mixture was extracted with ethyl acetate (50 ml×2). The combined ethyl acetate layers were washed with water (20 ml×1) and brine (20 ml×1), dried over anhydrous sodium sulfate, and concentrated. The residue was distilled under reduced pressure to give an oil of dimethyl 2-m-trifluoromethylphenyl-2-oxoethylphosphonate (4.72 g, 15.9 mmol, yield 65%, b.p. 198°-202° C./0.06 mmHg), which was assigned the structure by the following data:

IR(Liquid film method): 3450, 3070, 2860, 1680, 1610, 1590, 1440, 1405, 1330, 1305, 1250, 1165, 1120, 1090, 1065, 1030, 920, 875, 840, 825, 800, 755, 730, 690, 650 cm$^{-1}$.

NMR(90 MHz, CDCl$_3$, δ): 3.65(2H, d, J=22.9 Hz), 3.78(2H, d, J=11.2 Hz), 7.5-7.9(2H, m), 8.1-8.35(2H, m).

MASS(CI, m/e): 297(M$^+$+1)

REFERENCE EXAMPLE 71

Methyl o-chlorobenzoate (71)

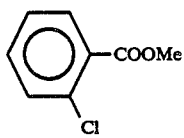

An excess solution of diazomethane in ether was added to an ice-cooled and stirred solution of o-chlorobenzoic acid (7.6 g, 48.6 mmol) in 50 ml of ether. After concentration, the residue was distilled under reduced pressure to give a colorless transparent oil of methyl o-chlorobenzoate (6.0 g, 35.2 mmol, yield 72.4%, b.p. 92°–93° C./7 mmHg), which was assigned the structure by the following data:

IR(Liquid film method): 3070, 2980, 2940, 2830, 1730, 1585, 1560, 1465, 1430, 1295, 1250, 1185, 1155, 1110, 1050, 1030, 950, 820, 780, 740, 715, 690, 670 cm$^{-1}$.

NMR(90 MHz, CDCl$_3$, δ): 3.93(3H, s), 7.18–7.55(3H, m), 7.70–7.90(1H, m).

MASS(EI, m/e): 170(M+).

REFERENCE EXAMPLE 72

Dimethyl 2-o-chlorophenyl-2-oxoethylphosphonate (72)

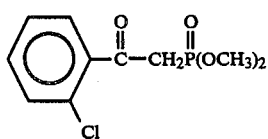

A solution of n-butyl lithium in hexane (1.58N, 55.6 ml, 88 mmol) was added dropwise to a solution of dimethyl methylphosphonate (10.9 g, 88 mmol) in 100 ml of anhydrous THF with stirring at −78° C. under argon atmosphere. After 30 minutes, a solution of methyl o-chlorobenzoate (6.0 g, 35.2 mmol) in 10 ml of anhydrous THF was added dropwise and the mixture was stirred for 30 minutes. The reaction mixture was allowed to warm to 0° C., diluted with 5.3 ml of acetic acid and 10 ml of water, and concentrated. 30 ml of water was added to the residue and the mixture was extracted with ethyl acetate (50 ml×2). The combined ethyl acetate layers were washed with water (20 ml×1) and brine (20 ml×1), dried over anhydrous sodium sulfate, and concentrated. The residue was distilled under reduced pressure to give a colorless transparent oil of dimethyl 2-o-chlorophenyl-2-oxoethylphosphonate (8.2 g, 31.2 mmol, yield 88.7%, b.p. 142°–145° C./0.09 mmHg), which was assigned the structure by the following data:

IR(Liquid film method): 3420, 3100, 3080, 3020, 2970, 2920, 2860, 2820, 1695, 1590, 1565, 1475, 1435, 1415, 1290, 1260, 1210, 1180, 1150, 1130, 1065, 1050, 1020, 1000, 960, 890, 870, 805, 780, 755, 720, 680, 650 cm$^{-1}$.

NMR(90 MHz, CDCl$_3$, δ): 3.72(2H, d, J=22.0 Hz), 3.76(6H, d, J=11.4 Hz), 7.25–7.65(4H, m).

MASS(EI, m/e): 262(M+).

REFERENCE EXAMPLE 73

Methyl m-chlorobenzoate (73)

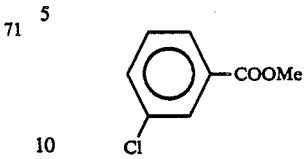

An excess solution of diazomethane in ether was added to an ice-cooled and stirred solution of m-chlorobenzoic acid (8.26 g, 52.8 mmol) in 50 ml of ether. The mixture was concentrated and distilled under reduced pressure to give a colorless transparent oil of methyl m-chlorobenzoate (6.1 g, 35.8 mmol, yield 67.8%, b.p. 116°–121° C./21 mmHg), which was assigned the structure by the following data:

IR(Liquid film method): 3080, 3000, 2960, 2860, 1730, 1595, 1570, 1470, 1430, 1420, 1290, 1270, 1255, 1190, 1160, 1125, 1080, 1075, 970, 900, 840, 805, 745, 675 cm$^{-1}$.

NMR(90 MHz, CDCl$_3$, δ): 3.92(3H, s), 7.25–7.6(2H, m), 7.85–8.1(2H, m).

MASS(EI, m/e): 170(M+).

REFERENCE EXAMPLE 74

Dimethyl 2-m-chlorophenyl-2-oxoethylphosphonate (74)

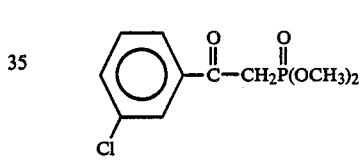

A solution of n-butyl lithium in hexane (1.63N, 45 ml, 73.3 mmol) was added dropwise to a solution of dimethyl methylphosphonate (9.1 g, 73.3 mmol) in 100 ml of anhydrous THF with stirring at −78° C. under argon atmosphere, and the mixture was stirred for 30 minutes. Then, methyl m-chlorobenzoate (5.0 g, 29.3 mmol) in 10 ml of anhydrous THF was further added dropwise and the mixture was stirred for 30 minutes. This reaction mixture was allowed to warm to 0° C., diluted with 4.4 ml of acetic acid and 10 ml of water, and concentrated. 30 ml of water was added to the residue and the mixture was extracted with ethyl acetate (50 ml×2). The combined ethyl acetate layers were washed with water (30 ml×1) and brine (30 ml×1), dried over anhydrous sodium sulfate, and concentrated. The residue was distilled under reduced pressure to give a colorless transparent oil of dimethyl 2-m-chlorophenyl-2-oxoethylphosphonate (6.5 g, 24.8 mmol, yield 84%, b.p. 144°–146° C./0.06 mmHg), which was assigned the structure by the following data:

IR(Liquid film method): 3070, 2960, 2850, 1680, 1590, 1570, 1460, 1470, 1375, 1250, 1195, 1180, 1135, 1040, 870, 840, 810, 750, 700, 680, 670 cm$^{-1}$.

NMR(90 MHz, CDCl$_3$, δ): 3.62(2H, d, J=22.6 Hz), 3.79(4H, d, J=11.2 Hz), 7.25–7.65(2H, m), 7.80–8.05(2H, m).

MASS(EI, m/e): 262(M+).

REFERENCE EXAMPLE 75

Methyl p-chlorobenzoate (75)

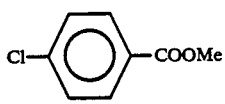

An excess solution of diazomethane in ether was slowly added to an ice-cooled and stirred solution of p-chlorobenzoic acid (6.2 g, 39.6 mmol) in 50 ml of ether and the mixture was concentrated. The residue was recrystallized from 5 ml of MeOH to give a white crystalline product of methyl p-chlorobenzoate (4.8 g, 28.2 mmol, yield 71%). m.p. 42.0°–43.0° C. (recrystallized from methanol)

IR(KBr): 3030, 3010, 2960, 2850, 1730, 1620, 1600, 1570, 1485, 1430, 1400, 1375, 1350, 1280, 1190, 1170, 1110, 1080, 1005, 960, 850, 830, 820, 760, 725, 680 cm$^{-1}$.

NMR(90 MHz, CDCl$_3$, δ3.91(3H, s), 7.40(2H, d, J=8.8 Hz), 7.97(2H, d, J=8.8 Hz).

MASS(EI, m/e): 170(M+).

REFERENCE EXAMPLE 76

Dimethyl 2-p-chlorophenyl-2-oxoethylphosphonate (76)

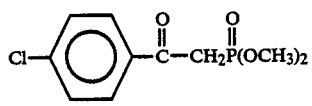

A solution of n-butyl lithium in hexane (1.63N, 43 ml, 70 mmol) was added dropwise to a solution of dimethyl methylphosphonate (8.68 g, 70 mmol) in 100 ml of anhydrous THF with stirring at −78° C. under argon atmosphere. After the mixture was stirred for 30 minutes, a solution of methyl p-chlorobenzoate (4.8 g, 28 mmol) in 10 ml of anhydrous THF was added dropwise and the mixture was stirred for 30 minutes. This reaction mixture was allowed to warm to 0° C., diluted with 4.2 ml of acetic acid and 10 ml of water, and concentrated. The residue was extracted with ethyl acetate (50 ml×2). The combined ethyl acetate layers were washed with water (20 ml×1) and brine (20 ml×1), dried over anhydrous sodium sulfate, and concentrated. The residue was distilled under reduced pressure to give a colorless transparent oil of dimethyl 2-p-chlorophenyl-2-oxoethylphosphonate (5.6 g, 21.3 mmol, yield 76.2%, b.p. 146°–149° C./0.07 mmHg), which was assigned the structure by the following data:

IR(Liquid film method): 2960, 2860, 1680, 1590, 1570, 1490, 1460, 1400, 1255, 1205, 1185, 1090, 1055, 1030, 1000, 885, 820, 785, 755, 710, 670 cm$^{-1}$.

NMR(90 MHz, CDCl$_3$, δ): 3.63(2H, d, J=12.6 Hz), 3.78(6H, d, J=11.2 Hz), 7.46(2H, d, J=8.7 Hz), 7.96(2H, d, J=8.7 Hz).

MASS(EI, m/e): 262(M+).

REFERENCE EXAMPLE 77

Methyl 2-phenylpropionate (77)

A solution of n-butyl lithium in hexane (1.44N, 75 ml, 108 mmol) was added to a solution of diisopropylamine (11.3 g, 112 mmol) in anhydrous THF (200 ml) cooled at −20° C. under argon atmosphere, and the mixture was stirred for 30 minutes. The reaction mixture was cooled to −78° C. To this solution were added a solution of methyl phenylacetate (12.0 g, 80.0 mmol) in 15 ml of anhydrous THF and HMPA (20.6 g, 115 mmol). The mixture was stirred at −78° C. for 1 hour and then at −30° C. for 30 minutes. To this reaction solution was added a solution of methyl iodide (17.0 g, 120 mmol) in anhydrous THF (30 ml) at −78° C., and the mixture was stirred at −78° C. for 1.5 hours. The reaction mixture was allowed to warm to room temperature and diluted with an aqueous saturated solution of ammonium chloride (300 ml) and water (150 ml). The mixture was extracted with ether (400 ml). The aqueous layer was further extracted with ether (200 ml×2). The combined organic layers were washed with water (200 ml) and brine, dried over anhydrous magnesium sulfate, and concentrated. The residue was distilled (b.p. 92°–93° C./10 mmHg) to give an oil of methyl 2-phenylpropionate (11.3 g, 68.9 mmol, 86.1%). This compound was assigned to the structure by the following data:

IR(Liquid film method):
3080, 3040, 2990, 2960, 1730, 1600, 1490, 1450, 1430, 1370, 1330, 1250, 1210, 1160, 1100, 1070, 1030, 1010, 970, 910, 860, 810, 770, 730, 700 cm$^{-1}$.

NMR(90 MHz, CDCl$_3$, δ): 1.50(3H, d, J=7.3 Hz), 3.65(3H, s), 3.72(1H, q, J=7.3 Hz), 7.1–7.4(5H, m).

MASS(EI, m/e): 164(M+).

REFERENCE EXAMPLE 78

Methyl 2-methyl-2-phenylpropionate (78)

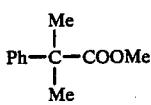

A solution of n-butyl lithium in hexane (1.44N, 60.0 ml, 86.4 mmol) was added to a solution of diisopropylamine (9.07 g, 89.6 mmol) in anhydrous THF (200 ml) cooled at −30° C. under argon atmosphere, and the mixture was stirred for 20 minutes. To this reaction mixture were added a solution of methyl 2-phenylpropionate (10.5 g, 64.0 mmol) in 10 ml of anhydrous THF and HMPA (16.5 g, 92.0 mmol), and the mixture was stirred at −30° C. for 10 minutes and then at 0° C. for 45 minutes. To this reaction solution was added a solution of methyl iodide (13.6 g, 96.0 mmol) in anhydrous THF (30 ml) at −30° C., and the mixture was stirred at −30° C. for 1 hour. This reaction mixture was added to an aqueous saturated solution of ammonium chloride (400 ml) and water (50 ml) was added. The mixture was extracted with ether (400 ml). The aqueous layer further extracted with ethyl acetate. The combined organic layers were washed with water (300 ml) and brine, dried over anhydrous magnesium sulfate, and concentrated. The residue was distilled (b.p. 99°–100° C./6 mmHg) to give an oil of methyl 2-methyl-2-phenylpropionate (7.63 g, 42.9 mmol, 67.0%). This compound was assigned the structure by the following data:

IR(Liquid film method): 2970, 1730, 1600, 1500, 1450, 1390, 1370, 1250, 1190, 1150, 1100, 1080, 1030, 1020, 990, 850, 770, 740, 700 cm$^{-1}$.

NMR(90 MHz, CDCl₃, δ): 1.58(6H, s), 3.64(3H, s), 7.1–7.4(5H, m).
MASS(EI, m/e): 178(M+).

REFERENCE EXAMPLE 79

Dimethyl 3-methyl-2-oxo-3-phenylbutylphosphonate (79)

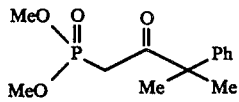                                79

A solution of n-butyl lithium in hexane (1.59N, 44.0 ml, 70.0 mmol) was added to a solution of dimethyl methylphosphonate (8.74 g, 70.0 mmol) in anhydrous THF (130 ml) cooled at −78° C. under argon atmosphere, and the mixture was stirred for 30 minutes. To this reaction mixture was added a solution of methyl 2-methyl-2-phenylpropionate (5.00 g, 28.0 mmol) in anhydrous THF (15 ml) at −78° C. The mixture was stirred for 2 hours, allowed to warm to room temperature and neutralized with acetic acid. The reaction mixture was diluted with water (10 ml), and concentrated. The residue was combined with ethyl acetate (100 ml) and water (30 ml). The separated organic layer was washed with water (30 ml) and brine, dried over anhydrous magnesium sulfate, and concentrated. The residue was distilled (b.p. 135°–141° C./0.05 mmHg) to give an oil of dimethyl 3-methyl-2-oxo-3-phenylbuthylphosphonate (5.73 g, 21.2 mmol, 75.7%). This compound was assigned the structure by the following data:

IR(Liquid film method): 3450, 2870, 1710, 1600, 1580, 1490, 1460, 1440, 1390, 1360, 1250, 1190, 1030, 1000, 910, 870, 800, 770, 700 cm⁻¹.

NMR(90 MHz, CDCl₃, δ): 1.44(6H, s), 2.80(2H, d, J=20.1 Hz), 3.65(6H, d, J=11.2 Hz), 7.0–7.5(5H, m).

MASS(EI, m/e): 270(M+).

REFERENCE EXAMPLE 80

Methyl 2-methyl-3-phenylpropionate (80)

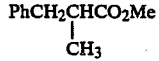                                80 n-Butyl lithium (1.49N, 49.2 ml, 73.3 mmol) was added dropwise to a solution of diisopropylamine (10.3 ml, 73.3 mmol) in 100 ml of anhydrous THF at 0° C. under argon atmosphere. After the mixture was stirred at 0° C. for 20 minutes, 3-phenylpropionic acid (5.00 g, 33.3 mmol) was added dropwise. After the mixture was stirred at 0° C. for 10 minutes, HMPA (12.7 ml, 73.3 mmol) was added dropwise and the mixture was further stirred for 20 minutes. Methyl iodide (4.4 ml, 69.9 mmol) was added dropwise at 0° C. and the mixture was stirred at room temperature for 3 hours. The reaction mixture was diluted with an aqueous saturated solution of ammonium chloride and acidified to pH2 with concentrated hydrochloric acid. The mixture was extracted with ethyl acetate (50 ml×4). The combined ethyl acetate layers were washed with water (50 ml) and brine (50 ml), dried over anhydrous sodium sulfate, and concentrated. To a solution of this residue in 100 ml of ether was added dropwise 50 ml of a solution of diazomethane in ether at 0° C. After concentration, the residue was distilled to give a colorless oil of methyl 2-methyl-3-phenylpropionate (5.6383 g, yield 95.0%, b.p. 122.5°–124.5° C./18 mmHg), which was assigned the structure by the following data:

IR(Liquid film method): 3070, 3030, 2975, 2950, 2880, 1735, 1605, 1585, 1495, 1455, 1435, 1375, 1360, 1283, 1255, 1215, 1193, 1165, 1119, 1090, 1080, 1063, 1042, 985, 905, 877, 835, 807, 745, 702 cm⁻¹.

NMR(100 MHz, CDCl₃, δ) 1.15(3H, d, J=6.37 Hz), 2.48–3.22(3H, m), 3.62(3H, s), 6.98–7.40(5H, m). MASS-(EI, m/e): 178(M+).

REFERENCE EXAMPLE 81

Methyl 2,2-dimethyl-3-phenylpropionate (81)

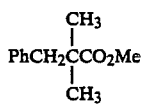                                81 n-Butyl lithium (1.49N, 28.3 ml, 42.2 mmol) was added dropwise to a solution of diisopropylamine (5.9 ml, 42.2 mmol) in 50 ml of anhydrous THF at −78° C. under argon atmosphere. After the mixture was stirred at −78° C. for 20 minutes, methyl 2-methyl-3-phenylpropionate (5.00 g, 28.1 mmol) was added dropwise. After the mixture was stirred at −78° C. for 30 minutes, a solution of methyl iodide (2.6 ml, 42.2 mmol) in HMPA (1.5 ml, 8.43 mmol) was added dropwise. The reaction mixture was further stirred at −78° C. for 2 hours, and 10 ml of an aqueous saturated solution of ammonium chloride was added. The mixture was extracted with ether (50 ml×4), and then, the combined ether layers were washed with water (50 ml) and brine (50 ml), dried over anhydrous sodium sulfate, and concentrated. This residue was distilled to give a colorless oil of methyl 2,2-dimethyl-3-phenylpropionate (1.8909 g, yield 51.7%, b.p. 127.5°–131° C./18 mmHg), which was assigned the structure by the following data:

IR(Liquid film method): 3025, 2960, 1725, 1488, 1445, 1429, 1380, 1360, 1318, 1278, 1243, 1188, 1118, 1068, 1015, 983, 893, 853, 798, 761, 733, 693 cm⁻¹.

NMR(100 MHz, CDCl₃, δ): 1.18(6H, s), 2.85(2H, s), 3.64(3H, s), 6.95–7.38(5H, m).

MASS(EI, m/e): 192(M+).

REFERENCE EXAMPLE 82

Dimethyl 3,3-dimethyl-2-oxo-4-phenylbutylphosphonate

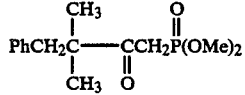                                82

To a solution of dimethyl methylphosphonate (2.4 ml, 21.8 mmol) in 100 ml of anhydrous THF was added dropwise n-butyl lithium (1.49N, 14.7 ml, 21.8 mmol) at −78° C. under argon atmosphere. After the mixture was stirred for 30 minutes, methyl 2,2-dimethyl-3-phenylpropionate (1.75 g, 10.0 mmol) was added dropwise and the mixture was stirred at −78° C. for 20 minutes and then at room temperature overnight. To this reaction mixture was added an aqueous saturated solution of ammonium chloride, and the mixture was extracted with ethyl acetate (50 ml×4). Then, the combined ethyl acetate layers were washed with water (50 ml) and brine (50 ml), dried over anhydrous sodium sulfate, and concentrated. Purification by column chromatography (silica gel, ethyl acetate) yielded a pure product of dimethyl 3,3-dimethyl-2-oxo-4-phenylbutylphosphonate (2.3144 g, 8.14 mmol, 89.5%). This compound was assigned the structure by the following data: m.p. 39°-46° C. (colorless needle-like crystal)

IR(KBr): 3370, 3055, 3025, 2970, 2900, 2855, 2820, 1698, 1603, 1495, 1468, 1418, 1393, 1375, 1335, 1283, 1263, 1243, 1208, 1183, 1158, 1128, 1038, 969, 919, 889, 849, 812, 797, 759, 729, 706, 664, 614 cm$^{-1}$.

NMR(100 MHz, CDCl$_3$, δ): 1.16(6H, s), 2.81(2H, s), 3.11(2H, d, J=21.55 Hz), 3.78(6H, d, J=11.21 Hz), 6.95-7.40(5H, m).

MASS(EI, m/e): 284(M+).

REFERENCE EXAMPLE 82

Methyl 2,2-dimethyl-4-oxapentanoate 83

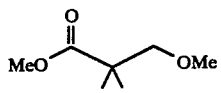

To a solution of diisopropylamine (8.71 g, 86.1 mmol) in anhydrous THF (130 ml) was added under argon atmosphere a solution of n-butyl lithium in hexane (1.62N, 53.1 ml, 86.1 mmol) at −20° C. The reaction mixture was stirred for 30 min. and cooled to −78° C. To the reaction mixture were added a solution of methyl isobutyrate (8.00 g, 78.3 mmol) in 15 ml of anhydrous THF and HMPA (14.0 g, 78.3 mmol), and the mixture was stirred for one hour at −78° C. To this was added a solution of chloromethyl methyl ether (7.57 g, 94.0 mmol) in 15 ml of anhydrous THF, and the reaction mixture was stirred for 2 hrs. at −78° C. To an aqueous saturated solution of ammonium chloride (300 ml) were added the above solution and water (100 ml). The resulting mixture was extracted with ether (400 ml). The aqueous layer was reextracted with ether (200 ml×2). The combined ether layers were washed with water (300 ml) and with brine, and dried over anhydrous magnesium sulfate. Ether was distilled out at normal pressure and the residue was distilled (b.p. 98°-99° C./107 mmHg) to give methyl 2,2-dimethyl-4-oxapentanoate (8.38 g, 57.4 mmol, 73.3%) as an oily material. The product was assigned the structure by the following data.

IR(liquid film): 2970, 2880, 1730, 1470, 1450, 1430, 1390, 1360, 1310, 1260, 1230, 1200, 1150, 1110, 1030, 1010, 980, 960, 930, 880, 810, 770 cm$^{-1}$.

NMR(90 MHz, CDCl$_3$, δ): 1.19(6H, s); 3.33(3H, s); 3.38(2H, s); 3.68(3H, s).

MASS(CI, m/e): 147(M++1).

REFERENCE EXAMPLE 84

Dimethyl 3,3-dimethyl-2-oxo-5-oxahexylphosphonate 84

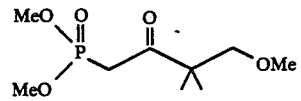

To a solution of dimethyl methylphosphonate (9.62 g, 77.0 mmol) in anhydrous THF (130 ml) was added under argon atmosphere a solution of n-butyl lithium in hexane (1.62N, 47.5 ml, 77.0 mmol) at −78° C. The reaction mixture was stirred for 30 min. and a solution of methyl 2,2-dimethyl-4-oxapentanoate (4.50 g, 30.8 mmol) in anhydrous THF (15 ml) was added at −78° C. This mixture was stirred for 30 min., allowed to warm to room temperature and stirred for 30 min. The resulting solution was neutralized with acetic acid, water (20 ml) was added, and the mixture was then concentrated. Ethyl acetate (120 ml) and water (20 ml) were added to the residue. The organic layer was separated from the aqueous layer, washed with water (50 ml), and with brine (50 ml), dried over anhydrous magnesium sulfate, and concentrated. Distillation of the residue (b.p. 104°-107° C./0.4 mmHg) gave dimethyl 3,3-dimethyl-2-oxo-5-oxahexylphosphonate (5.96 g, 25.0 mmol, 81.2%) as an oily material. The product was assigned the structure by the following data.

IR(liquid film): 3470, 2960, 1710, 1460, 1400, 1370, 1310, 1260, 1110, 1040, 960, 930, 870, 810, 730 cm$^{-1}$.

NMR(90 MHz, CDCl$_3$, δ): 1.17(6H, s); 3.23(2H, d, J=21.3 Hz); 3.32(3H, s); 3.36(2H, s); 3.79(6H, d, J=11.2 Hz).

MASS(EI, m/e): 238(M+).

REFERENCE EXAMPLE 85

Ethyl 2,2-dimethyl-4-oxahexanoate 85

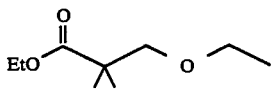

To a solution of diisopropylamine (4.36 g, 43.1 mmol) in 100 ml of anhydrous THF was added under argon atmosphere a solution of n-butyl lithium in hexane (1.61N, 26.8 ml, 43.1 mmol) at −20° C. The reaction mixture was stirred for one hour and cooled to −78° C. To the resulting mixture were added a solution of ethyl isobutyrate (5.00 g, 43.1 mmol) in anhydrous THF (15 ml) and HMPA (7.73 g, 43.1 mmol), and the mixture was stirred for 1.5 hrs. at −78° C. A solution of chloromethyl ethyl ether (4.89 g, 51.7 mmol) in 20 ml of anhydrous THF was added, stirred for 2 hrs. at −78° C., and then stirred for 2 hrs. at room temperature. To the resulting mixture were added an aqueous saturated solution of ammonium chloride (150 ml) and water (50 ml), and the mixture was extracted with ether (400 ml). The organic layer was washed with water (150 ml) and with brine, and dried over anhydrous magnesium sulfate. Ether was distilled out at normal pressure. Distillation of the resulting material (b.p. 80°-84° C./30 mmHg) gave ethyl 2,2-dimethyl-4-oxahexanoate (4.23 g, 24.3 mmol, 56.4%) as an oily material. The product was assigned the structure by the following data.

IR(liquid film): 2990, 2950, 2890, 1730, 1480, 1390, 1370, 1310, 1270, 1150, 1120, 1040, 940, 870, 770 cm$^{-1}$.

NMR(90 MHz, CDCl$_3$, δ): 1.0-1.4(6H, m); 1.18(6H, s); 3.41(2H, s); 3.47(2H, q, J=7.0 Hz); 4.14(2H, q, J=7.1 Hz).

MASS(CI, m/e): 175 (M++1).

REFERENCE EXAMPLE 86

Dimethyl 3,3-dimethyl-2-oxo-5-oxaheptylphosphonate 86

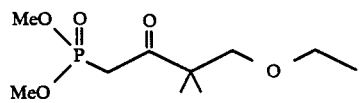

To a solution of dimethyl methylphosphonate (7.18 g, 57.5 mmol) in anhydrous THF (100 ml) was added under argon atmosphere a solution of n-butyl lithium in hexane (1.61N, 35.7 ml, 57.5 mmol) at 31 78° C. The reaction mixture was stirred for 30 min. and a solution of ethyl 2,2-dimethyl-4-oxahexanoate (4.00 g, 23.0 mmol) in anhydrous THF (15 ml) was added at −78° C. The resulting mixture was stirred for 30 min., allowed to warm to room temperature and stirred for one hour. The resulting mixture was then neutralized with acetic acid, then water (20 ml) was added, and the mixture was concentrated. Ethyl acetate (120 ml) and water (30 ml) were added to the residue. The organic layer was separated, washed with water (50 ml) and with brine, dried over anhydrous magnesium sulfate, and concentrated. Distillation of the residue (b.p. 106°-110° C./0.4 mmHg) gave dimethyl 3,3-dimethyl-2-oxo-5-oxaheptyl-phosphonate (4.19 g, 16.6 mmol, 72.2%) as an oily material. The product was assigned the structure by the following data.

IR(liquid film): 3480, 2980, 2880, 1710, 1470, 1390, 1370, 1320, 1260, 1190, 1120, 1040, 870, 810, 730 cm$^{-1}$.

NMR(90 MHz, CDCl$_3$, δ): 1.15(3H, t, J=7.0 Hz); 1.17(6H, s); 3.1-3.6(6H, m); 3.79(6H, d, J=11.0 Hz).

MASS(CI, m/e): 253(M$^+$+1).

REFERENCE EXAMPLE 87

Chloromethyl propyl ether 87

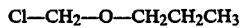

Anhydrous hydrogen chloride was passed through a solution of trioxan (15.0 g, 0.167 mol) in n-propanol (30.0 g, 0.5 mol) for 4 hrs. with stirring while being cooled in an ice bath. The upper layer was dried over calcium chloride, and distilled to give a colourless and transparent oil of chloromethyl propyl ether (29.8 g, 0.275 mol, b.p. 105°-110° C., yield: 55%). The product was assigned the structure by the following data.

IR(liquid film): 2950, 2870, 1450, 1380, 1310, 1280, 1240, 1110, 1050, 995, 940, 920, 890, 860 cm$^{-1}$.

NMR(90 MHz, CDCl$_3$, δ): 0.95(3H, t, J=7.3 Hz); 1.61 (2H, m); 3.65(2H, t, J=6.5 Hz); 5.51(2H, s).

MASS(EI, m/e): 79(M$^+$-C$_2$H$_5$). (CI, m/e): 73(M$^+$+1-HCl).

REFERENCE EXAMPLE 88

Methyl 2,2-dimethyl-4-oxaheptylate 88

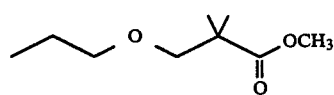

To a solution of anhydrous diisopropylamine (11.9 g, 0.118 mol) in 100 ml of anhydrous THF was added dropwise under argon atmosphere a solution of n-butyl lithium in hexane (1.59N, 74.2 ml, 0.118 mol) with stirring at −78° C. and further stirred for 30 min. To this solution was adddded dropwise a solution of methyl isobutyrate (10.0 g, 0.098 mol) in anhydrous THF (10 ml). The resulting mixture was stirred for 30 min. HMPA (7 g, 0.039 mol) and chloromethyl propyl ether (13.8 g, 0.127 mol) were added, and stirred for 30 min. The reaction mixture was allowed to warm to room temperature. To the mixture was then added an aqueous saturated solution of ammonium chloride (300 ml) cooled in an ice bath. The organic layer was washed with 30 ml of water and with 20 ml of brine, and dried over anhydrous sodium sulfate. The solvent was distilled out successively at normal pressure and then the residue was distilled in vacuo to give a colourless and transparent oil of methyl 2,2-dimethyl-4-oxaheptylate (12.6 g, 0.0724 mol, b.p. 84°-87° C./30 mmHg, yield: 73.9%). The product was assigned the structure by the following data.

IR(liquid film): 2960, 2870, 2800, 1730, 1460, 1430, 1380, 1360, 1340, 1300, 1220, 1185, 1150, 1110, 1050, 1030, 1005, 980, 950, 930, 865, 810, 770 cm$^{-1}$.

NMR(90 MHz, CDCl$_3$, δ): 0.88(3H, t, J=7.3 Hz); 1.19 (6H, s); 1.51(2H, m); 3.37(2H, t, J=6.5 Hz); 3.40(2H, s); 3.63(3H, s).

MASS(CI, m/e): 175(M$^+$+1).

REFERENCE EXAMPLE 89

Dimethyl 3,3-dimethyl-2-oxo-5-oxaoctylphosphonate 89

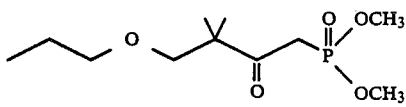

n-Butyl lithium in hexane (1.59N, 63.3 ml, 0.1 mol) was added dropwise under argon atmosphere with stirring to a solution of dimethyl methylphosphonate (12.4 g, 0.1 mol) in anhydrous THF (80 ml) at −78° C., and stirred for 30 min. To the reaction mixture was added dropwise a solution of methyl 2,2-dimethyl-4-oxahepty-late (7.0 g, 0.04 mol) in anhydrous THF (10 ml). The mixture was stirred for 30 min. and allowed to warm to 0° C. To the resulting mixture were added acetic acid (6.2 ml) and water (10 ml), and the mixture was concentrated. Water (20 ml) was added to the residue and the mixture was extracted with ethyl acetate (50 ml×2). The ethyl acetate layers were washed with water (20 ml) and with brine (20 ml), dried over anhydrous sodium sulfate, and concentrated to afford the residue. Column chromatography (silica gel; 200 g, ethyl acetate/cyclohexane: 2/1) of the residue gave a colourless and transparent oil of dimethyl 3,3-dimethyl-2-oxo-5-oxaoctylphosphonate (6.15 g, 0.023 mol, yield: 57.5%). The product was assigned the structure by the following data.

IR(liquid film): 3450, 2960, 2860, 2800, 1705, 1455, 1380, 1360, 1300, 1250, 1180, 1105, 1030, 950, 930, 800, 750, 720 cm$^{-1}$.

NMR(90 MHz, CDCl$_3$, δ): 0.89(3H, t, J=7.2 Hz); 1.17 (6H, s); 1.51(2H, m); 3.24(2H, d, J=20.9 Hz); 3.35(2H, t, J=6.5 Hz); 3.38(2H, s); 3.79(6H, d, J=11.0 Hz).

MASS(EI, m/e): 266(M$^+$).

REFERENCE EXAMPLE 90

Dimethyl 2-oxo-3-phenoxy-propylphosphonate 90

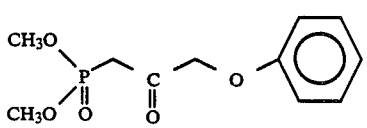

Dimethyl methylphosphonate (18 ml, 0.166 mol) was adddded to anhydrous THF (150 ml) under argon atmosphere and cooled to −78° C. After 20 min. a solution of n-butyl lithium in hexane (1.59N, 108.8 ml, 0.173 mmol) was added to the mixture. After being stirred for 30 min. a solution of methyl phenoxyacetate (10 ml, 0.069 mmol) in 10 ml of anhydrous THF was added, and the reaction mixture was stirred successively for 30 min. at −78° C. and for 30 min. at room temperature, and acidified with acetic acid. After confirming a weakly acidic pH of the solution thus obtained, THF was distilled out. Water (50 ml) was added to the residue, and the resulting mixture was extracted with ethyl acetate (150 ml×3). The combined organic layers were washed with 100 ml of water and with 100 ml of brine, dried over anhydrous sodium sulfate, and concentrated. The oily product was distilled under reduced pressure to afford dimethyl 2-oxo-3-phenoxypropylphosphonate (14.65 g, 0.057 mol, yield: 82.3%). B.p.: 145°–147° C./0.1 mmHg. The product was identified by the following data.

IR(liquid film): 3450, 3070, 3025, 2960, 2920, 2860, 1740, 1605, 1595, 1495, 1460, 1430, 1405, 1370, 1300, 1250, 1230, 1180, 1160, 1100, 1030, 890, 830, 810, 800 cm$^{-1}$.

NMR(90 MHz, CDCl$_3$, δ): 3.27(2H, d, J=22.7 Hz); 3.77(6H, d, J=11.2 Hz); 4.69(2H, s); 6.84–7.38 (5H, m).

MASS(EI, m/e): 258(M+).

REFERENCE EXAMPLE 91

Methyl 2-methyl-2-phenoxypropionate 91

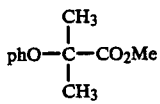

To a solution of diisopropylamine (37.00 ml, 0.264 mol) in anhydrous THF (200 ml) was added dropwise under argon atmosphere n-butyl lithium in hexane (1.62N, 163 ml, 0.264 mol) at 0° C. The reaction mixture was stirred for 30 min. at 0° C. To this was added dropwise a solution of 2-phenoxypropionic acid (20.00 g, 0.120 mol) in anhydrous THF (60 ml) and the mixture was stirred for 10 min. at 0° C. To the mixture was added dropwise HMPA (45.9 ml, 0.264 mol) and the resulting mixture was stirred for 20 min. To the mixture was added dropwise methyl iodide (15.7 ml, 0.252 mol) at 0° C. The mixture was then stirred for 4 hrs. at room temperature. The resulting mixture was acidified with 6N hydrochloric acid to pH 2 and extracted with ethyl acetate (50 ml×4). The ethyl acetate layers were washed with 50 ml of water and with 50 ml of brine, dried over anhydrous sodium sulfate, and concentrated. To the residue in 100 ml of ether was added dropwise a solution of diazomethane in ether (270 ml) at 0° C. Concentration and distillation of the solution thus obtained gave methyl 2-methyl-2-phenoxypropionate (22.8052 g, yield: 96.7%, b.p. 64.5°–75.3° C./0.22 mmHg) as a colourless oil. The product was assigned the structure by the following data.

IR(liquid film): 3000, 2950, 2900, 2820, 1735, 1595, 1490, 1460, 1385, 1365, 1288, 1233, 1193, 1175, 1140, 1066, 1023, 983, 885, 822, 750, 695 cm$^{-1}$.

NMR(100 MHz, CDCl$_3$, δ): 1.59(6H, s); 3.77(3H, s); 6.70–7.40(5H, m).

MASS(EI, m/e): 194(M+).

REFERENCE EXAMPLE 92

Dimethyl 3-methyl-2-oxo-3-phenoxybutylphosphonate 92

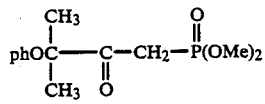

N-butyl lithium in hexane (1.62N, 38.1 ml, 0.0617 mol) was added dropwise under argon atmosphere to a solution of dimethyl methylphosphonate (7.0 ml, 0.0643 mol) in anhydrous THF (100 ml) at −78° C. The reaction mixture was stirred for 30 min. To the mixture was added dropwise methyl 2-methyl-2-phenoxypropionate (5.00 g, 0.0257 mol), and the mixture was stirred for 20 min. at −78° C. and further stirred for 30 min. at room temperature. To the resulting mixture were added 10 ml of water and acetic acid (3.2 ml, 0.0559 mol), and then the mixture was concentrated. The residue was extracted with ethyl acetate (50 ml×4). The combined ethyl acetate layers were washed with 50 ml of water and with 50 ml of brine, dried over anhydrous sodium sulfate, and concentrated. The residue thus obtained was purified by column chromatography (silica gel, ethyl acetate/cyclohexane: 3/1) to give a purified dimethyl 3-methyl-2-oxo-3-phenoxybutylphosphonate (6.5867 g, 0.0257 mol, 100%). The product was assigned the structure by the following data.

IR(liquid film): 3470, 3005, 2970, 1723, 1593, 1493, 1458, 1386, 1368, 1250, 1225, 1160, 1030, 957, 883, 840, 805, 760, 698 cm$^{-1}$.

NMR(100 MHz, CDCl$_3$, δ): 1.49(6H, s); 3.41(2H, d, J=20.89 Hz); 3.79(6H, d, J=11.22 Hz); 6.72–7.40(5H, m).

MASS(EI, m/e): 286(M+).

REFERENCE EXAMPLE 93

2-Pentyne-1-ol 93

To a stirred liquid ammonia (500 ml) were added a piece of lithium and a piece of ferric nitrate. After the blue color of the mixture had disappeared, lithium (8 g, 1.16 mol) was added to the mixture little by little. One hour after the completion of the above addition, 2-propyne-1-ol (16.3 g, 0.29 mol) was added to the mixture, and 30 min. later was further added ethyl bromide (37.6 g, 0.35 mol). 20 Min. later, an excess amount of ammonium chloride was added to the mixture and the liquid ammonia was evaporated over one day. To the residue was added water (100 ml) and the mixture was filtered and extracted with ether (150 ml×7). The combined ether layers were washed with brine (150 ml) and dried over anhydrous sodium sulfate. The ether was then distilled out under normal pressure. Distillation in vacuo of the residue gave 2-pentyne-1-ol (14.1 g, 0.17 mol, 57.9%, B.p.: 62°–65° C./20 mmHg). The product was assigned the structure by the following data.

IR (liquid film): 3300, 2970, 2930, 2875, 2295, 2225, 1450, 1415, 1315, 1225, 1130, 1060, 1005, 945, 780, 730 cm$^{-1}$.

NMR (90 MHz, CDCl$_3$, δ): 1.12 (3H, t, J=7.4 Hz); 1.8–2.4 (3H, m); 4.22 (2H, t, J=2.7 Hz).

MASS (EI, m/e): 84 (M+).

REFERENCE EXAMPLE 94

1-Bromo-2-pentyne 94

   94

Under argon atmosphere, to a stirred solution of 2-pentyne-1-ol (14 g, 0.17 mol) in anhydrous ether (60 ml) were added pyridine (1.2 ml) and phosphorus tribromide (16.2 g, 0.06 mol) at −30° C. and the reaction mixture was stirred for 2 hrs. at −30° C. and then one hour at room temperature. The resulting mixture was washed with brine (110 ml) and dried over anhydrous magnesium sulfate. Distillation out of the ether under normal pressure followed by distillation in vacuo of the residue gave 1-bromo-2-pentyne (12.8 g, 0.087 mol, 52.3%, B.p.: 80°–83° C./80 mmHg). The product was assigned the structure by the following data.

IR (liquid film): 2980, 2940, 2880, 2850, 2320, 2240, 1445, 1420, 1370, 1315, 1205, 1150, 1055, 950, 860, 710, 610 cm$^{-1}$.

NMR (90 MHz, CDCl$_3$, δ): 1.14 (3H, t, J=7.5 Hz); 2.26 (2H, t, q, J=2.3, 7.5 Hz); 3.92 (2H, t, J=2.3 Hz).

MASS (EI, m/e): 146 (M+).

REFERENCE EXAMPLE 95

Ethyl 2-methyl-4-heptynoate 95

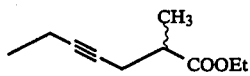   95

Under argon atmosphere a solution of diethyl methylmalonate (20.0 g, 0.114 mol) in anhydrous THF (20 ml) was added dropwise into a stirred solution of sodium hydride (60% mineral oil dispersion, 4.6 g, 0.114 mol) in anhydrous THF (200 ml) over one hour at room temperature. A solution of 1-bromo-2-pentyne (14.0 g, 0.095 mol) in anhydrous THF (15 ml) was then added dropwise over 20 min. at room temperature. To the resulting mixture was added water (30 ml), and the mixture was neutralized with 3N hydrochloric acid, and concentrated. The residue was extracted with ethyl acetate (200 ml×2). The combined ethyl acetate layers were washed with water (50 ml) and with brine (30 ml), dried over anhydrous sodium sulfate, and concentrated to give a crude material of ethyl 2-carboethoxy-2-methyl-4-heptynoate (26.0 g). To a stirred solution of the crude material in ethanol (200 ml) was added 0.994N aqueous NaOH solution (169 ml, 0.168 mol) under ice-cooling and the mixture was stirred for 14 hrs. at room temperature. After dilution with water (30 ml), the resulting mixture was concentrated, neutralized with 6N hydrochloric acid under ice-cooling and extracted with ethyl acetate (100 ml×3). The combined ethyl acetate layers were washed with brine (50 ml), dried over anhydrous sodium sulfate, and concentrated to give a crude material of 2-carboethoxy-2-methyl-4-heptynoic acid (22.1 g). The crude material was heated at 180° C. for 2 hrs., cooled and dissolved in 100 ml of ether. A solution of diazomethane in ether was added to the solution excessively. The resulting mixture was concentrated and distilled in vacuo to give ethyl 2-methyl-4-heptynoate (12.21 g, 0.073 mol, 76%, B.p.: 118°–125° C./56 mmHg) containing methyl 2-methyl-4-heptynoate in an amount of 10% by weight.

IR (liquid film): 2975, 2940, 2880, 2850, 1730, 1450, 1365, 1340, 1310, 1275, 1240, 1170, 1110, 1040, 1010, 920, 855, 780 cm$^{-1}$.

NMR (90 MHz, CDCl$_3$, δ): 1.10 (3H, t, J=7.2 Hz); 1.22 (3H, d, J=7.3 Hz); 1.27 (3H, t, J=6.2 Hz); 1.9–2.8 (5H, m); 4.15 (2H, q, J=7.2 Hz).

MASS (EI, m/e): 168 (M+)

REFERENCE EXAMPLE 96

Dimethyl 3-methyl-2-oxo-5-octynylphosphonate 96

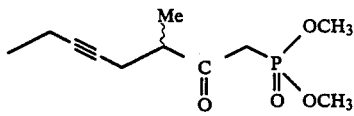   96

Under argon atmosphere, to a stirred solution of dimethyl methylphosphonate (7.91 ml, 0.074 mol) in anhydrous THF (150 ml) was added dropwise a solution of n-butyl lithium in hexane (1.71N, 43 ml, 0.074 mol) and the mixture was stirred for 30 min at −78° C. A solution of ethyl 2-methyl-4-heptynoate (5.0 g, 0.03 mol) in anhydrous THF (5 ml) was dropwise added into the mixture, and the resulting mixture was stirred for 30 min. at −78° C. The resulting mixture was allowed to room temperature and 30 min. later, to the solution were then added water (10 ml) and acetic acid (45 ml) under ice-cooling, and concentrated. The residue was diluted with water (20 ml) and extracted with ethyl acetate (50 ml×2). The combined ethyl acetate layers were washed with water (20 ml) and with brine (20 ml), dried over anhydrous sodium sulfate, and concentrated. The residue was distilled to give dimethyl 3-methyl-2-oxo-5-octynylphosphonate (6.55 g, 0.027 mol, 88%, B.p.: 118°–121° C./0.35 mmHg). The product was assigned the structure by the following data.

IR (liquid film): 3450, 2960, 2850, 1700, 1450, 1390, 1370, 1350, 1310, 1250, 1170, 1030, 870, 830, 805, 720 cm$^{-1}$.

NMR (90 MHz, CDCl$_3$, δ): 1.1 (3H, t, J=7.4 Hz); 1.19 (3H, d, J=6.8 Hz); 1.9–2.5 (4H, m); 2.7–3.1 (1H, m); 2.0–2.4 (2H, m); 3.79 (6H, d, J=11.2 Hz).

MASS (EI, m/e): 246 (M+).

REFERENCE EXAMPLE 97

Ethyl 2,2-dimethyl-4-hexynoate 97

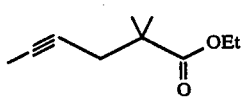   97

Under argon atmosphere, a solution of n-butyl lithium in hexane (1.64N, 26 ml, 0.043 mol) was dropwise added with stirring into a solution of anhydrous diisopropylamine (4.3 g, 0.043 mol) in anhydrous THF (35 ml) at −20° C. and the reaction mixture was stirred for 30 min. at −20° C. To the mixture was added dropwise a solution of ethyl 2-methyl-4-hexynoate (5.4 g, 0.035 mol) in anhydrous THF (15 ml) at −20° C. To the mixture was added anhydrous HMPA (2.25 ml, 0.013 mol). The reaction mixture was heated to room temperature and then stirred for 40 min. The mixture was again cooled to −30° C. and to the mixture was dropwise added a solution of methyl iodide (6.05 g, 0.043 mol) in anhydrous THF (5 ml). After warming to room temperature, the mixture was stirred for one hour, acetic acid (2.5 ml, 0.043 mol) was added, and the resulting mixture was concentrated. The residue was diluted with water (50 ml) and extracted with ethyl acetate (100 ml×2). The combined ethyl acetate layer were washed with water (30 ml) and with brine (20 ml), dried over anhydrous sodium sulfate, and concentrated. Distillation of the residue in vacuo give ethyl 2,2-dimethyl-4-hexynoate (3.7 g, 0.022 mol, 62%, B.p.: 65°–68° C./10 mmHg). The product was assigned the structure by the following data.

IR (liquid film): 2980, 2925, 2870, 2230, 1715, 1465, 1380, 1360, 1310, 1300, 1250, 1190, 1130, 1025, 980, 945, 910, 860, 770, 740 cm$^{-1}$.

NMR (90 MHz, CDCl$_3$, δ): 1.1–1.4 (9H, m); 1.77 (3H, t, J=2.5 Hz); 2.36 (2H, q, J=2.5 Hz); 4.14 (2H, q, J=7.1 Hz).

MASS (EI, m/e): 168 (M+).

REFERENCE EXAMPLE 98

Dimethyl 3,3-dimethyl-2-oxo-5-heptynylphosphonate 98

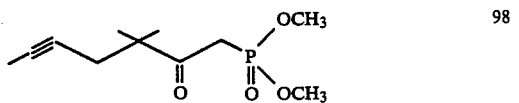

Under argon atmosphere, a solution of n-butyl lithium in hexane (33 ml, 0.054 mol, 1.04N) was added dropwise with stirring into a solution of dimethyl methylphosphonate (6.82 g, 0.055 mol) in anhydrous THF (100 ml) at −78° C. and the mixture was stirred for 30 min. at −78° C. To the mixture was added dropwise a solution of ethyl 2,2-dimethyl-4-hexynoate (3.7 g, 0.022 mol) in anhydrous THF (15 ml) and the mixture was stirred for 30 min. at −78° C. and then for one hour at room temperature. To the resulting mixture were added acetic acid (3.1 ml, 0.054 mol) and water (10 ml), and the mixture was then concentrated. The residue was diluted with water (20 ml) and extracted with ethyl acetate (100 ml×2). The combined ethyl acetate layers were washed with water (20 ml) and with brine (20 ml), dried over anhydrous sodium sulfate, and concentrated. Distillation of the residue in vacuo gave dimethyl 3,3-dimethyl-2-oxo-5-heptynylphosphonate (5.04 g, 0.020 mol, 93%, B.p.: 108°–110° C./0.15 mmHg). The product was assigned the structure by the following data.

IR (liquid film): 3450, 2950, 2905, 2850, 2220, 1700, 1455, 1375, 1355, 1240, 1175, 1020, 860, 835, 800, 710 cm$^{-1}$.

NMR (90 MHz, CDCl$_3$, δ): 1.23 (6H, m); 1.77 (3H, t, J=5.2 Hz); 3.24 (2H, d, J=21.3 Hz); 2.34 (2H, q, J=2.6 Hz); 3.80 (6H, d, J=11.2 Hz).

MASS (EI, m/e): 246 (M+).

REFERENCE EXAMPLE 99

2-Octyne-1-ol 99

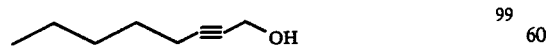

Under argon atmosphere, a piece of lithium was added to a liquid ammonia (250 ml) in a three neck distillation flask. After the reaction mixture had became dark blue, a catalytic amount of ferric nitrate nonahydrate was added thereto under argon atmosphere. A piece of lithium (2.75 g, 396 mmol) was successively added over 30 min. and the mixture was stirred for one hour. Propargyl alcohol (8.16 g, 146 mmol) was then added and the mixture was stirred for 30 min. Further, n-pentyl bromide (20 g, 132 mmol) was added and the mixture was stirred for 10 min. and allowed to stand overnight at room temperature. To the resulting mixture were added hydrated ether (50 ml) and water (200 ml), and the mixture was then extracted with ether (200 ml, 100 ml, 50 ml×3). The combined ether layers were washed with water (400 ml) and with brine (400 ml), dried over anhydrous sodium sulfate (50 g), and concentrated. Distillation of the residue gave a colorless oily product of 2-octyne-1-ol (9.5758 g, 52%, B.p.: 58°–61° C./0.3 mmHg). The product was assigned the structure by the following data.

IR (liquid film): 3400, 2910, 2850, 2278, 2216, 1447, 1423, 1374, 1323, 1223, 1131, 1102, 1060, 1000, 718 cm$^{-1}$.

NMR (100 MHz, CDCl$_3$, δ): 0.70–1.05 (3H, m), 1.09–1.23 (6H, m); 1.67 (1H, broad s); 1.97–2.39 (2H, m); 4.25 (2H, t, J=2.2 Hz).

MASS (CI, m/e): 144 (M++18).

REFERENCE EXAMPLE 100

1-Bromo-2-octyne 100

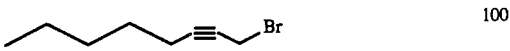

Under argon atmosphere, anhydrous pyridine (0.4 ml, 4.9 mmol) was added to a solution of 2-octyne-1-ol (9.4658 g, 75.0 mmol) in anhydrous ether (50 ml). To the mixture was added dropwise phosphorus tribromide (2.35 ml, 25.0 mmol) at −30° to −35° C. and the mixture was stirred at the same temperature for one hour and then stirred for one hour at room temperature under argon atmosphere. To the resulting mixture was added brine (100 ml), and the mixture was then extracted with ether (50 ml×4). The combined ether layers were washed with an aqueous saturated solution of sodium bicarbonate (150 ml), with water (150 ml) and with brine (150 ml), dried over anhydrous sodium sulfate (40 g), and concentrated. Distillation of the residue gave a colorless oily product of 1-bromo-2-octyne (9.1493 g, 65%, B.p.: 53°–58° C./0.39 mmHg). The product was assigned the structure by the following data.

IR (liquid film): 2949, 2850, 2300, 2220, 1458, 1427, 1379, 1325, 1302, 1283, 1210, 1150, 1105, 1085, 1015, 978, 904, 859, 775, 720, 700 cm$^{-1}$.

NMR (100 MHz, CDCl$_3$, δ): 0.70–1.07 (3H, m), 1.07–1.63 (6H, m); 2.02–2.41 (2H, m); 3.93 (2H, t, J=2.2 Hz).

MASS (CI, m/e): 189 (M++1).

REFERENCE EXAMPLE 101

Ethyl 2-methyl-4-decynoate 101

Under argon atmosphere, a solution of diethyl methylmalonate (12.3 ml, 71.52 mmol) in anhydrous THF (15 ml) was added to a suspension of sodium hydride (60% mineral oil dispersion, 2.67 g, 66.75 mmol) in anhydrous THF (90 ml) at room temperature and the mixture was stirred for 20 min. The mixture was cooled on an ice-bath and a solution of 1-bromo-2-octyne (9.011 g, 47.68 mmol) in anhydrous THF (10 ml) was added under argon atmosphere. The mixture was stirred for 30 min. at room temperature, 35 ml of 3N hydrochloric acid was added, and the resulting mixture was concentrated. The residue was diluted with water (50 ml) and extracted with ethyl acetate (40 ml×3). The combined ethyl acetate layers were washed with an aqueous saturated solution of sodium bicarbonate (100 ml), with water (100 ml) and with brine (100 ml), dried over anhydrous magnesium sulfate (30 g), and concentrated to give an oily material (18.3276 g).

To a solution of the oily material in ethanol (170 ml) was added a 1N aqueous NaOH solution (110 ml, 110 mmol) and the mixture was stirred under argon atmosphere for 18 hrs. at room temperature. The mixture was then mixed with a 1N aqueous NaOH solution (20 ml) and the mixture was stirred for 4 hrs. and 15 min. at 40°-45° C. To the resulting mixture was added 3N hydrochloric acid (80 ml), and the mixture was concentrated and extracted with ethyl acetate (70 ml, 50 ml×2). The combined ethyl acetate layers were washed with water (150 ml×2) and with brine (150 ml), dried over anhydrous sodium sulfate (50 g), and concentrated to give an oily material (13.8793 g).

The obtained oily material was heated under argon atmosphere at 180° C. for one hour and then 10 ml of ether was added. The mixture was treated with diazomethane under ice-cooling and concentrated to afford an oily material (9.1324 g), which was then distilled to give a colorless oily product of ethyl 2-methyl-4-decynoate (8.6349 g, 81%, B.p.: 94°-95° C./0.18 mmHg). GLC of the product revealed the ratio of ethyl ester to methyl ester to be 15. GLC: 3% OV-17; 1 m; column temperature of 60° C.; injection temperature of 180° C. The product was assigned the structure by the following data (NMR and Mass data shown only for ethyl ester).

IR (liquid film): 2925, 2870, 1735, 1458, 1374, 1350, 1305, 1250, 1228, 1173, 1110, 1050, 1024, 858 cm$^{-1}$.

NMR (100 MHz, CDCl$_3$, δ): 0.71-1.02 (3H, m); 1.02-1.71 (6H, m); 1.23 (3H, d, J=6.38 Hz); 1.26 (3H, t, J=7.03 Hz); 1.86-2.79 (5H, m); 4.14 (2H, q, J=7.03 Hz).

MASS (EI, m/e): 210 (M+).

REFERENCE EXAMPLE 102

Ethyl 2,2-dimethyl-4-decynoate 102

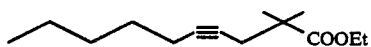

Diisopropylamine (6.4 ml, 45.6 mmol) was added under argon atmosphere into anhydrous THF (70 ml) in a three necked distillation flask. To the mixture was added 1.67N n-butyl lithium in hexane (27.3 ml, 45.6 mmol) at −20° C., and the resulting mixture was stirred for 20 min. under argon atmosphere. To the mixture was added a solution of ethyl 2-methyl-4-decynoate (8.5121 g, 38.0 mmol) in anhydrous THF (10 ml) and HMPA (7.93 ml, 45.6 mmol) and the mixture was stirred for 30 min. at room temperature. The mixture was cooled to −20° C., and methyl iodide (2.37 ml, 38.0 mmol) was added. The mixture was stirred for 10 min., 6N hydrochloric acid (12 ml) and water (50 ml) were added, and the resulting mixture was extracted with ethyl acetate (50 ml×3). The combined ethyl acetate layers were washed with a saturated aqueous solution of sodium bicarbonate (150 ml), with water (150 ml) and with brine (150 ml), dried over anhydrous magnesium sulfate (50 g), and concentrated to give an oily material (9.2804 g). The distillation of the material afforded a colorless oily product of ethyl 2,2-dimethyl-4-decynoate (7.9839 g, 88%). B.p.: 80°-84° C. (0.12 mmHg). The product was assigned the structure by the following data (NMR and MASS data shown only for ethyl ester).

IR (liquid film): 2951, 2925, 2853, 1725, 1462, 1383, 1362, 1319, 1300, 1258, 1199, 1130, 1026, 975, 906, 860, 768, 740 cm$^{-1}$.

NMR (100 MHz, CDCl$_3$, δ): 0.73-1.01 (3H, m); 1.05-1.73 (6H, m); 1.24 (6H, s); 1.24 (3H, t, J=7.03 Hz); 1.93-2.24 (2H, m); 2.38 (2H, t, J=2.2 Hz); 4.14 (2H, q, J=7.03 Hz).

MASS (EI, m/e): 224 (M+).

REFERENCE EXAMPLE 103

Dimethyl 3,3-dimethyl-2-oxo-5-undecynylphosphonate 103

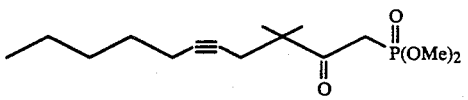

To a solution of dimethyl methylphosphonate (8.24 ml, 76.12 mmol) in anhydrous THF (250 ml) was added 1.71N n-butyl lithium in hexane (40.8 ml, 69.92 mmol) under argon atmosphere at −78° C. The mixture was stirred for 20 min. and then a solution of ethyl 2,2-dimethyl-4-decynoate (7.2468 g, 30.4 mmol) in anhydrous THF (10 ml) was added. The mixture was stirred for 30 min., acetic acid (2.2 ml) was added, and the resulting mixture was concentrated. The residue was diluted with water (40 ml) and extracted with ethyl acetate (40 ml×3). The combined ethyl acetate layers were washed with brine (100 ml×2), dried over anhydrous magnesium sulfate (40 g), and concentrated to give an oily material (9.8282 g). Distillation of the material gave a colorless oily product of dimethyl 3,3-dimethyl-2-oxo-5-undecynylphosphonate (7.0663 g, 75%, B.p.: 153° C./0.18 mmHg). The product was assigned the structure by the following data.

IR (liquid film): 3450, 2949, 2920, 2850, 1701, 1460, 1380, 1362, 1250, 1180, 1028, 870, 860, 804, 722 cm$^{-1}$.

NMR (100 MHz, CDCl$_3$, δ): 0.70-1.01 (3H, m); 1.01-1.65 (6H, m); 1.23 (6H, s); 1.90-2.26 (2H, m); 2.36 (2H, t, J=2.2 Hz); 3.23 (2H, d, J=21.33 Hz); 3.80 (6H, d, J=11.0 Hz).

MASS (EI, m/e): 302 (M+).

REFERENCE EXAMPLE 104

15-Oxo-2,5,6,7-tetranor-4-oxa-4,8-inter-m-phenylene PGI₂ methyl ester, 11-acetate (104)

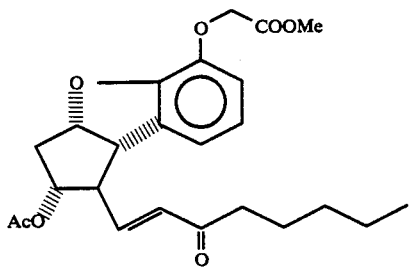

Methyl 2α-acetoxy-1β-hydroxymethyl-3aβH,8bβH-2,3,3a,8b-tetrahydro-1H-5-cyclopenta[b]benzofuranyloxyacetate (600 mg, 1.78 mmol) was dissolved in anhydrous THF (10 ml). Under argon atmosphere, anhydrous DMSO (1.26 ml, 17.8 mmol), anhydrous pyridine (0.07 ml, 0.89 mmol), trifluoroacetic acid (0.06 ml, 0.80 mmol), and D.C.C. (551 mg, 2.67 mmol) were added to the solution and the resulting mixture was stirred at room temperature for 2 hours.

To a suspension of sodium hydride (60% dispersion in mineral oil, 135 mg, 3.38 mmol) in anhydrous THF (5 ml) was added a solution of dimethyl 2-oxo-heptylphosphonate (791 mg, 3.56 mmol) in anhydrous THF (5 ml) under argon atmosphere. The resulting mixture was stirred at room temperature for 30 minutes. To the reaction mixture was added the aldehyde solution prepared above at 0° C. The resulting mixture was allowed to warm to room temperature and stirred for 30 minutes. The reaction mixture was neutralized with acetic acid. After concentration of the reaction mixture, ethyl acetate was added to the residue and the resulting mixture was then filtered. The filtrate was washed with water and with brine, and dried over anhydrous magnesium sulfate. After concentration, the residue was passed through a short silica gel column to remove solid materials. Purification of the product by column chromatography (Merck, Lobar column; ethyl acetate/cyclohexane 1/3) gave oily material, 15-oxo-2,5,6,7-tetranor-4-oxa-4,8-inter-m-phenylene PGI₂ methyl ester, 11-acetate (503 mg, 1.17 mmol, 65.6%). The structure was identified by the following data.

IR (liquid film): 3020, 2950, 2920, 2850, 1750, 1710, 1680, 1620, 1600, 1480, 1460, 1430, 1370, 1310, 1270, 1210, 1190, 1110, 1070, 1030, 980, 850, 750, 710, 670 cm$^{-1}$.

NMR (90 MHz, CDCl₃, δ): 0.8–1.0 (3H, m); 1.1–1.8 (6H, m); 1.81 (3H, s); 2.0–3.1 (5H, m); 3.6–3.9 (1H, m); 3.78 (3H, s); 4.72 (2H, s); 5.01 (1H, q, J=5.9 Hz); 5.15–5.5 (1H, m); 6.17 (1H, d, J=15.8 Hz); 6.6–6.9 (4H, m).

MASS (EI, m/e): 430 (M⁺).

REFERENCE EXAMPLE 105

15-Oxo-20a-homo-2,5,6,7-tetranor-4-oxa-4,8-inter-m-phenylene PGI₂ methyl ester, 11-benzoate (105)

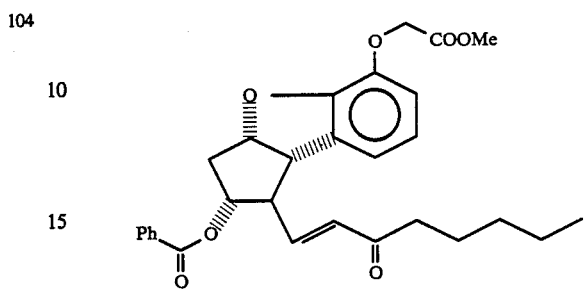

Methyl 2α-benzoyloxy-1β-hydroxymethyl-3aβH,8bβH-2,3,3a,8b-tetrahydro-1H-5-cyclopenta[b]benzofuranyloxyacetate (1.80 g, 4.52 mmol) was dissolved in anhydrous THF (25 ml). Under argon atmosphere, anhydrous DMSO (3.2 ml, 45 mmol), anhydrous pyridine (0.11 ml, 1.40 mmol), trifluoroacetic acid (0.098 ml, 1.27 mmol), and D.C.C. (1.40 g, 6.78 mmol) were added to the solution and the resulting mixture was stirred at room temperature for 3 hours.

To a suspension of sodium hydride (60% dispersion in mineral oil, 262 mg, 6.55 mmol) in anhydrous THF (10 ml), was added a solution of dimethyl 2-oxo-octylphosphonate (1.60 g, 6.78 mmol) in anhydrous THF (10 ml) under argon atmosphere. The resulting mixture was stirred at room temperature for 30 minutes. To the reaction mixture was added the aldehyde solution prepared above at 0° C. and stirred at 0° C. for 30 minutes. The resutling reaction mixture was neutralized with acetic acid. After concentration of the solution, ethyl acetate was added to the residue. The resulting mixture was then filtered, and the filtrate was washed with water and with brine, dried over anhydrous magnesium sulfate, and concentrated. The residue was passed through a short column of silica gel (ethyl acetate/cyclohexane 1/8) and then purified by Merck Lobar column (silica gel; ethyl acetate/cyclohexane 1/4.5) to give an oily product, 15-oxo-20a-homo-2,5,6,7-tetranor-4-oxa-4,8-inter-m-phenylene PGI₂ methyl ester, 11-benzoate (1.95 g, 3.85 mmol) with a yield of 85.3%. The structure of this product was identified by the following data.

IR (liquid film): 3020, 2950, 2920, 2860, 1760, 1720, 1670, 1620, 1600, 1480, 1460, 1430, 1370, 1310, 1270, 1210, 1190, 1110, 1070, 1020, 980, 850, 750, 710, 670 cm$^{-1}$.

NMR (400 MHz, CDCl₃, δ): 0.88 (3H, t, J=6.8 Hz); 1.2–1.4 (6H, m); 1.55–1.7 (2H, m); 2.4–2.45 (1H, m); 2.57 (2H, t, J=7.5 Hz); 2.66 (1H, ddd, J=5.6, 6.6, 15.1 Hz); 3.20 (1H, ddd, J=3.9, 4.4, 8.3 Hz); 3.75 (3H, s); 3.88 (1H, dd, J=4.4, 9.0 Hz); 4.64 (1H, d, J=16.4 Hz); 4.68 (1H, d, J=16.4 Hz); 5.35 (1H, dt, J=3.9, 5.6 Hz); 5.45 (1H, ddd, J=2.9, 6.6, 9.0 Hz); 6.26 (1H, dd, J=1.0, 16.1 Hz); 6.7–6.9 (3H, m); 6.81 (1H, dd, J=8.3, 16.1 Hz); 7.31 (2H, t, J=7.8 Hz); 7.49 (1H, tt, J=1.5, 7.8 Hz); 7.57 (2H, dt, J=1.5, 7.8 Hz).

MASS (EI, m/e): 506 (M⁺).

REFERENCE EXAMPLE 106

16-Methyl-15-oxo-2,5,6,7,18,19,20-heptanor-4-oxa-4,8-inter-m-phenylene PGI₂ methyl ester, 11-benzoate (106)

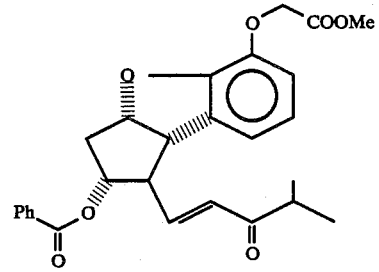

Methyl 2α-benzoyloxy-1β-hydroxymethyl-3aβH,8bβH-2,3,3a,8b-tetrahydro-1H-5-cyclopenta[b]benzofuranyloxyacetate (1.88 g, 4.72 mmol) was dissolved in anhydrous THF (25 ml). Under argon atmosphere, anhydrous DMSO (3.35 ml, 47 mmol), anhydrous pyridine (0.12 ml, 1.46 mmol), trifluoroacetic acid (0.10 ml, 1.32 mmol), and D.C.C. (1.46 g, 6.78 mmol) were added to the solution and the resulting mixture was stirred at room temperature for 3 hours.

To a suspension of sodium hydride (60% dispersion in mineral oil, 274 mg, 6.84 mmol) in anhydrous THF (10 ml), was added a solution of dimethyl 3-methyl-2-oxobutylphosphonate (1.38 g, 7.08 mmol) in anhydrous THF (10 ml) under argon atmosphere. The resulting mixture was stirred at room temperature for 30 minutes. To the reaction mixture was added the aldehyde solution prepared above at 0° C. The mixture was stirred at room temperature for 30 minutes. The resulting reaction mixture was neutralized with acetic acid. After concentration of the solution, ethyl acetate was added to the residue. The resulting mixture was filtered and the filtrate was washed with water and with brine, dried over anhydrous magnesium sulfate, and concentrated. The residue was passed through a short column of silica gel (ethyl acetate/cyclohexane 1/8) and then purified by Merck Lobar column (silica gel; ethyl acetate/cyclohexane 1/4.5) to give an oily product, 16-methyl-15-oxo-2,5,6,7,18,19,20-heptanor-4-oxa-4,8-inter-m-phenylene PGI₂ methyl ester, 11-benzoate (1.92 g, 4.14 mmol) with a yield of 87.7%. The structure of this product was confirmed by the following data.

IR (liquid film): 2980, 2880, 1760, 1720, 1670, 1630, 1600, 1490, 1470, 1380, 1320, 1280, 1220, 1200, 1120, 1070, 1060, 1030, 980, 940, 850, 760, 720, 670 cm⁻¹.

NMR (90 MHz, CDCl₃, δ): 1.13 (6H, d, J=6.8 Hz); 2.2–3.0 (3H, m); 3.05–3.35 (1H, m); 3.74 (3H, s); 3.88 (1H, dd, J=4.3, 8.6 Hz); 4.65 (2H, s); 5.2–5.6 (2H, m); 6.33 (1H, dd, J=1.0, 15.7 Hz); 6.7–7.05 (4H, m); 7.2–7.7 (5H, m).

MASS (EI, m/e): 464 (M⁺).

REFERENCE EXAMPLE 107

16,16-Dimethyl-15-oxo-2,5,6,7,18,19,20-heptanor-4-oxa-4,8-inter-m-phenylene PGI₂ methyl ester, 11-acetate (107)

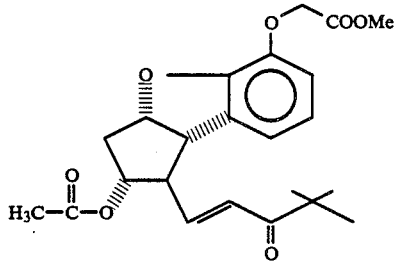

2α-Acetoxy-1β-hydroxymethyl-3aβH,8bβH-2,3,3a,8b-tetrahydro-1H-5-cyclopenta[b]benzofuranyloxyacetic acid methyl ester (1.5 g, 4.46 mmol) was dissolved in anhydrous THF (9 ml) under argon atmosphere. While stirring the solution, pyridine (0.108 ml, 1.34 mmol) and trifluoroacetic acid (0.101 ml, 1.31 mmol) were added, and then DMSO (3.11 ml, 43.8 mmol) and D.C.C. (1.22 g, 5.91 mmol) were further added. The mixture was stirred at room temperature for 2.5 hours.

To a suspension of sodium hydride (60% dispersion in mineral oil, 268 mg, 6.69 mmol) in anhydrous THF (8 ml), was added dropwise a solution of dimethyl 3,3-dimethyl-2-oxo-butylphosphonate (1.39 g, 6.69 mmol) in anhydrous THF (5 ml) under argon atmosphere while cooling with ice. The mixture was then stirred at room temperature for further 30 minutes. To the resulting solution was added the reaction mixture of the aldehyde ester prepared above while cooling with ice, and the mixture was stirred for 30 minutes. The reaction mixture was neutralized with acetic acid, filtered and then concentrated. Water (20 ml) was added to the residue and the mixture was extracted with ethyl acetate (50 ml×2). The combined ethyl acetate layers were washed with water (20 ml×1) and with brine (20 ml×1), dried over anhydrous sodium sulfate, and concentrated. Separation and purification of the residue by column chromatography (silica gel 60 g; ethyl acetate/cyclohexane 1/5) to give 16,16-dimethyl-15-oxo-2,5,6,7,18,19,20-heptanor-4-oxa-4,8-inter-m-phenylene PGI₂ methyl ester, 11-acetate (1.68 g, 4.04 mmol, yield: 90.5%). The structure of this product was confirmed by the following data.

IR (liquid film): 2960, 1755, 1735, 1685, 1620, 1480, 1460, 1435, 1370, 1320, 1290, 1240, 1190, 1110, 1070, 1000, 940, 845, 750, 730 cm⁻¹.

NMR (400 MHz, CDCl₃, δ): 1.18 (9H, s); 1.8 (3H, s); 2.1–2.3 (1H, m); 2.6–2.7 (1H, m); 2.9–3.1 (1H, m); 3.69 (1H, dd, J=6.1, 8.6 Hz); 3.79 (3H, s); 4.72 (1H, d, J=16.4 Hz); 4.73 (1H, d, J=16.1); 5.0 (1H, q, J=6.02 Hz); 5.2–5.4 (1H, m); 6.60 (1H, d, J=15.6 Hz); 6.7–6.9 (4H, m).

MASS (EI, m/e): 416 (M⁺).

REFERENCE EXAMPLE 108

16,16-Dimethyl-15-oxo-2,5,6,7,19,20-hexanor-4-oxa-4,8-inter-m-phenylene PGI$_2$ methyl ester, 11-acetate (108)

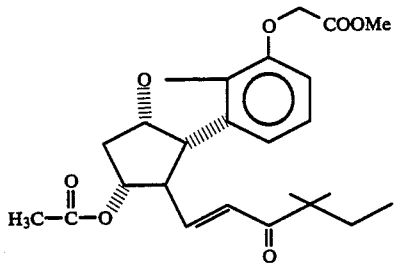

2α-Acetoxy-1β-hydroxymethyl-3aβH,8bβH-2,3,3a,8b-tetrahydro-1H-5-cyclopenta[b]benzofuranyloxyacetic acid methyl ester (1.5 g, 4.46 mmol) was dissolved in anhydrous THF (9 ml) under argon atmosphere. While stirring the solution, pyridine (0.108 ml, 1.34 mmol) and trifluoroacetic acid (0.101 ml, 1.31 mmol) were added and then DMSO (3.11 ml, 43.8 mmol) and D.C.C. (1.22 g, 5.91 mmol) were further added. The resulting mixture was stirred at room temperature for 2.5 hours.

To a suspension of sodium hydride (60% dispersion in mineral oil, 2.68 mg, 6.69 mmol) in anhydrous THF (8 ml), was added dropwise a solution of dimethyl 3,3-dimethyl-2-oxo-pentyl-phosphonate (1.49 g, 6.69 mmol) in anhydrous THF (5 ml) under argon atmosphere while cooling with ice. The mixture was then stirred at room temperature for 30 minutes. To the reaction mixture was added the solution of the aldehyde ester prepared above while cooling with ice. The mixture was then stirred at room temperature for 30 minutes. The reaction mixture was neutralized with acetic acid and subjected to filtration. The filtrate was concentrated. Water (20 ml) was added to the residue and the resulting mixture was then extracted with ethyl acetate (50 ml×2). The combined ethyl acetate layers were washed with water (20 ml×1) and with brine (20 ml×1), dried over anhydrous sodium sulfate, and concentrated. The residue was subjected to column chromatography (silica gel 50 g; ethyl acetate/cyclohexane 1/4) to separate by-products and excess Wordsworth agent and further separated and purified by Merck Lobar column (silica gel; ethyl acetate/cyclohexane 1/4) to give 16,16-dimethyl-15-oxo-2,5,6,7,19,20-hexanor-4-oxa-4,8-inter-m-phenylene PGI$_2$ methyl ester, 11-acetate (1.32 g, 3.07 mmol, yield: 68.8%). The structure of this product was confirmed by the following data.

IR (liquid film): 2960, 2880, 1740, 1690, 1620, 1595, 1480, 1460, 1440, 1375, 1320, 1290, 1240, 1190, 1110, 1070, 1030, 1000, 985, 945, 915, 890, 870, 845, 800, 765, 730 cm$^{-1}$.

NMR (400 MHz, CDCl$_3$, δ): 0.8 (3H, t, J=7.6 Hz); 1.13 (6H, s); 1.59 (2H, q, J=7.6 Hz); 1.81 (3H, s); 2.1–2.3 (1H, m); 2.6–2.7 (1H, m); 2.97 (1H, q, J=6.5 Hz); 3.69 (1H, dd, J=6.5, 8.5 Hz); 3.79 (3H, s); 4.72 (1H, d, J=16.1 Hz); 4.74 (1H, d, J=16.1 Hz); 4.9–5.1 (1H, m); 5.2–5.4 (1H, m); 6.58 (1H, d, J=14.7 Hz); 6.7–6.9 (4H, m).

MASS (EI, m/e): 430 (M$^+$).

REFERENCE EXAMPLE 109

16,16-Dimethyl-15-oxo-2,5,6,7,20-pentanor-4-oxa-4,8-inter-m-phenylene PGI$_2$ methyl ester, 11-acetate (109)

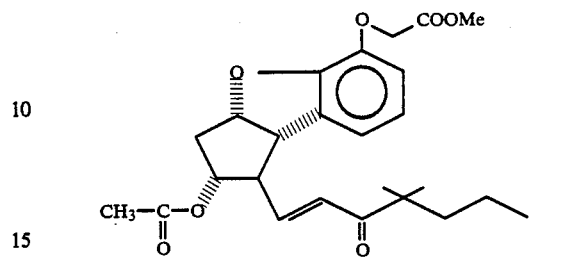

Under argon atmosphere, 2α-acetoxy-1β-hydroxymethyl-3aβH,8bβH-2,3,3a,8b-tetrahydro-1H-5-cyclopenta[b]benzofuranyloxyacetic acid methyl ester (1.5 g, 4.46 mmol) was dissolved in anhydrous THF (10 ml), and anhydrous pyridine (0.11 ml, 1.34 mmol), trifluoroacetic acid (0.10 ml, 1.34 mmol) and anhydrous DMSO (3 ml) were added, and then D.C.C. (1.38 g, 6.69 mmol) was further added to the solution. The mixture was stirred at room temperature for 2 hours.

Separately, sodium hydride (60% dispersion in mineral oil; 0.27 g, 6.69 mmol) was suspended in anhydrous THF (10 ml) in another reaction vessel. To the suspension was added a solution of dimethyl 3,3-dimethyl-2-oxo-hexylphosphonate (1.58 g, 6.69 mmol) in anhydrous THF (5 ml). The reaction mixture was stirred under argon atmosphere while cooling with ice for 30 minutes. To the reaction mixture, the supernatant of the aldehyde ester mixture prepared above was added by a syringe while cooling with ice. The residue was washed with anhydrous THF (5 ml×3). The resulting supernatant was also added to the reaction mixture and stirred at room temperature for 10 minutes. The reaction mixture was neutralized with acetic acid and then THF was distilled out. The precipitate was filtered and extracted with ethyl acetate (40 ml×3). The combined organic layers were washed with water (50 ml) and with brine (50 ml), dried over anhydrous sodium sulfate, and concentrated. The resulting oily material was purified by silica gel column chromatography (ethyl acetate/cyclohexane 1/9) to give a colorless oily product, 16,16-dimethyl-15-oxo-2,5,6,7,20-pentanor-4-oxa-4,8-inter-m-phenylene PGI$_2$ methyl ester, 11-acetate (1.77 g, 3.99 mmol, 89.4%). The structure of this product was confirmed by the following data.

IR (liquid film): 3020, 2950, 2930, 2870, 1750, 1730, 1680, 1620, 1590, 1480, 1460, 1430, 1370, 1290, 1230, 1190, 1160, 1110, 1090, 1050, 990, 980, 940, 860, 840, 750, 720 cm$^{-1}$.

NMR (400 MHz, CDCl$_3$, δ): 0.90 (3H, t, J=7.3 Hz); 1.13 (6H, s); 1.19 (2H, m); 1.51 (2H, m); 1.82 (3H, s); 2.20 (1H, ddd, J=3.5, 6.5, 14.6 Hz); 2.67 (1H, ddd, J=6.5, 7.1, 14.6 Hz); 2.97 (1H, q, J=6.5 Hz); 3.68 (1H, dd, J=6.5, 8.7 Hz); 3.79 (3H, s); 4.72 (1H, d, J=17.0 Hz); 4.76 (1H, d, J=17.0 Hz); 4.99 (1H, q, J=6.5 Hz); 5.33 (1H, ddd, J=3.5, 7.1, 8.7 Hz); 6.58 (1H, dd, J=15.1, 1.0 Hz); 6.72–6.84 (4H, m).

MASS (EI, m/e): 444 (M$^+$).

REFERENCE EXAMPLE 110

16,16-Dimethyl-15-oxo-2,5,6,7 tetranor-4-oxa-4,8-inter-m-phenylene PGI₂ methyl ester, 11-acetate (110)

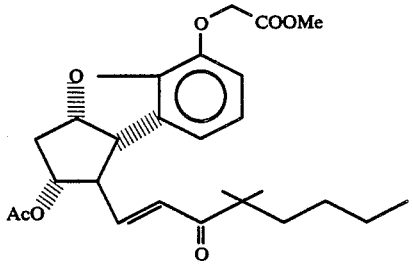

Methyl 2α-acetoxy-1β-hydroxymethyl-3aβH,8bβH-2,3,3a,8b-tetrahydro-1H-5-cyclopenta[b]benzofuranyloxyacetate (600 mg, 1.78 mmol) was dissolved in anhydrous THF (10 ml). To the solution were added anhydrous DMSO (1.26 ml, 17.8 mmol), anhydrous pyridine (0.07 ml, 0.89 mmol), trifluoroacetic acid (0.06 ml, 0.80 mmol), and D.C.C. (551 mg, 2.67 mmol) under argon atmosphere. The resulting mixture was stirred at room temperature for 2 hours.

Separately, sodium hydride (60% dispersion in mineral oil; 135 mg, 3.38 mmol) was suspended in anhydrous THF (5 ml) under argon atmosphere. To the solution was added a solution of dimethyl 3,3-dimethyl-2-oxo-heptylphosphonate (891 mg, 3.56 mmol) in anhydrous THF (5 ml). The resulting reaction mixture was stirred at room temperature for 30 minutes. To this reaction mixture, the solution of the aldehyde prepared above was added at 0° C. Then, the mixture was warmed to room temperature and stirred for 30 minutes. Acetic acid was added to neutralize the solution. After concentration, ethyl acetate was added to the residue and the mixture was filtered. The filtrate was washed with water and with brine, and dried over anhydrous magnesium sulfate. After concentration, the residue was separated and purified by silica gel column chromatography (ethyl acetate/cyclohexane 1/7) to give an oily product, 16,16-dimethyl-15-oxo-2,5,6,7-tetranor-4-oxa-4,8-inter-m-phenylene PGI₂ methyl ester, 11-acetate (764 mg, 1.67 mmol, 93.5%). The structure of this product was confirmed by the following data.

IR (liquid film): 2950, 2920, 2850, 1750, 1720, 1680, 1610, 1590, 1480, 1460, 1430, 1370, 1290, 1230, 1190, 1100, 1050, 990, 940, 840, 750, 720, 660 cm⁻¹.

NMR (90 MHz, CDCl₃, δ): 0.89 (3H, t, J=6.0 Hz); 1.13 (6H, s); 1.0–1.7 (6H, m); 1.81 (3H, s); 2.20 (1H, ddd, J=5, 7, 15 Hz); 2.68 (1H, ddd, J=6, 7, 15 Hz); 2.97 (1H, q, J=7 Hz); 3.68 (1H, dd, J=7, 9 Hz); 3.79 (3H, s); 4.73 (2H, s); 5.01 (1H, q, J=7 Hz); 5.33 (1H, ddd, J=5, 6, 9 Hz); 6.55 (1H, d, J=15 Hz); 6.76 (3H, s); 6.85 (1H, dd, J=7, 15 Hz).

MASS (EI, m/e): 458 (M⁺).

REFERENCE EXAMPLE 111

16,16-Dimethyl-15-oxo-20a-homo-2,5,6,7-tetranor-4-oxa-4,8-inter-m-phenylene PGI₂ methyl ester, 11-acetate (111)

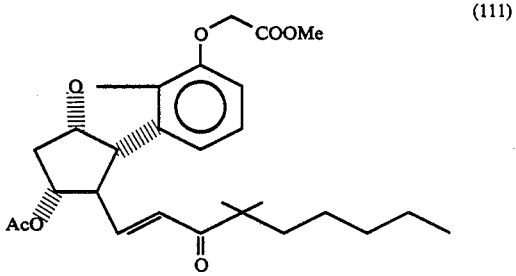

Under argon atmosphere, 2α-acetoxy-1β-hydroxymethyl-3aβH,8bβH-2,3,3a,8b-tetrahydro-1H-5-cyclopenta[b]benzofuranyloxyacetic acid methyl ester (1.2387 g, 3.69 mmol) was dissolved in anhydrous THF (10 ml). To the solution were added anhydrous pyridine (0.3 ml, 3.69 mmol), anhydrous DMSO (5 ml), and trifluoroacetic acid (0.14 ml, 1.85 mmol). Further, DCC (1.141 g, 5.53 mmol) was also added and the mixture was stirred at room temperature for 1.5 hours. After calcium carbonate (1.20 g, 11.99 mmol) was added, the reaction mixture was stirred for 20 minutes and then allowed to stand.

Separately, sodium hydride (60% dispersion in mineral oill; 221.4 mg, 5.53 mmol) was suspended in anhydrous THF (20 ml). To the suspension was added a solution of dimethyl 3,3-dimethyl-2-oxo-octylphosphonate (1.46 g, 5.53 mmol) in anhydrous THF (5 ml). The resulting reaction mixture was stirred at room temperature under argon atmosphere for 30 minutes. To this reaction mixture was added the supernatant of the aldehyde ester mixture prepared above by a syringe while cooling with ice. The residue was washed with anhydrous THF (10 ml; 5 ml×2). The resulting supernatant was also added to the reaction mixture and the thus resulting reaction mixture was stirred at room temperature for 10 minutes. After adding aqueous saturated ammonium chloride solution (50 ml), the mixture was extracted with ethyl acetate (40 ml×3). The combined organic layers were washed with water (100 ml) and with brine (100 ml), dried over anhydrous sodium sulfate (40 g), and concentrated. The residue was purified by silica gel column chromatography (ethyl acetate/cyclohexane ⅓) to give a colorless oily product, 16,16-dimethyl-15-oxo-20a-homo-2,5,6,7-tetranor-4-oxa-4,8-inter-m-phenylene PGI₂ methyl ester, 11-acetate (1.6659 g, 3.53 mmol, 96%). The structure of this product was confirmed by the following data.

IR (liquid film): 2952, 2935, 2860, 1759, 1739, 1686, 1621, 1482, 1461, 1420, 1374, 1295, 1240, 1192, 1112, 1053, 1000, 980, 943, 845, 738, 700 cm⁻¹.

NMR (100 MHz, CDCl₃, δ): 0.73–0.99 (3H, m); 1.13 (6H, s); 1.01–1.71 (8H, m); 1.80 (3H, s); 2.02–2.33 (1H, m); 2.46–3.09 (2H, m); 3.55–3.78 (1H, m); 3.78 (3H, s); 4.72 (2H, s); 4.98 (1H, q, J=5.38 Hz); 5.13–5.49 (1H, m); 6.46–6.98 (5H, m).

Mass (EI, m/e): 472 (M⁺).

REFERENCE EXAMPLE 112

16,16-Dimethyl-15-oxo-20a,20b-dihomo-2,5,6,7-tetranor-4-oxa-4,8-inter-m-phenylene PGI₂ methyl ester, 11-acetate (112)

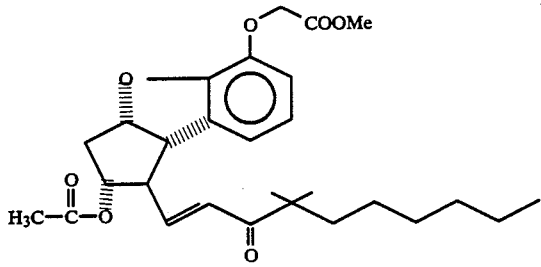

Under argon atmosphere, 2α-acetoxy-1β-hydroxymethyl-3aβH,8bβH-2,3,3a,8b-tetrahydro-1H-5-cyclopenta[b]benzofuranyloxyacetic acid methyl ester (1.5 g, 4.46 mmol) was dissolved in anhydrous THF (9 ml). While stirring, pyridine (0.108 ml, 1.34 mmol) and trifluoroacetic acid (0.101 ml, 1.31 mmol) were added, and then DMSO (3.11 ml, 43.8 mmol) and D.C.C. (1.22 g, 5.91 mmol) were also added to the solution. The mixture was stirred at room temperature for 2.5 hours.

Separately, sodium hydride (60% dispersion in mineral oil; 286 mg, 7.15 mmol) was suspended in anhydrous THF (8 ml) under argon atmosphere. To the suspension was added dropwise a solution of dimethyl 3,3-dimethyl-2-oxo-nonanylphosphonate (1.98 g, 7.14 mmol) in anhydrous THF (5 ml) while cooling with ice. The reaction mixture was stirred at room temperature for 30 minutes. To this reaction mixture was added the above prepared aldehyde ester while cooling with ice and the resulting mixture was stirred for 30 minutes. The reaction mixture was neutralized with acetic acid. After filtration the filtrate was concentrated. Water (20 ml) was added to the residue and the mixture was extracted with ethyl acetate (50 ml×2). The combined ethyl acetate layers were washed with water (20 ml×1) and with brine (20 ml×1), dried over anhydrous sodium sulfate, and concentrated. The residue was separated and purified by column chromatography (silica gel 60 g; ethyl acetate/cyclohexane 1/4) to give a colorless, transparent oily product, 16,16-dimethyl-15-oxo-20a,20b-dihomo-2,5,6,7-tetranor-4-oxa-4,8-inter-m-phenylene PGI₂ methyl ester, 11-acetate (1.68 g, 3.46 mmol, 77.5%). The structure of this product was confirmed by the following data.

IR (liquid film): 2930, 2860, 1755, 1730, 1680, 1620, 1590, 1480, 1455, 1430, 1370, 1290, 1230, 1190, 1110, 1090, 1050, 990, 940, 880, 840, 750, 720 cm$^{-1}$.

NMR (400 MHz, CDCl₃, δ): 0.8–0.9 (3H, m); 1.13 (6H, s); 1.0–1.4 (8H, m); 1.5–1.6 (2H, m); 1.81 (3H, s); 2.1–2.3 (1H, m); 2.6–2.7 (1H, m); 2.97 (1H, q, J=7.9 Hz); 3.6–3.7 (1H, m), 3.79 (3H, s); 4.72 (1H, d, J=16.1 Hz); 4.74 (1H, d), J=16.1 Hz); 4.99 (1H, q, J=6.0 Hz); 5.3–5.4 (1H, m); 6.58 (1H, d, J=15.1 Hz); 6.7–6.8 (3H, m); 6.82 (1H, dd, J=7.9, 15.1 Hz).

MASS (EI, m/e): 486 (M³⁰).

REFERENCE EXAMPLE 113

16,16-Dimethyl-15-oxo-20a,20,20c-trihomo-2,5,6,7-tetranor-4-oxa-4,8-inter-m-phenylene PGI₂ methyl ester, 11-acetate (113)

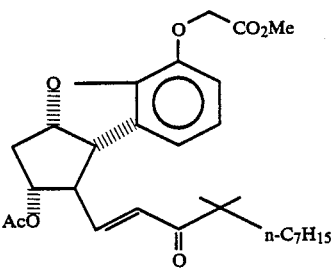

Under argon atmosphere, 2α-acetoxy-1β-hydroxymethyl-3aβH,8bβH-2,3,3a,8b-tetrahydro-1H-5-cyclopenta[b]benzofuranyloxyacetic acid methyl ester (1.20 g, 3.57 mmol) was dissolved in anhydrous THF (10 ml). To the solution were added anhydrous DMSO (5 ml, 70.8 mmol), anhydrous pyridine (0.3 ml, 3.71 mmol), anhydrous trifluoroacetic acid (0.14 ml, 1.79 mmol), and DCC (1.10 g, 5.36 mmol) at 0° C. The mixture was stirred at room temperature for one hour and 20 minutes.

Separately, sodium hydride (60% dispersion in mineral oil; 0.24 g, 6.00 mmol) was suspended in anhydrous THF (5 ml). To the suspension was added a solution of dimethyl 3,3-dimethyl-2-oxo-decylphosphonate (1.78 g, 6.09 mmol) in anhydrous THF (6 ml) under argon atmosphere at 0° C. The mixture was stirred at room temperature for 40 minutes. To the resulting mixture was added the above prepared aldehyde ester mixture through a syringe. Further, the residue was three times washed with anhydrous THF (5 ml). The washings were added to the reaction mixture. This mixture was then stirred at room temperature for one hour. Aqueous saturated ammonium chloride solution (10 ml) was added to the reaction mixture. The mixture was extracted with ethyl acetate (50 ml×4). The ethyl acetate layers were combined, washed with water (50 ml) and with brine (50 ml), dried over anhydrous sodium sulfate, and concentrated. The residue was subjected to silica gel column chromatography (ethyl acetate/cyclohexane 1/2) to eliminate byproducts. The resulting oily material was separated and purified by silica gel column chromatography (ethyl acetate/cyclohexane 1/5) to give a pure product, 16,16-dimethyl-15-oxo-20a,20b,20c-trihomo-2,5,6,7-tetranor-4-oxa-4,8-inter-m-phenylene PGI₂ methyl ester, 11-acetate (1.6481 g, 3.29 mmol, 92.2%). The structure of this product was confirmed by the following data.

IR (liquid film): 2920, 2845, 1734, 1682, 1616, 1477, 1454, 1364, 1291, 1231, 1188, 1110, 1056, 988, 942, 844, 762, 726 cm$^{-1}$.

NMR (100 MHz, CDCl₃, δ): 0.70–1.68 (21H, m); 1.81 (3H, s); 2.08–2.36 (1H, m); 2.49–3.10 (2H, m); 3.58–3.72 (1H, m); 3.79 (3H, s); 4.73 (2H, s); 4.85–5.12 (1H, m); 5.18–5.45 (1H, m); 6.42–6.99 (5H, m).

MASS (EI, m/e): 500 (M⁺).

REFERENCE EXAMPLE 114

16,16,17-Trimethyl-15-oxo-2,5,6,7,19,20-hexanor-4-oxa-4,8-inter-m-phenylene PGI$_2$ methyl ester, 11-acetate (114)

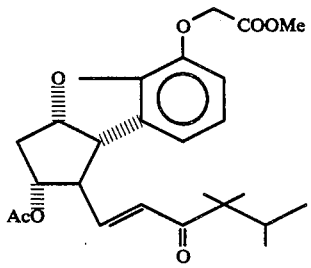

Under argon atmosphere, 2α-acetoxy-1β-hydroxymethyl-3aβH,8bβH-2,3,3a,8b-tetrahydro-1H-5-cyclopenta[b]benzofuranyloxyacetic acid methyl ester (1.2810 g, 3.81 mmol) was dissolved in anhydrous THF (10 ml), and anhydrous pyridine (0.31 ml, 3.69 mmol), anhydrous DMSO (5 ml), trifluoroacetic acid (0.15 ml, 1.91 mmol), and D.C.C. (1.18 g, 5.72 mmol) were added. The resulting mixture was stirred at room temperature for one hour. After adding calcium carbonate (1.24 g, 12.4 mmol), the reaction mixture was stirred for 20 minutes and allowed to stand.

Separately, sodium hydride (60% dispersion in mineral oil; 228.8 mg, 5.72 mmol) was suspended in anhydrous THF (20 ml). To the suspension was added a solution of dimethyl 3,3,4-trimethyl-2-oxo-pentylphosphonate (1.17 g, 5.72 mmol) in anhydrous THF (5 ml), and the mixture was stirred at room temperature under argon atmosphere for 30 minutes. To this reaction mixture, the supernatant of the above prepared aldehyde ester mixture was added through a syringe while cooling with ice. The remaining residue was washed with anhydrous THF (8 ml×2, 5 ml), and the resulting supernatant was added to the reaction mixture. The resulting mixture was stirred at room temperature for 10 minutes. Aqueous saturated ammonium chloride solution (50 ml) was added to the mixture and extracted with ethyl acetate (50 ml×3). The combined organic layers were washed with water (150 ml) and with brine (150 ml), dried over anhydrous sodium sulfate (40 g), and concentrated. The residue was purified by silica gel column chromatography (ethyl acetate/cyclohexane 1/3) to give a colorless oily product, 16,16,17-trimethyl-15-oxo-2,5,6,7,19,20-hexanor-4-oxa-4,8-inter-m-phenylene PGI$_2$ methyl ester, 11-acetate (1.6642 g, 3.75 mmol, 98%). The structure of this product was identified by the following data.

IR (liquid film): 2953, 1758, 1734, 1683, 1620, 1480, 1458, 1337, 1372, 1291, 1238, 1189, 1110, 1050, 1030, 984, 944, 888, 844, 760, 728 cm$^{-1}$.

NMR (100 MHz, CDCl$_3$, δ): 0.84 (6H, d, J=6.81); 1.05 (6H, s); 1.80 (3H, s); 1.80–3.10 (4H, m); 3.52–3.82 (1H, m); 3.79 (3H, s); 4.73 (2H, s); 4.99 (1H, q, J=5.38); 5.20–5.46 (1H, m); 6.46–6.98 (5H, m).

MASS (EI, m/e): 444 (M+).

REFERENCE EXAMPLE 115

17,17-Dimethyl-15-oxo-2,5,6,7-tetranor-4-oxa-4,8-inter-m-phenylene PGI$_2$ methyl ester, 11-benzoate (115)

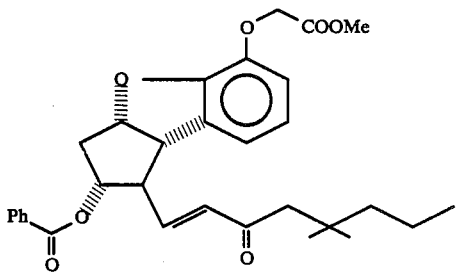

Methyl 2α-benzoyloxy-1β-hydroxymethyl-3aβH,8bβH-2,3,3a,8b-tetrahydro-1H-5-cyclopenta[b]benzofuranyloxyacetate (1.85 g, 4.65 mmol) was dissolved in anhydrous THF (25 ml). To this solution were added anhydrous DMSO (3.30 ml, 46.5 mmol), anhydrous pyridine (0.116 ml, 1.44 mmol), trifluoroacetic acid (0.10 ml, 1.30 mmol), and D.C.C. (1.44 g, 6.98 mmol) under argon atmosphere. The resulting mixture was stirred at room temperature for 2 hours.

Separately, sodium hydride (60% dispersion in mineral oil; 270 mg, 6.74 mmol) was suspended in anhydrous THF (10 ml) under argon atmosphere. To this suspension was added a solution of dimethyl 4,4-dimethyl-2-oxo-heptylphosphonate (1.74 g, 6.98 mmol) in anhydrous THF (5 ml). The resulting mixture was stirred at room temperature for 30 minutes. To this reaction mixture was added the above prepared aldehyde solution at 0° C. The mixture was warmed to room temperature and then stirred for 30 minutes. Acetic acid was added to the resulting solution to neutralize. After concentration, ethyl acetate (100 ml) was added and the mixture was filtered. The filtrate was washed with water (30 ml) and with brine (30 ml), dried over anhydrous magnesium sulfate, and concentrated. The residue was passed through a short column of silica gel (ethyl acetate/cyclohexane 1/8), and then purified by Merck Lobar column (silica gel; ethyl acetate/cyclohexane 1/4.5) to give an oily product, 17,17-dimethyl-15-oxo-2,5,6,7-tetranor-4-oxa-4,8-inter-m-phenylene PGI$_2$ methyl ester, 11-benzoate (2.38 g, 4.58 mmol, 98.4%). The structure of this product was confirmed by the following data.

IR (liquid film): 2970, 2880, 1760, 1730, 1660, 1620, 1550, 1490, 1460, 1370, 1320, 1270, 1220, 1200, 1120, 1070, 1060, 1030, 980, 860, 760, 720, 670 cm$^{-1}$.

NMR (400 MHz, CDCl$_3$, δ): 0.8–0.9 (3H, m); 0.97 (6H, s); 1.2–1.3 (4H, m); 2.35–2.45 (1H, m); 2.44 (2H, s); 2.66 (1H, ddd, J=5.5, 6.6, 15.1 Hz); 3.18 (1H, ddd, J=4.2, 4.7, 8.3 Hz); 3.75 (3H, s); 3.87 (1H, dd, J=4.7, 8.9 Hz); 4.64 (1H, d, J=16.1 Hz); 4.67 (1H, d, J=16.1 Hz); 5.34 (1H, dt, J=4.2, 5.5 Hz); 5.44 (1H, ddd, J=2.9, 6.6, 8.9 Hz); 6.25 (1H, dd, J=1.2, 15.9 Hz); 6.7–6.9 (4H, m); 7.31 (2H, t, J=7.8 Hz); 7.49 (1H, t, J=7.8 Hz); 7.56 (2H, d, J=7.8 Hz).

MASS (EI, m/e): 520 (M+).

REFERENCE EXAMPLE 116

18,18-Dimethyl-15-oxo-2,5,6,7-tetranor-4-oxa-4,8-inter-m-phenylene PGI₂ methyl ester, 11-benzoate (116)

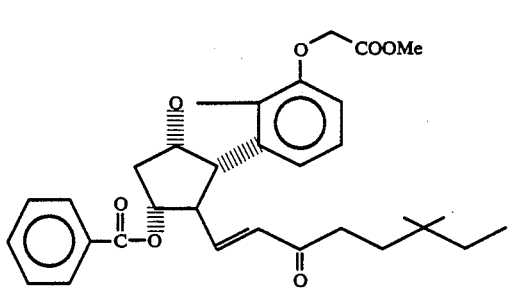

Under argon atmosphere, 2α-benzoyloxy-1β-hydroxymethyl-3aβH,8bβH-2,3,3a,8b-tetrahydro-1H-5-cyclopenta[b]benzofuranyloxyacetic acid methyl ester (1.7 g, 4.25 mmol) was dissolved in anhydrous THF (8 ml) and, while stirring, pyridine (0.103 ml, 1.27 mmol), trifluoroacetic acid (0.1 ml, 1.25 mmol), DMSO (2.97 ml, 41.8 mmol), and D.C.C. (1.16 g, 5.62 mmol) were added. The mixture was stirred at room temperature for 2 hours.

Separately, to a suspension of sodium hydride (60% dispersion in mineral oil; 261 mg, 6.8 mmol) in anhydrous THF (8 ml) was added dropwise a solution of dimethyl 5,5-dimethyl-2-oxo-heptylphosphonate (1.7 g, 6.8 mmol) in anhydrous THF (5 ml) under argon atmosphere while cooling with ice. The mixture was stirred at room temperature for 30 minutes. To this reaction mixture was added the above prepared aldehyde ester mixture while cooling with ice. The reaction mixture was stirred at room temperature for 30 minutes. Acetic acid was added to neutralize the reaction mixture. The mixture was filtered and the filtrate was concentrated. After adding water (20 ml) to the residue, the resulting mixture was extracted with ethyl acetate (50 m×2). The combined ethyl acetate layers were washed with water (20 ml×1) and with brine (20 ml×1), dried over anhydrous sodium sulfate, and concentrated. The residue was separated and purified by column chromatography (silica gel 50 g; ethyl acetate/cyclohexane 1/5) to give 18,18dimethyl-15-oxo-2,5,6,7-tetranor-4-oxa-4,8-inter-m-phenylene PGI₂ methyl ester, 11-benzoate (1.96 g, 3.77 mmol, 89%). The structure of this product was confirmed by the following data.

m.p.: 108.9°–109.2° C. (recrystallized from ethyl acetate/n-hexane 2/1).

IR (KBr): 3430, 2960, 1770, 1710, 1630, 1490, 1465, 1440, 1370, 1320, 1295, 1275, 1250, 1220, 1200, 1110, 1090, 1070, 1025, 990, 955, 915, 905, 860, 845, 780, 750, 715, 690 cm⁻¹.

NMR (400 MHz, CDCl₃, δ): 0.82 (3H, t, J=7.6 Hz); 0.85 (6H, s); 1.24 (2H, q, J=7.6 Hz); 1.4–1.6 (2H, m); 2.35–2.5 (3H, m); 2.6–2.7 (1H, m); 3.1–3.3 (1H, m); 3.75 (3H, s); 3.39 (1H, dd, J=4.4, 8.3 Hz); 4.63 (1H, d, J=16.5 Hz); 4.69 (1H, d, J=16.5 Hz); 5.3–5.4 (1H, m); 5.4–5.5 (1H, m); 6.27 (1H, dd, J=1.2, 15.9 Hz); 6.7–6.9 (4H, m); 7.31 (2H, t, J=7.8 Hz); 7.4–7.7 (3H, m).

MASS (EI, m/e): 520 (M⁺).

Elementary Analysis: Calcd. for C₃₁H₃₆O₇: C 71.52; H 6.97%. Found: C 71.54; H 6.97%.

REFERENCE EXAMPLE 117

16-Methyl-15-oxo-2,5,6,7-tetranor-4-oxa-4,8-inter-m-phenylene PGI₂ methyl ester, 11-benzoate (117)

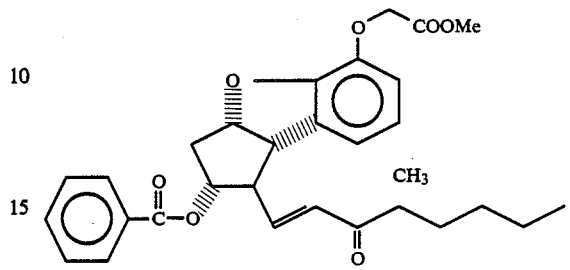

Under argon atmosphere, 2α-benzoyloxy-1β-hydroxymethyl-3aβH,8bβH-2,3,3a,8b-tetrahydro-1H-5-cyclopenta[b]benzofuranyloxy-acetic acid methyl ester (1.8 g, 4.52 mmol) was dissolved in anhydrous THF (9 ml) and, while stirring, pyridine (0.11 ml, 1.36 mmol), trifluoroacetic acid (0.102 ml, 1.27 mmol), DMSO (31.5 ml, 44.3 mmol) and D.C.C. (1.23 g, 5.96 mmol) were added. The resulting mixture was stirred at room temperature for 2.5 hours.

Under argon atmosphere, sodium hydride (60% dispersion in mineral oil; 325 mg, 8.14 mmol) was suspended in anhydrous THF (9 ml), and a solution of dimethyl 3-methyl-2-oxo-heptylphosphonate (1.92 g, 8.14 mmol) in anhydrous THF (5 ml) was dropwise added at room temperature. The reaction mixture was stirred for 30 minutes. To this reaction mixture cooled with ice, the above prepared aldehyde ester mixture was added, and the reaction mixture was stirred at room temperature for 30 minutes. Acetic acid was added to neutralize the reaction mixture. After filtration of the mixture, the filtrate was concentrated. Water (20 ml) was added to the filtrate and the resulting mixture was extracted with ethyl acetate (60 ml33 2). The combined ethyl acetate layers were washed with water (20 ml×1) and with brine (20 ml×1), dried over anhydrous sodium sulfate, and concentrated. The resulting residue was subjected to silica gel column chromatography (ethyl acetate/cyclohexane 1/5) to separate by-products and excess Wordsworth agents. Further separation and purification was done by Merck Lobar column (silica gel; ethyl acetate/cyclohexane 1/6) to give 16-methyl-15-oxo-2,5,6,7-tetranor-4-oxa-4,8-inter-m-phenylene PGI₂ methyl ester, 11-benzoate (1.71 g, 3.38 mmol, 74.8%). The structure of this product was confirmed by the following data.

IR (liquid film): 2950, 2920, 2850, 1750, 1710, 1660, 1620, 1600, 1480, 1450, 1370, 1310, 1270, 1210, 1185, 1110, 1060, 1050, 1020, 970, 845, 750, 710 cm⁻¹.

NMR (400 MHz, CDCl₃, δ): 0.87 (3H, t, J=6.8 Hz); 1.10 (3H, d, J=6.8 Hz); 1.1–1.4 (5H, m); 1.6–1.7 (1H, m); 2.3–2.5 (1H, m); 2.6–2.8 (2H, m); 3.1–3.2 (1H, m); 3.75 (3H, s); 3.88 (1H, dd, J=4.6, 8.5 Hz); 4.64 (1H, d, J=16.4 Hz); 4.68 (1H, d, J=16.4 Hz); 5.35 (1H, q, J=4.9 Hz); 6.34 (1H, d, J=15.6 Hz); 6.7–7.0 (4H, m); 7.31 (2H, t, J=7.1 Hz); 7.49 (1H, t, J=7.1 Hz); 7.57 (2H, d, J=7.1 Hz).

MASS (EI, m/e): 506 (M⁺).

REFERENCE EXAMPLE 118

(17S)-17-Methyl-15-oxo-2,5,6,7-tetranor-4-oxa-4,8-inter-m-phenylene PGI2 methyl ester, 11-benzoate (118)

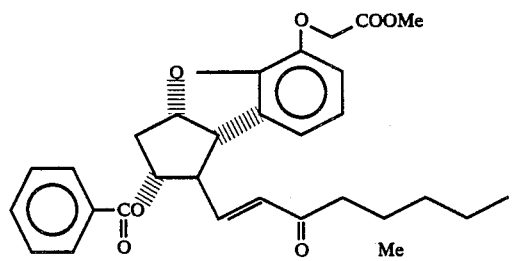

Under argon atmosphere, methyl 2α-benzoyloxy-1β-hydroxymethyl-3aβH,8bβH-2,3,3a,8b-tetrahydro-1H-5-cyclopenta[b]benzofuranyloxyacetate (3.6 g, 9.09 mmol) was dissolved in anhydrous THF (21 ml), and anhydrous DMSO (6.752 ml), anhydrous pyridine (0.234 ml, 2.89 mmol), anhydrous trifluoroacetic acid (0.218 ml, 2.83 mmol), and D.C.C. (2.94 g, 14.25 mmol) were added. The resulting mixture was stirred at room temperature fro 3 hours.

Separately, sodium hydride (60% dispersion in mineral oil; 576 mg, 13.82 mmol) was suspended in anhydrous THF (10 ml). To the suspension stirred while cooling with ice, a solution of dimethyl 4(S)-methyl-2-oxo-heptylphosphonate (3.2 g, 14.41 mmol) in anhydrous THF (10 ml) was added. The mixture was then stirred at room temperature for 30 minutes. The reaction mixture was again cooled with ice, and the above prepared aldehyde ester was added and stirred for 20 minutes. The reaction mixture was neutralized with acetic acid. The resulting precipitate was filtered out and the filtrate was concentrated. The resulting oily material was purified by silica gel column chromatography (ethyl acetate/cyclohexane 1/8) to give 17(S)-methyl-15-oxo-2,5,6,7-tetranor-4-oxa-4,8-inter-m-phenylene PGI2 methyl ester, 11-benzoate (3.59 g, 7.08 mmol, 77%). The structure of this product was confirmed by the following data.

IR (liquid film): 2930, 2870, 1760, 1720, 1680, 1620, 1600, 1485, 1455, 1370, 1315, 1270, 1210, 1070, 1055, 1025, 975, 850, 760, 715 cm$^{-1}$.

NMR (90 MHz, CDCl$_3$, δ): 0.90 (6H, m); 1.25 (4H, m); 2.00–3.00 (5H, m); 3.20 (1H, m); 3.78 (3H, s); 3.85 (1H, m); 4.65 (2H, s); 5.38 (2H, m); 6.25 (1H, dd, J=1.1, 16.0 Hz); 6.75 (2H, s); 6.79 (1H, m); 7.10–7.70 (8H, m).

MASS (EI, m/e): 507 (M$^+$).

REFERENCE EXAMPLE 119

(17S)-17-Methyl-15-oxo-20a-homo-2,5,6,7-tetranor-4-oxa-4,8-inter-m-phenylene PGI2 methyl ester, 11-benzoate (119)

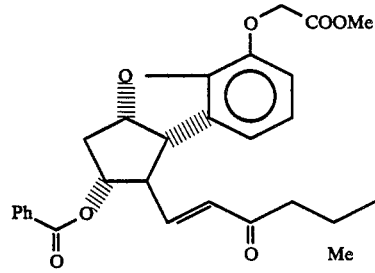

Methyl 2α-benzoyloxy-1β-hydroxymethyl-3aβH,8bβH-2,3,3a,8b-tetrahydro-1H-5-cyclopenta[b]benzofuranyloxyacetate (3.20 g, 8.04 mmol) was dissolved in anhydrous THF (40 ml). To this solution were added anhydrous DMSO (5.70 ml, 80.4 mmol), anhydrous pyridine (0.20 ml, 2.49 mmol), trifluoroacetic acid (0.17 ml, 2.25 mmol), and D.C.C. (2.49 g, 12.1 mmol) under argon atmosphere. The resultin mixture was stirred at room temperature for 3 hours.

Under argon atmosphere, sodium hydride (60% dispersion in mineral oil; 466 mg, 11.7 mmol) was suspended in anhydrous THF (20 ml), and a solution of dimethyl (4S)-4-methyl-2-oxo-octylphosphonate (3.02 g, 12.1 mmol) in THF (10 ml) was added. The mixture was stirred at room temperature for 30 minutes. To this reaction mixture was added the above prepared aldehyde solution at 0° C. The reaction mixture was warmed to room temperature and then stirred for 30 minutes. Acetic acid was added to neutralize the reaction mixture. After concentration of the mixture, ethyl acetate (100 ml) was added to the residue and filtered. The resulting crystals were washed with ethyl acetate (25 ml×2). The combined filtrates were washed with water (80 ml) and with brine (80 ml), dried over anhydrous magnesium sulfate, and concentrated. The residue was purified by silica gel column chromatography (ethyl acetate/cyclohexane 1/8–1/4) to give an oily product, (17S)-17-methyl-15-oxo-20a-homo-2,5,6,7-tetranor-4-oxa-4,8-inter-m-phenylene PGI2 methyl ester, 11-benzoate (3.94 g, 7.58 mmol, 94.2%). The structure of this product was confirmed by the following data.

IR (liquid film): 3030, 2970, 2940, 2870, 1770, 1720, 1670, 1620, 1490, 1470, 1380, 1320, 1280, 1220, 1200, 1120, 1080, 1060, 1030, 980, 860, 760, 720 cm$^{-1}$.

NMR (90 MHz, CDCl$_3$, δ): 0.7–1.5 (12H, m); 1.8–2.9 (5H, m); 3.0–3.4 (1H, m); 3.74 (3H, s); 3.88 (1H, dd, J=4.4, 8.6 Hz); 4.66 (2H, s); 5.2–5.6 (2H, m); 6.24 (1H, dd, J=1.1, 15.8 Hz); 6.6–7.0 (4H, m); 7.15–7.7 (5H, m).

MASS (EI, m/e): 520 (M$^+$).

REFERENCE EXAMPLE 120 d-15-Oxo-2,5,6,7-tetranor-4-oxa-4,8-inter-m-phenylene PGI₂ methyl ester, 11-acetate 120

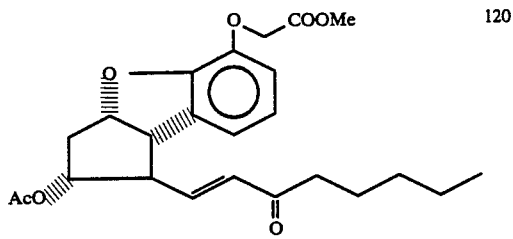

To a solution of methyl d-2α-acetoxy-1β-hydroxymethyl-3aβH,8bβH-2,3,3a,8b-tetrahydro-1H-5-cyclopenta[b]benzofuranyloxyacetate (700 mg, 2.08 mmol) in anhydrous THF (5 ml) were added under argon atmosphere anhydrous DMSO (1.48 ml, 20.8 mmol), anhydrous pyridine (0.05 ml, 0.62 mmol), trifluoroacetic acid (0.05 ml, 0.62 mmol) and D.C.C. (644 mg, 3.12 mmol) and the mixture was stirred for 2 hrs. at room temperature. On the other hand, to a suspension of sodium hydride (60% mineral oil dispersion, 120 mg, 3.12 mmol) in anhydrous THF (3 ml) in another flask was added under argon atmosphere a solution of dimethyl 2-oxo-heptylphosphonate (692 mg, 3.12 mmol) in anhydrous THF (3 ml) and the mixture was stirred for 30 min. at room temperature. To this was added the supernatant of the aldehyde ester reaction mixture prepared above by means of an injector. The residue of the aldehyde ester reaction mixture was washed with anhydrous THF (2 ml×4) and the combined washing solutions were also added into the said flask. The resulting mixture was stirred for 30 min. at room temperature and neutralized with acetic acid. The mixture was filtered. The filtrate was concentrated. The concentrate was diluted with water (10 ml) and extracted with ethyl acetate (30 ml×2). The combined ethyl acetate layers were washed with water (10 ml), and with brine (10 ml), dried over anhydrous sodium sulfate and concentrated. Column chromatography (silica gel, ethyl acetate/cyclohexane: 1/9) of the residue gave d-15-oxo-2,5,6,7-tetranor-4-oxa-4,8-inter-m-phenylene PGI₂ methyl ester, 11-acetate (813 mg, 1.89 mmol, 90.9%) as a colorless oily material. The product was assigned by the following data.

Optical rotation: $[\alpha]_D^{20} = +96.02$ (c=0.730, methanol).

IR (liquid film): 2965, 2940, 2880, 1760, 1740, 1695, 1675, 1630, 1595, 1490, 1465, 1440, 1375, 1295, 1240, 1190, 1115, 1060, 985, 950, 850, 860, 830 cm⁻¹.

NMR (400 MHz, CDCl₃, δ): 0.91 (3H, t, J=6.8 Hz); 1.24–1.33 (4H, m); 1.61–1.69 (2H, m); 1.81 (3H, s); 2.19–2.25 (1H, m); 2.56 (3H, t, J=7.5 Hz); 2.59–2.66 (1H, m); 2.96 (1H, q, J=6.3 Hz); 3.71 (1H, dd, J=6.3, 8.8 Hz); 3.79 (3H, s); 4.71 (1H, d, J=16.1 Hz); 4.74 (1H, d, J=16.1 Hz); 5.01 (1H, q, J=6.3 Hz); 5.30–5.35 (1H, m); 6.19 (1H, dd, J=1.0, 15.6 Hz); 6.72–6.78 (4H, m).

MASS (EI, m/e): 430M⁺.

REFERENCE EXAMPLE 121 d-16,16-Dimethyl-15-oxo-2,5,6,7-tetranor-4-oxa-4,8-inter-m-phenylene PGI₂ methyl ester, 11-acetate 121

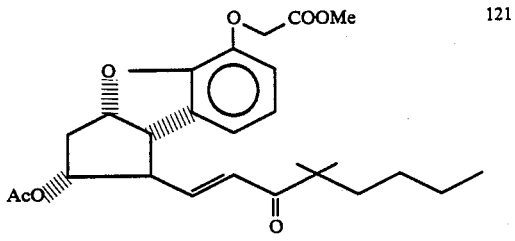

Under argon atmosphere to a solution of methyl d-2α-acetoxy-1β-hydroxymethyl-3aβH,8bβH-2,3,3a,8b-tetrahydro-1H-5-cyclopenta[b]benzofuranyloxyacetate (700 mg, 2.08 mmol) in anhydrous THF (5 ml) were added anhydrous DMSO (1.48 ml, 20.8 mmol), anhydrous pyridine (0.05 ml, 0.62 mmol), trifluoroacetic acid (0.05 ml, 0.62 mmol) and D.C.C. (644 mg, 3.12 mmol) and the mixture was stirred for 2 hrs. at room temperature. On the other hand, to a suspension of sodium hydride (60% mineral oil dispersion, 120 mg, 3.12 mmol) in anhydrous THF (5 ml) in another flask was added under argon atmosphere a solution of dimethyl 3,3-dimethyl-2-oxo-heptylphosphonate (780 mg, 3.12 mmol) in anhydrous THF (5 ml) and the mixture was stirred for 30 min. at room temperature. To this was added the supernatant of the aldehyde ester reaction mixture prepared above by means of an injector. The residue of the aldehyde ester reaction mixture was washed with anhydrous THF (2 ml×4) and the combined washing solutions were also added into the said flask. The resulting mixture was stirred for 30 min. at room temperature and neutralized with acetic acid. The mixture was filtered. The filtrate was concentrated. The concentrate was diluted with water (10 ml) and extracted with ethyl acetate (30 ml×2). The combined ethyl acetate layer was washed with water (10 ml), and with brine (10 ml), dried over anhydrous sodium sulfate and concentrated. Column chromatography (silica gel, ethyl acetate/cyclohexane: 1/9) of the residue gave d-16,16-dimethyl-15-oxo-2,5,6,7-tetranor-4-oxa-4,8-inter-m-phenylene PGI₂ methyl ester, 11-acetate (602 mg, 1.31 mmol, 63%). The product was assigned the structure by the following data.

Optical rotation: $[\alpha]_d^{20} = +97.97°$ (c=0.890, methanol).

IR (KBr): 2960, 2940, 2860, 1760, 1735, 1690, 1620, 1480, 1460, 1440, 1370, 1290, 1235, 1190, 1115, 1095, 1050, 990, 945, 845, 770, 730 cm⁻¹.

NMR (400 MHz, CDCl₃, δ): 0.89 (3H, t, J=7.3 Hz); 1.13 (6H, s); 1.15–1.18 (2H, m); 1.20–1.33 (2H, m); 1.51–1.55 (2H, m); 1.81 (3H, s); 2.20 (1H, ddd, J=3.4, 6.3, 14.8 Hz); 2.66 (1H, dt, J=6.8, 14.8 Hz); 2.97 (1H, q, J=6.3 Hz); 3.68 (1H, dd, J=6.3, 8.3 Hz); 3.79 (3H, s); 4.71 (1H, d, J=16.3 Hz); 4.74 (1H, d, J=16.3 Hz); 4.98 (1H, q, J=6.3 Hz); 5.29–5.34 (1H, m); 6.58 (1H, J=15.1 Hz); 6.72–6.85 (4H, m).

MASS (EI, m/e): 458M⁺.

REFERENCE EXAMPLE 122

15-cyclopentyl-15-oxo-2,5,6,7,16,17,18,19,20-nonanor-4-oxa-4,8-inter-m-phenylene PGI₂ methyl ester, 11-benzoate (122)

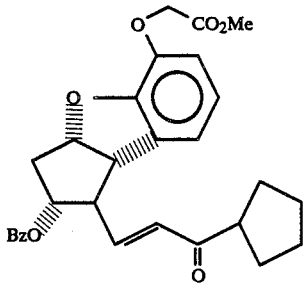

To a solution of methyl 2α-benzoyloxy-1β-hydroxymethyl-3aβH,8bβH-2,3,3a,8b-tetrahydro-1H-5-cyclopenta[b]benzofuranyloxyacetate (1.90 g, 4.77 mmol) in 10 ml of anhydrous THF were added anhydrous DMSO (4.0 ml, 56.7 mmol), anhydrous pyridine (0.12 ml, 1.48 mmol), anhydrous trifluoroacetic acid (0.20 ml, 2.60 mmol) and DCC (1.80 g, 8.72 mmol) under argon stream, and the mixture was stirred at room temperature under argon atmosphere for 2 hours and a half.

Sodium hydride (60% mineral oil dispersion, 0.38 g, 9.54 mmol) was suspended in 5 ml of anhydrous THF, and to this suspension was added a solution of dimethyl 2-cyclopentyl-2-oxoethylphosphonate (1.58 g, 7.16 mmol) in 11 ml of anhydrous THF with ice-cooling under argon atmosphere. The supernatant of the reaction mixture of aldehyde ester prepared in advance was added by an injector. The residue was washed three times each with 5 ml of anhydrous THF and the washings were also added. The mixture was stirred with ice-cooling for 5 minutes and then at room temperature for 1 hour and a half. Acetic acid was added to the reaction mixture, and the precipitate was filtered. The filtrate was combined with 10 ml of water and the mixture was extracted with ethyl acetate (30 ml×4). Then, the combined ethyl acetate layers were washed with brine (100 ml), dried over anhydrous sodium sulfate and concentrated. The residue was roughly purified by column chromatography (silica gel, ethyl acetate/cyclohexane=1:1) to afford an oily product, which was further purified by column chromatography (silica gel, ethyl acetate/cyclohexane=1:4) to give a pure product of 15-cyclopentyl-15-oxo-2,5,6,7,16,17,18,19,20-nonanor-4-oxa-4,8-inter-m-phenylene PGI₂ methyl ester, 11-benzoate (1.87 g, 3.81 mmol, 79.9%). This compound was assigned the structure by the following data:

m.p. 116°-117.5° C. (recrystallized from ethyl acetate and cyclohexane; colorless needle-like crystals).

IR(KBr): 3050, 2940, 2860, 1763, 1695, 1619, 1595, 1485, 1460, 1435, 1388, 1368, 1313, 1292, 1268, 1240, 1213, 1193, 1149, 1107, 1065, 1050, 1035, 1020, 1003, 990, 955, 918, 880, 840, 747, 705, 670, 603 cm$^{-1}$.

NMR(100 MHz, CDCl₃, δ): 1.43-2.05(8H, m), 2.21-3.32(4H, m), 3.63-4.00(4H, m), 4.65(2H, s), 5.20-5.59(2H, m), 6.30(1H, d, J=15.72 Hz), 6.62-7.00(4H, m), 7.12-7.69(5H, m).

MASS(EI, m/e): 490(M⁺).

REFERENCE EXAMPLE 123

15-cyclohexyl-15-oxo-2,5,6,7,16,17,18,19,20-nonanor-4-oxa-4,8-inter-m-phenylene PGI₂ methyl ester, 11-benzoate (123)

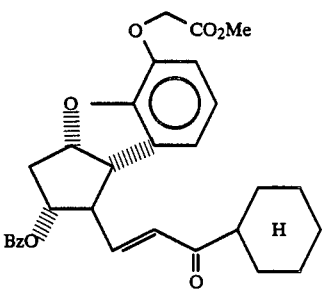

To a solution of methyl 2α-benzoyloxy-1β-hydroxymethyl-3aβH,8bβH-2,3,3a,8b-tetrahydro-1H-5-cyclopenta[b]benzofuranyloxyacetate (2.00 g, 5.03 mmol) in 10 ml of anhydrous THF were added anhydrous DMSO (40 ml, 56.7 mmol), anhydrous pyridine (0.12 ml, 1.48 mmol), anhydrous trifluoroacetic acid (0.23 ml, 2.86 mmol) and DCC (1.74 g, 8.43 mmol) under argon stream, and the mixture was stirred at room temperature for 1 hour and a half in the presence of argon. To the reaction mixture was added calcium carbonate (1.50 g, 15.0 mmol) with ice-cooling.

Sodium hydride (60% mineral oil dispersion, 0.32 g, 8.00 mmol) was suspended in 5 ml of anhydrous THF. To this suspension was added a solution of dimethyl 2-cyclohexyl-2-oxoethylphosphonate (1.41 g, 6.02 mmol) in 14 ml of anhydrous THF with ice-cooling under argon atmosphere. The supernatant of the reaction mixture of aldehyde ester prepared in advance was further added by an injector. The residue was washed three times each with 5 ml of anhydrous THF, and the supernatant of the washings was further added. The mixture was stirred with ice-cooling for 1 hour and then at room temperature for 1 hour. Acetic acid was added to the reaction mixture, and the precipitate was filtered. The filtrate was combined with 10 ml of water, and the mixture was extracted with ethyl acetate (30 ml×4). Then the combined ethyl acetate layers were washed with water (50 ml) and brine (100 ml), dried over anhydrous sodium sulfate and concentrated. The residue was roughly purified by column chromatography (silica gel, ethyl acetate/cyclohexane=1:5) to afford an oily product, which was further purified by column chromatography (silica gel, ethyl acetate/cyclohexane=1:5) to give a pure product of 15-cyclohexyl-15-oxo-2,5,6,7,16,17,18,19,20-nonanor-4-oxa-4,8-inter-m-phenylene PGI₂ methyl ester, 11-benzoate (1.74 g, 3.45 mmol) at a yield of 68.6%. This compound was assigned the structure by the following data: m.p. 69°-110° C. (recrystallized from ethyl acetate/n-hexane, colorless needle-like crystal)

IR(KBr): 2930, 2855, 1773, 1705, 1693, 1618, 1598, 1485, 1460, 1438, 1372, 1318, 1294, 1275, 1262, 1220, 1199, 1147, 1110, 1067, 1045, 1025, 997, 947, 917, 912, 847, 782, 754, 715 cm$^{-1}$.

NMR(100 MHz, CDCl₃, δ): 1.00-2.05(11H, m), 2.23-2.84(3H, m), 3.07-3.62(1H, m), 3.65-4.00(4H, m), 4.65(2H, s), 5.20-5.60(2H, m), 6.32(1H, d, J=16.16 Hz), 6.64-7.00(4H, m), 7.13-7.65(5H, m).

MASS(EI, m/e): 504(M⁺).

REFERENCE EXAMPLE 124

16-cyclopentyl-15-oxo-2,5,6,7,17,18,19,20-octanor-4-oxa-4,8-inter-m-phenylene $PGI_2$ methyl ester, 11-benzoate (124)

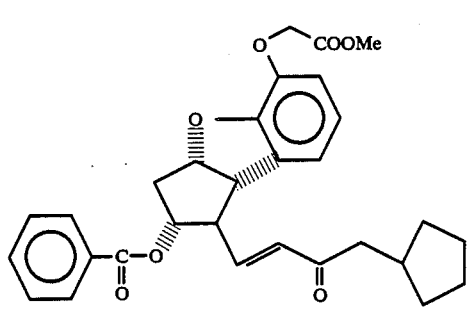

To a solution of methyl 2α-benzoyloxy-1β-hydroxymethyl-3aβH,8bβH-2,3,3a,8b-tetrahydro-1H-5-cyclopenta[b]benzofuranyloxyacetate (1.8670 g, 4.69 mmol) in 15 ml of anhydrous THF were added 5 ml of anhydrous DMSO, anhydrous pyridine (0.44 ml, 5.36 mmol), anhydrous trifluoroacetic acid (0.28 ml, 3.75 mmol) and DCC (1.45 g, 7.03 mmol) under argon stream, and the mixture was stirred at room temperature for 30 minutes. 2.35 g of calcium carbonate was added to the reaction mixture with ice-cooling and the mixture was stirred for 30 minutes.

Sodium hydride (60% mineral oil dispersion, 0.23 g, 5.70 mmol) was suspended in 10 ml of anhydrous THF, and to this suspension was added a solution of dimethyl 3-cyclopentyl-2-oxopropylphosphonate (1.76 g, 7.51 mmol) in 6 ml of anhydrous THF with ice-cooling, and the mixture was stirred under argon stream for 30 minutes. The supernatant of the reaction mixture of aldehyde ester synthesized in advance was added by an injector. The residue was washed with anhydrous THF (5 ml×4) and the supernatant of the washings was also added. The mixture was stirred at room temperature for 1 hour. To the reaction mixture was added 50 ml of a saturated aqueous solution of ammonium chloride and the mixture was extracted with ethyl acetate (50 ml×3). The combined organic layers were washed with water (100 ml) and brine (100 ml), dried over anhydrous sodium sulfate, and then concentrated. The residue was purified by column chromatography (silica gel, ethyl acetate/cyclohexane=½) to give a colorless oil of 16-cyclopentyl-15-oxo-2,5,6,7,17,18,19,20-octanor-4-oxa-4,8-inter-m-phenylene $PGI_2$ methyl ester, 11-benzoate (1.8597 g, 3.69 mmol) at a yield of 78.7%. This compound was assigned the structure by the following data:

IR(Liquid film method): 3060, 2940, 2850, 1757, 1712, 1620, 1480, 1445, 1364, 1315, 1270, 1212, 1185, 1108, 1064, 1020, 976, 844, 710 cm$^{-1}$.

NMR(100 MHz, CDCl$_3$, δ): 0.85–2.05(9H, m), 2.05–2.94(4H, m), 3.04–3.32(1H, m), 3.75(3H, s), 3.75–4.00(1H, m), 4.66(2H, s), 5.20–5.58(2H, m), 6.10–6.40(1H, m), 6.62–6.98(4H, m), 7.15–7.69(5H, m).

MASS(EI, m/e): 504(M$^+$).

REFERENCE EXAMPLE 125

16-cyclohexyl-15-oxo-2,5,6,7,17,18,19,20-octanor-4-oxa-4,8-inter-m-phenylene $PGI_2$ methyl ester, 11-benzoate (125)

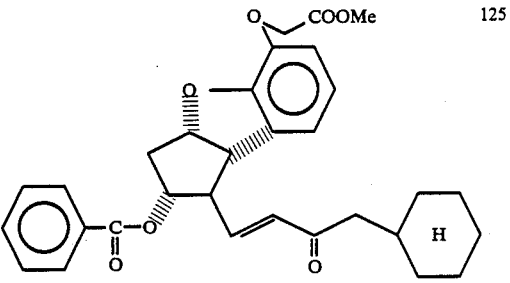

To a solution of methyl 2α-benzoyloxy-1β-hydroxymethyl-3aβH,8bβH-2,3,3a,8b-tetrahydro-1H-5-cyclopenta[b]benzofuranyloxyacetate (1.9497 mg, 4.90 mmol) in 15 ml of anhydrous THF were added 5 ml of anhydrous DMSO, anhydrous pyridine (0.46 ml, 5.69 mmol), anhydrous trifluoroacetic acid (0.25 ml, 3.25 mmol) and DCC (1.51 g, 7.32 mmol) under argon stream, and the mixture was stirred at room temperature for 30 minutes. To the reaction mixture was added 2.45 g of calcium carbonate with ice-cooling, and the mixture was stirred at 30 minutes.

Sodium hydride (60% mineral oil dispersion, 0.24 g, 6.26 mmol) was suspended in 10 ml of anhydrous THF, and to this suspension was added a solution of dimethyl 3-cyclohexyl-2-oxo-propylphosphonate (1.82 g, 7.35 mmol) in 9 ml of anhydrous THF. The mixture was stirred with ice-cooling for 30 minutes. The supernatant of the reaction mixture of aldehyde ester prepared in advance was added by an injector. The residue was washed with anhydrous THF (5 ml×3) and the supernatant of the washings was also added. The mixture was stirred at room temperature for 3.5 hours. To this reaction mixture was added 50 ml of a saturated aqueous solution of ammonium chloride and the mixture was extracted with ethyl acetate (40 ml×3). The combined organic layers were washed with water (100 ml) and brine (100 ml), dried over anhydrous sodium sulfate and then concentrated. The residue was purified by column chromatography (silica gel, ethyl acetate/cyclohexane=½) to obtain 16-cyclohexyl-15-oxo-2,5,6,7,17,18,19,20-octanor-4-oxa-4,8-inter-m-phenylene $PGI_2$ methyl ester, 11-benzoate (1.6107 g, 3.11 mmol) in a yield of 63.5%. This compound was assigned the structure by the following data:

IR(Liquid film method): 2920, 2840, 1755, 1722, 1660, 1615, 1595, 1475, 1440, 1368, 1312, 1267, 1212, 1185, 1108, 1062, 1020, 975, 938, 845, 755, 710 cm$^{-1}$.

NMR(400 MHz, CDCl$_3$, δ): 0.85–1.90(11H, m), 2.00–2.80(4H, m), 3.02–3.30(1H, m), 3,75(3H, s), 3.80–3.95(1H, m), 4.66(2H, s), 5.23–5.60(2H, m), 6.23(1H, dd, J=0.90, 15.8 Hz), 6.65–6.95(4H, m), 7.28–7.65(5H, m).

MASS(EI, m/e): 518(M$^+$).

REFERENCE EXAMPLE 126

17-cyclohexyl-15-oxo-2,5,6,7,18,19,20-heptanor-4-oxa-4,8-inter-m-phenylene PGI₂ methyl ester, 11-benzoate (126)

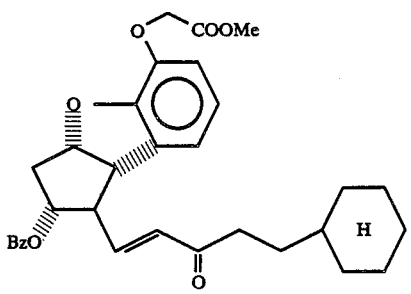

To a solution of methyl 2α-benzoyloxy-1β-hydroxymethyl-3aβH,8bβH-2,3,3a,8b-tetrahydro-1H-5-cyclopenta[b]benzofuranyloxyacetate (1.8159 g, 4.56 mmol) in 10 ml of anhydrous THF were added anhydrous pyridine (0.37 ml, 4.56 mmol), 5 ml of anhydrous DMSO, trifluoroacetic acid (0.18 ml, 2.28 mmol) and DCC (1.41 g, 6.84 mmol) under argon stream, and the mixture was stirred at room temperature for 1 hour and a half. To the reaction mixture was added calcium carbonate (1.48 g, 14.82 mmol), and the mixture was stirred for 20 minutes and allowed to stand.

Sodium hydride (60% mineral oil dispersion, 273.6 mg, 6.84 mmol) was suspended in 20 ml of anhydrous THF, and to this suspension was added a solution of dimethyl 4-cyclohexyl-2-oxo-butylphosphonate (1.57 g, 6.84 mmol) in 5 ml of anhydrous THF, and the mixture was stirred at room temperature under argon stream for 30 minutes. The supernatant of the reaction mixture of aldehyde ester prepared in advance was added by an injector with ice-cooling. The residue was washed with anhydrous THF (10 ml×2, 5 ml), and the supernatant of the washings was also added. The reaction mixture was stirred with ice-cooling for 10 minutes. 70 ml of a saturated aqueous solution of ammonium chloride was added to this reaction mixture and the mixture was extracted with ethyl acetate (50, 40, 30 ml). The combined organic layers were washed with 100 ml of water and 100 ml of brine, dried over anhydrous sodium sulfate (40 g), and then concentrated. The residue was purified through column chromatography (silica gel, ethyl acetate/cyclohexane=1:4), to give 17-cyclohexyl-15-oxo-2,5,6,7,18,19,20-heptanor-4-oxa-4,8-inter-m-phenylene PGI₂ methyl ester, 11-benzoate (2.0537 g, 3.86 mmol) in a yield of 85%. This compound was recrystallized from ethyl acetate/cyclohexane 1:1 to obtain a colorless needle-like crystal. The crystal was assigned the structure by the following data:

m.p. 79°–79.5° C.

IR(KBr): 3060, 2910, 2850, 1755, 1715, 1683, 1620, 1593, 1481, 1443, 1368, 1319, 1271, 1210, 1184, 1113, 1065, 1045, 1022, 970, 890, 844, 718 cm⁻¹.

NMR(400 MHz, CDCl₃, δ): 0.82–0.96(2H, m), 1.13–1.30(4H, m), 1.49–1.74(7H, m), 2.33–2.45(1H, m), 2.54–2.60(2H, m), 2.62–2.69(1H, m), 3.17–3.23(1H, m), 3.75(3H, s), 3.86–3.90(1H, m), 4.64(1H, d, J=16.6 Hz), 4.96(1H, d, J=16.6 Hz), 5.32–5.38(1H, m), 5.43–5.49(1H, m), 6.25(1H, d, J=16.1 Hz), 6.74–6.84(4H, m), 7.30–7.34(2H, m), 7.48–7.52(1H, m), 7.56–7.58(1H, m).

MASS(EI, m/e): 532(M+).

REFERENCE EXAMPLE 127

16-cyclohexyl-16-methyl-15-oxo-2,5,6,7,18,19,20-heptanor-4-oxa-4,8-inter-m-phenylene PGI₂ methyl ester, 11-acetate (127)

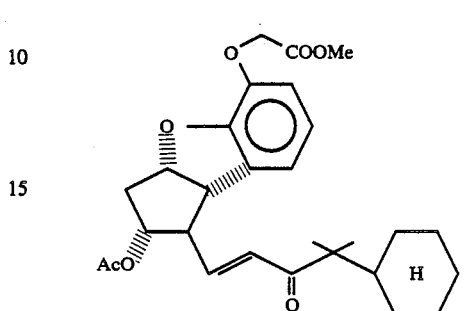

To a solution of methyl 2α-acetoxy-1β-hydroxymethyl-3aβH,8bβH-2,3,3a,8b-tetrahydro-1H-5-cyclopenta[b]benzofuranyloxyacetate (1.2164 g, 3.62 mmol) in 15 ml of anhydrous THF were added anhydrous pyridine (0.29 ml, 3.62 mmol), 5 ml of anhydrous DMSO, trifluoroacetic acid (0.14 ml, 1.81 mmol) and DCC (1.12 g, 5.43 mmol) under argon stream and the mixture was stirred at room temperature for 1 hour. To the reaction mixture was added calcium carbonate (1.18 g, 11.77 mmol), and the mixture was stirred for 20 minutes and allowed to stand.

Sodium hydride (60% mineral oil dispersion, 180 mg, 4.5 mmol) was suspended in 20 ml of anhydrous THF, and to this suspension was added a solugion of dimethyl 3-cyclohexyl-3-methyl-2-oxo-butylphosphonate (1.2424 g, 4.5 mmol) in 5 ml of anhydrous THF. The mixture was stirred at room temperature under argon stream for 30 minutes. The supernatant of the reaction mixture of aldehyde ester prepared in advance was added by an injector with ice-cooling. The residue was washed with anhydrous THF (10 ml, 8 ml×2) and the supernatant of the washings was also added. The reaction mixture was stirred with ice-cooling for 15 minutes. 40 ml of a saturated aqueous solution of ammonium chloride was added to this reaction mixture and the mixture was extracted with ethyl acetate (30 ml×3). The combined organic layers were washed with 100 ml of water and 100 ml of brine, dried over anhydrous sodium sulfate (30 g), and then concentrated. The residue was purified through column chromatography (silica gel, ethyl acetate/cyclohexane 1:3) to obtain a colorless oil of 16-cyclohexyl-16-methyl-15-oxo-2,5,6,7,18,19,20-heptanor-4-oxa-4,8-inter-m-phenylene PGI₂ methyl ester, 11-acetate (1.6175 g, 3.43 mmol, 95%). This compound was assigned the structure by the following data:

IR(Liquid film method): 2920, 2850, 1754, 1732, 1682, 1620, 1591, 1480, 1459, 1363, 1290, 1233, 1184, 1108, 1055, 992, 943, 885, 844, 764, 731, 701 cm⁻¹.

NMR(100 MHz, CDCl₃, δ): 0.81–1.95(11H, m), 1.06(6H, s), 1.82(3H, s), 2.05–2.35(1H, m), 2.51–3.09(2H, m), 3.56–3.81(1H, m), 3.79(3H, s), 4.73(2H, s), 4.99(1H, q, J=5.38 Hz), 5.17–5.44(1H, m), 6.47–6.98(5H, m).

MASS(EI, m/e): 484(M+).

REFERENCE EXAMPLE 128

17-cyclohexyl-16,16-dimethyl-15-oxo-2,5,6,7,18,19,20-heptanor-4-oxa-4,8-inter-m-phenylene PGI₂ methyl ester, 11-acetate (128)

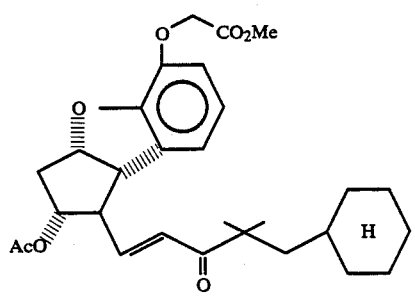

To a solution of methyl 2α-acetoxy-1β-hydroxymethyl-3aβH,8bβH-2,3,3a,8b-tetrahydro-1H-5-cyclopenta[b]benzofuranyloxyacetate (1.20 g, 3.57 mmol) in 10 ml of anhydrous THF were added anhydrous DMSO (5.0 ml, 70.8 mmol), anhydrous pyridine (0.3 ml, 3.71 mmol), anhydrous trifluoroacetic acid (0.14 ml, 1.79 mmol) and DCC (1.10 g, 5.36 mmol) under argon stream at 0° C., and the mixture was stirred at room temperature for 1 hour and a half.

Sodium hydride (60% mineral oil dispersion, 0.24 g, 6.00 mmol) was suspended in 5 ml of anhydrous THF, and to this suspension was added a solution of dimethyl 4-cyclohexyl-3,3-dimethyl-2-oxobutylphosphonate (1.76 g, 6.07 mmol) in 9 ml of anhydrous THF under argon stream at 0° C., and the mixture was stirred at room temperature for 45 minutes. The reaction mixture of aldehyde ester prepared in advance was added by an injector. The residue was washed three times each with 5 ml of anhydrous THF and the washings were also added. The mixture was stirred at room temperature for 1 hour and 20 minutes. The mixture was combined with 10 ml of a saturated aqueous solution of ammonium chloride, and the mixture was extracted with ethyl acetate (50 ml×4). The combined ethyl acetate layer was washed with water (50 ml) and brine (50 ml), dried over anhydrous sodium sulfate and concentrated. The residue was purified by column chromatography (silica gel, ethyl acetate/cyclohexane=1:2) to afford an oily product, which was further purified by column chromatography (silica gel, ethyl acetate/cyclohexane=1:4) to give a pure product of 17-cyclohexyl-16,16-dimethyl-15-oxo-2,5,6,7,18,19,20-heptanor-4-oxa-4,8-inter-m-phenylene PGI₂ methyl ester, 11-acetate in a yield of 93.3%. The compound was assigned the structure by the following data:

IR(Liquid film method): 2920, 2845, 1733, 1683, 1618, 1590, 1483, 1455, 1367, 1278, 1238, 1193, 1158, 1111, 1083, 1058, 1028, 995, 979, 940, 910, 845, 775, 758, 728, 685, 609 cm⁻¹.

NMR(100 MHz, CDCl₃ δ): 0.60–1.74(19H, m), 1.81(3H, s), 2.12–2.34(1H, m), 2.49–3.10(2H, m), 3.55–3.72(1H, m), 3.79(3H, s), 4.73(2H, s), 4.86–5.13(1H, m), 5.13–5.45(1H, m), 6.48–7.00(5H, m).

MASS(EI, m/e): 498(M⁺).

REFERENCE EXAMPLE 129

15-oxo-15-phenyl-2,5,6,7,16,17,18,19,20-nonanor-4-oxa-4,8-inter-m-phenylene PGI₂ methyl ester, 11-benzoate (129)

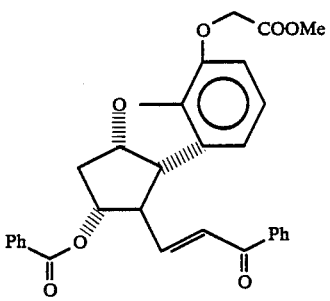

To a solution of methyl 2α-benzoyloxy-1β-hydroxymethyl-3aβH,8bβH-2,3,3a,8b-tetrahydro-1H-5-cyclopenta[b]benzofuranyloxyacetate (1.58 g, 3.97 mmol) in anhydrous THF (20 ml) were added anhydrous DMSO (2.8 ml, 39.7 mmol), anhydrous pyridine (0.10 ml, 1.23 mmol), trifluoroacetic acid (0.09 ml, 1.11 mmol), and DCC (1.23 g, 5.96 mmol) under argon atmosphere, and the mixture was stirred at room temperature for 2 hours.

Sodium hydride (60% mineral oil dispersion, 230 mg, 5.76 mmol) was suspended in anhydrous THF (10 ml) under argon atmosphere, and to this suspension was added a solution of dimethyl 2-oxo-2-phenylethylphosphonate (1.36 g, 5.96 mmol) in 5 ml of anhydrous THF, and the mixture was stirred at room temperature for 30 minutes. The aldehyde solution synthesized in advance was added to this reaction mixture at 0° C., and the mixture was allowed to warm to room temperature and stirred for 10 minutes. Thus obtained reaction solution was neutralized with acetic acid and concentrated. The residue was combined with ethyl acetate (50 ml), and then filtered. The resulting crystals were washed with ethyl acetate (20 ml×2). The washings and the filtrate were washed with water (50 ml) and brine, and dried over anhydrous magnesium sulfate. After concentration, the residue was purified by column chromatography (silica gel, ethyl acetate/cyclohexane=1:8–1:4) to give 15-oxo-15-phenyl-2,5,6,7,16,17,18,19,20-nonanor-4-oxa-4,8-inter-m-phenylene PGI₂ methyl ester, 11-benzoate (1.70 g, 85.9%) as an oil. This compound was assigned the structure by the following data:

IR(Liquid film method): 3030, 2960, 2870, 1760, 1720, 1680, 1620, 1600, 1580, 1490, 1470, 1450, 1380, 1320, 1280, 1220, 1200, 1120, 1070, 1060, 1030, 1010, 980, 940, 850, 760, 720, 700, 670 cm⁻¹.

NMR(90 MHz, CDCl₃, δ): 2.3–2.9(2H, m), 3.2–3.5(1H, m), 3.75(3H, s), 3.94(1H, dd, J=4.2, 8.4 Hz), 4.67(2H, s), 5.2–5.7(2H, m), 6.5–8.1(15H, m).

MASS(EI, m/e): 498(M⁺).

REFERENCE EXAMPLE 130

15-oxo-16-phenyl-2,5,6,7,17,18,19,20-octanor-4-oxa-4,8-inter-m-phenylene PGI₂ methyl ester, 11-benzoate (130)

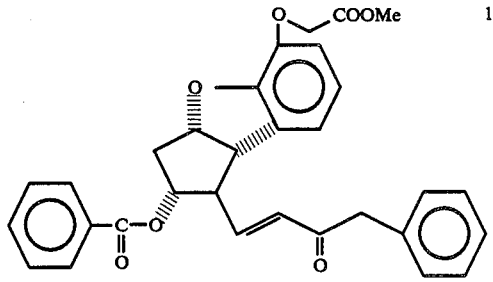

To an ice-cooled and stirred solution of methyl 2α-benzoyloxy-1β-hydroxymethyl-3aαH,8bβH-2,3,3a,8b-tetrahydro-1H-5-cyclopenta[b]benzofuranyloxyacetate (1.8 g, 4.52 mmol) in 10 ml of anhydrous THF were added anhydrous pyridine (0.11 ml, 1.36 mmol), anhydrous trifluoroacetic acid (0.1 ml, 1.30 mmol), anhydrous DMSO (4 ml, 56.3 mmol) and DCC (1.8 g, 8.72 mmol) under argon stream, and the mixture was stirred at room temperature for 3 hours.

Sodium hydride (60% mineral oil dispersion, 312 mg, 7.8 mmol) was suspended in 5 ml of anhydrous THF, and to this suspension was added a solution of dimethyl 2-oxo-3-phenylpropylphosphonate (1.8 g, 7.44 mmol) in 5 ml of anhydrous THF with ice-cooling and stirring. The mixture was stirred at room temperature for 30 minutes. This reaction mixture was ice-cooled and combined with the reaction solution of aldehyde ester synthesized in advance. The mixture was stirred for 10 minutes. This reaction mixture was neutralized with acetic acid. The precipitates were filtered and thoroughly washed with ethyl acetate. The washing and the filtrate were washed with water (30 ml) and brine (30 ml). After drying and concentration, 4.2 g of any oily product was obtained. This oily product was purified by column chromatography (silica gel, ethyl acetate/cyclohexane=1/9) to give 15-oxo-16-phenyl-2,5,6,7,17,18,19,20-octanor-4-oxa-4,8-inter-m-phenylene PGI₂ methyl ester, 11-benzoate (1.7 g, 3.32 mmol) in a yield of 71%. This compound was assigned the structure by the following data:

IR(Liquid film method): 3020, 2920, 2850, 1750, 1710, 1620, 1600, 1485, 1450, 1440, 1310, 1265, 1210, 1185, 1110, 1070, 1025, 965, 940, 850, 755, 710 cm$^{-1}$.

NMR(90 MHz, CDCl₃ δ): 2.20–3.30(2H, m), 3.30(1H, m), 3.70(1H, s), 3.80(1H, m), 3.85(2H, s), 4.65(2H, s), 5.30(2H, m), 6.30(1H, d, J=15.0 Hz), 6.72(3H, s), 6.85(1H, dd, J=7.9, 15.0 Hz), 7.10–7.70(10H, m).

MASS(EI, m/e): 512(M⁺).

REFERENCE EXAMPLE 131

15-oxo-17-phenyl-2,5,6,7,18,19,20-heptanor-4-oxa-4,8-inter-m-phenylene PGI₂ methyl ester, 11-benzoate (131)

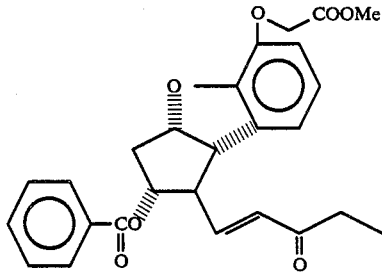

To an ice-cooled solution of methyl 2α-benzoyloxy-1β-hydroxymethyl-3aβH,8bβH-2,3,3a,8b-tetrahydro-1H-5-cyclopenta[b]benzofuranyloxyacetate (1.9 g, 4.8 mmol) in anhydrous THF were added anhydrous pyridine (0.11 ml, 1.36 mmol), trifluoroacetic acid (0.10 ml, 1.30 mmol), anhydrous DMSO (3.95 ml, 55.6 mmol) and DCC (1.7 g, 8.24 mmol) under argon stream, and the mixture was stirred at room temperature for 3 hours.

Sodium hydride (60% mineral oil dispersion, 312 mg, 7.8 mmol) was suspended in 5 ml of anhydrous THF, and to this suspension was added a solution of dimethyl 2-oxo-4-phenylbutylphosphonate (1.8 g, 7.0 mmol) in 5 ml of anhydrous THF with ice-cooling under argon stream. The mixture was stirred at room temperature for 30 minutes. The reaction solution of aldehyde ester synthesized in advance was added to this reaction mixture, and the mixture was stirred with ice-cooling for 10 minutes. Then, the mixture was adjusted to pH7 with acetic acid. The precipitate was filtered, thoroughly washed with ethyl acetate. The washing was combined with the filtrate. The solution was washed with water and brine, dried and then concentrated. Thus obtained oily product was separated and purified by column chromatography (silica gel: ethyl acetate/cyclohexane=1/9) to give 15-oxo-17-phenyl-2,5,6,7,18,19,20-heptanor-4-oxa-4,8-inter-m-phenylene PGI₂ methyl ester, 11-benzoate (2.2 g, 4.2 mmol) in a yield of 88%. This compound was assigned the structure by the following data:

IR(Liquid film method): 3025, 2930, 2850, 1760, 1715, 1675, 1620, 1600, 1485, 1450, 1370, 1315, 1270, 1215, 1190, 1115, 1070, 1025, 975, 940, 850, 755, 715, 700 cm$^{-1}$.

NMR(90 MHz, CDCl₃, δ): 2.50(2H, m), 2.92(4H, s), 3.15(1H, m), 3.75(3H, s), 3.80(1H, m), 4.66(2H, s), 5.35(2H, m), 6.22(1H, d, J=16.0 Hz), 6.72(1H, dd, J=7.9, 16.0 Hz), 7.30(8H, m), 7.55(2H, m).

MASS(EI, m/e): 526(M⁺).

REFERENCE EXAMPLE 132

15-o-methylphenyl-15-oxo-2,5,6,7,16,17,18,19,20-nonanor-4-oxa-4,8-inter-m-phenylene PGI$_2$ methyl ester, 11-benzoate (132)

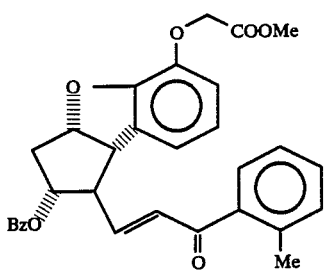

To a solution of methyl 2α-benzoyloxy-1β-hydroxymethyl-3aβH,8bβH-2,3,3a,8b-tetrahydro-1H-5-cyclopenta[b]benzofuranyloxyacetate (1.8520 g, 4.65 mmol) in 10 ml of anhydrous THF were added anhydrous pyridine (0.38 ml, 4.65 mmol), 5 ml of anhydrous DMSO, trifluoroacetic acid (0.18 ml, 2.33 mmol) and DCC (1.44 g, 6.98 mmol) under argon stream, and the mixture was stirred at room temperature for 1 hour and a half. Calcium carbonate (1.51 g, 15.1 mmol) was added to the reaction mixture, which was then stirred for 20 minutes and allowed to stand.

Sodium hydride (60% mineral oil dispersion, 279.2 mg, 6.98 mmol) was suspended in 20 ml of anhydrous THF, and to this suspension was added a solution of dimethyl 2-o-methylphenyl-2-oxo-ethylphosphonate (1.6892 g, 6.98 mmol) in 5 ml of anhydrous THF, and the mixture was stirred at room temperature under argon stream for 30 minutes. The supernatant of the reaction mixture of aldehyde ester prepared in advance was added by an injector with ice-cooling. The residue was washed with anhydrous THF (10 ml×2, 5 ml), and the supernatant of the washings was also added. The reaction mixture was stirred at room temperature for 20 minutes. 50 ml of a saturated aqueous solution of ammonium chloride were added and the mixture was extracted with ethyl acetate (30 ml×3). The combined organic layers were washed with 100 ml of water and 100 ml of brine, dried over anhydrous sodium sulfate (25 g), and then concentrated. This residue was purified by column chromatography (silica gel, ethyl acetate/cyclohexane 1:3) to give a colorless oily product of 15-o-methylphenyl-15-oxo-2,5,6,7,16,17,18,19,20-nonanor-4-oxa-4,8-inter-m-phenylene PGI$_2$ methyl ester, 11-benzoate (2.0058 g, 3.92 mmol) in a yield of 84%. This compound was assigned the structure by the following data:

IR(Liquid film method): 3080, 2970, 1761, 1728, 1678, 1657, 1623, 1499, 1465, 1386, 1330, 1282, 1225, 1202, 1123, 1078, 1059, 1034, 985, 940, 845, 780, 742, 721 cm$^{-1}$.

NMR(400 MHz, CDCl$_3$, δ): 2.43(3H, s), 2.40–2.49(1H, m), 2.63–2.72(1H, m), 3.25–3.30(1H, m), 3.75(3H, s), 3.88–3.93(1H, m), 4.63(1H, d, J=16.1 Hz), 4.69(1H, d, J=16.1 Hz), 5.33–5.40(1H, m), 5.42–5.48(1H, m), 6.67–6.89(5H, m), 7.24–7.52(7H, m), 7.55–7.60(2H, m).

MASS(EI, m/e): 512(M+).

REFERENCE EXAMPLE 133

15-p-methylphenyl-15-oxo-2,5,6,7,16,17,18,19,20-nonanor-4-oxa-4,8-inter-m-phenylene PGI$_2$ methyl ester, 11-benzoate (133)

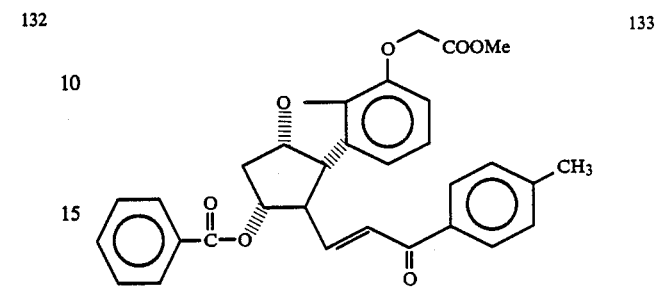

To a solution of methyl 2α-benzoyloxy-1β-hydroxymethyl-3aβH,8bβH-2,3,3a,8b-tetrahydro-1H-5-cyclopenta[b]benzofuranyloxyacetate (2.0 g, 5.03 mmol) in 10 ml of anhydrous THF were added pyridine (0.122 ml, 1.51 mmol), trifluoroacetic acid (0.144 ml, 1.87 mmol), DMSO (3.51 ml, 49.4 mmol) and DCC (1.37 g, 6.64 mmol) under argon atmosphere, and the mixture was stirred at room temperature for 3 hours.

Sodium hydride (60% mineral oil dispersion, 362 mg, 9.1 mmol) was suspended in 10 ml of anhydrous THF under argon atmosphere. To this suspension was added dropwise a solution of dimethyl 2-p-methylphenyl-2-oxoethylphosphonate (2.2 g, 9.1 mmol) in 5 ml of anhydrous THF with ice-cooling and stirring, and the mixture was stirred for 30 minutes. The preliminarily synthesized aldehyde ester was added to this reaction solution with ice-cooling and stirring, and the mixture was stirred for 30 minutes. This reaction mixture was neutralized with acetic acid. After filtration, the filtrate was concentrated. The concentrated residue was combined with 30 ml of water, and the mixture was extracted with ethyl acetate (50 ml×2). The ethyl acetate layers were washed with water (20 ml×1) and brine (20 ml×1), dried over anhydrous sodium sulfate, and then concentrated. The residue was separated and purified through column chromatography (silica gel 60 g, ethyl acetate/cyclohexane, 1/5) to give 15-p-methylphenyl-15-oxo-2,5,6,7,16,17,18,19,20-nonanor-4-oxa-4,8-inter-m-phenylene PGI$_2$ methyl ester, 11-benzoate (2.16 g, 4.21 mmol, yield 83.8%) as an oil. The structure was confirmed by the following data:

IR(Liquid film method): 3030, 2950, 1755, 1720, 1670, 1620, 1605, 1570, 1375, 1320, 1270, 1210, 1190, 1110, 1070, 1050, 1030, 980, 940, 890, 850, 815, 760, 715, 670 cm$^{-1}$.

NMR(400 MHz, CDCl$_3$, δ): 2.43(3H, s), 2.3–2.5(1H, m), 2.6–2.8(1H, m), 3.12–3.4(1H, m), 3.75(3H, s), 3.96(1H, dd, J=4.2, 8.5 Hz), 4.65(1H, d, J=16.4 Hz), 4.69(1H, d, J=16.4 Hz), 5.42(1H, q, J=4.6 Hz), 5.4–5.6(1H, m), 6.7–6.9(3H, m), 7.00(1H, dd, J=7.5, 15.6 Hz), 7.08(1H, d, J=15.6 Hz), 7.2–7.4(4H, m), 7.49(1H, t, J=7.6 Hz), 7.5–7.7(2H, m), 7.86(2H, d, J=8.3 Hz).

MASS(EI, m/e): 512(M+).

REFERENCE EXAMPLE 134

15-m-fluorophenyl-15-oxo-2,5,6,7,16,17,18,19,20-nonanor-4-oxa-4,8-inter-m-phenylene PGI₂ methyl ester, 11-benzoate (134)

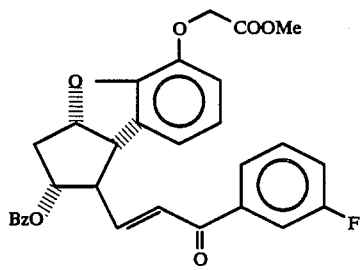

To a solution of methyl 2α-benzoyloxy-1β-hydroxymethyl-3aβH,8bβH-2,3,3a,8b-tetrahydro-1H-5-cyclopenta[b]benzofuranyloxyacetate (1.9421 g, 4.88 mmol) in 15 ml of anhydrous THF were added anhydrous pyridine (0.39 ml, 4.88 mmol), 5 ml of anhydrous DMSO, trifluoroacetic acid (0.19 ml, 2.44 mmol) and DCC (1.51 g, 7.32 mmol) under argon atmosphere, and the mixture was stirred at room temperature for 1 hour and a half. Calcium carbonate (1.59 g, 15.86 mmol) was added to the reaction mixture, and the mixture was stirred for 20 minutes and allowed to stand.

Sodium hydride (60% mineral oil dispersion, 292.8 mg, 7.32 mmol) was suspended in 30 ml of anhydrous THF, and to this suspension was added a solution of dimethyl 2-m-fluorophenyl-2-oxoethylphosphonate (1.57 g, 7.32 mmol) in 5 ml of anhydrous THF, and the mixture was stirred at room temperature under an argon stream for 30 minutes. The supernatant of the reaction mixture of aldehyde ester prepared in advance was added by an injector with ice-cooling. The residue was washed with anhydrous THF (10 ml, 5 ml×2), and the supernatant of the washings was also added. The reaction mixture was stirred at room temperature for 25 minutes, 50 ml of a saturated aqueous solution of ammonium chloride were added to the mixture, and the mixture was extracted with ethyl acetate (50 ml×3). The combined organic layers were washed with 150 ml of water and 150 ml of brine, dried over anhydrous sodium sulfate (40 g), and then concentrated. The residue was purified by column chromatography (silica gel, ethyl acetate/cyclohexane 1:3) to give a colorless oil of 15-m-fluoroophenyl-15-oxo-2,5,6,7,16,17,18,19,20-nonanor-4-oxa-4,8-inter-m-phenylene PGI₂ methyl ester, 11-benzoate (2.0346 g, 4.07 mmol) in a yield of 83%. This compound was assigned the structure by the following data:

IR(Liquid film method): 3060, 2950, 1752, 1709, 1662, 1619, 1582, 1480, 1440, 1365, 1270, 1214, 1190, 1108, 1061, 1050, 1021, 978, 943, 894, 850, 799, 610 cm⁻¹.

NMR(400 MHz, CDCl₃, δ): 2.43–2.52(1H, m), 2.68–2.77(1H, m), 3.30–3.34(1H, m), 3.76(3H, s), 3.92–3.97(1H, m), 4.65(1H, d, J=16.1 Hz), 4.70(1H, d, J=16.1 Hz), 5.41–5.46(1H, m), 5.46–5.52(1H, m), 6.75–6.82(2H, m), 6.84–6.89(1H, m), 6.98–7.10(2H, m), 7.26–7.35(4H, m), 7.43–7.54(2H, m), 7.60–7.66(2H, m), 7.72–7.75(1H, m).

MASS(EI, m/e): 516(M⁺).

REFERENCE EXAMPLE 135

15-m-trifluoromethylphenyl-15-oxo-2,5,6,7,16,17,18,19,20-nonanor-4-oxa-4,8-inter-m-phenylene PGI₂ methyl ester, 11-benzoate (135)

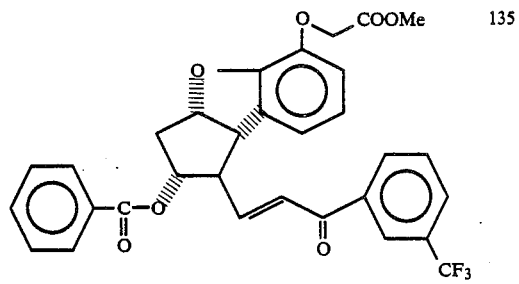

To a solution of methyl 2α-benzoyloxy-1β-hydroxymethyl-3aβH,8bβH-2,3,3a,8b-tetrahydro-1H-5-cyclopenta[b]benzofuranyloxyacetate (1.9995 g, 5.02 mmol) in 15 ml of anhydrous THF were added 5 ml of anhydrous DMSO, anhydrous pyridine (0.47 ml, 5.73 mmol), anhydrous trifluoroacetic acid (0.29 ml, 3.88 mmol) and DCC (1.48 g, 7.18 mmol) under argon stream, and the mixture was stirred at room temperature for 30 minutes. To this reaction mixture was added 2.51 g of calcium carbonate with ice-cooling and the mixture was stirred for 30 minutes.

Sodium hydride (60% mineral oil dispersion, 0.24 g, 5.95 mmol) was suspended in 10 ml of anhydrous THF, and to this suspension was added a solution of dimethyl 2-oxo-2-m-trifluoromethylphenylethylphosphonate (2.23 g, 7.54 mmol) in 5 ml of anhydrous THF with ice-cooling, and the mixture was stirred for 30 minutes under argon stream. The supernatant of the reaction mixture of aldehyde ester prepared in advance was added by an injector. The residue was washed with anhydrous THF (3 ml×3), and the supernatant of the washings was also added. The mixture was stirred at room temperature for 1.5 hours. 30 ml of a saturated aqueous solution of ammonium chloride were added to this reaction mixture and the mixture was extracted with ethyl acetate (50 ml×3). The combined organic layers were washed with water (100 ml) and brine (100 ml), dried over anhydrous sodium sulfate and then concentrated. The residue was purified by column chromatography (silica gel, ethyl acetate/cyclohexane=½) to give a colorless oil of 15-m-trifluoromethylphenyl-15-oxo-2,5,6,16,17,18,19,20-nonanor-4-oxa-4,8-inter-m-phenylene PGI₂ methyl ester, 11-benzoate (1.3387 g, 2.36 mmol) at a yield of 47.1%. This compound was assigned the structure by the following data:

IR(Liquid film method): 3055, 2950, 2860, 1752, 1710, 1665, 1615, 1480, 1460, 1437, 1375, 1328, 1260, 1215, 1170, 1120, 1065, 1020, 995, 972, 935, 845, 805, 770, 736, 715, 650 cm⁻¹.

NMR(100 MHz, CDCl₃, δ): 2.15–2.95(2H, m), 3.18–3.45(1H, m), 3.76(3H, s), 3.82–4.00(1H, m), 4.68(2H, s), 5.25–5.66(2H, m), 6.65–6.98(3H, m), 6.98–7.15(2H, m), 7.15–8.30(9H, m).

MASS(EI, m/e): 566(M⁺).

REFERENCE EXAMPLE 136

15-o-chlorophenyl-15-oxo-2,5,6,7,16,17,18,19,20-nonanor-4-oxa-4,8-inter-m-phenylene PGI₂ methyl ester, 11-benzoate (136)

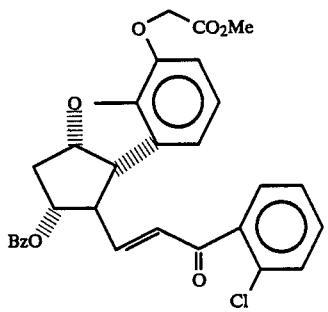

To a solution of methyl 2α-benzoyloxy-1β-hydroxymethyl-3aβH,8bβH-2,3,3a,8b-tetrahydro-1H-5-cyclopenta[b]benzofuranyloxyacetate (2.18 g, 5.48 mmol) in 10 ml of anhydrous THF were added anhydrous DMSO (4.0 ml, 56.7 mmol), anhydrous pyridine (0.12 ml, 1.48 mmol), anhydrous trifluoroacetic acid (0.22 ml, 2.86 mmol) and DCC (1.59 g, 7.71 mmol) under argon stream, and the mixture was stirred at room temperature under argon atmosphere for 2 hours and a half. To the reaction mixture was added calcium carbonate (1.65 g, 16.5 mmol) with ice-cooling.

Sodium hydride (60% mineral oil dispersion, 0.33 g, 8.25 mmol) was suspended in 5 ml of anhydrous THF, and to this suspension was added a solution of dimethyl 2-o-chlorophenyl-2-oxoethylphosphonate (1.59 g, 6.06 mmol) in 14 ml of anhydrous THF with ice-cooling under argon atmosphere. The supernatant of the reaction mixture of aldehyde ester prepared in advance was also added by an injector. The residue was washed three times each with 5 ml of anhydrous THF and the supernatant of the washings was also added. The mixture was stirred with ice-cooling for 10 minutes. To this reaction mixture were added 3 droplets of acetic acid and the precipitate was filtered. The filtrate was combined with 10 ml of water and the mixture was extracted ethyl acetate (50 ml×4). The combined ethyl acetate layers were washed with water (50 ml) and brine (50 ml), dried over anhydrous sodium sulfate and then concentrated. The residue was roughly purified by column chromatography (silica gel, ethyl acetate/cyclohexane=1:4) to afford an oily product which was purified by column chromatography (silica gel, ethyl acetate/cyclohexane=1:3) to give a pure product of 15-o-chlorophenyl-15-oxo-2,5,6,7,16,17,18,19,20-nonanor-4-oxa-4,8-inter-m-phenylene PGI₂ methyl ester 11-benzoate (1.39 g, 5.61 mmol, 47.6%). This compound was assigned the structure by the following data:

IR(Liquid film method): 3060, 2950, 1753, 1716, 1658, 1618, 1591, 1581, 1483, 1461, 1433, 1373, 1315, 1272, 1218, 1190, 1112, 1065, 1023, 978, 847, 762, 730, 672, 645 cm⁻¹.

NMR(100 MHz, CDCl₃, δ): 2.05–3.10(2H, m), 3.10–3.45(1H, m), 3.60–4.07(4H, m), 4.52–4.80(2H, m), 5.19–5.62(2H, m), 6.47–7.00(5H, m), 7.15–7.80(9H, m).

MASS(EI, m/e): 532(M⁺).

REFERENCE EXAMPLE 137

15-m-chlorophenyl-15-oxo-2,5,6,7,16,17,18,19,20-nananor-4-oxa-4,8-inter-m-phenylene PGI₂ methyl ester, 11-benzoate (137)

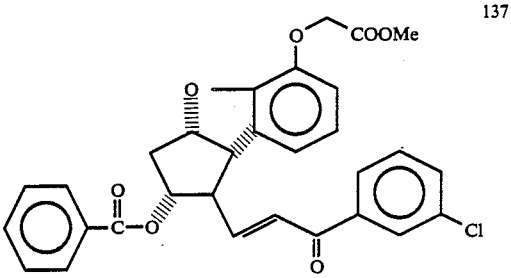

To a stirred solution of methyl 2α-benzoyloxy-1β-hydroxymethyl-3aβH,8bβH-2,3,3a,8b-tetrahydro-1H-5-cyclopenta[b]benzofuranyloxyacetate (1.8 g, 4.52 mmol) in 9 ml of anhydrous THF were added pyridine (0.11 ml, 1.36 mmol), trifluoroacetic acid (0.13 ml, 1.68 mmol), DMSO (3.15 ml, 44.3 mmol) and DCC (1.09 g, 5.28 mmol) under argon atmosphere, and the mixture was stirred at room temperature for 2.5 hours.

Sodium hydride (60% mineral oil dispersion, 289 mg, 7.23 mmol) was suspended in 9 ml of anhydrous THF under argon atmosphere, and to this suspension was added dropwise a solution of dimethyl 2-chlorophenyl-2-oxoethylphosphonate (1.9 g, 7.23 mmol) in 5 ml of anhydrous THF with ice-cooling under argon atmosphere, and the mixture was stirred for 30 minutes. The preliminarily synthesized aldehyde ester was added to this reaction mixture with ice-cooling, and this mixture was stirred at room temperature for 30 minutes. The reaction mixture was neutralized with acetic acid. After filtration, the filtrate was concentrated. The concentrated residue was combined with 20 ml of water, and the mixture was extracted with ethyl acetate (50 ml×2). The combined ethyl acetate layers were washed with water (20 ml×1) and brine (20 ml×1), dried over anhydrous sodium sulfate and then concentrated. The concentrated residue was roughly purified by column chromatography (silica gel 50 g, ethyl acetate/cyclohexane 1/5). The product was further purified by a Merck, Lobar column (silica gel, ethyl acetate/cyclohexane, ¼) to give 15-m-chlorophenyl-15-oxo-2,5,6,7,16,17,18,19,20-nonanor-4-oxa-4,8-inter-m-phenylene PGI₂ methyl ester, 11-benzoate (yielded amount 1.90 g, 3.56 mmol, yield 78.9%), which was assigned the structure by the following data:

IR(Liquid film method): 3070, 2960, 1760, 1710, 1615, 1570, 1490, 1470, 1450, 1430, 1370, 1350, 1320, 1270, 1220, 1190, 1120, 1070, 1030, 1000, 980, 910, 850, 790, 735, 710, 670 cm⁻¹.

NMR(90 MHz, CDCl₃, δ): 2.3–3.0(2H, m), 3.0–3.5(1H, m), 3.76(3H, s), 3.93(1H, dd, J=4.6, 8.6 Hz), 4.68(2H, s), 5.1–5.8(2H, m), 6.6–8.1(14H, m).

MASS(EI, m/e): 532(M⁺).

REFERENCE EXAMPLE 138

15-(p-chlorophenyl)-15-oxo-2,5,6,7,16,18,19,20-nonanor-4-oxa-4,8-inter-m-phenylene PGI₂ methyl ester, 11-benzoate (138)

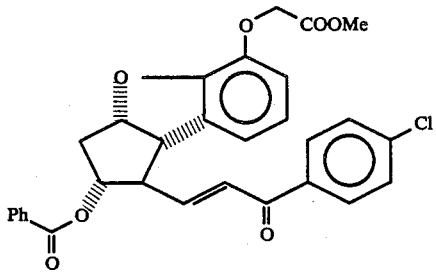

To a solution of methyl 2α-benzoyloxy-1β-hydroxymethyl-3aβH,8bβH-2,3,3a,8b-tetrahydro-1H-5-cyclopenta[b]benzofuranyloxyacetate (1.80 g, 4.52 mmol) in anhydrous THF (20 ml) were added anhydrous DMSO (3.2 ml, 45 mmol), anhydrous pyridine (0.11 ml, 1.40 mmol), trifluoroacetic acid (0.098 ml, 1.27 mmol) and DCC (1.40 g, 6.78 mmol) under argon atmosphere, and the mixture was stirred at room temperature for 3 hours.

Sodium hydride (60% mineral oil dispersion, 262 mg, 6.55 mmol) was suspended in anhydrous THF (10 ml), and to this suspension was added a solution of dimethyl 2-(p-chlorophenyl)-2-oxoethylphosphonate (1.78 g, 6.78 mmol) in 5 ml of anhydrous THF under argon atmosphere, and the mixture was stirred at room temperature for 30 minutes. To this reaction mixture was added the preliminarily synthesized aldehyde solution at 0° C. The reaction mixture was allowed to warm to room temperature and stirred for 1 hour. Thus obtained reaction solution was neutralized with acetic acid and concentrated. The residue was combined with ethyl acetate (60 ml) and filtered. The precipitated crystals were washed with ethyl acetate (20 ml×2). The ethyl acetate washings were combined with the filtrate, washed with water (30 ml) and brine (30 ml), and dried over anhydrous magnesium sulfate. After concentration, the residue was passed through a silica gel short column (ethyl acetate/cyclohexane 1:8), and then purified by a Merck, Lobar column (silica gel, ethyl acetate/cyclohexane 1:4) to give an oil of 15-(p-chlorophenyl)-15-oxo-2,5,6,7,16,17,18,19,20-nonanor-4-oxa-4,8-inter-m-phenylene PGI₂ methyl ester, 11-benzoate (1.70 g, 3.19 mmol) in a yield of 70.6%. This compound was assigned the structure by the following data:

IR(Liquid film method): 3020, 2950, 1760, 1720, 1670, 1620, 1590, 1490, 1460, 1400, 1270, 1220, 1190, 1120, 1090, 1070, 1030, 1010, 980, 760, 710 cm⁻¹.

NMR(90 MHz, CDCl₃, δ): 2.3–2.9(2H, m), 3.2–3.4(1H, m), 3.76(3H, s), 3.93(1H, dd, J=4.4, 8.6 Hz), 4.67(2H, s), 5.3–5.6(2H, m), 6.65–8.0(14H, m).

MASS(EI, m/e): 532(M⁺).

REFERENCE EXAMPLE 139

16-methyl-15-oxo-16-phenyl-2,5,6,7,18,19,20-heptanor-4-oxo-4,8-inter-m-phenylene PGI₂ methyl ester, 11-benzoate (139)

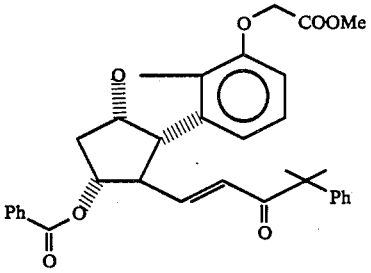

To a solution of methyl 2α-benzoyloxy-1β-hydroxymethyl-3aβH,8bβH-2,3,3a,8b-tetrahydro-1H-5-cyclopenta[b]benzofuranyloxyacetate (1.80 g, 4.52 mmol) in anhydrous THF (25 ml) were added anhydrous DMSO (3.2 ml, 45 mmol), anhydrous pyridine (0.11 ml, 1.40 mmol), trifluoroacetic acid (0.098 ml, 1.27 mmol) and DCC (1.40 g, 6.78 mmol) under argon atmosphere, and the mixture was stirred at room temperature for 4 hours. Then, under argon atmosphere, sodium hydride (60% mineral oil dispersion, 262 mg, 6.55 mmol) was suspended in anhydrous THF (10 ml), and to this suspension was added a solution of dimethyl 3-methyl-2-oxo-3-phenylbutylphosphonate (1.83 g, 6.78 mmol) in 10 ml of anhydrous THF. The mixture was stirred at room temperature for 30 minutes. the preliminarily prepared aldehyde solution was added to the reaction solution at 0° C. The mixture was stirred at 0° C. for 20 minutes and then at room temperature for 10 minutes. Thus obtained reaction solution was neutralized with acetic acid and concentrated. The residue was combined with ethyl acetate (60 ml) and filtered. The precipitated crystals were washed with ethyl acetate (20 ml×2). The washings were combined with the filtrate, washed with water (40 ml) and brine, and dried over anhydrous magnesium sulfate. After concentration, the residue was purified by column chromatography (silica gel, ethyl acetate/cyclohexane 1:8) to give an oil of 16-methyl-15-oxo-16-phenyl-2,5,6,7,18,19,20-heptanor-4-oxa-4,8-inter-m-phenylene PGI₂ methyl ester, 11-benzoate (2.39 g, 4.43 mmol) in a yield of 98.0%. This compound was assigned the structure by the following data:

IR(Liquid film method): 3030, 2980, 1760, 1720, 1630, 1600, 1490, 1460, 1380, 1370, 1320, 1270, 1220, 1190, 1110, 1070, 1050, 1030, 1000, 980, 950, 870, 850, 760, 720, 670 cm⁻¹.

NMR(90 MHz, CDCl₃, δ): 1.49(6H, s), 2.1–3.2(3H, m), 3.5–3.8(1H, m), 3.72(3H, s), 4.61(2H, s), 5.0–5.5(2H, m), 6.05(1H, dd, J=0.9, 15.5 Hz), 6.4–7.6(14H, m).

MASS(EI, m/e): 540(M⁺).

REFERENCE EXAMPLE 140

16,16-dimethyl-15-oxo-17-phenyl-2,5,6,7,18,19,20-heptanor-4-oxa-4,8-inter-m-phenylene PGI2 methyl ester, 11-acetate (140)

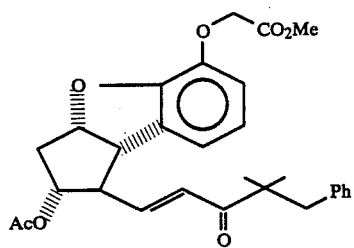

To a solution of methyl 2α-acetoxy-1β-hydroxymethyl-3aβH,8bβH-2,3,3a,8b-tetrahydro-1H-5-cyclopenta[b]benzofuranyloxyacetate (1.03 g, 3.06 mmol) in 10 ml of anhydrous THF were added anhydrous DMSO (4.3 ml, 60.9 mmol), anhydrous pyridine (0.26 ml, 3.21 mmol), anhydrous trifluoroacetic acid (0.12 ml, 1.56 mmol) and DCC (0.94 g, 4.56 mmol) under argon stream at 0° C., and the mixture was stirred at room temperature for 40 minutes. Sodium hydride (60% mineral oil dispersion, 0.21 g, 5.25 mmol) was suspended in 5 ml of anhydrous THF, and to this suspension was added dimethyl 3,3-dimethyl-2-oxo-4-phenylbutylphosphonate (1.48 g, 5.20 mmol) in 9 ml of anhydrous THF under argon stream at 0° C. The mixture was stirred at room temperature for 1 hour. The reaction mixture of aldehyde ester prepared in advance was added by an injector. The residue was washed three times each with 5 ml of anhydrous THF and the supernatant of the washings was also added. The mixture was stirred at room temperature for 1 hour. The reaction mixture was combined with 10 ml of a saturated aqueous solution of ammonium chloride, and the mixture was extracted with ethyl acetate (50 ml×4). The combined ethyl acetate layers were washed with water (50 ml) and brine (50 ml), dried over anhydrous sodium sulfate and concentrated. The residue was roughly purified by column chromatography (silica gel, ethyl acetate/cyclohexane=1:2). Thus obtained oily product was further purified by column chromatography (silica gel, ethyl acetate/cyclohexane=1:4) to give a pure product of 16,16-dimethyl-15-oxo-17-phenyl-2,5,6,7,18,19,20-heptanor-4-oxa-4,8-inter-m-phenylene PGI2 methyl ester, 11-acetate (1,2899 g, 2.62 mmol) in a yield of 85.6%. This compound was assigned the structure by the following data:

IR(Liquid film method): 3025, 2960, 1752, 1734, 1683, 1618, 1482, 1458, 1435, 1365, 1320, 1290, 1235, 1188, 1110, 1052, 998, 943, 843, 740, 700 cm$^{-1}$.

NMR(100 MHz, CDCl$_3$, δ): 1.15(6H, s), 1.80(3H, s), 2.08-2.33(1H, m), 2.38-3.10(4H, m), 3.53-3.70(1H, m), 3.78(3H, s), 4.72(2H, s), 5.00(1H, dd, J=12.09 Hz, 5.94 Hz), 5.15-5.43(1H, m), 6.43-7.40(10H, m).

MASS(EI, m/e): 492(M+).

REFERENCE EXAMPLE 141

16,16-Dimethyl-15-oxo-2,5,6,7,20-pentanor-4,18-dioxa-4,8-inter-m-phenylene PGI2 methyl ester, 11-benzoate 141

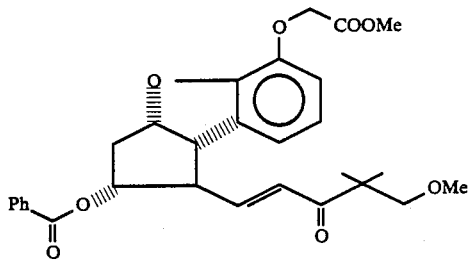

A solution of methyl 2α-benzoyloxy-1β-hydroxymethyl-3aβH,8bβH-2,3,3a,8b-tetrahydro-1H-5-cyclopenta[b]benzofuranyloxyacetate (1.80 g, 4.52 mmol) in 25 ml of anhydrous THF was mixed under argon atmosphere with anhydrous DMSO (3.2 ml, 45 mmol), anhydrous pyridine (0.11 ml, 1.40 mmol), trifluoroacetic acid (0.098 ml, 1.27 mmol) and D.C.C. (1.40 g, 6.78 mmol), and the mixture was stirred for 3 hrs. at room temperature. Under argon atmosphere sodium hydride (60% mineral oil dispersion, 262 mg, 6.55 mmol) was suspended in 10 ml of anhydrous THF. To this suspension was added a solution of dimethyl 3,3-dimethyl-2-oxo-5-oxahexylphosphonate (1.62 g, 6.78 mmol) in 10 ml of anhydrous THF, and the mixture was stirred for 30 min. at room temperature. At 0° C. this solution was mixed with the aldehyde solution prepared above, allowed to warm to room temperature and stirred for 30 min. The resulting solution was neutralized with acetic acid, and concentrated. The residue was triturated in ethyl acetate (30 ml), and the resulting crystals were filtered off and washed with ethyl acetate (20 ml×2). The combined filtrate was washed with water (30 ml×2), with brine (30 ml), dried over anhydrous magnesium sulfate and concentrated. The concentrate was passed through a short column of silica gel (ethyl acetate/cyclohexane: 1/10), then applied to Lobar column (Merck) of silica gel (ethyl acetate/cyclohexane:1/3.5) to give 16,16-dimethyl-15-oxo-2,5,6,7,20-pentanor-4,18-dioxa-4,8-inter-m-phenylene PGI2 methyl ester, 11-benzoate (2.11 g, 4.15 mmol) as an oily material with a yield of 91.8%. The product was assigned the structure by the following data.

IR(liquid film): 3030, 2970, 2880, 1760, 1720, 1690, 1620, 1480, 1460, 1400, 1370, 1320, 1270, 1220, 1190, 1110, 1070, 1030, 980, 850, 750, 710, 670 cm$^{-1}$.

NMR(90 MHz, CDCl$_3$, δ): 1.15(6H, s); 2.2-2.9(2H, m); 3.1-3.4(1H, m); 3.29(3H, s); 3.39(2H, s); 3.74(3H, s); 3.87(1H, dd, J=4.6, 8.6 Hz); 4.65(2H, s); 5.2-5.6(2H, m); 6.5-7.05(5H, m); 7.2-7.7(5H, m).

MASS (EI, m/e): 508(M+).

REFERENCE EXAMPLE 142

16,16-Dimethyl-15-oxo-2,5,6,7-tetranor-4,18-dioxa-4,8-inter-m-phenylene PGI₂ methyl ester, 11-benzoate 142

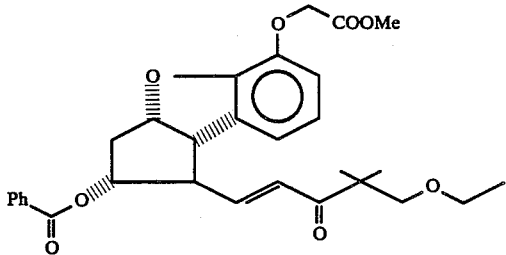

A solution of methyl 2α-benzoyloxy-1β-hydroxymethyl-3aβH,8bβH-2,3,3a,8b-tetrahydro-1H-5-cyclopenta[b]benzofuranyloxyacetate (1.80 g, 4.52 mmol) in anhydrous THF (25 ml) was mixed under argon atmosphere with anhydrous pyridine (0.11 ml, 1.40 mmol), anhydrous DMSO (3.2 ml, 45 mmol), trifluoroacetic acid (0.098 ml, 1.27 mmol) and D.C.C. (1.40 g, 6.78 mmol), and the mixture was stirred for 6 hrs. at room temperature. Under argon atmosphere sodium hydride (60% mineral oil dispersion, 262 mg, 6.55 mmol) was suspended in anhydrous THF (10 ml). To this suspension was added a solution of dimethyl 3,3-dimethyl-2-oxo-5-oxaheptylphosphonate (1.71 g, 6.78 mmol) in anhydrous THF (10 ml). The mixture was stirred for 30 min. at room temperature. At 0° C. this solution was mixed with the aldehyde solution prepared above, allowed to warm to room temperature and stirred for 30 min. The resulting solution was neutralized with acetic acid and concentrated. The residue was triturated in ethyl acetate (70 ml) and the resulting precipitate was filtered off. The filtrate was washed successively with 30 ml of water and brine, then dried over anhydrous magnesium sulfate and concentrated. The concentrate was passed through a short column of silica gel (ethyl acetate/cyclohexane: 1/8) and then purified by Lobar column of silica gel (Merck, ethyl acetate/cyclohexane: 1/4) to give 16,16-dimethyl-15-oxo-2,5,6,7-tetranor-4,18-dioxa-4,8-inter-m-phenylene PGI₂ methyl ester, 11-benzoate (1.90 g, 3.64 mmol) with a yield of 80.5% as an oily material. The product was identified by the following data. IR(liquid film): 2970, 2860, 1750, 1710, 1620, 1480, 1460, 1380, 1310, 1270, 1210, 1190, 1110, 1070, 1020, 970, 930, 840, 750, 710 cm⁻¹.

NMR(90 MHz, CDCl₃, δ): 1.12(3H, t, J=6.9 Hz); 1.15(6H, s); 2.2–2.9(2H, m); 3.1–3.4(1H, m); 3.425(2H, s); b 3.428(2H, q, J=6.9 Hz); 3.74(3H, s); 3.87(1H, dd, J=4.6, 8.6 Hz); 4.65(2H, s); 5.2–5.6(2H, m); 6.5–7.05(5H, m); 7.2–7.6(5H, m)

MASS(EI, m/e): 522(M⁺).

REFERENCE EXAMPLE 143

16,16-Dimethyl-15-oxo-20a-homo-2,5,6,7-tetranor-4,18-dioxa-4,8-inter-m-phenylene PGI₃ methyl ester, 11-benzoate 143

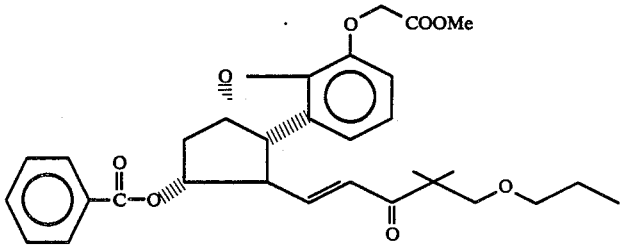

To a stirred solution of methyl 2α-benzoyloxy-1β-hydroxymethyl-3aβH,8bβH-2,3,3a,8b-tetrahydro-1H-5-cyclopenta[b]benzofuranyloxyacetate (1.8 g, 4.52 mmol) in 10 ml of anhydrous THF were added under argon atmosphere pyridine (0.11 ml, 1.36 mmol), trifluoroacetic acid (0.103 ml, 1.33 mmol), DMSO (3.19 ml, 44.9 mmol) and D.C.C. (1.39 g, 6.74 mmol). The reaction mixture was stirred for 2.5 hrs. at room temperature. Under argon atmosphere sodium hydride (60% mineral oil dispersion, 326 mg, 8.14 mmol) was suspended in 10 ml of anhydrous THF. To this suspension was added dropwise under ice-cooling a solution of dimethyl 3,3-dimethyl-2-oxo-5-oxaoctylate (2.16 g, 8.14 mmol) in 5 ml of anhydrous THF while stirring for 30 min. This solution was mixed under ice-cooling with the aldehyde ester prepared above and stirred for 30 min. while retaining at 0° C. The resulting solution was neutralized with acetic acid and filtered. The filtrate was concentrated. The concentrate was mixed with 20 ml of water and extracted with ethyl acetate (50 ml×2). The combined ethyl acetate layers were washed with water (20 ml), with brine (20 ml), dried over anhydrous sodium sulfate and concentrated. The concentrated residue was purified by column chromatography (silica gel 60 g, ethyl acetate/cyclohexane: 1/5) to afford a colourless and transparent oil of 16,16-dimethyl-15-oxo-20a-homo-2,5,6,7-tetranor-4,18-dioxa-4,8-inter-m-phenylene PGI₂ methyl ester, 11-benzoate (2.11 g, 3.94 mmol, yield 87.1%). The product was assigned the structure by the following data.

IR(liquid film): 2960, 2860, 1750, 1710, 1620, 1480, 1450, 1370, 1310, 1270, 1210, 1190, 1110, 1080, 1020, 970, 845, 750, 710 cm⁻¹.

NMR(400 MHz, CDCl₃, δ): 0.86(3H, t, J=7.0 Hz); 1.15(6H, s); 1.4–1.6(2H, m); 2.3–2.5(1H, m); 2.6–2.8(1H, m); 3.1–3.3(1H, m); 3.32(2H, t, J=7.0 Hz); 3.42 (2H, s); 3.74(3H, s); 3.87(1H, dd, J=4.4, 8.8 Hz); 4.63(1H, d, J=16.4 Hz); 4.67(1H, d, J=16.4 Hz); 5.3–5.5(2H, m); 6.6–6.9(5H, m); 7.2–7.5(5H, m).

MASS(EI, m/e): 536(M⁺).

REFERENCE EXAMPLE 144

15-Oxo-16-phenoxy-2,5,6,7,17,18,19,20-octanor-4-oxa-4,8-inter-m-phenylene PGI$_2$ methyl ester, 11-benzoate 144

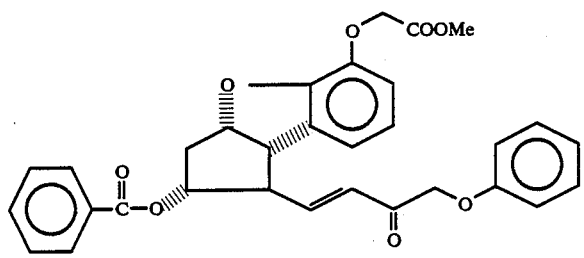

To a stirred solution of 2α-benzoyloxy-1β-hydroxymethyl-3aβH,8bβH-2,3,3a,8b-tetrahydro-1H-5-cyclopenta[b]benzofuranyloxyacetic acid methyl ester (1.7 g, 4.27 mmol) in anhydrous THF (9 ml) were added under argon atmosphere pyridine (0.104 ml, 1.29 mmol), trifluoroacetic acid (0.097 ml, 1.26 mmol), DMSO (3.01 ml, 42.4 mmol) and D.C.C. (1.31 g, 6.37 mmol), and the mixture was stirred for 2.5 hrs. at room temperature. Under argon atmosphere sodium hydride (60% mineral oil dispersion, 273 mg, 6.83 mmol) was suspended in 8 ml of anhydrous THF. To this suspension was added dropwise under ice-cooling a solution of dimethyl 2-oxo-3-phenoxypropylphosphonate (1.76 g, 6.83 mmol) in 5 ml of anhydrous THF while stirring for 20 min. This solution was mixed under ice-cooling with the aldehyde ester prepared above and stirred for 30 min. while retaining at 0° C. The resulting solution was neutralized with acetic acid and filtered. The filtrate was concentrated. The concentrated residue was mixed with 20 ml of water and extracted with ethyl acetate (50 ml33 2). The ethyl acetate layers were washed with 20 ml of water, with 20 ml of brine, dried over anhydrous sodium sulfate and concentrated. The concentrate was applied to column chromatography (silica gel 60 g, ethyl acetate/cyclohexane: 1/4) to give 15-oxo-16-phenoxy-2,5,6,7,17,18,19,20-octanor-4-oxa-4,8-inter-m-phenylene PGI$_2$ methyl ester, 11-benzoate (1.47 g, 2.78 mmol, yield 65.1%) as an oily material. The product was identified by the following data.

IR(liquid film): 2960, 2930, 2860, 1760, 1720, 1625, 1605, 1495, 1470, 1450, 1440, 1380, 1320, 1275, 1220, 1195, 1115, 1070, 1050, 1030, 980, 910, 850, 760, 730, 720, 690, 670 cm$^{-1}$.

NMR(90 MHz, CDCl$_3$, δ): 2.2–2.9(2H, m); 3.0–3.4(1H, m); 3.74(3H, s); 3.8–4.0(1H, m); 4.65(2H, s); 4.70 (2H, s); 5.2–5.6(2H, m); 6.4–7.7(15H, m).

MASS(EI, m/e): 528(M+).

REFERENCE EXAMPLE 145

16-Methyl-15-oxo-16-phenoxy-2,5,6,7,18,19,20-heptanor-4-oxa-4,8-inter-m-phenylene PGI$_2$ methyl ester, 11-acetate 145

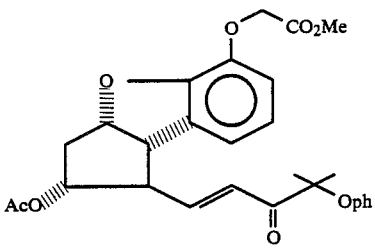

To a solution of 2α-acetoxy-1β-hydroxymethyl-3aβH, 8bβH-2,3,3a,8b-tetrahydro-1H-5-cyclopenta[b]benzofuranyloxyacetic acid methyl ester (1.20 g, 3.57 mmol) in 10 ml of anhydrous THF were added under argon atmosphere anhydrous DMSO (2.5 ml, 35.7 ml), anhydrous pyridine (0.09 ml, 1.07 mmol), anhydrous trifluoroacetic acid (0.14 ml, 1.07 mmol) and D.C.C. (1.10 g, 5.36 mmol) at 0° C., and the mixture was stirred for one hour at room temperature. Sodium hydride (60% mineral oil dispersion, 0.36 g, 8.93 mmol) was suspended in 5 ml of anhydrous THF. To this suspension was added under argon atmosphere a solution of dimethyl 3-methyl-2-oxo-3-phenoxybutylphosphonate (1.83 g, 7.14 mmol) in 11 ml of anhydrous THF at 0° C. This reaction mixture was allowed to warm to room temperature and stirred for 20 min. The aldehyde ester prepared above was injected into the above reaction mixture by means of an injector. The resulting mixture was stirred for 2 hrs. at room temperature, neutralized with acetic acid and concentrated. The residue was triturated in ethyl acetate (50 ml), and the resulting crystals were filtered off and washed with ethyl acetate (50 ml×3). The combined filtrate was washed with 50 ml of water, with 50 ml of brine, dried over anhydrous sodium sulfate and concentrated. Removal of by-products from the concentrated residue by column chromatography (silica gel, ethyl acetate/cyclohexane: 1/2) gave an oil, which was then further purified by column chromatography (silica gel, ether/n-hexane: 1/1) to afford a purified 16-methyl-15-oxo-16-phenoxy-2,5,6,7,18,19,20-heptanor-4-oxa-4,8-inter-m-phenylene PGI$_2$ methyl ester, 11-acetate (0.8705 g, 1.76 mmol) with a yield of 49.3%. The product was identified by the following data.

IR(liquid film): 2980, 2940, 1752, 1730, 1690, 1620, 1590, 1480, 1453, 1430, 1372, 1318, 1285, 1225, 1193, 1150, 1108, 1057, 1020, 990, 948, 883, 855, 843, 750, 725, 692 cm$^{-1}$.

NMR(100 MHz, CDCl$_3$, δ): 1.38–1.68(6H, m); 1.73(3H, s); 1.90–2.28(1H, m); 2.32–3.04(2H, m); 3.45–3.70 (1H, m); 3.77(3H, s); 4.69(2H, s); 4.80–5.30(2H, m); 6.30–6.57(1H, m); 6.60–7.40(9H, m).

MASS(EI, m/e): 494(M+).

REFERENCE EXAMPLE 146

16-Methyl-15-oxo-2,5,6,7-tetranor-4-oxa-18,18,19,19-tetradehydro-4,8-inter-m-phenylene PGI$_2$methyl ester, 11-benzoate 146

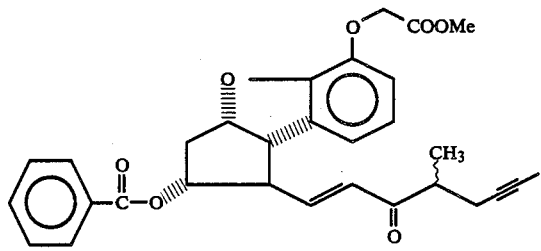

Under argon atmosphere to a solution of 2α-benzoyloxy-1β-hydroxymethyl-3aβH,8bβH-2,3,3a,8b-tetrahydro-1H-5-cyclopenta[b]benzofuranyloxyacetic acid methyl ester (2.0 g, 5.03 mmol) in anhydrous THF (10 ml) were added pyridine (0.122 ml, 1.51 mmol), trifluoroacetic acid (0.114 ml, 1.48 mmol), DMSO (3.51 ml, 49.4 mmol) and D.C.C. (1.37 g, 6.64 mmol) and the mixture was stirred for 2.5 hrs. at room temperature. On the other hand, a solution of dimethyl 3-methyl-2-oxo-5heptynylphosphonate (2.09 g, 9.05 mmol) in anhydrous THF (5 ml) was dropped under argon atmosphere into a suspension of sodium hydride (60% mineral oil dispersion, 362 mg, 9.05 mmol) in anhydrous THF (10 ml) under ice-cooling and the mixture was stirred for 30 min. To this solution was added the aldehyde ester prepared above and the mixture was stirred for 30 min. and neutralized with acetic acid. The mixture was filtered and the filtrate was concentrated. The concentrate was diluted with water (30 ml) and extracted with ethyl acetate (50 ml×2). The combined ethyl acetate layers were washed with water (20 ml), and with brine (20 ml), dried over anhydrous sodium sulfate and concentrated. The concentrate was passed through a column chromatography (silica gel 50 g, ethyl acetate/cyclohexane: 1/5) and then purified by column chromatography (Merck, Lobar, column, silica gel, ethyl acetate/cyclohexane: 1/4) to give 16-methyl-15-oxo-2,5,6,7-tetranor-4-oxa-18,18,19,19-tetradehydro-4,8-inter-m-phenylene PGI$_2$ methyl ester, 11-benzoate (2.49 g, 4.96 mmol, 98.6%) as an oily material. The product was assigned the structure by the following data.

IR (liquid film): 2960, 2930, 1760, 1710, 1660, 1620, 1600, 1480, 1450, 1370, 1315, 1270, 1215, 1190, 1110, 1065, 1030, 1025, 970, 935, 845, 760, 715, 670 cm$^{-1}$.

NMR (400 MHz, CDCl$_3$, δ): 1.20 (3H, d, J=6.8 Hz); 1.7–1.8 (3H, m); 2.2–2.3 (1H, m); 2.4–2.5 (2H, m); 2.6–2.7 (1H, m); 2.8–3.0 (1H, m); 3.1–3.3 (1H, m); 3.75 (3H, s); 3.8–4.0 (1H, m); 4.64 (1H, d, J=16.6 Hz); 4.68 (1H, d, J=16.6 Hz); 5.3–5.4 (1H, m); 5.4–5.5 (1H, m); 6.34, 6.36 (1H, d, J=15.6 Hz); 6.7–7.0 (4H, m); 7.31 (2H, t, J=7.8 Hz); 7.49 (1H, t, J=7.3 Hz); 7.56 (2H, d, J=7.8 Hz).

MASS (EI, m/e): 502 (M+).

REFERENCE EXAMPLE 147

16-Methyl-15-oxo-20a-homo-2,5,6,7-tetranor-4-oxa-18,18,19,19-tetradehydro-4,8-inter-m-phenylene PGI$_2$ methyl ester, 11-benzoate 147

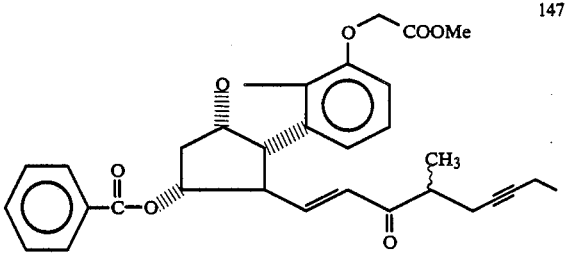

Under argon atmosphere to a solution of 2α-benzoyloxy-1β-hydroxymethyl-3aβH,8bβH-2,3,3a,8b-tetrahydro-1H-5-cyclopenta[b]benzofuranyloxyacetic acid methyl ester (1.7 g, 4.27 mmol) in anhydrous THF (9 ml) were added pyridine (0.104 ml, 1.29 mmol), trifluoroacetic acid (0.097 ml, 1.26 mmol), DMSO (3.01 ml, 42.4 mmol) and D.C.C. (1.31 g, 6.35 mmol) and the mixture was stirred for 3 hrs. at room temperature. On the other hand, a solution of dimethyl 3-methyl-2-oxo-5-octynylphosphonate (1.68 g, 6.83 mmol) in anhydrous THF (5 ml) was dropped into a suspension of sodium hydride (60% mineral oil dispersion, 273 mg, 6.83 mmol) in anhydrous THF (8 ml) under ice-cooling and the mixture was stirred for 30 min. To this solution was added the aldehyde ester prepared above under ice-cooling and the mixture was stirred for 30 min. and neutralized with acetic acid. The mixture was filtered and the filtrate was concentrated. The concentrate was diluted with water (30 ml) and extracted with ethyl acetate (50 ml×2). The combined ethyl acetate layers were washed with water (20 ml), and with brine (20 ml), dried over anhydrous sodium sulfate and concentrated. Column chromatography (silica gel 50 g, ethyl acetate/cyclohexane: 1/5) of the residue gave an oily product of 16-methyl-15-oxo-20a-homo-25,6,7-tetranor-4-oxa-18,18,19,19-tetradehydro-4,8-inter-m-phenylene PGI$_2$ methyl ester, 11-benzoate (1.88 g, 3.64 mmol, 85.2%). The product was assigned the structure by the following data.

IR (liquid film): 2970, 2930, 2870, 2850, 1755, 1510, 1665, 1610, 1480, 1450, 1430, 1370, 1310, 1270, 1210, 1190, 1110, 1065, 1050, 1025, 975, 940, 845, 750, 710, 690, 670 cm$^{-1}$.

NMR (400 MHz, CDCl$_3$, δ): 1.091, 1.094 (3H, t, J=7.3 Hz); 1.19, 1.21 (3H, d, J=6.8 Hz); 2.0–2.15 (2H, m); 2.2–2.3 (1H, m); 2.35–2.5 (2H, m); 2.6–2.7 (1H, m); 2.8–3.0 (1H, m); 3.1–3.3 (1H, m); 3.75 (3H, s); 3.8–4.0 (1H, m); 4.64 (1H, d, J=16.4 Hz); 4.68 (1H, d, J=16.4 Hz); 5.3–5.4 (1H, m); 5.45–5.55 (1H, m); 6.35–6.36 (1H, dd, J=1.5, 15.6 Hz); 6.7–7.0 (4H, m); 7.31 (2H, t, J=7.6 Hz); 7.45–7.6 (3H, m).

MASS (EI, m/e): 516 (M+).

REFERENCE EXAMPLE 148

16,16-Dimethyl-15-oxo-2,5,6,7-tetranor-4-oxa-18,18,19,19-tetradehydro-4,8-inter-m-phenylene PGI₂ methyl ester, 11-acetate 148

REFERENCE EXAMPLE 149

16,16-Dimethyl-15-oxo-20a,20b,20c,20d-tetrahomo-2,5,6,7-tetranor-4-oxa-18,18,19,19-tetradehydro-4,8-inter-m-phenylene PGI₂ methyl ester, 11-benzoate 149

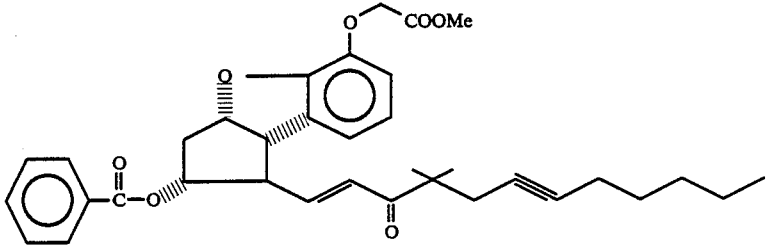

149

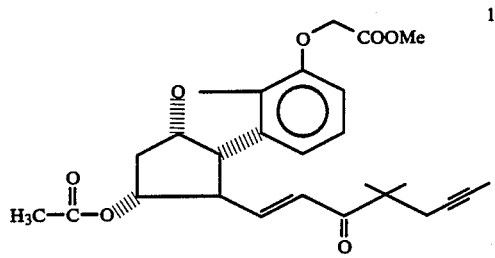

148

Under argon atmosphere to a solution of 2α-acetoxy-1β-hydroxymethyl-3aβH,8bβH-2,3,3a,8b-tetrahydro-1H-5-cyclopenta[b]benzofuranyloxyacetic acid methyl ester (1.5 g, 4.46 mmol) in anhydrous THF (10 ml) were added pyridine (0.108 ml, 1.34 mmol), trifluoroacetic acid (0.101 ml, 1.31 mmol), DMSO (3.11 ml, 43.8 mmol) and D.C.C. (1.22 g, 5.9 mmol) and the mixture was stirred for 2.5 hrs. at room temperature. On the other hand, a solution of dimethyl 3,3-dimethyl-2-oxo-5-heptynylphosphonate (1.84 g, 7.14 mmol) in anhydrous THF (5 ml) was dropped under argon atmosphere into a suspension of sodium hydride (60% mineral oil dispersion, 286 mg, 7.14 mmol) in anhydrous THF (8 ml) under ice-cooling and the mixture was stirred for 30 min. To this solution was added the aldehyde ester prepared above, and the mixture was stirred for 30 min. and neutralized with acetic acid. The mixture was filtered and the filtrate was concentrated. The concentrate was diluted with water (20 ml) and extracted with ethyl acetate (50 ml×2). The combined ethyl acetate layers were washed with water (20 ml), and with brine (20 ml), dried over anhydrous sodium sulfate and concentrated. Column chromatography (silica gel 55 g, ethyl acetate/cyclohexane: 1/4) of the residue gave an oily product of 16,16-dimethyl-15-oxo-2,5,6,7-tetranor-4-oxa-18,18,19,19-tetradehydro-4,8-inter-m-phenylene PGI₂ methyl ester, 11-acetate (1.87 g, 4.12 mmol, 92.4%). The product was assigned the structure by the following data.

IR (liquid film): 3020, 2960, 1730, 1680, 1610, 1480, 1450, 1430, 1370, 1320, 1290, 1230, 1185, 1050, 995, 940, 845, 750, 665 cm⁻¹.

NMR (400 MHz, CDCl₃, δ): 1.23 (6H, s); 1.77 (3H, t, J=2.5 Hz); 1.81 (3H, s); 2.15–2.25 (1H, m); 2.37 (2H, q, J=2.5 Hz); 2.6–2.7 (1H, m); 2.9–3.1 (1H, m); 3.65–3.75 (1H, m); 3.79 (3H, s); 4.72 (1H, d, J=16.4 Hz); 4.74 (1H, d, J=16.4 Hz); 5.00 (1H, q, J=6.1 Hz); 5.24–5.4 (1H, m); 6.6 (1H, d, J=14.2 Hz); 6.7–6.9 (4H, m).

MASS (EI, m/e): 454 (M⁺).

Under argon atmosphere to a solution of 2α-benzoyloxy-1β-hydroxymethyl-3aβH,8bβH-2,3,3a,8b-tetrahydro-1H-5-cyclopenta[b]benzofuranyloxyacetic acid methyl ester (1.9072 g, 4.79 mmol) in anhydrous THF (15 ml) were added anhydrous pyridine (0.39 ml, 4.79 mmol), anhydrous DMSO (5 ml), trifluoroacetic acid (0.18 ml, 2.40 mmol) and D.C.C. (1.48 g, 7.19 mmol) and the mixture was stirred for 30 min. at room temperature. The resulting solution was washed with calcium carbonate (1.56 g, 15.57 mmol). The mixture was stirred for 20 min. and allowed to stand. On the other hand, a solution of dimethyl 3,3-dimethyl-2-oxo-5-undecynylphosphonate (2.27 g, 7.19 mmol) in anhydrous THF (5 ml) was added under argon atmosphere to a suspension of sodium hydride (60% mineral oil dispersion, 287.4 mg, 7.10 mmol) in anhydrous THF (30 ml) and the mixture was stirred for 30 min. at room temperature. To this solution was added the supernatant of the aldehyde ester reaction mixture prepared above by means of an injector under ice-cooling. The residue of the aldehyde ester reaction mixture prepared above was washed with anhydrous THF (10 ml, 5 ml×2) and the supernatant of the washings was also added to the said mixture. The resulting mixture was stirred for 30 min. at room temperature and mixed with a saturated aqueous solution of ammonium chloride (50 ml). The mixture was extracted with ethyl acetate (40 ml×3). The combined ethyl acetate layers were washed with water (100 ml), and with brine (100 ml), dried over anhydrous sodium sulfate (30 g) and concentrated. Column chromatography (silica gel, ethyl acetate/cyclohexane: 1/3) of the residue gave 16,16-dimethyl-15-oxo-20a,20b,20c,20d-tetrahomo-2,5,6,7-tetranor-4-oxa-18,18,19,19-tetradehydro-4,8-inter-m-phenylene PGI₂ methyl ester, 11-benzoate (2.3689 g, 4.26 mmol, 89%) as a colorless oily product. The product was assigned the structure by the following data.

IR (liquid film): 3055, 2950, 2928, 2851, 1760, 1718, 1690, 1620, 1601, 1483, 1460, 1363, 1318, 1270, 1214, 1192, 1113, 1064, 1052, 1023, 1000, 972, 939, 843, 763, 712 cm⁻¹.

NMR (400 MHz, CDCl₃, δ): 0.88 (3H, t, J=7.33 Hz); 1.21 (6H, s); 1.25–1.39 (4H, m); 1.39–1.50 (2H, m); 2.08–2.15 (2H, m); 2.34–2.47 (3H, m); 2.63–2.72 (1H, m); 3.18–3.25 (1H, m); 3.75 (3H, s); 3.84–3.91 (1H, m); 4.63 (1H, d, J=16.11 Hz); 4.68 (1H, d, J=16.11 Hz); 5.30–5.36 (1H, m); 5.42–5.47 (1H, m); 6.67 (1H, d, J=15.13 Hz); 6.71–6.89 (3H, m); 6.88 (1H, dd, J=15.13, 8.30 Hz); 7.25–7.34 (2H, m); 7.44–7.58 (3H, m).

MASS (EI, m/e): 572 (M+).

REFERENCE EXAMPLE 150

15-Oxo-2,5,6,7-tetranor-3,3,4,4-tetradehydro-4,8-inter-m-phenylene PGI₂ methyl ester, 11-acetate 150

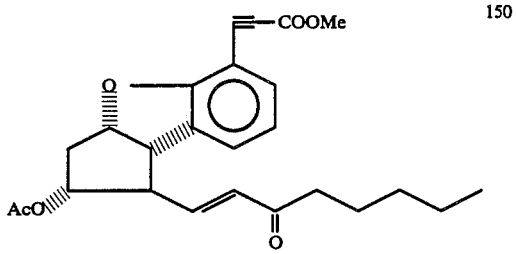

Under argon atmosphere to a solution of 2α-acetoxy-1β-hydroxymethyl-3aβH,8bβH-2,3,3a,8b-tetrahydro-1H-5-cyclopenta[b]benzofuranylpropynoic acid methyl ester (1.1804 g, 3.58 mmol) in anhydrous THF (15 ml) were added anhydrous pyridine (0.29 ml, 3.58 mmol), anhydrous DMSO (5 ml), trifluoroacetic acid (0.14 ml, 1.79 mmol) and D.C.C. (1.48 g, 7.16 mmol) and the mixture was stirred for 2 hrs. at room temperature. The solution was mixed with calcium carbonate (1.16 g, 11.6 mmol). The mixture was stirred for 20 min. and allowed to stand. On the other hand, to a suspension of sodium hydride (60% mineral oil dispersion, 214.8 mg, 5.37 mmol) in anhydrous THF (20 ml) was added a solution of dimethyl 2-oxo-heptylphosphonate (1.1921 g, 5.37 mmol) in anhydrous THF (5 ml) and the mixture was stirred under argon atmosphere for 30 min. at room temperature. To this solution was added the supernatant of the aldehyde ester reaction mixture prepared above by means of an injector under ice-cooling. The residue of the aldehyde ester reaction mixture was washed with anhydrous THF (10 ml×2, 5 ml) and the supernatant of the washings was also added to the reaction mixture. The resulting mixture was stirred for 10 min. at room temperature and mixed with a saturated aqueous solution of ammonium chloride (50 ml). The mixture was extracted with ethyl acetate (50 ml×3). The combined ethyl acetate layers were washed with water (100 ml), and with brine (100 ml), dried over anhydrous sodium sulfate (30 g) and concentrated. Column chromatography (silica gel, ethyl acetate/cyclohexane: 1/3) of the residue gave 15-oxo-2,5,6,7-tetranor-3,3,4,4-tetradehydro-4,8-inter-m-phenylene PGI₂ methyl ester, 11-acetate (1.3821 g, 3.26 mmol, 91%) as a colorless oily product. The product was assigned the structure by the following data.

IR (liquid film): 2950, 2855, 2205, 1730, 1701, 1664, 1623, 1463, 1443, 1364, 1322, 1284, 1205, 1202, 1050, 1004, 981, 942, 870, 745, 786, 742 cm⁻¹.

NMR (400 MHz, CDCl₃, δ): 0.91 (3H, t, J=6.84 Hz); 1.25–1.40 (4H, m); 1.60–1.68 (2H, m); 1.76 (3H, s); 2.27–2.34 (1H, m); 2.53–2.62 (3H, m); 2.93–2.99 (1H, m); 3.72–3.79 (1H, m); 3.84 (3H, s); 5.01–5.05 (1H, m); 5.38–5.43 (1H, m); 6.21 (1H, d, J=16.11 Hz); 6.74 (1H, dd, J=8.3, 16.11 Hz); 6.84 (1H, t, J=7.33 Hz); 7.18 (1H, d, J=7.33 Hz); 7.33 (1H, d, J=7.33 Hz).

MASS (EI, m/e): 424 (M+).

REFERENCE EXAMPLE 151

16,16-Dimethyl-15-oxo-2,5,6,7-tetranor-3,3,4,4-tetradehydro-4,8-inter-m-phenylene PGI₂ methyl ester, 11-acetate 151

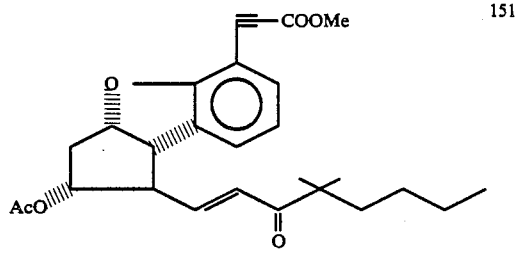

Under argon atmosphere to a solution of 2α-acetoxy-1β-hydroxymethyl-3aβH,8bβH-2,3,3a,8b-tetrahydro-1H-5-cyclopenta[b]benzofuranylpropynoic acid methyl ester (415.2 mg, 1.26 mmol) in anhydrous THF (7 ml) were added anhydrous pyridine (0.1 ml, 1.26 mmol), anhydrous DMSO (2.5 ml), trifluoroacetic acid (0.05 ml, 0.63 mmol) and D.C.C. (390 mg, 1.89 mmol) and the mixture was stirred for 3.5 hrs. at room temperature. The solution was mixed with calcium carbonate (410 mg, 4.10 mmol). The mixture was stirred for 20 min. and allowed to stand. On the other hand, to a suspension of sodium hydride (60% mineral oil dispersion, 75.6 mg, 1.89 mmol) in anhydrous THF (10 ml) was added a solution of dimethyl 3,3-dimethyl-2-oxo-heptylphosphonate (472.5 mg, 1.89 mmol) in anhydrous THF (5 ml) and the mixture was stirred under argon atmosphere for 30 min. at room temperature. To this solution was added the supernatant of the aldehyde ester reaction mixture prepared above by means of an injector under ice-cooling. The residue of the aldehyde ester reaction mixture was washed with anhydrous THF (5 ml×3) and the supernatant of the washings was also added to the reaction mixture. The resulting mixture was stirred for 20 min. at room temperature and mixed with a saturated aqueous solution of ammonium chloride (40 ml). The mixture was extracted with ethyl acetate (30 ml×3). The combined ethyl acetate layers were washed with water (100 ml), and with brine (100 ml), dried over anhydrous sodium sulfate (25 g) and concentrated. Column chromatography (silica gel, ethyl acetate/cyclohexane: 1/4) of the residue gave 16,16-dimethyl-15-oxo-2,5,6,7-tetranor-3,3,4,4-tetradehydro-4,8-inter-m-phenylene PGI₂ methyl ester, 11-acetate (435.5 mg, 1.03 mmol, 82%), which was then recrystallized from ethyl acetate/n-hexane (1/20) to give a colorless and needle-like crystal. M.p.: 78°–79° C. The product was assigned the structure by the following data.

IR (KBr): 2958, 2875, 2202, 1740, 1710, 1623, 1463, 1443, 1365, 1332, 1290, 1235, 1205, 1160, 1045, 1010, 983, 942, 870, 850, 784, 745, 701 cm⁻¹.

NMR (400 MHz, CDCl₃, δ): 0.89 (3H, t, J=7.32 Hz); 1.13 (6H, s); 1.08–1.18 (2H, m); 1.23–1.34 (2H, m); 1.51–1.58 (2H, m); 1.76 (3H, s); 2.23–2.32 (1H, m); 2.57–2.66 (1H, m); 2.95–3.02 (1H, m); 3.72–3.75 (1H, m); 3.84 (3H, s); 4.98–5.03 (1H, m); 5.37–5.44 (1H, m); 6.59 (1H, d, J=15.13 Hz); 6.80 (1H, dd, J=15.13, 8.3 Hz); 6.83 (1H, t, J=7.33 Hz); 7.18 (1H, d, J=7.33 Hz); 7.33 (1H, d, J=7.33 Hz).

MASS (EI, m/e): 452 (M+).

REFERENCE EXAMPLE 152

15-Oxo-16-phenoxy-2,5,6,7,17,18,19,20-octanor-3,3,4,4-tetradehydro-4,8-inter-m-phenylene PGI$_2$ methyl ester, 11-acetate 152

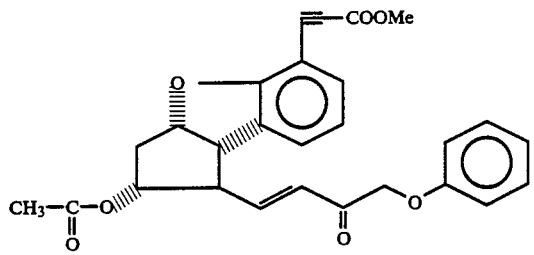

Under argon atmosphere to a solution of 2α-acetoxy-1β-hydroxymethyl-3aβH,8bβH-2,3,3a,8b-tetrahydro-1H-5-cyclopenta[b]benzofuranylpropynoic acid methyl ester (1.12 g, 3.39 mmol) in anhydrous THF (8 ml) were added anhydrous pyridine (0.082 ml, 1.02 mmol), anhydrous DMSO (2.41 ml, 33.9 mmol), anhydrous trifluoroacetic acid (0.079 ml, 1.02 mmol) and D.C.C. (1.05 g, 5.09 mmol) and the mixture was stirred for 3 hrs. at room temperature. On the other hand, to a suspension of sodium hydride (60% mineral oil dispersion, 0.204 g, 5.09 mmol) in anhydrous THF (10 ml) was added a solution of dimethyl 2-oxo-3-phenoxy-propylphosphonate (1.31 g, 5.09 mmol) in anhydrous THF (5 ml) and the mixture was stirred under argon atmosphere for 30 min. under ice-cooling. To this solution was added the supernatant of the aldehyde ester reaction mixture prepared above by means of an injector under ice-cooling. The residue of the aldehyde ester reaction mixture was washed with anhydrous THF (5 ml×3) and the supernatant of the washings was also added to the reaction mixture. The resulting mixture was stirred for 10 min. at room temperature and neutralized with acetic acid and concentrated. To the residue was added ethyl acetate. The resulting precipitate was filtered off and washed with ethyl acetate. The washings were mixed with water (50 ml) and extracted with ethyl acetate (40 ml×3). The combined ethyl acetate layers were washed with water (50 ml), and with brine (50 ml), dried over anhydrous sodium sulfate and concentrated. Column chromatography (silica gel, ethyl acetate/cyclohexane: 1/9) of the oily material gave 15-oxo-16-phenoxy-2,5,6,7,17,18,19,20-octanor-3,3,4,4-tetradehydro-4,8-inter-m-phenylene PGI$_2$ methyl ester, 11-acetate (870 mg, 1.89 mmol, 55.8%). The product was assigned the structure by the following data.

IR (liquid film): 3340, 3080, 3030, 2955, 2940, 2860, 2220, 1740, 1710, 1630, 1590, 1495, 1470, 1445, 1435, 1380, 1340, 1300, 1240, 1210, 1055, 1015, 985, 945, 890, 870, 850, 790, 760, 695, 675 cm$^{-1}$.

NMR (90 MHz, CDCl$_3$, δ): 1.74 (3H, s); 2.1–2.75 (2H, m); 2.95 (1H, m); 3.6–3.85 (1H, m); 3.83 (3H, s); 4.70 (2H, s); 5.00 (1H, q, J=5.6 Hz); 5.36 (1H, m); 6.54 (1H, dd, J=0.8, 15.7 Hz); 6.69–7.11 (7H, m); 7.20–7.40 (2H, m).

MASS (EI): 462 (M$^+$).

REFERENCE EXAMPLE 153

16-Methyl-15-oxo-16-phenoxy-2,5,6,7,18,19,20-heptanor-3,3,4,4-tetradehydro-4,8-inter-m-phenylene PGI$_2$ methyl ester, 11-acetate 153

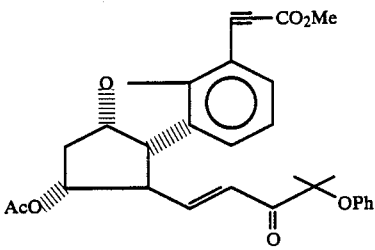

Under argon atmosphere to a solution of 2α-acetoxy-1β-hydroxymethyl-3aβH,8bβH-2,3,3a,8b-tetrahydro-1H-5-cyclopenta[b]benzofuranylpropynoic acid methyl ester (1.09 g, 3.30 mmol) in anhydrous THF (12 ml) were added anhydrous pyridine (0.3 ml, 3.71 mmol), anhydrous DMSO (5.0 ml, 70.8 mmol), anhydrous trifluoroacetic acid (0.14 ml, 1.82 mmol) and D.C.C. (1.10 g, 5.33 mmol) at 0° C. and the mixture was stirred for 2 hrs. at room temperature. On the other hand, to a suspension of sodium hydride (60% mineral oil dispersion, 0.24 g, 6.00 mmol) in anhydrous THF (5 ml) was added at 0° C. a solution of dimethyl 3-methyl-2-oxo-3-phenoxybutylphosphonate (1.70 g, 5.94 mmol) in anhydrous THF (12 ml) and the mixture was stirred under argon atmosphere for 1.5 hrs. To this solution was added the aldehyde ester reaction mixture prepared above by means of an injector under ice-cooling. The residue of the aldehyde ester reaction mixture was washed with anhydrous THF (3 ml×3) and the washings were also added to the reaction mixture. The resulting mixture was stirred for 30 min. at room temperature and mixed with a saturated aqueous solution of ammonium chloride (10 ml). The mixture was extracted with ethyl acetate (50 ml×4). The combined ethyl acetate layers were washed with water (50 ml), and with brine (50 ml), dried over anhydrous sodium sulfate and concentrated. Column chromatography (silica gel, ethyl acetate/cyclohexane: 1/2) of the residue removed the by-products. Column chromatography (silica gel, ethyl acetate/cyclohexane: 1/5) of the resulting oily material gave 16-methyl-15-oxo-16-phenoxy-2,5,6,7,18,19,20-heptanor-3,3,4,4-tetradehydro-4,8-inter-m-phenylene PGI$_2$ methyl ester, 11-acetate (1.1421 g, 2.34 mmol, 70.8%). The product was assigned the structure by the following data.

M.p.: 135°–135.5° C. (recrystallized from ethyl acetate/cyclohexane, white and needle-like crystal).

IR (KBr): 2980, 2940, 2205, 1738, 1708, 1633, 1598, 1486, 1468, 1436, 1378, 1336, 1285, 1232, 1202, 1155, 1057, 1007, 977, 939, 889, 869, 853, 822, 794, 759, 749, 727, 699, 632, 612 cm$^{-1}$.

NMR (100 MHz, CDCl$_3$, δ): 1.52 (3H, s); 1.56 (3H, s); 1.70 (3H, s); 1.94–2.70 (2H, m); 2.70–3.02 (1H, m); 3.47–3.73 (1H, m); 3.82 (3H, s); 4.79–5.10 (1H, m); 5.10–5.38 (1H, m); 6.50–7.40 (10H, m).

MASS (EI, m/e): 488 (M$^+$).

EXAMPLE 1

2,5,6,7-Tetranor-4-oxa-4,8-inter-m-phenylene PGI$_2$ methyl ester (154) and its 15-epimer (155)

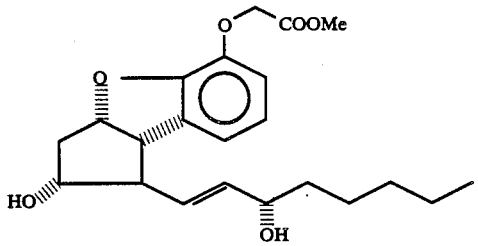

154

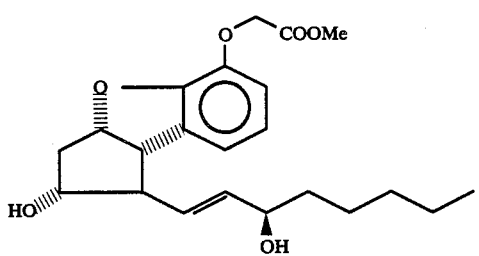

155

To a solution of 15-oxo-2,5,6,7-tetranor-4-oxa-4,8-inter-m-phenylene PGI$_2$ methyl ester, 11-acetate (470 mg, 1.09 mmol) in 20 ml of methanol was added cerium trichloride heptahydrate (528 mg, 1.42 mmol), and then the solution was cooled to 0° C. Sodium borohydride (50 mg, 1.31 mmol) was added to the solution. The reaction mixture was stirred for 10 min. at 0° C., diluted with a saturated aqueous solution of sodium bicarbonate (5 ml), and then concentrated. The residue was triturated in ethyl acetate, and the resulting precipitate was filtered off. The precipitate was washed with three portions of ethyl acetate. The combined filtrates were washed with water and with brine, dried over anhydrous magnesium sulfate and concentrated to give 470 mg of an oily material.

To a solution of the oily material dissolved in anhydrous methanol (10 ml) was added a solution of sodium methoxide in methanol (5.22N, 0.10 ml, 0.545 mmol) under argon atmosphere. The reaction mixture was stirred for 2 hrs. at room temperature, neutralized with acetic acid, and then concentrated. Water (20 ml) was added to the residue. Extraction with ethyl acetate followed by washing with brine, drying over anhydrous magnesium sulfate and concentration afforded a crude material. Column chromatography (Merck, Lobar column, silica gel; ethyl acetate/cyclohexane: 6/1) of the material gave less polar 15-epi-2,5,6,7-tetranor-4-oxa-4,8-inter-m-phenylene PGI$_2$ methyl ester (168 mg, 0.43 mmol, yield: 39.5%) as a white crystalline solid and more polar 2,5,6,7-tetranor-4-oxa-4,8-inter-m-phenylene PGI$_2$ methyl ester (141 mg, 0.36 mmol, yield: 33.1%) as a white crystalline solid. These compounds were assigned the corresponding structures by the following data. 2,5,6,7-Tetranor-4-oxa-4,8-inter-m-phenylene PGI$_2$ methyl ester M.p.: 98°–98.5° C. (recrystallized from ethyl acetate).

IR (KBr): 3400, 2970, 2940, 2870, 1740, 1620, 1490, 1470, 1440, 1380, 1310, 1280, 1270, 1250, 1200, 1110, 1080, 1030, 1010, 990, 960, 930, 900, 870, 840, 810, 770, 730, 700, 620, 590, 570 cm$^{-1}$.

NMR (400 MHz, CDCl$_3$, δ): 0.91(3H, t, J=6.8 Hz); 1.25–1.45 (6H, m); 1.45–2.65(2H, m); 1.95–2.0(1H, m); 2.05 (1H, ddd, J=5.4, 8.8, 13.7 Hz); 2.35–2.40(1H, m); 2.45(1H, q, J=8.4 Hz); 2.65(1H, ddd, J=6.4, 7.3, 13.7 Hz); 3.46(1H, t, J=8.4 Hz); 3.79(3H, s); 3.85–3.95(1H, m); 4.05–4.15(1H, m); 4.72(2H, s); 5.20(1H, ddd, J=5.4, 7.3, 8.4 Hz); 5.55–5.7(2H, m); 6.7–6.8(3H, m).

MASS(EI, m/e): 390(M+).

Elementary Analysis: Calcd. (as C$_{22}$H$_{30}$O$_6$): C: 67.67, H: 7.74. Found: C: 67.42, H: 7.64.

15-Epi-2,5,6,7-tetranor-4-oxa-4,8-inter-m-phenylene PGI$_2$ methyl ester

M.p.: 64°–65° C. (recrystallized from ether/hexane).

IR(KBr): 3350, 2940, 2870, 1760, 1740, 1620, 1590, 1490, 1460, 1440, 1370, 1280, 1220, 1190, 1120, 1020, 960, 890, 850, 790, 780, 760, 730, 600 cm$^{-1}$.

NMR(400 MHz, CDCl$_3$, δ): 0.90(3H, t, J=6.6 Hz); 1.25–1.5(6H, m); 1.5–1.65(2H, m); 1.65–1.7(1H, m); 1.9–1.95(1H, m); 2.07(1H, ddd, J=5.0, 8.3, 13.7 Hz); 2.45–2.55(1H, m); 2.62(1H, dt, J=6.5, 13.7 Hz); 3.51(1H, t, J=8.4 Hz); 3.79(3H, s); 3.9–4.0(1H, m); 4.1–4.2(1H, m); 4.72(2H, s); 5.22(1H, ddd, J=5.0, 6.5, 8.4 Hz); 5.6–5.75(2H, m); 6.73(1H, dd, J=1.5, 7.5 Hz); 6.77(1H, t, J=7.5 Hz); 6.82(1H, m).

MASS(EI, m/e): 390(M+).

HR MASS: Calcd. (C$_{22}$H$_{30}$O$_6$, M+): 390.2042. Found (M+): 390.2046.

EXAMPLE 2

2,5,6,7-Tetranor-4-oxa-4,8-inter-m-phenylene PGI$_2$ (156)

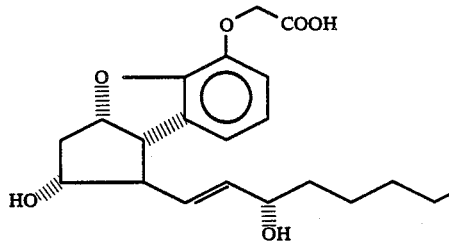

156

To a solution of 2,5,6,7-tetranor-4-oxa-4,8-inter-m-phenylene PGI$_2$ methyl ester (110 mg, 0.28 mmol) in methanol (10 ml) was added 1N aqueous NaOH solution (1.5 ml, 1.5 mmol), and the reaction mixture was stirred for 2 hrs. at room temperature. The reaction mixture was concentrated and 10 ml of water was added to the residue. After acidification to pH 4 with 1N hydrochloric acid, the mixture was extracted with ethyl acetate three times. The combined ethyl acetate layers were washed with brine, dried over anhydrous magnesium sulfate and concentrated to give 101 mg of a crude crystalline solid. Recrystallization of this material from ethyl acetate yielded 82 mg (0.22 mmol, 77.9%) of 2,5,6,7-tetranor-4-oxa-4,8-inter-m-phenylene PGI$_2$ as a white crystal, which was assigned the structure by the following data.

M.p.: 144°–144.5° C.

IR(KBr): 3400, 2930, 2860, 1770, 1610, 1590, 1490, 1460, 1430, 1290, 1200, 1120, 1080, 1010, 970, 940, 860, 790, 760, 720, 710 cm$^{-1}$.

NMR(400 MHz, DMSO-d$_6$, δ): 0.88(3H, t, J=6.4 Hz); 1.2–1.5 (8H, m); 1.65–1.75(1H, m); 2.16(1H, q, J=8.0 Hz); 2.4–2.6(1H, m); 3.35–3.45(1H, m); 3.7–3.8(1H, m); 3.9–4.0(1H, m); 4.64(2H, s); 4.55–4.7(1H, m); 4.8–4.9(1H, m); 5.07(1H, q, J=7.5 Hz);

5.46(1H, dd, J=6.2, 15.4 Hz); 5.61(1H, dd, J=8.0, 15.4 Hz); 6.70(3H, s).

MASS(EI, m/e): 376(M+).

HR MASS: Calcd. ($C_{21}H_{28}O_6$, M+): 376.1886. Found (M+): 376.1863.

EXAMPLE 3

15-Epi-2,5,6,7-tetranor-4-oxa-4,8-inter-m-phenylene $PGI_2$ (157)

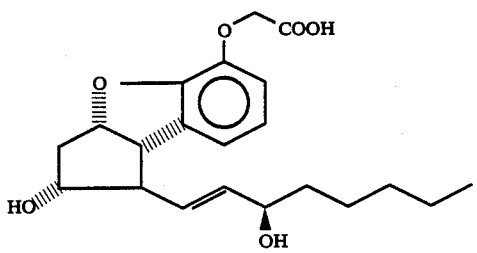

157

To a solution of 15-epi-2,5,6,7-tetranor-4-oxa-4,8-inter-m-phenylene $PGI_2$ methyl ester (120 mg, 0.31 mmol) in methanol (10 ml) was added 1N aqueous NaOH solution (1.5 ml, 1.5 mmol), and the reaction mixture was stirred for 2 hrs. at room temperature. The reaction mixture was concentrated and 10 ml of water was added to the residue. After acidification to pH 4 with 1N hydrochloric acid, the mixture was extracted with ethyl acetate three times. The combined ethyl acetate layers were washed with brine, dried over anhydrous magnesium sulfate and concentrated to give 112 mg of a crude crystalline solid. Recrystallization of this material from ethyl acetate yielded 82 mg (0.22 mmol, 70.4%) of 15-epi-2,5,6,7-tetranor-4-oxa-4,8-inter-m-phenylene $PGI_2$ as a white crystal, which was assigned the structure by the following data.

M.p.: 138°–138.5° C.

IR(KBr): 3470, 2950, 2920, 2850, 1740, 1710, 1620, 1590, 1490, 1460, 1420, 1170, 1160, 1120, 1280, 1190, 1160, 1120, 1060, 1020, 960, 880, 850, 790, 770, 730, 720, 600, 570, 490 $cm^{-1}$.

NMR(400 MHz, DMSO-$d_6$, δ): 0.87(3H, t, J=6.7 Hz); 1.2–1.5(8H, m); 1.6–1.8(1H, m); 2.16(1H, q, J=8.0 Hz); 2.4–2.6(1H, m); 3.35–3.45(1H, m); 3.7–3.8(1H, m); 3.9–4.0(1H, m); 4.63(2H, s); 4.55–4.7(1H, m); 4.8–4.9(1H, m); 5.07(1H, q, J=7.6 Hz); 5.47(1H, dd, J=5.9, 15.4 Hz); 5.62(1H, dd, J=8.0, 15.4 Hz); 5.65–5.8(3H, m).

MASS(EI, m/e): 376(M+).

Elementary Analysis: Calcd. (as $C_{21}H_{28}O_6$): C: 67.00, H: 7.50. Found: C: 66.61, H: 7.49.

EXAMPLE 4

20a-Homo-2,5,6,7-tetranor-4-oxa-4,8-inter-m-phenylene $PGI_2$ methyl ester (158) and its 15-epimer (159)

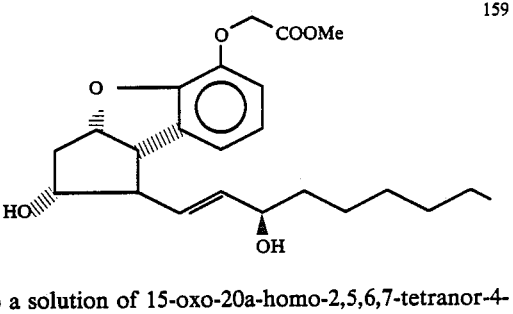

158

159

To a solution of 15-oxo-20a-homo-2,5,6,7-tetranor-4-oxa-4,8-inter-m-phenylene $PGI_2$ methyl ester, 11-benzoate (1.72 g, 3.40 mmol) in 70 ml of methanol was added cerium trichloride heptahydrate (1.65 g, 4.42 mmol), and then the solution was cooled to −20° C. Sodium borohydride (51.5 mg, 1.36 mmol) was added to the solution. The reaction mixture was stirred for 30 min. at −20° C., diluted with a saturated aqueous solution of sodium bicarbonate (15 ml), and then concentrated. The residue was triturated in ethyl acetate, and the resulting precipitate was filtered off. The precipitate was washed with three portions of ethyl acetate. The combined filtrates were washed with water and with brine, dried over anhydrous magnesium sulfate and concentrated to give an oily material.

To a solution of the oily material dissolved in anhydrous methanol (30 ml) was added a solution of sodium methoxide in methanol (5.22N, 0.33 ml, 1.70 mmol) under argon atmosphere. The reaction mixture was stirred for 20 hrs. at room temperature, neutralized with acetic acid, and then concentrated. Water was added to the residue. Extraction with ethyl acetate followed by washing with brine, drying over anhydrous magnesium sulfate and concentration afforded a crude material. Column chromatography (Merck, Lobar column, silica gel; ethyl acetate/cyclohexane: 4/1) of the material gave less polar 15-epi-20a-homo-2,5,6,7-tetranor-4-oxa-4,8-inter-m-phenylene $PGI_2$ methyl ester (655 mg, 1.62 mmol, yield: 47.7%) as a white crystalline solid and more polar 20a-homo-2,5,6,7-tetranor-4-oxa-4,8-inter-m-phenylene $PGI_2$ methyl ester (596 mg, 1.48 mmol, yield: 43.4%) as a white crystalline solid. These compounds were assigned the corresponding structures by the following data.

20a-Homo-2,5,6,7-tetranor-4-oxa-4,8-inter-m-phenylene $PGI_2$ methyl ester

M.p.: 95.5°–96° C. (recrystallized from ethyl acetate/hexane).

IR(KBr): 3300, 2950, 2920, 2850, 1750, 1620, 1590, 1480, 1460, 1430, 1370, 1320, 1290, 1220, 1190, 1180, 1110, 1060, 1030, 970, 960, 950, 920, 890, 860, 830, 790, 770, 730, 710, 670, 520, 360 $cm^{-1}$.

NMR(400 MHz, $CDCl_3$, δ): 0.90(3H, t, J=6.8 Hz); 1.2–1.7 (10H, m); 1.85–1.95(1H, m); 2.05(1H, ddd, J=4.9, 5.4, 13.9 Hz); 2.25–2.35(1H, m); 2.46(1H, q, J=8.3 Hz); 2.65(1H, dt, J=6.8, 13.9 Hz); 3.47(1H, t, J=8.3 Hz); 3.79(3H, s); 3.85–4.0(1H, m); 4.1–4.2(1H, m); 4.72(2H, s); 5.20(1H, ddd, J=4.9, 6.8, 8.3 Hz); 5.55–5.7(2H, m); 6.7–6.8(3H, m).

MASS(EI, m/e): 404(M+).

Elementary Analysis: Calcd. (as $C_{23}H_{32}O_6$): C: 68.29, H: 7.97. Found: C: 68.12, H: 8.13.

15-Epi-20a-homo-2,5,6,7-tetranor-4-oxa-4,8-inter-m-phenylene PGI$_2$ methyl ester M.p.: 92.5°–93° C. (recrystallized from ethyl acetate hexane).

IR(KBr): 3250, 2930, 2860, 1750, 1620, 1590, 1490, 1460, 1440, 1430, 1380, 1310, 1300, 1230, 1190, 1110, 1080, 1040, 1000, 980, 960, 890, 860, 830, 810, 680, 650, 580, 540, 480 cm$^{-1}$.

NMR(400 MHz, CDCl$_3$, δ): 0.89(3H, t, J=6.8 Hz); 1.2–1.7(11H, m); 1.8–1.9(1H, m); 2.08(1H, ddd, J=4.9, 8.3, 13.7 Hz); 2.45–2.55(1H, m); 2.62(1H, dt, J=6.8, 13.7 Hz); 3.51(1H, t, J=8.5 Hz); 3.79(3H, s); 3.9–4.0(1H, m); 4.1–4.2(1H, m); 4.72(2H, s); 5.22(1H, ddd, J=4.9, 6.8, 8.5 Hz); 5.6–5.7(2H, m); 6.73(1H, dd, J=1.5, 7.3 Hz); 6.77(1H, t, J=7.3 Hz); 6.82(1H, d, J=7.3 Hz).

MASS(EI, m/e): 404(M+).

Elementary Analysis: Calcd. (as C$_{23}$H$_{32}$O$_6$): C: 68.29, H: 7.97. Found: C: 68.09, H: 7.97.

EXAMPLE 5

20a-Homo-2,5,6,7-tetranor-4-oxa-4,8-inter-m-phenylene PGI$_2$ (160)

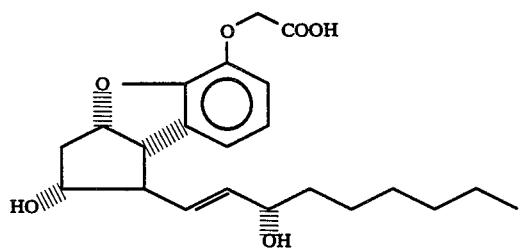

160

To a solution of 20a-homo-2,5,6,7-tetranor-4-oxa-4,8-inter-m-phenylene PGI$_2$ methyl ester (230 mg, 0.57 mmol) in methanol (20 ml) was added 1N aqueous NaOH solution (3 ml, 3 mmol), and the reaction mixture was stirred for 3 hrs. at room temperature. The reaction mixture was concentrated, and 15 ml of water was added to the residue. After acidification to pH 4 with 1N hydrochloric acid, the mixture was extracted with ethyl acetate three times. The combined ethyl acetate layers were washed with brine, dried over anhydrous magnesium sulfate and concentrated to give 214 mg of a crude cyrstalline solid. Recrystallization of this solid material from ethyl acetate yielded 161 mg (0.41 mmol, 72.0%) of 20a-homo-2,5,6,7-tetranor-4-oxa-4,8-inter-m-phenylene PGI$_2$ as a white crystal, which was assigned the structure by the following data.

M.p.: 136°–137° C.

IR(KBr): 3380, 2940, 2870, 1770, 1750, 1620, 1595, 1490, 1460, 1440, 1300, 1200, 1170, 1120, 1080, 1030, 990, 970, 950, 890, 860, 840, 800, 770, 730 cm$^{-1}$.

NMR(400 MHz, DMSO-d$_6$, δ): 0.8–0.9(3H, m); 1.2–1.5(10H, m); 1.65–1.75(1H, m); 2.16(1H, q, J=8.0 Hz); 2.45–2.6(1H, m); 3.35–3.45(1H, m); 3.65–3.8(1H, m); 3.9–4.0(1H, m); 4.55–4.65(1H, m); 4.63(2H, s); 4.8–4.9(1H, m); 5.07(1H, q, J=7.3 Hz); 5.48(1H, dd, J=6.3, 15.1 Hz); 5.61(1H, dd, J=8.0, 15.1 Hz); 6.70(3H, s).

MASS(EI, m/e): 390(M+).

HR MASS: Calcd. (C$_{22}$H$_{30}$O$_6$, M+): 390.2042. Found (M+): 390.2012.

EXAMPLE 6

15-Epi-20a-homo-2,5,6,7-tetranor-4-oxa-4,8-inter-m-phenylene PGI$_2$ (161)

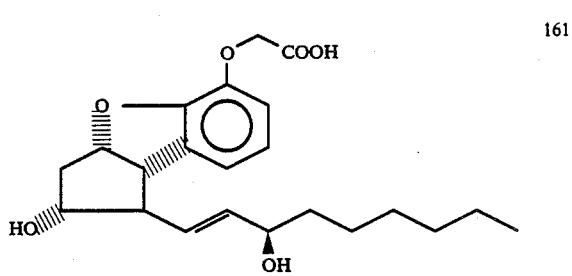

161

To a solution of 15-epi-20a-homo-2,5,6,7-tetranor-4-oxa-4,8-inter-m-phenylene PGI$_2$ methyl ester (350 mg, 0.87 mmol) in methanol (20 ml) was added 1N aqueous NaOH solution (3 ml, 3 mmol), and the reaction mixture was stirred for 3 hrs. at room temperature. The reaction mixture was concentrated, and 15 ml of water was added to the residue. After acidification to pH 4 with 1N hydrochloric acid, the mixture was extracted with ethyl acetate three times. The combined ethyl acetate layers were washed with brine, dried over anhydrous magnesium sulfate and concentrated to give 278 mg of a crude crystalline solid. Recrystallization of this solid material from ethyl acetate yielded 224 mg (0.57 mmol, 66.0%) of 15-epi-20a-homo-2,5,6,7-tetranor-4-oxa-4,8-inter-m-phenylene PGI$_2$ as a white crystal, which was assigned the structure by the following data.

M.p.: 136.5°–137.5° C.

IR(KBr): 3380, 2960, 2930, 2860, 1760, 1710, 1620, 1600, 1490, 1460, 1430, 1380, 1360, 1320, 1280, 1270, 1200, 1170, 1130, 1070, 1030, 1010, 960, 930, 890, 880, 860, 830, 800, 780, 740, 720, 610, 580 cm$^{-1}$.

NMR(400 MHz, DMSO-d$_6$, δ): 0.86(3H, t, J=6.8 Hz); 1.2–1.5(10H, m); 1.70(1H, ddd, J=5.9, 9.5, 12.9 Hz); 2.16(1H, q, J=8.3 Hz); 2.45–2.6(1H, m); 3.35–3.45(1H, m); 3.75–3.85(1H, m); 3.9–4.0(1H, m); 4.55–4.65(1H, m); 4.63(2H, s); 4.75–4.85(1H, m); 5.0–5.1(1H, m); 5.47(1H, dd, J=6.1, 15.4 Hz); 5.61(1H, dd, J=8.3, 15.4 Hz); 6.65–6.8(3H, m).

MASS(EI, m/e): 390(M+)

Elementary Analysis: Calcd. (as C$_{22}$H$_{30}$O$_6$): C: 67.67, H: 7.74. Found: C: 67.55, H: 7.82.

EXAMPLE 7

16-Methyl-2,5,6,7,18,19,20-heptanor-4-oxa-4,8-inter-m-phenylene PGI$_2$ methyl ester (162) and its 15-epimer (163)

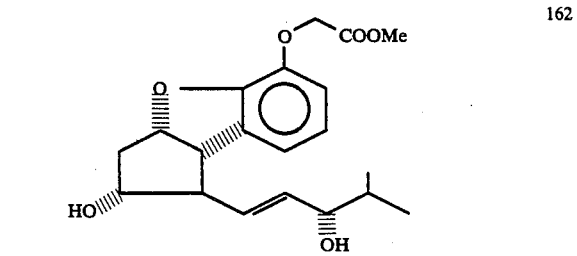

162

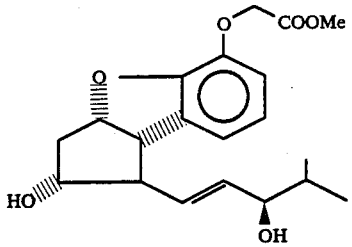

163

To a solution of 16-methyl-15-oxo-2,5,6,7,18,19,20-heptanor-4-oxa-4,8-inter-m-phenylene PGI₂ methyl ester, 11-benzoate (1.77 g, 3.81 mmol) in 70 ml of methanol was added cerium trichloride heptahydrate (1.85 g, 4.95 mmol) and then the solution was cooled to −25° C. Sodium borohydride (57.7 mg, 1.52 mmol) was added to the solution. The reaction mixture was stirred for 1 hr. at −25° C., diluted with a saturated aqueous solution of sodium bicarbonate (20 ml), and then concentrated. The residue was triturated in ethyl acetate, and the resulting precipitate was filtered off. The precipitate was washed with three portions of ethyl acetate. The combined filtrates were washed with water and with brine, dried over anhydrous magnesium sulfate and concentrated to give an oily material.

To a solution of the oily material dissolved in anhydrous methanol (30 ml) was added a solution of sodium methoxide in methanol (5.22N, 0.36 ml, 1.90 mmol) under argon atmosphere. The reaction mixture was stirred for 20 hrs. at room temperature, neutralized with acetic acid, and concentrated. Water was added to the residue. Extraction with ethyl acetate followed by washing with brine, drying over anhydrous magnesium sulfate and concentration afforded a crude material. Column chromatography (Merck, Lobar column, silica gel; ethyl acetate/cyclohexane: 4/1) of the material gave less polar 16-methyl-15-epi-2,5,6,7,18,19,20-heptanor-4-oxa-4,8-inter-m-phenylene PGI₂ methyl ester (653 mg, 1.80 mmol, yield: 47.3%) as a white crystalline solid and more polar 16-methyl-2,5,6,7,18,19,20-heptanor-4-oxa-4,8-inter-m-phenylene PGI₂ methyl ester (510 mg, 1.41 mmol, yield: 37.0%) as a white crystalline solid. These compounds were assigned the corresponding structures by the following data.

16-Methyl-2,5,6,7,18,19,20-heptanor-4-oxa-4,8-inter-m-phenylene PGI₂ methyl ester M.p.: 131°–132° C. (recrystallized from ethyl acetate)
IR(KBr): 3300, 2960, 2900, 1760, 1740, 1620, 1590, 1480, 1460, 1380, 1300, 1240, 1210, 1190, 1160, 1120, 1080, 1030, 1010, 980, 950, 900, 860, 850, 830, 790, 760, 730, 680, 610, 550, 360 cm⁻¹.
NMR(400 MHz, CDCl₃, δ): 0.93(3H, d, J=6.6 Hz); 0.97(3H, d, J=6.6 Hz); 1.65-1.8(1H, m); 2.0-2.1(1H, m); 2.04(1H, m, ddd, J=5.3, 8.5, 13.8 Hz); 2.46(1H, q, J=8.5 Hz); 2.5-2.6(1H, m); 2.66(1H, ddd, J=6.4, 7.3, 13.8 Hz); 3.46(1H, t, J=8.5 Hz); 3.79(3H, s); 3.86(1H, t, J=6.6 Hz); 3.92(1H, dt, J=6.4, 8.5 Hz); 4.72(2H, s); 5.19(1H, ddd, J=5.3, 7.3, 8.5 Hz); 5.55-5.7(2H, m); 6.7-6.8(3H, m).
MASS(EI, m/e): 362(M⁺).
Elementary Analysis: Calcd. (as C₂₀H₂₆O₆): C: 66.28, H: 7.23. Found: C: 66.46, H: 7.18.

16-Methyl-15-epi-2,5,6,7,18,19,20-heptanor-4-oxa-4,8-inter-m-phenylene PGI₂ methyl ester M.p.: 111.5°–112.5° C. (recrystallized from ethyl acetate/hexane).
IR(KBr): 3380, 3320, 2960, 2930, 2870, 1770, 1610, 1590, 1490, 1460, 1440, 1410, 1390, 1360, 1300, 1290, 1260, 1200, 1180, 1120, 1070, 1040, 970, 940, 900, 890, 860, 840, 800, 760, 730 cm⁻¹.
NMR(400 MHz, CDCl₃, δ): 0.94(3H, d, J=6.8 Hz); 0.96(3H, d, J=6.8 Hz); 1.55-1.65(1H, m); 1.7-1.9(2H, m); 2.08(1H, ddd, J=5.2, 8.6, 13.8 Hz); 2.45-2.55(1H, m); 2.63(1H, ddd, J=6.4, 7.3, 13.8 Hz); 3.52(1H, t, J=8.5 Hz); 3.79(3H, s); 3.9-4.0(2H, m); 4.72(2H, s); 5.23(1H, ddd, J=5.2, 7.3, 8.5 Hz); 5.6-5.75(2H, m); 6.73(1H, dd, J=1.5, 7.8 Hz); 6.77(1H, t, J=7.8 Hz); 6.8-6.85(1H, m).
MASS(EI, m/e): 362(M⁺).
Elementary Analysis: Calcd. (as C₂₀H₂₆O₆): C: 66.28, H: 7.23. Found: C: 66.17, H: 7.26.

EXAMPLE 8

16-Methyl-2,5,6,7,18,19,20-heptanor-4-oxa-4,8-inter-m-phenylene PGI₂ (164)

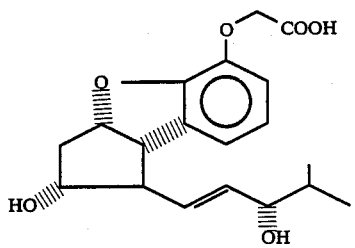

164

To a solution of 16-methyl-2,5,6,7,18,19,20-heptanor-4-oxa-4,8-inter-m-phenylene PGI₂ methyl ester (220 mg, 0.61 mmol) in methanol (120 ml) was added 1N aqueous NaOH solution (3 ml, 3 mmol), and the reaction mixture was stirred for 3 hrs. at room temperature. The reaction mixture was concentrated, and 15 ml of water was added to the residue. After acidification to pH 4 with 1N hydrochloric acid, the mixture was extracted with ethyl acetate three times. The combined ethyl acetate layers were washed with brine, dried over anhydrous magnesium sulfate and concentrated to give 219 mg of a crude crystalline solid. Recrystallization of this solid material from ethyl acetate/ethanol yielded 158 mg (0.45 mmol, 74.7%) of 16-methyl-2,5,6,7,18,19,20-heptanor-4-oxa-4,8-inter-m-phenylene PGI₂ as a white crystal, which was assigned the structure by the following data.

M.p.: 140°–141° C.
IR(KBr): 3370, 2960, 2930, 1770, 1750, 1615, 1590, 1490, 1460, 1430, 1380, 1290, 1250, 1200, 1110, 1080, 1030, 1010, 970, 950, 890, 860, 790, 760, 730, 710, 600, 440 cm⁻¹.
NMR(400 MHz, DMSO-d₆, δ): 0.86(3H, d, J=6.8 Hz); 0.88(3H, d, J=6.8 Hz); 1.55-1.65(1H, m); 1.71(1H, ddd, J=5.9, 9.8, 13.2 Hz); 2.18(1H, q, J=7.9 Hz); 2.45-2.55(1H, m); 3.35-3.45(1H, m); 3.65-3.8(2H, m); 4.55-4.65(1H, m); 4.64(2H, s); 4.8-4.9(1H, m); 5.0-5.1(1H, m); 5.46(1H, dd, J=6.6, 15.4 Hz); 5.61(1H, dd, J=7.9, 15.4 Hz); 6.65-6.75(3H, m).
MASS(EI, m/e): 348(M⁺).

EXAMPLE 9

16-Methyl-15-epi-2,5,6,7,18,19,20-heptanor-4-oxa-4,8-inter-m-phenylene PGI₂ (165)

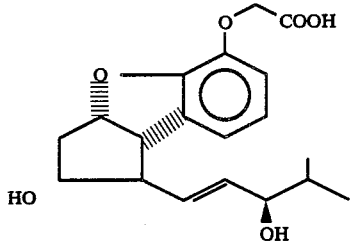

165

To a solution of 16-methyl-15-epi-2,5,6,7,18,19,20-heptanor-4-oxa-4,8-inter-m-phenylene PGI₂ methyl ester (280 mg, 0.77 mmol) in methanol (20 ml) was added 1N aqueous NaOH solution (3 ml, 3 mmol), and the reaction mixture was stirred for 3 hrs. at room temperature. The reaction mixture was concentrated, and 15 ml of water was added to the residue. After acidification to pH 4 with 1N hydrochloric acid, the mixture was extracted with ethyl acetate three times. The combined ethyl acetate layers were washed with brine, dried over anhydrous magnesium sulfate and concentrated to give 269 mg of a crude crystalline solid. Recrystallization of this material from ethanol yielded 160 mg (0.46 mmol, 59.5%) of 16-methyl-15-epi-2,5,6,7,18,19,20-heptanor-4-oxa-4,8-inter-m-phenylene PGI₂ as a white crystal, which was assigned the structure by the following data.

M.p.: 148°-149° C.

IR(KBr): 3360, 2960, 2930, 2890, 1740, 1710, 1620, 1590, 1490, 1460, 1425, 1360, 1320, 1280, 1260, 1200, 1070, 1020, 1010, 990, 960, 940, 890, 860, 810, 790, 780, 740, 720, 600, 570, 480 cm$^{-1}$.

NMR(400 MHz, DMSO-d₆, δ): 0.85(3H, d, J=6.8 Hz); 0.86(3H, d, J=6.8 Hz); 1.55-1.75(2H, m); 2.19(1H, q, J=8.3 Hz); 2.45-2.55(1H, m); 3.42(1H, t, J=8.3 Hz); 3.7-3.8(2H, m); 4.6-4.65(1H, m); 4.64(2H, s); 4.8-4.85(1H, m); 5.0-5.1(1H, m); 5.47(1H, dd, J=5.9, 15.6 Hz); 5.62(1H, dd, J=8.3, 15.6 Hz); 6.65-6.8(3H, m).

MASS(EI, m/e): 348(M+).

Elementary Analysis: Calcd. (as C₁₉H₂₄O₆): C: 65.50, H: 6.94. Found: C: 65.20, H: 6.94.

EXAMPLE 10

16,16-Dimethyl-2,5,6,7,18,19,20-heptanor-4-oxa-4,8-inter-m-phenylene PGI₂ methyl ester (166) and its 15-epimer (167)

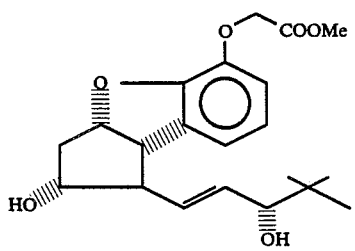

166

-continued

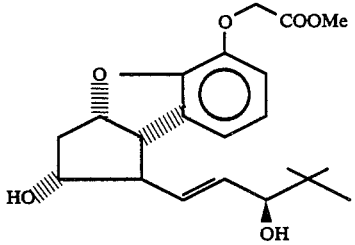

167

To a stirred solution of 16,16-dimethyl-15-oxo-2,5,6,7,18,19,20-heptanor-4-oxa-4,8-inter-m-phenylene PGI₂ methyl ester, 11-acetate (1.5 g, 4.46 mmol) in methanol was added cerium trichloride heptahydrate (1.76 g, 4.7 mmol), and then the solution was cooled to −10° C. Sodium borohydride (58.3 mg, 1.54 mmol) was added little by little to the solution. The reaction mixture was stirred for 20 min. at −10° C., brought to 0° C. and diluted with a saturated aqueous solution of sodium bicarbonate (15 ml). This solution was filtered and the filtrate was concentrated. The concentrate was mixed with 20 ml of water and extracted with ethyl acetate (50 ml×2). The combined ethyl acetate layers were washed with water (20 ml), and with brine (20 ml), dried over anhydrous sodium sulfate and concentrated to give 1.62 g of a colourless oily material.

To a solution of the oily material in anhydrous methanol was added with stirring a solution of sodium methoxide in methanol (5.22N, 0.19 mmol) under argon atmosphere. The reaction mixture was stirred for 2.5 hrs. at room temperature, neutralized with acetic acid, and then concentrated. Water (20 ml) was added to the residue. Extraction with ethyl acetate (50 ml×2) followed by washing with water (20 ml) and with brine (20 ml), drying over anhydrous sodium sulfate and concentration afforded a crude material. Column chromatography (Merck, Lobar column; silica gel, ethyl acetate/cyclohexane: 2/1) of the crude material gave less polar 16,16-dimethyl-15-epi-2,5,6,7,18,19,20-heptanor-4-oxa-4,8-inter-m-phenylene PGI₂ methyl ester (536 mg, 1.43 mmol, yield: 36.7%) and more polar 16,16-dimethyl-2,5,6,7,18,19,20-heptanor-4-oxa-4,8-inter-m-phenylene PGI₂ methyl ester (559 mg, 1.49 mmol, yield: 38.3%). These compounds were assigned the corresponding structures by the following data.

16,16-Dimethyl-2,5,6,7,18,19,20-heptanor-4-oxa-4,8-inter-m-phenylene PGI₂ methyl ester M.p.: 153.3°-154.8° C. (recrystallization solvent: ethyl acetate/n-hexane: 3/2).

IR(KBr): 3320, 2960, 2930, 2870, 1765, 1615, 1590, 1485, 1465, 1440, 1425, 1375, 1360, 1300, 1240, 1220, 1195, 1160, 1125, 1090, 1075, 1045, 1000, 975, 950, 895, 860, 830, 785, 755, 725, 710, 680, 645 cm$^{-1}$.

NMR(400 MHz, CDCl₃, δ): 0.93(9H, s); 1.5-2.2(3H, m); 2.46(1H, q, J=8.3 Hz); 2.6-2.7(1H, m); 3.46(1H, t, J=8.3 Hz); 3.77(1H, d, J=6.3 Hz); 3.79(3H, s); 3.8-4.0(1H, m); 4.72(2H, s); 5.1-5.3(1H, m); 5.6-5.8(2H, m); 6.7-6.9(3H, m).

MASS(EI, m/e): 376(M+).

Elementary Analysis: Calcd. (as C₂₁H₂₈O₆): C: 67.00, H: 7.50. Found: C: 66.95, H: 7.50.

16,16-Dimethyl-15-epi-2,5,6,7,18,19,20-heptanor-4-oxa-4,8-inter-m-phenylene PGI₂ methyl ester M.p.: 108.7°–110.0° C. (recrystallization solvent: ethyl acetate/n-hexane: 3/2).

IR(KBr): 3300, 2970, 2940, 2905, 2880, 1760, 1735, 1665, 1620, 1590, 1490, 1460, 1450, 1430, 1370, 1360, 1350, 1305, 1280, 1260, 1250, 1225, 1200, 1225, 1200, 1120, 1110, 995, 980, 960, 950, 890, 860, 830, 795, 765, 750, 725, 700 cm⁻¹.

NMR(400 MHz, CDCl₃, δ): 0.98(9H, s); 1.5–1.7(2H, m); 2.0–2.2(1H, m); 2.54(1H, q, J=7.9 Hz); 2.6–2.7(1H, m); 3.53(1H, t, J=7.9 Hz); 3.79(3H, s); 3.81(1H, d, J=5.4 Hz); 3.9–4.0(1H, m); 4.72(2H, s); 5.15–5.3(1H, m); 5.6–5.8(2H, m); 6.7–6.9(3H, m).

MASS(EI, m/e): 376(M⁺).

Elementary Analysis: Calcd. (as $C_{21}H_{28}O_6$): C: 67.00, H: 7.50. Found: C: 66.94, H: 7.52.

EXAMPLE 11

16,16-Dimethyl-2,5,6,7,18,19,20-heptanor-4-oxa-4,8-inter-m-phenylene PGI₂ (168)

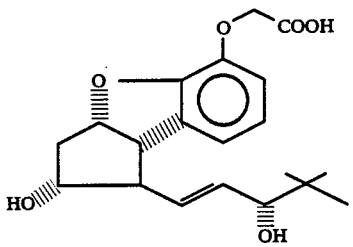

168

To a solution of 16,16-dimethyl-2,5,6,7,18,19,20-heptanor-4-oxa-4,8-inter-m-phenylene PGI₂ methyl ester (320 mg, 0.85 mmol) in methanol (30 ml) was added with stirring 0.725N aqueous NaOH solution (7.0 ml, 5.1 mmol) under ice-cooling, and then the reaction mixture was stirred for one hour at room temperature. The reaction mixture was concentrated, and 20 ml of water was added to the residue. After neutralization with 1N hydrochloric acid, the mixture was extracted with ethyl acetate (50 ml×2). The combined ethyl acetate layers were washed with 20 ml of water, and with 20 ml of brine, dried over anhydrous sodium sulfate and concentrated. Recrystallization of the residue from a mixture of 0.5 ml of ethyl acetate, 3 ml of chloroform and 1 ml of benzene yielded 272 mg (0.75 mmol, 88.2%) of 16,16-dimethyl-2,5,6,7,18,19,20-heptanor-4-oxa-4,8-inter-m-phenylene PGI₂ as a white crystal, which was assigned the structure by the following data.

M.p.: 159.9°–161.0° C. (recrystallization solvent: ethyl acetate/chloroform/benzene, 0.5/3/1).

IR(KBr): 3400, 3200, 2960, 2870, 2750, 2650, 2550, 1725, 1605, 1470, 1430, 1390, 1360, 1325, 1300, 1270, 1225, 1185, 1150, 1080, 1070, 1050, 1025, 1000, 955, 905, 880, 860, 830, 790, 770, 750, 725, 695, 650 cm⁻¹.

NMR(400 MHz, DMSO-d₆, δ): 0.86(9H, s); 1.6–1.8(1H, m); 2.19(1H, q, J=8.3 Hz); 2.4–2.6(1H, m); 3.42(1H, t, J=8.3 Hz); 3.59(1H, t, J=6.8 Hz); 3.7–3.8(1H, m); 4.5–4.6(1H, m); 4.64(2H, s); 4.7–4.9(1H, m); 5.0–5.2(1H, m); 5.56(1H, dd, J=6.8, 15.6 Hz); 5.61(1H, dd, J=8.3, 15.6 Hz); 6.6–6.9(3H, m).

MASS(EI, m/e): 362(M⁺).

HR MASS: Calcd. ($C_{20}H_{26}O_6$ M⁺): 362.1729. Found (M⁺): 362.1728.

EXAMPLE 12

16,16-Dimethyl-15-epi-2,5,6,7,18,19,20-heptanor-4-oxa-4,8-inter-m-phenylene PGI₂ (169)

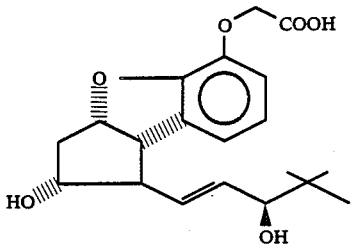

169

To a solution of 16,16-dimethyl-15-epi-2,5,6,7,18,19,20-heptanor-4-oxa-4,8-inter-m-phenylene PGI₂ methyl ester (310 mg, 0.82 mmol) in methanol was added with stirring 0.725N aqueous NaOH solution under ice-cooling, and then the reaction mixture was stirred for one hour at room temperature. After neutralization with 1N hydrochloric acid, the reaction mixture was concentrated, and 20 ml of water was added to the residue. The mixture was extracted with ethyl acetate (50 ml×2). The combined ethyl acetate layers were washed with 20 ml of water, and with 20 ml of brine, dried over anhydrous sodium sulfate and concentrated. Recrystallizaion of the residue from a mixture of 3 ml of ethyl acetate and 2 ml of n-hexane yielded 290 mg (0.8 mmol, 97.2%) of 16,16-dimethyl-15-epi-2,5,6,7,18,19,20-heptanor-4-oxa-4,8-inter-m-phenylene PGI₂ as a white crystal, which was assigned the structure by the following data.

M.p.: 150.1°–151.1° C. (recrystallization solvent: ethyl acetate/n-hexane: 3/2).

IR(KBr): 3300, 2970, 2920, 2870, 1750, 1700, 1610, 1590, 1480, 1460, 1430, 1410, 1320, 1305, 1280, 1250, 1200, 1180, 1150, 1115, 1100, 1070, 1050, 1030, 1010, 965, 925, 885, 860, 795, 770, 720, 695 cm⁻¹.

NMR(400 MHz, DMSO-d₆, δ): 0.85(9H, s); 1.6–1.8(1H, m); 2.2(1H, q, J=8.3 Hz); 2.4–2.6(1H, m); 3.42(1H, t, J=8.3 Hz); 3.5–3.8(2H, m); 4.64(2H, s); 4.5–4.7 (1H, m); 4.7–4.9(1H, m); 5.0–5.2(1H, m); 5.53(1H, dd, J=6.6, 15.4 Hz); 5.63(1H, dd, J=8.3, 15.4 Hz); 6.6–6.9(3H, m).

MASS(EI, m/e): 362(M⁺).

Elementary Analysis: Calcd. (as $C_{20}H_{26}O_6$): C: 66.28, H: 7.23. Found: C: 66.14, H: 7.32.

EXAMPLE 13

16,16-Dimethyl-2,5,6,7,19,20-hexanor-4-oxa-4,8-inter-m-phenylene PGI₂ methyl ester (170) and its 15-epimer (171)

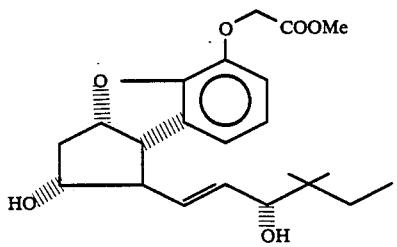

170

179

-continued

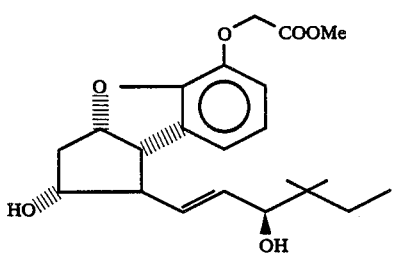

171

To a solution of 16,16-dimethyl-15-oxo-2,5,6,7,19,20-hexanor-4-oxa-4,8-inter-m-phenylene PGI₂ methyl ester, 11-acetate (1.22 g, 2.84 mmol) in methanol (80 ml) was added cerium trichloride heptahydrate (1.28 g, 3.41 mmol), and then the solution was cooled to −10° C. Sodium borohydride (42 mg, 1.13 mmol) was added little by little to the solution. The reaction mixture was stirred for 20 min. at −10° C., brought to 0° C. and diluted with a saturated aqueous solution of sodium bicarbonate (20 ml). This solution was filtered and the filtrate was concentrated. The concentrate was mixed with 20 ml of water and extracted with ethyl acetate (50 ml×2). The combined ethyl acetate layers were washed with water (20 ml), and with brine (20 ml), dried over anhydrous sodium sulfate and concentrated to give 1.2 g of an oily material.

To a solution of the oily material in anhydrous methanol (50 ml) was added with stirring a solution of sodium methoxide in methanol (5.22N, 0.13 ml, 0.7 mmol) under argon atmosphere. The reaction mixture was stirred for 14 hrs. at room temperature, neutralized with acetic acid, and concentrated. Water (20 ml) was added to the residue. Extraction with ethyl acetate (50 ml×2) followed by washing with water (20 ml) and with brine (20 ml), drying over anhydrous sodium sulfate and concentration afforded a crude material. Column chromatography (Merck, Lobar column, silica gel, ethyl acetate/cyclohexane: 2/1) of the material gave less polar 16,16-dimethyl-15-epi-2,5,6,7,19,20-hexanor-4-oxa-4,8-inter-m-phenylene PGI₂ methyl ester (476 mg, 1.22 mmol, yield: 43.6%) and more polar 16,16-dimethyl-2,5,6,7,19,20-hexanor-4-oxa-4,8-inter-m-phenylene PGI₂ methyl ester (493 mg, 1.26 mmol, yield: 45.1%). These compounds were assigned the corresponding structures by the following data.

16,16-Dimethyl-2,5,6,7,19,20-hexanor-4-oxa-4,8-inter-m-phenylene PGI₂ methyl ester M.p.: 132.6°–133.2° C. (recrystallization solvent: ethyl acetate/n-hexane, 2/3).

IR(KBr): 3350, 2970, 2930, 2880, 1765, 1620, 1595, 1490, 1465, 1440, 1380, 1300, 1240, 1195, 1160, 1125, 1090, 1075, 1050, 995, 980, 955, 895, 860, 830, 785, 760, 730, 710, 680 cm⁻¹.

NMR(400 MHz, CDCl₃, δ): 0.86(3H, s); 0.88(3H, t, J=7.8 Hz); 0.89 (3H, s); 1.2–1.5(2H, m); 1.7–1.9(1H, m); 2.0–2.2(1H, m); 2.2–2.4(1H, m); 2.49(1H, q, J=8.0 Hz); 2.6–2.8(1H, m); 3.48(1H, t, J=8.0 Hz); 3.79(3H, s); 3.87(1H, d, J=6.8 Hz); 3.9–4.0(1H, m); 4.73(2H, s); 5.1–5.3(1H, m); 5.63(1H, dd, J=8.0, 15.6 Hz); 5.69(1H, dd, J=6.8, 15.6 Hz); 6.7–6.9(3H, m).

MASS(EI, m/e): 390(M+).

Elementary Analysis: Calcd. (as C₂₂H₃₀O₆): C: 67.67, H: 7.74. Found: C: 67.62, H: 7.80.

180

16,16-Dimethyl-15-epi-2,5,6,7,19,20-hexanor-4-oxa-4,8-inter-m-phenylene PGI₂ methyl ester M.p.: 90.3°–91.2° C. (recrystallization solvent: ethyl acetate/n-hexane, 3/2).

IR(KBr): 3330, 2970, 2930, 1760, 1735, 1620, 1595, 1490, 1460, 1450, 1430, 1375, 1350, 1310, 1275, 1260, 1250, 1225, 1200, 1110, 1100, 1070, 1030, 1020, 980, 965, 950, 890, 855, 835, 800, 790, 765, 730, 705 cm⁻¹.

NMR(400 MHz, CDCl₃, δ): 0.855(3H, s); 0.898(3H, s); 0.873(3H, t, J=7.6 Hz); 1.2–1.5(2H, m); 1.4–1.6 (1H, m); 1.7–1.8(1H, m); 2.0–2.2(1H, m); 2.55(1H, q, J=7.7 Hz); 2.6–2.7(1H, m); 3.53(1H, t, J=7.7 Hz); 3.79(3H, s); 3.8–4.1(2H, m); 4.73(2H, s); 5.2–5.3(1H, m); 5.68(1H, dd, J=7.7, 15.6 Hz); 5.74(1H, dd, J=5.6, 15.6 Hz); 6.7–6.9(3H, m).

MASS(EI, m/e): 390(M+).

Elementary Analysis: Calcd. (as C₂₂H₃₀O₆): C: 67.67, H: 7.74. Found: C: 67.63, H: 7.79.

EXAMPLE 14

16,16-Dimethyl-2,5,6,7,19,20-hexanor-4-oxa-4,8-inter-m-phenylene PGI₂ (172)

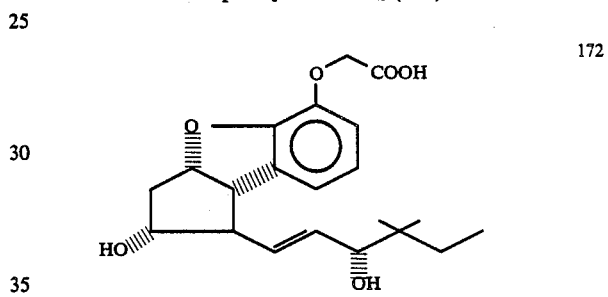

172

To a solution of 16,16-dimethyl-2,5,6,7,19,20-hexanor-4-oxa-4,8-inter-m-phenylene PGI₂ methyl ester (324 mg, 0.83 mmol) in methanol (30 ml) was added with stirring 0.725N aqueous NaOH solution (9.2 ml, 6.7 mmol) under ice-cooling, and then the reaction mixture was stirred for one hour at room temperature. After the solution was mixed with 1N hydrochloric acid (6.7 ml) under ice-cooling and concentrated, 20 ml of water was added to the residue and the mixture was extracted with ethyl acetate (50 ml×2). The combined ethyl acetate layers were washed with 20 ml of water, with 20 ml of brine, dried over anhydrous sodium sulfate and concentrated. Recrystallization of the residue from the mixture of 2 ml of chloroform and 1.5 ml of n-hexane yielded 287 mg (0.76 mmol, 91.9%) of 16,16-dimethyl-2,5,6,7,19,20-hexanor-4-oxa-4,8-inter-m-phenylene PGI₂ as a white crystal, which was assigned the structure by the following data.

M.p.: 78.2°–80.0° C. (recrystallization solvent: chloroform/n-hexane: 4/3).

IR(KBr): 3380, 2960, 1730, 1615, 1590, 1480, 1455, 1430, 1370, 1280, 1260, 1185, 1105, 1020, 965, 940, 880, 850, 820, 785, 760, 720 cm⁻¹.

NMR(400 MHz, CDCl₃, δ): 0.84(3H, s); 0.88(3H, s); 0.87 (3H, t, J=7.6 Hz); 1.2–1.5(2H, m); 1.9–2.1(1H, m); 2.45(1H, q, J=8.0 Hz); 2.5–2.7(1H, m); 3.45(1H, t, J=8.0 Hz); 3.4–3.8(2H, m); 3.85(1H, d, J=6.8 Hz); 3.8–4.0(1H, m); 4.65(1H, d, J=16.6 Hz); 4.73(1H, d, J=16.6 Hz); 5.1–5.3(1H, m); 5.5–5.7(2H, m); 6.7–6.9(3H, m).

MASS(EI, m/e): 376(M+).

EXAMPLE 15

16,16-Dimethyl-15-epi-2,5,6,7,19.20-hexanor-4-oxa-4,8-inter-m-phenylene PGI$_2$ (173)

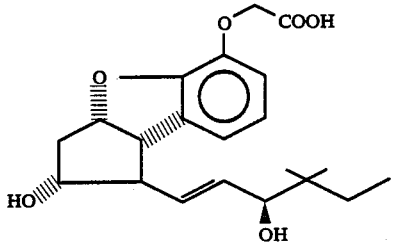

173

To a solution of 16,16-dimethyl-15-epi-2,5,6,7,19,20-hexanor-4-oxa-4,8-inter-m-phenylene PGI$_2$ methyl ester (316 mg, 0.81 mmol) in methanol (30 ml) was added with stirring 0.725N aqueous NaOH solution (9.2 ml, 6.7 mmol) under ice-cooling, and the reaction mixture was stirred for 30 min. The reaction mixture was concentrated, and 20 ml of water was added to the residue. After neutralization with 1N hydrochloric acid, the mixture was extracted with ethyl acetate (50 ml×2). The combined ethyl acetate layers were washed with 20 ml of water, and with 20 ml of brine, dried over anhydrous sodium sulfate and concentrated. Recrystallization of the residue from a mixture of 2.5 ml of ethyl acetate and 1.0 ml of n-hexane yielded 261 mg (0.69 mmol, 85.7%) of 16,16-dimethyl-15-epi-2,5,6,7,19,20-hexanor-4-oxa-4,8-inter-m-phenylene PGI$_2$ as a white crystal, which was assigned the structure by the following data.

M.p.: 129.5°–130.6° C. (recrystallization solvent: ethyl acetate/n-hexane: 5/2).

IR(KBr): 3320, 2970, 2940, 2880, 1755, 1705, 1620, 1605, 1590, 1480, 1460, 1430, 1415, 1375, 1340, 1325, 1285, 1270, 1200, 1190, 1155, 1120, 1105, 1075, 1050, 1040, 1030, 1010, 975, 950, 925, 890, 865, 830, 795, 770, 765, 730, 700, 660 cm$^{-1}$.

NMR(400 MHz, DMSO, δ): 0.77(3H, s); 0.8(3H, s); 0.7–0.9 (3H, m); 1.1–1.4(2H, m); 1.6–1.8(1H, m); 2.2(1H, q, J=8.3 Hz); 2.4–2.6(1H, m); 3.42(1H, t, J=8.3 Hz); 3.6–3.8(2H, m); 4.5–4.6(1H, m); 4.64(2H, s); 4.7–4.9(1H, m); 5.0–5.1(1H, m); 5.54(1H, dd, J=6.4, 15.1 Hz); 5.63(1H, dd, J=8.3, 15.1 Hz); 6.6–6.9(3H, m).

MASS(EI, m/e): 376(M+).

Elementary Analysis: Calcd. (as C$_{21}$H$_{28}$O$_6$): C: 67.00, H: 7.50. Found: C: 66.75, H: 7.50.

EXAMPLE 16

16,16-Dimethyl-2,5,6,7,20-pentanor-4-oxa-4,8-inter-m-phenylene PGI$_2$ methyl ester (174) and its 15-epimer (175)

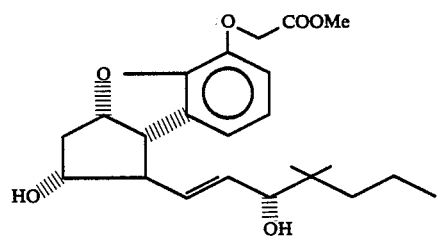

174

-continued

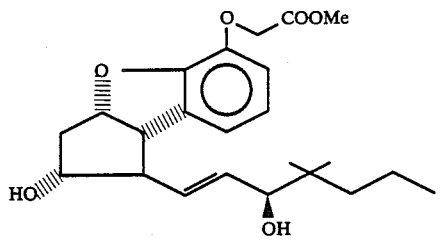

175

To a solution of 16,16-dimethyl-15-oxo-2,5,6,7,20-pentanor-4-oxa-4,8-inter-m-phenylene PGI$_2$ methyl ester, 11-acetate (1.77 g, 3.99 mmol) in methanol (100 ml) was added cerium trichloride heptahydrate (1.49 g, 3.99 mmol). Sodium borohydride (61 mg, 1.60 mmol) was added to the reaction mixture under ice-cooling, and the resulting mixture was stirred for 30 min. The solution was diluted with a saturated aqueous solution of sodium bicarbonate, and then methanol was removed off by an evaporator. The residue was triturated in 50 ml of ethyl acetate and the resulting precipitate was filtered off. The precipitate was washed with ethyl acetate (30 ml×3), and the combined filtrates were concentrated. The residue was diluted with 50 ml of water and extracted with ethyl acetate (80 ml×3). The combined ethyl acetate layers were washed with 50 ml of water, and with 50 ml of brine, dried over anhydrous sodium sulfate and concentrated to give an oily material (1.70 g).

After azeotropic distillation of the oily material with benzene (10 ml×2), the residue was dissolved in anhydrous methanol (70 ml). To this solution was added a solution of sodium methoxide in methanol (5.22N, 0.22 ml, 1.14 mmol). The reaction mixture was stirred under argon atmosphere for 3 hrs. at room temperature, neutralized with acetic acid, and then concentrated. Water (15 ml) was added to the residue. Extraction with ethyl acetate (30 ml×3) followed by washing with water (30 ml) and with brine (30 ml), drying over anhydrous sodium sulfate and concentration afforded a colourless oily material. Column chromatography (silica gel: ethyl acetate/cyclohexane: 2/1) of the material gave less polar 16,16-dimethyl-15-epi-2,5,6,7,20-pentanor-4-oxa-4,8-inter-m-phenylene PGI$_2$ methyl ester (673.8 mg, 1.67 mmol, 43.8%) and subsequently more polar 16,16-dimethyl-2,5,6,7,20-pentanor-4-oxa-4,8-inter-m-phenylene PGI$_2$ methyl ester (655.5 mg, 1.62 mmol, 42.6%). These compounds were assigned the corresponding structures by the following data.

16,16-Dimethyl-2,5,6,7,20-pentanor-4-oxa-4,8-inter-m-phenylene PGI$_2$ methyl ester M.p.: 117.5°–118.2° C. (recrystallized from ethyl acetate/cyclohexane: 2/1).

IR(KBr): 3310, 2970, 2940, 2880, 1770, 1620, 1600, 1490, 1470, 1440, 1435, 1380, 1360, 1310, 1300, 1260, 1250, 1220, 1200, 1190, 1170, 1120, 1090, 1040, 1020, 1000, 980, 970, 950, 860, 840, 790, 760, 730, 720, 690 cm$^{-1}$.

NMR(400 MHz, CDCl$_3$, δ): 0.87–0.94(9H, m); 1.19–1.34 (4H, m); 1.87(1H, broad s); 2.45(1H, ddd, J=5.0, 8.0, 13.7 Hz); 2.47(1H, q, J=8.0 Hz); 2.5(1H, broad s); 2.66(1H, dt, J=7.0, 13.7 Hz); 3.47(1H, t, J=8.0 Hz); 3.79(3H, s); 3.84(1H, d, J=6.8 Hz); 3.93(1H, m);

HR MASS: Calcd. (C$_{21}$H$_{28}$O$_6$, M+): 376.1871. Found: (M+): 376.1896.

4.73(2H, s); 5.20(1H, ddd, J=5.0, 7.0, 8.0 Hz); 5.66(2H, m); 6.71–6.79(3H, m).

MASS(EI, m/e): 404(M+).

Elementary Analysis: Calcd. (as $C_{23}H_{32}O_6$): C: 68.29, H: 7.97. Found: C: 68.27, H: 8.09.

16,16-Dimethyl-15-epi-2,5,6,7,20-pentanor-4-oxa-4,8-inter-m-phenylene PGI₂ methyl ester M.p.: 88.8°–89.5° C. (recrystallized from ethyl acetate/cyclohexane: 2/1).

IR(KBr): 3310, 2960, 2940, 2890, 2870, 1760, 1740, 1620, 1590, 1490, 1460, 1440, 1430, 1370, 1350, 1310, 1300, 1280, 1260, 1220, 1200, 1190, 1150, 1120, 1100, 1070, 1030, 1020, 990, 980, 960, 950, 880, 870, 860, 830, 780, 760, 720, 700, 610 cm⁻¹.

NMR(400 MHz, CDCl₃, δ): 0.88–0.93(9H, m); 1.20–1.36 (4H, m); 1.53(1H, broad s); 1.76(1H, broad s); 2.09(1H, ddd, J=4.9, 8.0, 13.5 Hz); 2.55(1H, q, J=8.0 Hz); 2.64(1H, dt, J=7.0, 13.5 Hz); 3.53(1H, t, J=8.0 Hz); 3.79(3H, s); 3.89(1H, d, J=5.4 Hz); 3.97 (1H, m); 4.73(2H, s); 5.23(1H, ddd, J=4.9, 7.0, 8.0 Hz); 5.66–5.77(2H, m); 6.72–6.84(3H, m).

MASS(EI, m/e): 404(M+).

Elementary Analysis: Calcd. (as $C_{23}H_{32}O_6$): C: 68.29, H: 7.97. Found: C: 68.24, H: 8.02.

EXAMPLE 17

16,16-Dimethyl-2,5,6,7,20-pentanor-4-oxa-4,8-inter-m-phenylene PGI₂ (176)

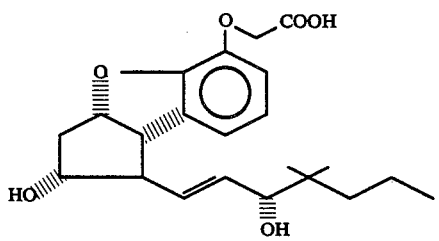

To a solution of 16,16-dimethyl-2,5,6,7,20-pentanor-4-oxa-4,8-inter-m-phenylene PGI₂ methyl ester (308 mg, 0.762 mmol) in methanol (70 ml) was added 1N aqueous NaOH solution (6.1 ml, 6.10 mmol), and the reaction mixture was stirred under argon atmosphere for 1.5 hrs. at room temperature. The solution was acidified with 1N hydrochloric acid to pH 4 and concentrated. After 10 ml of water was added to the residue, the resulting mixture was extracted with ethyl acetate (15 ml×3). The combined ethyl acetate layers were washed with 10 ml of water, and with 10 ml of brine, dried over anhydrous sodium sulfate and concentrated to give quantitatively 16,16-dimethyl-2,5,6,7,20-pentanor-4-oxa-4,8-inter-m-phenylene PGI₂ (297 mg, 0.761 mmol) as a single product. The product was assigned the structure by the following data.

M.p.: 99.0°–100.2° C. (recrystallized from ethyl acetate/cyclohexane: 3/1).

IR(KBr): 3430, 3360, 3230, 2960, 2920, 2870, 1760, 1750, 1680, 1620, 1590, 1490, 1460, 1430, 1360, 1300, 1250, 1210, 1180, 1160, 1120, 1090, 1080, 1060, 1030, 1000, 980, 960, 950, 920, 900, 880, 860, 830, 800, 760, 720, 690, 680, 540 cm⁻¹.

NMR(400 MHz, CDCl₃, δ): 0.86–0.93(9H, m); 1.18–1.31 (4H, m); 2.02(1H, ddd, J=4.9, 7.7, 13.7 Hz); 2.46 (1H, q, J=7.7 Hz); 2.61(1H, dt, J=7.7, 13.7 Hz); 3.04(2H, broad s); 3.46(1H, t, J=7.7 Hz); 3.84(1H, d, J=6.8 Hz); 3.93(1H, q, J=7.7 Hz); 4.66(1H, d, J=16.6 Hz); 4.73(1H, d, J=16.6 Hz); 5.18(1H, m); 5.57–5.68(2H, m); 6.73–6.78(3H, m).

MASS(EI, m/e): 390(M+).

HR MASS: Calcd. ($C_{22}H_{30}O_6$, M+): 390.2042. Found (M+): 390.2041.

EXAMPLE 18

16,16-Dimethyl-15-epi-2,5,6,7,20-pentanor-4-oxa-4,8-inter-m-phenylene PGI₂ (177)

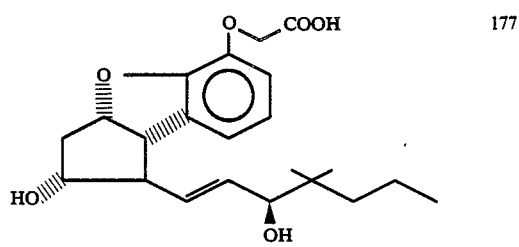

To a solution of 16,16-dimethyl-15-epi-2,5,6,7,20-pentanor-4-oxa-4,8-inter-m-phenylene PGI₂ methyl ester (308 mg, 0.762 mmol) in methanol (70 ml) was added 1N aqueous NaOH solution (6.1 ml, 6.10 mmmol), and the reaction mixture was stirred under argon atmosphere for 1.5 hrs. at room temperature. The solution was acidified with 1N hydrochloric acid to pH 4 and concentrated. After 20 ml of water was added to the residue, the resulting mixture was extracted with ethyl acetate (15 ml×3). The combined ethyl acetate layers were washed with 10 ml of water, and with 10 ml of brine, dried over anhydrous sodium sulfate and concentrated to give quantitatively 16,16-dimethyl-15-epi-2,5,6,7,20-pentanor-4-oxa-4,8-inter-m-phenylene PGI₂ (293 mg, 0.751 mmol) as a single product. The product was assigned the structure by the following data.

M.p.: 88.0°–88.9° C. (recrystallized from ethyl acetate/cyclohexane: 3/1).

IR(KBr): 3320, 2960, 2940, 2870, 1750, 1730, 1620, 1590, 1480, 1460, 1440, 1380, 1360, 1320, 1250, 1220, 1190, 1170, 1100, 1040, 1010, 1090, 1070, 1050, 1020, 990, 960, 930, 900, 830, 760, 720, 660, 610, 550 cm⁻¹.

NMR (400 MHz, CDCl₃, δ): 0.86–0.92(9H, m); 1.19–1.32(5H, m); 2.05(1H, m); 2.49–2.59(2H, m); 3.50(1H, t, J=7.0 Hz); 3.87(1H, d, J=4.9 Hz); 3.96(1H, q, J=7.0 Hz); 3.8–4.0(1H, broad s); 4.65(1H, d, J=16.40 Hz); 4.71 (1H, d, J=16.40 Hz); 5.20(1H, m); 5.63–5.73 (2H, m); 6.71–6.82(3H, m).

MASS(EI, m/e): 390(M+).

HR MASS: Calcd. ($C_{22}H_{30}O_6$, M+): 390.2042. Found (M+): 390.2018.

EXAMPLE 19

16,16-Dimethyl-2,5,6,7-tetranor-4-oxa-4,8-inter-m-phenylene PGI₂ methyl ester (178) and its 15-epimer (179)

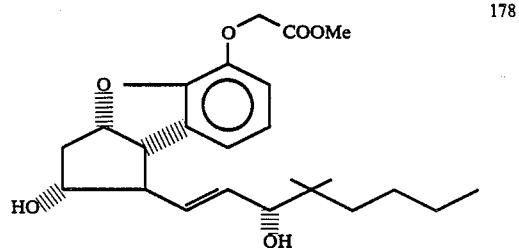

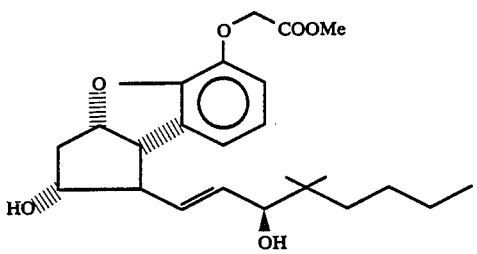

179

To a solution of 16,16-dimethyl-15-oxo-2,5,6,7-tetranor-4-oxa-4,8-inter-m-phenylene PGI₂ methyl ester, 11-acetate (690 mg, 1.50 mmol) in 30 ml of methanol was added cerium trichloride heptahydrate (838 mg, 2.25 mmol), and then the solution was cooled to −10° C. Sodium borohydride (68.1 mg, 1.80 mmol) was added to the solution. The reaction mixture was stirred for 10 min. at −10° C., diluted with a saturated aqueous solution of sodium bicarbonate (8 ml), and then concentrated. The residue was triturated in ethyl acetate, and the resulting precipitate was filtered off. The precipitate was washed with three portions of ethyl acetate. The combined filtrates were washed with water and with brine, dried over anhydrous magnesium sulfate and concentrated to give 699 mg of an oily material.

To a solution of the oily material in anhydrous methanol (15 ml) was added a solution of sodium methoxide in methanol (5.22N, 0.14 ml, 0.750 mmol) under argon atmosphere. The reaction mixture was stirred for 2 hrs. at room temperature, neutralized with acetic acid, and then concentrated. Water was added to the residue. Extraction with ethyl acetate followed by washing with brine, drying over anhydrous magnesium sulfate and concentration afforded a crude material. Column chromatography (Merck, Lobar column, silica gel; ethyl acetate/cyclohexane: 5/1) of the material gave less polar 16,16-dimethyl-15-epi-2,5,6,7-tetranor-4-oxa-4,8-inter-m-phenylene PGI₂ methyl ester (262 mg, 0.63 mmol, yield: 41.8%) as a white crystalline solid and more polar 16,16-dimethyl-2,5,6,7-tetranor-4-oxa-4,8-inter-m-phenylene PGI₂ methyl ester (248 mg, 0.59 mmol, yield: 39.6%) as a white crystalline solid. These compounds were assigned the corresponding structures by the following data.

16,16-Dimethyl-2,5,6,7-tetranor-4-oxa-4,8-inter-m-phenylene PGI₂ methyl ester

M.p.: 119°–120° C. (recrystallized from ethyl acetate).

IR(KBr): 3300, 2950, 2900, 2850, 1760, 1740, 1660, 1610, 1580, 1480, 1460, 1430, 1370, 1290, 1210, 1190, 1180, 1160, 1115, 1070, 1030, 1010, 990, 970, 960, 940, 880, 860, 830, 780, 750, 720, 710, 680, 270 cm⁻¹.

NMR(400 MHz, CDCl₃, δ): 0.87(3H, s); 0.90(3H, s); 0.92 (3H, t, J=6.8 Hz); 1.2–1.4(6H, m); 1.8–1.9(1H, m); 2.05(1H, ddd, J=5.4, 8.8, 13.6 Hz); 2.3–2.4(1H, m); 2.48(1H, q, J=8.5 Hz); 2.66(1H, dt, J=7.0, 13.6 Hz); 3.47(1H, t, J=8.5 Hz); 3.79(3H, s); 3.8–3.85(1H, m); 3.9–4.0(1H, m); 4.73(2H, s); 5.21(1H, ddd, J=5.4, 7.0, 8.5 Hz); 5.6–5.75(2H, m); 6.7–6.8(3H, m).

MASS(EI, m/e): 418(M⁺).

Elementary Analysis: Calcd. (as C₂₄H₃₄O₆); C: 68.87, H: 8.19. Found: C: 68.55, H: 8.22.

16,16-Dimethyl-15-epi-2,5,6,7-tetranor-4-oxa-4,8-inter-m-phenylene PGI₂ methyl ester M.p.: 80°–81° C. (recrystallized from ethyl acetate/hexane).

IR(KBr): 3330, 2950, 2930, 2870, 1760, 1735, 1620, 1590, 1490, 1460, 1370, 1340, 1300, 1270, 1260, 1220, 1200, 1120, 1030, 1020, 990, 960, 890, 860, 760, 720, 610 cm⁻¹.

NMR(400 MHz, CDCl₃, δ): 0.87(3H, s); 0.90(3H, s); 0.91(3H, t, J=6.8 Hz); 1.2–1.4(6H, m); 1.52(1H, d, J=4.4 Hz); 1.76(1H, d, J=4.5 Hz); 2.09(1H, ddd, J=4.9, 8.3, 13.7 Hz); 2.55(1H, q, J=8.2 Hz); 2.64 (1H, dt, J=7.0, 13.7 Hz); 3.53(1H, t, J=8.2 Hz); 3.79(3H, s); 3.85–3.9(1H, m); 3.9–4.0(1H, m); 4.73(2H, s); 5.23(1H, ddd, J=4.9, 7.0, 8.2 Hz); 5.67(1H, dd, J=8.2 Hz, 15.4 Hz); 5.74(1H, dd, J=5.6, 15.4 Hz); 6.73(1H, dd, J=1.5, 7.4 Hz); 6.77(1H, t, J=7.4 Hz); 6.83(1H, m).

MASS(EI, m/e): 418(M⁺).

Elementary Analysis: Calcd. (as C₂₄H₃₄O₆); C: 68.87, H: 8.19. Found: C: 68.53, H: 8.17.

EXAMPLE 20

16,16-Dimethyl-2,5,6,7-tetranor-4-oxa-4,8-inter-m-phenylene PGI₂ (180)

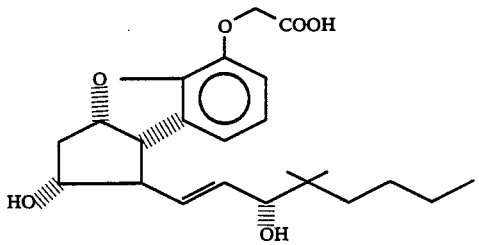

180

To a solution of 16,16-dimethyl-2,5,6,7-tetranor-4-oxa-4,8-inter-m-phenylene PGI₂ methyl ester (156 mg, 0.37 mmol) in methanol (15 ml) was added 1N aqueous NaOH solution (2 ml, 2 mmol), and the reaction mixture was stirred for 3 hrs. at room temperature. The reaction mixture was concentrated, and 15 ml of water was added to the residue. After acidification to pH 4 with 1N hydrochloric acid, the mixture was extracted with ethyl acetate three times. The combined ethyl acetate layers were washed with brine, dried over anhydrous magnesium sulfate and concentrated to give 142 mg of a crude crystalline solid. Recrystallization of this material from benzene yielded 115 mg (0.28 mmol, 76.9%) of 16,16-dimethyl-2,5,6,7-tetranor-4-oxa-4,8-inter-m-phenylene PGI₂ as a white crystal, which was assigned the structure by the following data.

M.p.: 119.5°–120.5° C.

IR(KBr): 3350, 2950, 2920, 2860, 1740, 1620, 1590, 1480, 1460, 1430, 1360, 1290, 1250, 1220, 1190, 1160, 1120, 1030, 1010, 1000, 980, 950, 900, 860, 830, 790, 760, 730 cm⁻¹.

NMR(400 MHz, CDCl₃, δ): 0.87(3H, s); 0.90(3H, s); 0.92(3H, t, J=6.8 Hz); 1.2–1.4(6H, m); 2.04(1H, ddd, J=5.0, 7.9, 13.7 Hz); 2.51(1H, q, J=7.9 Hz); 2.61(1H, ddd, J=6.2, 7.3, 13.7 Hz); 3.49(1H, t, J=7.9 Hz); 3.8–4.2(2H, m); 3.85(1H, d, J=6.4 Hz); 3.96(1H, dt, J=6.2, 7.9 Hz); 4.69(1H, d, J=16.1 Hz); 4.73(1H, d, J=16.1 Hz); 5.21(1H, ddd, J=5.0, 7.3, 7.9 Hz); 5.63(1H, dd, J=7.9, 15.2 Hz); 5.69(1H, dd, J=6.4, 15.2 Hz); 6.75–6.85(3H, m).

EXAMPLE 21

16,16-Dimethyl-15-epi-2,5,6,7-tetranor-4-oxa-4,8-inter-m-phenylene $PGI_2$ (181)

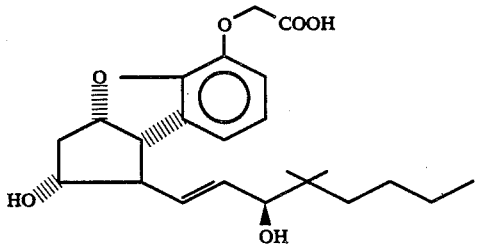

To a solution of 16,16-dimethyl-15-epi-2,5,6,7-tetranor-4-oxa-4,8-inter-m-phenylene $PGI_2$ methyl ester (161 mg, 0.39 mmol) in methanol (15 ml) was added 1N aqueous NaOH solution (2 ml, 2 mmol), and the reaction mixture was stirred for 3 hrs. at room temperature. The reaction mixture was concentrated, and 15 ml of water was added to the residue. After acidification to pH 4 with 1N hydrochloric acid, the mixture was extracted with ethyl acetate three times. The combined ethyl acetate layers were washed with brine, dried over anhydrous magnesium sulfate and concentrated to give 138 mg of a crude crystalline solid. Recrystallization of this material from ethyl acetate/hexane yielded 138 mg (0.34 mmol, 87.6%) of 16,16-dimethyl-15-epi-2,5,6,7-tetranor-4-oxa-4,8-inter-m-phenylene $PGI_2$ as a white crystal, which was assigned the structure by the following data.

M.p.: 83°–85° C.

IR(KBr): 3350, 2960, 2940, 1750, 1730, 1620, 1590, 1490, 1460, 1360, 1190, 1110, 1060, 970, 870, 760, 730 $cm^{-1}$.

NMR(400 MHz, $CDCl_3$, δ): 0.86(3H, s); 0.90(3H, s); 0.91(3H, t, J=6.8 Hz); 1.2–1.4(6H, m); 2.06(1H, ddd, J=4.9, 7.8, 13.7 Hz); 2.5–2.65(2H, m); 3.52(1H, t, J=7.8 Hz); 3.7–4.1(2H, m); 3.88(1H, d, J=4.9 Hz); 3.97(1H, q, J=7.8 Hz); 4.68(1H, d, J=16.6 Hz); 4.73(1H, d, J=16.6 Hz); 5.15–5.25(1H, m); 5.6–5.75(2H, m); 6.7–6.9(3H, m).

MS(EI, m/e): 404(M+).

Elementary Analysis: Calcd. (as $C_{23}H_{32}O_6$); C: 68.29, H: 7.97. Found: C: 68.21, H: 7.97.

EXAMPLE 22

16,16-Dimethyl-20a-homo-2,5,6,7-tetranor-4-oxa-4,8-inter-m-phenylene $PGI_2$ methyl ester (182) and its 15-epimer (183)

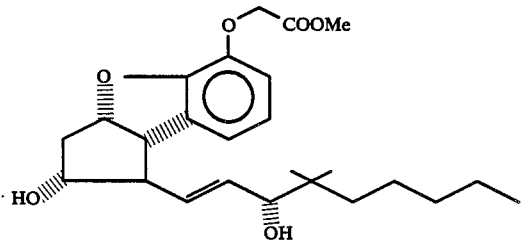

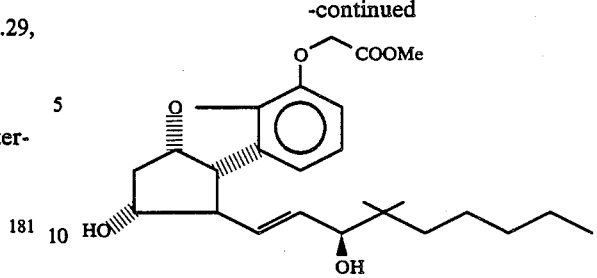

To a solution of 16,16-dimethyl-20a-homo-15-oxo-2,5,6,7-tetranor-4-oxa-4,8-inter-m-phenylene $PGI_2$ methyl ester, 11-acetate (1.6426 g, 3.48 mmol) in methanol (150 ml) was added cerium trichloride heptahydrate (1.30 g, 3.48 mmol). Sodium borohydride (87.8 mg, 2.08 mmol) was added to the reaction mixture under ice-cooling and the resulting mixture was stirred for 30 min. This solution was diluted with water (150 ml) and stirred for 10 min. The resulting precipitate was filtered off by suction using celite. The precipitate was washed with ethyl acetate (200 ml) and the combined filtrates were concentrated. The residue was extracted with ethyl acetate (80 ml×3). The combined ethyl acetate layers were washed with 250 ml of water, and with 250 ml of brine, dried over anhydrous sodium sulfate (40 g) and concentrated to given an oily material (1.6632 g).

After azeotropic distillation of the oil with benzene (10 ml×2), the residue was dissolved in anhydrous methanol (30 ml). To this solution was added a solution of sodium methoxide in methanol (5.22N, 0.03 ml, 0.174 mmol). The reaction mixture was stirred under argon atmosphere for 5 hrs. at room temperature, neutralized with acetic acid (0.1 ml), and concentrated. Water (15 ml) was added to the residue. Extraction with ethyl acetate (15 ml×3) followed by washing with water (50 ml) and with brine (50 ml), drying over anhydrous sodium sulfate (20 g) and concentration afforded an oily material (1.6382 g). Column chromatography (silica gel: ethyl acetate/cyclohexane: 2/1) of the material gave less polar 16,16-dimethyl-15-epi-20a-homo-2,5,6,7-tetranor-4-oxa-4,8-inter-m-phenylene $PGI_2$ methyl ester (654.2 mg, 1.51 mmol, 43%) and subsequently more polar 16,16-dimethyl-20a-homo-2,5,6,7-tetranor-4-oxa-4,8-inter-m-phenylene $PGI_2$ methyl ester (737.0 mg, 1.71 mmol, 49%). Recrystallization of these products from ethyl acetate/cyclohexane (2/1) gave colourless needle-like crystals. These products were assigned the corresponding structures by the following data.

16,16-Dimethyl-20a-homo-2,5,6,7-tetranor-4-oxa-4,8-inter-m-phenylene $PGI_2$ methyl ester M.p.: 105°–106° C.

IR(KBr): 3330, 2950, 2920, 2855, 1760, 1619, 1590, 1482, 1462, 1432, 1372, 1295, 1219, 1210, 1190, 1179, 1161, 1118, 1088, 1067, 1029, 998, 974, 948, 892, 860, 830, 785, 765, 728, 710, 680, 607 $cm^{-1}$.

NMR(400 MHz, $CDCl_3$, δ): 0.84–0.93(3H, m); 0.87(3H, s); 0.90(3H, s); 1.13–1.40 (8H, m); 1.5–1.9(2H, broad s); 2.04–2.10(1H, m); 2.47–2.53(H, m); 2.62–2.69(1H, m); 3.49(1H, t, J=8.3 Hz); 3.79(3H, s); 3.85(1H, d, J=6.35 Hz); 3.92–3.98(1H, m); 4.73(2H, s); 5.18–5.28(1H, m); 5.62–5.79(2H, m); 6.70–6.84(3H, m).

MASS(EI, m/e): 432(M+).

HR MASS: Calcd. ($C_{25}H_{36}O_6$, M+): 432.2512. Found (M+): 432.2503.

16,16-Dimethyl-15-epi-20a-homo-2,5,6,7-tetranor-4-oxa-4,8-inter-m-phenylene PGI₂ methyl ester M.p.: 95°–96° C.

IR(KBr): 3480, 2950, 2925, 2852, 2802, 1701, 1614, 1583, 1483, 1462, 1428, 1381, 1323, 1280, 1263, 1194, 1161, 1111, 1064, 1030, 1003, 981, 948, 864, 802, 761, 723, 605 cm$^{-1}$.

NMR(400 MHz, CDCl₃, δ): 0.89–0.93(3H, m); 0.87(3H, s); 0.91(3H, s); 1.20–1.38(8H, m); 1.5–1.8(2H, broad s); 2.05–2.13(1H, m); 2.53–2.60(1H, m); 2.60–2.68(1H, m); 3.53(1H, t, J=8.3 Hz); 3.87–3.91(1H, m); 3.79(3H, s); 3.94–4.01(1H, m); 4.73(2H, s); 5.21–5.28(1H, m); 5.64–5.78(2H, m); 6.71–6.86(3H, m).

MASS(EI, m/e): 432(M+).

HR MASS: Calcd. (C₂₅H₃₆O₆, M+): 432.2512. Found (M+): 432.2488.

EXAMPLE 23

16,16-Dimethyl-20a-homo-2,5,6,7-tetranor-4-oxa-4,8-inter-m-phenylene PGI₂ (184)

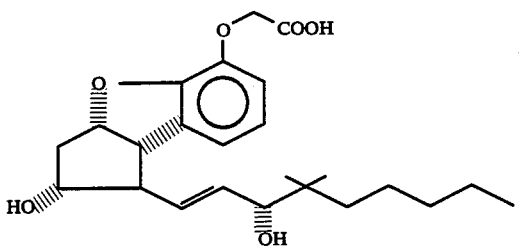

184

To a solution of 16,16-dimethyl-20a-homo-2,5,6,7-tetranor-4-oxa-4,8-inter-m-phenylene PGI₂ methyl ester (108.9 mg, 0.25 mmol) in methanol (15 ml) was added 1N aqueous NaOH solution (0.75 ml, 0.75 mmol), and then the reaction mixture was stirred under argon atmosphere overnight at room temperature. The solution was mixed with 0.75 ml of 1N hydrochloric acid, and then concentrated. After 10 ml of water and 0.1 ml of 1N hydrochloric acid were added to the residue, the resulting mixture was extracted with ethyl acetate (10 ml×3). The combined ethyl acetate layers were washed with 30 ml of water, and with 30 ml of brine, dried over anhydrous sodium sulfate (10 g) and concentrated to give quantitatively 103.9 mg (0.25 mmol) of 16,16-dimethyl-20a-homo-2,5,6,7-tetranor-4-oxa-4,8-inter-m-phenylene PGI₂ as a single product. Recrystallization of the product from ethyl acetate/cyclohexane: 3/1 gave a colourless needle-like crystal, which was assigned the structure by the following data.

M.p.: 65°–66° C.

IR(KBr): 3400(3655–2290), 2950, 2925, 2855, 1741, 1618, 1589, 1481, 1460, 1430, 1360, 1290, 1245, 1183, 1112, 1085, 1068, 1028, 974, 950, 860, 760, 728 cm$^{-1}$.

NMR(400 MHz, CDCl₃, δ): 0.88–0.93(3H, m); 0.86(3H, s); 0.91(3H, s); 1.15–1.38(8H, m); 2.00–2.10(1H, m); 2.43–2.54(1H, m); 2.60–2.70(1H, m); 3.46–3.53(1H, m); 3.83–3.87(1H, m); 3.93–3.98(1H, m); 3.7–4.5 (3H, broad s); 4.69(1H, d, J=16.6 Hz); 4.75(1H, d, J=16.6 Hz); 5.18–5.30(1H, m); 5.60–5.79(2H, m); 6.73–6.85(3H, m).

MASS(EI, m/e): 418(M+).

HR MASS: Calcd. (C₂₅H₃₄O₆, M+): 418.2355. Found (M+): 418.2372.

EXAMPLE 24

16,16-Dimethyl-15-epi-20a-homo-2,5,6,7-tetranor-4-oxa-4,8-inter-m-phenylene PGI₂ (185)

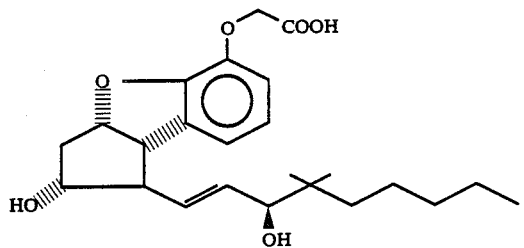

185

To a solution of 16,16-dimethyl-15-epi-20a-homo-2,5,6,7-tetranor-4-oxa-4,8-inter-m-phenylene PGI₂ methyl ester (103.1 mg, 0.24 mmol) in methanol (15 ml) was added 1N aqueous NaOH solution (0.72 ml, 0.72 mmol), and the reaction mixture was stirred under argon atmosphere overnight at room temperature. The solution was mixed with 0.72 ml of 1N hydrochloric acid, and concentrated. After 10 ml of water and 0.1 ml of 1N hydrochloric acid were added to the residue, the resulting mixture was extracted with ethyl acetate (10 ml×3). The combined ethyl acetate layers were washed with 30 ml of water, and with 30 ml of brine, dried over anhydrous sodium sulfate (10 g) and concentrated to give quantitatively 100.1 mg (0.24 mmol) of 16,16-dimethyl-15-epi-20a-homo-2,5,6,7-tetranor-4-oxa-4,8-inter-m-phenylene PGI₂ as a single product. Recrystallization of the product from ethyl acetate/cyclohexane: 5/3 gave a colourless needle-like crystal, which was assigned the structure by the following data.

M.p.: 72°–72.5° C.

IR(KBr): 3460(3700–2100), 2920, 2851, 1683, 1615, 1588, 1483, 1462, 1428, 1380, 1345, 1281, 1263, 1198, 1162, 1111, 1069, 1028, 978, 945, 860, 798, 761, 723 cm$^{-1}$.

NMR(400 MHz, CDCl₃, δ): 0.89–0.94(3H, m); 0.87(3H, s); 0.90(3H, s); 1.16–1.37(8H, m); 2.02–2.12(1H, m); 2.50–2.66(2H, m); 3.48–3.57(1H, m); 3.86–3.90(1H, m); 3.95–4.03(1H, m); 3.2–4.5(3H, broad s); 4.69(1H, d, J=16.6 Hz); 4.74(1H, d, J=16.6 Hz); 5.18–526(1H, m); 5.62–5.77(2H, m); 6.73–6.87(3H, m).

MASS(EI, m/e): 418(M+).

HR MASS: Calcd. (C₂₄H₃₄O₆, M+): 418.2355. Found (M+): 418.2332.

EXAMPLE 25

16,16-Dimethyl-20a,20b-dihomo-2,5,6,7-tetranor-4-oxa-4,8-inter-m-phenylene PGI₂ methyl ester (186) and its 15-epimer (187)

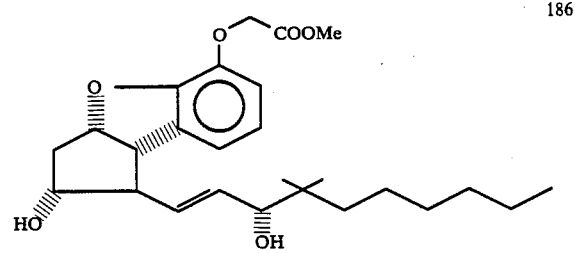

186

-continued

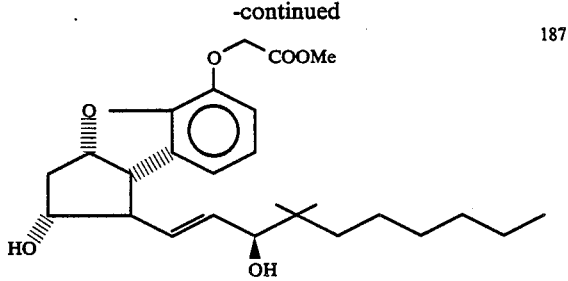

187

To a solution of 16,16-dimethyl-15-oxo-20a,20b-dihomo-2,5,6,7-tetranor-4-oxa-4,8-inter-m-phenylene PGI$_2$ methyl ester, 11-acetate (1.58 g, 3.25 mmol) in methanol (100 ml) was added with stirring cerium trichloride heptahydrate (1.46 g, 3.9 mmol), and then the solution was cooled to $-10°$ C. Sodium borohydride (48.3 mg, 1.3 mmol) was added little by little to the solution. The reaction mixture was stirred for 20 min. at $-10°$ C., brought to $0°$ C. and diluted with a saturated aqueous solution of sodium bicarbonate (15 ml). This solution was filtered and the filtrate was concentrated. The concentrate was mixed with 20 ml of water and extracted with ethyl acetate (50 ml×2). The combined ethyl acetate layers were washed with water (20 ml), and with brine (20 ml), dried over anhydrous sodium sulfate and concentrated to give 1.56 g of an oily material.

To a solution of the oily material in anhydrous methanol was added with stirring a solution of sodium methoxide in methanol (5.22N, 0.15 ml, 0.79 mmol) under argon atmosphere. The reaction mixture was stirred with 2.5 hrs. at room temperature, neutralized with acetic acid, and concentrated. Water (20 ml) was added to the residue. Extraction with ethyl acetate (50 ml×2) followed by washing with water (20 ml) and with brine (20 ml), drying over anhydrous sodium sulfate and concentration afforded a crude material. Column chromatography (Merck, Lobar column; silica gel, ethyl acetate/cyclohexane: 2/1) of the material gave less polar 16,16-dimethyl-15-epi-20a, 20b-dihomo-2,5,6,7-tetranor-4-oxa-4,8-inter-m-phenylene PGI$_2$ methyl ester (602 mg, 1.35 mmol, yield: 42.5%) and more polar 16,16-dimethyl-20a,20b-dihomo-2,5,6,7-tetranor-4-oxa-4,8-inter-m-phenylene PGI$_2$ methyl ester (642 mg, 1.44 mmol, yield: 45.3%). These compounds were assigned the corresponding structures by the following data.

16,16-Dimethyl-20a,20b-dihomo-2,5,6,7-tetranor-4-oxa-4,8-inter-m-phenylene PGI$_2$ methyl ester M.p.: 91.8°-92.5° C. (recrystallization solvent: ethyl acetate/n-hexane: 1/1).

IR(KBr): 3360, 3300, 2950, 2910, 2850, 1760, 1620, 1590, 1485, 1460, 1435, 1370, 1290, 1205, 1185, 1170, 1140, 1110, 1080, 1070, 1025, 990, 970, 945, 910, 885, 870, 820, 775, 750, 720, 670 cm$^{-1}$.

NMR(400 MHz, CDCl$_3$, δ): 0.86(3H, s); 0.9(3H, s); 0.8-1.0 (3H, m); 1.15-1.4(10H, m); 1.85-1.95(1H, m); 2.0-2.1(1H, m); 2.46(1H, q, J=8.3 Hz); 2.4-2.6(1H, m); 2.6-2.7(1H, m); 3.46(1H, t, J=8.3 Hz); 3.79(3H, s); 3.84(1H, d, J=6.8 Hz); 3.85-4.0(1H, m); 4.72(2H, s); 5.15-5.3(1H, m); 5.5-5.8(2H, m); 6.7-6.9(3H, m).

MASS(EI, m/e): 446(M+)

Elementary Analysis: Calcd. (as C$_{26}$H$_{38}$O$_6$): C: 69.93, H: 8.58. Found: C: 70.11, H:8.56.

16,16-Dimethyl-15-epi-20a,20b-dihomo-2,5,6,7-tetranor-4-oxa-4,8-inter-m-phenylene PGI$_2$ methyl ester M.p.: 79.8°-80.5° C. (recrystallization solvent: ethyl acetate/n-hexane: 3/2).

IR(KBr): 3350, 2960, 2920, 2860, 1750, 1730, 1610, 1585, 1480, 1455, 1370, 1300, 1270, 1260, 1210, 1190, 1110, 1060, 1020, 980, 960, 820, 850, 755, 720 cm$^{-1}$.

NMR(400 MHz, CDCl$_3$, δ): 0.87(3H, s); 0.90(3H, s); 0.8-0.9(3H, m); 1.15-1.4(10H, m); 1.45-1.55(1H, m); 1.7-1.8(1H, m); 2.0-2.15(1H, m); 2.55(1H, q, J=8.0 Hz); 2.6-2.7(1H, m); 3.53(1H, t, J=8.0 Hz); 3.85-4.05(2H, m); 3.79(3H, s); 4.73(2H, s); 5.2-5.3(1H, m); 5.6-5.8(2H, m); 6.7-6.9(3H, m).

MASS(EI, m/e): 446(M+).

Elementary Analysis: Calcd. (as C$_{26}$H$_{38}$O$_6$): C: 69.93, H: 8.58. Found: C: 70.22, H: 8.52.

EXAMPLE 26

16,16-Dimethyl-20a,20b-dihomo-2,5,6,7-tetranor-4-oxa-4,8-inter-m-phenylene PGI$_2$ (188)

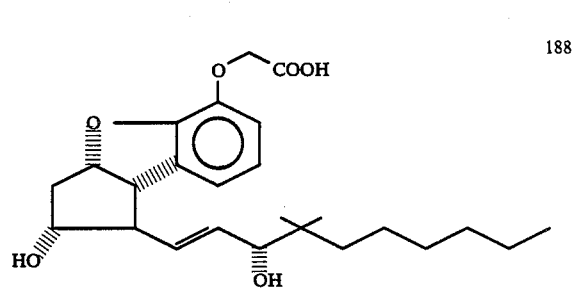

188

To a stirred solution of 16,16-dimethyl-20a,20b-dihomo-2,5,6,7-tetranor-4-oxa-4,8-inter-m-phenylene PGI$_2$ methyl ester (300 mg, 0.67 mmol) in methanol was added under ice-cooling 1N aqueous NaOH solution (5.15 ml, 5.15 mmol), and the reaction mixture was stirred for one hour at room temperature. The solution was neutralized with 1N hydrochloric acid under ice-cooling, and concentrated. After 20 ml of water was added to the residue, the resulting mixture was extracted with ethyl acetate (50 ml×2). The combined ethyl acetate layers were washed with 20 ml of water, and with 20 ml of brine, dried over anhydrous sodium sulfate and concentrated to give 253 mg (yield: 91%) of 16,16-dimethyl-20a,20b-dihomo-2,5,6,7-tetranor-4-oxa-4,8-inter-m-phenylene PGI$_2$ as an oily material, which was assigned the structure by the following data.

IR(liquid film): 3380, 2960, 2930, 2860, 1730, 1610, 1585, 1480, 1450, 1430, 1355, 1280, 1250, 1180, 1110, 1020, 970, 940, 980, 950, 920, 750, 720 cm$^{-1}$.

NMR(400 MHz, DMSO, δ): 0.79(3H, s); 0.813(3H, s); 0.85(3H, t, J=6.6 Hz); 1.1-1.4(10H, m); 1.65-1.75(1H, m); 2.15-2.25(1H, m); 2.4-2.6(1H, m); 3.42(1H, t, J=9.0 Hz); 3.6-3.8(2H, m); 4.5-4.6(1H, m); 4.64(2H, s); 4.7-4.85(1H, m); 5.0-5.15(1H, m); 5.54(1H, dd, J=7.1, 15.4 Hz); 5.63(1H, dd, J=6.1, 15.4 Hz); 6.65-6.8(3H, m).

MASS(EI, m/e): 432(M+).

HR MASS: Calcd. (C$_{25}$H$_{36}$O$_6$, M+): 432.2511. Found (M+): 432.2505.

EXAMPLE 27

16,16-Dimethyl-15-epi-20a,20b-dihomo-2,5,6,7-tetranor-4-oxa-4,8-inter-m-phenylene PGI₂ (189)

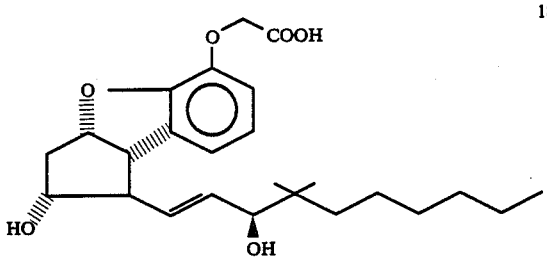

189

To a solution of 16,16-dimethyl-15-epi-20a,20b-dihomo-2,5,6,7-tetranor-4-oxa-4,8-inter-m-phenylene PGI₂ methyl ester (300 mg, 0.644 mmol) in methanol (40 ml) was added with stirring 1N aqueous NaOH solution (5.2 ml, 5.2 mmol) under ice-cooling, and the reaction mixture was stirred for one hour at room temperature. The solution was neutralized with 1N hydrochloric acid under ice-cooling, and then concentrated. After 20 ml of water was added to the residue, the resulting mixture was extracted with ethyl acetate (50 ml×2). The combined ethyl acetate layers were washed with 20 ml of water, and with 20 ml of brine, dried over anhydrous sodium sulfate and concentrated. Recrystallization of the residue from a mixture of 2 ml of ethyl acetate and 1 ml of n-hexane gave 16,16-dimethyl-15-epi-20a,20b-dihomo-2,5,6,7-tetranor-4-oxa-4,8-inter-m-phenylene PGI₂ (271 mg, 0.63 mmol, yield: 97.4%) as a white crystal, which was assigned the structure by the following data.

M.p.: 68.9°–70.8° C. (recrystallization solvent: ethyl acetate/n-hexane: 2/1).

IR(KBr): 3400, 2940, 2905, 2850, 1720, 1610, 1590, 1480, 1455, 1430, 1370, 1280, 1240, 1185, 1160, 1105, 1020, 970, 940, 885, 850, 820, 790, 755, 715, 680 cm$^{-1}$.

NMR(400 MHz, DMSO, δ): 0.85(3H, s); 0.88(3H, s); 0.8–1.0(3H, m); 1.15–1.4(10H, m); 1.9–2.1(1H, m); 2.4–2.5(1H, m); 2.55–2.65(1H, m); 3.43(1H, t, J=8.3 Hz); 3.83(1H, d, J=6.8 Hz); 3.85–3.95(1H, m); 4.0–4.5(2H, m); 4.63(b 1H, d, J=15.6 Hz); 4.72(1H, d, J=15.6 Hz); 5.1–5.2(1H, m); 5.5–5.7(2H, m); 6.6–6.9(3H, m).

MASS(EI, m/e): 432(M+).

Elementary Analysis: Calcd. (as $C_{25}H_{36}O_6$): C: 69.42, H: 8.39. Found: C: 69.73, H: 8.28.

EXAMPLE 28

16,16-Dimethyl-20a,20b,20c-trihomo-2,5,6,7-tetranor-4-oxa-4,8-inter-m-phenylene PGI₂ methyl ester (190) and its 15-epimer (191)

190

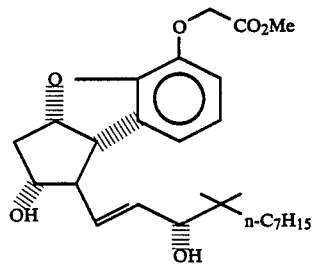

-continued

191

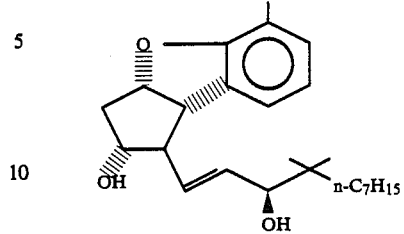

16,16-Dimethyl-15-oxo-20a,20b,20c-trihomo-2,5,6,7-tetranor-4-oxa-4,8-inter-m-phenylene PGI₂ methyl ester, 11-acetate (1.3476 g, 2.69 mmol) was dissolved in methanol (50 ml). Cerium trichloride heptahydrate (1.00 g, 2.69 mmol) was added to this solution. At −10° C., sodium borohydride (102.1 mg, 2.70 mmol) was added to the solution with stirring and agitation was further continued for 30 minutes. Water (10 ml) was added to the reaction mixture, and the solvent was distilled off. The resulting precipitate was filtered through Hyflo Super Cell, and the filtrate was extracted with ethyl acetate (50 ml×4). The combined ethyl acetate layers were washed with water (50 ml) and with brine (50 ml), dried over anhydrous sodium sulfate and concentrated. The resulting oily material was subjected to azeotropic distillation with benzene (20 ml×3). The residue was dried under vacuum and then dissolved in anhydrous methanol (40 ml). To this solution was added sodium methoxide (5.22N, 0.03 ml, 0.157 mmol) and the mixture was stirred overnight under argon atmosphere at room temperature. Acetic acid was added to neutralize the reaction mixture to pH 7 and then the mixture was concentrated. Water (20 ml) was added to the concentrate, and the mixture was extracted with ethyl acetate (50 ml×4). The combined ethyl acetate layers were washed with water (50 ml) and with brine (50 ml), dried over anhydrous sodium sulfate and concentrated. The resulting oily product was subjected to silica gel column chromatography (ethyl acetate/cyclohexane=2/1) to give less polar 16,16-dimethyl-15-ept-20a,20b,20c-trihomo-2,5,6,7-tetranor-4-oxa-4,8-inter-m-phenylene PGI₂ methyl ester (0.3535 g, 0.767 mmol, yield: 28.5%), and more polar 16,16-dimethyl-20a,20b,20c-trihomo-2,5,6,7-tetranor-4-oxa-4,8-inter-m-phenylene PGI₂ methyl ester (0.3651 g, 0.793 mmol, yield: 29.5%). These products were assigned the corresponding structures by the following data.

α-isomer 16,16-Dimethyl-20a,20b,20c-trihomo-2,5,6,7-tetranor-4-oxa-4,8-inter-m-phenylene PGI₂ methyl ester m.p.: 72°–74° C. (colorless needle-like crystal, recrystallized from ethyl acetate/cyclohexane).

IR(KBr): 3340, 2950, 2925, 2855, 1761, 1615, 1598, 1486, 1463, 1373, 1291, 1207, 1189, 1187, 1161, 1116, 1081, 1069, 1029, 994, 972, 948, 890, 860, 830, 780, 754, 722, 678, 603 cm$^{-1}$.

NMR (400 MHz, CDCl₃, δ): 0.83–0.95(9H, m); 1.18–1.39(12H, m); 1.88–2.11(3H, m); 2.44–2.52(1H, m); 2.62–2.72(1H, m); 3.47(1H, t, J=8.79 Hz); 3.79(3H, s); 3.84 (1H, d, J=6.35 Hz); 3.89–3.99 (1H, m); 4.73 (2H, s); 5.17–5.24 (1H, m); 5.58–5.74 (2H, m); 6.70–6.84 (3H, m).

MASS (EI, m/e): 460 (M+).

HR MASS Cacld. as $C_{27}H_{40}O_6$ (M+): 460.2824. Found: (M+): 460.2802.

β-isomer 16,16-Dimethyl-15-epi-20a,20b,20c-trihomo-2,5,6,7-tetranor-4-oxa-4,8-inter-m-phenylene PGI$_2$ methyl ester m.p.: 102°-103° C. (colorless needle-like crystal, recrystallized from ethyl acetate/cyclohexane).

IR (KBr): 3485, 2950, 2915, 2850, 2800, 1696, 1617, 1586, 1479, 1459, 1429, 1392, 1379, 1324, 1300, 1280, 1265, 1195, 1163, 1110, 1067, 1033, 1004, 983, 947, 865, 798, 739, 722, 609 cm$^{-1}$.

NMR (400 MHz, CDCl$_3$, δ): 0.83-0.94 (9H, m); 1.17-1.37 (12H, m); 1.61 (2H, broad s); 2.04-2.13 (1H, m); 2.52-2.59 (1H, m); 2.59-2.68 (1H, m); 3.53 (1H, t, J=8.30 Hz); 3.79 (3H, s); 3.89 (1H, d, J=5.37 Hz); 3.93-4.01 (1H, m); 4.73 (2H, s); 5.20-5.27 (1H, m); 5.64-5.78 (2H, m); 6.71-6.85 (3H, m).

MASS (EI, m/e): 460 (M+).

HR MASS: Cacld. as $C_{27}H_{40}O_6$ (M+): 460.2824. Found: (M+): 460.2819.

EXAMPLE 28

16,16-Dimethyl-20a,20b,20c-trihomo-2,5,6,7-tetranor-4-oxa-4,8-inter-m-phenylene PGI$_2$ (192)

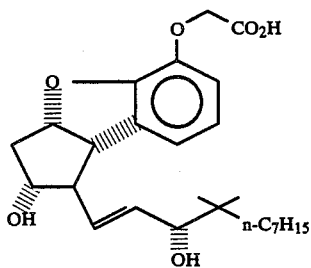

192

16,16-Dimethyl-20a,20b,20c-trihomo-2,5,6,7-tetranor-4-oxa-4,8-inter-m-phenylene PGI$_2$ methyl ester (118.5 mg, 0.257 mmol) was dissolved in methanol (20 ml). To this solution was added 1N aqueous sodium hydroxide solution (0.77 ml, 0.772 mmol) and the mixture was stirred overnight under argon atmosphere at room temperature. Hydrochloric acid (1N) was added to the reaction mixture to pH 2 and methanol was distilled off. Water (10 ml) was added to the residue and the resulting mixture was extracted with ethyl acetate (20 ml×4). The combined ethyl acetate layers were washed with water (20 ml) and with brine (20 ml), dried over anhydrous sodium sulfate and concentrated to give 111.1 mg of 16,16-dimethyl-20a,20b,20c-trihomo-2,5,6,7-tetranor-4-oxa-4,8-inter-m-phenylene PGI$_2$ as a single product with a yield of 96.8%. This product was assigned the structure by the following data.

m.p.: 61.5°-62.5° C. (colorless needle-like crystal, recrystallized from ethyl acetate/cyclohexane).

IR (KBr): 3400, 2925, 2860, 1741, 1623, 1593, 1588, 1565, 1538, 1295, 1245, 1189, 1110, 1070, 1028, 972, 942, 883, 858, 830, 760, 728 cm$^{-1}$.

NMR (400 MHz,

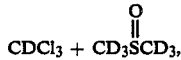

δ): 0.80-1.06 (9H, m); 1.10-1.40 (12H, m); 1.98-2.11 (1H, m); 2.40-3.55 (5H, m, broad); 3.85 (1H, d, J=5.86 Hz); 3.88-4.02 (1H, m); 4.64-4.79 (2H, m); 5.15-5.32 (1H, m); 5.55-5.72 (2H, m); 6.70-6.87 (3H, m).

MASS (EI, m/e): 446 (M+).

HR MASS: Calcd. as $C_{26}H_{38}O_6$ (M+): 446.2668. Found (M+): 446.2672.

EXAMPLE 30

16,16-Dimethyl-15-epi-20a,20b,20c-trihomo-2,5.6.7-tetranor-4-oxa-4,8-inter-m-phenylene PGI$_2$ (193)

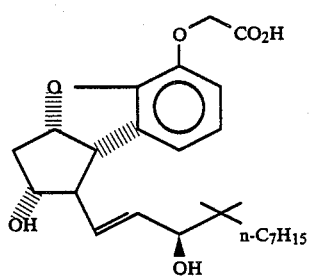

193

16,16-Dimethyl-15-epi-20a,20b,20c-trihomo-2,5,6,7-tetranor-4-oxa-4,8-inter-m-phenylene PGI$_2$ methyl ester (119.9 mg, 0.260 mmol) was dissolved in methanol (20 ml). To this solution was added 1N aqueous sodium hydroxide solution (0.78 ml, 0.781 mmol) and the mixture was stirred overnight under argon atmosphere at room temperature. Hydrochloric acid (1N) was added to the reaction mixture to pH 2 and methanol was distilled off. Water (10 ml) was added to the residue and the resulting mixture was extracted with ethyl acetate (20 ml×4). The combined ethyl acetate layers were washed with water (20 ml) and with brine (20 ml), dried over anhydrous sodium sulfate and concentrated to give 116.1 mg of 16,16-dimethyl-15-epi-20a,20b,20c-trihomo-2,5,6,7-tetranor-4-oxa-4,8-inter-m-phenylene PGI$_2$ as a single product with a yield of 100%. This product was assigned the structure by the following data.

m.p.: 69.5°-71.0° C. (colorless needle-like crystal, recrystallized from ethyl acetate/cyclohexane).

IR (KBr): 3470, 2955, 2920, 2850, 2805, 1687, 1617, 1592, 1487, 1462, 1432, 1382, 1352, 1307, 1280, 1262, 1205, 1163, 1112, 1073, 1029, 980, 949, 860, 795, 760, 724 cm$^{-1}$.

NMR (400 MHz,

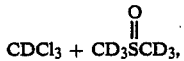

δ): 0.82-0.96 (9H, m); 1.18-1.38 (12H, m); 1.99-2.08 (1H, m); 2.43-2.51 (1H, m); 2.55-2.68 (1H, m); 3.44-3.51 (1H, m); 3.57-4.30 (4H, m, broad); 4.62-4.72 (2H, m); 5.14-5.21 (1H, m); 5.68-5.78 (2H, m); 6.68-6.74 (3H, m).

MASS (EI, m/e): 446 (M+).

HR MASS: Cacld. as $C_{26}H_{38}O_6$ (M+): 446.2669. Found: (M+): 446.2658.

EXAMPLE 31

16,16,16-Trimethyl-2,5,6,7,19,20-hexanor-4-oxa-4,8-inter-m-phenylene PGI₂ methyl ester (194) and its 15-epimer (195)

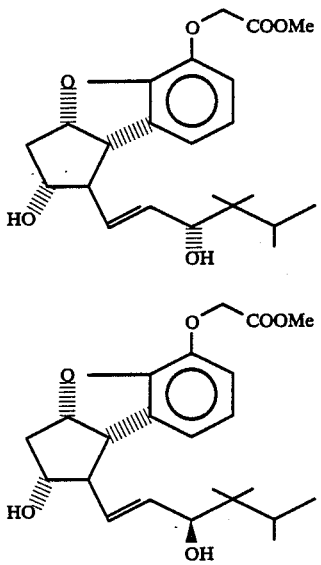

16,16,17-Trimethyl-15-oxo-2,5,6,7,19,20-hexanor-4-oxa-4,8-inter-m-phenylene PGI₂ methyl ester, 11-acetate (1.6428 g, 3.70 mmol) was dissolved in methanol (100 ml). To this solution was added cerium trichloride heptahydrate (1.3785 g, 3.70 mmol). While stirring under cooling with ice, sodium borohydride (113.4 mg, 3.00 mmol) was added to the solution and agitation was continued for 45 minutes. Water (50 ml) was added to the reaction mixture. After stirring for 10 minutes the reaction mixture was concentrated and filtered by suction through Celite. The residue was washed with ethyl acetate (200 ml) and the filtrate was concentrated. The resulting residue was extracted with ethyl acetate (40 ml×3). The combined ethyl acetate layers were washed with water (100 ml) and with brine (100 ml), dried over anhydrous sodium sulfate (30 g) and concentrated to give 1.6432 g of an oily material.

The oily material was then subjected to azeotropic distillation with benzene (10 ml×2). Anhydrous methanol (25 ml) was added to the residue. Sodium methoxide (5.22N, 0.018 ml, 0.93 mmol) was added to the solution and the mixture was stirred overnight under argon atmosphere at room temperature. Acetic acid (0.1 ml) was added to the reaction mixture and then the mixture was concentrated. Water (15 ml) was added to the residue, and the mixture was extracted with ethyl acetate (15 ml×3). The combined ethyl acetate layers were washed with water (45 ml) and with brine (45 ml), dried over anhydrous sodium sulfate (15 g) and concentrated to give 1.5701 g of an oily product. Column chromatography (silica gel, ethyl acetate/cyclohexane=2/1) of the oily product afforded less polar 16,16,17-trimethyl-15-epi-2,5,6,7,19,20-hexanor-4-oxa-4,8-inter-m-phenylene PGI₂ methyl ester (541.3 mg, 1.34 mmol: yield 43%), which gave a colorless needle-like crystal by recrystallization from ethyl acetate/cyclohexane (1/1), and subsequently more polar 16,16,17-trimethyl-2,5,6,7,19,20-hexanor-4-oxa-4,8-inter-m-phenylene PGI₂ methyl ester (655.5 mg, 1.62 mmol: yield 44%), which gave a colorless needle-like crystal by recrystallization from ethyl acetate/cyclohexane (1/1). These products were assigned the corresponding structures by the following data.

16,16,17-Trimethyl-2,5,6,7,19,20-hexanor-4-oxa-4,8-inter-m-phenylene PGI₂ methyl ester m.p.: 100°–100.5° C.

IR (KBr): 3330, 2953, 1759, 1605, 1584, 1480, 1459, 1433, 1365, 1285, 1206, 1186, 1155, 1118, 1085, 1063, 1024, 1005, 985, 969, 943, 891, 859, 825, 780, 751, 720, 680, 603 cm⁻¹.

NMR (400 MHz, CDCl₃, δ): 0.76 (3H, s); 0.86 (3H, s); 0.87 (3H, d, J=6.84 Hz); 0.90 (3H, d, J=6.84 Hz); 1.6–1.7 (1H, broad s); 1.69–1.80 (1H, m); 2.02–2.12 (1H, m); 2.2–2.3 (1H, broad s); 2.47–2.56 (1H, m); 2.62–2.72 (1H, m); 3.48 (1H, t, J=8.3 Hz); 3.79 (3H, s); 3.91–4.00 (1H, m); 4.03–4.09 (1H, m); 4.73 (2H, s); 5.17–5.27 (1H, m); 5.62–5.78 (2H, m); 6.72–6.83 (3H, m).

MASS (EI, m/e): 404 (M⁺).

HR MASS: Calcd. as C₂₃H₃₂O₆ (M⁺): 404.2199. Found: (M⁺): 404.2194.

16,16,17-Trimethyl-15-epi-2,5,6,7,19,20-hexanor-4-oxa-4,8-inter-m-phenylene PGI₂ methyl ester m.p.: 83.5°–84° C.

IR (KBr): 3325, 2960, 1750, 1732, 1616, 1584, 1483, 1460, 1366, 1342, 1270, 1223, 1195, 1115, 1024, 1012, 962, 885, 861, 841, 761, 722, 699, 619 cm⁻¹.

NMR (400 MHz, CDCl₃, δ): 0.75 (3H, s); 0.86 (3H, d, J=6.84 Hz); 0.89 (3H, d, J=6.84 Hz); 0.87 (3H, s); 1.42–1.48 (1H, broad s); 1.57–1.63 (1H, broad s); 1.68–1.80 (1H, m); 2.05–2.15 (1H, m); 2.51–2.60 (1H, m); 2.60–2.70 (1H, m); 3.53 (1H, t, J=8.3 Hz); 3.79 (3H, s); 3.94–4.03 (1H, m); 4.08–4.12 (1H, m); 4.73 (2H, s); 5.20–5.28 (1H, m); 5.65–5.82 (2H, m); 6.73–6.88 (3H, m).

MASS (EI, m/e): 404 (M⁺).

HR MASS: Calcd. as C₂₃H₃₂O₆ (M⁺): 404.2199. Found: 404.2214.

EXAMPLE 32

16,16,17-Trimethyl-2,5,6,7,19,20-hexanor-4-oxa-4,8 inter-m-phenylene PGI₂ (196)

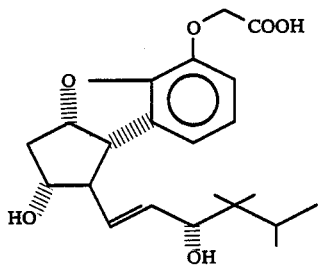

16,16,17-Trimethyl-2,5,6,7,19,20-hexanor-4-oxa-4,8-inter-m-phenylene PGI₂ methyl ester (113.3 mg, 0.28 mmol) was dissolved in methanol (15 ml). To this solution was added 1N aqueous sodium hydroxide solution (0.84 ml, 0.84 mmol) and then the mixture was stirred under argon atmosphere at room temperature for 2 hours. Hydrochloric acid (1N, 1 ml) was added to the reaction mixture and the mixture was concentrated. Water (15 ml) was added to the residue and the resulting mixture was extracted with ethyl acetate (15 ml×3). The combined ethyl acetate layers were washed with water (45 ml) and with brine (45 ml), dried over anhydrous sodium sulfate (10 g) and concentrated to give quantitatively 16,16,17-trimethyl-2,5,6,7,19,20-hexanor-4-oxa-4,8-inter-m-phenylene PGI$_2$ (109.2 mg, 0.28 mmol) as a single product. This was recrystallized from ethyl acetate/cyclohexane (3/1) to give a colorless needle-like crystal. This product was assigned the structure by the following data.

m.p.: 136°–138° C.

IR (KBr): 3350 (3650–2125), 3030, 2952, 2880, 1738, 1612, 1597, 1480, 1459, 1430, 1360, 1283, 1224, 1193, 1151, 1106, 1064, 1026, 1007, 967, 947, 894, 856, 786, 763, 724, 604 cm$^{-1}$.

NMR (400 MHz, CDCl$_3$, δ): 0.75 (3H, s); 0.85 (3H, s); 0.86 (3H, d, J=6.84 Hz); 0.89 (3H, d, J=6.84 Hz); 1.67–1.76 (1H, m); 2.01–2.08 (1H, m); 2.43–2.52 (1H, m); 2.58–2.66 (1H, m); 3.46 (1H, t, J=8.3 Hz); 3.5–4.1 (3H, broad s); 3.86–3.95 (1H, m); 4.04 (1H, d, J=6.35 Hz); 4.67 (1H, d, J=16.6 Hz); 4.74 (1H, d, J=16.6 Hz); 5.14–5.23 (1H, m); 5.58–5.70 (2H, m); 6.72–6.82 (3H, m).

MASS (EI, m/e): 390 (M+).

HR MASS: Calcd. as C$_{22}$H$_{30}$O$_6$ (M+): 390.2042. Found: (M+): 390.2056.

EXAMPLE 33

16,16,17-Trimethyl-15-epi-2,5,6,7,19,20-hexanor-4-oxa-4,8-inter-m-phenylene PGI$_2$ (197)

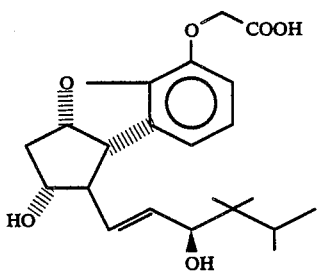

197

16,16,17-Trimethyl-15-epi-2,5,6,7,19,20-hexanor-4-oxa-4,8-inter-m-phenylene PGI$_2$ methyl ester (115.3 mg, 0.29 mmol) was dissolved in methanol (15 ml). To this solution was added 1N aqueous sodium hydroxide solution (0.86 ml, 0.86 mmol) and then the mixture was stirred under argon atmosphere at room temperature for 2 hours. Hydrochloric acid (1N, 1 ml) was added to the reaction mixture and the resulting mixture was concentrated. Water (15 ml) was added to the residue and the resulting mixture was extracted with ethyl acetate (15 ml×3). The combined ethyl acetate layers were washed with water (45 ml) and with brine (45 ml), dried over anhydrous sodium sulfate (10 g) and concentrated to give quantitatively 16,16,17-trimethyl-15-epi-2,5,6,7,19,20-hexanor-4-oxa-4,8-inter-m-phenylene PGI$_2$ (111.0 mg, 0.29 mmol) as a single product. This product was recrystallized from ethyl acetate/cyclohexane (3/1) to give a colorless needle-like crystal. The crystal was assigned the structure by the following data.

m.p.: 84°–85.5° C.

IR (liquid film): 3400 (3680–2180), 2954, 1735, 1614, 1584, 1480, 1458, 1432, 1371, 1280, 1243, 1184, 1104, 1022, 966, 880, 785, 763, 715 cm$^{-1}$.

NMR (400 MHz, CDCl$_3$, δ) 0.75 (3H, s); 0.86 (3H, d, J=6.83 Hz); 0.89 (3H, d, J=6.83 Hz); 0.85 (3H, s); 1.68–1.78 (1H, m); 2.03–2.13 (1H, m); 2.53–2.68 (2H, m); 3.50–3.58 (1H, m); 3.95–4.03 (1H, m); 3.2–4.1 (3H, broad s); 4.08–4.11 (1H, m); 4.65–4.82 (2H, m); 5.21–5.28 (1H, m); 5.65–5.80 (2H, m); 6.73–6.89 (3H, m).

MASS (EI, m/e): 390 (M+)

HR MASS: Calcd. as C$_{22}$H$_{30}$O$_6$ (M+): 390.2042. Found (M+): 390.2034.

EXAMPLE 34

17,17-Dimethyl-2,5,6,7-tetranor-4-oxa-4,8-inter-m-phenylene PGI$_2$ methyl ester (198) and its 15-epimer (199)

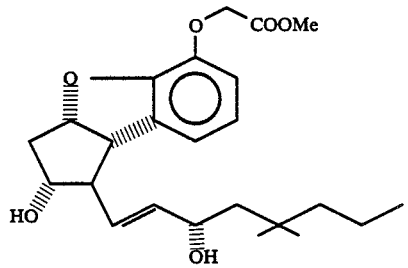

198

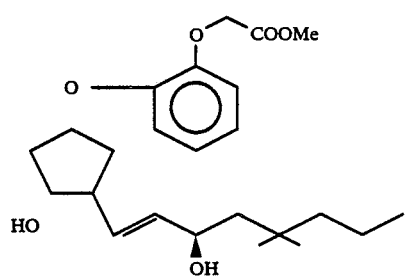

199

17,17-Dimethyl-15-oxo-2,5,6,7-tetranor-4-oxa-4,8-inter-m-phenylene PGI$_2$ methyl ester, 11-benzoate (2.21 g, 4.25 mmol) was dissolved in methanol (80 ml). To this solution was added cerium trichloride heptahydrate (2.06 g, 5.53 mmol) and then the mixture was cooled to −30° C. Sodium borohydride (96.5 mg, 2.55 mmol) was gradually added to the solution and the reaction mixture was stirred for 30 minutes at −30° C. A saturated aqueous sodium bicarbonate solution (20 ml) was added to the reaction mixture and then the mixture was concentrated. After ethyl acetate (50 ml) was added to the residue, the mixture was filtered and the resulting precipitate was washed with ethyl acetate (20 ml×3). The combined filtrates were washed with water (50 ml) and with brine (50 ml), dried over anhydrous magnesium sulfate and concentrated to give 2.27 g of an oily material.

The oily material was dissolved in anhydrous methanol (50 ml) under argon atmosphere. To this solution was added a solution of sodium methoxide in methanol (5.22N, 0.26 ml, 1.36 mmol) and the resulting mixture was stirred at room temperature for 21 hours. The reaction mixture was netralized with acetic acid and concentrated. To the residue was added water (30 ml), and the resulting mixture was extracted with ethyl acetate (80 ml). The organic layer was washed with brine, dried over anhydrous magnesium sulfate and concentrated. The resulting residue was purified by Merck Lobar column of silica gel (ethyl acetate/cyclohexane=4/1) to give less polar 17,17-dimethyl-15-epi-2,5,6,7-tetranor-4-oxa-4,8-inter-m-phenylene PGI$_2$ methyl ester (708 mg, 1.69 mmol: yield 39.8%) as a white crystal and more polar 17,17-dimethyl-2,5,6,7-tetranor-4-oxa-4,8-inter-m-phenylene PGI$_2$ methyl ester (687 mg, 1.64 mmol: yield 38.7%). These products were assigned the corresponding structures by the following data.

17,17-Dimethyl-2,5,6,7-tetranor-4-oxa-4,8-inter-m-phenylene PGI₂ methyl ester IR (liquid film): 3350, 2950, 1760, 1660, 1620, 1590, 1480, 1460, 1440, 1360, 1300, 1220, 1190, 1100, 1030, 970, 890, 860, 830, 760, 730, 670 cm⁻¹.

NMR (400 MHz, CDCl₃, δ): 0.90 (3H, t, J=6.6 Hz); 0.949 (3H, s); 0.954 (3H, s); 1.2-1.25 (4H, m); 1.46 (1H, dd, J=5.1, 14.3 Hz); 1.51 (1H, dd, J=6.8, 14.3 Hz); 1.6-1.9 (2H, m); 2.05 (1H, ddd, J=5.4, 8.8, 13.7 Hz); 2.4-2.5 (1H, m); 2.63 (1H, ddd, J=6.4, 7.3, 13.7 Hz); 3.48 (1H, t, J=8.8 Hz); 3.79 (3H, s); 3.9-4.0 (1H, m); 4.25-4.35 (1H, m); 4.72 (2H, s); 5.20 (1H, ddd, J=5.4, 7.3, 8.8 Hz); 5.55-5.7 (2H, m); 6.7-6.75 (3H, m).

MASS (EI, m/e): 418 (M+).

HR MASS: Calcd. as C₂₄H₃₄O₆ (M+): 418.2355. Found (M+): 418.2360.

17,17-Dimethyl-15-epi-2,5,6,7-tetranor-4-oxa-4,8-inter-m-phenylene PGI₂ methyl ester m.p.: 75°-76° C. (recrystallized from ethyl acetate).

IR (KBr): 3350, 2960, 2930, 1760, 1740, 1620, 1590, 1490, 1460, 1300, 1270, 1260, 1220, 1200, 1120, 1090, 1020, 980, 950, 890, 860, 760, 730 cm⁻¹.

NMR (400 MHz, CDCl₃, δ): 0.90 (3H, t, J=6.4 Hz); 0.949 (3H, s); 0.954 (3H, s); 1.2-1.3 (4H, m); 1.35-1.55 (3H, m); 1.65-1.75 (1H, m); 2.09 (1H, ddd, J=4.7, 7.3, 14.2 Hz); 2.53 (1H, q, J=8.3 Hz); 2.61 (1H, ddd, J=6.4, 7.3, 14.2 Hz); 3.52 (1H, t, J=8.3 Hz); 3.79 (3H, s); 3.9-4.0 (1H, m); 4.3-4.4 (1H, m); 4.73 (2H, s); 5.23 (1H, ddd, J=4.7, 7.3, 8.3 Hz); 5.6-5.7 (2H, m); 6.7-6.85 (3H, m).

MASS (EI, m/e): 418 (M+).

Elementary Analysis: Calcd. as C₂₄H₃₄O₆: C68.87; H 8.19. Found: C 68.75; H 8.29.

EXAMPLE 35

17,17-Dimethyl-2,5,6,7-tetranor-4-oxa-4,8-inter-m-phenylene PGI₂ (200)

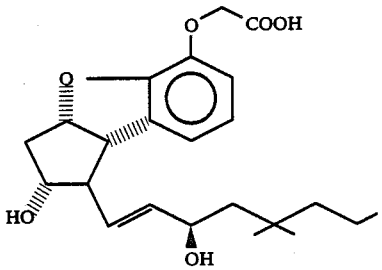

200

17,17-Dimethyl-2,5,6,7-tetranor-4-oxa-4,8-inter-m-phenylene PGI₂ methyl ester (420 mg, 1.00 mmol) was dissolved in methanol (30 ml). To this solution was added the aqueous sodium hdyroxide solution (0.75N, 6 ml, 4.5 mmol) and the resulting mixture was stirred at room temperature for 3 hours. After the concentration of the reaction mixture, water (30 ml) was added to the residue and 1N hydrochloric acid was also added to adjust the pH to 4. The resulting mixture was extrated with ethyl acetate three times (60 ml, 20 ml×2). The combined organic layers were washed with brine, dried over anhydrous magnesium sulfate and concentrated to give 403 mg of crude crystal. The crude crystal was recrystallized from ethyl acetate/hexane to afford white crystal of 17,17-dimethyl-2,5,6,7-tetranor-4-oxa-4,8-inter-m-phenylene PGI₂ (335 mg, 0.83 mmol) with a yield of 83.0%. This product was assigned the structure by the following data.

m.p.: 96°-97° C.

IR (KBr): 3360, 2960, 2930, 2870, 1770, 1740, 1620, 1590, 1490, 1460, 1430, 1380, 1370, 1340, 1280, 1250, 1200, 1170, 1120, 1070, 1030, 970, 940, 890, 870, 830, 790, 760, 730, 710, 610, 550, 520 cm⁻¹.

NMR (400 MHz, CDCl₃, δ): 0.90 (3H, t, J=6.6 Hz); 0.937 (3H, s); 0.942 (3H, s); 1.15-1.4 (4H, m); 1.43 (1H, dd, J=5.4, 14.6 Hz); 1.52 (1H, dd, J=6.8, 14.6 Hz); 1.99 (1H, ddd, J=4.9, 8.8, 13.5 Hz); 2.35-2.45 (1H, m); 2.57 (1H, dt, J=6.5, 13.5 Hz); 3.44 (1H, t, J=8.3 Hz); 3.6-3.8 (2H, m); 3.85-3.95 (1H, m); 4.2-4.3 (1H, m); 4.63 (1H, d, J=16.6 Hz); 4.71 (1H, d, J=16.6 Hz); 5.1-5.2 (1H, m); 5.5-5.65 (2H, m); 6.65-6.8 (3H, m).

MASS (EI, m/e): 404 (M+).

HR MASS: Calcd. as C₂₃H₃₂O₆ (M+): 404.2199. Found (M+): 404.2207.

EXAMPLE 36

17,17-Dimethyl-15-epi-2,5,6,7-tetranor-4-oxa-4,8-inter-m-phenylene PGI₂ (201)

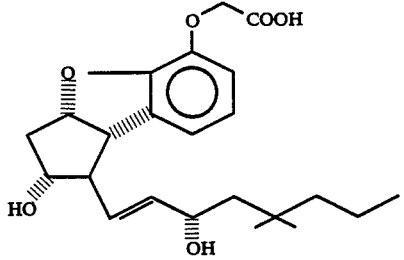

201

17,17-Dimethyl-15-epi-2,5,6,7-tetranor-4-oxa-4,8-inter-m-phenylene PGI₂ methyl ester (345 mg, 0.83 mmol) was dissolved in methanol (30 ml). To this solution was added 0.75N aqueous sodium hydroxide solution (6 ml, 4.5 mmol), and the mixture was stirred at room temperature for 2 hours. The reaction mixture was concentrated, and water (30 ml) was added to the residue. After 1N hydrochloric acid was added to adjust the pH to 4, the mixture was extracted with ethyl acetate (60 ml, 20 ml×2). The combined organic layers were washed with brine (30 ml), dried over anhydrous magnesium sulfate and concentrated to give 344 mg of crude crystal. The crude crystal was recrystallized from ethyl acetate to afford white crystal of 17,17-dimethyl-15-epi-2,5,6,7-tetranor-4-oxa-4,8-inter-m-phenylene PGI₂ (248 mg, 0.61 mmol) with a yield of 74.4%. This product was assigned the structure by the following data.

m.p.: 116°-117° C.

IR (KBr): 3370, 2970, 2940, 1740, 1710, 1620, 1590, 1490, 1470, 1430, 1370, 1340, 1310, 1280, 1260, 1200, 1170, 1120, 1080, 1060, 1040, 980, 960, 940, 920, 890, 860, 830, 790, 770, 730, 710, 630, 590 cm⁻¹.

NMR (400 MHz, CDCl₃, δ): 0.89 (3H, t, J=6.6 Hz); 0.941 (3H, s); 0.945 (3H, s); 1.15-1.3 (4H, m); 1.4-1.55 (2H, m); 2.0-2.1 (1H, m); 2.45-2.6 (2H, m); 3.2-3.4 (2H, m); 3.51 (1H, t, J=8.1 Hz); 3.97 (1H, q, J=7.0 Hz); 4.25-4.35 (1H, m); 4.65 (1H, d, J=16.4 Hz); 4.71 (1H, d, J=16.4 Hz); 5.15-5.3 (1H, m); 5.6-5.7 (2H, m); 6.7-6.9 (3H, m).

MASS (EI, m/e): 404 (M+).

Elementary Analysis: Calcd. as $C_{23}H_{32}O_6$: C 68.29; H 7.97. Found: C 68.03; H8.02.

EXAMPLE 37

18,18-Dimethyl-2,5,6,7-tetranor-4-oxa-4,8-inter-m-phenylene $PGI_2$ methyl ester (202) and its 15-epimer (203)

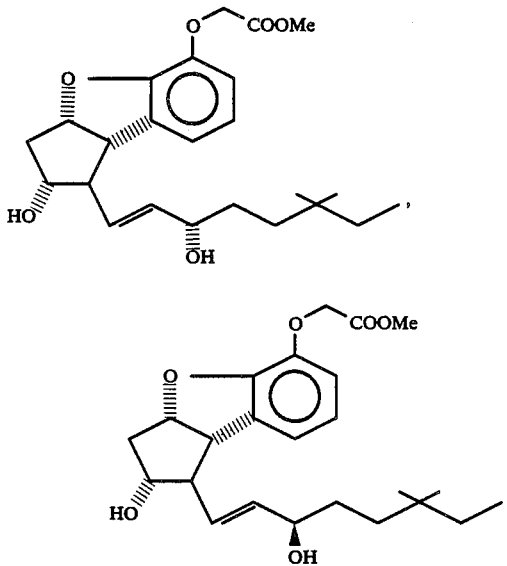

18,18-Dimethyl-15-oxo-2,5,6,7-tetranor-4-oxa-4,8-inter-m-phenylene $PGI_2$ methyl ester, 11-benzoate (1.88 g, 3.62 mmol) was dissolved in methanol (200 ml). Cerium trichloride heptahydrate (1.63 g, 4.38 mmol) was added to the solution and the resulting solution was cooled to $-20°$ C. Sodium borohydride (53.7 mg, 1.45 mmol) was gradually added to the solution. After stirring for 20 minutes at $-20°$ C. the reaction mixture was warmed to $0°$ C. A saturated aqueous sodium bicarbonate solution (15 ml) was added to the reaction mixture, and then the mixture was filtered and concentrated. After water (20 ml) was added to the residue, the mixture was extracted with ethyl acetate (50 ml×2). The combined ethyl acetate extracts were washed with water (20 ml) and with brine (20 ml), dried over anhydrous sodium sulfate and concentrated to give 1.86 g of an oily material.

The oily material was dissolved in anhydrous methanol (50 ml) under argon atmosphere. To this solution was added a solution of sodium methoxide in methanol (5.22N, 0.2 ml, 1.07 mmol), and then the resulting mixture was stirred at room temperature for 14 hours. The reaction mixture was neutralized with acetic acid. After concentration of the mixture water (20 ml) was added, and the resulting mixture was extracted with ethyl acetate (50 ml×2). The combined ethyl acetate layers were washed with water (20 ml) and with brine (20 ml), dried over anhydrous sodium sulfate and concentrated. The resulting residue was purified by Merck Lobar column of silica gel (ethyl acetate/cyclohexane=2/1) to give less polar 18,18-dimethyl-15-epi-2,5,6,7-tetranor-4-oxa-4,8-inter-m-phenylene $PGI_2$ methyl ester (645 mg, 1.54 mmol: yield 43.3%), and more polar 18,18-dimethyl-2,5,6,7-tetranor-4-oxa-4,8-inter-m-phenylene $PGI_2$ methyl ester (589 mg, 1.41 mmol: yield 39.6%). These products were assigned the corresponding structures by the following data.

18,18-Dimethyl-2,5,6,7-tetranor-4-oxa-4,8-inter-m-phenylene $PGI_2$ methyl ester m.p.: $113.2°-114.2°$ C. (recrystallized from ethyl acetate/n-hexane, 1/1).

IR (KBr): 3340, 2950, 2860, 1750, 1610, 1590, 1480, 1455, 1430, 1365, 1290, 1205, 1115, 1170, 1110, 1090, 1070, 1025, 970, 945, 885, 850, 820, 775, 750, 720, 670 cm$^{-1}$.

NMR (400 MHz, CDCl$_3$, δ): 0.82 (3H, t, J=7.6 Hz); 0.85 (6H, s); 1.24 (2H, q, J=7.6 Hz); 1.1–1.3 (2H, m); 1.35–1.6 (2H, m); 2.0–2.1 (2H, m); 2.45 (1H, q, J=8.2 Hz); 2.4–2.5 (1H, m); 2.6–2.8 (1H, m); 3.46 (1H, t, J=8.2 Hz); 3.79 (3H, s); 4.72 (2H, s); 5.1–5.3 (1H, m); 5.5–5.8 (2H, m); 6.7–6.9 (3H, m).

MASS (EI, m/e): 418 (M$^+$).

Elementary Analysis: Calcd. for $C_{24}H_{34}O_6$: C 68.87; H 8.19. Found: C 68.85; H 8.22.

18,18-Dimethyl-15-epi-2,5,6,7-tetranor-4-oxa-4,8-inter-m-phenylene $PGI_2$ methyl ester m.p.: $113.1°-113.5°$ C. (recrystallized from ethyl acetate/n-hexane, 4/3).

IR (KBr): 3300, 2960, 2870, 1760, 1610, 1590, 1490, 1460, 1430, 1370, 1290, 1205, 1190, 1170, 1160, 1110, 1080, 1070, 1025, 1000, 970, 945, 890, 855, 825, 780, 750, 715, 705, 670 cm$^{-1}$.

NMR (400 MHz, CDCl$_3$, δ): 0.82 (3H, t, J=7.6 Hz); 0.85 (6H, s); 1.24 (2H, q, J=7.6 Hz); 1.1–1.3 (2H, m); 1.4–1.6 (2H, m); 2.0–2.1 (2H, m); 2.45 (1H, q, J=8.3 Hz); 2.4–2.5 (1H, m); 2.6–2.7 (1H, m); 3.46 (1H, t, J=8.3 Hz); 3.79 (3H, s); 3.85–3.95 (1H, m); 4.0–4.1 (1H, m); 4.72 (2H, s); 5.1–5.3 (1H, m); 5.5–5.7 (2H, m); 6.7∝6.9 (3H, m).

MASS (EI, m/e): 418 (M$^+$).

Elementary Analysis: Calcd. for $C_{24}C_{34}O_6$: C 68.87; H 8.19. Found: C 68.98; H 8.25.

EXAMPLE 38

18,18-Dimethyl-2,5,6,7-tetranor-4-oxa-4,8-inter-m-phenylene $PGI_2$ (204)

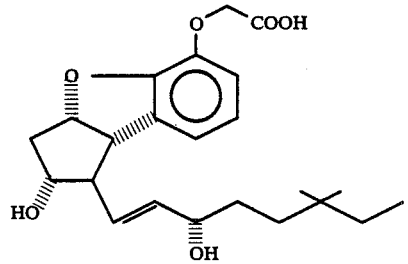

18,18-Dimethyl-2,5,6,7-tetranor-4-oxa-4,8-inter-m-phenylene $PGI_2$ methyl ester (332 mg, 0.797 mmol) was dissolved in methanol (40 ml). An aqueous sodium hydroxide solution (0.725N, 8.8 ml, 6.4 mmol) was added to the solution under cooling with ice while stirring. The resulting mixture was then stirred at room temperature for 1 hour. The reaction mixture was neutralized with 1N hydrochloric acid (6.4 ml) under cooling with ice. After concentration of the mixture, water (20 ml) was added to the residue. The resulting mixture was extracted with ethyl acetate (50 ml×2). The combined ethyl acetate layers were washed with water (20 ml)

and with brine (20 ml), dried over anhydrous sodium sulfate and concentrated. The resulting residue was recrystallized from a mixture of ethyl acetate (2 ml) and n-hexane (2 ml) to give white crystal of 18,18-dimethyl-2,5,6,7-tetranor-4-oxa-4,8-inter-m-phenylene PGI$_2$ (296 mg, 0.733 mmol) with a yield of 91.9%. This product was assigned the structure by the following data.

m.p.: 142.6°-143.9° C. (recrystallized from ethyl acetate/n-hexane, 1/1).

IR (KBr): 3400, 2960, 1730, 1610, 1585, 1480, 1475, 1420, 1280, 1250, 1190, 1110, 1060, 1020, 850, 790, 780, 720 cm$^{-1}$.

NMR (400 MHz, DMSO, δ): 0.81 (6H, s); 0.7-0.9 (3H, m); 1.19 (2H, q, J=7.5 Hz); 1.1-1.5 (4H, m); 1.6-1.8 (1H, m); 2.1-2.3 (1H, m); 2.4-2.6 (1H, m); 3.41 (1H, t, J=9.0 Hz); 3.6-3.8 (1H, m); 3.8-4.0 (1H, m); 4.64 (2H, s); 4.6-4.7 (1H, m); 4.8-4.9 (1H, m); 5.08 (1H, q, J=9.0 Hz); 5.48 (1H, dd, J=5.6, 15.4 Hz); 5.62 (1H, dd, J=7.6, 15.4 Hz); 6.6-6.9 (3H, m).

MASS (EI, m/e): 404 (M+).

Elementary Analysis: Calcd. for C$_{23}$H$_{32}$O$_6$: C 68.29; H 7.97. Found: C 68.01; H 7.98.

EXAMPLE 39

18,18-Dimethyl-15-epi-2,5,6,7-tetranor-4-oxa-4,8-inter-m-phenylene PGI$_2$ (205)

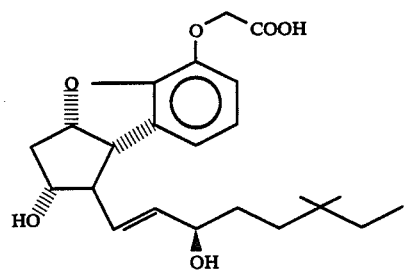

18,18-Dimethyl-15-epi-2,5,6,7-tetranor-4-oxa-4,8-inter-m-phenylene PGI$_2$ methyl ester (408 mg, 0.98 mmol) was dissolved in methanol (40 ml). To the stirred solution cooled with ice-bath was added 0.725N aqueous sodium hydroxide solution (10.8 ml, 7.8 mmol). The mixture was then stirred at room temperature for 1 hour. Hydrochloric acid (1N, 7.8 ml) was added to neutralize the reaction mixture under ice-cooling. After concentrating the reaction mixture, water (20 ml) was added to the residue. The mixture was extracted with ethyl acetate (50 ml×2). The combined ethyl acetate layers were washed with water (20 ml) and with brine (20 ml), dried over anhydrous sodium sulfate and concentrated. The resulting residue was recrystallized from a mixture of ethyl acetate (3 ml) and n-hexane (2 ml) to give white crystal of 18,18-dimethyl-15-epi-2,5,6,7-tetranor-4-oxa-4,8-inter-m-phenylene PGI$_2$ (371 mg, 9.18 mmol) with a yield of 94.1%. This product was assigned the structure by the following data.

m.p.: 143.2°-144.1° C. (recrystallized from ethyl acetate/n-hexane, 3/2).

IR (KBr): 3400, 2950, 1740, 1705, 1610, 1590, 1490, 1460, 1425, 1360, 1280, 1260, 1200, 1170, 1110, 1070, 1025, 960, 855, 790, 775, 735, 720 cm$^{-1}$.

NMR (400 MHz, DMSO, δ): 0.81 (6H, s); 0.7-0.9 (3H, m); 1.19 (2H, q, J=7.5 Hz); 1.0-1.5 (4H, m); 2.1-2.3 (1H, m); 2.4-2.6 (1H, m); 3.4 (1H, t, J=8.8 Hz); 3.65-3.8 (1H, m); 3.85-4.0 (1H, m); 4.64 (2H, s); 4.7-4.9 (1H, m); 5.0-5.1 (1H, m); 5.48 (1H, dd, J=5.9, 15.1 Hz); 5.62 (1H, dd, J=7.6, 15.1 Hz); 6.6-6.8 (3H, m).

MASS (EI, m/e): 404 (M+).

Elementary Analysis: Calcd. for C$_{23}$H$_{32}$O$_6$: C 68.29; H 7.97. Found: C 68.03; H 7.99.

EXAMPLE 40

16-Methyl-2,5,6,7-tetranor-4-oxa-4,8-inter-m-phenylene PGI$_2$ methyl ester 206 and its 15-epimer 207

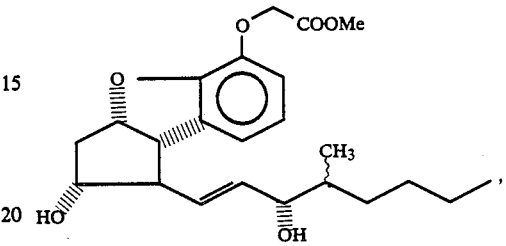

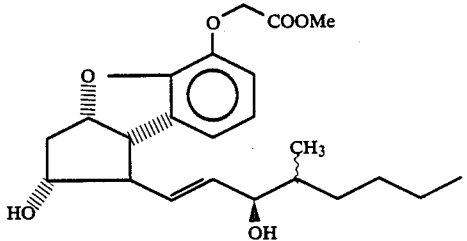

To a solution of 16-methyl-15-oxo-2,5,6,7-tetranor-4-oxa-4,8-inter-m-phenylene PGI$_2$ methyl ester, 11-benzoate (1.68 g, 3.32 mmol) in methanol (70 ml) was added with stirring cerium trichloride heptahydrate (2.49 g, 6.69 mmol) and then the solution was cooled to −10° C. Sodium borohydride (188 mg, 4.97 mmol) was added little by little to the solution. The reaction mixture was stirred for 20 min. at −10° C. and diluted with a saturated aqueous solution of sodium bicarbonate (30 ml). This mixture was filtered and the filtrate was concentrated. The concentrate was mixed with 20 ml of water and extracted with ethyl acetate (50 ml×2). The combined ethyl acetate layers were washed with water (20 ml), and with brine (20 ml), dried over anhydrous sodium sulfate and concentrated to give 1.7 g of an oily material. To a solution of the oil in anhydrous methanol (30 ml) was added under argon atmosphere a solution of sodium methoxide in methanol (5.22N, 0.17 ml, 0.84 mmol). The reaction mixture was stirred for 14 hrs. at room temperature, neutralized with acetic acid and concentrated. 20 ml of water was added to the residue. Extraction with ethyl acetate (50 ml×2) followed by washing with water (20 ml) and with brine (20 ml), drying over anhydrous sodium sulfate and concentration gave a crude material. Column chromatography (Merck, Lobar column: silica gel, ethyl acetate/cyclohexane: 2/1) of the material afforded less polar 16-methyl-15-epi-2,5,6,7-tetranor-4-oxa-4,8-inter-m-phenylene PGI$_2$ methyl ester (539 mg, 1.33 mmol, yield: 40%) and more polar 16-methyl-2,5,6,7-tetranor-4-oxa-4,8-inter-m-phenylene PGI$_2$ methyl ester (495 mg, 1.23 mmol, yield: 36.9%). These compounds were assigned the corresponding structures by the following data.

16-methyl-2,5,6,7-tetranor-4-oxa-4,8-inter-m-phenylene PGI$_2$ methyl ester

M.p.: 107.2°–123.4° C. (recrystallization solvent, ethyl acetate/n-hexane: 5/2).

IR (KBr): 3400, 2910, 2920, 2860, 1730, 1610, 1590, 1480, 1450, 1430, 1370, 1280, 1245, 1195, 1060, 1110, 1015, 960, 940, 890, 855, 820, 785, 755, 730 cm$^{-1}$.

NMR (400 MHz, CDCl$_3$, δ): 0.8–1.0 (6H, m); 1.0–1.8 (7H, m); 1.8–2.1 (2H, m); 2.46 (1H, q, J=8.3 Hz); 2.3–2.6 (1H, m); 2.6–2.7 (1H, m); 3.4 (1H, t, J=8.3 Hz); 3.79 (3H, s); 3.8–4.1 (2H, m); 4.72 (2H, s); 5.1–5.3 (1H, m); 5.5–5.7 (2H, m); 6.7–6.9 (3H, m).

MASS (EI, m/e): 404 (M+).

Elemental analysis: Calcd. (as C$_{23}$H$_{32}$O$_6$): C: 68.29, H: 7.97. Found: C: 68.25, H: 8.01.

16-Methyl-15-epi-2,5,6,7-tetranor-4-oxa-4,8-inter-m-phenylene PGI$_2$ methyl ester IR (liquid film): 3350, 2940, 2905, 2860, 1750, 1610, 1585, 1480, 1455, 1430, 1345, 1290, 1230, 1210, 1190, 1175, 1160, 1110, 1065, 1025, 970, 945, 910, 890, 860, 830, 780, 755, 720, 710, 675 cm$^{-1}$.

NMR (400 MHz, CDCl$_3$, δ): 0.8–1.0 (6H, m); 1.0–1.7 (7H, m); 1.8–2.1 (2H, m); 2.2–2.4 (1H, m); 2.5 (1H, q, J=8.1 Hz); 2.5–2.7 (1H, m); 3.49 (1H, t, J=8.1 Hz); 3.78 (3H, s); 3.94 (1H, q, J=8.1 Hz); 4.0–4.1 (1H, m); 4.72 (2H, s); 5.1–5.3 (1H, m); 5.6–5.8 (2H, m); 6.7–6.9 (3H, m)

MASS (EI, m/e): 404 (M+).

HR MASS: Calcd. (C$_{23}$H$_{32}$O$_6$, M+): 404.2199. Found (M+): 404.2211.

EXAMPLE 41

16-Methyl-2,5,6,7-tetranor-4-oxa-4,8-inter-m-phenylene PGI$_2$ 208

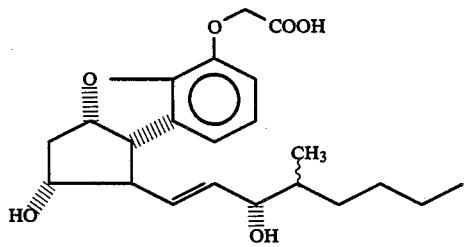

To a solution of 16-methyl-2,5,6,7-tetranor-4-oxa-4,8-inter-m-phenylene PGI$_2$ methyl ester (405 mg, 1.0 mmol) in methanol (30 ml) was added with stirring 0.973N aqueous NaOH solution (8.2 ml, 8.0 mmol) under ice-cooling and the reaction mixture was stirred for 14 hrs. The solution was mixed with 1N hydrochloric acid under ice-cooling and concentrated. 20 ml of water was added to the residue and the mixture was extracted with ethyl acetate (50 ml×2). The combined ethyl acetate layers were washed with water (20 ml), and with brine (20 ml), dried over anhydrous sodium sulfate and concentrated. Recrystallization of the residue from a mixture of 2 ml of ethyl acetate and 0.8 ml of n-hexane yielded 353 mg (0.91 mmol, 90.5%) of 16-methyl-2,5,6,7-tetranor-4-oxa-4,8-inter-m-phenylene PGI$_2$ as a white crystal, which was assigned the structure by the following data.

M.p.: 117.2°–120.1° C. (recrystallization solvent, ethyl acetate/n-hexane: 5/2).

IR (KBr): 3400, 2940, 2900, 2850, 1750, 1660, 1610, 1585, 1475, 1450, 1430, 1370, 1240, 1100, 1020, 960, 890, 850, 825, 750, 720 cm$^{-1}$.

NMR (400 MHz, CDCl$_3$, δ): 0.8–1.0 (6H, m); 1.0–1.7 (7H, m); 1.9–2.1 (1H, m); 2.44 (1H, q, J=8.0 Hz); 2.5–2.7 (1H, m); 3.45 (1H, t, J=8.0 Hz); 3.92 (1H, q, J=7.5 Hz); 3.96 (1H, t, J=5.9 Hz); 3.5–4.3 (3H, m); 4.66 (1H, d, J=16.1 Hz); 4.72 (1H, d, J=16.1 Hz); 5.1–5.2 (1H, m); 5.5–5.7 (2H, m); 6.6–6.9 (3H, m).

MASS (EI, m/e): 390 (M+).

HR MASS: Calcd. (C$_{22}$H$_{30}$O$_6$, M+): 390.2042. Found (M+): 390.2043.

EXAMPLE 42

15-Methyl-2,5,6,7-tetranor-4-oxa-4,8-inter-m-phenylene PGI$_2$ methyl ester 209

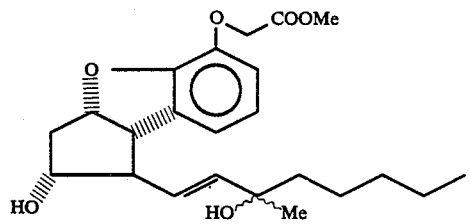

To a solution of 15-oxo-2,5,6,7-tetranor-4-oxa-4,8-inter-m-phenylene PGI$_2$ methyl ester, 11-benzoate (2.2 g, 4.45 mmol) in anhydrous THF (80 ml) was added dropwise with stirring a solution of methylmagnesium bromide in THF (0.683N, 20 ml, 13.66 mmol) under argon atmosphere at −78° C. and the mixture was stirred for 2 hrs. A saturated aqueous solution of ammonium chloride (14 ml) was added to the reaction mixture at −78° C. and then the reaction mixture was further stirred until it was warmed to room temperature. The solution was mixed with water (30 ml) and extracted with ethyl acetate (50 ml×3). The combined ethyl acetate layers were washed with water (30 ml), and with brine (30 ml), dried and concentrated to give an oily material (2.2 g). After three times repeated azeotropic distillation of the oil with benzene, the residue was dissolved in anhydrous methanol (80 ml). To this solution was added a solution of sodium methoxide in methanol (5.22N, 0.6 ml, 3.13 mmol). The reaction mixture was allowed to stand under argon atmosphere for 14 hrs. at room temperature, neutralized with acetic acid to pH 7 and concentrated. Water was added to the residue. Extraction with ethyl acetate (three times) followed by washing with water and with brine, drying and concentration gave 2.6 g of an oily material. Column chromatography (silica gel, ethyl acetate/cyclohexane: 8/1) of the oil afforded 15-methyl-2,5,6,7-tetranor-4oxa-4,8-inter-m-phenylene PGI$_2$ methyl ester (400 mg, 0.99 mmol, 22.2%). The compound was assigned the structure by the following data.

IR (liquid film): 3360, 2950, 2930, 2850, 1750, 1615, 1595, 1485, 1455, 1420, 1375, 1280, 1190, 1100, 1025, 970, 950, 920, 890, 860, 830, 765, 725 cm$^{-1}$.

NMR (400 Hz, CDCl$_3$, δ): 0.87–0.93 (3H, m); 1.22–1.40 (9H, m); 1.50–1.55 (2H, m); 2.00–2.10 (3H, m); 2.41–2.47 (1H, m); 2.60–2.68 (1H, m); 3.43–3.49 (1H, m); 3.78 (3H, s); 3.90–4.00 (1H, m); 4.72 (2H, s); 5.17–5.22 (1H, m); 5.55–5.70 (2H, m); 6.66–6.80 (3H, m).

MASS (EI, m/e): 404 (M+).

HR MASS: Calcd. (C$_{23}$H$_{32}$O$_6$, M+): 404.2199. Found (M+): 404.2201.

EXAMPLE 43

15-Methyl-2,5,6,7-tetranor-4-oxa-4,8-inter-m-phenylene PGI$_2$ 210

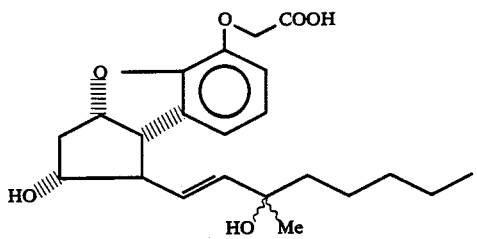

210

To a solution of 15-methyl-2,5,6,7-tetranor-4-oxa-4,8-inter-m-phenylene PGI$_2$ methyl ester (400 mg, 0.99 mmol) in methanol (70 ml) was added under argon atmosphere 1N aqueous NaOH solution (10 ml, 10 mmol) and the reaction mixture was allowed to stand for 14 hrs. at room temperature. The reaction mixture was then concentrated and 1N hydrochloric acid (10 ml) was added to the residue under ice-cooling. The mixture was extracted with ethyl acetate (100 ml). The ethyl acetate layer was back-extracted with a saturated aqueous solution of sodium bicarbonate and with water. The combined aqueous layers were acidified to pH 4 with 1N hydrochloric acid and extracted with ethyl acetate (100 ml, 50 ml, 10 ml). The combined ethyl acetate layers were washed with brine (30 ml), dried and concentrated to give 15-methyl-2,5,6,7-tetranor-4-oxa-4,8-inter-m-phenylene PGI$_2$ (340 mg, 0.87 mmol). The compound was assigned the structure by the following data.

IR (liquid film): 3700–2200, 1740, 1620, 1595, 1495, 1460, 1380, 1285, 1250, 1195, 1170, 1030, 975, 950, 895, 865, 825, 760, 720 cm$^{-1}$.

NMR (400 MHz, CDCl$_3$, δ): 0.90 (3H, m); 1.20–1.40 (9H, m); 1.54 (2H, m); 2.03 (1H, m); 2.42 (1H, m); 2.56 (1H, m); 3.44 (1H, t, J=8.3 Hz); 3.90 (1H, m); 4.62 (1H, d, J=16.6 Hz); 4.69 (1H, d, J=16.6 Hz); 5.17 (1H, m); 5.62 (2H, m); 6.75 (3H, m).

MASS (EI, m/e): 390 (M+).

HR MASS: Calcd. (C$_{22}$H$_{30}$O$_6$, M+): 390.2042. Found (M+): 390.2054.

EXAMPLE 44

15-Methyl-20a-homo-2,5,6,7-tetranor-4-oxa-4,8-inter-m-phenylene PGI$_2$ methyl ester 211

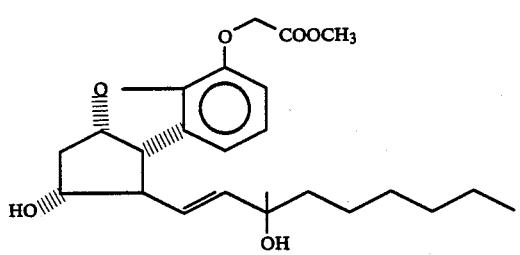

211

Cerium trichloride heptahydrate (69.2 mg, 0.186 mmol) was rapidly ground in a mortar and transferred into a two-necked flask (50 ml), which was then heated over 1 hour to 140° C. while being sucked by a vaccum pump. After drying in vacuo at 140° C. for one hour, the two necked flask was filled with argon gas to normal pressure. A teflon stirring bar was set in the flask and the flask was further dried in vacuo for 2 hours at 140° C. while stirring. The flask was then filled with argon gas to normal pressure and cooled on an ice-bath. To this was added with stirring 20 ml of THF at a stretch. After the solution was warmed to room temperature, the mixture was stirred overnight and cooled to −78° C. To this solution was dropped over 5 min. a solution of methyl lithium in n-hexane (0.86N, 0.22 ml, 0,186 mmol) and the mixture was stirred for 2 hrs. A solution of 15-oxo-20a-homo-2,5,6,7-tetranor-4-oxa-4,8-inter-m-phenylene PGI$_2$ methyl ester (50 mg, 0.124 mmol) in THF (10 ml) was dropped to the mixture prepared above over 10 min. at −78° C. and the resulting mixture was stirred for one hour at −78° C. The solution was allowed to warm to room temperature, mixed with a saturated aqueous solution of ammonium chloride with stirring and mixed with acetic acid until the mixture became transparent. The thus obtained solution was extracted with ethyl acetate. The ethyl acetate layer was washed with brine four times, and dried over anhydrous sodium sulfate. Ethyl acetate was distilled off in vacuo to give a yellow oily material. Column chromatography (Merck, Lobar column A type, methylene chloride/acetonitorile/acetic acid: 10/1/1) of the material gave 15-methyl-20a-homo-2,5,6,7-tetranor-4-oxa-4,8-inter-m-phenylene PGI$_2$ methyl ester (5.24 mg, 0.013 mmol, 10%). The product was assigned the structure by the following data.

IR (liquid film): 3430, 2990, 2960, 2890, 1750, 1630, 1619, 1600, 1500, 1475, 1380, 1375, 1340, 1260, 1210, 1180, 1118, 1060, 988, 960, 900, 870, 840, 795, 775, 745 cm$^{-1}$.

NMR (400 MHz, CDCl$_3$, δ): 0.90 (3H, s); 1.26–1.33 (11H, m); 1.43–1.60 (3H, m); 1.75–1.80 (1H, m); 2.03–2.09 (1H, m); 2.46–2.52 (1H, m); 2.62–2.69 (1H, m); 3.47–3.52 (1H, m); 3.79 (3H, s); 3.95–3.97 (1H, m); 4.63–4.72 (2H, m); 5.19–5.25 (1H, m); 5.63–5.71 (2H, m); 6.67–6.81 (3H, m).

MASS (EI, m/e): 418 (M+).

HR MASS: Calcd. (C$_{24}$H$_{34}$O$_6$, M+): 418.2355. Found (M+): 418.2361.

EXAMPLE 45

17-(S)-methyl-2,5,6,7-tetranor-4-oxa-4,8-inter-m-phenylene PGI$_2$ methyl ester 212

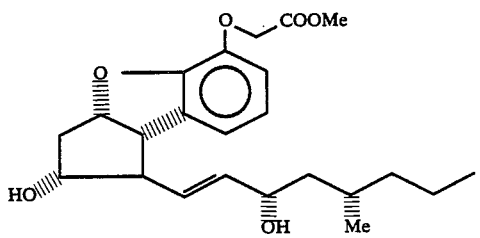

212

To a solution of 17-(S)-methyl-15-oxo-2,5,6,7-tetranor-4-oxa-4,8-inter-m-phenylene PGI$_2$ methyl ester, 11-benzoate (3.5 g, 6.90 mmol) in methanol (144 ml) was added cerium trichloride heptahydrate (5.4 g, 14.49 mmol). To the solution at −30° C. was added sodium borohydride (125 mg, 3.30 mmol). The reaction mixture was stirred for 10 min. and diluted with an aqueous saturated solution of sodium bicarbonate. The solution was concentrated and to the residue ethyl acetate was added. The resulting precipitate was filtered off. The filtrate was concentrated. After three times repeated azeotropic distillation of the residue with benzene, the residue was dissolved in anhydrous methanol (144 ml). To this solution was added a solution of sodium methoxide (5.22N, 0.864 ml, 4.5 mmol). The reaction mixture was allowed to stand under argon atmosphere for 16 hrs. at room temperature, neutralized with acetic acid to pH 7 and concentrated. Water was added to the residue. Extraction with three portions of ethyl acetate followed by washing with water and with brine, drying and concentration gave a crude material. Column chromatography (silica gel, ethyl acetate/cyclohexane: 1/1) of the material yielded 250 mg of 17-(S)-methyl-2,5,6,7-tetranor-4-oxa-4,8-inter-m-phenylene $PGI_2$ methyl ester (0.619 mmol, 9.0%). The product was assigned the structure by the following data.

M.p.: 68°–69° C. (recrystallized from ethyl acetate/n-hexane).

IR (KBr): 3350, 2950, 2920, 2850, 1755, 1610, 1595, 1485, 1450, 1380, 1280, 1225, 1195, 1160, 1115, 1095, 1025, 965, 950, 890, 850, 765, 725 $cm^{-1}$.

NMR (400 MHz, $CDCl_3$, δ): 0.90 (6H, m); 1.15 (1H, m); 1.20–1.50 (6H, m); 1.90 (1H, m); 2.32 (1H, q, J=8.8 Hz); 2.42 (1H, broad s); 2.65 (1H, m); 3.18 (1H, broad s); 3.38 (1H, m); 3.78 (3H, s); 3.80 (1H, m); 4.13 (1H, m); 4.70 (2H, s); 5.13 (1H, m); 5.48 (1H, dd, J=7.3, 15.1 Hz); 5.53 (1H, dd, J=8.8, 15.1 Hz); 6.70 (3H, broad s).

MASS (EI, m/e): 404 (M+).

EXAMPLE 46

17-(S)-Methyl-2,5,6,7-tetranor-4-oxa-4,8-inter-m-phenylene $PGI_2$ 213

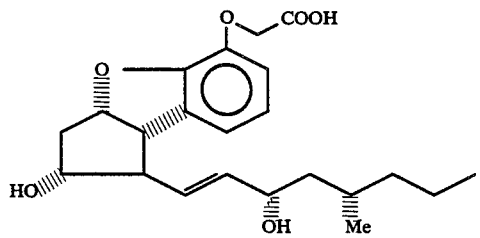

To a solution of 17-(S)-methyl-2,5,6,7-tetranor-4-oxa-4,8-inter-m-phenylene $PGI_2$ methyl ester (120 mg, 0.30 mmol) in methanol (12 ml) was added 1N aqueous NaOH solution (3 ml, 3 mmol) and the reaction mixture was allowed to stand for 20 hrs. under argon atmosphere at room temperature. The reaction mixture was then concentrated. The residue was cooled with ice and adjusted to pH 3 with 1N hydrochloric acid. The mixture was extracted with three portions of ethyl acetate. The combined ethyl acetate layers were washed with water, and with brine, dried and concentrated to give quantitatively a single product of 17-(S)-methyl-2,5,6,7-tetranor-4-oxa-4,8-inter-m-phenylene $PGI_2$ (120 mg, 0.30 mmol). The compound was assigned the structure by the following data.

Optical rotation: $[\alpha]_D^{23} = +62.26°$ (c=0.212, $CHCl_3$).

M.p.: 76°–78° C. (recrystallized from ethyl acetate/n-hexane).

IR (KBr): 3650–2250, 1760, 1740, 1620, 1590, 1495, 1465, 1435, 1385, 1350, 1310, 1295, 1225, 1195, 1150, 1115, 1090, 1030, 995, 970, 925, 860, 825, 795, 765, 725 $cm^{-1}$.

NMR (400 MHz, $CDCl_3$, δ): 0.90 (6H, m); 1.15 (1H, m); 1.20–1.45 (6H, m); 1.93 (1H, broad s); 2.32 (1H, m); 2.56 (1H, broad s); 3.35 (1H, m); 3.82 (1H, m); 4.16 (1H, m); 4.63 (2H, m); 4.75 (3H, broad s); 5.10 (1H, m); 5.48 (1H, dd, J=7.3, 15.1 Hz); 5.53 (1H, dd, J=8.8, 15.1 Hz); 6.70 (3H, broad s).

MASS (EI, m/e): 390 (M+).

HR MASS: Calcd. ($C_{22}H_{30}O_6$, M+): 390.2042. Found (M+): 390.2042.

EXAMPLE 47

(17S)-17-Methyl-20a-homo-2,5,6,7-tetranor-4-oxa-4,8-inter-m-phenylene $PGI_2$ methyl ester (214), and its 15-epimer (215), (8R, 9R, 11S, 12S, 15R) isomer (216) and (8R, 9R, 11S, 12S) isomer (217)

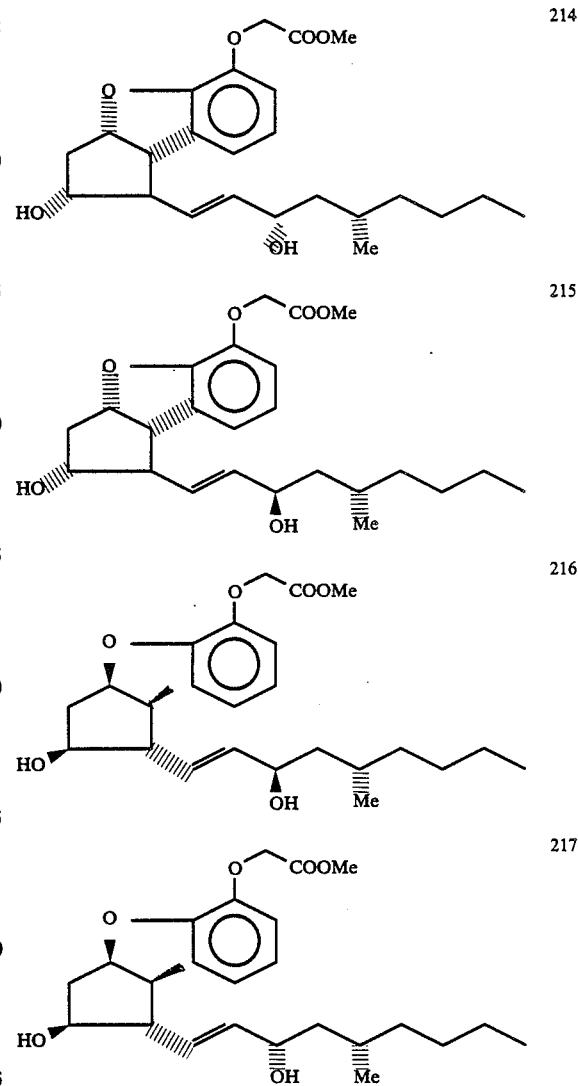

To a solution of 17(S)-methyl-15-oxo-20a-homo-2,5,6,7-tetranor-4-oxa-4,8-inter-m-phenylene $PGI_2$ methyl ester, 11-benzoate (3.93 g, 7.55 mmol) in methanol (120 ml) was added cerium trichloride heptahydrate (3.66 g, 9.82 mmol) and the reaction mixture was cooled to −20° C. Sodium borohydride (188 mg, 4.97 mmol) was added slowly to the mixture. The reaction mixture was stirred for 20 min. at −20° C., diluted with an aqueous saturated solution of sodium bicarbonate (30 ml), and concentrated. To the residue ethyl acetate was added (150 ml) and the resulting precipitate was filtered off. The precipitate was washed with ethyl acetate (50 ml×2). The ethyl acetate layers were combined with the filtrate, washed with water (50 ml), and with brine, dried over anhydrous magnesium sulfate and concentrated to give 3.8 g of an oily material. The oil was dissolved under argon atmosphere in anhydrous methanol (80 ml). To this solution was added a solution of sodium methoxide in methanol (5.22N, 0.36 ml, 1.89 mmol). The reaction mixture was stirred for 48 hrs. at room temperature, neutralized with acetic acid, and concentrated. Water (50 ml) was added to the residue. Extraction with ethyl acetate (50 ml, 15 ml×2) followed by washing with brine, drying over anhydrous magnesium sulfate and concentration afforded a crude material. Column chromatography (Merck, Lobar column, silica gel: acetonitrile/methylene chloride: 1/4–1/3) of the residue gave the least polar (17S)-17-methyl-15-epi-20a-homo-2,5,6,7-tetranor-4-oxa-4,8-inter-m-phenylene PGI$_2$ methyl ester (580 mg, 1.39 mmol, 18.4%) as a white crystal, less polar (8R, 9R, 11S, 12S, 15S, 17S)-17-methyl-20a-homo-2,5,6,7-tetranor-4-oxa-4,8-inter-m-phenylene PGI$_2$ methyl ester (629 mg, 1.50 mmol, 19.9%) as a white crystal; the most polar (8R, 9R, 11S, 12S, 15R, 17S)-17-methyl-20a-homo-2,5,6,7-tetranor-4-oxa-4,8-inter-m-phenylene PGI$_2$ methyl ester (605 mg, 1.45 mmol, 19.2%) as a white crystal; and (17S)-17-methyl-20a-homo-2,5,6,7-tetranor-4-oxa-4,8-inter-m-phenylene PGI$_2$ methyl ester (610 mg, 1.46 mmol, 19.3%) as oil. These compounds were assigned the corresponding structures by the following data.

(17S)-17-Methyl-20a-homo-2,5,6,7-tetranor-4-oxa-4,8-inter-m-phenylene PGI$_2$ methyl ester Optical rotation: $[\alpha]_D^{25} = +71.18°$ (c=0.354, methanol).

IR (liquid film): 3370, 2960, 2930, 2870, 1760, 1660, 1620, 1600, 1480, 1460, 1380, 1300, 1220, 1200, 1120, 1100, 1030, 970, 890, 860, 830, 770, 730 cm$^{-1}$.

NMR (400 MHz, CDCl$_3$, δ): 0.91 (3H, t, J=6.8 Hz); 0.92 (3H, d, J=6.4 Hz); 1.1–1.6 (9H, m); 2.02 (1H, ddd, J=5.1, 9.0, 13.8 Hz); 2.3–2.4 (1H, m); 2.40 (1H, q, J=8.5 Hz); 2.66 (1H, dt, J=6.8, 13.8 Hz); 2.85–3.0 (1H, m); 3.42 (1H, t, J=8.5 Hz); 3.79 (3H, s); 3.85–3.95 (1H, m); 4.1–4.2 (1H, m); 4.72 (2H, s); 5.1–5.2 (1H, m); 5.53 (1H, dd, J=7.3, 15.1 Hz); 5.61 (1H, dd, J=8.5, 15.1 Hz); 6.7–6.8 (3H, m).

MASS (EI, m/e): 418 (M+).

HR MASS: Calcd. (C$_{24}$H$_{34}$O$_6$, M+): 418.2355. Found (M+): 418.2378.

(17S)-17-Methyl-15-epi-20a-homo-2,5,6,7-tetranor-4,8-inter-m-phenylene PGI$_2$ methyl ester M.p.: 81.5°–82.5° C. (recrystallized from ether).
Optical rotation $[\alpha]_D^{25}$=74.99° (c=0.408, methanol).
IR (KBr): 3450, 2970, 2930, 1740, 1720, 1620, 1600, 1490, 1465, 1440, 1380, 1300, 1280, 1265, 1200, 1120, 1090, 1070, 1030, 990, 970, 940, 890, 860, 830, 800, 780, 740, 560 cm$^{-1}$.

NMR (400 MHz, CDCl$_3$, δ): 0.90 (3H, t, J=6.6 Hz); 0.93 (3H, d, J=6.4 Hz); 1.1–1.4 (7H, m); 1.5–1.8 (4H, m); 2.08 (1H, ddd, J=5.0, 8.5, 13.8 Hz); 2.45–2.55 (1H, m); 2.62 (1H, ddd, J=6.1, 7.2, 13.8 Hz); 3.52 (1H, t, J=8.6 Hz); 3.79 (3H, s); 3.9–4.0 (1H, m); 4.2–4.3 (1H, m); 4.72 (2H, s); 5.23 (1H, ddd, J=5.0, 7.2, 8.6 Hz); 5.6–5.7 (2H, m); 6.73 (1H, dd, J=1.2, 7.5 Hz); 6.77 (1H, t, J=7.5 Hz); 6.82 (1H, dd, J=1.2, 6.5 Hz).

MASS (EI, m/e): 418 (M+).

HR MASS: Calcd. (C$_{24}$H$_{34}$O$_6$, M+): 418.2355. Found (M+): 418.2375.

(8R, 9R, 11S, 12S, 15R, 17S)-17-Methyl-20a-homo-2,5,6,7-tetranor-4-oxa-4,8-inter-m-phenylene PGI$_2$ methyl ester M.p.: 69°–70° C. (recrystallized from ether/n-hexane).
Optical rotation: $[\alpha]_D^{25}$=80.43° (c=0.368, methanol).

IR (KBr): 3450, 3200, 2960, 2930, 1740, 1720, 1680, 1620, 1590, 1490, 1470, 1430, 1400, 1380, 1320, 1300, 1280, 1260, 1220, 1190, 1170, 1110, 1070, 1030, 1010, 970, 950, 900, 870, 860, 830, 800, 770, 730, 610, 560 cm$^{-1}$.

NMR (400 MHz, CDCl$_3$, δ): 0.90 (3H, t, J=6.4 Hz); 0.93 (3H, d, J=6.4 Hz); 1.1–1.4 (7H, m); 1.5–1.7 (2H, m); 1.8–2.1 (1H, m); 2.03 (1H, ddd, J=5.4, 8.8, 13.7 Hz); 2.4–2.5 (1H, m); 2.5–2.7 (1H, m); 2.64 (1H, dt, J=6.3, 13.7 Hz); 3.45 (1H, t, J=8.5 Hz); 3.79 (3H, s); 3.9–4.0 (1H, m); 4.2–4.3 (1H, m); 4.72 (2H, s); 5.15–5.25 (1H, m); 5.55–5.7 (2H, m); 6.7–6.8 (3H, m).

MASS (EI, m/e): 418(M+).

Elemental analysis: Calcd. (as C$_{24}$H$_{34}$O$_6$) C: 68.87, H: 8.19. Found C: 68.61, H: 8.24.

(8R, 9R, 11S, 12S, 15S, 17S)-17-Methyl-20a-homo-2,5,6,7-tetranor-4-oxa-4,8-inter-m-phenylene PGI$_2$ methyl ester M.p.: 83.5°–84.5° C. (recrystallized from ethyl acetate/n-hexane).
Optical rotation: $[\alpha]_D^{25}$= −69.89° (c=0.392, methanol).

IR (KBr): 3300, 2960, 2930, 2870, 1740, 1620, 1490, 1470, 1450, 1430, 1380, 1360, 1310, 1290, 1280, 1260, 1210, 1190, 1170, 1110, 1070, 1030, 1020, 1000, 970, 950, 890, 870, 850, 830, 790, 760, 730, 700, 660, 510, 360 cm$^{-1}$.

NMR (400 MHz, CDCl$_3$, δ): 0.90 (3H, t, J=6.8 Hz); 0.92 (3H, d, J=6.4 Hz); 1.1–1.8 (11H, m); 2.08 (1H, ddd, J=5.0, 8.6, 13.9 Hz); 2.5–2.7 (2H, m); 3.52 (1H, t, J=8.3 Hz); 3.79 (3H, s); 3.9–4.0 (1H, m); 4.2–4.3 (1H, m); 4.73 (2H, s); 5.2–5.3 (1H, m); 5.6–5.8 (2H, m); 6.7–6.9 (3H, m).

MASS (EI, m/e): 418 (M+).

Elemental Analysis: Calcd. (C$_{24}$H$_{34}$O$_6$) C: 68.87, H: 8.19. Found C: 69.08, H: 8.27.

EXAMPLE 48

(17S)-17-Methyl-20a-homo-2,5,6,7-tetranor-4-oxa-4,8-inter-m-phenylene PGI$_2$ (218)

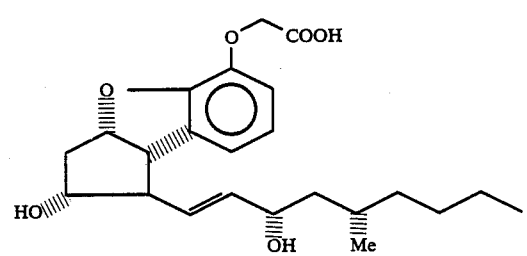

218

To a solution of (17S)-17-methyl-20a-homo-2,5,6,7-tetranor-4-oxa-4,8-inter-m-phenylene PGI$_2$ methyl ester (196 mg, 0.469 mmol) in methanol (20 ml) was added 1N aqueous NaOH solution (3 ml, 3 mmol) and the reaction mixture was stirred for 3 hrs. at room temperature. The solution was concentrated and 15 ml of water was added to the residue. After neutralization with 1N hydrochloric acid (3 ml), the mixture was extracted with ethyl acetate (25 ml×3). The combined ethyl acetate layers were washed with brine, dried over anhydrous magnesium sulfate, and concentrated to give 193 mg of a crude crystalline solid. Recrystallization of the crude crystal from ethyl acetate yielded 120 mg (0.297 mmol, 63.3%) of (17S)-17-methyl-20a-homo-2,5,6,7-tetranor-4-oxa-4,8-inter-m-phenylene PGI$_2$ as a white crystal. The compound was assigned the structure by the following data.

M.p.: 75°-77° C.

Optical rotation: $[\alpha]_D^{25} = +79.83°$ (c=0.238, methanol).

IR (KBr): 3580, 3420, 3250, 2970, 2930, 1760, 1740, 1630, 1600, 1500, 1470, 1440, 1380, 1350, 1300, 1240, 1200, 1170, 1120, 1040, 970, 940, 860, 830, 800, 770, 730, 610 cm$^{-1}$.

NMR (400 MHz, CDCl$_3$, δ): 0.85-1.0 (6H, m); 1.1-1.6 (9H, m); 1.9-2.0 (1H, m); 2.38 (1H, q, J=8.3 Hz); 2.55-2.7 (1H, m); 3.41 (1H, t, J=8.3 Hz); 3.5-4.0 (4H, m); 4.1-4.3 (1H, m); 4.63 (1H, d, J=16.1 Hz); 4.72 (1H, d, J=16.1 Hz); 5.1-5.2 (1H, m); 5.49 (1H, dd, J=7.6, 15.2 Hz); 5.59 (1H, dd, J=8.3, 15.2 Hz); 6.73 (3H, s).

MASS (EI, m/e): 404 (M+).

HR MASS: Calcd. (C$_{23}$H$_{32}$O$_6$, M+): 404.2199 Found (M+): 404.2222.

EXAMPLE 49

(17S)-17-Methyl-15-epi-20a-homo-2,5,6,7-tetranor-4-oxa-4,8-inter-m-phenylene PGI$_2$ (219)

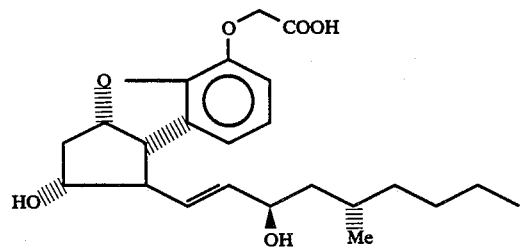

To a solution of (17S)-17-methyl-15-epi-20a-homo-2,5,6,7-tetranor-4-oxa-4,8-inter-m-phenylene PGI$_2$ methyl ester (200 mg, 0.478 mmol) in methanol (20 ml) was added 1N aqueous NaOH solution (3 ml, 3 mmol) and the reaction mixture was stirred for 3 hrs. at room temperature. The solution was concentrated and 15 ml of water was added to the residue. After neutralization with 1N hydrochloric acid (3 ml), the mixture was extracted with ethyl acetate (25 ml, 15 ml×2). The combined ethyl acetate layers were washed with brine, dried over anhydrous magnesium sulfate, and concentrated to give 188 mg of a crude crystalline solid. Recrystallization of the crude crystal from ethyl acetate/n-hexane yielded 91 mg (0.225 mmol, 47.1%) of (17S)-17-methyl-15-epi-20a-homo-2,5,6,7-tetranor-4-oxa-4,8-inter-m-phenylene PGI$_2$ as a white crystal. The compound was assigned the structure by the following data.

M.p.: 113°-114° C.

Optical rotation: $[\alpha]_D^{25} = +78.01°$ (c=0.232, methanol).

IR (KBr): 3450, 2970, 2940, 1730, 1620, 1600, 1490, 1470, 1420, 1380, 1280, 1200, 1170, 1120, 1100, 1030, 990, 970, 940, 900, 860, 800, 780, 740, 710, 630 cm$^{-1}$.

NMR (400 MHz, DMSO-d$_6$, δ): 0.8-1.0 (6H, m); 1.0-1.35 (7H, m); 1.4-1.5 (1H, m); 1.6-1.8 (2H, m); 2.16 (1H, q, J=8.1 Hz); 2.45-2.6 (1H, m); 3.35-3.45 (1H, m); 3.7-3.8 (1H, m); 3.95-4.1 (1H, m); 4.55-4.6 (1H, m); 4.63 (2H, s); 4.75-4.85 (1H, m); 5.0-5.1 (1H, m); 5.48 (1H, dd, J=6.1, 15.6 Hz); 5.62 (1H, dd, J=7.6, 15.6 Hz); 6.7-6.8 (3H, m).

MASS (EI, m/e): 404 (M+).

HR MASS: Calcd. (C$_{23}$H$_{32}$O$_6$, M+): 404.2199. Found (M+): 404.2193.

EXAMPLE 50

(8R, 9R, 11S, 12S, 15R, 17S)-17-Methyl-20a-homo-2,5,6,7-tetranor-4-oxa-4,8-inter-m-phenylene PGI$_2$ (220)

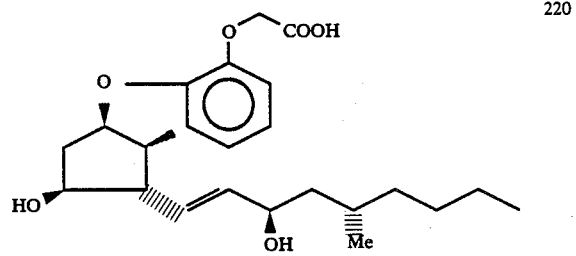

To a solution of (8R, 9R, 11S, 12S, 15R, 17S)-17-methyl-20a-homo-2,5,6,7-tetranor-4-oxa-4,8-inter-m-phenylene PGI$_2$ methyl ester (256 mg, 0.612 mmol) in methanol (20 ml) was added 1N aqueous NaOH solution (3 ml, 3 mmol) and the reaction mixture was stirred for 3 hrs. at room temperature. The solution was concentrated and 15 ml of water was added to the residue. After neutralization with 1N hydrochloric acid (3 ml), the mixture was extracted with ethyl acetate (25 ml, 15 ml×2). The combined ethyl acetate layers were washed with brine, dried over anhydrous magnesium sulfate, and concentrated to give 242 mg of a crude crystalline solid. Recrystallization of the crude crystal from ethyl acetate/n-hexane yielded 101.7 mg (0.252 mmol, 41.2%) of (8R, 9R, 11S, 12S, 15R, 17S)-17-methyl-20a-homo-2,5,6,7-tetranor-4-oxa-4,8-inter-m-phenylene PGI$_2$ as a white crystal. The compound was assigned the structure by the following data.

M.p.: 106°-107° C.

Optical rotation: $[\alpha]_D^{25} = -82.26°$ (c=0.282, methanol).

IR (KBr): 3350, 2960, 2940, 1750, 1700, 1620, 1590, 1490, 1470, 1440, 1290, 1200, 1170, 1120, 1030, 970, 860, 760, 730 cm$^{-1}$.

NMR (400 MHz, CDCl$_3$, δ): 0.90 (3H, t, J=6.6 Hz); 0.94 (3H, d, J=6.8 Hz); 1.1-1.4 (7H, m); 1.5-1.7 (2H, m); 1.9-2.1 (1H, m); 2.4-2.55 (1H, m); 2.6-2.7 (1H, m); 2.8-3.4 (3H, m); 3.4-3.5 (1H, m); 3.9-4.0 (1H, m); 4.2-4.3 (1H, m); 4.66 (1H, d, J=16.6 Hz); 4.73 (1H, d, J=16.6 Hz); 5.15-5.3 (1H, m); 5.5-5.7 (2H, m); 6.7-6.8 (3H, m).

MASS (EI, m/e): 404 (M+).

HR MASS: Calcd. (C$_{23}$H$_{32}$O$_6$, M+): 404.2199. Found (M+): 404.2224.

EXAMPLE 51

(8R, 9R, 11S, 12S, 15S, 17S)-17-Methyl-20a-homo-2,5,6,7-tetranor-4-oxa-4,8-inter-m-phenylene PGI₂ (221)

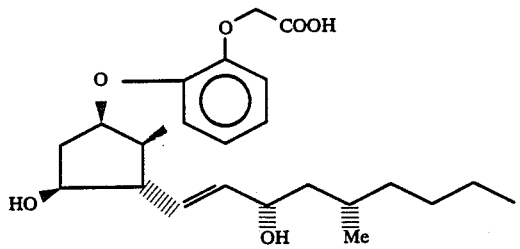

To a solution of (8R, 9R, 11S, 12S, 15S, 17S)-17-methyl-20a-homo-2,5,6,7-tetranor-4-oxa-4,8-inter-m-phenylene PGI₂ methyl ester (200 mg, 0.478 mmol) in methanol (20 ml) was added 1N aqueous NaOH solution (3 ml, 3 mmol) and the reaction mixture was stirred for 3 hrs. at room temperature. The solution was concentrated and 15 ml of water was added to the residue. After recyrstallization with 1N hydrochloric acid (3 ml), the mixture was extracted with ethyl acetate (25 ml, 15 ml×2). The combined ethyl acetate layers were washed with brine, dried over anhydrous magnesium sulfate, and concentrated to give 197 mg of a crude crystalline solid. Recrystallization of the crude crystal from ethyl acetate/n-hexane yielded 180 mg (0.446 mmol. 93.3%) of (8R, 9R, 11S, 12S, 15S, 17S)-17-methyl-20a-homo-2,5,6,7-tetranor-4-oxa-4,8-inter-m-phenylene PGI₂ as a white crystal. The compound was assigned the structure by the following data.

M.p.: 97°–98° C.

Optical rotation: $[\alpha]_D^{25} = -71.56°$ (c=0.204, methanol).

IR (KBr): 3370, 2970, 2940, 2870, 1770, 1750, 1730, 1700, 1620, 1590, 1490, 1470, 1440, 1380, 1280, 1200, 1170, 1120, 1030, 970, 950, 900, 860, 800, 780, 760, 730, 600, 570 cm⁻¹.

NMR (400 MHz, CDCl₃, δ): 0.90 (3H, t, J=6.8 Hz); 0.92 (3H, d, J=6.3 Hz); 1.1–1.6 (9H, m); 2.0–2.1 (1H, m); 2.5–2.7 (2H, m); 3.51 (1H, t, J=8.5 Hz); 3.6–3.9 (3H, m); 3.96 (1H, q, J=7.0 Hz); 4.2–4.3 (1H, m); 4.65 (1H, d, J=16.4 Hz); 4.72 (1H, d, J=16.4 Hz); 5.21 (1H, ddd, J=4.7, 7.3, 8.5 Hz); 5.6–5.8 (2H, m); 6.7–6.9 (3H, m).

MASS (EI, m/e): 404 (M⁺).

HR MASS: Calcd. (C₂₃H₃₂O₆, M⁺): 404.2199. Found (M⁺): 404.2208.

EXAMPLE 52 d-2,5,6,7-Tetranor-4-oxa-4,8-inter-m-phenylene PGI₂ methyl ester 222 and its 15-epimer 223

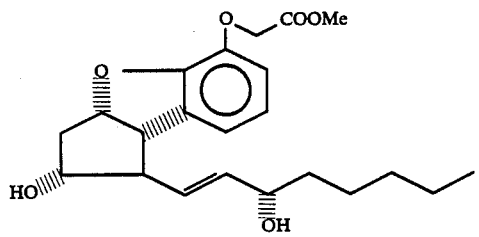

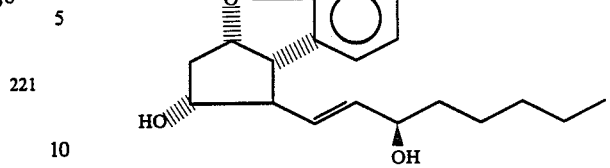

To a solution of d-15-oxo-2,5,6,7-tetranor-4-oxa-4,8-inter-m-phenylene PGI₂ methyl ester, 11-acetate (750 mg, 1.74 mmol) in methanol (50 ml) was added cerium trichloride heptahydrate (972 mg, 2.61 mmol) and the mixture was cooled to 0° C. Sodium borohydride (50 mg, 1.32 mmol) was added to the mixture. The mixture was then stirred for 10 min. and diluted with an aqueous saturated solution of sodium bicarbonate (10 ml). The mixture was filtered and the filtrate was concentrated. The concentrate was extracted with ethyl acetate (30 ml×3). The combined ethyl acetate layers were washed with water (30 ml), and with brine (30 ml), dried over anhydrous sodium sulfate, and concentrated to give an oil.

After azeotropic distillation of the oil with benzene, the residue was dissolved in anhydrous methanol (25 ml) under argon atmosphere. To the solution was added a solution of sodium methoxide in methanol (5.22N, 0.08 ml, 0.435 mmol) and the mixture was stirred overnight. The reaction mixture was neutralized with acetic acid and concentrated. The concentrate was diluted with water (20 ml) and the solution extracted with ethyl acetate (30 ml×3). The combined ethyl acetate layers were washed with brine (20 ml), dried over anhydrous sodium sulfate, and concentrated to give an oil. Column chromatography (Merck, Lobar column, silica gel, ethyl acetate/cyclohexane: 2/1) of the oil afforded less polar d-15-epi-2,5,6,7-tetranor-4-oxa-4,8-inter-m-phenylene PGI₂ methyl ester (239 mg, 0.61 mmol, 35.2%) and more polar d-2,5,6,7-tetranor-4-oxa-4,8-inter-m-phenylene PGI₂ methyl ester (224 mg, 0.57 mmol, 33.0%). These compounds were assigned the corresponding structures by the following data.

d-2,5,6,7-Tetranor-4-oxa-4,8-inter-m-phenylene PGI₂ methyl ester

Optical rotation $[\alpha]_D^{20} = +90.35$ (c=0.912, methanol).

M.p.: 88.5°–89.0° C.

IR (KBr): 3600–3200, 2970, 2940, 2865, 1735, 1620, 1595, 1495, 1465, 1435, 1360, 1310, 1290, 1270, 1245, 1200, 1170, 1140, 1115, 1100, 1070, 1050, 1025, 1015, 990, 890, 865, 830, 770, 735, 730 cm⁻¹.

NMR (400 MHz, CDCl₃, δ): 0.91 (3H, t, J=6.8 Hz); 1.25–1.40 (6H, m); 1.47–1.60 (2H, m); 1.93 (1H, bs); 2.05 (1H, ddd, J=4.9, 8.8, 14.0 Hz); 2.34 (1H, bs); 2.46 (1H, q, J=8.3 Hz); 2.64 (1H, ddd, J=6.4, 7.3, 14.0 Hz); 3.46 (1H, t, J=8.3 Hz); 3.79 (1H, s); 3.92–3.94 (1H, m); 4.72 (2H, s); 5.20 (1H, ddd, J=4.8, 7.3, 8.3 Hz); 5.56–5.67 (2H, m); 6.71–6.79 (3H, m).

MASS (EI, m/e): 390(M⁺).

HR MASS: Calcd. (C₂₂H₃₀O₆, M⁺): 390.2043. Found (M⁺): 390.2074.

d-15-Epi-2,5,6,7-tetranor-4-oxa-4,8-inter-m-phenylene PGI₂ methyl ester

Optical rotation: $[\alpha]_D^{20} = +69.45$ (c=0.838, methanol).

M.p.: 68.5°–69.5° C.

IR (KBr): 3700–3200, 2975, 2945, 2870, 1745, 1620, 1595, 1490, 1465, 1440, 1380, 1350, 1305, 1285, 1265, 1200, 1170, 1120, 1095, 1070, 1030, 1015, 965, 915, 895, 865, 860, 800, 780, 735 cm⁻¹.

NMR (400 MHz, CDCl₃, δ): 0.90 (3H, t, J=6.8 Hz); 1.24–1.50 (6H, m); 1.52–1.60 (3H, m); 1.80 (1H, bs); 2.08 (1H, ddd, J=4.9, 8.3, 13.2 Hz); 2.49–2.55 (1H, m); 2.59–2.66 (1H, m); 3.56 (1H, t, J=8.3 Hz); 3.78 (1H, s); 3.95–3.96 (1H, s); 4.14–4.18 (1H, m); 4.72 (2H, s); 5.22 (1H, ddd, J=4.9, 6.8, 8.3 Hz); 5.62–5.71 (2H, m); 6.71–6.82 (3H, m).

MASS (EI, m/e): 390(M+).

HR MASS: Calcd. (C₂₂H₃₀O₆, M+): 390.2043. Found (M+): 390.2045.

EXAMPLE 53 d-2,5,6,7-Tetranor-4-oxa-4,8-inter-m-phenylene PGI₂ 224

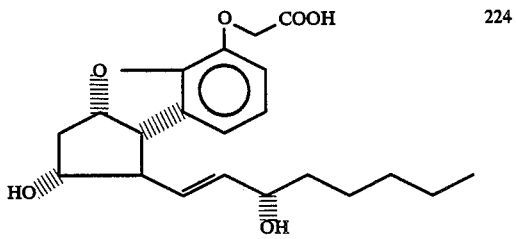

To a solution of d-2,5,6,7-tetranor-4-oxa-4,8-inter-m-phenylene PGI₂ methyl ester (130 mg, 0.33 mmol) in methanol (30 ml) was added 1N aqueous NaOH solution (2.6 ml, 2.6 mmol) and the reaction mixture was stirred for 3 hrs. at room temperature. The solution was neutralized with 1N hydrochloric acid (2.6 ml) and concentrated. The concentrate was extracted with ethyl acetate (50 ml, 30 ml×2). The combined ethyl acetate layers were washed with water (20 ml), and with brine (20 ml), dried over anhydrous sodium sulfate, and concentrated to give an oil. Recrystallization of the material from ethyl acetate/cyclohexane (1/1) gave d-2,5,6,7-tetranor-4-oxa-4,8-inter-m-phenylene PGI₂ (98 mg, 0.26 mmol, 79%) as a white crystal. The product was assigned the structure by the following data.

Optical rotation: $[\alpha]_D^{20} = +89.33$ (c=0.778, methanol).

M.p.: 128°–128.5° C.

IR (KBr): 3575, 3500–3100, 2965, 2935, 2870, 1760, 1735, 1660, 1615, 1590, 1490, 1460, 1435, 1350, 1295, 1240, 1205, 1105, 1075, 1025, 990, 965, 940, 920, 895, 865, 805, 795, 765, 725, 675 cm⁻¹.

NMR (400 MHz, CDCl₃/DMSO-d₆, δ): 0.91 (3H, t, J=7.1 Hz); 1.25–1.47 (8H, m); 1.91 (1H, ddd, J=5.3, 10.3, 13.2 Hz); 2.30 (1H, q, J=8.8 Hz); 2.58–2.65 (1H, m); 3.38–3.58 (3H, m); 3.84 (1H, dt, J=5.8, 8.8 Hz); 4.02 (1H, q, J=6.8 Hz); 4.2–4.4 (1H, m); 4.63 (2H, s); 5.10–5.16 (1H, m); 5.54 (1H, dd, J=6.8, 15.1 Hz); 5.61 (1H, dd, J=8.8, 15.1 Hz); 6.69–6.76 (3H, m).

MASS (EI, m/e): 376(M+).

HR MASS: Calcd. (C₂₁H₂₈O₆, M+): 376.1886. Found (M+): 376.1907.

EXAMPLE 54 d-16,16-Dimethyl-2,5,6,7-tetranor-4-oxa-4,8-inter-m-phenylene PGI₂ methyl ester 225 and its 15-epimer 226

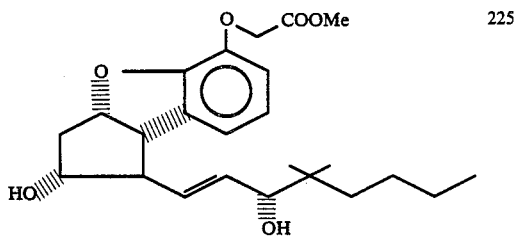

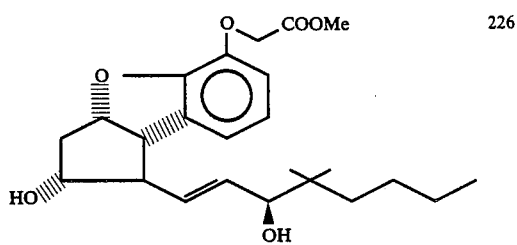

To a solution of d-16,16-dimethyl-15-oxo-2,5,6,7-tetranor-4-oxa-4,8-inter-m-phenylene PGI₂ methyl ester, 11-acetate (528 mg, 1.15 mmol) in methanol (50 ml) was added cerium trichloride heptahydrate (428 mg, 1.15 mmol) and the mixture was cooled to 0° C. Sodium borohydride (17 mg, 0.46 mmol) was added to the mixture. The resulting mixture was stirred for 10 min. and diluted with a saturated aqueous solution of sodium bicarbonate (10 ml). The mixture was filtered and the filtrate was concentrated. The residue was extracted with ethyl acetate (30 ml×3). The combined ethyl acetate layers were washed with water (30 ml) and with brine (30 ml), dried over anhydrous sodium sulfate, and concentrated. After azeotropic distillation of the oily residue with benzene, the resulting material was dissolved in anhydrous methanol (25 ml) under argon atmosphere. To the solution was added a solution of sodium methoxide in methanol (5.22N, 0.07 ml, 0.36 mmol) and the mixture was stirred overnight. The resulting mixture was neutralized with acetic acid, and concentrated. The residue was diluted with water (20 ml) and the mixture was extracted with ethyl acetate (30 ml×3). The combined ethyl acetate layers were washed with brine (20 ml), dried over anhydrous sodium sulfate, and concentrated to give an oil. Column chromatography (Merck, Lobar column, silica gel, ethyl acetate/cyclohexane: 2/1) of the oil gave less polar d-15-epi-16,16-dimethyl-2,5,6,7-tetranor-4-oxa-4,8-inter-m-phenylene PGI₂ methyl ester (153 mg, 0.37 mmol, 31.8%) and more polar d-16,16-dimethyl-2,5,6,7-tetranor-4-oxa-4,8-inter-m-phenylene PGI₂ methyl ester (149 mg, 0.36 mmol, 31.0%). These compounds were assigned the corresponding structures by the following data.

d-16,16-Dimethyl-2,5,6,7-tetranor-4-oxa-4,8-inter-m-phenylene PGI₂ methyl ester

Optical rotation: $[\alpha]_D^{20} = +96.32°$ (c=1.332, methanol).

M.p.: 46.5°–47.5° C.

IR (KBr): 3550, 3420, 3200, 2970, 2940, 2880, 1825, 1615, 1595, 1490, 1465, 1435, 1390, 1365, 1325, 1300, 1285, 1270, 1260, 1195, 1165, 1105, 1060, 1050, 1030, 1015, 980, 955, 870, 860, 840, 800, 770, 735 cm$^{-1}$.

NMR (400 MHz, CDCl$_3$, δ): 0.88 (3H, s); 0.91 (3H, s); 0.92–0.93 (3H, m); 1.25–1.31 (6H, m); 1.57 (1H, bs); 1.98 (1H, bs); 2.07 (1H, ddd, J=4.9, 8.8, 14.1 Hz); 2.51 (1H, q, J=7.8 Hz); 2.65 (1H, d, q, J=6.8, 14.1 Hz); 3.50 (1H, t, J=7.8 Hz); 3.79 (1H, s); 3.82–3.86 (1H, m); 3.96–4.02 (1H, m); 4.72 (2H, s); 5.19–5.24 (1H, m); 5.65 (1H, dd, J=7.3, 15.1 Hz); 5.69 (1H, dd, J=6.3, 15.1 Hz); 6.72–6.80 (3H, m).

MASS (EI, m/e): 418(M+).

HR MASS: Calcd. (C$_{24}$H$_{34}$O$_6$, M+): 418.2356. Found (M+): 418.2348.

d-15-Epi-16,16-dimethyl-2,5,6,7-tetranor-4-oxa-4,8-inter-m-phenylene PGI$_2$ methyl ester Optical rotation: $[\alpha]_D^{20}$= +61.94° (c=0.770, methanol).

M.p.: 83°–83.5° C.

IR (KBr): 3490, 2960, 2930, 2880, 2960, 1805, 1620, 1590, 1490, 1465, 1455, 1435, 1390, 1375, 1360, 1325, 1295, 1275, 1200, 1165, 1115, 1105, 1085, 1075, 1030, 1005, 980, 965, 945, 870, 805, 765, 740, 725 cm$^{-1}$.

NMR (400 MHz, CDCl$_3$, δ): 0.88 (3H, s); 0.90 (3H, s); 0.91 (3H, t, J=6.8 Hz); 1.21–1.35 (6H, m); 1.46 (1H, d, J=4.4 Hz); 1.67 (1H, d, J=5.4 Hz); 2.09 (1H, ddd, J=4.8, 8.3, 13.9 Hz); 2.55 (1H, q, J=7.3 Hz); 2.63 (1H, dt, J=6.8, 13.9 Hz); 3.51–3.55 (1H, m); 3.79 (3H, s); 3.89 (1H, t, J=5.4 Hz); 3.94–4.00 (1H, m); 4.73 (2H, s); 5.23 (1H, ddd, J=4.8, 6.8, 8.9 Hz); 5.67 (1H, dd, J=7.3, 15.1 Hz); 5.72 (1H, dd, J=5.4, 15.1 Hz); 6.72–6.83 (3H, m).

MASS (EI, m/e): 418(M+).

HR MASS: Calcd. (C$_{24}$H$_{34}$O$_6$, M+): 418.2356. Found (M+): 418.2378.

EXAMPLE 55 d-16,16-Dimethyl-2,5,6,7-tetranor-4-oxa-4,8-inter-m-phenylene PGI$_2$ 227

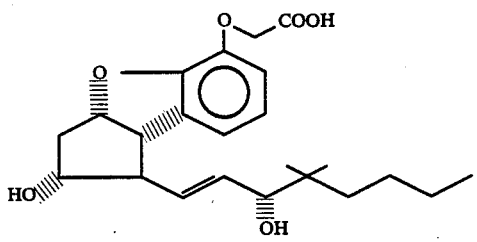

To a solution of d-16,16-dimethyl-2,5,6,7-tetranor-4-oxa-4,8-inter-m-phenylene PGI$_2$ methyl ester (93.4 mg, 0.22 mmol) in methanol (20 ml) was added 1N aqueous NaOH solution 1.8 ml, 1.8 mmol) and the reaction mixture was stirred for 3 hrs. at room temperature. The solution was neutralized with 1N hydrochloric acid (1.8 ml) and concentrated. The concentrate was extracted with ethyl acetate (50 ml, 30 ml×2). The combined ethyl acetate layers were washed with water (20 ml), and with brine (20 ml), dried over anhydrous sodium sulfate, and concentrated to give d-16,16-dimethyl-2,5,6,7-tetranor-4-oxa-4,8-inter-m-phenylene PGI$_2$ (85.7 mg, 0.21 mmol, 96.4%). The product was assigned the structure by the following data.

Optical rotation: $[\alpha]_D^{20}$= +91.48 (c=1.714, methanol).

IR (liquid film): 3700–3200, 2960, 2930, 2870, 1740, 1625, 1595, 1490, 1460, 1440, 1380, 1290, 1240, 1195, 1165, 1115, 1100, 1070, 1020, 965, 955, 890, 860, 835, 790, 765, 735 cm$^{-1}$.

NMR (400 MHz, CDCl$_3$, δ): 0.86 (3H, s); 0.89 (3H, s); 0.92 (3H, t, J=7.1 Hz); 1.19–1.32 (6H, m); 1.97–2.03 (1H, m); 2.45 (1H, q, J=8.3 Hz); 2.57–2.64 (1H, m); 3.44 (1H, t, J=8.3 Hz); 3.60–3.69 (3H, bs); 3.83 (1H, d, J=6.8 Hz); 3.88–3.94 (1H, m); 4.64 (1H, d, J=16.2 Hz); 4.71 (1H, d, J=16.2 Hz); 5.14–5.19 (1H, m); 5.59 (1H, dd, J=7.8, 15.1 Hz); 5.65 (1H, dd, J=6.8, 15.1 Hz); 6.71–6.77 (3H, m).

MASS (EI, m/e): 404(M+).

HR MASS: Calcd. (C$_{23}$H$_{32}$O$_6$, M+): 404.2198. Found (M+): 404.2174.

EXAMPLE 56

15-cyclopentyl-2,5,6,7,16,17,18,19,20-nonanor-4-oxa-4,8-inter-m-phenylene PGI$_2$ methyl ester (228) and its 15-epimer (229)

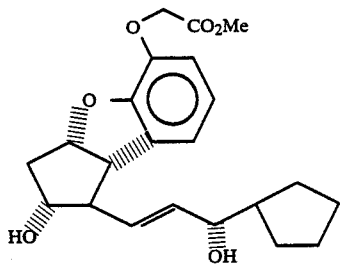

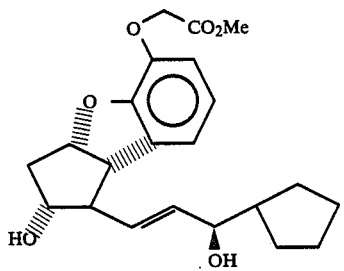

Cerium trichloride heptahydrate (1.19 g, 3.20 mmol) was dissolved into a solution of 15-cyclopentyl-15-oxo-2,5,6,7,16,17,18,19,20-nonanor-4-oxa-4,8-inter-m-phenylene PGI$_2$ methyl ester, 11-benzoate (1.57 g, 3.20 mmol) in 50 ml of methanol. While this solution was being stirred with ice-cooling, sodium borohydride (125.5 mg, 3.32 mmol) was added thereinto. The mixture was stirred for 1 hour. To the reaction mixture was added 10 ml of water and the solvent was distilled off. The residue was mixed with ethyl acetate (50 ml), and the resulting precipitate was filtered by Hyflo Super Cel. The precipitate was washed with ethyl acetate (50 ml×3). The combined ethyl acetate layer was washed with brine (100 ml), dried over anhydrous sodium sulfate and concentrated to give an oily product. This oily product was dried by azeotropic distillation with benzene (20 ml×3), and under reduced pressure, and dissolved into 100 ml of anhydrous methanol. Sodium methoxide (5.22N, 0.06 ml, 0.313 mmol) was added to this solution and the mixture was stirred overnight at room temperature under argon atmosphere. To this reaction mixture were added 3 droplets of acetic acid and 2 ml of a solution of diazomethane in ether. After concentration, 30 ml of water were added and the mixture was extracted with ethyl acetate (30 ml×4). The ethyl acetate layer was washed with brine (50 ml), dried over anhydrous sodium sulfate and concentrated to give an oily product.

This oily product was purified by column chromatography (silica gel, ethyl acetate/cyclohexane=4:1) to give less polar 15-cyclopentyl-15-epi-2,5,6,7,16,17,18,19,20-nonanor-4-oxa-4,8-inter-m-phenylene PGI$_2$ methyl ester (319.4 mg, 0.822 mmol) and more polar 15-cyclopentyl-2,5,6,7,16,17,18,19,20-nonanor-4-oxa-4,8-inter-m-phenylene PGI$_2$ methyl ester (297.0 mg, 0.765 mmol) in 49.6% yield. These compounds were assigned the corresponding structures by the following data:

α-isomer 15-cyclopentyl-2,5,6,7,16,17,18,19,20-nonanor-4-oxa-4,8-inter-m-phenylene PGI$_2$ methyl ester m.p. 108°–109° C. (recrystallized from ethyl acetate and cyclohexane; colorless needle-like crystal).

IR(KBr): 3410, 3350, 2950, 2875, 1738, 1623, 1595, 1493, 1465, 1433, 1385, 1310, 1280, 1245, 1203, 1175, 1108, 1078, 1035, 1017, 987, 965, 953, 906, 865, 821, 770, 738, 706 cm$^{-1}$.

NMR(400 MHz, CDCl$_3$, δ): 1.20;14 1.33(1H, m), 1.34–1.46(1H, m), 1.50–1.88(6H, m), 1.92–2.19(3H, m), 2.38–2.60(2H, m), 2.60–2.70(1H, m), 3.41–3.48(1H, m), 3.79(3H, s), 3.83–3.98(2H, m), 4.72(2H, s); 5.15–5.23(1H, m), 5.56–5.67(2H, m), 6.70–6.82(3H, m).

MASS(EI, m/e): 388(M+).

HR MASS: Calcd. (C$_{22}$H$_{28}$O$_6$, M+): 388.1885. Found (M+): 388.1912.

β-isomer 15-cyclohexyl-15-epi-2,5,6,7,16,17,18,19,20-nonanor-4-oxa-4,8-inter-m-phenylene PGI$_2$ methyl ester m.p. 105.5°–106.5° C. (recrystallized from ethyl acetate and cyclohexane; colorless needle-like crystal).

IR(KBr): 3485, 2935, 2880, 2865, 2825, 1701, 1618, 1595, 1481, 1461, 1428, 1393, 1379, 1325, 1313, 1301, 1281, 1263, 1261, 1200, 1163, 1111, 1068, 1031, 1006, 980, 945, 902, 890, 865, 829, 800, 760, 732, 722, 699, 665, 607 cm$^{-1}$.

NMR(400 MHz, CDCl$_3$, δ): 1.21–1.32(1H, m), 1.35–1.46(1H, m), 1.51–1.87(6H, m), 1.94–2.12(2H, m), 2.48–2.57(1H, m), 2.58–2.67(1H, m), 3.48–3.55(1H, m), 3.79(3H, s), 3.93–4.01(2H, m), 4.73(2H, s), 5.19–5.26(1H, m), 5.63–5.74(2H, m), 6.72–6.84(3H, m)

MASS(EI, m/e): 388(M+).

HR MASS: Calcd. (C$_{22}$H$_{28}$O$_6$, M+): 388.1885. Found (M+): 388.1870.

EXAMPLE 57

15-cyclopentyl-2,5,6,7,16,17,18,19,20-nonanor-4-oxa-4,8-inter-m-phenylene PGI$_2$ (230)

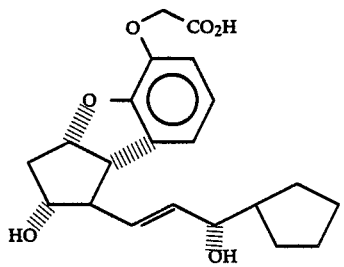

230

To a solution of 15-cyclopentyl-2,5,6,7,16,17,18,19,20-nonanor-4-oxa-4,8-inter-m-phenylene PGI$_2$ methyl ester (118.7 mg, 0.306 mmol) in 20 ml of methanol was added an aqueous solution of sodium hydroxide (1N, 0.92 ml, 0.918 mmol), and the mixture was stirred overnight at room temperature under argon atmosphere. Hydrochloric acid (1N, 0.92 ml) was added to the reaction mixture and methanol was distilled off. 10 ml of water was added and the mixture was extracted with ethyl acetate (30 ml×4). The combined ethyl acetate layer was washed with brine (30 ml), dried over anhydrous sodium sulfate and concentrated to give 115.0 mg of 15-cyclopentyl-2,5,6,7,16,17,18,19,20-nonanor-4-oxa-4,8-inter-m-phenylene PGI$_2$ as a single product (yield 100%). This compound was assigned the structure by the following data:

m.p. 152.5°–153° C. (recrystallized from acetone and n-hexane; colorless needle-like crystal).

IR(KBr): 3475, 3300, 2950, 2870, 1745, 1608, 1592, 1480, 1455, 1428, 1283, 1275, 1220, 1200, 1158, 1110, 1070, 1022, 980, 964, 942, 892, 857, 832, 790, 760, 730, 711 cm$^{-1}$.

NMR(CDCl$_3$, δ): 1.20–1.34(1H, m); 1.37–1.71(6H, m), 1.78–1.89(1H, m), 1.91–2.07(2H, m); 2.32–2.42(1H, m), 2.60–2.71(1H, m); 2.97–4.18(5H, broad m), 4.67(2H, s), 5.12–5.21(1H, m), 5.54–5.64(2H, m), 6.70–6.78(3H, m).

MASS(EI, m/e): 374(M+).

HR MASS: Calcd. (C$_{21}$H$_{26}$O$_6$, M+): 374.1729. Found (M+): 374.1734.

EXAMPLE 58

15-cyclopentyl-15-epi-2,5,6,7,16,17,18,19,20-nonanor-4-oxa-4,8-inter-m-phenylene PGI$_2$ (231)

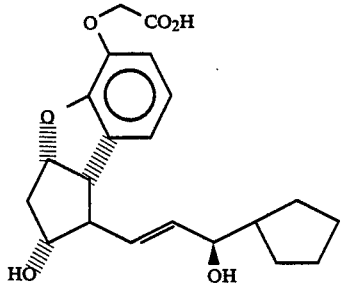

231

To a solution of 15-cyclopentyl-15-epi-2,5,6,7,16,17,18,19,20-nonanor-4-oxa-4,8-inter-m-phenylene PGI$_2$ methyl ester (121.5 mg, 0.313 mmol) in 20 ml of methanol was added an aqueous solution of sodium hydroxide (1N, 0.94 ml, 0.939 mmol), and the mixture was stirred overnight at room temperature under argon atmosphere. Hydrochloric acid (1N, 0.94 ml) was added to the reaction mixture and methanol was distilled off. 20 ml of water was added and the mixture was extracted with ethyl acetate (30 ml×4). The combined ethyl acetate layer was washed with brine (50 ml), dried over anhydrous sodium sulfate and concentrated to give 117.4 mg of 15-cyclopentyl-15-epi-2,5,6,7,16,17,18,19,20-nonanor-4-oxa-4,8-inter-m-phenylene PGI$_2$ as a single product (yield 100%), which was assigned the structure by the following data:

m.p. 151°–152° C. (recrystallized from acetone and n-hexane; colorless needle-like crystal).

IR(KBr): 3360, 2945, 1733, 1703, 1615, 1588, 1482, 1455, 1420, 1353, 1315, 1275, 1189, 1162, 1120, 1102, 1060, 1020, 992, 955, 929, 880, 850, 820, 790, 775, 737, 720, 625, 600 cm$^{-1}$.

NMR(CDCl$_3$, δ): 1.23–1.35(1H, m), 1.38–1.72(6H, m), 1.74–1.88(1H, m), 1.94–2.08(2H, m), 2.40–2.49(1H, m), 2.55–2.68(1H, m), 3.20–4.40(5H, broad m), 4.66(2H, s), 5.13–5.21(1H, m), 5.65–5.78(2H, m), 6.68–6.84(3H, m).

MASS(EI, m/e): 374(M+).

HR MASS: Calcd. (C$_{21}$H$_{26}$O$_6$, M+): 374.1729. Found (M+): 374.1748.

EXAMPLE 59

15-cyclohexyl-2,5,6,7,16,17,18,19,20-nonanor-4-oxa-4,8-inter-m-phenylene PGI$_2$ methyl ester (232) and its 15-epimer (233)

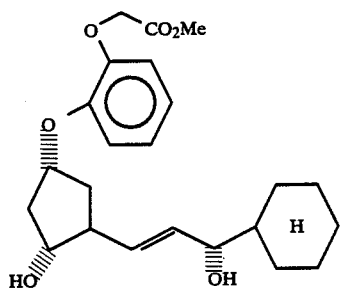

232

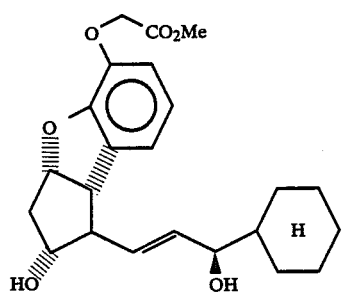

233

Cerium trichloride heptahydrate (1.14 g, 3.07 mmol) was dissolved into a solution of 15-cyclohexyl-15oxo-2,5,6,7,16,17,18,19,20-nonanor-4-oxa-4,8-inter-m-phenylene PGI$_2$ methyl ester, 11-benzoate (1.55 g, 3.97 mmol) in 50 ml of methanol. While this solution was being stirred at −20° C., sodium borohydride (108.7 mg, 2.87 mmol) was added thereinto, and the mixture was stirred for 1 hour. 10 ml of water was added to the reaction mixture and the solvent was distilled off. The residue was mixed with ethyl acetate (50 ml), and the resulting precipitate was filtered by Hyflo Super Cel. The precipitate was washed with ethyl acetate (50 ml×3). The combined ethyl acetate layer was washed with brine (100 ml), dried over anhydrous sodium sulfate and concentrated to give an oily product. This oily product was dried by azeotropic distillation with benzene (20 ml×3), and further dried under reduced pressure and dissolved into 50 ml of anhydrous methanol. To this solution was added sodium methoxide (5.22N, 0.05 ml, 0.261 mmol) and the mixture was stirred overnight at room temperature under argon atmosphere. To the reaction mixture were added 0.1 ml of acetic acid and 10 ml of a solution of diazomethane in ether. After concentration, 30 ml of water was added and the mixture was extracted with ethyl acetate (30 ml×4). The ethyl acetate layer was washed with brine (50 ml), dried over anhydrous sodium sulfate and concentrated to give an oily product. This oily product was separated and purified through column chromatography (silica gel, ethyl acetate/cyclohexane=5:1) to give less polar 15-cyclohexyl-15-epi-2,5,6,7,16,17,18,19,20-nonanor-4-oxa-4,8-inter-m-phenylene PGI$_2$ methyl ester (239.8 mg, 0.596 mmol) and more polar 15-cyclohexyl-2,5,6,7,16,17,18,19,20-nonanor-4-oxa-4,8-inter-m-phenylene PGI$_2$ methyl ester (207.8 mg, 0.516 mmol) in 36.2% yield. These compounds were assigned the corresponding structures by the following data:

α-isomer 15-cyclohexyl-2,5,6,7,16,17,18,19,20-nonanor-4-oxa-4,8-inter-m-phenylene PGI$_2$ methyl ester m.p. 91°–92° C. (recrystallized from ethyl acetate and cyclohexane; colorless needle-like crystal).

IR(KBr): 3360, 2920, 2860, 1769, 1732, 1609, 1587, 1483, 1459, 1434, 1364, 1293, 1236, 1196, 1178, 1113, 1103, 1066, 1027, 1007, 981, 975, 950, 920, 908, 890, 860, 827, 805, 783, 758, 722, 700, 680, 608 cm$^{-1}$.

NMR(400 MHz, CDCl$_3$, δ): 0.93–1.97(12H, m), 2.00–2.10(1H, m), 2.34–2.42(1H, m), 2.43–2.51(1H, m), 2.60–2.69(1H, m), 3.44–3.51(1H, m), 3.79(3H, s), 3.80–3.98(2H, m), 4.72(2H, s), 5.15–5.24(1H, m), 5.55–5.66(2H, m), 6.70–6.83(3H, m).

MAS(EI, m/e): 402(M+).

HR MASS: Calcd. (C$_{23}$H$_{30}$O$_6$, M+): 402.2042. Found (M+): 402.2052.

β-isomer 15-cyclohexyl-15-epi-2,5,6,7,16,17,18,19,20-nonanor-4-oxa-4,8-inter-m-phenylene PGI$_2$ methyl ester m.p. 102.5°–103.5° C. (recrystallized from ethyl acetate and cyclohexane; colorless needle-like crystal).

IR(KBr): 3380, 2920, 2845, 1735, 1615, 1590, 1482, 1456, 1431, 1375, 1297, 1275, 1260, 1193, 1163, 1108, 1092, 1060, 1018, 1003, 963, 888, 858, 827, 796, 771, 728, 656, 610 cm$^{-1}$.

NMR(400 MHz, CDCl$_3$, δ): 0.94–1.90(13H, m), 2.04–2.13(1H, m), 2.50–2.67(2H, m), 3.48–3.56(1H, m), 3.79(3H, s), 3.87–4.01(2H, m), 4.72(2H, s), 5.19–5.27(1H, m), 5.61–5.71(2H, m), 6.70–6.85(3H, m).

MASS(EI, m/e): 402(M+).

HR MASS: Calcd. (C$_{23}$H$_{30}$O$_6$, M+): 402.2042. Found (M+): 402.2051.

EXAMPLE 60

15-cyclohexyl-2,5,6,7,16,17,18,19,20-nonanor-4-oxa-4,8-inter-m-phenylene PGI$_2$ (234)

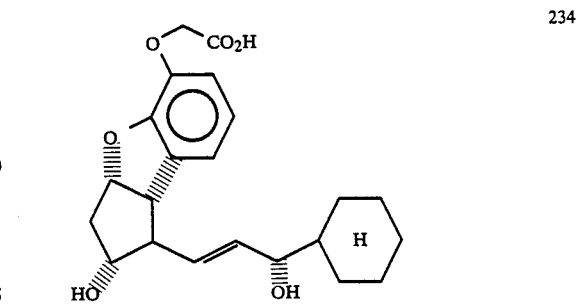

234

To a solution of 15-cyclohexyl-2,5,6,7,16,7,18,19,20-nonanor-4-oxa-4,8-inter-m-phenylene PGI$_2$ methyl ester (119.1 mg, 0.296 mmol) in 20 ml of methanol was added an aqueous solution of sodium hydroxide (1N, 0.89 ml, 0.888 mmol), and the mixture was stirred overnight at room temperature under argon atmosphere. Hydrochloric acid (1N, 0.89 ml) was added to the reaction mixture and methanol was distilled off. 10 ml of water was added and the mixture was extracted with ethyl acetate (30 ml×4). The combined ethyl acetate layer was washed with brine (50 ml), dried over anhydrous sodium sulfate and concentrated to give 105.3 mg of 15-cyclohexyl-2,5,6,7,16,17,18,19,20-nonanor-4-oxa-4,8-inter-m-phenylene PGI$_2$ as a single product (yield 91.6%), which was assigned the structure by the following data:

m.p. 138°-139° C. (recrystallized from acetone and n-hexane; colorless needle-like crystal).

IR(KBr): 3380, 2925, 2860, 1755, 1740, 1612, 1595, 1483, 1450, 1433, 1305, 1278, 1253, 1201, 1161, 1110, 1068, 1027, 1001, 969, 939, 917, 891, 857, 829, 792, 783, 729, 711 cm$^{-1}$.

NMR(400 MHz,

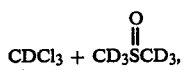

δ): 0.92–1.47(5H, m), 1.63–1.82(5H, m), 1.88–1.97(1H, m), 1.97–2.07(1H, m), 2.34–2.43(1H, m), 2.62–2.71(1H, m), 3.10–4.00(5H, broad m), 4.67(2H, s), 5.13–5.22(1H, m), 5.53–5.63(2H, m), 6.71–6.84(3H, m).

MASS(EI, m/e): 388(M+).

HR MASS: Calcd. (C$_{22}$H$_{28}$O$_6$, M+): 388.1886. Found (M+): 388.1911.

EXAMPLE 61

15-cyclohexyl-15-epi-2,5,6,7,16,17,18,19,20-nonanor-4-oxa-4,8-inter-m-phenylene PGI$_2$ (235)

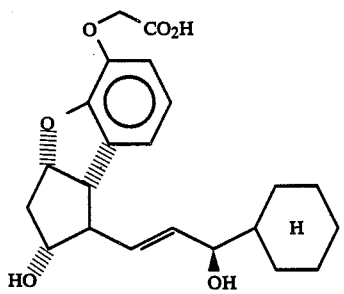

To a solution of 15-cyclohexyl-15-epi-2,5,6,7,16,17,18,19,20-nonanor-4-oxa-4,8-inter-m-phenylene PGI$_2$ methyl ester (124.6 mg, 0.310 mmol) in 20 ml of methanol was added an aqueous solution of sodium hydroxide (1N, 0.93 ml, 0.929 mmol), and the mixture was stirred overnight at room temperature under argon atmosphere. Hydrochloric acid (1N, 0.93 ml) was added to the reaction mixture and methanol was distilled off. 10 ml of water was added and the mixture was extracted with ethyl acetate (30 ml×4). The combined ethyl acetate layer was washed with brine (50 ml), dried over anhydrous sodium sulfate and concentrated to give 105.3 mg of 15-cyclohexyl-15-epi-2,5,6,7,16,17,18,19,20-nonanor-4-oxa-4,8-inter-m-phenylene PGI$_2$ as a single product (yield 87.4%), which was assigned the structure by the following data:

m.p. 170° C. (recrystallized from acetone and n-hexane; colorless needle-like crystal).

IR(KBr): 3350, 2915, 2845, 1734, 1704, 1614, 1589, 1482, 1464, 1454, 1419, 1354, 1317, 1275, 1190, 1181, 1116, 1060, 1016, 996, 980, 957, 929, 884, 849, 819, 789, 774, 732, 719, 624 cm$^{-1}$.

NMR(400 MHz,

δ): 0.94–1.35(5H, m), 1.38–1.49(1H, m), 1.63–1.82(4H, m), 1.83–1.92(1H, m), 2.01–2.10(1H, m), 2.47–2.54(1H, m), 2.57–2.66(1H, m), 2.80–3.85(3H, broad m), 3.85–3.97(2H, m), 4.63–4.73(2H, m), 5.17–5.23(1H, m), 5.63–5.74(2H, m), 6.70–6.86(3H, m).

MASS(EI, m/e): 388(M+).

HR MASS: Calcd. (C$_{22}$H$_{28}$O$_6$, M+): 388.1886. Found (M+): 388.1881.

EXAMPLE 62

16-cyclopentyl-2,5,6,7,17,18,19,20-octanor-4-oxa-4,8-inter-m-phenylene PGI$_2$ methyl ester (236) and its 15-epimer (237)

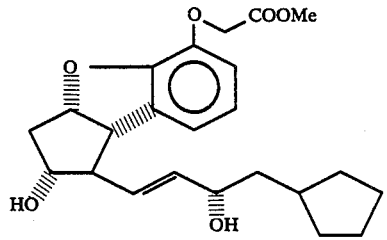

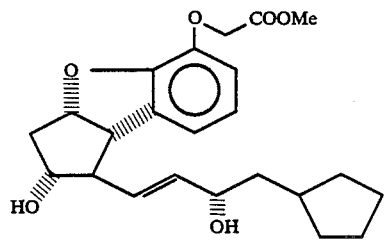

Cerium trichloride heptahydrate (1.35 g, 3.61 mmol) was dissolved into a solution of 16-cyclopentyl-15-oxo-2,5,6,7,17,18,19,20-octanor-4-oxa-4,8-inter-m-phenylene PGI$_2$ methyl ester, 11-benzoate (1.8217 g, 3.61 mmol) in 50 ml of methanol. While this solution was being stirred with ice-cooling, sodium borohydride (54.5 g, 1.44 mmol) was added thereinto, and the mixture was stirred for 30 minutes. To the reaction mixture was added 10 ml of water. After concentration, 10 ml of water was added and the mixture was extracted with ethyl acetate (50 ml×3). The combined organic layers were washed with water (100 ml) and brine (100 ml), dried over anhydrous sodium sulfate and concentrated to give 1.31 g of an oily product.

This oily product was dissolved into 40 ml of anhydrous methanol, and to this solution was added 5.22N sodium methoxide (50 µl, 0.26 mmol). The mixture was stirred overnight at room temperature under argon stream.

The reaction mixture was mixed with 0.1 ml of acetic acid and concentrated. 30 ml of water was added and the mixture was extracted with ethyl acetate (30 ml×3).

The combined organic layers were washed with water (60 ml) and brine (60 ml), dried over anhydrous sodium sulfate and concentrated to give 1.21 g of an oily product. This oily product was purified by column chromatography (silica gel, ethyl acetate/cyclohexane=6/1) to give as first eluted fraction less polar 16-cyclopentyl-15-epi-2,5,6,7,17,18,19,20-octanor-4-oxa-4,8-inter-m-phenylene $PGI_2$ methyl ester (435 mg, 1.08 mmol) in a yield of 30.0%, and as second eluted fraction more polar 16-cyclopentyl-2,5,6,7,17,18,19,20-octanor-4-oxa-4,8-inter-m-phenylene $PGI_2$ methyl ester (407.6 mg, 1.01 mmol) in 28.1% yield.

These compounds were assigned the corresponding structures by the following data:

16-cyclopentyl-2,5,6,7,17,18,19,20-octanor-4-oxa-4,8-inter-m-phenylene $PGI_2$ methyl ester m.p. 105.0°–106.0° C. (recrystallized from ethyl acetate).

IR(KBr): 3300, 2950, 2925, 2855, 1765, 1735, 1613, 1598, 1480, 1459, 1365, 1320, 1282, 1203, 1185, 1160, 1112, 1080, 1063, 1043, 1024, 970, 940, 892, 855, 825, 778, 755, 720, 680, 608, 530 cm$^{-1}$.

NMR(400 MHz, CDCl$_3$, δ): 1.03–1.30(2H, m), 1.45–1.76(8H, m), 1.76–1.95(3H, m), 2.03–2.15(1H, m), 2.42–2.55(1H, m), 2.58–2.69(1H, m), 3.45–3.54(1H, m), 3.79(3H, s), 3.92–4.00(1H, m), 4.09–4.22(1H, m), 4.72(2H, s), 5.15–5.29(1H, m), 5.60–5.75(2H, m), 6.70–6.90(3H, m).

MASS(EI, m/e): 402(M+).

HR MASS: Calcd. (C$_{23}$H$_{30}$O$_6$, M+): 402.2042. Found (M+): 402.2065.

16-cyclopentyl-15-epi-2,5,6,7,17,18,19,20-octanor-4-oxa-4,8-inter-m-phenylene $PGI_2$ methyl ester m.p. 72.5°–74.0° C. (recrystallized from ethyl acetate/n-hexane=1/2).

IR(KBr): 3325, 2940, 2860, 1755, 1735, 1618, 1591, 1488, 1460, 1375, 1330, 1308, 1275, 1220, 1192, 1118, 1070, 1018, 976, 958, 890, 860, 830, 760, 725, 700, 555 cm$^{-1}$.

NMR(400 MHz, CDCl$_3$, δ): 1.05–1.20(2H, m), 1.45–1.71(8H, m), 1.75–1.96(3H, m), 2.05–2.15(1H, m), 2.48–2.57(1H, m), 2.57–2.67(1H, m), 3.48–3.56(1H, m), 3.79(3H, s), 3.94–4.03(1H, m), 4.16–4.23(1H, broad s), 4.73(2H, s), 5.18–5.28(1H, m), 5.65–5.75(2H, m), 6.70–6.85(3H, m).

MASS(EI, m/e): 402(M+).

HR MASS: Calcd. (C$_{23}$H$_{30}$O$_6$, M+): 402.2042. Found (M+): 402.2056.

EXAMPLE 63

16-cyclopentyl-2,5,6,7,17,18,19,20-octanor-4-oxa-4,8-inter-m-phenylene $PGI_2$ (238)

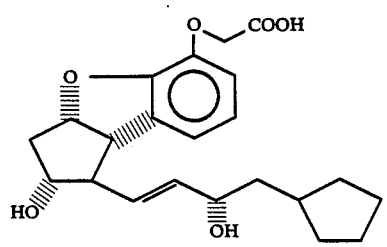

238

To a solution of 16-cyclopentyl-2,5,6,7,17,18,19,20-octanor-4-oxa-4,8-inter-m-phenylene $PGI_2$ methyl ester (199.5 mg, 0.496 mmol) in 20 ml of methanol was added 1N aqueous solution of sodium hydroxide (1.5 ml, 1.5 mmol), and the mixture was stirred overnight at room temperature under argon stream, 1N hydrochloric acid (1.5 ml, 1.5 mmol) and 30 ml of water were added to the reaction mixture, and the mixture was extracted with ethyl acetate (30 ml×3). The combined organic layers were washed with water (50 ml) and brine (50 ml), dried over anhydrous sodium sulfate and concentrated to give quantitatively 16-cyclopentyl-2,5,6,7,17,18,19,20-octanor-4-oxa-4,8-inter-m-phenylene $PGI_2$ (184.0 mg, 0.474 mmol) as a single product. This compound was assigned the structure by the following data:

m.p. 156.0°–157.0° C. (recrystallized from THF/n-hexane=1/2).

IR(KBr): 3380, 2940, 2860, 1760, 1740, 1613, 1585, 1484, 1430, 1280, 1200, 1160, 1112, 1080, 1025, 980, 960, 938, 885, 820, 785, 760, 728 cm$^{-1}$.

NMR(400 MHz, CDCl$_3$, δ): 1.08–1.22(2H, m), 1.47–1.71(6H, m), 1.75–1.95(1H, m), 1.95–2.06(1H, m), 2.31–2.42(1H, m), 2.60–2.62(1H, m), 2.62–2.73(1H, m), 3.37–3.47(1H, m), 3.55–4.05(2H, m), 4.05–4.16(1H, m), 4.66(2H, s), 5.13–5.20(1H, m), 5.55–5.68(2H, m), 6.66–6.78(3H, m).

MASS(EI, m/e): 388(M+).

HR MASS: Calcd. (C$_{22}$H$_{28}$O$_6$, M+): 388.1885. Found (M+): 388.1891.

EXAMPLE 64

16-cyclohexyl-2,5,6,7,17,18,19,20-octanor-4-oxa-4,8-inter-m-phenylene $PGI_2$ methyl ester (239) and its 15-epimer (240)

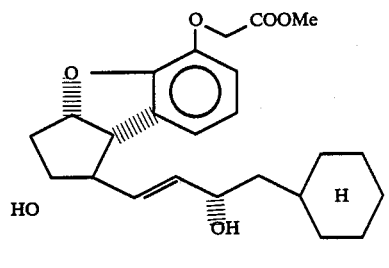

239

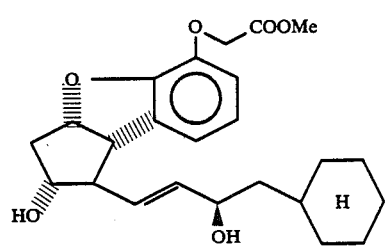

240

Cerium trichloride heptahydrate (1.14 g, 3.05 mmol) was dissolved into a solution of 16-cyclohexyl-15-oxo-2,5,6,7,17,19,20-octanor-4-oxa-4,8-inter-m-phenylene $PGI_2$ methyl ester, 11-benzoate (1.5917 g, 3.05 mmol) in 50 ml of methanol. While this solution was being stirred with ice-cooling, sodium borohydride (34.7 mg, 0.92 mmol) was added thereinto and the mixture was stirred for 10 minutes. To the reaction mixture was added 10 ml of water. After concentration, 10 ml of water was added and the mixture was extracted with ethyl acetate (50 ml×3). The combined organic layers were washed with water (100 ml) and brine (100 ml), dried over anhydrous sodium sulfate and concentrated to give 1.54 g of an oily product.

This oily product was dissolved into 40 ml of anhydrous methanol. To this solution was added 5.22N sodium methoxide (54 μl, 0.28 mmol). The mixture was stirred overnight at room temperature under argon stream.

This reaction mixture was combined with 0.1 ml of acetic acid and concentrated. 30 ml of water was added and the mixture was extracted with ethyl acetate (30 ml×3). The combined organic layers were washed with water (60 ml) and brine (60 ml), dried over anhydrous sodium sulfate and concentrated to give 1.15 g of an oily product. This oily product was purified by column chromatography (silica gel, ethyl acetate/cyclohexane=6/1) to give as first eluted fraction less polar 16-cyclohexyl-15-epi-2,5,6,7,17,18,19,20-octanor-4-oxa-4,8-inter-m-phenylene PGI$_2$ methyl ester (456.2 mg, 1.10 mmol) in a yield Of 35.9%, and as second eluted fraction more polar 16-cyclohexyl-2,5,6,7,17,18,19,20-octanor-4-oxa-4,8-inter-m-phenylene PGI$_2$ methyl ester (501.4 mg, 1.21 mmol) in 39.5% yield.

These compounds were assigned the corresponding structures by the following data:

16-cyclohexyl-2,5,6,7,17,18,19,20-octanor-4-oxa-4,8-inter-m-phenylene PGI$_2$ methyl ester m.p. 122.5°–123.0° C. (recrystallized from acetone/n-hexane-3/1).

IR(KBr): 3400, 2920, 2850, 1762, 1735, 1620, 1590, 1490, 1460, 1432, 1280, 1260, 1240, 1198, 1110, 1023, 1002, 962, 861, 762, 605, 520 cm$^{-1}$.

NMR(400 MHz, CDCl$_3$, δ): 0.88–1.04(2H, m), 1.11–1.32(3H, m), 1.32–1.56(3H, m), 1.62–1.83(6H, m), 2.02–2.10(1H, m), 2.10–2.25(1H, broad s), 2.43–2.52(1H, m), 2.61–2.70(1H, m), 3.44–3.50(1H, m), 3.79(3H, s), 3.91–4.00(1H, broad s), 4.21–4.29(1H, broad s), 4.72(2H, s), 5.17–5.25(1H, m), 5.57–5.70(2H, m), 6.73–6.82(3H, m).

MASS(EI, m/e): 416(M+).

HR MASS: Calcd. (C$_{24}$H$_{32}$O$_6$, M+): 416.2199. Found (M+): 416.2183.

16-cyclohexyl-15-epi-2,5,6,7,17,18,19,20-octanor-4-oxa-4,8-inter-m-phenylene PGI$_2$ methyl ester m.p. 78.5–81.0° C. (recrystallized from acetone/n-hexane=1/2).

IR(KBr): 3260, 2910, 2845, 1738, 1612, 1583, 1480, 1442, 1356, 1302, 1282, 1265, 1237, 1197, 1155, 1108, 1072, 1017, 988, 963, 940, 880, 957, 840, 822, 778, 753, 720, 655 cm$^{-1}$.

NMR(400 MHz, CDCl$_3$, δ): 0.88–1.04(2H, m), 1.10–1.32(3H, m), 1.32–1.55(4H, m), 1.62–1.84(6H, m), 2.40–2.51(1H, m), 2.51–2.59(1H, m), 2.60–2.68(1H, m), 3.50–3.56(1H, m), 3.79(3H, s), 3.94–4.02(1H, m), 4.24–4.31(1H, broad s), 4.72(2H, s), 5.20–5.27(1H, m), 5.63–5.75(2H, m), 6.72–6.86(3H, m).

MASS(EI, m/e): 416(M+).

HR MASS: Calcd. (C$_{24}$H$_{32}$O$_6$, M+): 416.2199. Found (M+): 416.2186.

EXAMPLE 65

16-cyclohexyl-2,5,6,7,17,18,19,20-octanor-4-oxa-4,8-inter-m-phenylene PGI$_2$ (241)

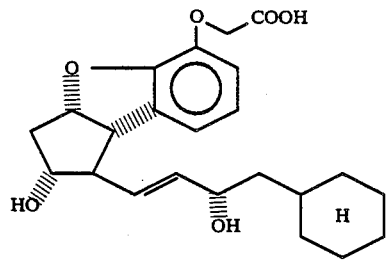

To a solution of 16-cyclohexyl-2,5,6,7,17,18,19,20-octanor-4-oxa-4,8-inter-m-phenylene PGI$_2$ methyl ester (253.0 mg, 0.61 mmol) in 20 ml of methanol was added 1N aqueous solution of sodium hydroxide (1.8 ml, 1.8 mmol), and the mixture was stirred overnight at room temperature under argon stream. To this reaction mixture were added 1.8 ml of 1N hydrochloric acid and 30 ml of water, and the mixture was extracted with ethyl acetate (30 ml×3). The combined organic layers were washed with water (50 ml) and brine (50 ml), dried over anhydrous sodium sulfate and concentrated to give quantitatively 16-cyclohexyl-2,5,6,7,17,18,19,20-octanor-4-oxa-4,8-inter-m-phenylene PGI$_2$ (244.2 mg, 0.61 mmol) as a single product, which was assigned the structure by the following data:

m.p. 162.0°–163.0° C. (recrystallized from ethyl acetate/n-hexane=3/1).

IR(KBr): 3380, 2920, 2848, 1768, 1735, 1610, 1585, 1480, 1428, 1282, 1250, 1192, 1110, 1073, 1015, 973, 940, 882, 858, 820, 782, 758, 725, 600, 520 cm$^{-1}$.

NMR(400 MHz, CDCl$_3$, δ): 0.88–1.03(2H, m), 1.22–1.37(4H, m), 1.37–1.56(2H, m), 1.62–1.88(5H, m), 1.86–2.06(1H, m), 2.31–2.40(1H, m), 2.62–2.70(1H, m), 3.20–3.60(3H, m), 3.78–3.91(1H, m), 4.15–4.23(1H, m), 4.67(2H, s), 5.12–5.20(1H, m), 5.51–5.65(2H, m), 6.70–6.78(3H, m).

MASS(EI, m/e): 402(M+).

HR MASS: Calcd. (C$_{23}$H$_{30}$O$_6$, M+): 402.2042. Found (M+): 402.2021.

EXAMPLE 66

17-cyclohexyl-2,5,6,7,18,19,20-heptanor-4-oxa-4,8-inter-m-phenylene PGI$_2$ methyl ester (242) and its 15-epimer (243)

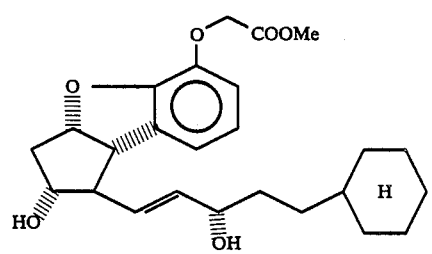

-continued

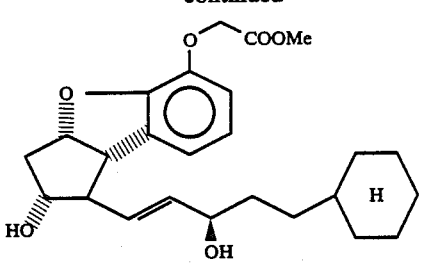

243

Cerium trichloride heptahydrate (1.4158 g, 3.80 mmol) was dissolved into a solution of 17-cyclohexyl-15-oxo-2,5,6,7,18,19,20-heptanor-4-oxa-4,8-inter-m-phenylene PGI₂ methyl ester, 11-benzoate (2.0237 g, 3.80 mmol) in 50 ml of methanol. While this solution was being stirred at −10° C., sodium borohydride (48.0 mg, 1.14 mmol) was added thereinto, and the mixture was stirred for 10 minutes. 50 ml of water was further added and the mixture was stirred for 10 minutes. The reaction mixture was concentrated and the residue was extracted with ethyl acetate (40 ml×3). The combined organic layers were washed with 100 ml of water and 100 ml of brine, dried over anhydrous sodium sulfate (35 g) and concentrated to give 2.0312 g of an oily product.

This oily product was dried by aceotropic distillation with benzene (10 ml×2) and dissolved into 15 ml of anhydrous methanol. 5.22N sodium methoxide (0.07 ml, 0.38 mmol) was added to the solution, which was then stirred overnight at room temperature under argon stream. The reaction mixture was treated with 0.1 ml of acetic acid and concentrated. 15 ml of water was added to the residue, which was extracted with ethyl acetate (15 ml×3). The combined organic layers were washed with 50 ml of water and 50 ml of brine, dried over anhydrous sodium sulfate (30 g) and concentrated to give 1.9191 g of an oily product. This oily product was purified by column chromatography (silica gel, ethyl acetate/cyclohexane=3:1), to give at first less polar 17-cyclohexyl-15-epi-2,5,6,7,18,19,20-heptanor-4-oxa-4,8-inter-m-phenylene PGI₂ methyl ester (613.2 mg, 1.43 mmol) in a yield of 38%. This product was recrystallized from ethyl acetate/cyclohexane (1:1) to yield colorless needle-like crystals. Then, more polar 17-cyclohexyl-2,5,6,7,18,19,20-heptanor-4-oxa-4,8-inter-m-phenylene PGI₂ methyl ester (557.3 mg, 1.30 mmol) was yielded in 34% yield. This was recrystallized from ethyl acetate/cyclohexane (1:1) to yield colorless needle-like crystals. These compounds were assigned the corresponding structures by the following data:

17-cyclohexyl-2,5,6,7,18,19,20-heptanor-4-oxa-4,8-inter-m-phenylene PGI₂ methyl ester m.p. 99°–100° C.

IR(KBr): 3425, 2910, 2850, 1739, 1603, 1582, 1482, 1451, 1428, 1402, 1367, 1335, 1300, 1274, 1260, 1240, 1190, 1272, 1105, 1023, 1001, 971, 886, 864, 840, 825, 803, 764, 727, 616, 608 cm⁻¹.

NMR(400 MHz, CDCl₃, δ): 0.84–0.95(2H, m), 1.11–1.35(6H, m), 1.48–1.76(7H, m), 1.76–1.81(1H, broad s), 2.01–2.09(1H, m), 2.08–2.13(1H, broad s), 2.44–2.52(1H, m), 2.62–2.68(1H, m), 3.47(1H, t, J=8.3 Hz), 3.79(3H, s), 3.92–3.99(1H, m), 4.06–4.13(1H, m), 4.73(2H, s), 5.16–5.23(1H, m), 5.58–5.68(2H, m), 6.73–6.83(3H, m).

MASS(EI, m/e): 430(M⁺).

HR MASS: Calcd. (C₂₅H₃₄O₆, M⁺) 430.2355. Found (M⁺) 430.2340.

17-cyclohexyl-15-epi-2,5,6,7,18,19,20-pentanor-4-oxa-4,8-inter-m-phenylene PGI₂ methyl ester m.p. 104.5–105° C.

IR(KBr): 3300, 2905, 2850, 1740, 1618, 1580, 1481, 1452, 1443, 1345, 1310, 1292, 1271, 1202, 1181, 1162, 1109, 1072, 1023, 998, 965, 943, 882, 863, 844, 825, 783, 760, 724, 660 cm⁻¹.

NMR(400 MHz, CDCl₃, δ): 0.83–0.94(2H, m), 1.11–1.37(6H, m), 1.52–1.78(9H, m), 2.04–2.11(1H, m), 2.50–2.55(1H, m), 2.60–2.68(1H, m), 3.52(1H, t, J=8.3 Hz), 3.79(3H, s), 3.95–4.01(1H, m), 4.11–4.16(1H, m), 4.73(2H, s), 5.20–5.25(1H, m), 5.62–5.72(2H, m), 6.72–6.84(3H, m).

MASS(EI, m/e): 430(M⁺).

HR MASS: Calcd. (C₂₅H₃₄O₆, M⁺) 430.2355. Found (M⁺) 430.2327.

EXAMPLE 67

17-cyclohexyl-2,5,6,7,18,19,20-heptanor-4-oxa-4,8-inter-m-phenylene PGI₂ (244)

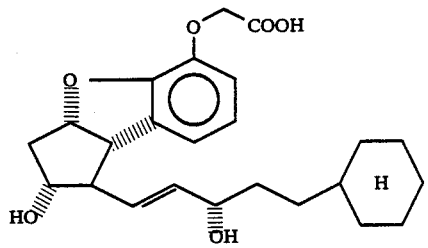

244

To a solution of 17-cyclohexyl-2,5,6,7,18,19,20-heptanor-4-oxa-4,8-inter-m-phenylene PGI₂ methyl ester (221.2 mg, 0.51 mmol) in 10 ml of methanol was added 1N aqueous solution of sodium hydroxide (1.54 ml, 1.54 mmol), and the mixture was stirred overnight at room temperature undre argon stream. To this reaction mixture were added 1.7 ml of 1N hydrochloric acid and 15 ml of water, and the mixture was extracted with ethyl acetate (15 ml×3). The combined organic layers were washed with 50 ml of water and 50 ml of brine, dried over anhydrous sodium sulfate (25 g) and concentrated to give quantitatively 17-cyclohexyl-2,5,6,7,18,19,20-heptanor-4-oxa-4,8-inter-m-phenylene PGI₂ (211.9 mg, 0.51 mmol) as a single product. This product was recrystallized from THF/cyclohexane (3:2) to yield a colorless needle-like crystal, which was assigned the structure by the following data:

m.p. 158°–159° C.

IR(KBr): 3400(3700–2250), 2910, 2840, 1742, 1611, 1585, 1482, 1452, 1433, 1292, 1258, 1202, 1168, 1121, 1022, 960, 940, 883, 855, 823, 788, 760, 721 cm⁻¹.

NMR(400 MHz, CDCl₃, δ): 0.84–0.95(2H, m), 1.10–1.35(6H, m), 1.42–1.77(7H, m), 1.97–2.05(1H, m), 2.32–2.40(1H, m), 2.59–2.68(1H, m), 3.39–3.44(1H, m), 3.82–3.99(1H, m), 4.02–4.08(1H, m), 5.13–5.18(1H, m), 5.56–5.64(2H, m), 6.73–6.76(3H, m).

MASS(EI, m/e): 416(M⁺).

HR MASS: Calcd. (C₂₄H₃₂O₆, M⁺): 416.2198. Found (M⁺): 416.2175.

EXAMPLE 68

17-cyclohexyl-15-epi-2,5,6,7,18,19,20-heptanor-4-oxa-4,8-inter-m-phenylene PGI₂ (245)

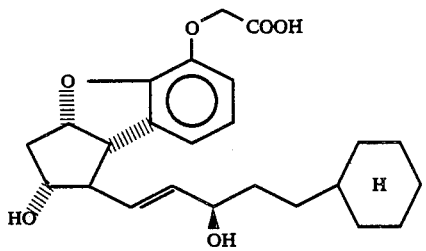

245

To a solution of 17-cyclohexyl-15-epi-2,5,6,7,18,19,20-heptanor-4-oxa-4,8-inter-m-phenylene PGI₂ methyl ester (226.4 mg, 0.53 mmol) in 10 ml of methanol was added 1N aqueous solution of sodium hydroxide (1.58 ml, 1.58 mmol), and the mixture was stirred overnight at room temperature under argon stream. To this reaction mixture was added 1.7 ml of 1N hydrochloric acid and 15 ml of water, and the mixture was extracted with ethyl acetate (15 ml×3). The combined organic layers were washed with 50 ml of water and 50 ml of brine, dried over anhydrous sodium sulfate (25 g) and concentrated to give 17-cyclohexyl-15-epi-2,5,6,7,18,19,20-heptanor-4-oxa-4,8-inter-m-phenylene PGI₂ (204.8 mg, 0,49 mmol) as a single product in a yield of 93%. This product was recrystallized from acetone/cyclohexane (2:1) to yield a colorless needle-like crystal, which was assigned the structure by the following data:

m.p. 142°–143.5° C.

IR(KBr): 3400(3700–2200), 2910, 2850, 1735, 1703, 1610, 1596, 1482, 1452, 1285, 1195, 1263, 1164, 1063, 1021, 996, 959, 883, 796, 778, 733 cm⁻¹.

NMR(400 MHz, CDCl₃, δ): 0.83–0.95(2H, m), 1.08–1.39(6H, m), 1.50–1.77(7H, m), 2.01–2.10(1H, m), 2.43–2.49(1H, m), 2.57–2.67(1H, m), 2.0–4.0(3H, broad s), 3.48(1H, t, J=8.3 Hz), 3.90–3.97(1H, m), 4.06–4.12(1H, m), 4.67(2H, s), 5.17–5.22(1H, m), 5.63–5.74(2H, m), 6.70–6.85(3H, m).

MASS(EI, m/e): 416(M⁺).

HR MASS: Calcd. (C₂₄H₃₂O₆, M⁺): 416.2198. Found (M⁺): 416.2206.

EXAMPLE 69

16-cyclohexyl-16-methyl-2,5,6,7,18,19,20-heptanor-4-oxa-4,8-inter-m-phenylene PGI₂ methyl ester (246) and its 15-epimer (247)

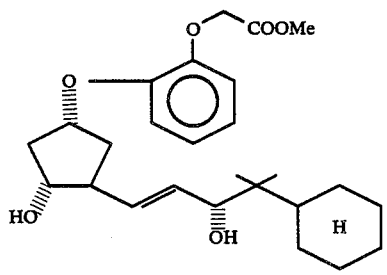

246

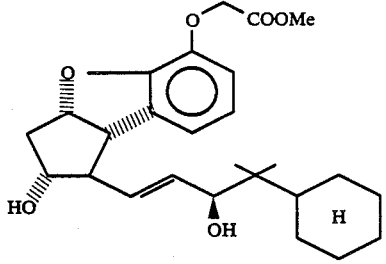

247

Cerium trichloride heptahydrate (1.248 g, 3.35 mmol) was dissolved into a solution of 16-cyclohexyl-16-methyl-15-oxo-2,5,6,7,18,19,20-heptanor-4-oxa-4,8-inter-m-phenylene PGI₂ methyl ester, 11-acetate (1.5841 g, 3.35 mmol) in 70 ml of methanol. While this solution was being stirred with ice-cooling, sodium borohydride (84.4 mg, 2.02 mmol) was added thereinto, and the mixture was stirred for 30 minutes. Further, 30 ml of a saturated aqueous solution of sodium bicarbonate was added and the mixture was stirred for 10 minutes. The reaction mixture was filtered by suction using celite and washed with 200 ml of ethyl acetate. The filtrate was concentrated and the residue was extracted with ethyl acetate (30 ml×3). The combined organic layers were washed with 100 ml of water and 100 ml of brine, dried over anhydrous sodium sulfate (30 g) and concentrated to give 1.5321 g of an oily product.

This oily product was dried by azeotropic distillation with benzene (10 ml×2) and dissolved into 20 ml of anhydrous methanol. To this solution was added 5.22N sodium methoxide (0.03 ml, 0.17 mmol), and the mixture was stirred at room temperature for 3 hours under argon stream. 0.05 ml of acetic acid was added to the reaction mixture, which was then concentrated. The residue was mixed with 15 ml of water and extracted with ethyl acetate (15 ml×3). The combined organic layers were washed with 50 ml of water and 50 ml of brine, dried over anhydrous sodium sulfate (20 g) and concentrated to give 1.4918 g of an oily product. This oily product was purified by column chromatography (silica gel, ethyl acetate/cyclohexane=1:1) to yield at first less polar 16-cyclohexyl-16-methyl-15-epi-2,5,6,7,18,19,20-heptanor-4-oxa-4,8-inter-m-phenylene PGI₂ methyl ester (454.7 mg, 1.05 mmol) in 31% yield. This product was recrystallized from THF/n-hexane (2:3) to yield colorless needle-like crystals. Then, more polar 16-cyclohexyl-16-methyl-2,5,6,7,18,19,20-heptanor-4-oxa-4,8-inter-m-phenylene PGI₂ methyl ester (563.8 mg, 1.31 mmol) was yielded in 39% yield. This product was recrystallized from THF/n-hexane (1:1) to yield colorless needle-like crystals. These compounds were assigned the corresponding structures by the following data:

16-cyclohexyl-16-methyl-2,5,6,7,19,20-heptanor-4-oxa-4,8-inter-m-phenylene PGI₂ methyl ester m.p. 132°–133° C.

IR(KBr): 3350, 2920, 2850, 1760, 1613, 1588, 1481, 1460, 1404, 1368, 1290, 1218, 1199, 1181, 1160, 1119, 1075, 1025, 1005, 990, 973, 942, 891, 860, 830, 780, 758, 721, 680, 640, 603 cm⁻¹.

NMR(400 MHz, CDCl₃, δ): 0.78(3H, s), 0.87(3H, s), 0.93–1.38(7H, m), 1.4–1.88(6H, m), 2.04–2.11(1H, m), 2.47–2.54(1H, m), 2.61–2.68(1H, m), 3.49(1H, t, J=8.3

Hz), 3.79(3H, s), 3.92–3.99(1H, m), 4.09(1H, d, J=6.84 Hz), 4.73(2H, s), 5.18–5.26(1H, m), 5.63–5.80(2H, m), 6.71–6.86(3H, m).

MASS(EI, m/e): 444(M+).

HR MASS: Calcd. ($C_{26}H_{36}O_6$, M+): 444.2512. Found (M+): 444.2519.

16-cyclohexyl-16-methyl-15-epi-2,5,6,7,18,19,20-heptanor-4-oxa-4,8-inter-m-phenylene PGI$_2$ methyl ester m.p. 111°–112.5° C.

IR(KBr): 3380, 2980, 2925, 2856, 1761, 1609, 1591, 1488, 1462, 1342, 1310, 1294, 1243, 1215, 1190, 1178, 1161, 1119, 1088, 1068, 1048, 997, 964, 952, 892, 864, 790, 760, 723, 680, 619 cm$^{-1}$.

NMR(400 MHz, CDCl$_3$, δ): 0.77(3H, s), 0.88(3H, s), 0.93–1.38(7H, m), 1.4–1.7(2H, broad s), 1.61–1.83(4H, m), 2.07–2.14(1H, m), 2.53–2.67(2H, m), 3.53(1H, t, J=8.3 Hz), 3.79(3H, s), 3.94–4.00(1H, m), 4.11(1H, d, J=5.86 Hz), 4.73(2H, s), 5.22–5.28(1H, m), 5.65–5.78(2H, m), 6.72–6.84(3H, m).

MASS(EI, m/e): 444(M+).

HR MASS: Calcd. ($C_{26}H_{36}O_6$, M+): 444.2512. Found (M+): 444.2510.

EXAMPLE 70

16-cyclohexyl-16-methyl-2,5,6,7,18,19,20-heptanor-4-oxa-4,8-inter-m-phenylene PGI$_2$ (248)

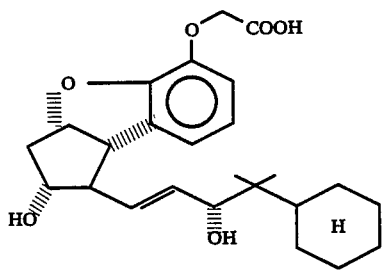

248

To a solution of 16-cyclohexyl-16-methyl-2,5,6,7,18,19,20-heptanor-4-oxa-4,8-inter-m-phenylene PGI$_2$ methyl ester (224 mg, 0.52 mmol) in 20 ml of methanol was added 1N aqueous solution of sodium hydroxide (1.56 ml, 1.56 mmol), and the mixture was stirred overnight at room temperature under argon stream. 2 ml of 1N hydrochloric acid was added to the reaction mixture, which was then concentrated. 10 ml of water was added to the residue, which was extracted with ethyl acetate (10 ml×3). The combined organic layers were washed with 30 ml of water and 30 ml of brine, dried over anhydrous sodium sulfate (10 g) and concentrated to yield quantitatively 16-cyclohexyl-16-methyl-2,5,6,7,18,19,20-heptanor-4-oxa-4,8-inter-m-phenylene PGI$_2$ (217.2 mg, 0.52 mmol) as a single product. This product was recrystallized from ethyl acetate/n-hexane (1:1) to give a colorless needle-like crystal, which was assigned the structure by the following data:

m.p. 143°–144° C.

IR(KBr): 3400(3655–2290), 2950, 2925, 2855, 1741, 1618, 1589, 1481, 1460, 1430, 1360, 1290, 1245, 1183, 1112, 1085, 1068, 1028, 974, 950, 860, 760, 728 cm$^{-1}$.

NMR(400 MHz, CDCl$_3$, δ): 0.76(3H, s), 0.86(3H, s), 0.90–1.40(7H, m), 1.60–1.85(4H, m), 1.98–2.08(1H, m), 2.43–2.55(1H, m), 2.56–2.67(2H, m), 3.42–3.54(1H, m), 3.85–3.94(1H, m), 3.7–4.3(3H, broad s), 4.67(1H, d, J=16.6 Hz), 4.75(1H, d, J=16.6 Hz), 5.14–5.23(1H, m), 5.56–5.71(2H, m), 6.70–6.86(3H, m).

MASS(EI, m/e): 430(M+).

HR MASS: Calcd. ($C_{25}H_{34}O_6$, M+): 430.2355. Found (M+): 430.2342.

EXAMPLE 71

16-cyclohexyl-16-methyl-15-epi-2,5,6,7,18,19,20-heptanor-4-oxa-4,8-inter-m-phenylene PGI$_2$ (249)

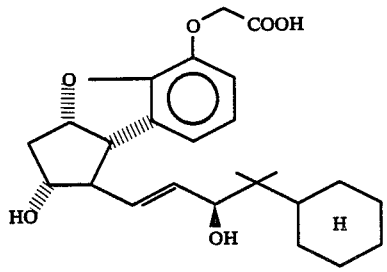

249

To a solution of 16-cyclohexyl-16-methyl-15-epi-2,5,6,7,18,19,20-heptanor-4-oxa-4,8-inter-m-phenylene PGI$_2$ methyl ester (118.1 mg, 0.27 mmol) in 15 ml of methanol was added 1N aqueous solution of sodium hydroxide (0.82 ml, 0.82 mmol), and the mixture was stirred for 9 hours at room temperature under argon stream. 1 ml of 1N hydrochloric acid was added to the reaction mixture, which was then concentrated. The residue was mixed with 10 ml of water and extracted with ethyl acetate (10 ml×3). The combined organic layers were washed with 30 ml of water and 30 ml of brine, dried over anhydrous sodium sulfate (10 g) and concentrated to yield quantitatively 16-cyclohexyl-16-methyl-2,5,6,7,18,19,20-heptanor-4-oxa-4,8-inter-m-phenylene PGI$_2$ (112.2 mg, 0.27 mmol) as a single product. This product was recrystallized from ethyl acetate/cyclohexane (5:1) to yield a colorless needle-like crystal, which was assigned the structure by the following data:

m.p. 89°–90° C.

IR(KBr): 3370(3675–2180), 2905, 2852, 1735, 1685, 1601, 1453, 1362, 1323, 1273, 1249, 1190, 1178, 1150, 1093, 1018, 983, 964, 954, 888, 864, 741, 728, 785, 761, 719, 624 cm$^{-1}$.

NMR(400 MHz, CDCl$_3$, δ): 0.77(3H, s), 0.88(3H, s), 0.93–1.38(7H, m), 1.4–1.7(2H, broad s), 1.01–1.83(4H, m), 2.07–2.14(1H, m), 2.53–2.67(2H, m), 3.53(1H, t, J=8.3 Hz), 3.79(3H, s), 3.94–4.00(1H, m), 4.11(1H, d, J=5.86 Hz), 4.73(2H, s), 5.22–5.28(1H, m), 5.65–5.78(2H, m), 6.72–6.84(3H, m).

MASS(EI, m/e) 430(M+).

HR MASS: Calcd. ($C_{25}H_{34}O_6$, M+): 430.2355. Found (M+): 430.2353.

EXAMPLE 72

17-cyclohexyl-16,16-dimethyl-2,5,6,7,18,19,20-heptanor-4-oxa-4,8-inter-m-phenylene PGI$_2$ methyl ester (250) and its 15-epimer (251)

Cerium trichloride heptahydrate (1.03 g, 2.77 mmol) was dissolved into a solution of 17-cyclohexyl-16,16-dimethyl-15-oxo-2,5,6,7,18,19,20-heptanor-4-oxa-4,8-inter-m-phenylene PGI$_2$ methyl ester, 11-acetate (1.3136 g, 2.77 mmol) in 50 ml of methanol. While this solution was being stirred at $-15°$ C., sodium borohydride (63.5 mg, 1.68 mmol) was added thereinto, and the mixture was stirred for 30 minutes. To the reaction mixture was added 10 ml of water and the solvent was distilled off. The residue was mixed with ethyl acetate (50 ml), and resulting precipitate was filtered by Hyflo Super Cel. The precipitate was washed with ethyl acetate (50 ml×3). The ethyl acetate layer was washed with water (50 ml) and brine (50 ml), dried over anhydrous sodium sulfate and concentrated to give an oily product. This oily product was dried by azeotropic distillation with benzene (20 ml×3), further dried under reduced pressure and dissolved into 40 ml of anhydrous methanol. To this solution was added sodium methoxide (5.22N, 0.03 ml, 0.157 mmol), and the mixture was stirred overnight at room temperature under argon atmosphere. After being neutralized to pH 7 with acetic acid and concentrated, the reaction mixture was diluted with 20 ml of water, and extracted with ethyl acetate (50 ml×4). The combined ehtyl acetate layers were dried over anhydrous sodium sulfate and concentrated to give an oily product. This oily product was separated and purified through column chromatography (silica gel, ethyl acetate/cyclohexane=3:1) to give less polar 17-cyclohexyl-16,16-dimethyl-15-epi-2,5,6,7,18,19,20-heptanor-4-oxa-4,8-inter-m-phenylene PGI$_2$ methyl ester (0.4594 g, 1.00 mmol) and more polar 17-cyclohex-

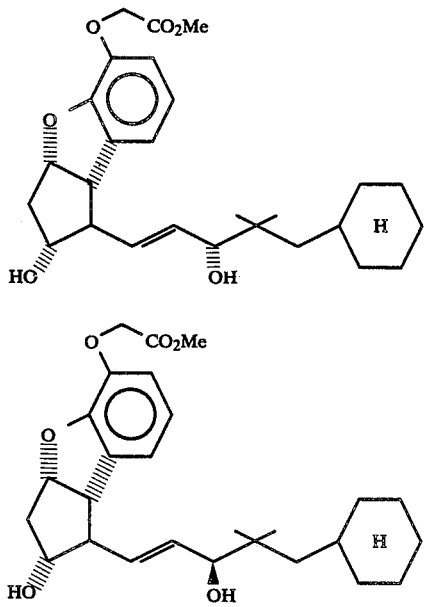

yl-16,16-dimethyl-2,5,6,7,18,19,20-heptanor-4-oxa-4,8-inter-m-phenylene PGI$_2$ methyl ester (0.3806 g, 0.830 mmol) in a yield of 66.1%. These compounds were assigned the corresponding structures by the following data:

α-isomer 17-cyclohexyl-16,16-dimethyl-2,5,6,7,18,19,20-heptanor-4-oxa-4,8-inter-m-phenylene PGI$_2$ methyl ester m.p. 109°–110.5° C. (recrystallized from ethyl acetate and n-hexane; colorless needle-like crystal).

IR(KBr):
3305, 2925, 1850, 1756, 1611, 1586, 1481, 1459, 1441, 1371, 1291, 1255, 1248, 1211, 1189, 1173, 1163, 1118, 1088, 1081, 1031, 1015, 995, 968, 948, 893, 861, 840, 785, 758, 725, 711, 678 cm$^{-1}$.

NMR (400 MHz, CDCl$_3$, δ): 0.85–1.43(14H, m), 1.58–1.92(6H, m), 2.00–2.10(1H, m), 2.30–2.42(1H, broad s), 2.43–2.52(1H, m), 2.61–2.70(1H, m), 3.47(1H, t, J=8.79 Hz), 3.79(3H, s), 3.82(1H, d, J=6.84 Hz), 3.89–3.97(1H, m), 4.72(2H, s), 5.17–5.23(1H, m), 5.58–5.71(2H, m), 6.71–6.82(3H, m).

MASS(EI, m/e): 458(M+).

HR MASS: Calcd. (C$_{27}$H$_{38}$O$_6$, M+): 458.2668. Found (M+): 458.2696.

β-isomer 17-cyclohexyl-16,16-dimethyl-15-epi-2,5,6,7,18,19,20-heptanor-4-oxa-4,8-inter-m-phenylene PGI$_2$ methyl ester m.p. 107.5°–108.5° C. (recrystallized from acetone and n-hexane; colorless needle-like crystal).

IR(KBr): 3485, 2920, 2850, 1698, 1616, 1588, 1488, 1461, 1428, 1381, 1356, 1321, 1285, 1273, 1195, 1160, 1100, 1065, 1025, 1000, 975, 958, 943, 860, 798, 760, 735, 720 cm$^{-1}$.

NMR(400 MHz, CDCl$_3$, δ): 0.86–1.04(8H, m), 1.04–1.43(6H, m), 1.47–1.80(7H, m), 2.04–2.12(1H, m), 2.51–2.58(1H, m), 2.59–2.68(1H, m), 3.52(1H, d, J=8.30 Hz), 3.79(3H, s), 3.86(1H, d, J=5.37 Hz), 3.93–4.01(1H, m), 4.73(2H, s), 5.20–5.27(1H, m), 5.63–5.77(2H, m), 6.71–6.85(3H, m).

MASS(EI, m/e): 458(M+).

HR MASS: Calcd. (C$_{27}$H$_{38}$O$_6$, M+): 458.2667. Found (M+): 458.2664.

EXAMPLE 73

17-cyclohexyl-16,16-dimethyl-2,5,6,7,18,19,20-heptanor-4-oxa-4,8-inter-m-phenylene PGI$_2$ (252)

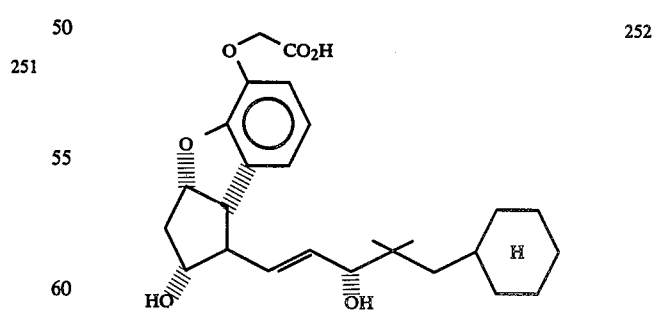

To a solution of 17-cyclohexyl-16,16-dimethyl-2,5,6,7,18,19,20-heptanor-4-oxa-4,8-inter-m-phenylene PGI$_2$ methyl ester (136.5 mg, 0.298 mmol) in 20 ml of methanol was added an aqueous solution of sodium hydroxide (1N, 0.89 ml, 0.894 mmol), and the mixture was stirred overnight at room temperature under argon atmosphere. The reaction mixture was acidified to pH 2 with hydrochloric acid (1N), and methanol was distilled off. 10 ml of water was added and the mixture was extracted with ethyl acetate (20 ml×4). The combined ethyl acetate layer was washed with water (20 ml) and brine (20 ml), dried over anhydrous sodium sulfate and concentrated to give 132.4 mg of 17-cyclohexyl-16,16-dimethyl-2,5,6,7,18,19,20-heptanor-4-oxa-4,8-inter-m-phenylene PGI$_2$ as a single product (yield 99.9%), which was assigned the structure by the following data:

m.p. 151°–153° C. (recrystallized from ethyl acetate and n-hexane; colorless needle-like crystal).

IR(KBr): 3420, 2930, 2860, 1738, 1615, 1588, 1483, 1448, 1428, 1385, 1363, 1282, 1242, 1182, 1160, 1115, 1025, 990, 972, 952, 892, 857, 830, 792, 761, 728 cm$^{-1}$.

NMR(400 MHz,

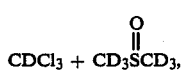

δ): 0.83–1.45(14H, m), 1.58–1.79(5H, m), 1.95–2.06(1H, m), 2.32–2.41(1H, m), 2.62–2.71(1H, m), 3.38–3.45(1H, m), 3.76(1H, d, J=7.81 Hz), 3.80–3.88(1H, m), 3.90–4.60(2H, broad s), 4.67(2H, s), 5.12–5.20(1H, m), 5.52–5.69(2H, m), 6.68–6.80(3H, m).

MASS(EI, m/e): 444(M+).

HR MASS: Calcd. (C$_{26}$H$_{36}$O$_6$, M+): 444.2512. Found (M+): 444.2482.

EXAMPLE 74

17-cyclohexyl-16,16-dimethyl-15-epi-2,5,6,7,18,19,20-heptanor-4-oxa-4,8-inter-m-phenylene PGI$_2$ (253)

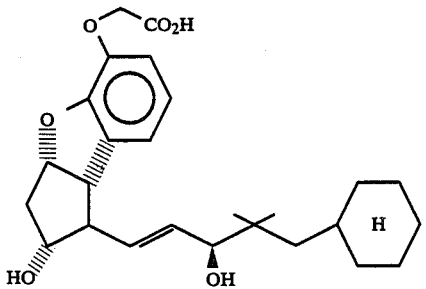

To a solution of 17-cyclohexyl-16,16-dimethyl-15-epi-2,5,6,7,18,19,20-heptanor-4-oxa-4,8-inter-m-phenylene PGI$_2$ methyl ester (146.9 mg, 0.320 mmol) in 20 ml of methanol was added an aqueous solution of sodium hydroxide (1N, 0.96 ml, 0.961 mmol), and the mixture was stirred overnight at room temperature under argon atmosphere. The reaction mixture was acidified to pH 2 by addition of hydrochloric acid (1N), and methanol was distilled off. 10 ml of water was added and the mixture was extracted with ethyl acetate (20 ml×4). The combined ethyl acetate layer was washed with water (20 ml) and brine (20 ml), dried over anhydrous sodium sulfate and concentrated to give 138.6 mg of 17-cyclohexyl-16,16-dimethyl-15-epi-2,5,6,7,18,19,20-heptanor-4-oxa-4,8-inter-m-phenylene PGI$_2$ as a single product (yield 97.4%), which was assigned the structure by the following data:

m.p. 77°–78° C. (recrystallized from acetone and n-hexane; colorless needle-like crystal).

IR(KBr): 3375, 2925, 2845, 1735, 1618, 1591, 1483, 1461, 1443, 1381, 1361, 1277, 1247, 1190, 1110, 1027, 971, 891, 861, 795, 763, 728 cm$^{-1}$.

NMR(400 MHz,

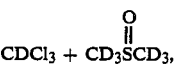

δ): 0.84–1.04(8H, m), 1.04–1.42(6H, m), 1.58–1.76(5H, m), 2.00–2.10(1H, m), 2.49–2.63(2H, m), 3.40–3.78(3H, broad m), 3.85(1H, d, J=4.88 Hz), 3.93–4.01(1H, m), 4.64–4.76(2H, m), 5.18–5.24(1H, m), 5.62–5.75(2H, m), 6.70–6.85(3H, m).

MASS(EI, m/e): 444(M+).

HR MASS: Calcd. (C$_{26}$H$_{36}$O$_6$, M+): 444.2512. Found (M+): 444.2513.

EXAMPLE 75

15-phenyl-2,5,6,7,16,17,18,19,20-nonanor-4-oxa-4,8-inter-m-phenylene PGI$_2$ methyl ester (254) and its 15-epimer (255)

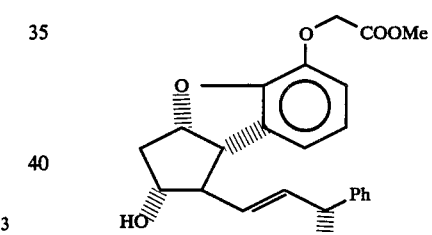

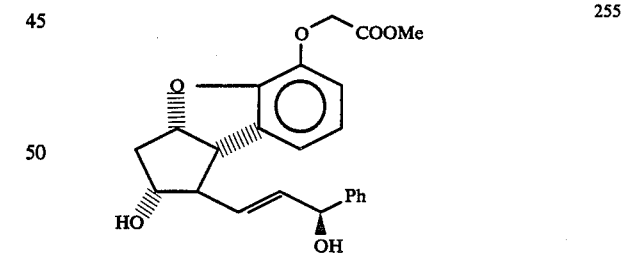

Cerium trichloride heptahydrate (1.58 g, 3.17 mmol) was added to a solution of 15-oxo-15-phenyl-2,5,6,7,16,17,18,19,20-nonanor-4-oxa-4,8-inter-m-phenylene PGI$_2$ methyl ester, 11-benzoate (1.58 g, 3.17 mmol) in methanol (120 ml). The mixture was cooled to 0° C. and sodium borohydride (60.0 mg, 1.59 mmol) was slowly added. After being stirred for 5 minutes at 0° C., the mixture was diluted with a saturated aqueous solution of sodium bicarbonate (10 ml) and concentrated. Ethyl acetate (80 ml) was added to the residue, which was then filtered. The precipitate was washed with ethyl acetate (20 ml×2). The combined ethyl acetate layers were washed with water and brine. After being dried over anhydrous magnesium sulfate and concentration, 1.72 g of an oily product was obtained. This oily product was dissolved into anhydrous methanol (40 ml) under argon atmosphere. To this solution was added a solution of sodium methoxide in methanol (5.22N, 0.15 ml, 0.793 mmol). The mixture was stirred for 15 hours at room temperature, neutralized with acetic acid and concentrated. Water (20 ml) was added and the mixture was extracted with ethyl acetate (40 ml). The aqueous layer was further extracted with ethyl acetate (15 ml×2). The combined organic layers were washed with brine (30 ml), dried over anhydrous magnesium sulfate and concentrated. The residue was separated and purified through column chromatography (Merck, Lobar column; silica gel, ethyl acetate/cyclohexane=4:1) to give less polar 15-phenyl-15-epi-2,5,6,7,16,17,18,19,20-nonanor-4-oxa-4,8-inter-m-phenylene PGI$_2$ methyl ester (451 mg, 1.14 mmol, yield 36.0%) as a white crystalline solid and more polar 15-phenyl-2,5,6,7,16,17,18,19,20-nonanor-4-oxa-4,8-inter-m-phenylene PGI$_2$ methyl ester (470 mg, 1.19 mmol, yield 37.5%) as a white crystalline solid. These compounds were assigned the corresponding structures by the following data:

15-phenyl-2,5,6,7,16,17,18,19,20-nonanor-4-oxa-4,8-inter-m-phenylene PGI$_2$ methyl ester m.p. 135°–136° C. (recrystallized from ethyl acetate).
IR(KBr): 3270, 2970, 1750, 1620, 1600, 1490, 1460, 1440, 1400, 1350, 1310, 1280, 1250, 1220, 1200, 1110, 1050, 1000, 990, 970, 940, 870, 840, 810, 770, 730, 710, 610, 550, 520 cm$^{-1}$.
NMR(400 MHz, CDCl$_3$, δ): 2.06(1H, ddd, J=4.9, 8.3, 13.7 Hz), 2.19(1H, d, J=4.9 Hz), 2.30(1H, d, J=3.7 Hz), 2.52(1H, d, J=8.0 Hz), 2.63(1H, J=6.4, 7.3, 13.7 Hz), 3.49(1H, t, J=8.0 Hz), 3.77(3H, s,), 3.9–4.0(1H, m), 4.71(2H, s), 5.20(1H, ddd, J=4.9, 7.3, 8.0 Hz), 5.25(1H, dd, J=3.7, 5.4 Hz), 5.75–5.9(2H, m), 6.71(3H, s), 7.25–7.4(5H, m).
MASS(EI, m/e): 396(M+).
Elementary analysis: Calcd. (as C$_{23}$H$_{24}$O$_6$): C: 69.68 H: 6.10. Found: C: 69.72 H: 6.06.

15-phenyl-15-epi-2,5,6,7,16,17,18,19,20-nonanor-4-oxa-4,8-inter-m-phenylene PGI$_2$ methyl ester m.p. 110.5°–111.5° C. (recrystallized from ethyl acetate).
IR(KBr): 3300, 2970, 2880, 1770, 1740, 1620, 1600, 1490, 1460, 1440, 1390, 1340, 1330, 1300, 1280, 1270, 1220, 1200, 1120, 1110, 1040, 1000, 970, 960, 900, 870, 860, 840, 820, 790, 770, 760, 750, 730, 700, 660, 640, 610, 550, 530 cm$^{-1}$.
NMR(400 MHz, CDCl$_3$, δ): 1.87(1H, d, J=5.4 Hz), 2.0–2.15(2H, m), 2.55(1H, q, J=8.2 Hz), 2.61(1H, ddd, J=6.4, 7.3, 13.7 Hz), 3.54(1H, t, J=8.2Hz), 3.78(3H, s), 3.9–4.0(1H, m), 4.71(2H, s), 5.22(1H, ddd, J=4.9, 7.3, 8.2 Hz), 5.25–5.3(1H, m), 5.79(1H, dd, J=8.2, 15.1 Hz), 5.86(1H, dd, J=5.4, 15.1 Hz), 6.7–6.85(3H, m), 7.3–7.5(5H, m).
MASS(EI, m/e): 396 (M+).
Elementary analysis: Calcd. (as C$_{23}$H$_{24}$O$_6$): C: 69.68 H: 6.10. Found: C: 69.85 H: 6.05.

EXAMPLE 76

15-phenyl-2,5,6,7,16,17,18,19,20-nonanor-4-oxa-4,8-inter-m-phenylene PGI$_2$ (256)

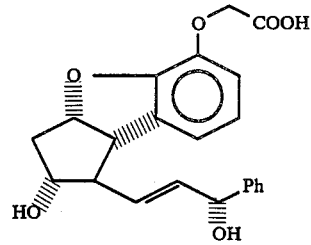

256

To a solution of 15-phenyl-2,5,6,7,16,17,18,19,20-nonanor-4-oxa-4,8-inter-m-phenylene PGI$_2$ methyl ester (200 mg, 0.505 mmol) in methanol (20 ml) was added an aqueous solution of sodium hydroxide (1N, 3 ml, 3 mmol), and the mixture was stirred for 2 hours at room temperature. The reaction mixture was concentrated. The residue was diluted with water (20 ml), neutralized with 1N hydrochloric acid (3 ml) and extracted with ethyl acetate (40 ml, 20 ml×2). The combined organic layers were washed with brine, dried over anhydrous magnesium sulfate and concentrated to give 210 mg of crude crystals. The crude crystals were recrystallized from ethyl acetate-ethanol-hexane to give 15-phenyl-2,5,6,7,16,17,18,19,20-nonanor-4-oxa-4,8-inter-m-phenylene PGI$_2$ (128 mg, 0.335 mmol) in a yield of 66.4% as a white crystal, which was assigned the structure by the following data:
m.p. 136°–137° C.
IR(KBr): 3430, 3050, 2970, 2940, 1740, 1630, 1600, 1490, 1470, 1440, 1390, 1350, 1300, 1290, 1230, 1200, 1170, 1110, 1080, 1020, 970, 950, 910, 870, 770, 730, 700, 580, 570, 550, 500 cm$^{-1}$.
NMR(400 MHz, DMSO-d$_6$, δ): 1.71(1H, ddd, J=5.9, 9.8, 13.2 Hz), 2.15–2.25(1H), m), 2.45–2.6(1H, m), 3.40(1H, t, J=9.0 Hz), 3.7–3.8(1H, m), 4.62(2H, s), 4.8–4.9(1H, m), 5.0–5.15(2H, m), 5.4–5.5(1H, m), 5.63(1H, dd, J=6.1, 15.2 Hz), 5.75(1H, dd, J=7.8, 15.2 Hz), 6.5–6.7(3H, m), 7.2–7.25(1H, m), 7.3–7.45(4H, m).
MASS(EI, m/e): 346(M-2H$_2$O)+.
Elementary analysis: Calcd. (as C$_{22}$H$_{22}$O$_6$): C: 69.10, H: 5.80. Found: C: 68.86, H: 5.87.

EXAMPLE 77

15-phenyl-15-epi-2,5,6,7,16,17,18,19,20-nonanor-4-oxa-4,8-inter-m-phenylene PGI$_2$ (257)

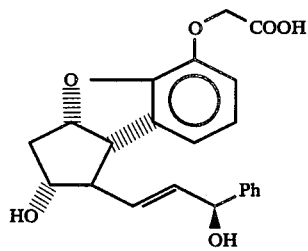

257

To a solution of 15-phenyl-15-epi-2,5,6,7,16,17,18,19,20-nonanor-4-oxa-4,8-inter-m-phenylene PGI₂ methyl ester (200 mg, 0.505 mmol) in methanol (20 ml) was added an aqueous solution of sodium hydroxide (1N, 3 ml, 3 mmol), and the mixture was stirred for 2 hours at room temperature. The reaction mixture was concentrated, and water (20 ml) was added to the residue. The aqueous mixture was neutralized with 1N hydrochloric acid (3 ml) and extracted with ethyl acetate (40 ml, 20 ml×2). The combined organic layers were washed with brine, dried over anhydrous magnesium sulfate and concentrated to give 203 mg of crude crystals. The crude crystals were recrystallized from ethanol/ethyl acetate to give 15-phenyl-15-epi-2,5,6,7,16,17,18,19,20-nonanor-4-oxa-4,8-inter-m-phenylene PGI₂ (119 mg, 0.312 mmol) as a white crystal in a yield of 61.8%. This compound was assigned the structure by the following data:

m.p. 140°–141° C.

IR(KBr): 3450, 3030, 2940, 1730, 1620, 1590, 1490, 1470, 1430, 1380, 1350, 1320, 1300, 1280, 1240, 1200, 1110, 1090, 1070, 1030, 980, 950, 900, 860, 800, 770, 730, 700, 600, 500, 480 cm$^{-1}$.

NMR(400 MHz, DMSO-d₆, δ): 1.71(1H, ddd, J=5.9, 9.3, 13.2 Hz), 2.15–2.3(1H, m), 2.45–2.6(1H, m), 3.43(1H, t, J=9.0 Hz), 3.7–3.8(1H, m), 4.63(2H, s), 4.8–4.9(1H, m), 5.0–5.15(2H, m), 5.4–5.5(1H, dd, J=6.3, 15.1 Hz), 5.77(1H, dd, J=7.8, 15.1 Hz), 6.65–6.8(3H, m), 7.2–7.25(1H, m), 7.3–7.45(4H, m).

MASS(EI, m/e): 346(M-2H₂O)⁺.

Elementary analysis: Calcd. (C₂₂H₂₂O₆): C: 69.10, H: 5.80. Found: C: 68.86; H: 5.89.

EXAMPLE 78

16-phenyl-2,5,6,7,17,18,19,20-octanor-4-oxa-4,8-inter-m-phenylene PGI₂ methyl ester (258) and its 15-epimer (259)

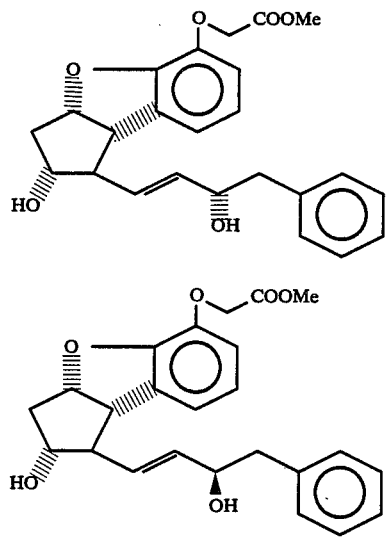

To a solution of 15-oxo-16-phenyl-2,5,6,7,17,18,19,20-octanor-4-oxa-4,8-inter-m-phenylene PGI₂ methyl ester, 11-benzoate (1.7 g, 332 mmol) in 90 ml of methanol was added cerium trichloride heptahydrate (3.4 g, 9.13 mmol). Sodium borohydride (80 mg, 2.11 mmol) was further added at −20° C., and the mixture was stirred for 10 minutes and 6 ml of a saturated aqueous solution of sodium bicarbonate was added to the reaction mixture, which was then concentrated. The residue was triturated with ethyl acetate and filtered. The residue was further washed with ethyl acetate (20 ml×3). The combined organic layers were washed with water (30 ml) and brine (10 ml), dried and concentrated. The resulting oily product was dried by azeotropic distillation with benzene (50 ml×3) and dissolved into 80 ml of anhydrous methanol. 5.22N sodium methoxide (0.6 ml, 3.13 mmol) was added to this solution and the mixture was allowed to stand at room temperature for 14 hours under argon stream. The reaction solution was neutralized with acetic acid and concentrated. 30 ml of water was added to the residue, which was extracted with ethyl acetate (100 ml, 50 ml). The combined ethyl acetate layer was washed with water (10 ml) and brine (10 ml), dried and concentrated. The resulting oily product was separated and purified through column chromatography (silica gel, ethyl acetate) to give as first eluted fraction less polar 16-phenyl-15-epi-2,5,6,7,17,18,19,20-octanor-4-oxa-4,8-inter-m-phenylene PGI₂ methyl ester (425 mg, 0.965 mmol) in a yield of 29.1%, and as second eluted fraction more polar 16-phenyl-2,5,6,7,17,18,19,20-octanor-4-oxa-4,8-inter-m-phenylene PGI₂ methyl ester (500 mg, 1.22 mmol) in 36.7% yield. These compounds were assigned the corresponding structures by the following data:

16-phenyl-2,5,6,7,17,18,19,20-octanor-4-oxa-4,8-inter-m-phenylene PGI₂ methyl ester m.p. 129.5°–131.5° C. (recrystallized from ethyl acetate).

IR(KBr): 3270, 2980, 2930, 1770, 1615, 1590, 1485, 1465, 1430, 1375, 1290, 1235, 1190, 1178, 1118, 1075, 1040, 990, 975, 945, 895, 895, 855, 785, 760, 745, 725, 700 cm$^{-1}$.

NMR(400 MHz, CDCl₃, δ): 1.94(1H, m), 2.32(1H, m), 2.58(1H, m), 2.82(4H, m), 3.28(1H, t, J=8.8 Hz), 3.77(3H, s), 3.76(1H, m), 4.32(1H, m), 4.68(2H, s), 5.07(1H, m), 5.53(2H, m), 6.50(1H, m), 6.70(2H, m), 7.25(5H, m).

MASS(EI, m/e): 410(M⁺).

16-phenyl-15-epi-2,5,6,7,17,18,19,20-octanor-4-oxa-4,8-inter-m-phenylene PGI₂ methyl ester IR(Liquid film method): 3200, 3030, 2920, 2850, 1740, 1730, 1620, 1595, 1485, 1460, 1435, 1280, 1220, 1190, 1110, 1090, 1025, 970, 895, 860, 830, 750, 730, 700 cm$^{-1}$ NMR(400 MHz, CDCl₃, δ): 1.77–1.85(1H, broad s), 2.00(2H, m), 2.42(1H, t, J=8.1 Hz), 2.57(1H, dt, J=6.5, 13.3 Hz), 2.87(2H, m), 3.42(1H, t, J=8.1 Hz), 3.78(1H, s), 3.80(1H, m), 4.38(1H, q, J=6.5 Hz), 4.71(2H, s), 5.15(1H, m), 5.57(1H, dd, J=8.1, 15.8 Hz), 5.62(1H, dd, J=5.9, 15.8 Hz), 6.68–6.80(3H, m), 7.2–7.35(5H, m).

MASS(EI, m/e): 410(M⁺).

EXAMPLE 79

16-phenyl-2,5,6,7,17,18,19,20-octanor-4-oxa-4,8-inter-m-phenylene PGI₂ (260)

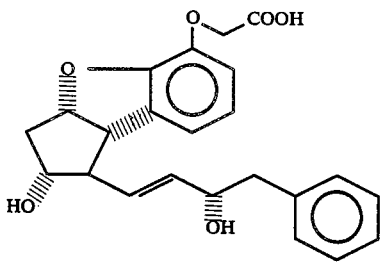
260

To a solution of 16-phenyl-2,5,6,7,17,18,19,20-octanor-4-oxa-4,8-inter-m-phenylene PGI₂ methyl ester (200 mg, 0.488 mmol) in 20 ml of methanol was added an aqueous solution of sodium hydroxide (0.725N, 5.3 ml, 3.84 mmol), and the mixture was allowed to stand under argon stream at room temperature for 14 hours. The reaction solution was concentrated, and the residue was acidified to pH4 by addition of 3.84 ml of 1N hydrochloric acid with ice-cooling, and extracted with ethyl acetate (50 ml, 30 ml, 10 ml). The combined organic layers were washed with water (10 ml) and brine (10 ml), dried and concentrated to give quantitatively 16-phenyl-2,5,6,7,17,18,19,20-octanor-4-oxa-4,8-inter-m-phenylene PGI₂ as a single product, which was assigned the structure by the following data:

m.p. 143°–144° C. (recrystallized from chloroform).
IR(KBr): 3350, 3030, 2910, 2880, 1770, 1750, 1615, 1590, 1485, 1460, 1430, 1350, 1285, 1260, 1190, 1165, 1120, 1075, 1020, 995, 980, 960, 940, 890, 880, 860, 830, 795, 770, 750, 730, 700 cm⁻¹.

NMR(40 MNz, CDCl₃, δ): 1.68(1H, ddd, J=5.7, 9.3, 14.2 Hz), 2.12(1H, t, J=8.3 Hz), 2.42–2.50(1H, m), 2.69(1H, dd, J=6.8, 13.4 Hz), 2.79(1H, dd, J=6.8, 13.4 Hz), 3.29(1H, t, J=8.3 Hz), 3.68(1H, m), 4.20(1H, m), 4.63(2H, s), 4.77–4.88(2H, broad s), 5.03(1H, m), 5.46–5.59(2H, m), 6.49(1H, t, J=3.9 Hz), 6.69(2H, d, J=3.9 Hz), 7.16–7.30(5H, m).

MASS(EI, m/e): 396(M+).

HR MASS: Calcd. (C₂₃H₂₄O₆, M+): 396.1573. Found (M+): 396.1579.

EXAMPLE 80

17-phenyl-2,5,6,7,18,19,20-heptanor-4-oxa-4,8-inter-m-phenylene PGI₂ methyl ester (261) and its 15-epimer (262)

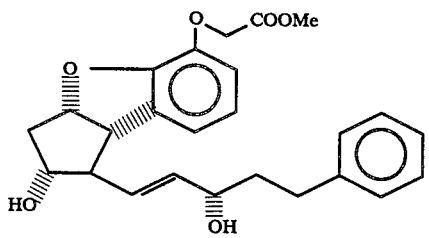
261

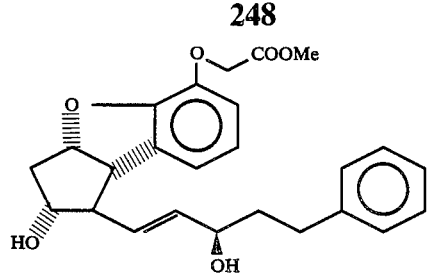
262

Cerium trichloride heptahydrate (3.4 g, 9.1 mmol) was added to a solution of 15-oxo-17-phenyl-2,5,6,7,18,19,20-heptanor-4-oxa-4,8-inter-m-phenylene PGI₂ methyl ester, 11-benzoate (2.2 g, 4.2 mmol) in 90 ml of methanol, and the mixture was cooled to −20° C. Sodium borohydride (80 mg, 2.1 mmol) was further added. The mixture was stirred for 5 minutes, diluted with 9 ml of a saturated aqueous solution of sodium bicarbonate and concentrated. The resulting precipitate was filtered and washed with ethyl acetate (100 ml×2). The combined ethyl acetate layers were washed with water (30 ml) and brine (30 ml), dried and concentrated to give 2.3 g of an oily product. This only product was dried by azeotropic distillation with benzene three times and dissolved into 80 ml of anhydrous methanol. 5.22N sodium methoxide (0.6 ml, 3.13 mmol) was added to this solution and the mixture was allowed to stand under argon atmosphere at room temperature for 14 hours. The reaction mixture was neutralized to pH7 with acetic acid and concentrated. 30 ml of water was added to the residue, which was extracted with ethyl acetate (100 ml, 50 ml). The combined ethyl acetate layers were washed with water (10 ml) and brine (10 ml), dried and concentrated to give 2.3 g of an oily product. This oily product was purified by column chromatography (silica gel, ethyl acetate) to give as first eluted fraction less polar 17-phenyl-15-epi-2,5,6,7,18,19,20-heptanor-4-oxa-4,8-inter-m-phenylene PGI₂ methyl ester (593.3 mg, 1.40 mmol) in a yield of 33.3% and as second eluted one, more polar 17-phenyl-2,5,6,7,18,19,20-heptanor-4-oxa-4,8-inter-m-phenylene PGI₂ methyl ester (660 mg, 1.56 mmol) in 37.3% yield. These compounds were assigned the corresponding structures by the following data:

17-phenyl-2,5,6,7,18,19,20-heptanor-4-oxa-4,8-inter-m-phenylene PGI₂ methyl ester m.p. 104°–106° C. (recrystallized from ethyl acetate).
IR(KBr): 3350, 3020, 2925, 2850, 1747, 1620, 1590, 1490, 1440, 1350, 1288, 1240, 1195, 1110, 1070, 1030, 975, 860, 765, 725, 700 cm⁻¹.

NMR(400 MHz, CDCl₃, δ): 1.75–2.05(4H, m), 2.4(1H, m), 2.6–2.75(3H, m), 3.05–3.2 (1H, m), 3.4(1H, t, J=8.8 Hz), 3.78(3H, s), 3.8–3.9(1H, m), 4.70(2H, s), 5.11–5.2(1H, m), 5.5–5.6(2H, m), 6.7–6.8(3H, m), 7.16–7.23(3H, m), 7.25–7.31(2H, m).

MASS(EI, m/e): 424(M+).

17-phenyl-15-epi-2,5,6,7,18,19,20-heptanor-4-oxa-4,8-inter-m-phenylene PGI₂ methyl ester m.p. 95°–97° C. (recrystallized from ethyl acetate).

IR(KBr): 3400, 3030, 2960, 2920, 2880, 2850, 1780, 1760, 1740, 1730, 1615, 1590, 1490, 1460, 1435, 1300, 1280, 1240, 1230, 1195, 1170, 1110, 1090, 1070, 1030, 985, 955, 940, 890, 865, 860, 770, 755, 740, 700 cm$^{-1}$.

NMR(400 MHz, CDCl$_3$, δ): 1.69(broad s), 1.80–1.83(3H, m), 2.07(1H, ddd, J=4.9, 8.3, 13.7 Hz), 2.51(1H, m), 2.62(1H, ddd, J=6.4, 7.3, 13.7 Hz), 2.68–2.82(2H, m), 3.50(1H, t, J=8.5 Hz), 3.78(3H, s), 3.95(1H, m), 4.18(1H, m), 4.72(1H, s), 5.21(1H, ddd, J=4.9, 7.3, 8.5 Hz), 5.64–5.74(2H, m), 6.71–6.84(3H, m), 7.17–7.24(3H, m), 7.25–7.32(2H, m).

MASS(EI, m/e): 424(M$^+$).

EXAMPLE 81

17-phenyl-2,5,6,7,18,19,20-heptanor-4-oxa-4,8-inter-m-phenylene PGI$_2$ (263)

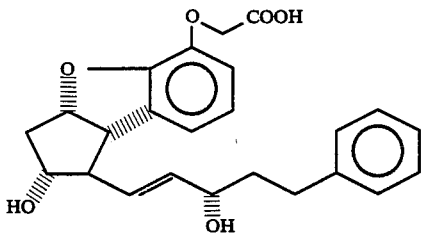

263

To a solution of 17-phenyl-2,5,6,7,18,19,20-heptanor-4-oxa-4,8-inter-m-phenylene PGI$_2$ methyl ester (300 mg, 0.708 mmol) in 30 ml of methanol was added an aqueous solution of sodium hydroxide (0.725N, 8 ml, 5.8 mmol), and the mixture was allowed to stand under argon atmosphere at room temperature for 14 hours. The reaction mixture was concentrated. The residue was acidified to pH4 by addition of 5.8 ml of 1N hydrochloric acid with ice-cooling, and extracted with ethyl acetate three times. The combined organic layers were washed with water and brine, and dried to give quantitatively 17-phenyl-2,5,6,7,18,19,20-heptanor-4-oxa-4,8-inter-m-phenylene PGI$_2$ as a single product, which was assigned the structure by the following data:

m.p. 162°–164° C. (recrystallized from ethyl acetate/methanol).

IR(KBr): 3650–2250, 1735, 1620, 1592, 1490, 1465, 1425, 1380, 1345, 1290, 1265, 1220, 1185, 1105, 1080, 1055, 1020, 965, 960, 945, 900, 860, 830, 795, 765, 745, 725, 700 cm$^{-1}$.

NMR(400 MHz, CDCl$_3$, δ): 1.77–1.81(3H, m), 2.19(1H, q, J=8.3 Hz), 2.45–2.55(1H, m), 2.58–2.63(2H, m), 3.42(1H, t, J=8.3 Hz), 3.75(1H, m), 3.97(1H, m), 4.64(2H, s), 4.78(1H, broad s), 4.85(1H, broad s), 5.08(1H, m), 5.53(1H, dd, J=6.1, 15.3 Hz), 5.65(1H, dd, J=7.8, 15.3 Hz), 6.69–6.76(3H, m), 7.13–7.25(3H, m), 7.27–7.31(2H, m).

MASS(EI, m/e): 410(M$^+$).

Elementary analysis: Calcd. (as C$_{24}$H$_{26}$O$_6$): C: 70.23, H: 6.39. Found: C: 70.07, H: 6.36.

EXAMPLE 82

15-(o-methylphenyl)-2,5,6,7,16,17,18,19,20-nonanor-4-oxa-4,8-inter-m-phenylene PGI$_2$ methyl ester (264) and its 15-epimer (265)

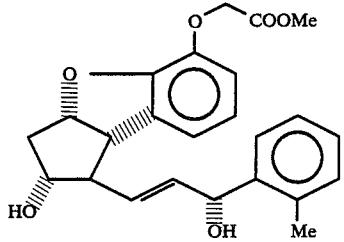

264

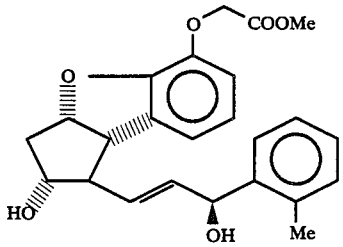

265

Cerium trichloride heptahydrate (1.4233 g, 3.82 mmol) was dissolved into a solution of 15-o-methylphenyl-15-oxo-2,5,6,7,16,17,18,19,20-nonanor-4-oxa-4,8-inter-m-phenylene PGI$_2$ methyl ester, 11-benzoate (1.9562 g, 3.82 mmol) in 50 ml of methanol. While the solution was being stirred with ice-cooling, sodium borohydride (48.3 mg, 1.15 mmol) was added thereinto, and the mixture was stirred for 10 minutes. 20 ml of water was further added and the mixture was concentrated. The reaction mixture was filtered by suction using celite and washed with 200 ml of ethyl acetate. The filtrate was concentrated and the residue was extracted with ethyl acetate (40 ml×3). The combined organic layers were washed with 100 ml of water and 100 ml of brine, dried over anhydrous sodium sulfate (40 g) and concentrated to give 1.9624 g of an oily product.

This oily product was dried by azeotropic distillation with benzene (20 ml×2) and dissolved into 15 ml of anhydrous methanol. 5.22N sodium methoxide (0.073 ml, 0.38 mmol) was added to this solution and the mixture was stirred overnight under argon stream at room temperature. 0.1 ml of acetic acid was added to the reaction mixture, which was then concentrated. The residue was combined with 20 ml of water and extracted with ethyl acetate (20 ml×3). The combined organic layers were washed with 60 ml of water and 60 ml of brine, dried over anhydrous sodium sulfate (25 g) and concentrated to give 1.9261 g of an oily product. This oily product was purified by column chromatography (silica gel, ethyl acetate/cyclohexane=6:1) to give as first eluted fraction less polar 15-(o-methylphenyl)-15-epi-2,5,6,7,16,17,18,19,20-nonanor-4-oxa-4,8-inter-m-phenylene PGI$_2$ methyl ester (702.2 mg, 1.71 mmol) in a yield of 45%. This product was recrystallized from ethyl acetate/cyclohexane (4:3) to give a colorless needle-like crystal. Second eluted fraction afforded more polar 15-(o-methylphenyl)-2,5,6,7,16,17,18,19,20-nonanor-4-oxa-4,8-inter-m-phenylene PGI$_2$ methyl ester (706.2 mg, 1.72 mmol) in 45% yield. This product was recrystallized from ethyl acetate/cyclohexane (4:3) to yield a colorless needle-like crystal. These compounds were assigned the corresponding structures by the following data:

15-(o-methylphenyl)-2,5,6,7,16,17,18,19,20-nonanor-4-oxa-4,8-inter-m-phenylene $PGI_2$ methyl ester m.p. 132°–133° C.

IR(KBr): 3400, 2980, 2945, 1748, 1602, 1482, 1462, 1381, 1266, 1253, 1220, 1199, 1183, 1160, 1112, 1085, 1040, 1019, 985, 950, 890, 860, 799, 764, 740, 704, 650, 610 cm$^{-1}$.

NMR(400 HMz, CDCl$_3$, δ): 2.02–2.10(1H, m), 2.20–2.28(2H, broad s), 2.37(3H, s), 2.50–2.56(1H, m), 2.59–2.66(1H, m), 3.48(1H, t, J=8.3 Hz), 3.77(3H, s), 3.93–4.02(1H, m), 4.70(2H, s), 5.15–5.23(1H, m), 5.42–5.48(1H, m), 5.73–5.83(2H, m), 6.67–6.73(3H, m), 7.16–7.25(3H, m), 7.46–7.48(1H, m).

MASS(EI, m/e): 410(M+).

HR MASS: Calcd. (C$_{24}$H$_{26}$O$_6$, M+): 410.1729. Found (M+): 410.1703.

15-(o-methylphenyl)-15-epi-2,5,6,7,16,17,18,19,20-nonanor-4-oxa-4,8-inter-m-phenylene $PGI_2$ methyl ester m.p. 97°–98° C.

IR(KBr): 3360, 2960, 2900, 1741, 1623, 1600, 1482, 1460, 1442, 1368, 1300, 1224, 1204, 1120, 1102, 1040, 1005, 983, 950, 900, 859, 824, 782, 770, 760, 739, 703, 668, 617 cm$^{-1}$.

NMR(400 MHz, CDCl$_3$, δ): 1.92–1.96(1H, broad s), 2.03–2.07(1H, broad s), 2.02–2.11(1H, m), 2.37(3H, s), 2.53–2.64(2H, m), 3.51(1H, t, J=8.3 Hz), 3.78(3H, s), 3.93–3.99(1H, m), 4.71(2H, s), 5.16–5.23(1H, m), 5.44–5.49(1H, m), 5.68–5.76(1H, m), 5.83–5.89(1H, m), 6.72–6.81(3H, m), 7.14–7.28(3H, m), 7.45–7.48(1H, m).

MASS(EI, m/e): 410(M+).

HR MASS: Calcd. (C$_{24}$H$_{26}$O$_6$, M+): 410.1729. Found (M+): 410.1749.

EXAMPLE 83

15-(o-methylphenyl)-2,5,6,7,16,17,18,19,20-nonanor-4-oxa-4,8-inter-m-phenylene $PGI_2$ (266)

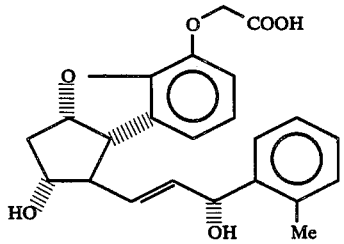

266

To a solution of 15-(o-methylphenyl)-2,5,6,7,16,17,18,19,20-nonanor-4-oxa-4,8-inter-m-phenylene $PGI_2$ methyl ester (225.0 mg, 0.55 mmol) in 10 ml of methanol was added an aqueous solution of sodium hydroxide (1N, 1.65 ml, 1.65 mmol), and the mixture was stirred under argon stream at room temperature for 3 hours. To this reaction mixture were added 1.65 ml of 1N hydrochloric acid and 15 ml of water, and the mixture was extracted with ethyl acetate (15 ml×3). The combined organic layers were washed with 50 ml of water and 50 ml of brine, dried over anhydrous sodium sulfate (25 g) and concentrated to give 15-(o-methylphenyl)-2,5,6,7,16,17,18,19,20-nonanor-4-oxa-4,8-inter-m-phenylene $PGI_2$ (214.9 mg, 0.54 mmol) as a single product in a yield of 99%. This product was recrystallized from acetone/n-hexane (2:1) to give a colorless needle-like crystal, which was assigned the structure by the following data:

m.p. 130° C. (dec.).

IR(KBr): 3400(3700–2250), 2960, 2920, 1740, 1619, 1590, 1484, 1462, 1432, 1375, 1344, 1284, 1244, 1193, 1104, 1063, 1023, 965, 942, 856, 762, 724, 636 cm$^{-1}$.

NMR(400 MHz, CDCl$_3$, δ): 1.97–2.07(1H, m), 2.41(3H, s), 2.35–2.45(1H, m), 2.58–2.68(1H, m), 1.9–4.3(3H, broad s), 3.42–3.46(1H, m), 3.87–3.92(1H, m), 4.64(2H, s), 5.12–5.20(1H, m), 5.35–5.40(1H, m), 5.67–5.79(2H, m), 6.63–6.73(3H, m), 7.13–7.25(3H, m), 7.53–7.58(1H, m).

MASS(EI, m/e): 360(M+-36).

HR MASS: Calcd. (C$_{24}$H$_{24}$O$_5$, M+-H$_2$O: 378.1467. Found (M+-H$_2$O): 378.1445.

EXAMPLE 84

15-(o-methylphenyl)-15-epi-2,5,6,7,16,17,18,19,20-nonanor-4-oxa-4,8-inter-m-phenylene $PGI_2$ (267)

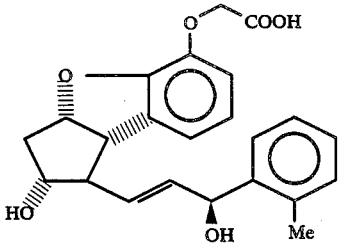

267

To a solution of 15-(o-methylphenyl)-15-epi-2,5,6,7,16,17,18,19,20-nonanor-4-oxa-4,8-inter-m-phenylene $PGI_2$ methyl ester (235.0 mg, 0.57 mmol) in 10 ml of methanol was added an aqueous solution of sodium hydroxide (1N, 1.72 ml, 1.72 mmol), and the mixture was stirred under argon stream at room temperature for 3 hours. To this reaction mixture were added 1.69 ml of 1N hydrochloric acid and 15 ml of water, and the mixture was extracted with ethyl acetate (15 ml×3). The combined organic layers were washed with 50 ml of water and 50 ml of brine, dried over anhydrous sodium sulfate (25 g) and concentrated to give 15-(o-methylphenyl)-15-epi-2,5,6,7,16,17,18,19,20-nonanor-4-oxa-4,8-inter-m-phenylene $PGI_2$ (225.6 mg, 0.57 mmol) as a single product in a yield of 99%. This product was recrystallized from acetone/n-hexane (2:1) to give a colorless needle-like crystal, which was assigned the structure by the following data:

m.p. 130° C.(dec.).

IR(KBr): 3350(3700–2200), 2930, 1740, 1710, 1620, 1595, 1484, 1461, 1424, 1283, 1262, 1199, 1123, 1044, 1023, 1004, 974, 961, 940, 883, 859, 793, 781, 769, 748, 734, 630, 603 cm$^{-1}$.

NMR(400 MHz, CDCl$_3$, δ): 1.98–2.07(1H, m), 2.36(3H, s), 2.42–2.49(1H, m), 2.57–2.66(1H, m), 3.42–3.47(1H, m), 3.83–3.90(1H, m), 2.2–2.4(3H, broad s), 4.65(2H, s), 5.12–5.19(1H, m), 5.38–5.42(1H, m), 5.60–5.68(1H, m), 5.83–5.89(1H, m), 6.70–6.77(3H, m), 7.13–7.27(3H, m), 7.52–7.54(1H, m).

MASS(EI, m/e): 360(M+-36).

HR MASS: Calcd. (C$_{24}$H$_{24}$O$_5$, M+-H$_2$O): 378.1467. Found (M+-H$_2$O): 378.1448.

EXAMPLE 85

15-(p-methylphenyl)-2,5,6,7,16,17,18,19,20-nonanor-4-oxa-4,8-inter-m-phenylene PGI$_2$ methyl ester (268) and its 15-epimer (269)

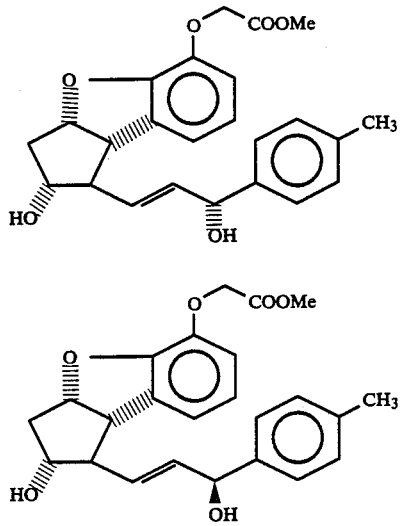

Cerium trichloride heptahydrate (1.81 g, 4.86 mmol) was dissolved into a stirred solution of 15-(p-methylphenyl)-15-oxo-2,5,6,7,16,17,18,19,20-nonanor-4-oxa-4,8-inter-m-phenylene PGI$_2$ methyl ester, 11-benzoate (1.95 g, 4.03 mmol) in 100 ml of methanol. The solution was cooled to −10° C. Sodium borohydride (59.6 mg, 1.58 mmol) was slowly added with stirring and then, the mixture was stirred for 20 minutes. The reaction mixture was allowed to warm to 0° C. and mixed with 13 ml of a saturated aqueous solution of sodium bicarbonate. After filtration, the filtrate was concentrated. The concentrated residue was diluted with 20 ml of water, and extracted with ethyl acetate (50 ml×2). The combined ethyl acetate layer was washed with water (20 ml×1) and brine (20 ml×1), dried over anhydrous sodium sulfate and concentrated to give an oily product (1.94 g). This oily product was dissolved into 50 ml of anhydrous methanol under argon atmosphere. A solution of sodium methoxide in methanol (5.22N, 0.36 ml, 1.89 mmol) was added with stirring, and the mixture was stirred at room temperature for 14 hours. This reaction solution was neutralized with acetic acid and concentrated. The concentrated residue was mixed with 20 ml of water, and extracted with ethyl acetate (50 ml×2). The ethyl acetate layer was washed with water (20 ml×1) and brine (20 ml×1), dried over anhydrous sodium sulfate and concentrated. The concentrated residue was separated and purified through column chromatography (Merck, Lobar column; silica gel, ethyl acetate/cyclohexane=2/1) to give less polar 15-p-methylphenyl-15-epi-2,5,6,7,16,17,18,19,20-nonanor-4-oxa-4,8-inter-m-phenylene PGI$_2$ methyl ester (yielded amount 571 mg, 1.39 mmol, yield 36.9%) and more polar 15-p-methylphenyl-2,5,6,7,16,17,18,19,20-nonanor-4-oxa-4,8-inter-m-phenylene PGI$_2$ methyl ester (yielded amount 616 mg, 1.5 mmol, yield 39.9%). These compounds were assigned the corresponding structures by the following data:

15-(p-methylphenyl)-2,5,6,7,16,17,18,19,20-nonanor-4-oxa-4,8-inter-m-phenylene PGI$_2$ methyl ester m.p. 152.1°–153.0° C. (recrystallized from THF/n-hexane 2/1).

IR(KBr): 3300, 2930, 1755, 1605, 1495, 1475, 1455, 1435, 1170, 1130, 1275, 1240, 1215, 1175, 1160, 1090, 1065, 1030, 1005, 970, 950, 855, 820, 800, 735 cm$^{-1}$.

NMR(400 MHz, CDCl$_3$, δ): 2.0–2.1(1H, m), 2.1–2.3(2H, m), 2.36(3H, s), 2.53(1H, q, J=7.6 Hz), 2.6–2.7(1H, m), 3.51(1H, t, J=7.6 Hz), 3.78(3H, s), 3.9–4.1(1H, m), 4.71(2H, s), 5.1–5.3(2H, m), 5.76(1H, dd, J=7.6, 15.4 Hz), 5.83(1H, dd, J=5.6, 15.4 Hz), 6.6–6.8(3H, m), 7.19(2H, d, J=7.6 Hz), 7.27(2H, d, J=7.6 Hz).

MASS(EI, m/e): 410(M+).

Elementary analysis: Calcd. (as C$_{24}$H$_{26}$O$_6$): C(%) 70.23 H(%) 6.39. Found: 70.12 6.42.

15-(p-methylphenyl)-15-epi-2,5,6,7,16,17,18,19,20-nonanor-4-oxa-4,8-inter-m-phenylene PGI$_2$ methyl ester m.p. 108.3°–109.0° C. (recrystallized from ethyl acetate/n-hexane 2/1).

IR(KBr): 3330, 2950, 2870, 1755, 1600, 1480, 1450, 1430, 1375, 1320, 1285, 1255, 1225, 1190, 1175, 1160, 1100, 1020, 990, 975, 940, 915, 890, 855, 825, 790, 775, 730, 705, 670 cm$^{-1}$.

NMR(400 MHz, CDCl$_3$, δ): 1.7–1.9(1H, m), 1.9–2.1(1H, m), 2.0–2.2(1H, m), 2.36(3H, s), 2.5–2.7(2H, m), 3.55(1H, t, J=8.3 Hz), 3.78(3H, s), 3.9–4.1(1H, m), 4.72(2H, s), 5.1–5.3(2H, m), 5.78(1H, dd, J=5.4, 15.7 Hz), 5.85(1H, dd, J=7.6, 15.7 Hz), 6.7–6.9(3H, m), 7.19(2H, d, J=8.3 Hz), 7.27(2H, d, J=8.3 Hz).

MASS(EI, m/e): 410(M+).

Elementary analysis: Calcd. (as C$_{24}$H$_{26}$O$_6$): C(%) 70.23 H(%) 6.39. Found: 70.25 6.35.

EXAMPLE 86

15-(p-methylphenyl)-2,5,6,7,16,17,18,19,20-nonanor-4-oxa-4,8-inter-m-phenylene PGI$_2$ (270)

To an ice-cooled and stirred solution of 15-(p-methylphenyl)-2,5,6,7,16,17,18,19,20-nonanor-4-oxa-4,8-inter-m-phenylene PGI$_2$ methyl ester (148 mg, 0.36 mmol) in 20 ml of methanol was added an aqueous solution of sodium hydroxide (0.725N, 3.97 ml, 2.88 mmol), and the mixture was stirred for 3 hours at room temperature, then concentrated, and diluted with 50 ml of ethyl acetate and 20 ml of water. The reaction mixture was neutralized by slow addition of 2.88 ml of 1N hydrochloric acid with ice-cooling and stirring. The ethyl acetate layer was washed with water (20 ml×1) and brine (20 ml×1), dried over anhydrous sodium sulfate and concentrated. The concentrated residue was recrystallized from 2.5 ml of ethyl acetate and 1.5 ml of n-hexane to yield 15-(p-methylphenyl)-2,5,6,7,16,17,18,19,20-nonanor-4-oxa-4,8-inter-m-phenylene PGI₂ (yielded amount 102 mg, 0.26 mmol, 71.5% yield) as a white crystal, which was assigned the structure by the following data:

m.p. 109.3°–112.6° C. (recrystallized from ethyl acetate/n-hexane 5/3).

IR(KBr): 3400, 2920, 1725, 1700, 1610, 1485, 1460, 1430, 1370, 1280, 1240, 1190, 1105, 1080, 1070, 850, 760, 720 cm⁻¹.

NMR(400 MHz, DMSO, δ): 1.6–1.8(1H, m), 2.20(1H, q, J=8.3 Hz), 2.3(3H, s), 2.4–2.6(1H, m), 3.39(1H, t, J=8.3 Hz), 3.7–3.8(1H, m), 4.62(2H, s), 4.8–4.9(1H, m), 5.0–5.1(2H, m), 5.2–5.4(1H, m), 5.62(1H, dd, J=8.3, 15.4 Hz), 5.72(1H, dd, J=6.1, 15.4 Hz), 6.5–6.7(3H, m), 7.14(2H, d, J=7.8 Hz), 7.25(2H, d, J=7.8 Hz).

MASS(FAB, m/e): 396(M+).

Elementary analysis: Calcd. (as C₂₃H₂₄O₆): C(%) 69.68, H(%) 6.10. Found: 69.92, 6.45.

EXAMPLE 87

15-(p-methylphenyl)-15-epi-2,5,6,7,16,17,18,19,20-nonanor-4-oxa-4,8-inter-m-phenylene PGI₂ (271)

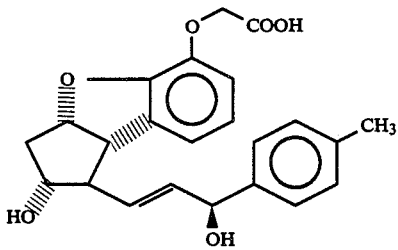

271

To an ice-cooled and stirred solution of 15-(p-methylphenyl)-15-epi-2,5,6,7,16,17,18,19,20-nonanor-4-oxa-4,8-inter-m-phenylene PGI₂ methyl ester (131 mg, 0.32 mmol) in 20 ml of MeOH was added an aqueous solution of sodium hydroxide (0.725N, 3.5 ml, 2.55 mmol), and the mixture was stirred for 3 hours at room temperature. This reaction solution was concentrated. 50 ml of ethyl acetate and 20 ml of water were added to the residue. Further, 2.55 ml of 1N hydrochloric acid was slowly added with ice-cooling and stirring. The ethyl acetate layer was washed with water (20 ml×1) and brine (20 ml×1), dried over anhydrous sodium sulfate and concentrated. The concentrated residue was recrystallized from 2 ml of ethyl acetate and 2 ml of n-hexane to yield 15-(p-methylphenyl)-15-epi-2,5,6,7,16,17,18,19,20-nonanor-4-oxa-4,8-inter-m-phenylene PGI₂ (yielded amount 107 mg, 0.27 mmol, yield 84.6%), which was assigned the structure by the following data:

m.p. 124.3°–126.7° C. (recrystallized from ethyl acetate/n-hexane 1/1).

IR(KBr): 3450, 2920, 1730, 1710, 1615, 1590, 1485, 1455, 1420, 1280, 1260, 1190, 1120, 1060, 1020, 960, 880, 850, 810, 790, 770, 750, 730 cm⁻¹.

NMR(400 MHz, DMSO, δ): 1.6–1.8(1H, m), 2.1–2.3(1H, m), 2.29(3H, s), 2.4–2.6(1H, m), 3.43(1H, t, J=9.0 Hz), 3.7–3.8(1H, m), 4.62(2H, s), 4.8–4.9(1H, m), 5.0–5.1(2H, m), 5.61(1H, dd, J=6.1, 15.6 Hz), 5.74(1H, dd, J=7.6, 15.6 Hz), 6.6–6.8(3H, m), 7.13(2H, d, J=8.1 Hz), 7.25(2H, d, J=8.1 Hz)

MASS(FAB, m/e): 396(M+).

Elementary analysis: Calcd. (as C₂₃H₂₄O₆): C(%) 69.28, H(%) 6.10. Found: 69.29, 6.05.

EXAMPLE 88

15-(m-fluorophenyl)-2,5,6,7,16,17,18,19,20-nonanor-4-oxa-4,8-inter-m-phenylene PGI₂ methyl ester (272) and its 15-epimer (273)

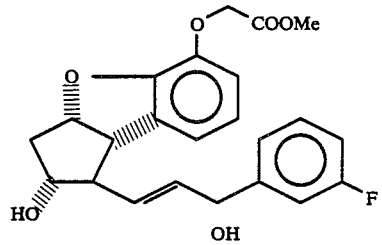

272

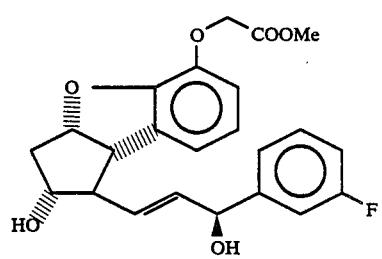

273

Cerium trichloride heptahydrate (1.7884 g, 4.80 mmol) was dissolved into a solution of 15-(m-fluorophenyl)-15-oxo-2,5,6,7,16,17,18,19,20-nonanor-4-oxa-4,8-inter-m-phenylene PGI₂ methyl ester, 11-benzoate (2.0012 g, 4.00 mmol) in 50 ml of methanol. While this solution was being stirred at −10° C., sodium borohydride (50.4 mg, 1.20 mmol) was added. The mixture was stirred for 30 minutes, diluted with 40 ml of water and then concentrated. Then, the mixture was extracted with ethyl acetate (40 ml×3). The combined organic layers were washed with 100 ml of water and 100 ml of brine, dried over anhydrous sodium sulfate (35 g) and concentrated to give 2.2078 g of an oily product.

This oily product was dried by azeotropic distillation with benzene (10 ml×2) and dissolved into 15 ml of anhydrous methanol. 5.22N sodium methoxide (0.23 ml, 1.20 mmol) was added to this solution and the mixture was stirred overnight under argon stream at room temperature. 0.4 ml of acetic acid was added to the reaction mixture, which was then concentrated. The residue was combined with 15 ml of water and extracted with ethyl acetate (15 ml×3). The combined organic layers were washed with 50 ml of water and 50 ml of brine, dried over anhydrous sodium sulfate (20 g) and concentrated to give 1.9824 g of an oily product. This oily product was purified by column chromatography (silica gel, ethyl acetate/cyclohexane 6:1) to give a first eluted fraction less polar 15-m-fluorophenyl-15-epi-2,5,6,7,16,17,18,19,20-nonanor-4-oxa-4,8-inter-m-phenylene PGI₂ methyl ester (755.5 mg, 1.91 mmol) in 48% yield. This product was recrystallized from ethyl acetate/cyclohexane (2:1) to yield a colorless needle-like crystal. Second eluted fraction afforded more polar 15-(m-fluorophenyl)-2,5,6,7,16,17,18,19,20-nonanor-4-oxa-4,8-inter-m-phenylene PGI₂ methyl ester (748.9 mg, 1.89 mmol) in 47% yield. This product was recrystallized from ethyl acetate/cyclohexane (2:1) to yield a colorless needle-like crystal. These compounds were assigned the corresponding structures by the following data:

15-(m-fluorophenyl)-2,5,6,7,16,17,18,19,20-nonanor-4-oxa-4,8-inter-m-phenylene PGI₂ methyl ester m.p. 143.5°–144° C.

IR(KBr): 3250, 2980, 2950, 2910, 2880, 1755, 1610, 1583, 1480, 1457, 1369, 1285, 1242, 1204, 1183, 1154, 1114, 1064, 1025, 1005, 983, 964, 944, 915, 885, 865, 830, 780, 755, 723, 704, 694, 680, 603 cm⁻¹.

NMR(400 MHz, CDCl₃, δ): 1.98–2.06(1H, broad s), 2.02–2.08(1H, m), 2.24–2.29(1H, broad s), 2.50–2.57(1H, m), 2.59–2.68(1H, m), 3.48–3.53(1H, m), 3.78(3H, s), 3.94–4.03(1H, m), 4.71(2H, s), 5.18–5.26(2H, m), 5.73–5.83(2H, m), 6.68–6.75(3H, m), 6.96–7.03(1H, m), 7.10–7.18(2H, m), 7.31–7.37(1H, m).

MASS(EI, m/e): 414(M⁺).

HR MASS: Calcd. (C₂₃H₂₃O₆F, M⁺): 414.1478. Found (M⁺): 414.1489.

15-(m-fluorophenyl)-15-epi-2,5,6,7,16,17,18,19,20-nonanor-4-oxa-4,8-inter-m-phenylene PGI₂ m.p. 93°–94° C.

IR(KBr): 3470, 2950, 2900, 2854, 1725, 1612, 1583, 1482, 1453, 1431, 1370, 1290, 1274, 1260, 1238, 1188, 1160, 1138, 1105, 1069, 1025, 1003, 984, 970, 915, 885, 861, 843, 799, 763, 730, 700, 630, 608 cm⁻¹.

NMR(400 MHz, CDCl₃, δ): 1.77–1.80(1H, broad s), 2.10–2.12(1H, broad s), 2.52–2.67(2H, m), 3.51–3.55(1H, m), 3.78(3H, s), 3.97–4.03(1H, m), 4.71(2H, s), 5.20–5.28(2H, m), 5.77–5.86(2H, m), 6.71–6.80(3H, m), 6.97–7.03(1H, m), 7.10–7.17(2H, m), 7.31–7.38(1H, m).

MASS(EI, m/e): 414(M⁺).

HR MASS: Calcd. (C₂₃H₂₃O₆F, M⁺): 414.1478. Found (M⁺): 414.1475.

EXAMPLE 89

15-(m-fluorophenyl)-2,5,6,7,16,17,18,19,20-nonanor-4-oxa-4,8-inter-m-phenylene PGI₂ (274)

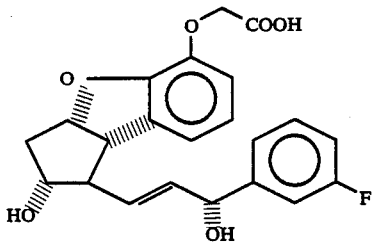

274

To a solution of 15-(m-fluorophenyl)-2,5,6,7,16,17,18,19,20-nonanor-4-oxa-4,8-inter-m-phenylene PGI₂ methyl ester (217.2 mg, 0.55 mmol) in 10 ml of methanol was added an aqueous solution of sodium hydroxide (1N, 2.7 ml, 2.7 mmol), and the mixture was stirred for 3 hours under argon stream at room temperature. To this reaction mixture was added 2.7 ml of 1N hydrochloric acid and 10 ml of water, and the mixture was extracted with ethyl acetate (10 ml×3). The combined organic layers were washed with 30 ml of water and 30 ml of brine, dried over anhydrous sodium sulfate (10 g) and concentrated to give quantitatively 15-(m-fluorophenyl)-2,5,6,7,16,17,18,19,20-nonanor-4-oxa-4,8-inter-m-phenylene PGI₂ (208.2 mg, 0.55 mmol) as a single product. This product was recrystallized from ethyl acetate/n-hexane (1:1) to yield a colorless needle-like crystal, which was assigned the structure by the following data:

m.p. 130° C.(dec.).

IR(KBr): 3400(3700-2220), 2920, 1730, 1620, 1591, 1482, 1462, 1428, 1380, 1344, 1300, 1283, 1237, 1186, 1163, 1104, 1077, 1022, 970, 960, 941, 910, 886, 860, 830, 784, 765, 732, 700, 622 cm⁻¹.

NMR(400 MHz, CDCl₃, δ): 1.98–2.06(1H, m), 2.37–2.43(1H, m), 2.58–2.69(1H, m), 2.0–4.4(3H, broad s), 3.42–3.46(1H, m), 3.88–3.93(1H, m), 4.66(2H, s), 5.15–5.25(2H, m), 5.70–5.81(2H, m), 6.67–6.75(3H, m), 6.93–6.98(1H, m), 7.12–7.19(2H, m), 7.29–7.37(1H, m).

MASS(EI, m/e): 364(M⁺-2H₂O).

HR MASS: Calcd. (C₂₂H₂₁O₆F, M⁺-2H₂O): 364.1111. Found (M⁺-2H₂O): 364.1115.

EXAMPLE 90

15-(m-fluorophenyl)-15-epi-2,5,6,7,16,17,18,19,20-nonanor-4-oxa-4,8-inter-m-phenylene PGI₂ (275)

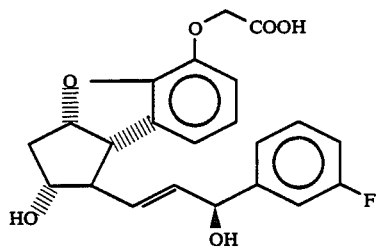

275

To a solution of 15-(m-fluorophenyl)-15-epi-2,5,6,7,16,17,18,19,20-nonanor-4-oxa-4,8-inter-m-phenylene PGI₂ methyl ester (250.3 mg, 0.63 mmol) in 10 ml of methanol was added an aqueous solution of sodium hydroxide (1N, 3.2 ml, 3.2 mmol), and the mixture was stirred under argon stream at room temperature for 3 hours. To this reaction mixture were added 3.2 ml of 1N hydrochloric acid and 10 ml of water, and the mixture was extracted with ethyl acetate (10 ml×3). The organic layer was washed with 30 ml of water and 30 ml of brine, dried over anhydrous sodium sulfate (10 g) and concentrated to give quantitatively 15-(m-fluorophenyl)-15-epi-2,5,6,7,16,17,18,19,20-nonanor-4-oxa-4,8-inter-m-phenylene PGI₂ (240.8 mg, 0.63 mmol) as a single product. This product was recrystallized from THF/n-hexane (1:1) to yield a colorless needle-like crystal, which was assigned the structure by the following data:

m.p. 155° C.(dec.).

IR(KBr): 3400(3700-2200), 2920, 1720, 1620, 1585, 1481, 1463, 1443, 1430, 1379, 1340, 1310, 1290, 1272, 1241, 1220, 1200, 1163, 1119, 1084, 1072, 1022, 965, 953, 940, 906, 883, 871, 858, 831, 786, 768, 743, 730, 701, 625, 600 cm⁻¹.

NMR(400 MHz, CDCl₃, δ): 1.97–2.07(1H, m), 2.43–2.51(1H, m), 2.57–2.67(1H, m), 2.0–4.6(3H, broad s), 3.43–3.48(1H, m), 3.89–3.94(1H, m), 4.65(2H, s), 5.13–5.22(2H, m), 5.72–5.88(2H, m), 6.70–6.78(3H, m), 6.92–6.98(1H, m), 7.12–7.18(2H, m), 7.28–7.36(1H, m).

MASS(EI, m/e): 364(M⁺-36).

HR MASS: Calcd. (C₂₂H₂₁O₆F, M⁺-2H₂O): 364.1111. Found (M⁺-2H₂O): 364.1085.

EXAMPLE 91

15-(m-trifluoromethylphenyl)-2,5,6,7,16,17,18,19,20-nonanor-4-oxa-4,8-inter-m-phenylene PGI$_2$ methyl ester (276) and its 15-epimer (277)

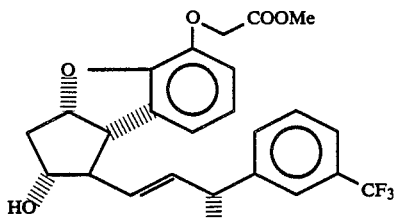

276

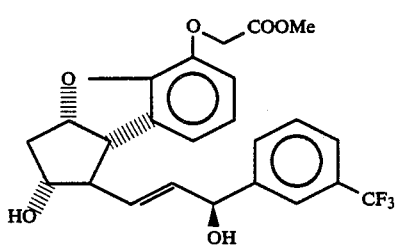

277

837 mg of cerium trichloride heptahydrate (2.25 mmol) were dissolved into a solution of 15-(m-trifluoromethylphenyl)-15-oxo-2,5,6,7,16,17,18,19,20-nonanor-4-oxa-4,8-inter-m-phenylene PGI$_2$ methyl ester, 11-benzoate (1.2711 g, 2.25 mmol) in 50 ml of methanol. Sodium borohydride (33.8 mg, 0.89 mmol) was added into this solution which was being stirred with ice-cooling, and this mixture was stirred for 10 minutes. 10 ml of water was added to this reaction mixture, which was concentrated. Further, 10 ml of water was added and the mixture was extracted with ethyl acetate (30 ml×3). The combined organic layers were washed with water (50 ml) and brine (50 ml), dried over anhydrous sodium sulfate and concentrated to give 1.27 g of an oily product.

To a solution of the oily product in 40 ml of anhydrous methanol was added 5.22N sodium methoxide (47 μl, 0.25 mmol). The mixture was stirred overnight under argon atmosphere at room temperature, quenched with 0.1 ml of acetic acid, and then concentrated. The residue was mixed with 30 ml of water and extracted with ethyl acetate (30 ml×3). The combined organic layers were washed with 50 ml of water and 50 ml of brine, dried over anhydrous sodium sulfate and concentrated to give 1.00 g of an oily product. This oily product was purified by column chromatography (silica gel, ethyl acetate/cyclohexane=6/1) to give as first eluted fraction less polar 15-(m-trifluoromethylphenyl)-15-epi-2,5,6,7,16,17,18,19,20-nonanor-4-oxa-4,8-inter-m-phenylene PGI$_2$ methyl ester (299.6 mg, 0.59 mmol) in a yield of 26.3%, and as second eluted fraction more polar 15-(m-trifluoromethylphenyl)-2,5,6,7,16,17,18,19,20-nonanor-4-oxa-4,8-inter-m-phenylene PGI$_2$ methyl ester (262.7 mg, 0.57 mmol) in 25.2% yield.

These compounds were assigned the corresponding structures by the following data:

15-(m-trifluoromethylphenyl)-2,5,6,7,16,17,18,19,20-nonanor-4-oxa-4,8-inter-m-phenylene PGI$_2$ methyl ester m.p. 84.5°–86.0° C. (recrystallized from acetone/n-hexane=1/1).

IR(KBr): 3545, 3380, 2960, 2900, 2850, 1760, 1740, 1615, 1585, 1485, 1455, 1435, 1385, 1330, 1300, 1235, 1190, 1155, 1110, 1065, 1020, 978, 958, 940, 900, 882, 852, 825, 800, 760, 720, 698, 600 cm$^{-1}$.

NMR(400 MHz, CDCl$_3$, δ): 1.91–1.98(1H, broad s), 2.04–2.13(1H, m), 2.28–2.34(1H, broad s), 2.51–2.58(1H, m), 2.62–2.71(1H, m), 3.47–3.52(1H, m), 3.78(3H, s), 3.96–4.05(1H, m), 4.71(2H, s), 5.16–5.26(1H, m), 5.29–5.37(1H, m), 5.76–5.88(2H, m), 6.67–6.76(3H, m), 7.47–7.68(4H, m).

MASS(EI, m/e): 464(M+).

HR MASS: Calcd. (C$_{24}$H$_{23}$O$_6$F$_3$, M+): 464.1446. Found (M+): 464.1466.

15-(m-trifluoromethylphenyl)-15-epi-2,5,6,7,16,17,18,19,20-nonanor-4-oxa-4,8-inter-m-phenylene PGI$_2$ methyl ester m.p. 133.0°–134.5° C. (recrystallized from acetone/n-hexane=2/3).

IR(KBr): 3320, 2975, 2920, 2870, 1755, 1615, 1590, 1485, 1458, 1435, 1370, 1332, 1305, 1285, 1255, 1222, 1190, 1165, 1118, 1065, 1020, 980, 960, 935, 885, 850, 808, 780, 760, 745, 708, 685, 655 cm$^{-1}$.

NMR(400 MHz, CDCl$_3$, δ): 1.56(1H, s), 1.68–1.77(1H, broad s), 2.04–2.18(2H, m), 2.52–2.69(2H, m), 3.51–3.57(1H, m), 3.78(3H, s), 3.96–4.05(1H, m), 4.72(2H, s), 5.20–5.27(1H, m) 5.31–5.36(1H, m), 5.77–5.92(2H, m), 6.69–6.78(3H, m), 7.47–7.71(4H, m).

MASS(EI, m/e): 464(M+).

HR MASS: Calcd. (C$_{24}$H$_{23}$O$_6$F$_3$, M+): 464.1446. Found (M+): 464.1462.

EXAMPLE 92

15-(m-trifluoromethylphenyl)-2,5,6,7,16,17,18,19,20-nonanor-4-oxa-4,8-inter-m-phenylene PGI$_2$ (278)

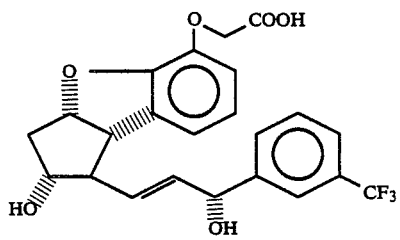

278

To a solution of 15-(m-trifluoromethylphenyl)-2,5,6,7,16,17,18,19,20-nonanor-4-oxa-4,8-inter-m-phenylene PGI$_2$ methyl ester (165.4 mg, 0.36 mmol) in 20 ml of methanol was added an aqueous solution of sodium hydroxide (1N, 1.1 ml, 1.1 mmol). The mixture was stirred overnight under argon atmosphere, quenched with 1.1 ml of 1N hydrochloric acid, diluted with 30 ml of water, and extracted with ethyl acetate (30 ml×3). The combined organic layers were washed with water (60 ml) and brine (60 ml), dried over anhydrous sodium sulfate and concentrated to give quantitatively 15-(m-trifluoromethylphenyl)-2,5,6,7,16,17,18,19,20-nonanor-4-oxa-4,8-inter-m-phenylene PGI$_2$ (139.5 mg, 0.31 mmol) as a single compound, which was assigned the structure by the following data:

m.p. 156.0°–158.0° C. (recrystallized from acetone/n-hexane=1/1).

IR(KBr): 3440, 2925, 1725, 1615, 1588, 1485, 1462, 1432, 1380, 1350, 1328, 1290, 1240, 1178, 1110, 1065, 1020, 980, 940, 898, 855, 828, 804, 765, 728, 700 cm$^{-1}$.

NMR(400 MHz, CDCl₃, δ): 1.93–2.03(1H, m), 2.36–2.45(1H, m), 2.57–2.68(1H, m), 2.68–3.40(2H, broad s), 3.41–3.47(1H, m), 3.85–3.94(1H, m), 4.62(2H, s), 5.10–5.18(1H, m), 5.22–5.28(1H, m), 5.68–5.86(2H, m), 6.62–6.74(2H, m), 7.45–7.73(4H, m).

MASS(EI, m/e): 450(M+).

HR MASS: Calcd. (C₂₃H₂₁O₆F₃, M+): 450.1290. Found (M+): 450.1280.

EXAMPLE 93

15-(o-chlorophenyl)-2,5,6,7,16,17,18,19,20-nonanor-4-oxa-4,8-inter-m-phenylene PGI₂ methyl ester (279) and its 15-epimer (280)

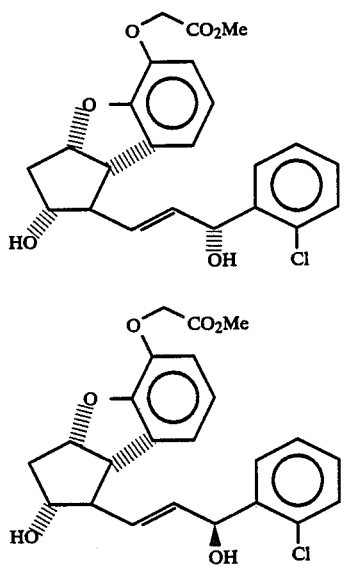

Cerium trichloride heptahydrate (0.90 g, 2.42 mmol) was dissolved into a solution of 15-(o-chlorophenyl)-15-oxo-2,5,6,7,16,17,18,19,20-nonanor-4-oxa-4,8-inter-m-phenylene PGI₂ methyl ester, 11-benzoate (1.29 g, 2.42 mmol) in 50 ml of methanol. While this solution was being stirred at −14° C., sodium borohydride (52.5 mg, 1.39 mmol) was added thereto and the mixture was stirred for 1 hour, diluted with 10 ml of water, concentrated and mixed with 50 ml ethyl acetate. Resulting precipitate was filtered by Hyflo Super Cel, and washed with ethyl acetate (50 ml×3). The combined ethyl acetate layer was washed with brine (50 ml), dried over anhydrous sodium sulfate and concentrated to give an oily product. This oily product was dried by azeotropic distillation with benzene (20 ml×3), further dried under reduced pressure and dissolved into 50 ml of anhydrous methanol. To the solution was added sodium methoxide (5.22N, 0.05 ml, 0.261 mmol), and the mixture was stirred overnight under argon atmosphere at room temperature, 0.1 ml of acetic acid and 10 ml of a solution of diazomethane in ether were added to this reaction mixture, which was then concentrated. 30 ml of water was added and the mixture was extracted with ethyl acetate (30 ml×4). The combined ethyl acetate layer was washed with brine (50 ml), dried over anhydrous sodium sulfate and concentrated to give an oily product. This oily product was separated and purified through column chromatography (silica gel, ethyl acetate/cyclohexane=5:1) to give less polar 15-o-chlorophenyl-15-epi-2,5,6,7,16,17,18,19,20-nonanor-4-oxa-4,8-inter-m-phenylene PGI₂ methyl ester (0.32 g, 0.74 mmol) and more polar 15-o-chlorophenyl-2,5,6,7,16,17,18,19,20-nonanor-4-oxa-4,8-inter-m-phenylene PGI₂ methyl ester (0.41 g, 0.95 mmol) in a yield of 70%. These compounds were assigned the corresponding structures by the following data:

α-isomer 15-(o-chlorophenyl)-2,5,6,7,16,17,18,19,20-nonanor-4-oxa-4,8-inter-m-phenylene PGI₂ methyl ester m.p. 120° C. (recrystallized from ethyl acetate and cyclohexane; colorless needle-like crystal).

IR(KBr): 3380, 1735, 1618, 1588, 1482, 1460, 1435, 1278, 1260, 1235, 1192, 1113, 1010, 978, 943, 860, 760, 730 cm⁻¹.

NMR(400 MHz, CDCl₃, δ): 2.01–2.09(1H, m), 2.28–2.33(1H, broad s), 2.44–2.52(1H, m), 2.58–2.68(2H, m), 3.45–3.51(1H, m), 3.77(3H, s), 3.92–4.00(1H, m), 4.70(2H, s), 5.15–5.22(1H, m), 5.61–5.67(1H, m), 5.67–5.74(1H, m), 5.63(1H, dd, J=6.35, 2.45 Hz), 5.71(1H, dd, J=15.14, 6.35 Hz), 5.83(1H, dd, J=15.14, 8.79 Hz), 6.65–6.74(3H, m), 7.21–7.40(3H, m), 7.56–7.60(1H, m).

MASS(EI, m/e): 430(M+).

HR MASS: Calcd. (C₂₃H₂₃O₆Cl, M+): 430.1183. Found (M+): 430.1164.

β-isomer 15-(o-chlorophenyl)-15-epi-2,5,6,7,16,17,18,19,20-nonanor-4-oxa-4,8-inter-m-phenylene PGI₂ methyl ester m.p. 113°–114° C. (recrystallized from ethyl acetate and cyclohexane; colorless needle-like crystal).

IR(KBr): 3785, 1755, 1613, 1590, 1480, 1458, 1435, 1369, 1285, 1238, 1189, 1178, 1118, 1075, 1048, 1018, 980, 964, 940, 892, 852, 757, 727, 705 cm⁻¹.

NMR(400 MHz, CDCl₃, δ): 1.85–1.94(1H, broad s), 2.03–2.11(1H, m), 2.28–2.33(1H, broad s), 2.49–2.56(1H, m), 2.57–2.66(1H, m), 3.50(1H, t, J=8.30 Hz), 3.78(3H, s), 3.92–3.99(1H, m), 4.71(2H, s), 5.18–5.24(1H, m), 5.63–5.68(1H, m), 5.72–5.85(1H, m), 6.69–6.80(3H, m), 7.22–7.38(3H, m), 7.56–7.61(1H, m).

MASS(EI, m/e): 430(M+).

HR MASS: Calcd. (C₂₃H₂₃O₆Cl, M+): 430.1183. Found (M+): 430.1167.

EXAMPLE 94

15-(o-chlorophenyl)-2,5,6,7,16,17,18,19,20-nonanor-4-oxa-4,8-inter-m-phenylene PGI₂ (281)

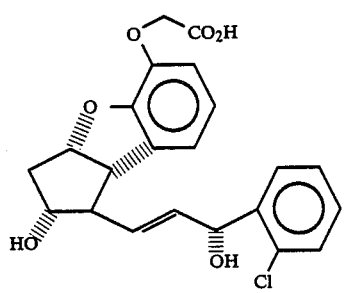

To a solution of 15-(o-chlorophenyl)-2,5,6,7,16,17,18,19,20-nonanor-4-oxa-4,8-inter-m-phenylene PGI₂ methyl ester (121.4 mg, 0.282 mmol) in 20 ml of methanol was added an aqueous solution of sodium hydroxide (1N, 0.85 ml, 0.846 mmol), and the mixture was stirred overnight under argon atmosphere at room temperature. Hydrochloric acid (1N, 0.85 ml) was added to the reaction mixture and methanol was distilled off. 10 ml of water was added and the mixture was extracted with ethyl acetate (30 ml×4). The combined ethyl acetate layer was washed with brine (50 ml), dried over anhydrous sodium sulfate and concentrated to give 117.7 mg of 15-(o-chlorophenyl)-2,5,6,7,16,17,18,19,20-nonanor-4-oxa-4,8-inter-m-phenylene PGI$_2$ as a single product (yield 100%), which was assigned the structure by the following data:

m.p. 147°–149° C. (recrystallized from acetone and n-hexane; colorless needle-like crystal).

IR(KBr): 3430, 2980, 1736, 1626, 1598, 1490, 1470, 1438, 1381, 1348, 1280, 1238, 1101, 1063, 1048, 1016, 960, 945, 860, 765, 750, 732, 710, 636 cm$^{-1}$.

NMR(400 MHz,

δ): 1.94–2.05(1H, m), 2.30–2.40(1H, m), 2.57–2.70(2H, m), 3.25–4.35(4H, broad m), 4.64(2H, s), 5.11–5.20(1H, m), 5.53–5.65(2H, m), 5.78–5.88(1H, m), 6.51–6.73(3H, m), 7.18–7.25(1H, m), 7.27–7.40(2H, m), 7.62–7.70(1H, m).

MASS(EI, m/e): 416(M$^+$).

HR MASS: Calcd. (C$_{22}$H$_{21}$O$_6$Cl, M$^+$): 416.1026. Found (M$^+$): 416.1047.

EXAMPLE 95

15-(o-chlorophenyl)-15-epi-2,5,6,7,16,17,18,19,20-nonanor-4-oxa-4,8-inter-m-phenylene PGI$_2$ (282)

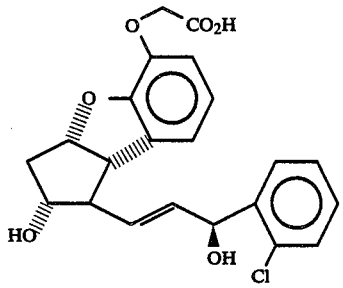

To a solution of 15-(o-chlorophenyl)-15-epi-2,5,6,7,16,17,18,19,20-nonanor-4-oxa-4,8-inter-m-phenylene PGI$_2$ methyl ester (278.8 mg, 0.647 mmol) in 30 ml of methanol was added an aqueous sodium hydroxide solution (1N, 1.94 ml, 1.94 mmol), and the mixture was stirred overnight under argon atmosphere at room temperature. To this reaction mixture was added hydrochloric acid (1N, 1.94 ml) and methanol was distilled off. 20 ml of water was added and the mixture was extracted with ethyl acetate (30 ml×4). The combined ethyl acetate layer was washed with brine (50 ml), dried over anhydrous sodium sulfate and concentrated to give 243.3 mg of 15-(o-chlorophenyl)-15-epi-2,5,6,7,16,17,18,19,20-nonanor-4-oxa-4,8-inter-m-phenylene PGI$_2$ as a single product (yield 90.2%). This compound was assigned the structure by the following data:

m.p. 137.5°–139.5° C. (recrystallized from acetone and n-hexane; colorless needle-like crystal).

IR(KBr): 3355, 3060, 2955, 2925, 1738, 1705, 1617, 1590, 1567, 1483, 1461, 1435, 1420, 1365, 1317, 1281, 1261, 1190, 1166, 1120, 1063, 1053, 1021, 967, 954, 934, 884, 854, 803, 787, 772, 759, 742, 727, 701, 629, 602 cm$^{-1}$.

NMR(400 MHz,

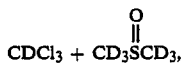

δ): 1.98–2.08(1H, m), 2.43–2.52(1H, m), 2.56–2.65(1H, m), 2.98–3.78(2H, broad s), 3.43(1H, t, J=8.79 Hz), 3.85–3.93(1H, m), 4.62–4.72(2H, m), 5.13–5.20(1H, m), 5.59–5.69(2H, m), 5.85(1H, dd, J=15.14, 5.86 Hz), 6.68–6.77(3H, m), 7.20–7.38(3H, m), 7.58–7.64(1H, m).

MASS(EI, m/e): 416(M$^+$).

HR MASS: Calcd. (C$_{22}$H$_{21}$O$_6$Cl, H$^+$): 416.1027. Found (M$^+$): 416.1050.

EXAMPLE 96

15-(m-chlorophenyl)-2,5,6,7,16,17,18,19,20-nonanor-4-oxa-4,8-inter-m-phenylene PGI$_2$ methyl ester (283) and its 15-epimer (284)

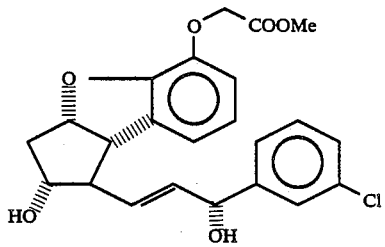

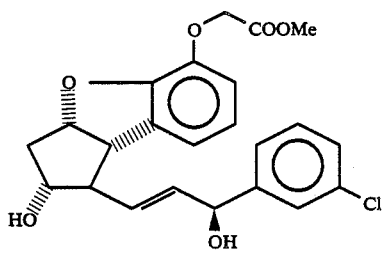

Cerium trichloride heptahydrate (1.58 g, 4.24 mmol) was dissolved into a stirred solution of 15-(m-chlorophenyl)-15-oxo-2,5,6,7,16,17,18,19,20-nonanor-4-oxa-4,8-inter-m-phenylene PGI$_2$ methyl ester, 11-benzoate (1.87 g, 3.5 mmol) in 80 ml of methanol. The solution was cooled to −10° C. Sodium borohydride (52 mg, 1.4 mmol) was slowly added and the mixture was stirred in situ for 20 minutes. This reaction mixture was allowed to warm to 0° C., and 15 ml of a saturated aqueous solution of sodium bicarbonate was added. After filtration, the filtrate was concentrated. The concentrated residue was combined with 20 ml of water and extracted with ethyl acetate (50 ml×2). The combined ethyl acetate layer was washed with water (20 ml×1) and brine (20 ml×1), dried over anhydrous sodium sulfate and concentrated to give an oily product (1.81 g). To a solution of the oily product in 50 ml of methanol was added sodium methoxide (5.22N, 0.2 ml, 1.04 mmol) under argon atmosphere and the mixture was stirred at room temperature for 14 hours. This reaction mixture was neutralized with acetic acid and concentrated. The residue was combined with 20 ml of water and extracted with ethyl acetate (50 ml×2). The combined ethyl acetate layer was washed with water (20 ml×1) and brine (20 ml×1), dried over anhydrous sodium sulfate and concentrated. The concentrated residue was separated and purified through column chromatography (Merck, Lobar column; silica gel, ethyl acetate/cyclohexane 2/1) to give less polar 15-(m-chlorophenyl)-15-epi-2,5,6,7,16,17,18,19,20-nonanor-4-oxa-4,8-inter-m-phenylene PGI₂ methyl ester (yielded amount 545 mg, 1.27 mmol, yield 37.4%) and more polar 15-m-chlorophenyl-2,5,6,7,16,17,18,19,20-nonanor-4-oxa-4,8-inter-m-phenylene PGI₂ methyl ester (yielded amount 566 mg, 1.31 mmol, yield 38.9%). These compounds were assigned the corresponding structures by the following data:

15-(m-chlorophenyl)-2,5,6,7,16,17,18,19,20-nonanor-4-oxa-4,8-inter-m-phenylene PGI₂ methyl ester m.p. 134.8°–135.5° C. (recrystallized from ethyl acetate/n-hexane 2/1).

IR(KBr): 3250, 2970, 2930, 1755, 1610, 1595, 1570, 1480, 1460, 1425, 1370, 1290, 1235, 1210, 1190, 1155, 1120, 1105, 1070, 1030, 1005, 985, 970, 960, 950, 880, 860, 830, 780, 760, 725, 710, 690, 675 cm⁻¹.

NMR(400 MHz, CDCl₃, δ): 2.0–2.1(1H, m), 2.48(1H, q, J=8.1 Hz), 2.5–2.9(3H, m), 3.47(1H, t, J=8.1 Hz), 3.77(3H, s), 3.8–4.0(1H, m), 4.7(2H, s), 5.1–5.3(2H, m), 5.7–5.9(2H, m), 6.6–6.8(3H, m), 7.2–7.4(3H, m), 7.39(1H, s).

MASS(EI, m/e): 430(M+).

Elementary analysis: Calcd. (as C₂₃H₂₁O₆Cl₁): C(%) 64.11, H(%) 5.38. Found: 64.08, 5.45.

15-(m-chlorophenyl)-15-epi-2,5,6,7,16,17,18,19,20-nonanor-4-oxa-4,8-inter-m-phenylene PGI₂ methyl ester m.p. 128.2°–129.6° C. (recrystallized from ethyl acetate/n-hexane 2/1).

IR(KBr): 3270, 2970, 2920, 2860, 1750, 1665, 1600, 1590, 1565, 1485, 1460, 1430, 1410, 1370, 1345, 1305, 1290, 1255, 1240, 1220, 1190, 1165, 1115, 1090, 1045, 1010, 980, 960, 935, 920, 885, 870, 850, 805, 790, 775, 755, 720, 680 cm⁻¹.

NMR(400 MHz, CDCl₃, δ): 2.0–2.2(2H, m), 2.3–2.4(1H, m), 2.5–2.7(2H, m), 3.51(1H, t, J=8.3 Hz), 3.78(3H, s), 3.97(1H, q, J=7.3 Hz), 4.71(2H, s), 5.1–5.3(2H, m), 5.7–5.9(2H, m), 6.6–6.9(3H, m), 7.2–7.4(3H, m), 7.39(1H, s).

MASS(EI, m/e): 430(M+).

Elementary analysis: Calcd. (as C₂₃H₂₃O₆Cl₁): C(%) 64.11, H(%) 5.38. Found: 64.09, 5.53.

EXAMPLE 97

15-(m-chlorophenyl)-2,5,6,7,16,17,18,19,20-nonanor-4-oxa-4,8-inter-m-phenylene PGI₂ (285)

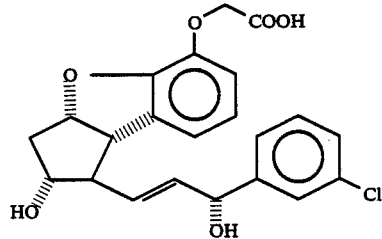

To an ice-cooled and stirred solution of 15-(m-chlorophenyl)-2,5,6,7,16,17,18,19,20-nonanor-4-oxa-4,8-inter-m-phenylene PGI₂ methyl ester (302 mg, 0.7 mmol) in 100 ml of methanol was added 0.725N sodium hydroxide (7.74 ml, 5.6 mmol), and the mixture was stirred for 2 hours at room temperature. The reaction mixture was concentrated, then diluted with 20 ml of water and neutralized with 1N hydrochloric acid. The mixture was extracted with ethyl acetate (50 ml×2). The combined ethyl acetate layer was washed with water (20 ml×1) and brine (20 ml×1), dried over anhydrous sodium sulfate and concentrated. The concentrated residue was recrystallized from 2 ml of methanol, 1 ml of ethyl acetate and 1 ml of n-hexane to give 15-(m-chlorophenyl)-2,5,6,7,16,17,18,19,20-nonanor-4-oxa-4,8-inter-m-phenylene PGI₂ as a white crystal (yielded amount 280 mg, 0.67 mmol, yield 96.2%). This compound was assigned the structure by the following data:

m.p. 137.4°–139.1° C. (recrystallized from methanol/ethyl acetate/n-hexane, 2/1/1).

IR(KBr): 3420, 2930, 1725, 1615, 1590, 1485, 1465, 1430, 1380, 1350, 1320, 1290, 1260, 1220, 1105, 1080, 1020, 985, 970, 880, 860, 820, 780, 765, 720, 705, 670 cm⁻¹.

NMR(400 MHz,, DMSO, δ): 1.6–1.8(1H, m), 2.2(1H, q, J=8.6Hz), 2.4–2.6(1H, m), 3.41(1H, t, J=8.6 Hz), 3.7–3.9(1H, m), 4.62(2H, s), 5.06(1H, q, J=8.6 Hz), 5.10(1H, d, J=6.6 Hz), 4.8–5.0(1H, m), 5.60(1H, dd, J=6.6, 15.1 Hz), 5.80(1H, dd, J=8.6, 15.1 Hz), 5.5–5.7(1H, m), 6.5–6.8(3H, m), 7.2–7.5(3H, m), 7.41(1H, s).

MASS(FAB, m/e): 416(M+).

Elementary analysis: Calcd. (as C₂₂H₂₁O₆Cl₁): C(%) 63.38, H(%) 5.08. Found: 63.19, 5.09.

EXAMPLE 98

15-(m-chlorophenyl)-15-epi-2,5,6,7,16,17,18,19,20-nonanor-4-oxa-4,8-inter-m-phenylene PGI₂ (286)

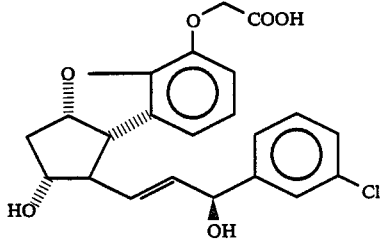

To an ice-cooled and stirred solution of 15-(m-chlorophenyl)-15-epi-2,5,6,7,16,17,18,19,20-nonanor-4-oxa-4,8-inter-m-phenylene PGI₂ methyl ester (301 mg, 0.699 mmol) in 100 ml of methanol was added an aqueous solution of sodium hydroxide (0.725N, 7.72 ml, 5.59 mmol). The mixture was stirred at room temperature for 2 hours, concentrated, diluted with 20 ml of water and neutralized with 1N hydrochloric acid. The mixture was extracted with ethyl acetate (50 ml×2). The combined ethyl acetate layer was washed with water (20 ml×1) and brine (20 ml×1), dried over anhydrous sodium sulfate and concentrated. The concentrated residue was recrystallized from 2 ml of methanol, 1 ml of ethyl acetate and 1 ml of n-hexane to give 15-(m-chlorophenyl)-15-epi-2,5,6,7,16,17,18,19,20-nonanor-4-oxa-4,8-inter-m-phenylene PGI₂ as a white crystal (yielded amount 239 mg, 0.57 mmol, yield 82%), which was assigned the structure by the following data:

m.p. 163.8°–165.2° C. (recrystallized from methanol-/ethyl acetate/n-hexane 2/1/1).

IR(KBr): 3430, 2930, 2870, 1720, 1625, 1590, 1490, 1465, 1450, 1380, 1350, 1310, 1290, 1280, 1270, 1250, 1200, 1105, 1075, 1060, 1010, 990, 950, 880, 850, 810, 790, 760, 720, 700, 980 cm$^{-1}$.

NMR(400 MHz, DMSO, δ): 1.6–1.8(1H, m), 2.1–2.3(1H, m), 2.4–2.6(1H, m), 3.43(1H, t, J=9.0 Hz), 3.7–3.9(1H, m), 4.63(2H, s), 4.8–4.9(1H, m), 5.0–5.2(3H, m), 5.60(1H, dd, J=6.3, 15.1 Hz), 5.80(1H, dd, J=8.3, 15.1 Hz), 6.6–6.8(3H, m), 7.2–7.5(3H, m), 7.41(1H, s).

MASS(FAB, m/e): 415(M$^+$-1)

Elementary analysis: Calcd. (as $C_{22}H_{21}O_6Cl_1$): C(%) 63.38, H(%) 5.08. Found: 63.22, 5.13.

EXAMPLE 99

15-(p-chlorophenyl)-2,5,6,7,16,17,18,19,20-nonanor-4-oxa-4,8-inter-m-phenylene PGI$_2$ methyl ester (287) and its 15-epimer (288)

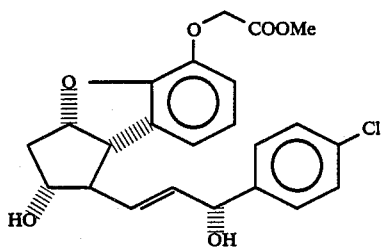

287

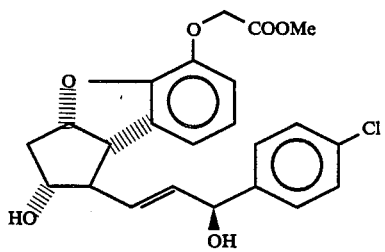

288

Cerium trichloride heptahydrate (1.34 g, 3.60 mmol) was added to a solution of 15-(p-chlorophenyl)-15-oxo-2,5,6,7,16,17,18,19,20-nonanor-4-oxa-4,8-inter-m-phenylene PGI$_2$ methyl ester, 11-benzoate (1.60 g, 3.00 mmol) in methanol (120 ml), and the mixture was cooled to −3° C. Sodium borohydride (56.7 mg, 1.50 mmol) was added to this mixture, which was then stirred at −3° C. for 10 minutes. A saturated aqueous solution of sodium bicarbonate (20 ml) was added to the mixture, which was then concentrated. The residue was combined with ethyl acetate (60 ml) and filtered. The precipitate was washed with ethyl acetate (20 ml×2). The combined ethyl acetate layers were washed with water (30 ml) and brine (30 ml), and dried over anhydrous magnesium sulfate and concentrated. Thus obtained oily product was dissolved into anhydrous methanol (40 ml) under argon atmosphere. To this solution was added a solution of sodium methoxide in methanol (5.22N, 0.14 ml, 0.75 mmol), and the mixture was stirred at room temperature for 20 hours. This reaction solution was neutralized with acetic acid. After concentration, water (40 ml) was added and the mixture was extracted with ethyl acetate (80 ml, 20 ml×2). The combined organic layers were washed with brine (40 ml), dried over anhydrous magnesium sulfate and concentrated. Thus obtained residue was separated and purified through column chromatography (Merck, Lobar column; silica gel, ethyl acetate/cyclohexane 2:1) to give less polar 15-(p-chlorophenyl)-15-epi-2,5,6,7,16,17,18,19,20-nonanor-4-oxa-4,8-inter-m-phenylene PGI$_2$ methyl ester (549 mg, 1.27 mmol, yield 42.5%) as a white crystal and more polar 15-(p-chlorophenyl)-2,5,6,7,16,17,18,19,20-nonanor-4-oxa-4,8-inter-m-phenylene PGI$_2$ methyl ester (500 mg, 1.16 mmol, yield 38.7%) as a white crystal. These compounds were assigned the corresponding structures by the following data:

15-(p-chlorophenyl)-2,5,6,7,16,17,18,19,20-nonanor-4-oxa-4,8-inter-m-phenylene PGI$_2$ methyl ester m.p. 101°–102° C. (recrystallized from ethanol/ethyl acetate).

IR(KBr): 3300, 2930, 1760, 1600, 1480, 1450, 1410, 1370, 1330, 1280, 1250, 1210, 1180, 1160, 1100, 1070, 1030, 1010, 970, 950, 890, 850, 830, 800, 780, 740, 720, 700, 600, 550, 490, 460 cm$^{-1}$.

NMR(400 MHz, CDCl$_3$, δ): 2.06(1H, ddd, J=4.9, 8.3, 14.0 Hz), 2.16(1H, d, J=5.4 Hz), 2.37(1H, d, J=3.4 Hz), 2.45–2.55(1H, m), 2.63(1H, ddd, J=6.4, 7.3, 14.0 Hz), 3.48(1H, t, J=8.5 Hz), 3.78(3H, s), 3.9–4.0(1H, m), 4.71(2H, s), 5.15–5.25(2H, m), 5.7–5.8(2H, m), 6.65–6.8(3H, m), 7.3–7.4(4H, m).

MASS(EI, m/e): 430(M$^+$).

Elementary analysis: Calcd. (as $C_{23}H_{23}O_6Cl$) C: 64.11, H: 5.38. Found C:63.97, H: 5.41.

15-(p-chlorophenyl)-15-epi-2,5,6,7,16,17,18,19,20-nonanor-4-oxa-4,8-inter-m-phenylene PGI$_2$ methyl ester m.p. 150°–151° C. (recrystallized from ethyl acetate/hexane).

IR(KBr): 3490, 2960, 2900, 1700, 1620, 1590, 1490, 1470, 1435, 1400, 1380, 1330, 1300, 1280, 1270, 1200, 1170, 1110, 1090, 1070, 1010, 980, 950, 870, 860, 820, 800, 790, 770, 730, 610, 590, 550, 490 cm$^{-1}$.

NMR(400 MHz, CDCl$_3$, δ): 2.0–2.1(2H, m), 2.3–2.4(1H, m), 2.53(1H, q, J=7.7 Hz), 2.61(1H, dt, J=6.8, 13.2 Hz), 3.50(1H, t, J=7.7 Hz), 3.78(3H, s), 3.9–4.0(1H, m), 4.71(2H, s), 5.1-5.25(2H, m), 5.75(1H, dd, J=7.7, 15.4 Hz), 5.80(1H, dd, J=5.4, 15.4 Hz), 6.7–6.8(3H, m), 7.3–7.4(4H, m).

MASS(EI, m/e): 430(M$^+$)

Elementary analysis: Calcd. (as $C_{23}H_{23}O_6Cl$): C: 64.11, H:5.38. Found: C: 64.05, H: 5.40.

EXAMPLE 100

15-(p-chlorophenyl)-2,5,6,7,16,17,18,19,20-nonanor-4-oxa-4,8-inter-m-phenylene PGI$_2$(289)

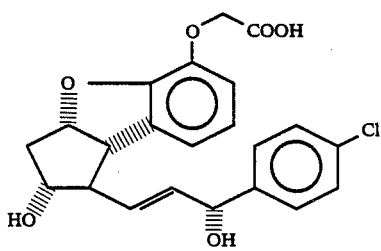

289

To a solution of 15-(p-chlorophenyl)-2,5,6,7,16,17,18,19,20-nonanor-4-oxa-4,8-inter-m-phenylene PGI$_2$ methyl ester (200 mg, 0.464 mmol) in methanol (20 ml) was added an aqueous solution of sodium hydroxide (1N, 3 ml, 3 mmol), and the mixture was stirred at room temperature for 14 hours. The reaction mixture was concentrated, diluted with water (20 ml), neutralized with 1N hydrochloric acid (3 ml) and extracted with ethyl acetate (80 ml, 20 ml×2). The combined organic layers was washed with brine, dried over anhydrous magnesium sulfate and concentrated to give 194 mg of crude crystals. These crude crystals were recrystallized from ethanol/ethyl acetate/hexane to give 15-(p-chlorophenyl)-2,5,6,7,16,17,18,19,20-nonanor-4-oxa-4,8-inter-m-phenylene PGI$_2$ (114 mg, 0.273 mmol) in a yield of 58.8% as a white crystal, which was assigned the structure by the following data:

m.p. 133°–135° C.

IR(KBr): 3430, 2930, 1730, 1620, 1590, 1490, 1470, 1430, 1380, 1350, 1290, 1200, 1110, 1010, 980, 870, 850, 830, 810, 770, 730, 500 cm$^{-1}$.

NMR(400 MHz, DMSO-d$_6$, δ): 1.71(1H, ddd, J=5.9, 9.3, 13.2 Hz), 2.19(1H, q, J=8.6 Hz), 2.4–2.6(1H, m), 3.40(1H, t, J=8.6 Hz), 3.7–3.8(1H, m), 4.61(2H, s), 4.8–4.9(1H, m), 5.0–5.1(1H, m), 5.11(1H, d, J=6.4 Hz), 5.5–5.6(1H, m), 5.60(1H, dd, J=6.4, 15.1 Hz), 5.77(1H, dd, J=7.6, 15.1 Hz), 6.5–6.7(3H, m), 7.40(4H, s).

MASS(EI, m/e): 380(M-2H$_2$O)$^+$.

Elementary analysis: Calcd. (as C$_{22}$H$_{21}$O$_6$Cl): C: 63.89, H: 5.08. Found: C: 63.07, H: 5.15.

EXAMPLE 101

15-(p-chlorophenyl)-15-epi-2,5,6,7,16,17,18,19,20-nonanor-4-oxa-4,8-inter-m-phenylene PGI$_2$ (290)

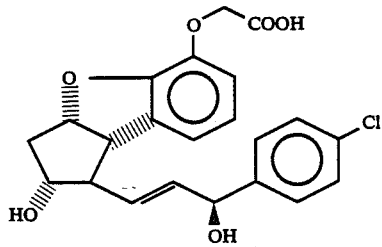

290

To a solution of 15-(p-chlorophenyl)-15-epi-2,5,6,7,16,17,18,19,20-nonanor-4-oxa-4,8-inter-m-phenylene PGI$_2$ methyl ester (255 mg, 0.592 mmol) in methanol (20 ml) was added an aqueous solution of sodium hydroxide (1N, 3 ml, 3 mmol), and the mixture was stirred for 4 hours at room temperature. The reaction mixture was concentrated, diluted with water (20 ml), neutralized with 1N hydrochloric acid (3 ml) and extracted with ethyl acetate (80 ml, 20 ml×2). The combined organic layers were washed with brine, dried over anhydrous magnesium sulfate and concentrated to give 239 mg of crude crystals. These crude crystals were recrystallized from ethanol/ethyl acetate to give 15-(p-chlorophenyl)-15-epi-2,5,6,7,16,17,18,19,20-nonanor-4-oxa-4,8-inter-m-phenylene PGI$_2$ (112 mg, 0.269 mmol) as a white crystal in a yield of 45.4%. This compound was assigned the structure by the following data:

m.p. 143°–144° C.

IR(KBr): 3430, 2930, 1730, 1620, 1600, 1490, 1470, 1430, 1380, 1350, 1320, 1300, 1280, 1260, 1200, 1110, 1090, 1010, 980, 950, 850, 820, 800, 790, 770, 730, 590, 480 cm$^{-1}$.

NMR(400 MHz, DMSO-d$_6$, δ): 1.71(1H, ddd, J=5.9, 9.3, 13.2 Hz), 2.19(1H, q, J=8.8 Hz), 2.45–2.6(1H, m), 3.43(1H, t, J=8.8 Hz), 3.7–3.8(1H, m), 4.63(2H, s), 4.8–4.9(1H, m), 5.0–5.15(2H, m), 5.5–5.6(1H, m), 5.60(1H, dd, J=6.6, 15.4 Hz), 5.77(1H, dd, J=8.0, 15.4 Hz), 6.65–6.8(3H, m), 7.38(4H, s).

MASS(EI, m/e): 380(M-2H$_2$O)$^+$. Elementary analysis: Calcd. (as C$_{22}$H$_{21}$O$_6$Cl) C: 63.39, H: 5.08. Found C: 63.10, H:5.07.

EXAMPLE 102

16-methyl-16-phenyl-2,5,6,7,18,19,20-heptanor-4-oxa-4,8-inter-m-phenylene PGI$_2$ methyl ester (291) and its 15-epimer (292)

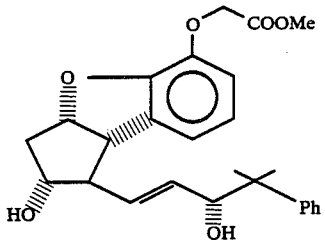

291

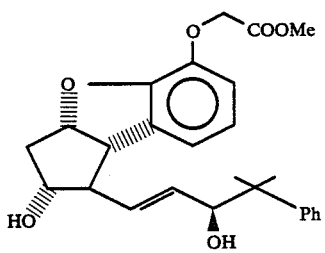

292

To a precooled solution of 16-methyl-15-oxo-16-phenyl-2,5,6,7,18,19,20-heptanor-4-oxa-4,8-inter-m-phenylene PGI$_2$ methyl ester, 11-benzoate (2.28 g, 4.22 mmol) and cerium trichloride heptahydrate (2.05 g, 5.49 mmol) in methanol (120 ml) at −5° C. was added, sodium borohydride (178 mg, 4.71 mmol). The mixture was stirred at −5° C. for 20 minutes, diluted with a saturated aqueous solution of sodium bicarbonate (20 ml) and concentrated. The residue was triturated with ethyl acetate (60 ml) and filtered. The precipitate was washed with ethyl acetate (20 ml×2). The combined ethyl acetate layers were washed with water (40 ml) and brine, dried over anhydrous magnesium sulfate and concentrated. To a solution of the residual oily product in anhydrous methanol (50 ml) was added a solution of sodium methoxide in methanol (5.22N, 0.32 ml, 1.69 mmol) under argon atmosphere. The mixture was stirred at room temperature for 18 hours, neutralized with acetic acid, concentrated, diluted with water (30 ml) and extracted with ethyl acetate (100 ml, 20 ml×2). The combined organic layers were washed with brine, dried over anhydrous magnesium sulfate and concentrated. Thus obtained residue was separated and purified through column chromatography (Merck, Lobar column; silica gel, ethyl acetate/cyclohexane 4:1) to give less polar 16-methyl-16-phenyl-15-epi-2,5,6,7,18,19,20-heptanor-4-oxa-4,8-inter-m-phenylene PGI$_2$ methyl ester (769 mg, 1.76 mmol, yield 41.7%) as white crystals and more polar 16-methyl-16-phenyl-2,5,6,7,18,19,20-heptanor-4-oxa-4,8-inter-m-phenylene PGI$_2$ methyl ester (653 mg, 1.49 mmol, yield 35.3%) as white crystals. These compounds were assigned the corresponding structures by the following data:

16-methyl-16-phenyl-2,5,6,7,18,19,20-heptanor-4-oxa-4,8-inter-m-phenylene PGI₂ methyl ester m.p. 134°–134.5° C. (recrystallized from ethyl acetate).

IR(KBr): 3420, 3250, 2970, 2940, 2880, 1770, 1615, 1590, 1490, 1460, 1430, 1390, 1360, 1280, 1240, 1210, 1200, 1160, 1120, 1100, 1080, 1060, 1030, 980, 970, 890, 860, 820, 790, 760, 730, 700, 620, 600, 570cm⁻¹.

NMR(400 MHz, CDCl₃, δ): 1.34(3H, s), 1.35(3H, s), 1.6–1.9(1H, m), 1.98(1H, ddd, J=5.3, 9.0, 13.8 Hz), 2.3–2.5(2H, m), 2.59(1H, ddd, J=6.4, 7.3, 13.8 Hz), 3.37(1H, t, J=9.1 Hz), 3.78(3H, s), 3.75–3.9(1H, m), 4.14(1H, d, J=5.9 Hz), 4.71(2H, s), 5.14(1H, ddd, J=5.3, 7.3, 9.1 Hz), 5.45–5.6(2H, m), 6.6–6.65(1H, m), 6.7–6.8(2H, m), 7.15–7.25(1H, m), 7.3–7.4(4H, m).

MASS(EEI, m/e): 438(M+).

Elementary analysis: Calculated (as C₂₆H₃₀O₆) C: 71.21, H: 6.90. Found C: 71.16, H: 6.92.

16-methyl-16-phenyl-15-epi-2,5,6,7,18,19,20-heptanor-4-oxa-4,8-inter-m-phenylene PGI₂ methyl ester m.p. 107°–108° C. (recrystallized from ethyl acetate).

IR(KBr): 3560, 3500, 3400, 2970, 1740, 1720, 1620, 1590, 1490, 1460, 1360, 1310, 1280, 1190, 1170, 1110, 1070, 1020, 980, 950, 860, 790, 760, 730, 700, 600 cm⁻¹.

NMR(400 MHz, CDCl₃, δ): 1.35(3H, s), 1.40(3H, s), 1.5–1.7(2H, m), 2.00(1H, ddd, J=5.3, 8.5, 13.7 Hz), 2.35–2.45(1H, m), 2.56(1H, ddd, J=6.4, 7.3, 13.7 Hz), 3.41(1H, t, J=8.7 Hz), 3.7–3.8(1H, m), 3.78(3H, s), 4.2–4.25(1H, m), 4.71(2H, s), 5.16(1H, ddd, J=5.3, 7.3, 8.7 Hz), 5.5–5.6(2H, m), 6.7–6.8(3H, m), 7.2–7.25(1H, m), 7.3–7.4(4H, m).

MASS(EI, m/e): 438(M+).

Elementary analysis: Calcd. (as C₂₆H₃₀O₆) C: 71.21, H: 6.90. Found C: 71.23, H: 6.90.

EXAMPLE 103

16-methyl-16-phenyl-2,5,6,7,18,19,20-heptanor-4-oxa-4,8-inter-m-phenylene PGI₂ (293)

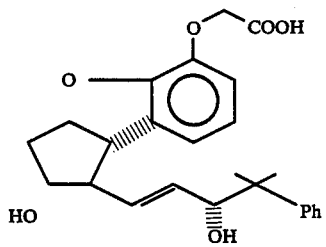

293

To a solution of 16-methyl-16-phenyl-2,5,6,7,18,19,20-heptanor-4-oxa-4,8-inter-m-phenylene PGI₂ methyl ester (220 mg, 0.502 mmol) in methanol (20 ml) was added an aqeuous solution of sodium hydroxide (1N, 3 ml, 3 mmol). The mixture was stirred for 3 hours at room temperature, concentrated, diluted with water (20 ml), neutralized with 1N hydrochloric acid (3 ml) and then extracted with ethyl acetate (30 ml, 15 ml×2). The combined organic layers were washed with brine, dried over anhydrous magnesium sulfate and concentrated to give 240 mg of crude crystals. These crude crystals were recrystallized from ethanol/hexane to give 16-methyl-16-phenyl-2,5,6,7,18,19,20-heptanor-4-oxa-4,8-inter-m-phenylene PGI₂ (170 mg, 0.401 mmol) as a white crystal in a yield of 79.9%. This compound was assigned the structure by the following data:

m.p. 187°–188° C.

IR(KBr): 3350, 2970, 2870, 1740, 1620, 1590, 1490, 1430, 1360, 1290, 1250, 1200, 1160, 1120, 1030, 990, 970, 950, 860, 790, 760, 730, 700 cm⁻¹.

NMR(400 MHz, DMSO-d₆, δ): 1.24(3H, s), 1.29(3H, s), 1.65(1H, ddd, J=5.9, 9.3, 13.2 Hz), 2.06(1H, q, J=8.4 Hz), 2.4–2.55(1H, m), 3.22(1H, t, J=8.4 Hz), 3.6–3.7(1H, m), 4.05–4.15(1H, m), 4.62(2H, m), 4.7–4.8(2H, m), 4.95–5.05(1H, m), 5.26(1H, dd, J=6.8, 15.1 Hz), 5.50(1H, dd, J=8.4, 15.1 Hz), 6.42(1H, dd, J=3.4, 5.2 Hz), 6.671(1H, d, J=5.2 Hz), 6.674(1H, d, J=3.4 Hz), 7.16(1H, t, J=7.5 Hz), 7.29(2H, t, J=7.5 Hz), 7.39(2H, d, J=7.5 Hz).

MASS(EI, m/e): 424(M+).

HR MASS: Calcd. (C₂₅H₂₈O₆, M+): 424.1886. Found (M+): 424.1915.

EXAMPLE 104

16-methyl-16-phenyl-15-epi-2,5,6,7,18,19,20-heptanor-4-oxa-4,8-inter-m-phenylene PGI₂ (294)

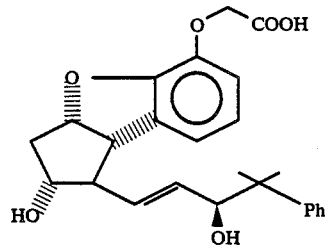

294

To a solution of 16-methyl-16-phenyl-15-epi-2,5,6,7,18,19,20-heptanor-4-oxa-4,8-inter-m-phenylene PGI₂ methyl ester (220 mg, 0.502 mmol) in methanol (20 ml) was added an aqueous solution of sodium hydroxide (1N, 3 ml, 3 mmol). The mixture was stirred for 3 hours at room temperature, concentrated, diluted with water (20 ml), neutralized with 1N hydrochloric acid (3 ml) and extracted with ethyl acetate (30 ml, 15 ml×2). The combined organic layers were washed with brine (20 ml), dried over anhydrous magnesium sulfate and concentrated to give 229 mg of crude crystals. These crude crystals were recrystallized from ethanol/ethyl acetate/hexane to give 16-methyl-16-15-epi-2,5,6,7,18,19,20-heptanor-4-oxa-4,8-inter-m-phenylene PGI₂ (180 mg, 0.425 mmol) as a white crystal in a yield of 84.7%. This compound was assigned the structure by the following data:

m.p. 173°–174° C.

IR(KBr): 3400, 2970, 1740, 1620, 1590, 1490, 1460, 1430, 1300, 1250, 1200, 1120, 1080, 1070, 1030, 970, 950, 860, 800, 770, 730, 700 cm⁻.

NMR(400 MHz, DMSO-d₆, δ): 1.23(3H, s), 1.29(3H, s), 1.65(1H, ddd, J=5.9, 9.3, 13.2 Hz), 2.07(1H, q, J=8.2 Hz), 2.4–2.55(1H, m), 3.30(1H, t, J=8.2 Hz), 3.6–3.7(1H, m), 4.0–4.1(1H, m), 4.62(2H, s), 4.65–4.75(1H, m), 4.75–4.85(1H, m), 4.95–5.05(1H, m), 5.24(1H, dd, J=5.9, 15.5 Hz), 5.57(1H, dd, J=8.2, 15.5 Hz), 6.57(1H, t, J=4.4 Hz), 6.69(2H, d, J=4.4 Hz), 7.15(1H, t, J=7.3 Hz), 7.28(2H, dd, J=7.3, 7.8 Hz), 7.38(2H, d, J=7.8 Hz).

MASS(EI, m/e): 424(M+).

HR MASS: Calcd. (C₂₅H₂₈O₆, M+): 424.1886. Found (M+): 424.1883.

EXAMPLE 105

16,16-dimethyl-17-phenyl-2,5,6,7,18,19,20-heptanor-4-oxa-4,8-inter-m-phenylene PGI$_2$ methyl ester (295) and its 15-epimer (296)

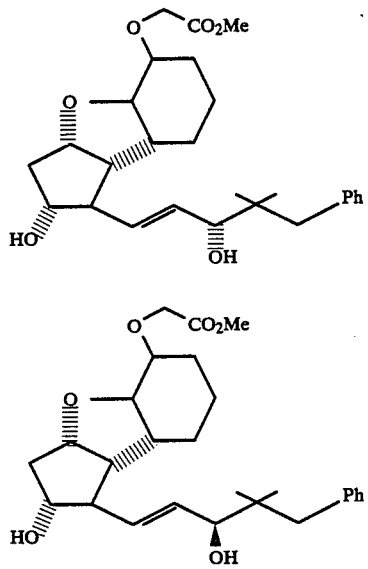

Cerium trichloride heptahydrate (0.90 g, 2.43 mmol) was dissolved into a solution of 16,16-dimethyl-15-oxo-17-phenyl-2,5,6,7,18,19,20-heptanor-4-oxa-4,8-inter-m-phenylene PGI$_2$ methyl ester, 11-acetate (1.1946 g, 2.43 mmol) in 50 ml of methanol. While this solution was being stirred at −15° C., sodium borohydride (66.0 mg, 1.74 mmol) was added thereinto, and the mixture was stirred for 1 hour. 10 ml of water was added to the reaction mixture and the solvent was distilled off. The residue was triturated with ethyl acetate and resulting precipitate was filtered off by Hyflo Super Cel. The precipitate was washed with ethyl acetate (50 ml×3). The combined ethyl acetate layer was washed with water (50 ml) and brine (50 ml), dried over anhydrous sodium sulfate and concentrated to give an oily product. This oily product dried by azeotropic distillation with benzene (20 ml×3), dried under reduced pressure and dissolved into 40 ml of anhydrous methanol. To the solution was added sodium methoxide (5.22N, 0.02 ml, 0.104 mmol), and the mixture was stirred overnight under argon atmosphere at room temperature, neutralized to pH7 with acetic acid and concentrated. 20 ml of water was added and the mixture was extracted with ethyl acetate (50 ml×4). The combined ethyl acetate layer was washed with water (50 ml) and brine (50 ml), dried over anhydrous sodium sulfate and concentrated to give an oily product. This oily product was separated and purified through column chromatography (silica gel, ethyl acetate/cyclohexane=2:1) to give less polar 16,16-dimethyl-17-phenyl-15-epi-2,5,6,7,18,19,20-heptanor-4-oxa-4,8-inter-m-phenylene PGI$_2$ methyl ester (0.1483 g, 0.328 mmol) and more polar 16,16-dimethyl-17-phenyl-2,5,6,7,18,19,20-heptanor-4-oxa-4,8-inter-m-phenylene PGI$_2$ methyl ester (0.1792 g, 0.396 mmol) in a yield of 29.8%. These compounds were assigned the corresponding structures by the following data:

α-isomer 16,16-dimethyl-17-phenyl-2,5,6,7,18,19,20-heptanor-4-oxa-4,8-inter-m-phenylene PGI$_2$ methyl ester m.p. 98°–99° C. (recrystallized from ethyl acetate and n-hexane; colorless needle-like crystal).

IR(KBr): 3330, 3020, 2950, 2860, 1750, 1608, 1582, 1478, 1453, 1428, 1368, 1286, 1203, 1186, 1175, 1158, 1112, 1081, 1068, 1035, 988, 962, 942, 887, 852, 825, 772, 753, 721, 692, 669, 631 cm$^{-}$.

NMR(400 MHz, CDCl$_3$, δ): 0.85(3H, s), 0.93(3H, s), 1.50–2.30(3H, m), 2.45–2.58(2H, m), 2.60–2.71(1H, m), 2.75–2.83(1H, m), 3.42–3.50(1H, m), 3.79(3H, s), 3.84(1H, d, J=7.32 Hz), 3.89–3.98(1H, m), 4.72(2H, s), 5.16–5.24(1H, m), 5.62(1H, dd, J=15.13, 8.30 Hz), 5.73(1H, dd, J=15.63, 7.33 Hz), 6.69–6.82(3H, m), 7.15–7.34(5H, m).

MASS(EI, m/e): 452(M+).

HR MASS: Calcd. (C$_{27}$H$_{32}$O$_6$, M+): 452.2199. Found (M+): 452.2188.

β-isomer 16,16-dimethyl-17-phenyl-15-epi-2,5,6,7,18,19,20-heptanor-4-oxa-4,8-inter-m-phenylene PGI$_2$ methyl ester IR(Liquid film method): 3365, 3030, 2960, 2875, 1750, 1617, 1592, 1482, 1458, 1437, 1380, 1362, 1288, 1263, 1220, 1191, 1111, 1093, 1068, 1028, 1003, 973, 890, 857, 785, 760, 732, 700, 662 cm$^{-1}$.

NMR(400 MHz, CDCl$_3$, δ): 0.84(3H, s), 0.93(3H, s), 1.50–1.80(2H, broad s), 2.03–2.13(1H, m), 2.48–2.69(3H, m), 2.75–2.83(1H, m), 3.52(1H, t, J=8.30 Hz), 3.79(3H, s), 3.86(1H, d, J=5.86 Hz), 3.90–4.00(1H, m), 4.67–4.80(2H, m), 5.19–5.28(1H, m), 5.63–5.73(1H, m), 5.78(1H, dd, J=15.62 Hz, 6.35 Hz), 6.68–6.88(3H, m), 7.15–7.33(5H, m).

MASS(EI, m/e): 452(M+).

HR MASS: Calcd. (C$_{27}$H$_{32}$O$_6$, M+): 452.2199. Found (M+): 452.2184.

EXAMPLE 106

16,16-dimethyl-17-phenyl-2,5,6,7,18,19,20-heptanor-4-oxa-4,8-inter-m-phenylene PGI$_2$ (297)

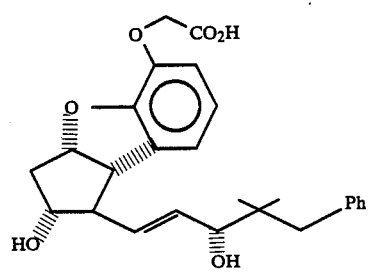

To a solution of 16,16-dimethyl-17-phenyl-2,5,6,7,18,19,20-heptanor-4-oxa-4,8-inter-m-phenylene PGI$_2$ methyl ester (98.8 mg, 0.218 mmol) in 20 ml of methanol was added an aqueous solution of sodium hydroxide (1N, 0.65 ml, 0.655 mmol). The mixture was stirred overnight under argon atmosphere at room temperature, acidified to pH2 with hydrochloric acid (1N), concentrated to remove methanol, diluted with 10 ml of water, and extracted with ethyl acetate (20 ml×4). The combined ethyl acetate layer was washed with water (20 ml) and brine (20 ml), dried over anhydrous sodium sulfate and concentrated to give 95.6 mg of 16,16- dimethyl-17-phenyl-2,5,6,7,18,19,20-heptanor-4-oxa-4,8-inter-m-phenylene PGI₂ as a single product (yield 100%). This compound was assigned the structure by the following data:

m.p. 144°–145° C. (recrystallized from ethyl acetate and n-hexane; colorless needle-like crystal).

IR(KBr): 3360, 3025, 2960, 2870, 1732, 1614, 1584, 1479, 1454, 1427, 1361, 1284, 1244, 1191, 1159, 1111, 1074, 1024, 992, 963, 890, 856, 826, 788, 758, 723, 694 cm⁻¹.

NMR(400 MHz,

δ): 0.82(3H, s), 0.92(3H, s), 1.97–2.08(1H, m), 2.49–2.72(3H, m), 2.75–2.84(1H, m), 3.00–4.50(2H, broad s), 3.36–3.44(1H, m), 3.75–3.91(2H, m), 4.67(2H, s), 5.12–5.20(1H, m), 5.58(1H, dd, J=15.14, 8.79 Hz), 5.72(1H, dd, J=15.14, 7.81 Hz), 6.68–6.78(3H, m), 7.16–7.34(5H, m).

MASS(EI, m/e): 438(M+).

HR MASS: Calcd. (C₂₆H₃₀O₆, M+): 438.2048. Found (M+): 438.2047.

EXAMPLE 107

16,16-dimethyl-17-phenyl-15-epi-2,5,6,7,18,19,20-heptanor-4-oxa-4,8-inter-m-phenylene PGI₂ (298)

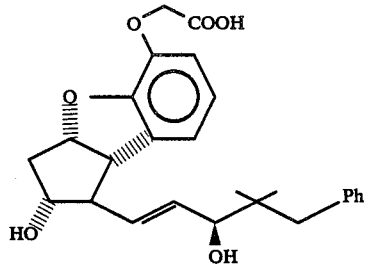

To a solution of 16,16-dimethyl-17-phenyl-15-epi-2,5,6,7,18,19,20-heptanor-4-oxa-4,8-inter-m-phenylene PGI₂ methyl ester (112.5 mg, 0.249 mmol) in 20 ml of methanol was added an aqueous solution of sodium hydroxide (1N, 0.75 ml, 0.746 mmol). The mixture was stirred overnight under argon atmosphere at room temperature, acidified to pH2 with hydrochloric acid (1N), concentrated to remove methanol, diluted with 10 ml of water, and extracted with ethyl acetate (20 ml×4). Then, the combined ethyl acetate layer was washed with water (20 ml) and brine (20 ml), dried over anhydrous sodium sulfate and concentrated to give 99.0 mg of 16,16-dimethyl-17-phenyl-15-epi-2,5,6,7,18,19,20-heptanor-4-oxa-4,8-inter-m-phenylene PGI₂ as a single product (yield 90.7%). This compound was assigned the structure by the following data:

m.p. 71°–74° C. (recrystallized from ethyl acetate and n-hexane; colorless needle-like crystal).

IR(KBr): 3380, 3025, 2960, 2865, 1729, 1616, 1591, 1483, 1459, 1436, 1361, 1281, 1245, 1185, 1108, 1025, 970, 857, 792, 764, 728, 710 cm⁻¹.

NMR(400 MHz,

δ): 0.83(3H, s), 0.90(3H, s), 2.00–2.10(1H, m), 2.45–2.62(3H, m), 2.72–2.81(1H, m), 3.46–3.53(1H, m), 3.70–4.20(4H, broad m), 4.63–4.75(2H, m), 5.16–5.23(1H, m), 5.65(1H, dd, J=15.62, 7.81 Hz), 5.74(1H, dd, J=15.63, 6.35 Hz), 6.66–6.86(3H, m), 7.13–7.32(5H, m).

MASS(EI, m/e): 438(M+).

HR MASS: Calcd. (C₂₆H₃₀O₆, M+): 438.2048. Found (M+): 438.2020.

EXAMPLE 108

16,16-Dimethyl-2,5,6,7,20-pentanor-4,18-dioxa-4,8-inter-m-phenylene PGI₂ methyl ester (299) and its 15-epimer (300)

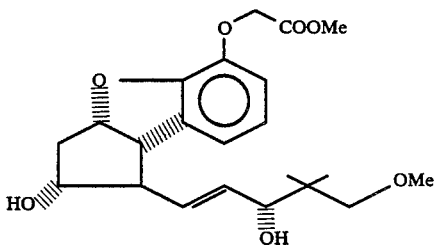

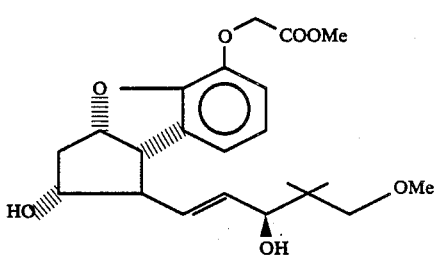

To a solution of 16,16-dimethyl-15-oxo-2,5,6,7,20-pentanor-4,18-dioxa-4,8-inter-m-phenylene PGI₂ methyl ester, 11-benzoate (2.05 g, 4.04 mmol) in methanol (100 ml) was added cerium trichloride heptahydrate (1.96 g, 5.25 mmol). The reaction mixture was cooled to −25° C. and mixed with sodium borohydride (91.7 mg, 2.42 mmol). The mixture was stirred for 10 min. at −25° C., diluted with a saturated aqueous solution of sodium bicarbonate (20 ml), and concentrated. The residue was triturated in 70 ml of ethyl acetate and the resulting precipitate was filtered off. The precipitate was washed with three portions of ethyl acetate (20 ml). The combined filtrates were washed with 50 ml of water and with 50 ml of brine, dried over anhydrous magnesium sulfate, and concentrated to give an oily material. The oily material was dissolved in anhydrous methanol (50 ml) under argon atmosphere. This solution was mixed with a solution of sodium methoxide in methanol (5.22N, 0.31 ml, 1.62 mmol) and stirred for 72 hrs. The resulting solution was neutralized with acetic acid and concentrated. The residue was mixed with 70 ml of ethyl acetate and washed with 30 ml of water. The aqueous layer was re-extracted with ethyl acetate (15 ml×2). The combined ethyl acetate layers were washed with 50 ml of brine, dried over anhydrous magnesium sulfate and concentrated. Column chromatography (Merck, Lobar column, silica gel, ethyl acetate/cyclohexane: 4/1) of the residue gave less polar 16,16-dimethyl-15-epi-2,5,6,7,20-pentanor-4,18-dioxa-4,8-inter-m-phenylene PGI₂ methyl ester (618 mg, 1.52 mmol, yield 37.6%) as an oily product and more polar 16,16-dimethyl-2,5,6,7,20-pentanor-4,18-dioxa-4,8-inter-m-phenylene PGI₂ methyl ester (557 mg, 1.37 mmol, yield 33.9%) as a white crystal. These compounds were assigned the corresponding structures by the following data.

16,16-Dimethyl-2,5,6,7,20-pentanor-4,18-dioxa-4,8-inter-m-phenylene PGI₂ methyl ester M.p.: 91°–92° C. (recrystallized from ethyl acetate/hexane).

IR(KBr): 3330, 2970, 2930, 2870, 2800, 1760, 1620, 1590, 1490, 1470, 1430, 1370, 1300, 1210, 1190, 1120, 1030, 1000, 970, 950, 890, 860, 830, 780, 760, 730, 710, 680, 640, 600, 490 cm⁻¹.

NMR(400 MHz, CDCl₃, δ): 0.92(3H, s); 0.94(3H, s); 2.05(1H, ddd, J=5.3, 9.0, 13.8 Hz); 2.4–2.55 (1H, m); 2.65(1H, dt, J=7.0, 13.8 Hz); 2.7–2.8(1H, m); 3.24(1H, d, J=8.8 Hz); 3.32(1H, d, J=8.8 Hz); 3.35(3H, s); 3.48(1H, t, J=8.7 Hz); 3.6–3.7(1H, m); 3.79(3H, s); 3.9–4.0(2H, m); 4.73(2H, s); 5.20(1H, ddd, J=5.3, 7.0, 8.7 Hz); 5.6–5.7(2H, m); 6.7–6.8 (3H, m).

MASS(EI, m/e): 406(M⁺).

Elementary Analysis: Calcd. (as C₂₀H₃₀O₇): C: 65.01, H: 7.44. found: C: 64.86, H: 7.48.

16,16-Dimethyl-15-epi-2,5,6,7,20-pentanor-4,18-dioxa-4,8-inter-m-phenylene PGI₂ methyl ester IR(liquid film): 3400, 2950, 1750, 1620, 1590, 1480, 1460, 1290, 1220, 1190, 1100, 1030, 970, 860, 750, 670 cm⁻¹.

NMR(400 MHz, CDCl₃, δ): 0.92(6H, s); 2.07(1H, ddd, J=5.0, 8.5, 13.7 Hz); 2.05–2.15(1H, m); 2.5–2.6 (1H, m); 2.63(1H, ddd, J=6.2, 7.3, 13.7 Hz); 3.25 (1H, d, J=8.8 Hz); 3.33(1H, d, J=8.8 Hz); 3.36(3H, s); 3.5–3.6(2H, m); 3.79(3H, s); 3.9–4.0(2H, m); 4.72(2H, s); 5.22(1H, ddd, J=5.0, 7.3, 8.8 Hz); 5.65–5.8(2H, m); 6.7–6.9(3H, m).

MASS(EI, m/e): 406(M⁺).

HR MASS: Calcd. (C₂₂H₃₀O₇, M⁺): 406.1992. Found (M⁺): 406.1971.

EXAMPLE 109

16,16-Dimethyl-2,5,6,7,20-pentanor-4,18-dioxa-4,8-inter-m-phenylene PGI₂ (301)

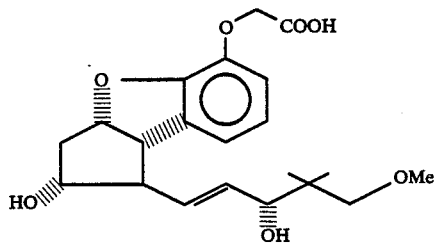

To a solution of 16,16-dimethyl-2,5,6,7,20-pentanor-4,18-dioxa-4,8-inter-m-phenylene PGI₂ methyl ester (285 mg, 0.702 mmol) in 20 ml of methanol was added a 1N aqueous NaOH solution (3.5 ml, 3.5 mmol). The reaction mixture was stirred for 3 hrs. at room temperature. The resulting solution was concentrated. The residue was mixed with water (20 ml) and neutralized with 1N hydrochloric acid (3.5 ml). This solution was extracted with ethyl acetate (30 ml, 15 ml×2). The combined organic layers were washed with 20 ml of water, with 30 ml of brine, dried over anhydrous magnesium sulfate and concentrated to give 16,16-dimethyl-2,5,6,7,20-pentanor-4,18-dioxa-4,8-inter-m-phenylene PGI₂ (272 mg, 0.694 mmol) as a white crystal with a yield of 98.9%. The product was identified by the following data.

M.p.: 72°–73° C. (recrystallized from ethyl acetate/hexane)

IR(IBr): 3320, 2960, 2930, 1740, 1720, 1610, 1590, 1490, 1460, 1370, 1300, 1280, 1190, 1160, 1110, 1090, 1030, 1000, 970, 920, 890, 850, 830, 760, 730 cm⁻¹.

NMR(400 MHz, CDCl₃, δ): 0.91(3H, s); 0.92(3H, s); 2.01 (1H, ddd, J=5.1, 8.5, 13.7 Hz); 2.4–2.55(1H, m); 2.60(1H, dt, J=6.8, 13.7 Hz); 3.24(1H, d, J=8.8 Hz); 3.32(1H, d, J=8.8 Hz); 3.35(3H, s); 3.44(1H, t, J=8.3 Hz); 3.85–3.95(1H, m); 3.98(1H, d, J=5.9 Hz); 4.65(1H, d, J=16.6 Hz); 4.71(1H, d, J=16.6 Hz); 4.8–5.1(3H, m); 5.1–5.2(1H, m); 5.55–5.7(2H, m); 6.7–6.8(3H, m).

MASS(EI, m/e): 392(M⁺).

HR MASS: Calcd. (C₂₁H₂₈O₇, M⁺): 392.1835. Found (M⁺): 392.1813.

EXAMPLE 110

16,16-Dimethyl-15-epi-2,5,6,7,20-pentanor-4,18-dioxa-4,8-inter-m-phenylene PGI₂ (302)

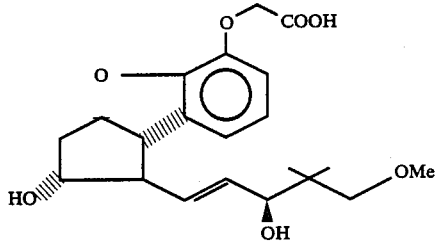

To a solution of 16,16-dimethyl-15-epi-2,5,6,7,20-pentanor-4,18-dioxa-4,8-inter-m-phenylene PGI₂ methyl ester (355 mg, 0.875 mmol) in 20 ml of methanol was added a 1N aqueous NaOH solution (4 ml, 4 mmol). The reaction mixture was stirred for 4 hrs. at room temperature. The resulting solution was concentrated. The residue was mixed with water (20 ml) and neutralized with 1N hydrochloric acid (4 ml). This solution was extracted with ethyl acetate (30 ml, 15 ml×2). The combined organic layers were washed with 20 ml of water, with 30 ml of brine, dried over anhydrous magnesium sulfate and concentrated to give 16,16-dimethyl-15-epi-2,5,6,7,20-pentanor-4,18-dioxa-4,8-inter-m-phenylene PGI₂ (314 mg, 0.801 mmol) as a white crystal with a yield of 91.5%. The product was identified by the following data.

M.p.: 51°–52.5° C. (recrystallized from ethyl acetate)

IR(KBr): 3400, 2960, 1740, 1620, 1590, 1480, 1460, 1370, 1190, 1110, 1030, 970, 920, 860, 760, 730 cm⁻¹.

NMR(400 MHz, CDCl₃, δ): 0.91(3H, s), 0.92(3H, s); 2.0–2.1(1H, m); 2.5–2.7(2H, m); 3.25(1H, d, J=8.8 Hz); 3.33(1H, d, J=8 Hz); 3.36(3H, s); 3.45–3.6(1H, m); 3.85–3.95(1H, m); 4.00(1H, d, J=7.3 Hz); 4.4–4.8(5H, m); 5.15–5.25(1H, m); 5.6–5.8(2H, m); 6.65–6.9(3H, m).

MASS(EI, m/e): 392(M⁺).

HR MASS: Calcd. (C₂₁H₂₈O₇, M⁺): 392.1835. Found (M⁺): 392.1810.

EXAMPLE 111

16,16-Dimethyl-2,5,6,7-tetranor-4,18-dioxa-4,8-inter-m-phenylene PGI₂ methyl ester (303) and its 15-epimer (304)

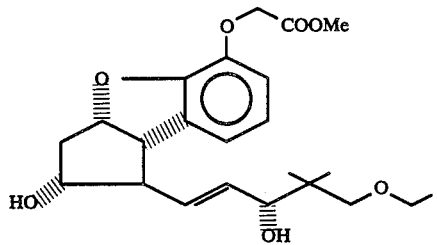

303

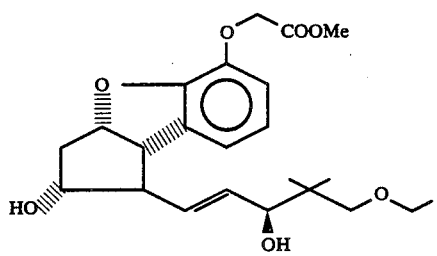

304

To a solution of 16,16-dimethyl-15-oxo-2,5,6,7-tetranor-4,18-dioxa-4,8-inter-m-phenylene PGI₂ methyl ester, 11-benzoate (1.82 g, 3.48 mmol) in methanol (80 ml) was added cerium trichloride heptahydrate (1.68 g, 4.52 mmol). The reaction mixture was cooled to −25° C. and mixed with sodium borohydride (105 mg, 2.78 mmol). The mixture was stirred for 30 min. at −25° C., diluted with a saturated aqueous solution of sodium bicarbonate (20 ml) and concentrated. The residue was triturated in 80 ml of ethyl acetate and the resulting precipitate was filtered off. The precipitate was twice washed with ethyl acetate. The combined filtrates were washed with 30 ml of water and with 50 ml of brine, dried over anhydrous magnesium sulfate and concentrated to give an oily material. The oily material was dissolved in anhydroud methanol (50 ml) under argon atmosphere. This solution was mixed with a solution of sodium methoxide in methanol (5.22N, 0.17 ml, 0.87 mmol) and stirred for 20 hrs. at room temperature. The resulting solution was neutralized with acetic acid and concentrated. The residue was mixed with 100 ml of ethyl acetate and washed with 40 ml of water. The ethyl acetate layer was washed with 40 ml of brine and dried over anhydrous magnesium sulfate and concentrated. Column chromatography (Merck, Lobar column, silica gel, ethyl acetate/cyclohexane: 4/1) of the residue gave less polar 16,16-dimethyl-15-epi-2,5,6,7-tetranor-4,18-dioxa-4,8-inter-m-phenylene PGI₂ methyl ester (623 mg, 1.48 mmol, yield 42.5%) as a white crystal and more polar 16,16-dimethyl-2,5,6,7-tetranor-4,18-dioxa-4,8-inter-m-phenylene PGI₂ methyl ester (618 mg, 1.47 mmol, yield 42.2%) as a white crystal. These compounds were assigned the corresponding structures by the following data.

16,16-Dimethyl-2,5,6,7-tetranor-4,18-dioxa-4,8-inter-m-phenylene PGI₂ methyl ester M.p.: 95.5°–96° C. (recrystallized from ethyl acetate/hexane)

IR(KBr): 3300, 2970, 2860, 1760, 1620, 1590, 1490, 1470, 1380, 1300, 1220, 1200, 1190, 1130, 1090, 1030, 1000, 970, 950, 900, 860, 760, 730 cm⁻¹.

NMR(400 MHz, CDCl₃, δ): 0.92(3H, s); 0.95(3H, s); 1.20 (3H, t, J=7.1 Hz); 2.06(1H, ddd, J=5.0, 8.8, 14.5 Hz); 2.3–2.55(2H, m); 2.64(1H, dt, J=7.1, 14.5 Hz); 3.29(1H, d, J=9.3 Hz); 3.36(1H, d, J=9.3 Hz); 3.45–3.6(3H, m); 3.79(3H, s); 3.9–4.0(3H, m); 4.73(2H, s); 5.21(1H, ddd, J=5.0, 7.1, 8.8 Hz); 5.6–5.8(2H, m); 6.7–6.9(3H, m).

MASS(EI, m/e): 420(M+).

Elementary Analysis: calcd. (as C₂₃H₃₂O₇): C: 65.69, H: 7.67. found: C: 65.57, H: 7.66.

16,16-Dimethyl-15-epi-2,5,6,7-tetranor-4,18-dioxa-4,8-inter-m-phenylene PGI₂ methyl ester M.p.: 81.5°–82.5° C. (recrystallized from ethyl acetate/hexane).

IR(KBr): 3380, 2970, 2870, 1730, 1620, 1590, 1490, 1470, 1440, 1410, 1370, 1360, 1300, 1280, 1260, 1200, 1110, 1060, 1030, 1000, 980, 950, 900, 860, 800, 770, 750, 730, 620, 550, 500 cm⁻¹.

NMR(400 MHz, CDCl₃, δ): 0.92(3H, s); 0.93(3H, s); 1.22 (3H, t, J=6.8 Hz); 1.8–1.9(1H, m); 2.08(1H, ddd, J=4.9, 8.3, 13.7 Hz); 2.5–2.6(1H, m); 2.63(1H, ddd, J=4.9, 8.3, 13.7 Hz); 3.30(1H, d, J=8.8 Hz); 3.37 (1H, d, J=8.8 Hz); 3.45–3.6(3H, m); 3.79(3H, s); 3.91(1H, d, J=3.9 Hz); 3.95–4.05(2H, m); 4.73(2H, s); 5.23(1H, ddd, J=4.9, 7.3, 8.8 Hz); 5.65–5.8(2H, m); 6.7–6.9(3H, m).

MASS(EI, m/e): 420(M+).

Elementary Analysis: calcd. (as C₂₃H₃₂O₇): C: 65.69, H: 7.67. found: C: 65.67, H: 7.68.

EXAMPLE 112

16,16-Dimethyl-2,5,6,7-tetranor-4,18-dioxa-4,8-inter-m-phenylene PGI₂ (305)

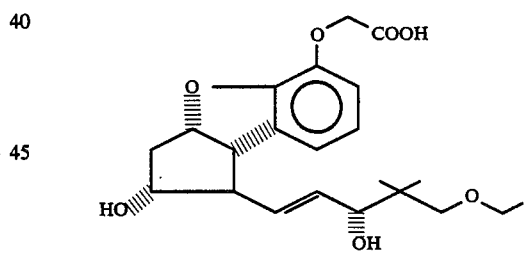

305

To a solution of 16,16-dimethyl-2,5,6,7,-tetranor-4,18-dioxa-4,8-inter-m-phenylene PGI₂ methyl ester (214 mg, 0.510 mmol) in 20 ml of methanol was added a 1N aqueous NaOH solution (3 ml, 3 mmol). The reaction mixture was stirred for 3 hrs. at room temperature. The resulting solution was concentrated. The residue was mixed with 20 ml of water and neutralized with 1N hydrochloric acid (3 ml). This solution was extracted with ethyl acetate (25 ml, 15 ml×2). The combined organic layers were washed with brine, dried over anhydrous magnesium sulfate and concentrated to give 221 mg of a crude crystal. Recrystallization of the crude crystal from ethyl acetate/hexane gave 16,16-dimethyl-2,5,6,7-tetranor-4.18-dioxa-4,8-inter-m-phenylene PGI₂ (93 mg, 0.229 mmol) as a white crystal with a yield of 44.9%. The product was assigned the structure by the following data.

M.p.: 77°–78° C.

IR(KBr): 3400, 2970, 2870, 1760, 1720, 1620, 1590, 1490, 1460, 1410, 1380, 1360, 1290, 1230, 1180, 1110, 1070, 1030, 1010, 970, 950, 890, 860, 760, 720 cm$^{-1}$.

NMR(400 MHz, CDCl$_3$, δ): 0.92(3H, s); 0.93(3H, s); 1.20 (3H, t, J=7.1 Hz); 2.0–2.1(1H, m); 2.45–2.6(1H, m); 2.60(1H, ddd, J=6.4, 7.3, 13.7 Hz); 3.29(1H, d, J=9.1 Hz); 3.36(1H, d, J=9.1 Hz); 3.4–3.6(3H, m); 3.9–4.0(1H, m); 3.99(1H, d, J=5.9 Hz); 4.0–4.5(3H, m); 4.67(1H, d, J=16.4 Hz); 4.72(1H, d, J=16.4 Hz); 5.15–5.3(1H, m); 5.6–5.8(2H, m); 6.7–6.9(3H, m).

MASS(EI, m/e): 406(M$^+$).

HR MASS: Calcd. (C$_{22}$H$_{30}$O$_7$, M$^+$): 406.1992. Found (M$^+$): 406.1970.

EXAMPLE 113

16,16-Dimethyl-15-epi-2,5,6,7-tetranor-4,18-dioxa-4,8-inter-m-phenylene PGI$_2$ (306)

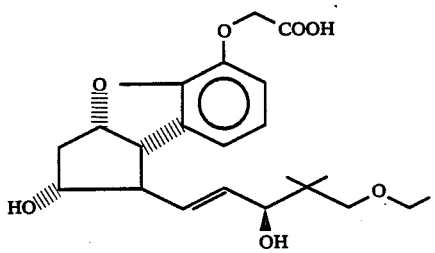

306

To a solution of 16,16-dimethyl-15-epi-2,5,6,7-tetranor-4,18-dioxa-4,8-inter-m-phenylene PGI$_2$ methyl ester (213 mg, 0.507 mmol) in 20 ml of methanol was added a 1N aqueous NaOH solution (3 ml, 3 mmol). The reaction mixture was stirred for 3 hrs. at room temperature. The resulting solution was concentrated. The residue was mixed with water (20 ml) and neutralized with 1N hydrochloric acid (3 ml). This solution was extracted with ethyl acetate (25 ml, 15 ml×2). The combined organic layers were washed with brine, dried over anhydrous magnesium sulfate and concentrated to give 16,16-dimethyl-15-epi-2,5,6,7-tetranor-4,18-dioxa-4,8-inter-m-phenylene PGI$_2$(201 mg, 0.495 mmol) as an oily material with a yield of 97.6%. The product was identified by the following data.

IR(liquid film): 3400, 2970, 2930, 2870, 1740, 1620, 1590, 1480, 1460, 1280, 1190, 1110, 1030, 970, 860, 760 cm$^{-1}$.

NMR(400 MHz, CDCl$_3$, δ): 0.91(3H, s); 0.93(3H, s); 1.22 (3H, t, J=7.1 Hz); 2.05(1H, ddd, J=5.0, 8.2, 13.6 Hz); 2.5–2.7(2H, m); 3.30(1H, d, J=9.1 Hz); 3.37 (1H, d, J=9.1 Hz); 3.4–3.6(3H, m); 3.9–4.0(1H, m); 4.00(1H, d, J=4.9 Hz); 4.1–4.6(3H, m); 4.66(1H, d, J=16.6 Hz); 4.71(1H, d, J=16.6 Hz); 5.20(1H, ddd, J=5.0, 7.3, 8.8 Hz); 5.6–5.8(2H, m); 6.7–6.9(3H, m).

MASS(EI, m/e): 406(M$^+$).

HR MASS: Calcd. (C$_{22}$H$_{30}$O$_7$, M$^+$): 406.1992. Found (M$^+$): 406.1978.

EXAMPLE 114

16,16-Dimethyl-20a-homo-2,5,6,7-tetranor-4,18-dioxa-4,8-inter-m-phenylene PGI$_2$ methyl ester (307) and its 15-epimer (308)

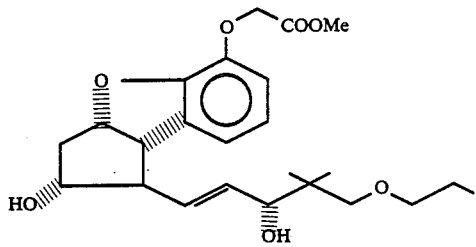

307

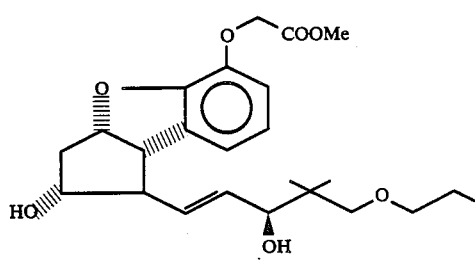

308

To a solution of 16,16-dimethyl-15-oxo-20a-homo-2,5,6,7-tetranor-4,18-dioxa-4,8-inter-m-phenylene PGI$_2$ methyl ester, 11-benzoate (2.1 g, 3.93 mmol) in methanol (120 ml) was added cerium trichloride (1.77 g, 4.75 mmol). The resulting solution was cooled to $-10°$ C. and mixed slowly with sodium borohydride (58.4 g, 154 mmol). The reaction mixture was stirred for 20 min. at $-10°$ C. and diluted with a saturated aqueous solution of sodium bicarbonate (15 ml). The solution was filtered and the filtrate was concentrated. The residue was mixed with 20 ml of water and extracted with ethyl acetate (50 ml×2). The combined ethyl acetate layers were washed with 20 ml of water and with 20 ml of brine, dried over anhydrous sodium sulfate and concentrated to give an oily material (2.08 g). The oily material was dissolved in anhydrous methanol (100 ml) under argon atmosphere. To this solution was added with stirring a solution of sodium methoxide in methanol (5.22N, 0.223 ml, 1.16 mmol) and the mixture was stirred for 14 hrs. at room temperature. The resulting solution was neutralized with acetic acid and concentrated. The residue was mixed with water (20 ml) and the solution was extracted with ethyl acetate (50 ml×2). The combined ethyl acetate layers were washed with 20 ml of water, with 20 ml of brine, dried over anhydrous sodium sulfate and concentrated. Column chromatography (Merck, Lobar column, silica gel, ethyl acetate/cyclohexane: 2/1) of the residue gave less polar 16,16-dimethyl-15-epi-20a-homo-2,5,6,7-tetranor-4,18-dioxa-4,8-inter-m-phenylene PGI$_2$ methyl ester (671 mg, 1.55 mmol, yield: 39.8%) and more polar 16,16-dimethyl-20a-homo-2,5,6,7-tetranor-4,18-dioxa-4,8-inter-m-phenylene PGI$_2$ methyl ester (668 mg, 1.54 mmol, yield: 39.7%). These compounds were assigned the corresponding structures by the following data.

16,16-Dimethyl-20a-homo-2,5,6,7-tetranor-4,18-dioxa-4,8-inter-m-phenylene PGI$_2$ methyl ester M.p.: 100.0°–100.8° C. (recrystallization solvent, ethyl acetate/n-hexane: 1/2).

IR(KBr): 3380, 2950, 2870, 1735, 1615, 1590, 1485, 1460, 1430, 1360, 1290, 1245, 1190, 1105, 1030, 1010, 990, 965, 950, 855, 790, 760, 725 cm$^{-1}$.

NMR(400 MHz, CDCl$_3$, δ): 0.92(3H, s); 0.94(3H, s); 0.9–1.0(3H, m); 1.5–1.7(2H, m); 2.06(1H, ddd, J=5.1, 9.0, 13.9 Hz); 2.4–2.5(1H, m); 2.5–2.7(2H, m); 3.3(1H, d, J=9.0 Hz); 3.36(1H, d, J=9.0 Hz); 3.3–3.5 (2H, m); 3.49(1H, t, J=8.5Hz); 3.79(3H, s); 3.8–4.0(2H, m); 4.02(1H, d, J=4.4 Hz); 4.73(2H, s); 5.1–5.3(1H, m); 5.6–5.8(2H, m); 6.7–6.9(3H, m).

MASS(EI, m/e): 434(M+).

Elementary Analysis: calcd. (as C$_{24}$H$_{34}$O$_7$): C: 66.34, H: 7.89. found: C: 66.30, H: 7.90.

16,16-Dimethyl-15-epi-20a-homo-2,5,6,7-tetranor-4,18-dioxa-4,8-inter-m-phenylene PGI$_2$ methyl ester M.p.: 83.1°–84.2° C. (recrystallization solvent, ethyl acetate/n-hexane: 1/4).

IR(KBr): 3370, 2950, 2920, 2860, 1730, 1615, 1585, 1480, 1455, 1430, 1410, 1370, 1330, 1290, 1270, 1255, 1190, 1105, 1060, 1020, 1000, 970, 950, 855, 830, 785, 750, 720 cm$^{-1}$.

NMR(400 MHz, CDCl$_3$, δ): 0.927(3H, s); 0.937(3H, s); 0.937(3H, t, J=7.3 Hz); 1.5–1.7(2H, m); 1.8–2.0 (1H, m); 2.0–2.2(1H, m); 2.55(1H, q, J=7.8 Hz); 2.5–2.7(1H, m); 3.3(1H, d, J=9.0 Hz); 3.37(1H, d, J=9.0 Hz); 3.3–3.5(2H, m); 3.54(1H, t, J=7.8 Hz); 3.79(3H, s); 3.9–4.1(3H, m); 4.73(2H, s); 5.1–5.3 (1H, m); 5.6–5.8(2H, m); 6.7–6.9(3H, m).

MASS(EI, m/e): 434(M+).

Elementary Analysis: calcd. (as C$_{24}$H$_{34}$O$_7$): C: 66.34, H: 7.89. found: C: 66.57, H: 7.93.

EXAMPLE 115

16,16-Dimethyl-20a-homo-2,5,6,7-tetranor-4,18-dioxa-4,8-inter-m-phenylene PGI$_2$ (309)

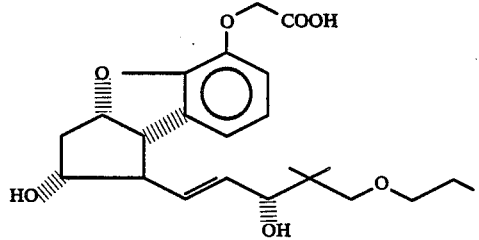

To a solution of 16,16-dimethyl-20a-homo-2,5,6,7-tetranor-4,18-dioxa-4,8-inter-m-phenylene PGI$_2$ methyl ester (317 mg, 0.73 mmol) in 40 ml of methanol was added with stirring 1N aqueous NaOH solution (3.7 ml, 3.7 mmol) under ice-cooling. After being stirred for 1 hrs. at room temperature the reaction mixture was concentrated. The residue was mixed with water (20 ml) and neutralized with 1N hydrochloric acid. This solution was extracted with ethyl acetate (50 ml×2). The combined ethyl acetate layers were washed with 20 ml of water, with 20 ml of brine, dried over anhydrous sodium sulfate and concentrated. Recrystallization of the residue from a mixture of 2 ml of ether and 1.5 ml of n-hexane gave 16,16-dimethyl-20a-homo-2,5,6,7-tetranor-4,18-dioxa-4,8-inter-m-phenylene PGI$_2$ as a white crystal (278 mg, 0.662 mmol, yield: 90.7%). The product was assigned the structure by the following data.

M.p.: 106.1°–107.2° C. (recrystallization solvent, ether/n-hexane: 4/3).

IR(KBr): 3380, 2950, 2860, 1715, 1615, 1590, 1485, 1460, 1430, 1360, 1290, 1245, 1190, 1105, 1030, 1010, 990, 965, 950, 855, 830, 790, 760, 730 cm$^{-1}$.

NMR(400 MHz, CDCl$_3$, δ): 0.92(3H, s); 0.93(3H, s); 0.92 (3H, t, J=7.3 Hz); 1.5–1.7(2H, m); 2.0–2.1(1H, m); 2.50(1H, q, J=7.4 Hz); 2.6–2.7(1H, m); 3.30(1H, d, J=9.0 Hz); 3.36(1H, d, J=9.0 Hz); 2.3–2.4(2H, m); 3.48(1H, t, J=8.3 Hz); 3.94(1H, q, J=7.4 Hz), 3.99 (1H, d, J=5.9 Hz); 3.5–4.1(2H, m); 4.67(1H, d, J=16.1 Hz); 4.71(1H, d, J=16.1 Hz); 5.1–5.3(1H, m); 5.5–5.8(2H, m); 6.7–6.9(3H, m).

MASS(EI, m/e): 420(M+).

HR MASS: Calcd. (C$_{23}$H$_{32}$O$_7$, M+): 420.2148. Found (M+): 420.2159.

EXAMPLE 116

16,16-Dimethyl-15-epi-20a-homo-2,5,6,7-tetranor-4,18-dioxa-4,8-inter-m-phenylene PGI$_2$ (310)

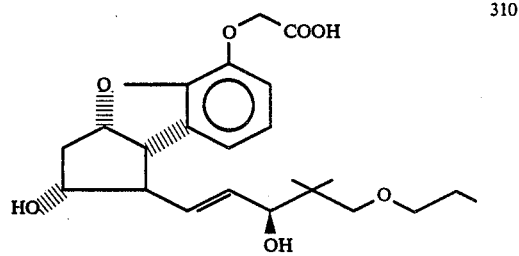

To a solution of 16,16-dimethyl-15-epi-20a-homo-2,5,6,7-tetranor-4,18-dioxa-4,8-inter-m-phenylene PGI$_2$ methyl ester (305 mg, 0.703 mmol) in 40 ml of methanol was added with stirring 1N aqueous NaOH solution (3.5 ml, 3.5 mmol) under ice-cooling. After being stirred for 1 hrs. at room temperature the reaction mixture was concentrated. The residue was mixed with water (20 ml) and neutralized with 1N hydrochloric acid. This solution was extracted with ethyl acetate (50 ml×2). The combined ethyl acetate layers were washed with 20 ml of water, with 20 ml of brine, dried over anhydrous sodium sulfate and concentrated to give 16,16-dimethyl-15-epi-20a-homo-2,5,6,7-tetranor-4,18-dioxa-4,8-inter-m-phenylene PGI$_2$ as a colourless and transparent oil (285 mg, 0.68 mmol, yield: 96.7%). The product was assigned the structure by the following data.

IR(liquid film): 3400, 2960, 1735, 1615, 1590, 1475, 1450, 1380, 1350, 1280, 1240, 1180, 1100, 1025, 970, 880, 850, 830, 750, 725 cm$^{-1}$.

NMR(400 MHz, CDCl$_3$, δ): 0.91(3H, s); 0.93(3H, s); 0.8–1.0(3H, m); 1.5–1.7(2H, m); 2.0–2.1(1H, m); 2.5–2.7(2H, m); 3.31(1H, d, J=9.3 Hz); 3.37(1H, d, H=9.3 Hz); 3.3–3.5(2H, m); 3.52(1H, t, J=8.3 Hz); 3.9–4.0(1H, m); 4.01(1H, d, J=4.9 Hz); 4.1–4.6 (2H, m); 4.66(1H, d, J=16.6 Hz); 4.7(1H, d, J=16.6 Hz); 5.1–5.3(1H, m); 5.6–5.8(2H, m); 6.7–6.9(3H, m).

MASS(EI, m/e): 420(M+).

HR MASS: Calcd. (C$_{23}$H$_{32}$O$_7$, M+): 420.2148. Found (M+): 420.2127.

EXAMPLE 117

16-Phenoxy-2,5,6,7,17,18,19,20-octanor-4-oxa-4,8-inter-m-phenylene PGI₂ methyl ester (311) and its epimer (312)

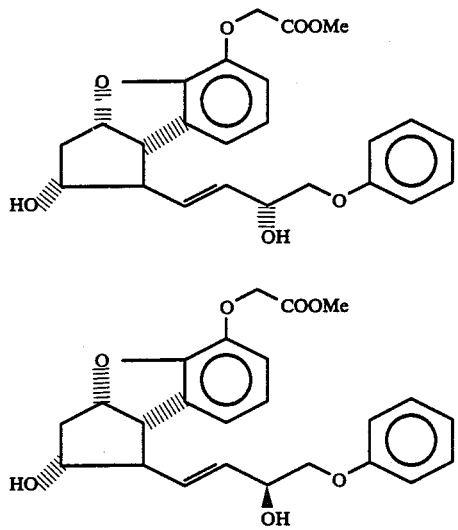

To a solution of 15-oxo-16-phenoxy-2,5,6,7,17,18,19,20-octanor-4-oxa-4,8-inter-m-phenylene PGI₂ methyl ester, 11-benzoate (1.44 g, 2.72 mmol) in methanol (100 ml) was added cerium trichloride heptahydrate (1.22 g, 3.27 mmol). The resulting solution was cooled to −10° C. To this solution was added slowly sodium borohydride (40.5 mg, 1.07 mmol) and the mixture was stirred for 20 min. at −10° C. This solution was brought to 0° C., diluted with a saturated aqueous solution of sodium bicarbonate (15 ml) and concentrated. The residue was triturated in 50 ml of ethyl acetate and the resulting precipitate was filtered off. The precipitate was washed with five portions of ethyl acetate (10 ml). The combined ethyl acetate layers were washed with 30 ml of water, with 30 ml of brine, dried over anhydrous sodium sulfate and concentrated to give an oily material (1.38 g). The oily material was dissolved in anhydrous methanol (70 ml) under argon atmosphere. To this solution was added with stirring a solution of sodium methoxide in methanol (5.22N, 0.15 ml, 0.783 mmol) and the mixture was stirred for 14 hrs. The resulting solution was neutralized with acetic acid and concentrated. The residue was mixed with 20 ml of water and extracted with ethyl acetate (50 ml×2). The combined ethyl acetate layers were washed with 20 ml of water, with 20 ml of brine, dried over anhydrous sodium sulfate and concentrated. Column chromatography (Merck, Lobar column, silica gel: ethyl acetate/cyclohexane: 2/1) of the residue gave less polar 16-phenoxy-15-epi-2,5,6,7,17,18,19,20-octanor-4-oxa-4,8-inter-m-phenylene PGI₂ methyl ester (487 mg, 1.15 mmol, yield: 43.9%) and more polar 16-phenoxy-2,5,6,7,17,18,19,20-octanor-4-oxa-4,8-inter-m-phenylene PGI₂ methyl ester (413 mg, 0.97 mmol, yield: 37.2%). These compounds were assigned the corresponding structures by the following data.

16-Phenoxy-2,5,6,7,17,18,19,20-octanor-4-oxa-4,8-inter-m-phenylene PGI₂ methyl ester M.p.: 132.7°–133.9° C. (recrystallization solvent, ethyl acetate).

IR(KBr): 3480, 3420, 2950, 2930, 2910, 2870, 1730, 1620, 1595, 1590, 1495, 1460, 1430, 1375, 1335, 1320, 1295, 1270, 1260, 1240, 1200, 1170, 1145, 1110, 1100, 1090, 1070, 1065, 1040, 1030, 1010, 975, 970, 950, 905, 890, 860, 830, 815, 770, 750, 735, 725, 690 cm⁻¹.

NMR(400 MHz, CDCl₃, δ): 2.0–2.2(1H, m); 2.4–2.5(1H, m); 2.51(1H, q, J=8.3 Hz); 2.6–2.7(1H, m); 2.8–2.9(1H, m); 3.50(1H, t, J=8.3 Hz); 3.78(3H, s); 3.92(1H, dd, J=7.5, 9.5 Hz); 3.7–4.0(1H, m); 4.03(1H, dd, J=3.6, 9.5 Hz); 4.5–4.7(1H, m); 4.72(2H, s); 5.1–5.3(1H, m); 5.70(1H, dd, J=6.4, 15.4 Hz); 5.87(1H, dd, J=8.3, 15.4 Hz); 5.7–5.9(3H, m); 5.9–7.1(3H, m); 7.2–7.4(2H, m).

MASS(EI, m/e): 426(M⁺).

Elementary Analysis: calcd. (C₂₄H₂₆O₇): C: 67.59, H: 6.15. found: C: 67.60, H: 6.12.

16-Phenoxy-15-epi-2,5,6,7,17,18,19,20-octanor-4-oxa-4,8-inter-m-phenylene PGI₂ methyl ester M.p.: 102.2°–102.9° C. (recrystallization solvent, ethyl acetate/chloroform: 2/1).

IR(KBr): 3330, 2920, 1755, 1735, 1620, 1600, 1490, 1460, 1435, 1380, 1300, 1265, 1250, 1230, 1200, 1170, 1110, 1090, 1045, 950, 910, 895, 865, 845, 820, 765, 730, 690 cm⁻¹.

NMR(400 MHz, CDCl₃, δ): 1.7–1.9(1H, m); 2.0–2.2(1H, m); 2.5–2.7(3H, m); 3.55(1H, t, J=8.3 Hz); 3.79(3H, s); 3.92(1H, dd, J=7.6, 9.4 Hz); 3.95–4.05(1H, m); 4.06 (1H, dd, J=3.4, 9.4 Hz); 4.5–4.7(1H, m); 4.73(2H, s); 5.2–5.3(1H, m); 5.73(1H, dd, J=5.1, 15.9 Hz); 5.90(1H, ddd, J=1.2, 8.3, 15.9 Hz); 6.7–7.1(6H, m); 7.2–7.4(2H, m).

MASS(EI, m/e): 394(M-CH₃OH)⁺.

HR MASS: Calcd. (C₂₄H₂₆O₇, M⁺): 426.1679. Found (M⁺): 426.1672.

EXAMPLE 118

16-Phenoxy-2,5,6,7,17,18,19,20-octanor-4-oxa-4,8-inter-m-phenylene PGI₂ (313)

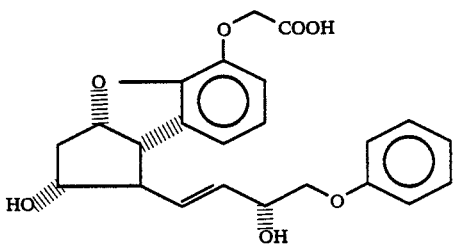

To a solution of 16-phenoxy-2,5,6,7,17,18,19,20-octanor-4-oxa-4,8-inter-m-phenylene PGI₂ methyl ester (250 mg, 0.59 mmol) in 80 ml of methanol was added with stirring 0.725N aqueous NaOH solution (6.5 ml, 4.7 mmol) under ice-cooling. After being stirred for 1 hr. at room temperature the reaction mixture was concentrated. The residue was mixed with 20 ml of water and neutralized under ice-cooling with 1N hydrochloric acid. This solution was extracted with ethyl acetate (50 ml×2). The combined ethyl acetate layers were washed with 20 ml of water, with 20 ml of brine, dried over anhydrous sodium sulfate and concentrated. Recrystallization of the residue from a mixture of 3 ml of ethyl acetate and 0.1 ml of methanol gave 16-phenoxy-2,5,6,7,17,18,19,20-octanor-4-oxa-4,8-inter-m-phenylene PGI₂ (229 mg, 0.558 mmol, yield: 94.7%) as a white crystal. The product was identified by the following data.

M.p.: 164.9°–166.5° C. (recrystallization solvent, ethyl acetate/methanol: 30/1).

IR(KBr): 3400, 3040, 2970, 2925, 1735, 1710, 1620, 1600, 1490, 1465, 1430, 1370, 1290, 1250, 1200, 1110, 1085, 1040, 970, 950, 910, 890, 860, 830, 790, 770, 755, 730, 690 cm⁻¹.

NMR(400 MHz, DMSO-d₆, δ): 1.6–1.8(1H, m); 2.1–2.3(1H, m); 2.4–2.6(1H, m); 3.39(1H, t, J=9.3 Hz); 3.7–3.9 (1H, m); 3.9(2H, d, J=5.9 Hz); 4.3–4.5(1H, m); 4.63(2H, s); 4.8–5.0(1H, m); 5.0–5.3(1H, m); 5.62(1H, dd, J=5.9, 15.6 Hz); 5.82(1H, dd, J=7.6, 15.6 Hz); 6.6–6.8(3H, m); 6.8–7.0(3H, m); 7.28 (1H, d, J=7.8 Hz); 7.3(1H, d, J=8.3 Hz).

MASS(EI, m/e): 412(M+).

Elementary Analysis: calcd. (as C₂₃H₂₄O₇): C: 66.98, H: 5.87. found: C: 66.81, H: 5.90.

EXAMPLE 119

16-Phenoxy-15-epi-2,5,6,7,17,18,19,20-octanor-4-oxa-4,8-inter-m-phenylene PGI₂ (314)

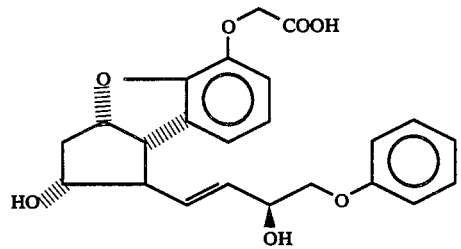

To a solution of 16-phenoxy-15-epi-2,5,6,7,17,18,19,20-octanor-4-oxa-4,8-inter-m-phenylene PGI₂ methyl ester (253 mg, 0.596 mmol) in 80 ml of methanol was added with stirring a 0.725N aqueous NaOH solution (6.6 ml, 4.8 mmol) under ice-cooling. After being stirred for 1 hr. at room temperature the reaction mixture was concentrated. The residue was mixed with 20 ml of water and neutralized under ice-cooling with 1N hydrochloric acid. This solution was extracted with ethyl acetate (50 ml×2). The combined ethyl acetate layers were washed with 20 ml of water, with 20 ml of brine, dried over anhydrous sodium sulfate and concentrated. Recrystallization of the residue from a mixture of 3 ml of ethyl acetate and 0.5 ml of methanol gave 16-phenoxy-15-epi-2,5,6,7,17,18,19,20-octanor-4-oxa-4,8-inter-m-phenylene PGI₂ (229 mg, 0.56 mmol, yield: 94%) as a white crystal. The product was identified by the following data.

M.p.: 152.1°–154.0° C. (recrystallization solvent, ethyl acetate/methanol: 30/5).

IR(KBr): 3400, 2920, 1735, 1710, 1620, 1600, 1490, 1460, 1430, 1370, 1290, 1250, 1200, 1120, 1080, 1040, 970, 950, 890, 860, 830, 790, 770, 750, 730, 690 cm⁻¹.

NMR(400 MHz, DMSO-d₆, δ): 1.6–1.8(1H, m); 2.2(1H, q, J=8.3 Hz); 2.4–2.6(1H, m); 3.43(1H, t, J=8.3 Hz); 3.7–4.0(3H, m); 4.3–4.4(1H, m); 4.63(2H, s); 4.8–5.0(1H, m); 5.0–5.1(1H, m); 5.15–5.2(1H, m); 5.64(1H, dd, J=5.4, 15.4 Hz); 5.84(1H, dd, J=8.3, 15.4 Hz); 6.6–6.8(3H, m); 6.9–7.0(3H, m); 7.28 (1H, d, J=7.3 Hz); 7.30(1H, d, J=8.8 Hz).

MASS(EI, m/e): 412(M+).

HR MASS: Calcd. (C₂₃H₂₄O₇, M+): 412.1522. Found (M+): 412.1534.

EXAMPLE 120

16-Methyl-16-phenoxy-2,5,6,7,18,19,20-heptanor-4-oxa-4,8-inter-m-phenylene PGI₂ methyl ester (315) amd its 15-epimer (316)

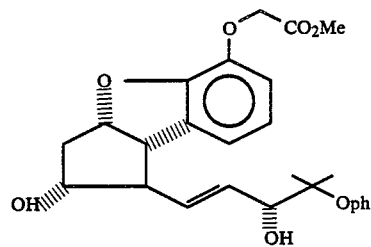

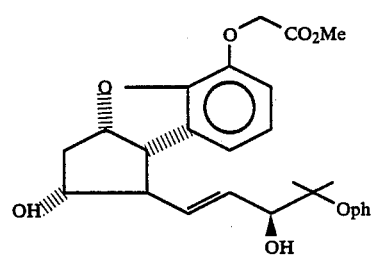

To a solution of 16-methyl-15-oxo-16-phenoxy-2,5,6,7,18,19,20-heptanor-4-oxa-4,8-inter-m-phenylene PGI₂ methyl ester, 11-acetate (0.8647 g, 1.75 mmol) in methanol (50 ml) was added cerium trichloride heptahydrate (0.65 g, 1.75 mmol). To this stirred solution was added sodium borohydride (93.2 mg, 2.46 mmol) at −15° C. and the mixture was stirred for 3.5 hrs. This solution was mixed with 10 ml of water and the solvent was distilled out. The resulting precipitate was filtered off by Hyflo Super Cel and the filtrate was extracted with ethyl acetate (50 ml×4). The combined ethyl acetate layers were washed with 50 ml of water, with 50 ml of brine, dried over anhydrous sodium sulfate and concentrated to give an oily material. After azeotropic distillation of the oil with benzene (20 ml×3), the resultant residue was dried under reduced pressure and dissolved in 40 ml of anhydrous methanol. To this solution was added sodium methoxide in methanol (5.22N, 0.02 ml, 0.104 mmol) and the mixture was stirred under argon atmosphere overnight at room temperature. After addition of three drops of acetic acid, the resulting solution was concentrated. The residue was mixed with 20 ml of water and extracted with ethyl acetate (50 ml×4). The combined ethyl acetate layers were washed with 50 ml of water, with 50 ml of brine, dried over anhydrous sodium sulfate and concentrated to give an oily material. Column chromatography (silica gel, ethyl acetate/cyclohexane: 4/1) of the oily material gave less polar 16-methyl-16-phenoxy-15-epi-2,5,6,7,18,19,20-heptanor-4-oxa-4,8-inter-m-phenylene PGI₂ methyl ester (0.2962 g, 0.652 mmol: 37.3%) and more polar 16-methyl-16-phenoxy-2,5,6,7,18,19,20-heptanor-4-oxa-4,8-inter-m-phenylene PGI₂ methyl ester (0.3175 g, 0.699 mmol: 39.9%). These compounds were assigned the corresponding structures by the following data.

α-Epimer

16-Methyl-16-phenoxy-2,5,6,7,18,19,20-heptanor-4-oxa-4,8-inter-m-phenylene PGI₂ methyl ester M.P.: 107.5–108° C. (recrystallized from a mixture of ethyl acetate and cyclohexane, a colourless needle-like crystal)

IR(KBr): 3270, 2955, 2925, 1765, 1737, 1615, 1587, 1484, 1457, 1434, 1378, 1283, 1216, 1199, 1153, 1115, 1093, 1068, 1026, 966, 844, 855, 787, 759, 727, 699 cm⁻¹.

NMR(400 MHz, CDCl₃, δ): 1.24(3H, s); 1.26(3H, s); 1.95–2.15(3H, broad, s); 2.49–2.57(1H, m); 2.62–2.71(1H, m); 3.47–3.54(1H, m); 3.79(3H, s); 3.93–4.02(1H, m); 4.20(1H, d, J=6.35 Hz); 4.73(2H, s); 5.18–5.25(1H, m); 5.72(1H, dd, J=15.14 Hz, 6.84 Hz); 5.83(1H, dd, J=15.63 Hz, 8.30 Hz); 6.71–6.79(3H, m); 6.97–7.02(2H, m); 7.10–7.16(1H, m); 7.25–7.33(2H, m).

MASS(EI, m/e): 454(M⁺).

HR MASS: Calcd. (C₂₆H₃₀O₇, M⁺): 454.1991. Found (M⁺): 454.2000.

β-Epimer

16-Methyl-16-phenoxy-15-epi-2,5,6,7,18,19,20-heptanor-4-oxa-4,8-inter-m-phenylene PGI₂ methyl ester M.p.: 103°–104° C. (recrystallized from a mixture of ethyl acetate and cyclohexane, a colourless needle-like crystal).

IR(KBr): 3475, 3050, 2970, 2940, 2850, 1670, 1613, 1586, 1481, 1460, 1428, 1369, 1320, 1293, 1280, 1253, 1230, 1198, 1173, 1153, 1113, 1071, 1023, 1008, 993, 981, 969, 944, 902, 884, 864, 837, 805, 763, 729, 689, 609 cm⁻¹.

NMR(400 MHz, CDCl₃, δ): 1.24(3H, s); 1.25(3H, s); 1.88–2.14(3H, m); 2.53–2.70(2H, m); 3.56(1H, t, J=8.30 Hz); 3.79(3H, s); 3.96–4.03(1H, m); 4.20–4.24(1H, m); 4.73(2H, s); 5.21–5.28(1H, m); 5.70–5.78(1H, m); 5.82–5.91(1H, m); 6.71–6.86(3H, m); 6.98–7.03(2H, m); 7.10–7.16(1H, m); 7.25–7.34(2H, m).

MASS(EI, m/e): 454(M⁺).

HR MASS: Calcd. (C₂₆H₃₀O₇, M⁺): 454.1991. Found (M⁺): 454.1982.

EXAMPLE 121

16-Methyl-16-phenoxy-2,5,6,7,18,19,20-heptanor-4-oxa-4,8-inter-m-phenylene PGI₂ (317)

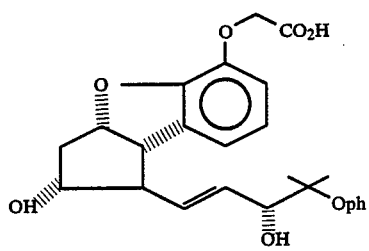

317

To a solution of 16-methyl-16-phenoxy-2,5,6,7,18,19,20-heptanor-4-oxa-4,8-inter-m-phenylene PGI₂ methyl ester (134.1 mg, 0.295 mmol) in methanol (20 ml) was added 1N aqueous NaOH solution (0.89 ml, 0.855 mmol). The reaction mixture was stirred under argon atmosphere overnight at room temperature. To the resulting solution was added hydrochloric acid (1N, 0.89 ml, 0.885 mmol). Methanol was distilled out, and the residue was mixed with 30 ml of water and extracted with ethyl acetate (20 ml×4). The combined ethyl acetate layers were washed with 20 ml of water, with 20 ml of brine, dried over anhydrous sodium sulfate and concentrated to give 16-methyl-16-phenoxy-2,5,6,7,18,19,20-heptanor-4-oxa-4,8-inter-m-phenylene PGI₂ as a single product (130.4 mg, yield: 100%). The product was identified by the following data.

M.p.: 150°–152° C. (recrystallized from a mixture of acetone and n-hexane, a colourless needle-like crystal).

IR(KBr): 3430, 2960, 2925, 1735, 1612, 1587, 1482, 1454, 1427, 1372, 1362, 1285, 1245, 1220, 1190, 1152, 1115, 1093, 1068, 1039, 1022, 965, 951, 882, 853, 826, 785, 758, 725, 697 cm⁻¹.

NMR(400 MHz,

CDCl₃ + CD₃SCD₃,

δ): 1.25(3H, s); 1.27(3H, s); 1.98–2.08(1H, m); 2.42–2.50(1H, m); 2.62–2.71(1H, m); 3.43–3.50(1H, m); 3.87–3.96(1H, m); 4.17(1H, d, J=6.35 Hz); 4.62–5.13(4H, broad, m); 5.14–5.22(1H, m); 5.70–5.84(2H, m); 6.70–6.78(3H, m); 6.99–7.06(2H, m); 7.07–7.14(1H, m); 7.24–7.34(2H, m).

MASS(EI, m/e): 440(M⁺).

HR MASS: Calcd. (C₂₅H₂₈O₇, M⁺): 440.1835. Found (M⁺): 440.1844.

EXAMPLE 122

16-Methyl-16-phenoxy-15-epi-2,5,6,7,18,19,20-heptanor-4-oxa-4,8-inter-m-phenylene PGI₂ (318)

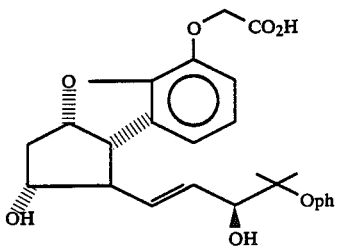

318

To a solution of 16-methyl-16-phenoxy-15-epi-2,5,6,7,18,19,20-heptanor-4-oxa-4,8-inter-m-phenylene PGI₂ methyl ester (128.5 mg, 0.283 mmol) in methanol (20 ml) was added 1N aqueous NaOH solution (0.85 ml, 0.848 mmol). The reaction mixture was stirred under argon atmosphere overnight at room temperature. To the resulting solution was added hydrochloric acid (1N, 0.85 ml, 0.848 mmol). Methanol was distilled out, and the residue was mixed with 10 ml of water and extracted with ethyl acetate (20 ml×4). The combined ethyl acetate layers were washed with 20 ml of water, with 20 ml of brine, dried over anhydrous sodium sulfate and concentrated to give 16-methyl-16-phenoxy-15-epi-2,5,6,7,18,19,20-heptanor-4-oxa-4,8-inter-m-phenylene PGI₂ as a single product (124.7 mg, yield: 100%). The product was identified by the following data.

M.p.: 130°–132° C. (recrystallized from a mixture of acetone and n-hexane, a colourless needle-like crystal).

IR(KBr): 3400, 2970, 2925, 1720, 1615, 1585, 1478, 1451, 1423, 1382, 1262, 1218, 1182, 1107, 1062, 1006, 957, 932, 867, 785, 765, 721, 687 cm⁻¹.

NMR(400 MHz,

δ): 1.24(3H, s); 1.28(3H, s); 1.99–2.11(1H, m); 2.48–2.58(1H, m); 2.58–2.69(1H, m); 3.49–3.55(1H, m); 3.80–4.60(4H, broad m); 4.67(2H, s); 5.15–5.23(1H, m); 5.73–5.82(1H, m); 5.84–5.93(1H, m); 6.70–6.86(3H, m); 6.97–7.05(2H, m); 7.08–7.15(1H, m); 7.24–7.34(2H, m).

MASS(EI, m/e): 440(M+).

HR MASS: Calcd. ($C_{25}H_{28}O_7$, M+): 440.1835. Found (M+): 440.1861.

EXAMPLE 123

16-Methyl-2,5,6,7-tetranor-4-oxa-18,18,19,19-tetradehydro-4,8-inter-m-phenylene PGI$_2$ methyl ester 391 and its epimer 320

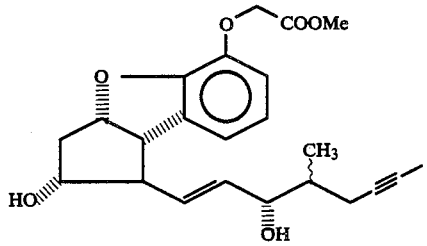

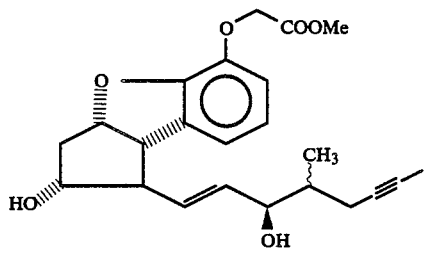

To a solution of 16-methyl-15-oxo-2,5,6,7-tetranor-4-oxa-18,18,19,19-tetradehydro-4,8-inter-m-phenylene PGI$_2$ methyl ester, 11-benzoate (2.49 g, 4.96 mmol) in methanol (50 ml) was added with stirring cerium trichloride (2.23 g, 5.98 mmol) and the solution was cooled to −10° C. Sodium borohydride (73.3 mg, 1.94 mmol) was added little by little to the solution and the reaction mixture was stirred for 20 min. at −10° C. The resulting solution was brought to 0° C. and diluted with a saturated aqueous solution of sodium bicarbonate (15 ml). The mixture was filtered and the filtrate was concentrated. The concentrate was diluted with water (20 ml) and extracted with ethyl acetate (50 ml×2). The combined ethyl acetate layers were washed with water (20 ml), with brine (20 ml), dried over anhydrous sodium sulfate and concentrated to give an oily material (2.47 g). The oily material was dissolved in methanol (40 ml) under argon atmosphere. To this was added a solution of sodium methoxide in methanol (0.48 ml, 2.5 mmol) and the mixture was stirred for 7.5 hrs. at room temperature. The solution was neutralized with acetic acid and concentrated. The residue was mixed with water (30 ml) and the solution was extracted with ethyl acetate (50 ml×2). The combined ethyl acetate layers were washed with water (20 ml), with brine (20 ml), dried over anhydrous sodium sulfate and concentrated to give a crude material. Column chromatography (Merck, Lobar column, silica gel, ethyl acetate/cyclohexane: 2/1) of the material afforded less polar 16-methyl-15-epi-2,5,6,7-tetranor-4-oxa-18,18,19,19-tetradehydro-4,8-inter-m-phenylene PGI$_2$ methyl ester (715 mg, 1.79 mmol, 36.4%) and more polar 16-methyl-2,5,6,7-tetranor-4-oxa-18,18,19,19-tetradehydro-4,8-inter-m-phenylene PGI$_2$ methyl ester (689 mg, 1.72 mmol, 35.1%). These compounds were assigned the corresponding structures by the following data.

16-Methyl-2,5,6,7-tetranor-4-oxa-18,18,19,19-tetradehydro-4,8-inter-m-phenylene PGI$_2$ methyl ester IR(liquid film): 3380, 2970, 2930, 1750, 1620, 1595, 1490, 1460, 1440, 1380, 1295, 1210, 1200, 1120, 1020, 970, 890, 855, 830, 760, 730, 665 cm$^{-1}$.

NMR(400 MHz, CDCl$_3$, δ): 0.983, 1.02(3H, d, J=6.8 Hz); 1.7–2.0(4H, m); 1.9–2.2(2H, m); 2.2–2.3(1H, m); 2.3–2.5(1H, m); 2.6–2.7(1H, m); 2.5–3.1(2H, m); 3.44, 3.45(1H, t, J=8.6 Hz); 3.79(3H, s); 3.8–4.0(1H, m); 4.0–4.2(1H, m); 4.72(2H, s); 5.1–5.3(1H, m); 5.5–5.8(2H, m); 6.6–6.9(3H, m).

MASS(EI, m/e): 400 (M+)

HR MASS: Calcd. ($C_{23}H_{28}O_6$, M+): 400.1886. Found (M+): 400.1892.

16-Methyl-15-epi-2,5,6,7-tetranor-4-oxa-18,18,19,19-tetradehydro-4,8-inter-m-phenylene PGI$_2$ methyl ester M.p.: 74.6°–78.2° C. (recrystallization solvent, ethyl acetate/n-hexane=2/1).

IR(KBr): 3300, 2970, 2930, 1740, 1620, 1595, 1490, 1460, 1435, 1380, 1280, 1265, 1250, 1200, 1115, 1070, 1010, 965, 890, 865, 770, 730 cm$^{-1}$.

NMR(400 MHz, CDCl$_3$, δ): 1.00(3H, d, J=6.8 Hz); 1.6–1.8(1H, m); 1.7–1.8(4H, m); 1.8–2.2(3H, m); 2.1–2.3(1H, m); 2.4–2.6(1H, m); 2.6–2.7(1H, m); 3.52(1H, t, J=7.6 Hz); 3.79(3H, s); 3.9–4.0(1H, m); 4.0–4.3(1H, m); 4.72(2H, s); 5.1–5.3(1H, m); 5.6–5.8(2H, m); 6.73(1H, d, J=7.2 Hz); 6.77(1H, t, J=7.2 Hz); 6.82(1H, d, J=7.2 Hz).

MASS(EI, m/e): 400 (M+).

HR MASS: Calcd. ($C_{23}H_{28}O_6$, M+): 400.1886. Found (M+): 400.1899.

EXAMPLE 124

16-Methyl-2,5,6,7-tetranor-4-oxa-18,18,19,19-tetradehydro-4,8-inter-m-phenylene PGI$_2$ 321

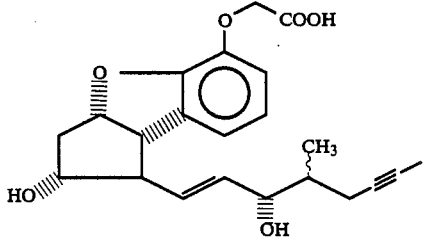

To a solution of 16-methyl-2,5,6,7-tetranor-4-oxa-18,18,19,19-tetradehydro-4,8-inter-m-phenylene PGI$_2$ methyl ester (536 mg, 1.34 mmol) in methanol (30 ml) was added 1N aqueous NaOH (11 ml, 11 mmol) with stirring under ice-cooling and the reaction mixture was stirred for 3.5 hrs. at room temperature. The solution was concentrated and 20 ml of water was added to the residue. After neutralization with 1N hydrochloric acid, the resulting mixture was extracted with ethyl acetate (50 ml×2). The combined ethyl acetate layers were washed with water (20 ml), with brine (20 ml), dried over anhydrous sodium sulfate and concentrated. Recrystallization of the residue from a mixture of 2.5 ml of ethyl acetate and 1 ml of n-hexane yielded 476 mg (1.23 mmol, 92%) of 16-methyl-2,5,6,7-tetranor-4-oxa-18,18,19,19-tetradehydro-4,8-inter-m-phenylene PGI$_2$ as a white crystal. The product was assigned the structure by the following data.

M.p.: 71.3°–73.2° C. (recrystallization solvent, ethyl acetate/n-hexane=5/2).

IR(KBr): 3410, 2950, 2905, 1730, 1610, 1585, 1485, 1455, 1430, 1280, 1250, 1195, 1160, 1110, 1065, 1020, 970, 940, 850, 790, 755, 720 cm$^{-1}$.

NMR(400 MHz, DMSO, δ): 0.92(3H, d, J=6.8 Hz); 1.5–1.7(1H, m); 1.6–1.8(4H, m); 1.8–2.1(1H, m); 2.1–2.4(2H, m); 2.4–2.6(1H, m); 3.42(1H, t, J=9.0 Hz); 3.7–3.8(1H, m); 3.8–4.0(1H, m); 4.64(2H, s); 4.6–4.8(1H, m); 4.7–4.9(1H, m); 5.0–5.1(1H, m); 5.45(1H, dd, J=8.3, 15.1 Hz); 5.6–5.7(1H, m); 6.6–6.8(3H, m).

MASS(EI, m/e): 386 (M+).

HR MASS: Calcd. (C$_{22}$H$_{26}$O$_6$, M+): 386.1729. Found (M+): 386.1746.

EXAMPLE 125

16-Methyl-15-epi-2,5,6,7-tetranor-4-oxa-18,18,19,19-tetradehydro-4,8-inter-m-phenylene PGI$_2$ 322

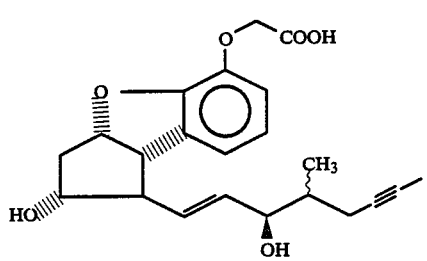

322

To a solution of 16-methyl-15-epi-2,5,6,7-tetranor-4-oxa-18,18,19,19-tetradehydro-4,8-inter-m-phenylene PGI$_2$ methyl ester (552 mg, 1.38 mmol) in methanol (30 ml) was added 1N aqueous NaOH (11.4 ml, 11.4 mmol) with stirring under ice-cooling and the reaction mixture was stirred for 3 hrs. at room temperature. The solution was concentrated and 20 ml of water was added to the residue. After neutralization with 1N hydrochloric acid under ice-cooling with stirring, the resulting mixture was extracted with ethyl acetate (50 ml×2). The combined ethyl acetate layers were washed with water (20 ml), with brine (20 ml), dried over anhydrous sodium sulfate and concentrated. Recrystallization of the residue from 2.5 ml of ethyl acetate yielded 420 mg (1.09 mmol, 81.2%) of 16-methyl-15-epi-2,5,6,7-tetranor-4-oxa-18,18,19,19-tetradehydro-4,8-inter-m-phenylene PGI$_2$ as a white crystal. The product was assigned the structure by the following data.

M.p.: 131.8°–133.5° C. (recrystallization solvent, ethyl acetate).

IR (KBr): 3380, 2960, 2930, 1740, 1705, 1620, 1590, 1485, 1460, 1425, 1370, 1320, 1280, 1270, 1195, 1125, 1020, 1010, 960, 930, 855, 790, 775, 735 cm$^{-1}$.

NMR (400 MHz, DMSO, δ): 0.896, 0.914 (3H, d, J=7.3 Hz); 1.5–1.7 (1H, m); 1.6–1.8 (4H, m); 1.8–2.1 (1H, m); 2.1–2.4 (2H, m); 2.4–2.6 (1H, m); 3.42 (1H, t, J=9 Hz); 3.6–3.8 (1H, m); 3.8–4.0 (1H, m); 4.64 (2H, s); 4.7–4.8 (1H, m); 4.8–4.9 (1H, m); 5.0–5.2 (1H, m); 5.4–5.5 (1H, m); 5.6–5.7 (1H, m); 6.6–6.9 (3H, m).

MASS (EI, m/e): 386 (M+).

HR MASS: Calcd. (C$_{22}$H$_{26}$O$_6$, M+): 386.1729. Found: (M+): 386.1751.

EXAMPLE 126

16-Methyl-20a-homo-2,5,6,7-tetranor-4-oxa-18,18,19,19-tetradehydro-4,8-inter-m-phenylene PGI$_2$ methyl ester 323 and its epimer 324

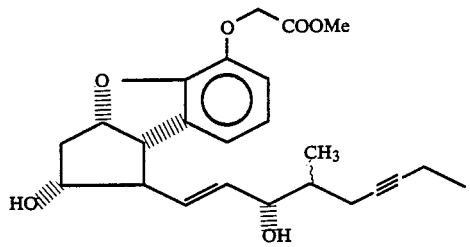

323

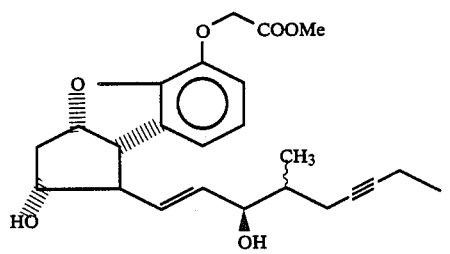

324

To a solution of 16-methyl-15-oxo-20a-homo-2,5,6,7-tetranor-4-oxa-18,18,19,19-tetradehydro-4,8-inter-m-phenylene PGI$_2$ methyl ester, 11-benzoate (1.88 g, 3.73 mmol) in methanol (100 ml) was added with stirring cerium trichloride (1.68 g, 4.5 mmol) and the solution was cooled to −10° C. Sodium borohydride (55.2 mg, 1.49 mmol) was added little by little to the stirred solution and the reaction mixture was stirred for 20 min. at −10° C. The resulting solution was brought to 0° C. and diluted with a saturated aqueous solution of sodium bicarbonate (15 ml). The mixture was filtered and the filtrate was concentrated. The concentrate was diluted with water (20 ml) and extracted with ethyl acetate (50 ml×2). The combined ethyl acetate layers were washed with water (20 ml), with brine (20 ml), dried over anhydrous sodium sulfate and concentrated to give an oily material (1.76 g). The oily material was dissolved in anhydrous methanol (80 ml) under argon atmosphere. To this was added a solution of sodium methoxide in methanol (5.22N, 0.2 ml, 1.04 mmol) and the mixture was stirred for 14 hrs. at room temperature. The solution was neutralized with acetic acid and concentrated. The residue was mixed with water (20 ml) and the solution was extracted with ethyl acetate (50 ml×2). The combined ethyl acetate layer was washed with water (20 ml), with brine (20 ml), dried over anhydrous sodium sulfate and concentrated to give a crude material. Column chromatography (Merck, Lobar column, silica gel, ethyl acetate/cyclohexane: 3/1) of the material afforded less polar 16-methyl-15-epi-20a-homo-2,5,6,7-tetranor-4-oxa-18,18,19,19-tetradehydro-4,8-inter-m-phenylene PGI$_2$ methyl ester (583 mg, 1.41 mmol, 40.6%) and more polar 16-methyl-20a-homo-2,4,6,7-tetranor-4-oxa-18,18,19,19-tetradehydro-4,8-inter-m-phenylene PGI$_2$ methyl ester (614 mg, 1.48 mmol, 42.7%). These compounds were assigned the corresponding structures by the following data.

16-Methyl-20a-homo-2,5,6,7-tetranor-4-oxa-18,18,19,19-tetradehydro-4,8-inter-m-phenylene PGI$_2$ methyl ester IR (liquid film): 3450, 2970, 2930, 1745, 1660, 1615, 1590, 1490, 1460, 1440, 1330, 1290, 1245, 1195, 1115, 1040, 970, 865, 765, 730, 690 cm$^{-1}$.

NMR (400 MHz, CDCl$_3$, δ): 1.00, 1.03 (3H, d, J=6.8 Hz); 1.12, 1.13 (3H, t, J=7.3 Hz); 1.7–1.9 (1H, m); 1.9–2.3 (5H, m); 2.3–2.5 (1H, m); 2.6–3.1 (3H, m); 3.44, 3.45 (1H, t, J=8.8 Hz); 3.79 (3H, s); 3.8–3.95 (1H, m); 4.0–4.2 (1H, m); 4.72 (2H, s); 5.1–5.3 (1H, m); 5.5–5.7 (2H, m); 6.7–6.9 (3H, m).

MASS (EI, m/e): 414 (M+).

HR MASS: Calcd. (C$_{24}$H$_{30}$O$_6$, M+): 414.2042. Found (M+): 414.2042.

16-Methyl-15-epi-20a-homo-2,5,6,7-tetranor-4-oxa-18,18,19,19-tetradehydro-4,8-inter-m-phenylene PGI$_2$ methyl ester M.p.: 90.2°–91.3° C. (recrystallization solvent, ethyl acetate/n-hexane=3/2).

IR (KBr): 3490, 2960, 2920, 1705, 1615, 1590, 1490, 1470, 1430, 1380, 1330, 1285, 1270, 1255, 1200, 1190, 1165, 1115, 1070, 1010, 980, 950, 850, 805, 760, 725 cm$^{-1}$.

NMR (400 MHz, CDCl$_3$, δ): 1.02 (3H, d, J=6.8 Hz); 1.13 (3H, t, J=7.3 Hz); 1.7–1.9 (2H, m); 1.9–2.4 (6H, m); 2.5–2.7 (2H, m); 3.52, 3.53 (1H, t, J=8.2 Hz); 3.79 (3H, s); 3.9–4.0 (1H, m); 4.1–4.4 (1H, m); 4.73 (2H, s); 5.1–5.3 (1H, m); 5.6–5.8 (2H, m); 6.7–6.9 (3H, m).

MASS (EI, m/e): 414 (M+).

Elemental Analysis: Calcd. (as C$_{24}$H$_{30}$O$_6$): C(%): 69.54, H(%): 7.30. Found: C(%): 69.55, H(%): 7.33.

EXAMPLE 127

16-Methyl-20a-homo-2,5,6,7-tetranor-4-oxa-18,18,19,19-tetradehydro-4,8-inter-m-phenylene PGI$_2$

325

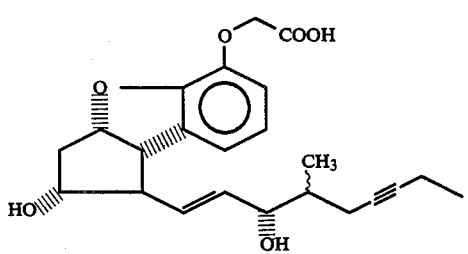

325

To a solution of 16-methyl-20a-homo-2,5,6,7-tetranor-4-oxa-18,18,19,19-tetradehydro-4,8-inter-m-phenylene PGI$_2$ methyl ester (350 mg, 0.844 mmol) in methanol (80 ml) was added 0.725N aqueous NaOH (9.3 ml, 6.8 mmol) with stirring under ice-cooling and the reaction mixture was stirred for 2 hrs. at room temperature. The solution was concentrated and 20 ml of water was added to the residue. After neutralization with 1N hydrochloric acid, the resulting mixture was extracted with ethyl acetate (50 ml×2). The combined ethyl acetate layers were washed with water (20 ml), with brine (20 ml), dried over anhydrous sodium sulfate and concentrated. Recrystallization of the residue from a mixture of 2 ml of ethyl acetate and 1 ml of n-hexane yielded 327 mg (0.82 mmol, 97.2%) of 16-methyl-20a-homo-2,5,6,7-tetranor-4-oxa-18,18,19,19-tetradehydro-4,8-inter-m-phenylene PGI$_2$ as a white crystal. The product was assigned the structure by the following data.

M.p.: 123.8°–125.5° C. (recrystallization solvent, ethyl acetate/n-hexane=2/1).

IR (KBr): 3420, 2970, 2930, 1730, 1610, 1585, 1480, 1450, 1430, 1370, 1280, 1250, 1190, 1160, 1110, 1010, 965, 940, 855, 785, 755, 730 cm$^{-1}$.

NMR (400 MHz, DMSO, δ): 0.92, 0.93 (3H, d, J=6.8 Hz); 1.05, 1.06 (3H, t, J=7.3 Hz); 1.5–1.8 (2H, m); 1.9–2.4 (5H, m); 2.4–2.6 (1H, m); 3.42 (1H, t, J=8.8 Hz); 3.6–4.0 (2H, m); 4.64 (2H, s); 4.6–4.9 (2H, m); 5.08 (1H, q, J=7.3 Hz); 5.4–5.5 (1H, m); 5.6–5.7 (1H, m); 6.71 (3H, s).

MASS (EI, m/e): 400 (M+).

HR MASS: Calcd. (C$_{23}$H$_{28}$O$_6$, M+): 400.1886. Found (M+): 400.1910.

EXAMPLE 128

16-Methyl-15-epi-20a-homo-2,5,6,7-tetranor-4-oxa-18,18,19,19-tetradehydro-4,8-inter-m-phenylene PGI$_2$

326

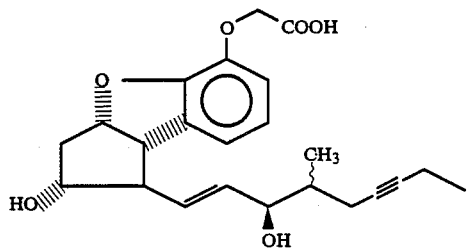

326

To a solution of 16-methyl-15-epi-20a-homo-2,5,6,7-tetranor-4-oxa-18,18,19,19-tetradehydro-4,8-inter-m-phenylene PGI$_2$ methyl ester (358 mg, 0.86 mmol) in methanol was added 0.725N aqueous NaOH (9.5 ml, 6.9 mmol) with stirring under ice-cooling and the reaction mixture was stirred for 1.5 hrs. at room temperature. The solution was concentrated and 20 ml of water was added to the residue. After neutralization with 1N hydrochloric acid under ice-cooling and stirring, the resulting mixture was extracted with ethyl acetate (50 ml×2). The combined ethyl acetate layers were washed with water (20 ml), with brine (20 ml), dried over anhydrous sodium sulfate and concentrated. Recrystallization of the residue from a mixture of 3 ml of ethyl acetate and 1.5 ml of n-hexane yielded 332 mg (0.81 mmol, 93.2%) of 16-methyl-15-epi-20a-homo-2,5,6,7-tetranor-4-oxa-18,18,19,19-tetradehydro-4,8-inter-m-phenylene PGI$_2$ as a white crystal. The product was assigned the structure by the following data.

M.p.: 125.2°–126.2° C. (recrystallization solvent, ethyl acetate/n-hexane=2/1).

IR (KBr): 3370, 2970, 2930, 1740, 1710, 1620, 1590, 1485, 1460, 1425, 1370, 1320, 1285, 1270, 1195, 1165, 1125, 1065, 1025, 1010, 965, 935, 885, 855, 795, 775, 735 cm$^{-1}$.

NMR (400 MHz, DMSO, δ): 0.91, 0.92 (3H, d, J=8.7 Hz); 1.05 (3H, t, J=7.3 Hz); 1.5–1.8 (2H, m); 1.8–2.4 (5H, m); 2.4–2.6 (1H, m); 3.42 (1H, t, J=9.0 Hz); 3.6–4.0 (2H, m); 4.63 (2H, s); 4.6–5.0 (2H, m); 5.08 (1H, q, J=7.5 Hz); 5.4–5.5 (1H, m); 5.6–5.7 (1H, m); 6.7–6.9 (3H, m);

MASS (EI, m/e): 400 (M+).

HR MASS: Calcd. (C$_{23}$H$_{28}$O$_6$, M+): 400.1886. Found (M+): 400.1903.

EXAMPLE 129

16,16-Dimethyl-2,5,6,7-tetranor-4-oxa-18,18,19,19-tetradehydro-4,8-inter-m-phenylene PGI₂ methyl ester 327 and its epimer 328

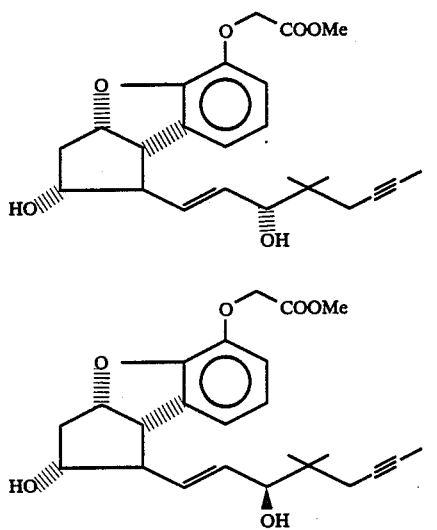

To a solution of 16,16-dimethyl-15-oxo-2,5,6,7-tetranor-4-oxa-18,18,19,19-tetradehydro-4,8-inter-m-phenylene PGI₂ methyl ester, 11-acetate (1.85 g, 4.07 mmol) in methanol (70 ml) was added with stirring cerium trichloride (1.83 g, 4.91 mmol) and the solution was cooled to −10° C. Sodium borohydride (75.8 mg, 2.0 mmol) was added little by little with stirring to the solution and the reaction mixture was stirred for 20 min. at −10° C. The resulting solution was brought to 0° C. and diluted with a saturated aqueous solution of sodium bicarbonate (15 ml). The mixture was filtered and the filtrate was concentrated. The concentrate was diluted with water (20 ml) and extracted with ethyl acetate (50 ml×2). The combined ethyl acetate layers were washed with water (20 ml), with brine (20 ml), dried over anhydrous sodium sulfate and concentrated to give an oily material (1.85 g). The oily material was dissolved in anhydrous methanol (60 ml) under argon atmosphere. To this was added a solution of sodium methoxide in methanol (0.133 ml, 0.69 mmol) and the mixture was stirred for 14 hrs. at room temperature. The solution was neutralized with acetic acid and concentrated. The residue was mixed with water (20 ml) and the solution was extracted with ethyl acetate (50 ml×2). The combined ethyl acetate layers were washed with water (20 ml), with brine (20 ml), dried over anhydrous sodium sulfate and concentrated to give a crude material. Column chromatography (Merck, Lobar column, silica gel, ethyl acetate/cyclohexane: 2/1) of the material afforded less polar 16,16-dimethyl-15-epi-2,5,6,7-tetranor-4-oxa-18,18,19,19-tetradehydro-4,8-inter-m-phenylene PGI₂ methyl ester (584 mg, 1.41 mmol, 40.8%) and more polar 16,16-dimethyl-2,5,6,7-tetranor-4-oxa-18,18,19,19-tetradehydro-4,8-inter-m-phenylene PGI₂ methyl ester (668 mg, 1.61 mmol, 46.5%). These compounds were assigned the corresponding structures by the following data.

16,16-Dimethyl-2,5,6,7-tetranor-4-oxa-18,18,19,19-tetradehydro-4,8-inter-m-phenylene PGI₂ methyl ester M.p.: 115.0°–116.1° C. (recrystallization solvent, ethyl acetate/n-hexane=1/1).

IR (KBr): 3340, 2950, 2905, 2860, 1755, 1610, 1685, 1480, 1455, 1430, 1370, 1290, 1210, 1190, 1160, 1110, 1080, 1070, 1025, 1010, 995, 970, 945, 855, 775, 755, 730, 710, 670, 660 cm⁻¹.

NMR (400 MHz, CDCl₃, δ): 0.969 (3H, s); 0.972 (3H, s); 1.80 (3H, t, J=2.7 Hz); 2.0–2.5 (3H, m); 2.4–2.5 (2H, m); 2.6–2.75 (2H, m); 3.47 (1H, t, J=8.5 Hz); 3.79 (3H, s); 3.85–4.05 (2H, m); 4.72 (2H, s); 5.15–5.25 (1H, m); 5.6–5.7 (2H, m); 6.7–6.8 (3H, m).

MASS (EI, m/e): 414 (M⁺).

Elemental Analysis: Calcd. (as C₂₄H₃₀O₆): C(%): 69.54, H(%): 7.30. Found: C(%): 69.49, H(%): 7.34.

16,16-Dimethyl-15-epi-2,5,6,7-tetranor-4-oxa-18,18,19,19-tetradehydro-4,8-inter-m-phenylene PGI₂ methyl ester M.p.: 99.0°–99.5° C. (recrystallization solvent, ethyl acetate/n-hexane=3/4).

IR (KBr): 3470, 2950, 2920, 1740, 1695, 1615, 1585, 1485, 1460, 1430, 1380, 1325, 1275, 1190, 1110, 1065, 1030, 1005, 970, 950, 865, 800, 760, 725 cm⁻¹.

NMR (400 MHz, CDCl₃, δ): 0.975 (6H, s); 1.81 (3H, t, J=2.5 Hz); 1.75–1.85 (1H, m); 1.95–2.3 (4H, m); 2.5–2.7 (2H, m); 3.53 (1H, t, J=8.3 Hz); 3.79 (3H, s); 3.9–4.1 (2H, m); 4.73 (2H, s); 5.1–5.3 (1H, m); 5.7–5.8 (2H, m); 6.7–6.9 (3H, m).

MASS (EI, m/e): 414 (M⁺).

Elemental Analysis Calcd. (as C₂₄H₃₀O₆): C(%): 69.54, H(%): 7.30. Found: C(%): 69.58, H(%): 7.39.

EXAMPLE 130

16,16-Dimethyl-2,5,6,7-tetranor-4-oxa-18,18,19,19-tetradehydro-4,8-inter-m-phenylene PGI₂ 329

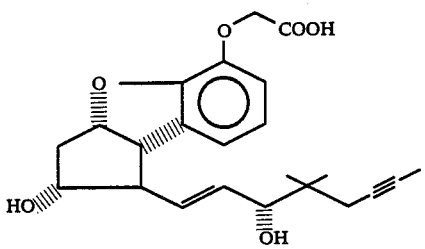

To a solution of 16,16-dimethyl-2,5,6,7-tetranor-4-oxa-18,18,19,19-tetradehydro-4,8-inter-m-phenylene PGI₂ methyl ester (365 mg, 0.882 mmol) in methanol (40 ml) was added 1N aqueous NaOH (7 ml, 7 mmol) with stirring under ice-cooling and the reaction mixture was stirred for one hour at room temperature. The solution was concentrated and 20 ml of water was added to the residue. After neutralization with 1N hydrochloric acid, the resulting mixture was extracted with ethyl acetate (50 ml×2). The combined ethyl acetate layers were washed with water (20 ml), with brine (20 ml), dried over anhydrous sodium sulfate and concentrated to give 345 mg (0.86 mmol, 97.8%) of 16,16-dimethyl-2,5,6,7-tetranor-4-oxa-18,18,19,19-tetradehydro-4,8-inter-m-phenylene PGI₂ as an oily material. The product was assigned the structure by the following data.

M.p.: 78.3°–79.5° C. (recrystallization solvent, ethyl acetate/n-hexane=1.1).

IR (KBr): 3400, 3010, 2960, 1730, 1615, 1590, 1480, 1455, 1430, 1280, 1210, 1185, 1110, 1020, 970, 855, 750, 665 cm$^{-1}$.

NMR (400 MHz, CDCl$_3$, δ): 0.96 (6H, s); 1.80 (3H, t, J=2.4 Hz); 1.95–2.25 (3H, m); 2.4–2.5 (1H, m); 2.55–2.65 (1H, m); 3.46 (1H, t, J=8.3 Hz); 3.5–3.9 (2H, m); 3.9–4.1 (2H, m); 4.65 (1H, d, J=16.6 Hz); 4.71 (1H, d, J=16.6 Hz); 5.1–5.25 (1H, m); 5.6–5.7 (2H, m); 6.7–6.85 (3H, m).

MASS (EI, m/e): 400 (M+).

HR MASS: Calcd. (C$_{23}$H$_{28}$O$_6$, M+): 400.1886. Found (M+): 400.1884.

EXAMPLE 131

16,16-Dimethyl-15-epi-2,5,6,7-tetranor-4-oxa-18,18,19,19-tetradehydro-4,8-inter-m-phenylene PGI$_2$ 330

330

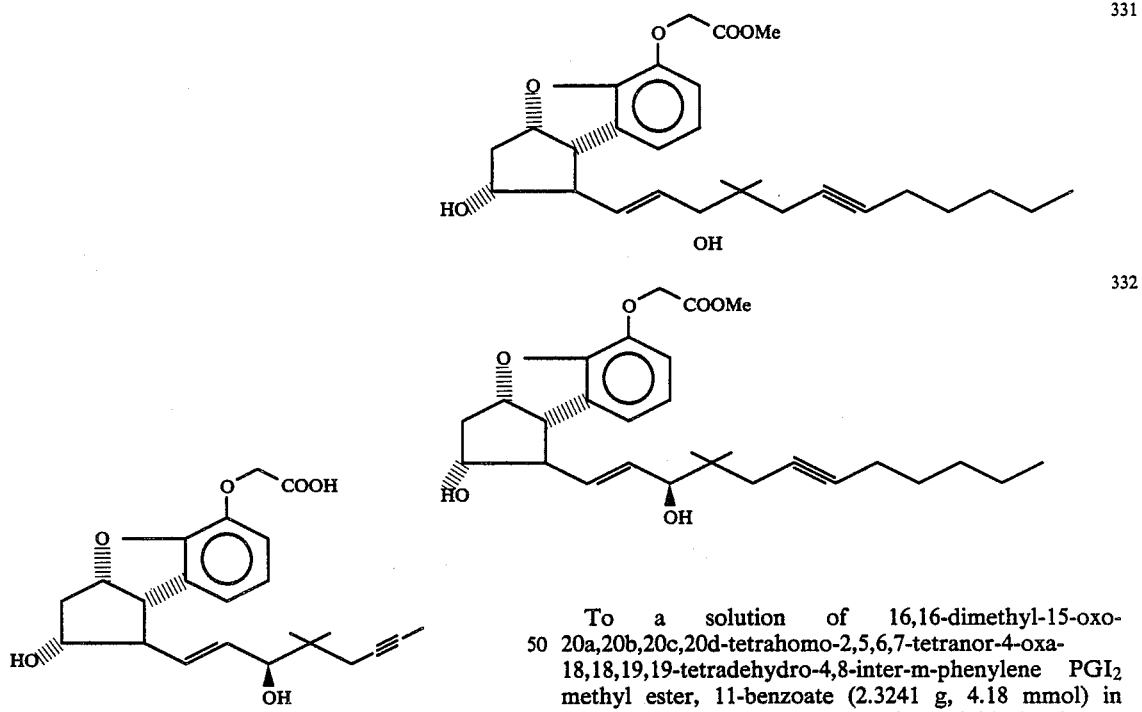

To a solution of 16,16-dimethyl-15-epi-2,5,6,7-tetranor-4-oxa-18,18,19,19-tetradehydro-4,8-inter-m-phenylene PGI$_2$ methyl ester (340 mg, 0.82 mmol) in methanol (40 ml) was added 1N aqueous NaOH (5 ml, 5 mmol) with stirring under ice-cooling and the reaction mixture was stirred for one hour at room temperature. The solution was concentrated and 20 ml of water was added to the residue. After neutralization with 1N hydrochloric acid under ice-cooling and stirring, the resulting mixture was extracted with ethyl acetate (50 ml×2). The combined ethyl acetate layers were washed with water (20 ml), with brine (20 ml), dried over anhydrous sodium sulfate and concentrated. Recrystallization of the residue from a mixture of 1 ml of ethyl acetate and 1 ml of n-hexane yielded 280 mg (0.7 mmol, 85.4%) of 16,16-dimethyl-15-epi-2,5,6,7-tetranor-4-oxa-18,18,19,19-tetradehydro-4,8-inter-m-phenylene PGI$_2$ as a white crystal. The product was assigned the structure by the following data.

M.p.: 66.0°–67.2° C. (recrystallization solvent, ethyl acetate/n-hexane=1/1).

IR (KBr): 3450, 2960, 2920, 1730, 1685, 1615, 1590, 1480, 1460, 1430, 1370, 1275, 1185, 1110, 1070, 1025, 970, 950, 890, 855, 830, 795, 760, 725 cm$^{-1}$.

NMR (400 MHz, DMSO, δ): 0.86 (3H, s); 0.88 (3H, s); 1.65–1.8 (4H, m); 2.0–2.3 (3H, m); 2.45–2.6 (1H, m); 3.43 (1H, t, J=9.0 Hz); 3.65–3.8 (2H, m); 4.64 (2H, s); 4.65–4.85 (2H, m); 5.0–5.15 (1H, m); 5.52 (1H, dd, J=6.6, 15.6 Hz); 5.65 (1H, dd, J=7.8, 15.6 Hz); 6.65–6.8 (3H, m).

MASS (EI, m/e): 400 (M+).

Elemental Analysis: Calcd. (as C$_{23}$H$_{28}$O$_6$): C(%): 68.98, H(%): 7.05. Found: C(%): 68.63, H(%): 7.10.

EXAMPLE 132

16,16-Dimethyl-20a,20b,20c,20d-tetrahomo-2,5,6,7-tetranor-4-oxa-18,18,19,19-tetradehydro-4,8-inter-m-phenylene PGI$_2$ methyl ester 331 and its 15-epimer 332

To a solution of 16,16-dimethyl-15-oxo-20a,20b,20c,20d-tetrahomo-2,5,6,7-tetranor-4-oxa-18,18,19,19-tetradehydro-4,8-inter-m-phenylene PGI$_2$ methyl ester, 11-benzoate (2.3241 g, 4.18 mmol) in methanol (50 ml) was added cerium trichloride heptahydrate (1.5574 g, 4.18 mmol) and the solution was cooled to −10° C. Sodium borohydride (52.7 mg, 1.25 mmol) was added to the stirred solution and the reaction mixture was stirred for 10 min. The solution was mixed with water (30 ml), filtered by means of suction using celite and washed with ethyl acetate (200 ml). The filtrate was concentrated and the residue was extracted with ethyl acetate (30 ml×3). The combined ethyl acetate layers were washed with water (100 ml), with brine (100 ml), dried over anhydrous sodium sulfate (30 g) and concentrated to give an oily material (2.5501 g).

After drying the oil with azeotropic distillation of benzene (10 ml×2), the residue was dissolved in anhydrous methanol (15 ml). To this was added a solution of sodium methoxide in methanol (5.22N, 0.24 ml, 1.25 mmol). The reaction mixture was stirred under argon atmosphere overnight at room temperature, mixed with acetic acid (0.4 ml) and concentrated. Water (15 ml) was added to the residue. Extraction with ethyl acetate (15 ml×3) followed by washing with water (50 ml) and with brine (50 ml), drying over anhydrous sodium sulfate (20 g) and concentration afforded an oily material (2.0014 g). Column chromatography (silica gel, ethyl acetate/cyclohexane: 3/1) of the oil gave first less polar 16,16-dimethyl-15-epi-20a,20b,20c,20d-tetrahomo-2,5,6,7-tetranor-4-oxo-18,18,19,19-tetradehydro-4,8-inter-m-phenylene PGI$_2$ methyl ester (884.1 mg, 1.95 mmol, 47%), which was recrystallized from a mixture of ethyl acetate and cyclohexane (3/2) to give a colourless and needle-like crystal. Subsequently, the column chromatography gave more polar 16,16-dimethyl-20a,20b,20c,20d-tetrahomo-2,5,6,7-tetranor-4-oxa-18,18,19,19-tetradehydro-4,8-inter-m-phenylene PGI$_2$ methyl ester (888.5 mg, 1.96 mmol, 47%), which was recrystallized from a mixture of ethyl acetate and cyclohexane (3/2) to give a colourless and needle-like crystal. These compounds were assigned the corresponding structures by the following data.

16,16-Dimethyl-20a,20b,20c,20d-tetrahomo-2,5,6,7-tetranor-4-oxa-18,18,19,19-tetradehydro-4,8-inter-m-phenylene PGI$_2$ methyl ester M.p.: 76° C.

IR (KBr): 3310, 2951, 2915, 2855, 1755, 1612, 1585, 1482, 1460, 1425, 1371, 1295, 1205, 1185, 1118, 1083, 1065, 1025, 994, 971, 944, 892, 861, 832, 781, 752, 721, 681, 603 cm$^{-1}$.

NMR (400 MHz, CDCl$_3$, δ): 0.88–0.92 (3H, m); 0.98 (3H, s); 0.99 (3H, s); 1.28–1.63 (7H, m); 2.02–2.88 (6H, m); 2.47–2.53 (1H, m); 2.61–2.70 (1H, m); 3.50 (1H, t, J=8.3 Hz); 3.79 (3H, s); 3.90–4.01 (1H, m); 4.02–4.07 (1H, m); 4.73 (2H, s); 5.18–5.25 (1H, m); 5.55–5.74 (2H, m); 6.72–6.83 (3H, m).

MASS (EI, m/e): 470 (M+).

HR MASS: Calcd. (C$_{28}$H$_{38}$O$_6$, M+): 470.2668. Found: 470.2649.

16,16-Dimethyl-15-epi-20a,20b,20c,20d-tetrahomo-2,5,6,7-tetranor-4-oxa-18,18,19,19-tetradehydro-4,8-inter-m-phenylene PGI$_2$ methyl ester M.p.: 83°–84° C.

IR (KBr): 3480, 2950, 2870, 2803, 1699, 1619, 1584, 1482, 1461, 1425, 1391, 1380, 1323, 1301, 1281, 1264, 1201, 1163, 1104, 1063, 1030, 1002, 984, 950, 890, 866, 832, 802, 764, 722, 704, 614 cm$^{-1}$.

NMR (400 MHz, CDCl$_3$, δ): 0.88–0.92 (3H, m); 0.98 (6H, s); 1.25–1.42 (4H, m); 1.45–1.55 (2H, m); 1.72–1.75 (1H, m); 1.97–2.01 (1H, m); 2.04–2.29 (5H, m); 2.52–2.59 (1H, m); 2.60–2.67 (1H, m); 3.53 (1H, t, J=8.3 Hz); 3.79 (3H, s); 3.93–4.01 (1H, m); 4.05–4.08 (1H, m); 4.73 (2H, s); 5.16–5.31 (1H, m); 5.68–5.77 (2H, m); 6.62–6.86 (3H, m).

MASS (EI, m/e): 470 (M+).

HR MASS: Calcd. (C$_{28}$H$_{38}$O$_6$, M+): 470.2668. Found: (M+): 470.2657.

EXAMPLE 133

16,16-Dimethyl-20a,20b,20c,20d-tetrahomo-2,5,6,7-tetranor-4-oxa-18,18,19,19-tetradehydro-4,8-inter-m-phenylene PGI$_2$ 333

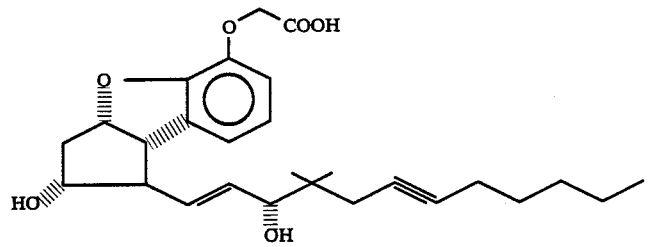

To a solution of 16,16-dimethyl-20a,20b,20c,20d-tetrahomo-2,5,6,7-tetranor-4-oxa-18,18,19,19-tetradehydro-4,8-inter-m-phenylene PGI$_2$ methyl ester (227.1 mg, 0.50 mmol) in methanol (8 ml) was added 1N aqueous NaOH (2.5 ml, 2.5 mmol) and the reaction mixture was stirred under argon atmosphere for 3 hrs. at room temperature. The solution was mixed with 1N hydrochloric acid (2.8 ml) and water (10 ml) and the mixture was extracted with ethyl acetate (10 ml×3). The combined ethyl acetate layers were washed with water (30 ml), with brine (30 ml), dried over anhydrous sodium sulfate (15 g) and concentrated to give quantitatively 16,16-dimethyl-20a,20b,20c,20d-tetrahomo-2,5,6,7-tetranor-4-oxa-18,18,19,19-tetradehydro-4,8-inter-m-phenylene PGI$_2$ (220.8 mg, 0.50 mmol) as a single product, which was assigned the structure by the following data.

IR (liquid film): 3375 (3700–2200), 2951, 2918, 2852, 1727, 1611, 1584, 1480, 1457, 1426, 1375, 1361, 1282, 1242, 1184, 1104, 1063, 1022, 998, 964, 940, 881, 853, 828, 785, 760, 723 cm$^{-1}$.

NMR (400 MHz, CDCl$_3$, δ): 0.88–0.91 (3H, m); 0.97 (6H, s); 1.24–1.42 (4H, m); 1.46–1.55 (2H, m); 2.02–2.28 (5H, m); 2.45–2.53 (1H, m); 2.57–2.67 (1H, m); 2.77–3.39 (3H, broad s); 3.46–3.50 (1H, m); 3.92–3.99 (1H, m); 4.01–4.05 (1H, m); 4.66 (1H, d, J=16.1 Hz); 4.73 (1H, d, J=16.1 Hz); 5.15–5.23 (1H, m); 5.61–5.71 (2H, m); 6.72–6.83 (3H, m).

MASS (EI, m/e): 456 (M+).

HR MASS: Calcd. (C$_{27}$H$_{36}$O$_6$, M+): 456.2512. Found (M+): 456.2512.

EXAMPLE 134

16,16-Dimethyl-15-epi-20a,20b,20c,20d-tetrahomo-2,5,6,7-tetranor-4-oxa-18,18,19,19-tetradehydro-4,8-inter-m-phenylene PGI₂ 334

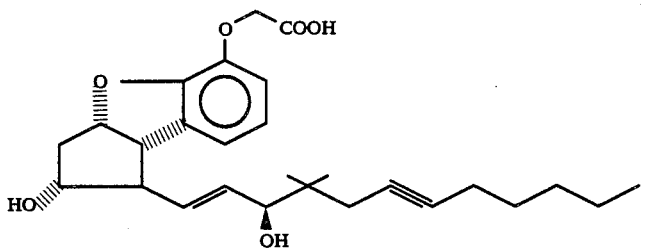

To a solution of 16,16-dimethyl-15-epi-20a,20b,20c,20d-tetrahomo-2,5,6,7-tetranor-4-oxa-18,18,19,19-tetradehydro-4,8-inter-m-phenylene PGI₂ methyl ester (227.3 mg, 0.50 mmol) in methanol (8 ml) was added 1N aqueous NaOH (2.5 ml, 2.5 mmol) and the reaction mixture was stirred under argon atmosphere for 3 hrs. at room temperature. The solution was mixed with 1N hydrochloric acid (2.8 ml) and water (10 ml) and the mixture was extracted with ethyl acetate (10 ml × 3). The combined ethyl acetate layers were washed with water (30 ml), with brine (30 ml), dried over anhydrous sodium sulfate (15 g) and concentrated to give quantitatively 16,16-dimethyl-15-epi-20a,20b,20c,20d-tetrahomo-2,5,6,7-tetranor-4-oxa-18,18,19,19-tetradehydro-4,8-inter-m-phenylene PGI₂ (221.2 mg, 0.50 mmol) as a single product, which was recrystallized from a mixture of ethyl acetate and cyclohexane (1/3) to give a colourless and needle-like crystal. The product was assigned the structure by the following data.

M.p.: 63°–65° C.

IR (KBr): 3428 (3725–2250), 2952, 2925, 2854, 1740, 1619, 1586, 1483, 1461, 1432, 1377, 1361, 1283, 1257, 1199, 1108, 1022, 966, 945, 861, 831, 800, 764, 735 cm⁻¹.

NMR (400 MHz, CDCl₃, δ): 0.88–0.92 (3H, m); 0.98 (6H, s); 1.24–1.42 (4H, m); 1.47–1.56 (2H, m); 2.04–2.27 (5H, m); 2.32–2.60 (3H, broad s); 2.53–2.66 (2H, m); 3.53–3.57 (1H, m); 3.95–4.03 (1H, m); 4.03–4.07 (1H, m); 4.69 (1H, d, J=16.6 Hz); 4.74 (1H, d, J=16.6 Hz); 5.22–5.28 (1H, m); 5.68–5.77 (2H, m); 6.74–6.88 (3H, m).

MASS (EI, m/e): 456 (M⁺).

HR MASS: Calcd. (C₂₇H₃₆O₆, M⁺): 456.2512. Found (M⁺): 456.2485.

EXAMPLE 135

16-Methyl-2,5,6,7,18,19,20-heptanor-4-oxa-13,14-dihydro-4,8-inter-m-phenylene PGI₂ methyl ester 335

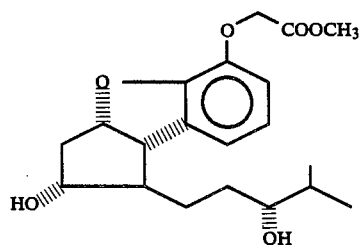

In a flask (25 ml), 16-methyl-2,5,6,7,18,19,20-heptanor-4-oxa-4,8-inter-m-phenylene PGI₂ methyl ester (86.1 mg, 0.238 mmol) was dissolved into ethyl acetate (10 ml). 40 mg of 10% palladium on carbon was then added into the solution and the atmosphere in the flask was substituted by hydrogen gas. Hydrogenation was performed for 4 hrs. at room temperature under atmospheric pressure. The catalyst was removed by filtration with celite and ethyl acetate was distilled out in vacuo. The resulting yellow and oily material was purified by column chromatography (Merck, Lobar column B type, cyclohexane/ethyl acetate: 1/2) to give 16-methyl-2,5,6,7,18,19,20-heptanor-4-oxa-13,14-dihydro-4,8-inter-m-phenylene PGI₂ methyl ester (69 mg, 0.190 mmol, 80%), which was recrystallized from ethyl acetate/n-hexane to afford a white crystal. The product was assigned the structure by the following data.

M.p.: 110.5°–111.5° C.

IR (KBr): 3375, 2960, 2920, 2890, 1750, 1610, 1585, 1485, 1439, 1380, 1359, 1303, 1288, 1268, 1250, 1220, 1190, 1180, 1115, 1090, 1075, 1050, 1020, 1008, 985, 958, 888, 862, 847, 835, 790, 770, 748, 722, 710 cm⁻¹.

NMR (400 MHz, CDCl₃, δ): 0.92 (3H, d, J=1.47 Hz); 0.95 (3H, d, J=1.47 Hz); 1.44–1.60 (3H, m); 1.62–1.73 (4H, m); 2.05–2.08 (1H, m); 2.14–2.20 (1H, m); 2.40–2.46 (1H, m); 3.40–3.45 (2H, m); 3.78 (3H, s); 4.00–4.03 (1H, m); 4.68–4.76 (2H, m); 5.26–5.30 (1H, m); 6.71–6.88 (3H, m).

MASS (EI, m/e): 364 (M⁺).

HR MASS: Calcd. (C₂₀H₂₈O₆, M⁺): 364.1855. Found (M⁺): 364.1893.

EXAMPLE 136

16,16-Dimethyl-2,5,6,7-tetranor-4-oxa-13,14-dihydro-4,8-inter-m-phenylene PGI₂ methyl ester 336

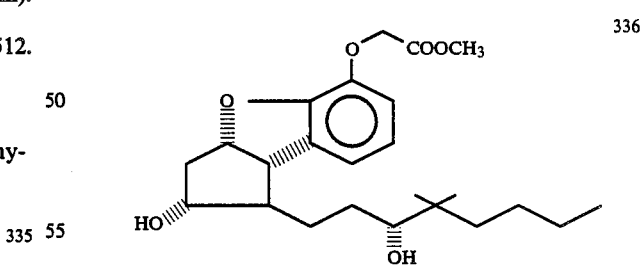

In a flask (25 ml), 16,16-dimethyl-2,5,6,7-tetranor-4-oxa-4,8-inter-m-phenylene PGI₂ methyl ester (39 mg, 0.093 mmol) was dissolved into ethyl acetate (5 ml). 15 mg of 10% palladium on carbon was then added into the solution and the atmosphere in the flask was substituted by hydrogen gas. Hydrogenation was performed for 4 hrs. at room temperature under atmospheric pressure. The catalyst was removed by filtration with celite and ethyl acetate was distilled out in vacuo. The resulting colourless and oily material was purified by column chromatography (Merck, Lobar column B type, cyclohexane/ethyl acetate: 1/6) to give 16,16-dimethyl-2,5,6,7-tetranor-4-oxa-13,14-dihydro-4,8-inter-m-phenylene PGI$_2$ methyl ester (27.7 mg, 0.066 mmol, 71%). The product was assigned the structure by the following data.

IR (liquid film): 3370, 2970, 2930, 2875, 1740, 1620, 1611, 1595, 1480, 1460, 1440, 1375, 1300, 1245, 1220, 1198, 1100, 1045, 955, 915, 850, 845, 780, 760, 730 cm$^{-1}$.

NMR (400 MHz, CDCl$_3$, δ): 0.86 (3H, s); 0.88 (3H, s); 0.89–0.93 (3H, m); 1.19–1.33 (6H, m); 1.42–1.52 (2H, m); 1.59 (2H, s); 1.68–1.75 (2H, m); 2.05–2.07 (1H, m); 2.16–2.21 (1H, m); 2.40–2.47 (1H, m); 3.29–3.31 (1H, m); 3.42–3.45 (1H, m); 3.78 (3H, s); 4.01–4.05 (1H, m); 4.70–4.72 (2H, m); 5.26–5.31 (1H, m); 6.71–6.89 (3H, m).

MASS (EI, m/e): 420 (M+).

HR MASS: Calcd. (C$_{24}$H$_{36}$O$_6$, M+): 420.2511. Found (M+): 420.2536.

EXAMPLE 137

16,16-Dimethyl-2,5,6,7-tetranor-20a-homo-4-oxa-13,14-dihydro-4,8-inter-m-phenylene PGI$_2$ methyl ester 337

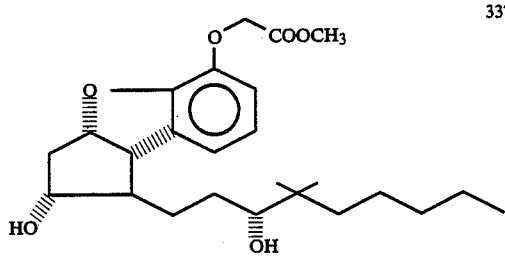

In a flask (25 ml), 16,16-dimethyl-2,5,6,7-tetranor-20a-homo-4-oxa-4,8-inter-m-phenylene PGI$_2$ methyl ester (79 mg, 0.183 mmol) was dissolved into ethyl acetate (10 ml). 39 mg of 10% palladium on carbon was then added into the solution and the atmosphere in the flask was substituted by hydrogen gas. Hydrogenation was performed for 5 hrs. at room temperature under atmospheric pressure. The catalyst was removed by filtration with celite and ethyl acetate was distilled out in vacuo. The resulting colorless and oily material was purified by column chromatography (Merck, Lobar column B type, cyclohexane/ethyl acetate: 1/2) to give 16,16-dimethyl-2,5,6,7-tetranor-20a-homo-4-oxa-13,14-dihydro-4,8-inter-m-phenylene PGI$_2$ methyl ester (53.7 mg, 0.124 mmol, 68%). The product was assigned the structure by the following data.

IR (liquid film): 3470, 2970, 2940, 2870, 1755, 1612, 1599, 1490, 1465, 1440, 1375, 1300, 1220, 1195, 1115, 960, 915, 855, 800, 730 cm$^{-1}$.

NMR (400 MHz, CDCl$_3$, δ): 0.86–0.91 (9H, m); 1.18–1.32 (8H, m); 1.40–1.52 (2H, m); 1.57 (2H, m); 1.67–1.77 (2H, m); 2.04–2.09 (1H, m); 2.15–2.21 (1H, m); 2.40–2.47 (1H, m); 3.28 –3.31 (1H, m); 3.41–3.45 (1H, m); 3.78 (3H, s); 4.01–4.05 (1H, m); 4.67–4.76 (2H, m); 5.26–5.31 (1H, m); 6.71–6.88 (3H, m).

MASS (EI, m/e): 434 (M+).

HR MASS: Calcd. (C$_{25}$H$_{38}$O$_6$, M+): 434.2668. Found (M+): 434.2659.

EXAMPLE 138

16,16,17-Trimethyl-2,5,6,7,19,20-hexanor-4-oxa-13,14-dihydro-4,8-inter-m-phenylene PGI$_2$ methyl ester 338

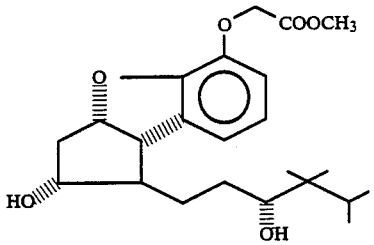

In a flask (25 ml), 16,16,17-trimethyl-2,5,6,7,19,20-hexanor-4-oxa-4,8-inter-m-phenylene PGI$_2$ methyl ester (121.3 mg, 0.300 mmol) was dissolved into ethyl acetate (15 ml). 39 mg of 10% palladium on carbon was then added into the solution and the atmosphere in the flask was substituted by hydrogen gas. Hydrogenation was performed for 4 hrs. at room temperature under atmosphere pressure. The catalyst was removed by filtration with celite and ethyl acetate was distilled out in vacuo. The resulting colourless and oily material was purified by column chromatography (Merck, Lobar column B type, cyclohexane/ethyl acetate: 1/2) to give 16,16,17-trimethyl-2,5,6,7,19,20-hexanor-4-oxa-13,14-dihydro-4,8-inter-m-phenylene PGI$_2$ methyl ester (101.4 mg, 0.250 mmol, 80%), which was recrystallized from ethyl acetate/n-hexane to afford a white crystal. The product was assigned the structure by the following data.

M.p.: 94°–95° C.

IR (liquid film): 3425, 2980, 2900, 2870, 1740, 1620, 1610, 1598, 1438, 1462, 1450, 1422, 1390, 1372, 1300, 1245, 1220, 1193, 1110, 1048, 958, 915, 854, 838, 790, 772, 734, 710, 639, 610 cm$^{-1}$.

NMR (400 MHz, CDCl$_3$, δ): 0.76 (3H, s); 0.81–0.90 (9H, m); 1.37–1.53 (3H, m); 1.67–1.80 (3H, m); 1.98–2.06 (2H, m); 2.14–2.20 (1H, m); 2.40–2.46 (1H, m); 3.41–3.49 (2H, m); 3.78 (3H, s); 3.95–4.02 (1H, m); 4.67–4.76 (2H, m); 5.26–5.30 (1H, m); 6.71–6.88 (3H, m).

MASS (EI, m/e): 406 (M+).

HR MASS: Calcd. (C$_{23}$H$_{34}$O$_6$, M+): 406.2355. Found (M+): 406.2375.

EXAMPLE 139

17-Cyclohexyl-2,5,6,7,18,19,20-heptanor-4-oxa-13,14-dihydro-4,8-inter-m-phenylene PGI$_2$ methyl ester 339

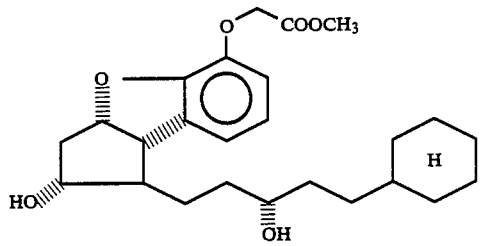

In a flask (25 ml), 17-cyclohexyl-2,5,6,7,18,19,20-heptanor-4-oxa-4,8-inter-m-phenylene PGI$_2$ methyl ester (81.3 mg, 0.189 mmol) was dissolved into ethyl acetate (10 ml). 34 mg of 10% palladium on carbon was then added into the solution and the atmosphere in the flask was substituted by hydrogen gas. Hydrogenation was performed for 4 hrs. at room temperature under atmosphere pressure. The catalyst was removed by filtration with celite and ethyl acetate was distilled out in vacuo. The resulting colourless and oily material was purified by column chromatography (Merck, Lobar column B type, cyclohexane/ethyl acetate: 1/2) to give 17-cyclohexyl-2,5,6,7,18,19,20-heptanor-4-oxa-13,14-dihydro-4,8-inter-m-phenylene PGI$_2$ methyl ester (58.7 mg, 0.136 mmol, 72%), which was recrystallized from ethyl acetate/n-hexane to afford a white crystal. The product was assigned the structure by the following data.

M.p.: 88.5°–90° C.

IR (KBr): 3320, 2930, 2860, 1740, 1620, 1590, 1490, 1463, 1457, 1396, 1369, 1357, 1300, 1282, 1250, 1222, 1202, 1168, 1152, 1115, 1065, 1052, 1035, 1012, 958, 906, 870, 858, 808, 756, 722 cm$^{-1}$.

NMR (400 MHz, CDCl$_3$, δ): 0.88–0.96 (2H, m); 1.10–1.34 (6H, m); 1.49–1.72 (13H, m); 2.04–2.10 (1H, m); 2.16–2.20 (1H, m); 2.41–2.46 (1H, m); 3.43–3.46 (1H, m); 3.60–3.65 (1H, m); 3.78 (3H, s); 4.00–4.05 (1H, m); 4.68–4.76 (2H, m); 5.25–5.30 (1H, m); 6.70–6.87 (3H, m).

MASS (EI, m/e): 432 (M$^+$).

HR MASS: Calcd. (C$_{25}$H$_{36}$O$_6$, M$^+$): 432.2511. Found (M$^+$): 432.2529.

EXAMPLE 140

16,16-Dimethyl-2,5,6,7-tetranor-4,18-dioxa-13,14-dihydro-4,8-inter-m-phenylene PGI$_2$ methyl ester 340

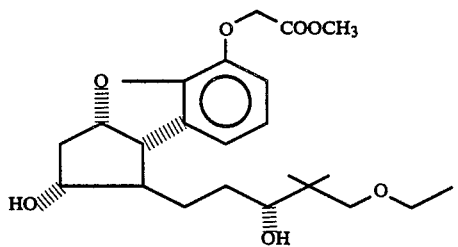

In a flask (25 ml), 16,16-dimethyl-2,5,6,7-tetranor-4,18-dioxa-4,8-inter-m-phenylene PGI$_2$ methyl ester (84.7 mg, 0.201 mmol) was dissolved into ethyl acetate (12 ml). 12 mg of 10% palladium on carbon was then added into the solution and the atmosphere in the flask was substituted by hydrogen gas. Hydrogenation was performed for 3 hrs. at room temperature under atmosphere pressure. The catalyst was removed by filtration with celite and ethyl acetate was distilled out in vacuo. The resulting colourless and oily material was purified by column chromatography (Merck, Lobar column B type, cyclohexane/ethyl acetate: 1/2) to give 16,16-dimethyl-2,5,6,7-tetranor-4,18-dioxa-13,14-dihydro-4,8-inter-m-phenylene PGI$_2$ methyl ester (64.2 mg, 0.152 mmol, 76%). The product was assigned the structure by the following data.

IR (liquid film): 3400, 2960, 2930, 2880, 1760, 1620, 1595, 1485, 1465, 1440, 1390, 1295, 1250, 1220, 1190, 1110, 1070, 1030, 980, 955, 910, 850, 835, 770, 730 cm$^{-1}$.

NMR (400 MHz, CDCl$_3$, δ): 0.88 (3H, s); 0.93 (3H, s); 1.18–1.20 (3H, m); 1.45–1.75 (6H, m); 2.01–2.04 (1H, m); 2.14–2.20 (1H, m); 2.42–2.49 (1H, m); 3.28–3.35 (2H, m); 3.41–3.52 (4H, m); 3.78 (3H, s); 4.10–4.15 (1H, m); 4.70–4.72 (2H, m); 5.25–5.30 (1H, m); 6.71–6.80 (2H, m); 6.87–6.89 (1H, m).

MASS (EI, m/e): 422 (M$^+$).

HR MASS: Calcd. (C$_{23}$H$_{34}$O$_7$, M$^+$): 422.2304. Found (M$^+$): 422.2293.

EXAMPLE 141

16,16-Dimethyl-2,5,6,7-tetranor-4,18-dioxa-13,14-dihydro-4,8-inter-m-phenylene PGI$_2$ 341

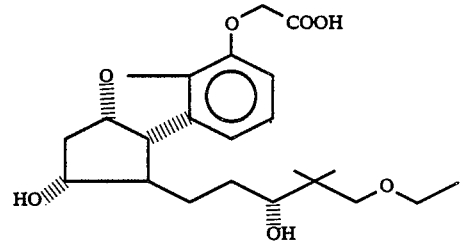

16,16-Dimethyl-2,5,6,7-tetranor-4,18-dioxa-13,14-dihydro-4,8-inter-m-phenylene PGI$_2$ methyl ester (45 mg, 0.107 mmol) was dissolved in methanol (4 ml) in a flask (25 ml). To this was added 1N aqueous NaOH (0.36 ml). The atmosphere in the flask was substituted by argon gas and the reaction mixture was then stirred for 3 hrs. at room temperature. After distillation in vacuo of methanol, the residue was diluted with water (3 ml) and acidified to pH 2 with 1N hydrochloric acid. The solution was extracted with ethyl acetate. The ethyl acetate layers were washed with brine, dried over anhydrous sodium sulfate and concentrated in vacuo to give 16,16-dimethyl-2,5,6,7-tetranor-4,18-dioxa-13,14-dihydro-4,8-inter-m-phenylene PGI$_2$ (39.3 mg, 0.963 mmol, 90%), which was recrystallized from n-hexane/ethyl acetate to afford a white crystal. The product was assigned the structure by the following data.

M.p.: 125°–126° C.

IR (KBr): 3350, 3230, 2980, 2950, 2920, 2900, 2880, 1725, 1680, 1620, 1610, 1595, 1485, 1465, 1440, 1380, 1365, 1325, 1305, 1285, 1255, 1240, 1195, 1185, 1170, 1105, 1070, 1045, 1020, 980, 935, 895, 870, 845, 825, 795, 750, 729, 682 cm$^{-1}$.

NMR (400 MHz, CDCl$_3$, δ): 0.88 (3H, s); 0.93 (3H, s); 1.20 (3H, t, J=6.83 Hz); 1.44–1.56 (2H, m); 1.63–1.72 (2H, m); 2.03–2.10 (1H, m); 2.12–2.17 (1H, m); 2.37–2.44 (1H, m); 2.45–2.74 (3H, m); 3.32 (2H, q, J=9.28 Hz); 3.42–3.52 (4H, m); 4.03–4.06 (1H, m); 4.66 (2H, dd, J=16.6 Hz); 5.25–5.30 (1H, m); 6.72–6.81 (2H, m); 6.89 (1H, d, J=7.33 Hz).

MASS (EI, m/e): 408 (M$^+$).

HR MASS: Calcd. (C$_{22}$H$_{32}$O$_7$, M$^+$): 408.2148. Found (M$^+$): 408.2178.

EXAMPLE 142

16,16-Dimethyl-2,5,6,7-tetranor-4,18-dioxa-4,8-inter-m-phenylene PGI$_2$ ethyl ester 342

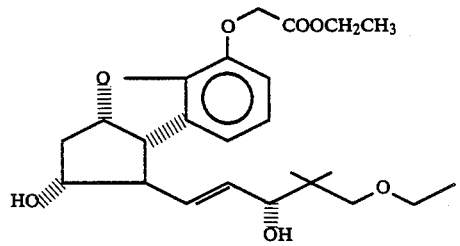

16,16-Dimethyl-2,5,6,7-tetranor-4,18-dioxa-4,8-inter-m-phenylene PGI$_2$ (63.8 mg, 0.152 mmol) was dissolved into anhydrous tetrahydrofuran (7 ml) into a two-neck flask (30 ml) which was filled with argon gas. To this were added under ice-cooling triethylamine (0.028 ml, 0.201 mmol) and ethyl chloroformate (0.016 ml, 0.168 mmol). The mixture was then allowed to warm to room temperature and stirred for 4 hrs. Anhydrous ethanol (0.046 ml, 1.52 mmol) was added to the solution and the mixture was stirred at 60° C. overnight. After cooling, the resulting solution was mixed with ethyl acetate (10 ml), washed with a saturated aqueous solution of sodium bicarbonate and with brine, dried over anhydrous sodium sulfate and concentrated in vacuo to give an oily and yellow material. Column chromatography (Merck, Lobar column B type, cyclohexane/ethyl acetate: 1/4) of the material gave 16,16-dimethyl-2,5,6,7-tetranor-4,18-dioxa-4,8-inter-m-phenylene PGI$_2$ ethyl ester (53.5 mg, 0.123 mmol, 81%), which was recrystallized from n-hexane/ethyl acetate to afford a white crystal. The product was assigned the structure by the following data.

M.p.: 94.5°–95° C.

IR (KBr): 3380, 3300, 2975, 2940, 2875, 1762, 1620, 1595, 1495, 1470, 1450, 1440, 1380, 1365, 1298, 1240, 1210, 1185, 1118, 1090, 1070, 1045, 1025, 1005, 989, 950, 905, 895, 865, 835, 790, 780, 760, 730 cm$^{-1}$.

NMR (400 MHz, CDCl$_3$, δ): 0.92 (3H, s); 0.95 (3H, s); 1.19–1.23 (3H, m); 1.28 (3H, t, J=7.32 Hz); 1.58 (2H, broad s); 2.05–2.12 (1H, m); 2.51–2.56 (1H, m); 2.60–2.67 (1H, m); 3.33 (2H, dd, J=8.78 Hz); 3.46–3.54 (3H, m); 3.94–3.99 (2H, m); 4.22–4.28 (2H, m); 4.70 (2H, s); 5.20–5.25 (1H, m); 5.67–5.69 (2H, m); 6.72–6.81 (3H, m).

MASS (EI, m/e): 434 (M+).

HR MASS: Calcd. (C$_{24}$H$_{34}$O$_7$, M+): 434.2304. Found (M+): 434.2292.

EXAMPLE 143

16,16-Dimethyl-2,5,6,7-tetranor-4,18-dioxa-4,8-inter-m-phenylene PGI$_2$ cyclohexylmethyl ester 343

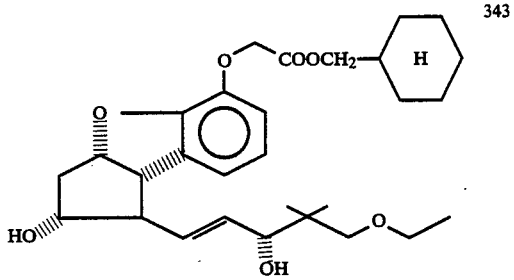

16,16-Dimethyl-2,5,6,7-tetranor-4,18-dioxa-4,8-inter-m-phenylene PGI$_2$ (84 mg, 0.197 mmol) was dissolved into anhydrous tetrahydrofuran (8 ml) in a two-neck flask (30 ml) which was filled with argon gas. To this were added under ice-cooling triethylamine (0.034 ml, 0.236 mmol) and ethyl chloroformate (0.02 ml, 0.217 mmol). The mixture was then allowed to warm to room temperature and stirred for 4 hrs. Cyclohexylmethyl alcohol (0.24 ml, 1.97 mmol) was added to the solution and the mixture was stirred at 60° C. overnight. After cooling, the resulting solution was mixed with ethyl acetate (10 ml), washed with a saturated aqueous solution of sodium bicarbonate and with brine, dried over anhydrous sodium sulfate and concentrated in vacuo to give an oily and yellow material. Column chromatography (Merck, Lobar column B type, cyclohexane/ethyl acetate: 1/4) of the material gave 16,16-dimethyl-2,5,6,7-tetranor-4,18-dioxa-4,8-inter-m-phenylene PGI$_2$ cyclohexylmethyl ester (75.2 mg, 0.150 mmol, 76%), which was recrystallized from n-hexane/ethyl acetate to afford a white crystal. The product was assigned the structure by the following data.

M.p.: 107°–109° C.

IR (KBr): 3330, 2970, 2930, 2860, 1758, 1678, 1620, 1596, 1490, 1470, 1435, 1420, 1400, 1380, 1370, 1330, 1303, 1280, 1260, 1240, 1210, 1188, 1165, 1158, 1119, 1100, 1080, 1046, 1039, 1031, 1010, 990, 978, 960, 910, 893, 870, 838, 790, 762, 732, 700 cm$^{-1}$.

NMR (400 MHz, CDCl$_3$, δ): 0.88–0.95 (8H, m); 1.14–1.26 (6H, m); 1.59–1.71 (7H, m); 2.05–2.11 (2H, m); 2.51–2.53 (1H, m); 2.60–2.67 (1H, m); 3.28–3.38 (2H, m); 3.46–3.53 (3H, m); 3.95–3.99 (4H, m); 4.73 (2H, s); 5.18–5.24 (1H, m); 5.67–5.69 (2H, m); 6.72–6.80 (3H, m).

MASS (EI, m/e): 502 (M+).

HR MASS: Calcd. (C$_{29}$H$_{42}$O$_7$, M+): 502.2937. Found (M+): 502.2930.

EXAMPLE 144

16,16-Dimethyl-2,5,6,7-tetranor-4,18-dioxa-4,8-inter-m-phenylene PGI$_2$ furfuryl ester 344

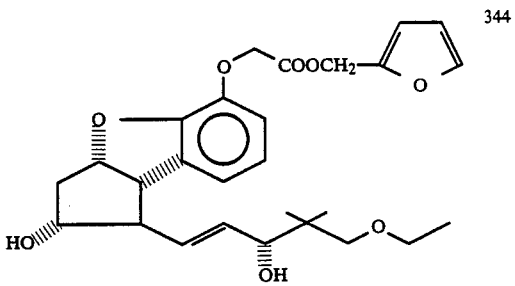

16,16-Dimethyl-2,5,6,7-tetranor-4,18-dioxa-4,8-inter-m-phenylene PGI$_2$ (84 mg, 0.207 mmol) was dissolved into anhydrous tetrahydrofuran (8 ml) in a two-neck flask (30 ml) which was filled with argon gas. To this were added under ice-cooling triethylamine (0.035 ml, 0.249 mmol) and ethyl chloroformate (0.022 ml, 0.228 mmol). The mixture was then allowed to warm to room temperature and stirred for 3 hrs. Furfuryl alcohol (0.18 ml, 2.07 mmol) was added to the solution and the mixture was stirred at 60° C. overnight. After cooling, the resulting solution was mixed with ethyl acetate (10 ml), washed with a saturated aqueous solution of sodium bicarbonate and with brine, dried over anhydrous sodium sulfate and concentrated in vacuo to give an oily and yellow material. Column chromatography (Merck, Lobar column B type, cyclohexane/ethyl acetate: 1/4) of the material gave 16,16-dimethyl-2,5,6,7-tetranor-4,18-dioxa-4,8-inter-m-phenylene PGI$_2$ furfuryl ester (96.5 mg, 0.199 mmol, 96%), which was recrystallized from n-hexane/ethyl acetate to afford a white crystal. The product was assigned the structure by the following data.

M.p.: 95.5°–96° C.

IR (KBr): 3320, 3070, 3040, 2970, 2930, 2860, 1758, 1670, 1619, 1592, 1485, 1465, 1435, 1420, 1380, 1365, 1298, 1280, 1238, 1210, 1180, 1162, 1120, 1090, 1075, 1040, 1032, 1005, 985, 975, 955, 905, 890, 862, 835, 790, 782, 739, 730 cm$^{-1}$.

NMR (400 MHz, CDCl$_3$, δ): 0.92 (3H, s); 0.95 (3H, s); 1.21 (3H, t, J=7.33 Hz); 1.63 (2H, broad s); 2.02–2.09

(1H, m); 2.49–2.54 (1H, m); 2.59–2.65 (1H, m); 3.33 (2H, dd, J=8.79 Hz); 3.45–3.52 (3H, m); 3.90–3.96 (2H, m); 4.73 (2H, s); 5.17–5.22 (3H, m); 5.63–5.71 (2H, m); 6.36–6.37 (1H, m); 6.42–6.43 (1H, m); 6.70–6.80 (3H, m); 7.42–7.43 (1H, m).

MASS (EI, m/e): 486 (M+).

HR MASS: Calcd. ($C_{27}H_{34}O_8$, M+): 486.2253. Found (M+): 486.2236.

EXAMPLE 145

16,16-Dimethyl-2,5,6,7-tetranor-4,18-dioxa-4,8-inter-m-phenylene PGI$_2$ (1-carbomethoxyethyl) ester 345

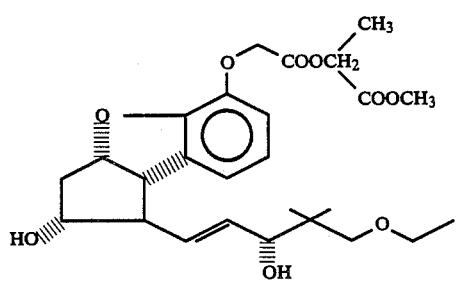

16,16-Dimethyl-2,5,6,7-tetranor-4,18-dioxa-4,8-inter-m-phenylene PGI$_2$ (109.1 mg, 0.269 mmol) was dissolved into anhydrous tetrahydrofuran (10 ml) in a two-neck flask (30 ml) which was filled with argon gas. To this were added under ice-cooling triethylamine (0.045 ml, 0.322 mmol) and ethyl chloroformate (0.028 ml, 0.296 mmol). The mixture was then allowed to warm to room temperature and stirred for 5 hrs. Methyl lactate (0.256 ml, 2.69 mmol) was added to the solution and the mixture was stirred at 60° C. overnight. After cooling, the resulting solution was mixed with ethyl acetate (20 ml), washed with a saturated aqueous solution of sodium bicarbonate and with brine, dried over anhydrous sodium sulfate and concentrated in vacuo to give an oily and yellow material. Column chromatography (Merck, Lobar column A type, cyclohexane/ethyl acetate: 1/4) of the material gave 16,16-dimethyl-2,5,6,7-tetranor-4,18-dioxa-4,8-inter-m-phenylene PGI$_2$ (1-carbomethoxyethyl) ester (35.1 mg, 0.071 mmol, 26%), which was recrystallized from n-hexane/ethyl ether to afford a white crystal. The product was assigned the structure by the following data.

M.p.: 89.5°–90.5° C.

IR (KBr): 3330, 3270, 2980, 2940, 2880, 1775, 1750, 1620, 1590, 1490, 1465, 1438, 1380, 1360, 1298, 1280, 1238, 1175, 1120, 1070, 1045, 1030, 1005, 975, 965, 950, 890, 860, 850, 835, 790, 780, 760, 730 cm$^{-1}$.

NMR (400 MHz, CDCl$_3$, δ): 0.92 (3H, s); 0.95 (3H, s) 1.20 (3H, t, J=7.02 Hz); 1.24–1.30 (3H, m); 1.70 (1H, broad s); 2.04–2.10 (1H, m); 2.34 (1H, broad s); 2.48–2.54 (1H, m); 2.60–2.67 (1H, m); 3.30 (2H, dd, J=8.85 Hz); 3.46–3.52 (3H, m); 3.74 (3H, s); 3.91–3.97 (1H, m); 4.22–4.28 (2H, m); 4.71–4.82 (2H, m); 5.19–5.24 (1H, m); 5.63–5.71 (2H, m); 6.72–6.80 (3H, m).

MASS (EI/ m/e): 492 (M+).

HR MASS: Calcd. ($C_{26}H_{36}O_9$, M+): 492.2359. Found (M+): 492.2358.

EXAMPLE 146

16,16-Dimethyl-2,5,6,7-tetranor-4,18-dioxa-4,8-inter-m-phenylene PGI$_2$ benzyl ester 346

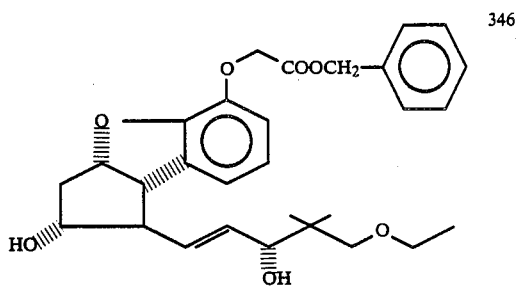

16,16-dimethyl-2,5,6,7-tetranor-4,18-dioxa-4,8-inter-m-phenylene PGI$_2$ (70 mg, 0.172 mmol) was dissolved into anhydrous tetrahydrofuran (6 ml) in a two-neck flask (30 ml) which was filled with argon gas. To this were added under ice-cooling triethylamine (0.029 ml, 0.206 mmol) and ethyl chloroformate (0.018 ml, 0.189 mmol). The mixture was then allowed to warm to room temperature and stirred for 4 hrs. Benzyl alcohol (0.18 ml, 1.72 mmol) was added to the solution and the mixture was stirred at 60° C. overnight. After cooling, the resulting solution was mixed with ethyl acetate (10 ml), washed with a saturated aqueous solution of sodium bicarbonate and with brine, dried over anhydrous sodium sulfate and concentrated in vacuo to give an oily and yellow material. Column chromatography (Merck, Lobar column B type, cyclohexane/ethyl acetate: 1/4) of the material gave 16,16-dimethyl-2,5,6,7-tetranor-4,18-dioxa-4,8-inter-m-phenylene PGI$_2$ benzyl ester (75.2 mg, 0.152 mmol, 88%), which was recrystallized from n-hexane/ethyl acetate to afford a white crystal. The product was assigned the structure by the following data.

M.p.: 74.5°–75° C.

IR (KBr): 3325, 3050, 2980, 2940, 2880, 2820, 1760, 1620, 1590, 1485, 1465, 1435, 1380, 1365, 1298, 1238, 1215, 1180, 1165, 1120, 1090, 1070, 1045, 1035, 1005, 985, 975, 955, 905, 890, 862, 835, 780, 760, 738, 730, 700 cm$^{-1}$.

NMR (400 MHz, CDCl$_3$, δ): 0.92 (3H, s); 0.95 (3H, s); 1.19–1.23 (3H, m); 1.58 (2H, broad s); 2.01–2.08 (1H, m); 2.51–2.53 (1H, m); 2.58–2.64 (1H, m); 3.29 (1H, d, J=8.79 Hz); 3.37 (1H, d, J=9.23 Hz); 3.46–3.52 (3H, m); 3.90–3.98 (2H, m); 4.76 (2H, s); 5.15–5.22 (3H, m); 5.66–5.68 (2H, m); 6.70–6.80 (3H, m); 7.32–7.37 (5H, m).

MASS (EI, m/e): 496 (M+).

HR MASS: Calcd. ($C_{29}H_{36}O_7$, M+): 496.2461. Found (M+): 496.2444.

EXAMPLE 147

16,16-Dimethyl-2,5,6,7-tetranor-4,18-dioxa-4,8-inter-m-phenylene PGI$_2$ p-bromophenacyl ester 347

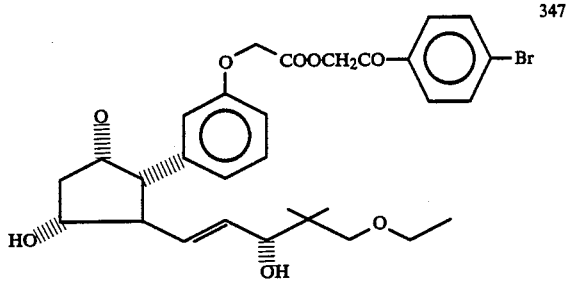

16,16-Dimethyl-2,5,6,7-tetranor-4,18-dioxa-4,8-inter-m-phenylene PGI$_2$ (80 mg, 0.197 mmol) was dissolved into anhydrous dimethylformamide (3 ml) in a two-neck flask (30 ml) filled with argon gas. To this were added under ice-cooling triethylamine (0.030 ml, 0.217 mmol) and p-bromophenacyl bromide (55 mg, 0.200 mmol) and the reaction mixture was stirred for 6 hrs. at room temperature. Water (5 ml) was added to the solution and the mixture was extracted with ethyl ether. The ethyl ether layers were dried over anhydrous sodium sulfate and concentrated in vacuo to give a colourless and oily material. Column chromatography (Merck, Lobar column, B type, cyclohexane/ethyl acetate: 1/4) of the material gave 16,16-dimethyl-2,5,6,7-tetranor-4,18-dioxa-4,8-inter-m-phenylene PGI$_2$ p-bromophenacyl ester (91.1 mg, 0.151 mmol, 77%), which was recrystallized from n-hexane/ethyl acetate to afford a white crystal. The product was assigned the structure by the following data.

M.p.: 103°–105° C.

IR (KBr): 3400, 2980, 2930, 2850, 1775, 1700, 1620, 1590, 1485, 1460, 1445, 1420, 1400, 1360, 1290, 1280, 1245, 1010, 970, 895, 865, 835, 820, 800, 795, 770, 730, 710 cm$^{-1}$.

NMR (400 MHz, CDCl$_3$, δ): 0.92 (3H, s); 0.95 (3H, s); 1.19–1.24 (3H, m); 1.58 (2H, broad s); 2.06–2.13 (1H, m); 2.54 (1H, q, J=7.32 Hz); 2.61–2.67 (1H, m); 3.33 (2H, dd, J=8.79 Hz); 3.46–3.55 (3H, m); 3.94–4.00 (2H, m); 4.88–5.00 (2H, m); 5.21–5.26 (1H, m); 5.39 (2H, s); 5.64–5.74 (2H, m); 6.77–6.86 (3H, m); 7.64 (2H, d, J=8.79 Hz); 7.76 (2H, d, J=8.79 Hz).

MASS (EI, m/e): 602 (M+).

HR MASS: Calcd. (C$_{30}$H$_{35}$O$_8$Br): 602.1372. Found (M+): 602.1489.

EXAMPLE 148

16,16-Dimethyl-2,5,6,7-tetranor-4,18-dioxa-4,8-inter-m-phenylene PGI$_2$ carboxamide 348

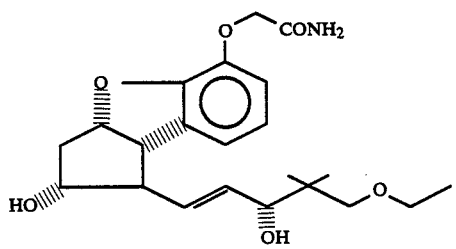

16,16-dimethyl-2,5,6,7-tetranor-4,18-dioxa-4,8-inter-m-phenylene PGI$_2$ (80 mg, 0.197 mmol) was dissolved into anhydrous tetrahydrofuran (8 ml) in a two-neck flask (30 ml) filled with argon gas. To this were added under ice-cooling triethylamine (0.25 ml, 1.79 mmol) and ethyl chloroformate (0.16 ml, 1.68 mmol) and the mixture was stirred for 4 hrs. at room temperature. The resulting solution was dropped over 15 min. into a liquid ammonia (8 ml) in a two-neck flask (100 ml) filled with argon gas at −33° C. The reaction mixture was stirred for 2 hrs. at −33° C. and the liquid ammonia was removed. The solution was mixed with brine (5 ml) and extracted with three portions of ethyl ether. The combined ethyl ether layers were washed with brine, dried over anhydrous sodium sulfate and concentrated in vacuo. Column chromatography (Merck, Lobar column A type, ethyl acetate/acetonitrile: 4/1) of the residue followed by recrystallization from n-hexane/ethyl acetate gave 16,16-dimethyl-2,5,6,7-tetranor-4,18-dioxa-4,8-inter-m-phenylene PGI$_2$ carboxamide (12 mg, 0.030 mmol, 15%). The product was assigned by the following data.

IR (liquid film): 3340, 3200, 2980, 2880, 1655, 1610, 1488, 1465, 1392, 1355, 1290, 1197, 1170, 1155, 1102, 1070, 1030, 1010, 972, 945, 859, 830, 790, 763, 728 cm$^{-1}$.

NMR (400 MHz, CDCl$_3$, δ): 0.92 (3H, s); 0.95 (3H, s); 1.19–1.23 (3H, m); 1.76 (2H, s); 2.45–2.55 (2H, m); 2.62–2.69 (1H, m); 3.34 (2H, dd, J=8.79 Hz); 3.46–3.55 (3H, m); 3.96–3.98 (2H, m); 4.56 (2H, s); 5.19–5.25 (1H, m); 5.50 (2H, broad s); 5.66–5.68 (2H, m); 6.76–6.85 (3H, m).

MASS (EI, m/e): 405 (M+).

HR MASS: Calcd. (C$_{22}$H$_{31}$O$_6$N, M+): 405.2151. Found (M+): 405.2160.

EXAMPLE 149

3-Decarboxy-3-hydroxymethyl-20a-homo-2,5,6,7-tetranor-4-oxa-4,8-inter-m-phenylene PGI$_2$ 349

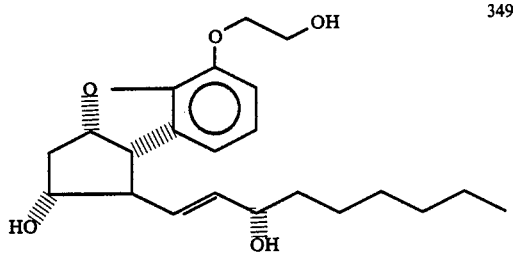

To a solution of 20a-homo-2,5,6,7-tetranor-4-oxa-4,8-inter-m-phenylene PGI$_2$ methyl ester (95 mg, 0.24 mmol) in methanol (10 ml) was added cerium trichloride heptahydrate (105 mg, 0.29 mmol). To this mixture was added sodium borohydride (290 mg, 7.7 mmol) little by little at room temperature. The resulting mixture was stirred for 2 hrs. at room temperature, mixed with a saturated aqueous solution of sodium bicarbonate (5 ml) and concentrated. The residue was mixed with ethyl acetate and the mixture was filtered. The resulting precipitate was washed with three portions of ethyl acetate. The combined ethyl acetate filtrates were washed with water (20 ml), with brine, dried over anhydrous magnesium sulfate and concentrated to give a crude material (96 mg). Column chromatography (silica gel, acetonitrile/methylene chloride: 1/1) of the material gave 3-decarboxy-3-hydroxymethyl-20a-homo- 2,5,6,7-tetranor-4-oxa-4,8-inter-m-phenylene PGI₂ (63 mg, 0.17 mmol, 69.8%) as a white crystal. The product was assigned the structure by the following data.

M.p.: 143.5°–144° C. (recrystallized from ethyl acetate).

IR (KBr): 3490, 3400, 2960, 2940, 2860, 1620, 1590, 1495, 1470, 1300, 1270, 1230, 1200, 1170, 1100, 1080, 990, 970, 950, 910, 880, 840, 790, 770, 730, 640, 560, 460 cm$^{-1}$.

NMR (400 MHz, CDCl₃, δ): 0.90 (3H, t, J=6.8 Hz); 1.2–1.7 (10H, m); 2.0–2.1 (1H, m); 2.3–2.5 (1H, m); 2.43 (1H, q, J=8.6 Hz); 2.66 (1H, dt, J=7.0, 13.7 Hz); 2.7–2.85 (1H, m); 2.9–3.0 (1H, m); 3.45 (1H, t, J=8.6 Hz); 3.85–3.95 (3H, m); 4.0–4.1 (3H, m); 5.17 (1H, ddd, J=5.4, 7.0, 8.6 Hz); 5.5–5.7 (2H, m); 6.7–6.85 (3H, m).

MASS (EI, m/e): 376 (M+).

HR MASS: Calcd. (C₂₂H₃₂O₅, M+): 376.2250. Found (M+): 376.2238.

EXAMPLE 150

3-Decarboxy-3-hydroxymethyl-16-methyl-2,5,6,7-tetranor-4-oxa-4,8-inter-m-phenylene PGI₂ 350

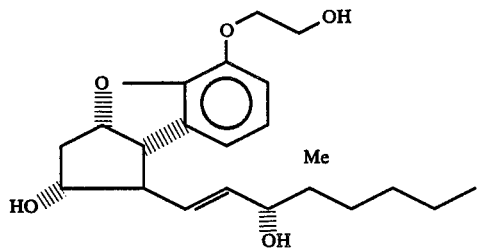

To a solution of 16-methyl-2,5,6,7-tetranor-4-oxa-4,8-inter-m-phenylene PGI₂ methyl ester (75.3 mg, 0.19 mmol) in methanol (38 ml) was added cerium trichloride heptahydrate (80.5 mg, 0.22 mmol). To the stirred mixture was added sodium borohydride (432.44 mg, 10.3 mmol) at room temperature and the mixture was stirred for one hour and 45 min. The resulting solution was mixed with water (30 ml), stirred for 10 min. and filtered by means of suction using celite. The precipitate was washed with ethyl acetate (200 ml). The filtrate was concentrated and the residue was extracted with ethyl acette (30 ml×3). The combined ethyl acetate layers were washed with water (100 ml), with brine (100 ml), dried over anhydrous sodium sulfate (20 g) and concentrated to give an oily material (80.6 mg). Column chromatography (silica gel, 5% methanol-ethyl acetate) of the material gave 3-decarboxy-3-hydroxymethyl-16-methyl-2,5,6,7-tetranor-4-oxa-4,8-inter-m-phenylene PGI₂ (51.3 mg, 0.14 mmol, 73%). The product was assigned the structure by the following data.

IR (KBr): 3475, 2950, 2915, 2860, 1619, 1588, 1485, 1453, 1368, 1290, 1223, 1190, 1160, 1084, 1063, 1023, 983, 940, 895, 865, 824, 781, 760, 721 cm$^{-1}$.

NMR (400 MHz, CDCl₃, δ): 0.88–0.97 (6H, m); 1.15–1.69 (7H, m); 2.02–2.11 (1H, m); 2.11–2.23 (1H, broad s); 2.44–2.52 (1H, m); 2.53–2.59 (1H, broad s); 2.64–2.72 (1H, m); 2.83–2.91 (1H, broad s); 3.47 (1H, t, J=8.30 Hz); 3.88–4.01 (4H, m); 4.11–4.18 (2H, m); 5.16–5.22 (1H, m); 5.57–5.67 (2H, m); 6.74–6.85 (3H, m).

MASS (m/e): 376 (M+).

HR MASS: Calcd. (C₂₂H₃₂O₅, M+): 376.2250. Found (M+): 376.2265.

EXAMPLE 151

3-Decarboxy-3-hydroxymethyl-16,16-dimethyl-2,5,6,7-tetranor-4-oxa-4,8-inter-m-phenylene PGI₂ 351

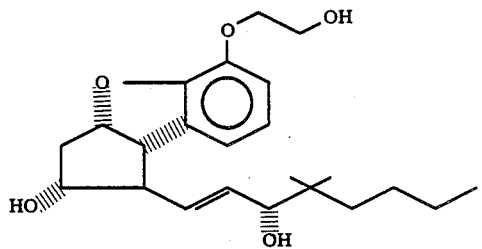

To a solution of 16,16-dimethyl-2,5,6,7-tetranor-4-oxa-4,8-inter-m-phenylene PGI₂ methyl ester (192.8 mg, 0.461 mmol) in methanol (20 ml) was added cerium trichloride heptahydrate (206.0 mg, 0.553 mmol) and the mixture was stirred at −15° C. To this solution was added sodium borohydride (663.4 mg, 19.5 mmol) and the mixture was stirred for 2 hrs. The solution was mixed with water (10 ml) and the solvent was distilled out. The resulting precipitate was filtered out by Hyflo Super Cel and the filtrate was extracted with ethyl acetate (20 ml×4). The combined ethyl acetate layers were washed with water (20 ml), with brine (20 ml), dried over anhydrous sodium sulfate and concentrated to give an oily material. Column chromatography (silica gel, ethyl acetate) of the material gave 3-decarboxy-3-hydroxymethyl-16,16-dimethyl-2,5,6,7-tetranor-4-oxa-4,8-inter-m-phenylene PGI₂ (160.4 mg, 0.411 mmol, 89.1%). The product was assigned the structure by the following data.

M.p.: 111.0°–120.0° C. (a colourless and needle-like crystal, recrystallized from ethyl acetate/n-hexane).

IR (KBr): 3480, 3350, 2955, 2930, 2870, 1620, 1590, 1487, 1460, 1410, 1380, 1360, 1284, 1193, 1163, 1098, 1068, 1031, 993, 943, 903, 873, 826, 783, 763, 728 cm$^{-1}$.

NMR (400 MHz, CDCl₃, δ): 0.80–1.10 (9H, m); 1.10–1.40 (6H, m); 1.80–2.38 (4H, broad m); 2.38–2.55 (1H, m); 2.60–2.72 (1H, m); 3.40–3.53 (1H, m); 3.78–4.00 (4H, m); 4.05–4.20 (2H, m); 5.13–5.27 (1H, m); 5.45–5.82 (2H, m); 6.68–6.84 (3H, m).

MASS (EI, m/e): 390 (M+).

HR MASS: Calcd. (C₂₃H₃₄O₅, M+): 390.2411. Found (M+): 390.2408.

EXAMPLE 152

3-Decarboxy-3-hydroxymethyl-16,16-dimethyl-20a-homo-2,5,6,7-tetranor-4-oxa-4,8-inter-m-phenylene PGI₂ 352

To a solution of 16,16-dimethyl-20a-homo-2,5,6,7-tetranor-4-oxa-4,8-inter-m-phenylene PGI₂ methyl ester (98.4 mg, 0.23 mmol) in methanol (18 ml) was added cerium trichloride heptahydrate (101.8 mg, 0.27 mmol). To the stirred solution was added sodium borohydride (271.0 mg, 6.4 mmol) at room temperature and the mixture was stirred for one hour and 15 min. The solution was mixed with water (20 ml) and stirred for 10 min. The resulting mixture was filtered by means of suction using celite and the precipitate was washed with ethyl acetate (100 ml). The filtrate was concentrated and the residue was extracted with ethyl acetate (15 ml×3). The combined ethyl acetate layers were washed with water (50 ml), with brine (50 ml), dried over anhydrous sodium sulfate (20 g) and concentrated to give an oily material (98.4 mg). Column chromatography (silica gel, ethyl acetate) of the material gave 3-decarboxy-3-hydroxymethyl-16,16-dimethyl-20a-homo-2,5,6,7-tetranor-4-oxa-4,8-inter-m-phenylene $PGI_2$ (82.4 mg, 0.20 mmol, 89%), which was recrystallized from ethyl acetate/cyclohexane (6/1) to afford a colourless and needle-like crystal. The product was assigned the structure by the following data.

M.p.: 117°–117.5° C.

IR (KBr): 3475, 3350, 3048, 2947, 2920, 2855, 1618, 1585, 1483, 1452, 1424, 1405, 1378, 1355, 1280, 1224, 1190, 1161, 1090, 1061, 1024, 983, 940, 901, 865, 822, 778, 756, 721, 623 cm$^{-1}$.

NMR (400 MHz, CDCl$_3$, δ): 0.84–0.94 (3H, m); 0.87 (3H, s); 0.91 (3H, s); 1.13–1.40 (8H, m); 1.58–2.26 (3H, broad s); 2.02–2.11 (1H, m); 2.40–2.55 (1H, m); 2.63–2.73 (1H, m); 3.43–3.56 (1H, m); 3.83–3.99 (1H, m); 3.99–4.02 (3H, m); 4.10–4.20 (2H, m); 5.17–5.28 (1H, m); 5.48–5.78 (2H, m); 6.72–6.93 (3H, m).

MASS (EI, m/e): 404 (M+).

HR MASS: Calcd. ($C_{24}H_{36}O_5$, M+): 404.2563. Found (M+): 404.2572.

EXAMPLE 153

3-Decarboxy-3-hydroxymethyl-17-phenyl-2,5,6,7,18,19,20-heptanor-4-oxa-4,8-inter-m-phenylene $PGI_2$ 353

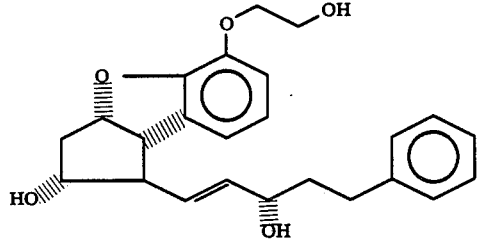

To a solution of 17-phenyl-2,5,6,7,18,19,20-heptanor-4-oxa-4,8-inter-m-phenylene $PGI_2$ methyl ester (120 mg, 0.283 mmol) in methanol (60 ml) was added with stirring cerium trichloride heptahydrate (127 mg, 0.34 mmol). To the stirred mixture was added under ice-cooling sodium boronydride (725 mg, 19.2 mmol) little by little and the mixture was stirred for 30 min. at 0° C. The solution was mixed with a saturated aqueous solution of sodium bicarbonate (40 ml) and filtered. The resulting precipitate was washed with ethyl acetate (5 ml×7) and the combined filtrates were concentrated. The concentrate was mixed with water (20 ml) and extracted with ethyl acetate (50 ml×2). The combined ethyl acetate layers were washed with water (20 ml), with brine (20 ml), dried over anhydrous sodium sulfate and concentrated. Column chromatography (Merck, Lobar column, silica gel, acetonitrile/methylene chloride: 5/1) of the residue followed by recrystallization from a mixture of 3 ml of ethyl acetate and 0.1 ml of methanol gave 3-decarboxy-3-hydroxymethyl-17-phenyl-2,5,6,7,18,19,20-heptanor-4-oxa-4,8-inter-m-phenylene $PGI_2$ (82.6 mg, 0.21 mmol, 73.7%) as a white crystal. The product was assigned the structure by the following data.

M.p.: 144.6°–146.0° C. (recrystallization solvent, ethyl acetate/methanol: 30/1).

IR (KBr): 3470, 3030, 2930, 2870, 1620, 1590, 1485, 1450, 1290, 1220, 1190, 1160, 1090, 1070, 1030, 985, 970, 945, 900, 870, 830, 760, 725, 700 cm$^{-1}$.

NMR (400 MHz, CDCl$_3$, δ): 1.75–2.1 (3H, m); 2.35–2.5 (2H, m); 2.6–2.8 (4H, m); 2.9–3.0 (1H, m); 3.45 (1H, t, J=8.5 Hz); 3.85–4.0 (3H, m); 4.1–4.25 (3H, m); 5.1–5.2 (1H, m); 5.5–5.7 (2H, m); 6.7–6.85 (3H, m); 7.15–7.35 (5H, m).

MASS (EI, m/e): 396 (M+).

HR MASS: Calcd. ($C_{24}H_{28}O_5$, M+): 396.1937. Found (M+): 396.1946.

EXAMPLE 154

3-Decarboxy-3-hydroxymethyl-16-phenoxy-2,5,6,7,17,18,19,20-octanor-4-oxa-4,8-inter-m-phenylene $PGI_2$ 354

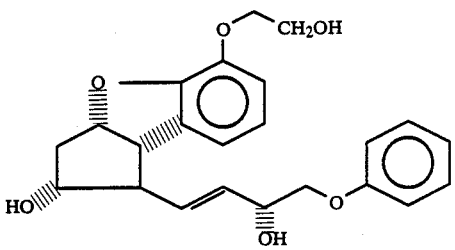

To a solution of 16-phenoxy-2,5,6,7,17,18,19,20-octanor-4-oxa-4,8-inter-m-phenylene $PGI_2$ methyl ester (42 mg, 0.99 mmol) in methanol (20 ml) was added with stirring cerium trichloride heptahydrate (52.4 mg, 0.14 mmol). To the stirred mixture was added under ice-cooling sodium borohydride (494 mg, 13 mmol) little by little and the mixture was stirred for 30 min at 0° C. The solution was mixed with a saturated aqueous solution of sodium bicarbonate (10 ml) and filtered. The resulting precipitate was washed with ethyl acetate (5 ml×5) and the combined filtrates were concentrated. The concentrate was mixed with water (10 ml) and extracted with ethyl acetate (50 ml×2). The combined ethyl acetate layers were washed with water (20 ml), with brine (20 ml), dried over anhydrous sodium sulfate and concentrated. Recrystallization of the residue from a mixture of 2 ml of ethyl acetate and 0.5 ml of n-hexane gave 3-decarboxy-3-hydroxymethyl-16-phenoxy-2,5,6,7,17,18,19,20-octanor-4-oxa-4,8-inter-m-phenylene $PGI_2$ (23.6 mg, 0.062 mmol, 62.4%) as a white crystal. The product was assigned the structure by the following data.

M.p.: 145.7°–147.2° C. (recrystallization solvent, ethyl acetate/n-hexane: 4/1).

IR (KBr): 3470, 2920, 2870, 1615, 1590, 1480, 1450, 1280, 1240, 1185, 1085, 1030, 965, 940, 890, 870, 740, 720, 685 cm$^{-1}$.

NMR (400 MHz, DMSO-d$_6$, δ): 1.6–1.8 (1H, m); 2.20 (1H, q, J=8.5 Hz); 2.4–2.6 (1H, m); 3.40 (1H, t, J=9.0

Hz); 3.68 (2H, q, J=5.2 Hz); 3.7–3.9 (1H, m); 3.90 (2H, d, J=5.9 Hz); 3.97 (2H, t, J=5.2 Hz); 4.3–4.5 (1H, m); 4.7–4.9 (2H, m); 5.05 (1H, q, J=7.3 Hz); 5.18 (1H, d, J=4.9 Hz); 5.62 (1H, dd, J=15.4, 5.9 Hz); 5.82 (1H, dd, J=15.4, 7.8 Hz); 6.65 (1H, t, J=7.6 Hz); 6.70 (1H, d, J=6.8 Hz); 6.78 (1H, d, J=7.6 Hz); 6.9–7.0 (3H, m); 7.3 (2H, t, J=7.6 Hz).

MASS (EI, m/e): 398 (M+).

HR MASS: Calcd. (C23H26O6): 398.1730. Found (M+): 398.1703.

EXAMPLE 155

3-Decarboxy-3-hydroxymethyl-16-methyl-2,5,6,7-tetranor-4-oxa-18,18,19,19-tetradehydro-4,8-inter-m-phenylene PGI2 355

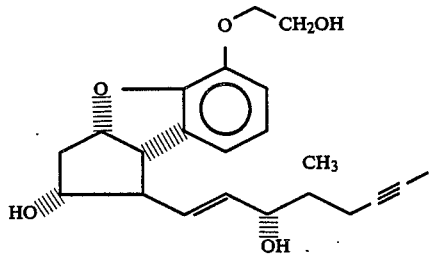

To a solution of 16-methyl-2,5,6,7-tetranor-4-oxo-18,18,19,19-tetradehydro-4,8-inter-m-phenylene PGI2 methyl ester (124 mg, 0.31 mmol) in methanol (30 ml) was added cerium trichloride heptahydrate (171 mg, 0.46 mmol). To the stirred mixture was added under ice-cooling sodium borohydride (517 mg, 15.1 mmol) little by little and the mixture was stirred for 30 min. at 0° C. The solution was mixed with a saturated aqueous solution of sodium bicarbonate (15 ml) and filtered. The resulting precipitate was washed with ethyl acetate (5 ml×5) and the combined filtrates were concentrated. The concentrate was mixed with water (10 ml) and extracted with ethyl acetate (60 ml×2). The combined ethyl acetate layers were washed with water (20 ml), with brine (20 ml), dried over anhydrous sodium sulfate and concentrated. Column chromatography (Merck, Lobar column, silica gel, acetonitrile/ethyl acetate: 1/1) of the residue followed by recrystallization from a mixture of 1.5 ml of ethyl acetate and 1 ml of n-hexane gave 3-decarboxy-3-hydroxymethyl-16-methyl-2,5,6,7-tetranor-4-oxa-18,18,19,19-tetradehydro-4,8-inter-m-phenylene PGI2 (62 mg, 0.167 mmol, 53.8%) as a white crystal. The product was assigned the structure by the following data.

M.p.: 106.5°–107.8° C. (recrystallization solvent-=ethyl acetate/n-hexane: 3/2).

IR (KBr): 3470, 3370, 2960, 2920, 2870, 1620, 1585, 1480, 1450, 1380, 1290, 1185, 1160, 1085, 1065, 1020, 980, 890, 865, 820, 760, 720 cm$^{-1}$.

NMR (400 MHz, CDCl3, δ): 1.01 (3H, t, J=7.1 Hz); 1.7–1.9 (4H, m); 2.0–2.2 (2H, m); 2.2–2.6 (4H, m); 2.6–2.8 (2H, m); 3.50 (1H, t, J=8.6 Hz); 3.8–4.0 (3H, m); 4.0–4.3 (1H, m); 4.06 (2H, t, J=6.8 Hz); 5.1–5.3 (1H, m); 5.5–5.8 (2H, m); 6.7–6.9 (3H, m).

MASS (EI, m/e): 372 (M+).

HR MASS: Calcd. (C22H28O5): 372.1934. Found (M+): 372.1931.

EXAMPLE 156

3-Decarboxy-3-hydroxymethyl-16,16-dimethyl-20a,20b,20c,20d-tetrahomo-2,5,6,7-tetranor-4-oxa-18,18,19,19-tetradehydro-4,8-inter-m-phenylene PGI2 356

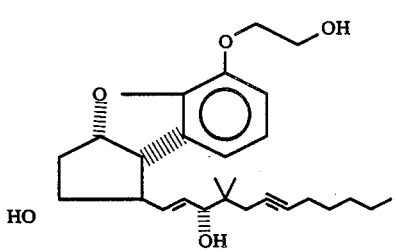

To a solution of 16,16-dimethyl-20a,20b,20c,20d-tetrahomo-2,5,6,7-tetranor-4-oxa-18,18,19,19-tetradehydro-4,8-inter-m-phenylene PGI2 methyl ester (80.6 mg, 0.18 mmol) in methanol (26 ml) was added cerium trichloride heptahydrate (66.13 mg, 0.18 mmol). To the stirred mixture was added sodium borohydride (388.6 mg, 10.3 mmol) at room temperature and the mixture was stirred for 45 min. The solution was mixed with water (20 ml), stirred for 10 min. and filtered by means of suction with celite. The resulting precipitate was washed with ethyl acetate (100 ml) and the filtrate was concentrated. The concentrate was extracted with ethyl acetate (15 ml×3). The combined ethyl acetate layers were washed with water (50 ml), with brine (50 ml), dried over anhydrous sodium sulfate (25 g) and concentrated to give an oily material (64.9 mg). Column chromatography (silica gel, ethyl acetate) of the material gave 3-decarboxy-3-hydroxymethyl-20a,20b,20c,20d-tetrahomo-2,5,6,7-tetranor-4-oxa-18,18,19,19-tetradehydro-4,8-inter-m-phenylene PGI2 (62.1 mg, 0.15 mmol, 82%), which was recrystallized from ethyl acetate/n-hexane (2/3) to afford a colourless and needle-like crystal. The product was assigned the structure by the following data.

M.p.: 91.5°–92° C.

IR (KBr): 3350, 2950, 2920, 2853, 1614, 1583, 1482, 1455, 1372, 1280, 1189, 1160, 1090, 1064, 1023, 999, 965, 943, 893, 869, 824, 760, 725, 696 cm$^{-1}$.

NMR (400 MHz, CDCl3, δ): 0.88–0.92 (3H, m); 0.98 (6H, s); 1.23–1.42 (4H, m); 1.47–1.55 (2H, m); 2.02–2.28 (5H, m); 2.34–2.39 (2H, broad s); 2.45–2.54 (1H, m); 2.64–2.74 (2H, m); 3.48–3.52 (1H, m); 3.89–4.01 (3H, m); 4.01–4.06 (1H, m); 4.12–4.17 (2H, m); 5.16–5.23 (1H, m); 565–5.73 (2H, m); 6.77–6.83 (3H, m).

MASS (EI, m/e): 442 (M+).

HR MASS: Calcd. (C27H38O5, M+): 442.2719. Found (M+): 442.2710.

EXAMPLE 157

2,5,6,7-Tetranor-3,3,4,4-tetradehydro-4,8-inter-m-phenylene PGI$_2$ methyl ester 357 and its 15epimer 358

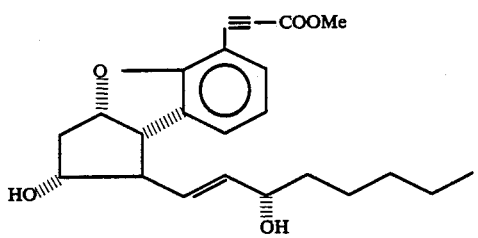

357

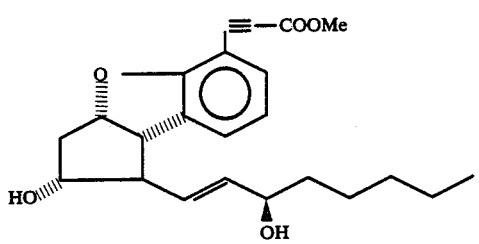

358

To a solution of 15-oxo-2,5,6,7-tetranor-3,3,4,4-tetradehydro-4,8-inter-m-phenylene PGI$_2$ methyl ester, 11-acetate (1.3562 g, 3.20 mmol) in methanol (20 ml) was added cerium trichloride heptahydrate (1.43 g, 3.84 mmol). Sodium borohydride (134.5 mg, 3.2 mmol) was added to the stirred mixture under ice-cooling and the resulting mixture was stirred for 5 min. This solution was diluted with water (30 ml) and extracted with ethyl acetate (30 ml×3). The combined ethyl acetate layers were washed with water (80 ml), with brine (80 ml), dried over anhydrous sodium sulfate (25 g) and concentrated to give an oily material (1.4321 g).

After azeotropic distillation of the oily material with benzene (10 ml×2), the residue was dissolved in anhydrous methanol (15 ml). To this solution was added a solution of sodium methoxide in methanol (5.22N, 0.025 ml, 0.13 mmol). The reaction mixture was stirred under argon atmosphere for one hour at room temperature, mixed with acetic acid (0.1 ml) and concentrated. Water (15 ml) was added to the residue. Extraction with ethyl acetate (15 ml×3) followed by washing with water (50 ml) and with brine (50 ml), drying over anhydrous sodium sulfate (20 g) and concentration afforded an oily material (1.3026 g). Column chromatography (silica gel, ethyl acetate/cyclohexane: 3/1) of the material first gave less polar 15-epi-2,5,6,7-tetranor-3,3,4,4-tetradehydro-4,8-inter-m-phenylene PGI$_2$ methyl ester (542.2 mg, 1.41 mmol, 44%), which was recrystallized from ethyl acetate/cyclohexane (3/1) to afford a colourless and needle-like crystal. Subsequently, the column chromatography gave more polar 2,5,6,7-tetranor-3,3,4,4-tetradehydro-4,8-inter-m-phenylene PGI$_2$ methyl ester (490.1 mg, 1.27 mmol, 40%), which was recrystallized from ethyl acetate/cyclohexane (2/1) to afford a colourless and needle-like crystal. These compounds were assigned the corresponding structures by the following data.

2,5,6,7-Tetranor-3,3,4,4-tetradehydro-4,8-inter-m-phenylene PGI$_2$ methyl ester M.p.: 103.5°–104° C.

IR (KBr): 3350, 2950, 2920, 2201, 1699, 1603, 1585, 1462, 1439, 1324, 1292, 1260, 1202, 1159, 1123, 1090, 1049, 1002, 980, 961, 939, 908, 863, 828, 790, 763, 741, 610 cm$^{-1}$.

NMR (400 MHz, CDCl$_3$, δ): 0.88–0.93 (3H, m); 1.27–1.45 (5H, m); 1.45–1.65 (3H, m); 1.57–1.87 (1H, broad s); 2.05–2.12 (2H, m); 2.41–2.48 (1H, m); 2.62–2.70 (1H, m); 3.83 (3H, s); 3.93–3.99 (1H, m); 4.12–4.18 (1H, m); 5.17–5.30 (1H, m); 5.58–5.68 (2H, m); 6.82 (1H, t, J=7.33 Hz); 7.17 (1H, d, J=7.33 Hz); 7.33 (1H, d, J=7.33 Hz).

MASS (EI, m/e): 384 (M+).

HR MASS: Calcd. (C$_{23}$H$_{28}$O$_5$, M+): 384.1972. Found (M+): 384.1964.

15-Epi-2,5,6,7-tetranor-3,3,4,4-tetradehydro-4,8-inter-m-phenylene PGI$_2$ methyl ester M.p.: 109°–109.5° C.

IR (KBr): 3250, 2925, 2860, 2200, 1699, 1602, 1583, 1439, 1343, 1327, 1292, 1263, 1203, 1160, 1130, 1090, 1062, 1050, 1020, 992, 965, 948, 893, 866, 848, 830, 780, 739, 610 cm$^{-1}$.

NMR (400 MHz, CDCl$_3$, δ): 0.88–0.96 (3H, m); 1.24–1.48 (5H, m); 1.48–1.63 (4H, m); 1.74–1.78 (1H, broad s); 2.05–2.13 (1H, m); 2.44–2.52 (1H, m); 2.62–2.68 (1H, m); 3.50 (1H, t, J=8.3 Hz); 3.83 (3H, s); 3.95–4.03 (1H, m); 4.13–4.18 (1H, m); 5.23–5.29 (1H, m); 5.62–5.71 (2H, m); 6.82 (1H, t, J=7.33 Hz); 7.20 (1H, d, J=7.33 Hz); 7.32 (1H, t, J=7.33 Hz).

MASS (EI, m/e): 384 (M+).

HR MASS: Calcd. (C$_{23}$H$_{28}$O$_5$, M+): 384.1972. Found (M+): 384.1973.

EXAMPLE 158

2,5,6,7-Tetranor-3,3,4,4-tetradehydro-4,8-inter-m-phenylene PGI$_2$ 359

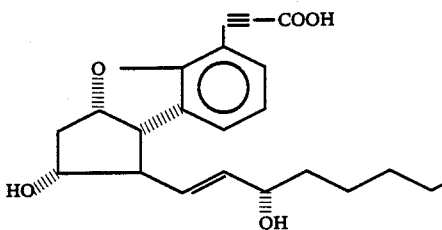

359

To a solution of 2,5,6,7-tetranor-3,3,4,4-tetradehydro-4,8-inter-m-phenylene PGI$_2$ methyl ester (224.0 mg, 0.58 mmol) in methanol (10 ml) was added 1N aqueous NaOH (2.9 ml) and the reaction mixture was stirred under argon atmosphere at room temperature overnight. The solution was mixed with 1N hydrochloric acid (4 ml) and then with water (30 ml). The mixture was extracted with ethyl acetate (30 ml×3). The combined ethyl acetate layers were washed with water (90 ml), with brine (90 ml), dried over anhydrous sodium sulfate (25 g) and concentrated to give quantitatively 2,5,6,7-tetranor-3,3,4,4-tetradehydro-4,8-inter-m-phenylene PGI$_2$ (214.1 mg, 0.58 mmol) as a single product, which was assigned the structure by the following data.

M.p.: 146.5°–147° C.

IR (KBr): 3330 (3700–2200), 2910, 2860, 2201, 1720, 1660, 1602, 1585, 1463, 1436, 1345, 1310, 1255, 1197, 1088, 1068, 1050, 1030, 968, 939, 868, 846, 822, 786, 753, 740, 611 cm$^{-1}$.

NMR (400 MHz, CDCl$_3$, δ): 0.89–0.95 (3H, m); 1.29–1.67 (8H, m); 2.01–2.08 (1H, m); 2.32–2.40 (1H, m); 2.62–2.70 (1H, m); 3.43 (1H, t, J=8.3 Hz); 3.83–3.92

(1H, m); 4.05–4.12 (1H, m); 5.17–5.23 (1H, m); 5.53–5.63 (2H, m); 6.80 (1H, t, J=7.33 Hz); 7.13 (1H, d, J=7.33 Hz); 7.29 (1H, d, J=7.33 Hz).

MASS (EI, m/e): 326 (M+-CO₂).

HR MASS: Calcd. (C₂₁H₂₆O₃, M+-CO₂): 326.1881. Found (M+-CO₂): 326.1855.

EXAMPLE 159

15-Epi-2,5,6,7-tetranor-3,3,4,4-tetradehydro-4,8-inter-m-phenylene PGI₂ 360

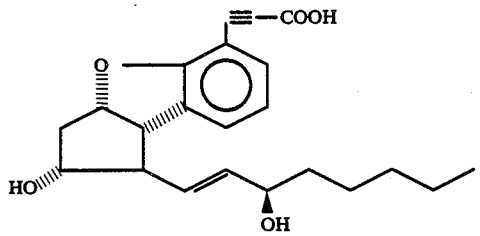
360

To a solution of 15-epi-2,5,6,7-tetranor-3,3,4,4-tetradehydro-4,8-inter-m-phenylene PGI₂ methyl ester (221.2 mg, 0.58 mmol) in methanol (9 ml) was added 1N aqueous NaOH (2.88 ml) and the reaction mixture was stirred under argon atmosphere at room temperature overnight. The solution was mixed with 1N hydrochloric acid (4 ml) and then with water (30 ml). The mixture was extracted with ethyl acetate (30 ml×3). The combined ethyl acetate layers were washed with water (90 ml), with brine (90 ml), dried over anhydrous sodium sulfate (25 g) and concentrated to give quantitatively 15-epi-2,5,6,7-tetranor-3,3,4,4-tetradehydro-4,8-inter-m-phenylene PGI₂ (213.9 mg, 0.58 mmol) as a single product, which was recrystallized from ethyl acetate/cyclohexane (2/1) to afford a colourless and needle-like crystal. The product was assigned the structure by the following data.

M.p.: 155°–155.5° C.

IR (KBr): 3400 (3700–2250), 2910, 2860, 2200, 1670, 1603, 1584, 1464, 1440, 1345, 1290, 1200, 1135, 1067, 1050, 1017, 960, 940, 918, 899, 869, 845, 783, 765, 735 cm⁻¹.

NMR (400 MHz, CDCl₃, δ): 0.87–0.95 (3H, m); 1.25–1.64 (8H, m); 2.03–2.12 (1H, m); 2.42–2.50 (1H, m); 2.55–2.65 (1H, m); 3.49 (1H, t, J=8.3 Hz); 3.92–3.99 (1H, m); 4.09–4.15 (1H, m); 5.22–5.38 (1H, m); 5.63–5.74 (2H, m); 6.80 (1H, t, J=7.33 Hz); 7.22 (1H, d, J=7.33 Hz); 7.28 (1H, d, J=7.33 Hz).

MASS (EI, m/e): 326 (M+-CO₂).

HR MASS: Calcd. (C₂₁H₂₆O₃, M+-CO₂): 326.1881. Found (M+-CO₂): 326.1889.

EXAMPLE 160

16,16-Dimethyl-2,5,6,7-tetranor-3,3,4,4-tetradehydro-4,8-inter-m-phenylene PGI₂ methyl ester 361 and its 15-epimer 362

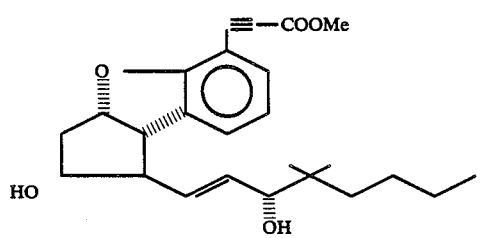
361

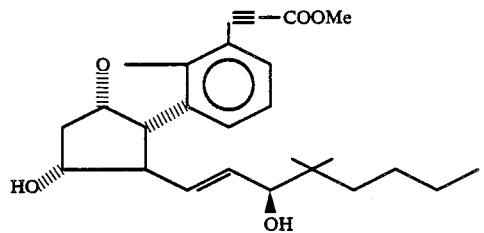
362

To a solution of 16,16-dimethyl-15-oxo-2,5,6,7-tetranor-3,3,4,4-tetradehydro-4,8-inter-m-phenylene PGI₂ methyl ester, 11-acetate (400.6 mg, 0.945 mmol) in methanol (10 ml) was added cerium trichloride heptahydrate (352.1 mg, 0.95 mmol). Sodium borohydride (11.9 mg, 0.28 mmol) was added to the stirred mixture under ice-cooling and the resulting mixture was stirred for 5 min. This solution was diluted with water (15 ml) and extracted with ethyl acetate (15 ml×3). The combined ethyl acetate layers were washed with water (50 ml), with brine (50 ml), dried over anhydrous sodium sulfate (20 g) and concentrated to give an oily material (407.4 mg).

After azeotropic distillation of the oily material with benzene (10 ml×2), the residue was dissolved in anhydrous methanol (10 ml). To this solution was added a solution of sodium methoxide in methanol (5.22N, 0.0072 ml, 0.038 mmol). The reaction mixture was stirred under argon atmosphere for 2 hrs. at room temperature, mixed with acetic acid (0.01 ml) and concentrated. Water (15 ml) was added to the residue. Extraction with ethyl acetate (15 ml×3) followed by washing with water (50 ml) and with brine (50 ml), drying over anhydrous sodium sulfate (25 g) and concentration afforded an oily material (374.2 mg). Column chromatography (silica gel, ethyl acetate/cyclohexane: 2/1) of the material first gave less polar 16,16-dimethyl-15-epi-2,5,6,7-tetranor-3,3,4,4-tetradehydro-4,8-inter-m-phenylene PGI₂ methyl ester (153.7 mg, 0.40 mmol, 43%), which was recrystallized from ethyl acetate/cyclohexane (1/1) to afford a colourless and needle-like crystal. Subsequently, the column chromatography gave more polar 16,16-dimethyl-2,5,6,7-tetranor-3,3,4,4-tetradehydro-4,8-inter-m-phenylene PGI₂ methyl ester (169.9 mg, 0.44 mmol, 47%), which was recrystallized from ethyl acetate/n-hexane (1/2) to afford a colourless and needle-like crystal. These compounds were assigned the corresponding structures by the following data.

16,16-Dimethyl-2,5,6,7-tetranor-3,3,4,4-tetradehydro-4,8-inter-m-phenylene PGI₂ methyl ester M.p.: 145.5°–146.5° C.

IR (KBr): 3390, 2951, 2930, 2860, 2210, 1718, 1602, 1588, 1463, 1440, 1408, 1359, 1334, 1293, 1266, 1247, 1200, 1100, 1070, 1045, 1038, 1002, 967, 946, 862, 837, 795, 762, 740, 680, 619 cm⁻¹.

NMR (400 MHz, CDCl₃, δ): 0.87 (3H, s); 0.90 (3H, s); 0.90–0.95 (3H, m); 1.17–1.36 (6H, m); 1.74–1.80 (1H, broad s); 2.03–2.10 (1H, m); 2.22–2.28 (1H, broad s); 2.42–2.48 (1H, m); 2.63–2.72 (1H, m); 3.47 (1H, t, J=8.3 Hz); 3.83 (3H, s); 3.84–3.88 (1H, m); 3.93–3.99 (1H, m); 5.22–5.28 (1H, m); 5.60–5.73 (2H, m); 6.82 (1H, t, J=7.32 Hz); 7.16 (1H, d, J=7.32 Hz); 7.32 (1H, t, J=7.32 Hz).

MASS (EI, m/e): 412 (M+).

HR MASS: Calcd. (C25H32O5, M+): 412.2249 Found (M+): 412.2230.

16,16-Dimethyl-15-epi-2,5,6,7-tetranor-3,3,4,4-tetradehydro-4,8-inter-m-phenylene PGI2 methyl ester M.p.: 106°–107° C.

IR (KBr): 3470, 3360, 2950, 2920, 2880, 2855, 2201, 1683, 1602, 1438, 1381, 1369, 1292, 1254, 1220, 1199, 1160, 1144, 1111, 1093, 1076, 1054, 1022, 1003, 990, 959, 940, 882, 864, 855, 829, 785, 766, 743, 735, 652, 611 cm$^{-1}$.

NMR (400 MHz, CDCl3, δ): 0.87 (3H, s); 0.91 (3H, s); 0.89–0.93 (3H, m); 1.23–1.38 (6H, s); 1.50–1.52 (1H, broad s); 1.65–1.70 (1H, broad s); 2.04–2.13 (1H, m); 2.47–2.53 (1H, m); 2.63–2.69 (1H, m); 3.52 (1H, t, J=8.3 Hz); 3.83 (3H, s); 3.87–3.92 (1H, m); 3.94–4.02 (1H, m); 5.23–5.30 (1H, m); 5.63–5.78 (2H, m); 6.82 (1H, t, J=7.33 Hz); 7.21 (1H, d, J=7.33 Hz); 7.32 (1H, t, J=7.33 Hz).

MASS (EI, m/e): 412 (M+).

HR MASS: Calcd. (C25H32O5, M+): 412.2249. Found (M+): 412.2263.

EXAMPLE 161

16,16-Dimethyl-2,5,6,7-tetranor-3,3,4,4-tetradehydro-4,8-inter-m-phenylene PGI2 363

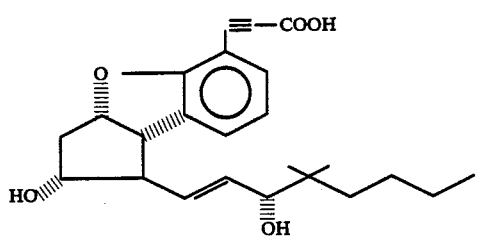

To a solution of 16,16-dimethyl-2,5,6,7-tetranor-3,3,4,4-tetradehydro-4,8-inter-m-phenylene PGI2 methyl ester (118.7 mg, 0.31 mmol) in methanol (10 ml) was added 1N aqueous NaOH (0.91 ml) and the reaction mixture was stirred under argon atmosphere at room temperature overnight. The solution was mixed with 1N hydrochloric acid (1 ml) and water (30 ml). The mixture was extracted with ethyl acetate (30 ml×3). The combined ethyl acetate layers were washed with water (100 ml), with brine (100 ml), dried over anhydrous sodium sulfate (25 g) and concentrated to give 16,16-dimethyl-2,5,6,7-tetranor-3,3,4,4-tetradehydro-4,8-inter-m-phenylene PGI2 (114.0 mg, 0.31 mmol) quantitatively as a single product, which as recrystalized from acetone/n-hexane (2/1) to afford a colourless and needle-like crystal. The product was assigned the structure by the following data.

M.p.: 159.5°–160° C.

IR (KBr): 3400 (3700–2100), 2952, 2930, 2870, 2210, 1678, 1602, 1588, 1464, 1443, 1379, 1352, 1323, 1299, 1260, 1224, 1203, 1064, 1053, 1020, 993, 964, 921, 765, 741, 780, 753, 740, 605 cm$^{-1}$.

NMR (400 MHz, CDCl3, δ): 0.86 (3H, s); 0.90 (3H, s); 0.89–0.95 (3H, m); 1.17–1.38 (6H, m); 1.97–2.06 (1H, m); 2.33–2.38 (1H, m); 2.63–2.71 (1H, m); 3.43 (1H, t, J=8.3 Hz); 3.79 (1H, d, J=7.81 Hz); 3.82–3.90 (1H, m); 5.18–5.23 (1H, m); 5.58 (1H, dd, J=15.14, 8.3 Hz); 5.67 (1H, dd, J=15.14, 7.81 Hz); 6.79 (1H, t, J=7.33 Hz); 7.12 (1H, d, J=7.33 Hz); 7.31 (1H, d, J=7.33 Hz).

MASS (EI, m/e): 354 (M+-CO2).

HR MASS: Calcd. (C23H30O3, M+-CO2): 354.2198. Found: (M+-CO2): 354.2214.

EXAMPLE 162

16,16-Dimethyl-15-epi-2,5,6,7-tetranor-3,3,4,4-tetradehydro-4,8-inter-m-phenylene PGI2 364

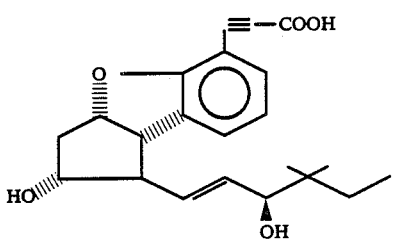

To a solution of 16,16-dimethyl-15-epi-2,5,6,7-tetranor-3,3,4,4-tetradehydro-4,8-inter-m-phenylene PGI2 methyl ester (108.0 mg, 0.28 mmol) in methanol (10 ml) was added 1N aqueous NaOH (0.83 ml) and the reaction mixture was stirred under argon atmosphere at room temperature overnight. The solution was mixed with 1N hydrochloric acid (1 ml) and water (30 ml). The mixture was extracted with ethyl acetate (30 ml×3). The combined ethyl acetate layers were washed with water (100 ml), with brine (100 ml), dried over anhydrous sodium sulfate (20 g) and concentrated to give quantitatively 16,16-dimethyl-15-epi-2,5,6,7-tetranor-3,3,4,4-tetradehydro-4,8-inter-m-phenylene PGI2 (104.1 mg, 0.28 mmol) as a single product, which was recrystallized from acetone/n-hexane (10/1) to afford a colourless and needle-like crystal. The product was assigned the structure by the following data.

M.p.: 167°–168° C.

IR (KBr): 3425 (3725–2100), 2950, 2925, 2870, 2210, 1679, 1468, 1440, 1381, 1342, 1290, 1260, 1221, 1203, 1100, 1045, 1012, 993, 963, 943, 889, 870, 851, 832, 812, 783, 750, 739, 600 cm$^{-1}$.

NMR (400 MHz, CDCl3, δ): 0.87 (3H, s); 0.90 (3H, s); 0.86–0.95 (3H, m); 1.20–1.38 (6H, m); 2.04–2.12 (1H, m); 2.46–2.52 (1H, m); 2.58–2.67 (1H, m); 3.50 (1H, t, J=7.33 Hz); 3.86 (1H, d, J=4.89 Hz); 3.93–3.99 (1H, m); 5.18–5.32 (1H, m); 5.65–5.78 (1H, m); 6.79 (1H, t, J=7.33 Hz); 7.20 (1H, d, J=7.33 Hz); 7.29 (1H, d, J=7.33 Hz).

MASS (EI, m/e): 354 (M+-44)

HR MASS: Calcd. (C23H30O3, M+-CO2): 354.2198. Found: (M+-CO2): 354.2198.

EXAMPLE 163

16-Phenoxy-2,5,6,7,17,18,19,20-octanor-3,3,4,4-tetradehydro-4,8-inter-m-phenylene PGI2 methyl ester 365 and its 15-epimer 366

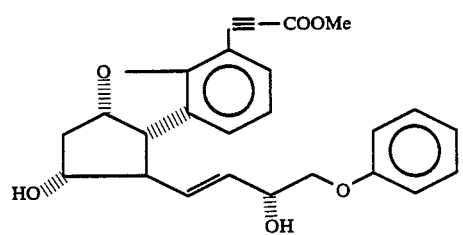

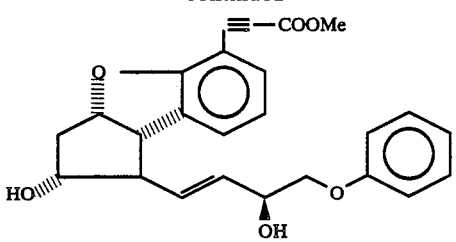

366

To a solution of 15-oxo-16-phenoxy-2,5,6,7,17,18,19,20-octanor-3,3,4,4-tetradehydro-4,8-inter-m-phenylene PGI$_2$ methyl ester, 11-acetate (840 mg, 1.82 mmol) in methanol (50 ml) was added cerium trichloride heptahydrate (1.02 g, 2.73 mmol). Sodium borohydride (103 mg, 2.73 mmol) was added to the stirred mixture under ice-cooling and the resulting mixture was stirred for 10 min. This solution was mixed with a saturated aqueous solution of sodium bicarbonate and methanol was distilled out from the mixture. The residue was triturated in ethyl acetate (30 ml). The resulting precipitate was filtered off and washed with ethyl acetate (20 ml×3). The combined filtrates were concentrated. The concentrate was mixed with water (30 ml) and extracted with ethyl acetate (50 ml×3). The combined ethyl acetate layers were washed with water (30 ml), with brine (30 ml), dried over anhydrous sodium sulfate and concentrated to give an oily material (835 mg).

After azeotropic distillation of the oily material with benzene (10 ml×2), the residue was dissolved in anhydrous methanol (50 ml). To this solution was added a solution of sodium methoxide in methanol (5.22N, 0.10 ml, 0.542 mmol). The reaction mixture was stirred under argon atmosphere for 1.5 hrs. at room temperature, neutralized with acetic acid and concentrated. Water (15 ml) was added to the residue. Extraction with ethyl acetate (30 ml×3) followed by washing with water (30 ml) and with brine (30 ml), drying over anhydrous sodium sulfate and concentration afforded a colourless and oily material. Column chromatography (silica gel, ethyl acetate/cyclohexane: 2/1) of the material gave less polar 16-phenoxy-15-epi-2,5,6,7,17,18,19,20-octanor-3,3,4,4-tetradehydro-4,8-inter-m-phenylene PGI$_2$ methyl ester (254 mg, 0.606 mmol, 33.2%) and then more polar 16-phenoxy-2,5,6,7,17,18,19,20-octanor-3,3,4,4-tetradehydro-4,8-inter-m-phenylene PGI$_2$ methyl ester (210 mg, 0.507 mmol, 27.9%). These compounds were assigned the corresponding structures by the following data.

16-Phenoxy-2,5,6,7,17,18,19,20-octanor-3,3,4,4-tetradehydro-4,8-inter-m-phenylene PGI$_2$ methyl ester M.p.: 160.3°–161.0° C. (recrystallized from ethyl acetate).

IR (KBr): 3450, 2990, 2950, 2930, 2890, 2870, 2215, 1720, 1600, 1585, 1495, 1470, 1440, 1370, 1350, 1320, 1295, 1240, 1200, 1155, 1085, 1040, 1005, 960, 940, 910, 865, 815, 790, 760, 740, 735, 685 cm$^{-1}$.

NMR (400 MHz, CDCl$_3$, δ): 2.09 (1H, ddd, J=5.1, 8.3, 13.7 Hz); 2.20 (1H, d, J=4.4 Hz); 2.48 (1H, q, J=8.3 Hz); 2.67 (1H, dt, J=6.8, 13.7 Hz); 2.71 (1H, d, J=3.4 Hz); 3.50 (1H, t, J=8.3 Hz); 3.83 (3H, s); 3.92 (1H, dd, J=7.6, 9.3 Hz); 3.95–4.05 (1H, m); 4.04 (1H, dd, J=3.4, 9.3 Hz); 4.55–4.63 (1H, m); 5.25 (1H, m); 5.71 (1H, dd, J=6.1, 15.3 Hz); 5.87 (1H, dd, J=8.3, 15.3 Hz); 6.79 (1H, t, J=7.3 Hz); 6.92 (2H, dd, J=1.0, 8.8 Hz); 6.99 (1H, t, J=7.3 Hz); 7.17 (1H, d, J=7.3 Hz); 7.25–7.34 (3H, m).

MASS (EI, m/e): 420 (M+).

HR MASS: Calcd. (C$_{25}$H$_{24}$O$_6$, M+): 420.1573. Found (M+): 420.1596.

16-Phenoxy-15-epi-2,5,6,7,17,18,19,20-octanor-3,3,4,4-tetradehydro-4,8-inter-m-phenylene PGI$_2$ methyl ester M.p.: 154.7°–155.4° C. (recrystallized from ethyl acetate).

IR (KBr): 3300, 2970, 2950, 2920, 2875, 2210, 1705, 1595, 1580, 1495, 1470, 1440, 1380, 1330, 1300, 1250, 1225, 1180, 1080, 1050, 1040, 1005, 990, 970, 945, 905, 885, 860, 850, 830, 795, 760, 755, 740, 690 cm$^{-1}$.

NMR (400 MHz, CDCl$_3$, δ): 1.80 (1H, d, J=3.9 Hz); 2.10 (1H, ddd, J=5.1, 8.3, 13.7 Hz); 2.51 (1H, q, J=8.3 Hz); 2.54 (1H, d, J=3.9 Hz); 2.67 (1H, dt, J=6.8, 13.7 Hz); 3.53 (1H, t, J=8.3 Hz); 3.83 (3H, s); 3.92 (1H, dd, J=7.3, 9.3 Hz); 3.96–4.06 (1H, m); 4.06 (1H, dd, J=3.6, 9.3 Hz); 4.56–4.64 (1H, m); 5.27 (1H, m); 5.73 (1H, dd, J=5.4, 15.6 Hz); 5.89 (1H, dd, J=8.3, 15.6 Hz); 6.80 (1H, t, J=7.3 Hz); 6.93 (2H, d, J=7.8 Hz); 7.00 (1H, t, J=7.3 Hz); 7.21 (1H, d, J=7.3 Hz); 7.28–7.34 (3H, m).

MASS (EI, m/e): 420.

HR MASS: Calcd. (C$_{25}$H$_{24}$O$_6$, M+): 420.1573. Found (M+): 420.1590.

EXAMPLE 164

16-Phenoxy-2,5,6,7,17,18,19,20-octanor-3,3,4,4-tetradehydro-4,8-inter-m-phenylene PGI$_2$ 367

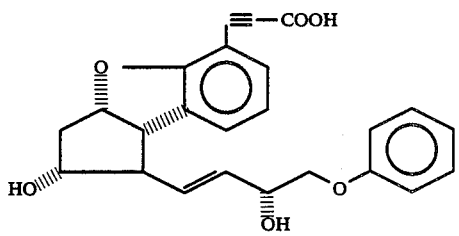

367

To a solution of 16-phenoxy-2,5,6,7,17,18,19,20-octanor-3,3,4,4-tetradehydro-4,8-inter-m-phenylene PGI$_2$ methyl ester (197.5 mg, 0.470 mmol) in methanol (50 ml) was added 1N aqueous NaOH (2.3 ml, 2.35 mmol) and the reaction mixture was stirred under argon atmosphere at room temperature overnight. The soluton was acidified to pH 4 with 1N hydrochloric acid and concentrated. The concentrate was mixed with water (10 ml) and extracted with ethyl acetate (20 ml×3). The combined ethyl acetate layers were washed with water (10 ml), with brine (10 ml), dried over anhydrous sodium sulfate and concentrated to give quantitatively 16-phenoxy-2,5,6,7,17,18,19,20-octanor-3,3,4,4-tetradehydro-4,8-inter-m-phenylene PGI$_2$ (177.3 mg, 0.437 mmol) as a single product. The product was assigned the structure by the following data.

M.p.: 174.5°–176.5° C. (recrystallized from ethyl acetate/ethanol).

IR (KBr): 3450, 3250, 2970, 2940, 2920, 2870, 2200, 1675, 1600, 1585, 1500, 1485, 1465, 1450, 1440, 1380, 1335, 1290, 1280, 1260, 1245, 1200, 1170, 1130, 1110, 1080, 1065, 1040, 1030, 1005, 975, 870, 850, 795, 750, 740, 695 cm$^{-1}$.

NMR (400 MHz, CDCl$_3$/DMSO-d$_6$, δ): 2.03 (1H, ddd, J=4.7, 9.3, 14.4 Hz); 2.42 (1H, q, J=8.3 Hz); 2.55–2.70 (1H, broad s); 2.63 (1H, dt, J=7.3, 14.4 Hz);

3.48 (1H, t, J=8.3 Hz); 3.89-4.02 (4H, m); 4.52 (1H, q, J=6.1 Hz); 5.73 (1H, dd, J=6.1, 15.1 Hz); 5.84 (1H, dd, J=8.3, 15.1 Hz); 6.77 (1H, t, J=7.3 Hz); 6.92-6.98 (3H, m); 7.17 (1H, d, J=7.3 Hz); 7.25-7.33 (3H, m).

MASS (EI, m/e): 362 (M+-CO2).

HR MASS: Calcd. (C23H22O4, M+-CO2): 362.1518. Found (M+-CO2): 362.1547.

EXAMPLE 165

16-Phenoxy-15-epi-2,5,6,7,17,18,19,20-octanor-3,3,4,4-tetradehydro-4,8-inter-m-phenylene PGI2 368

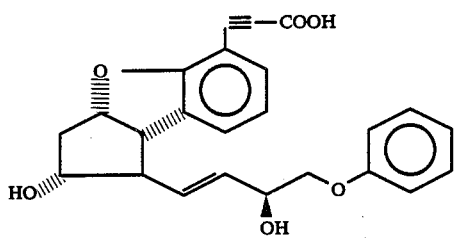

To a solution of 16-phenoxy-15-epi-2,5,6,7,17,18,19,20-octanor-3,3,4,4-tetradehydro-4,8-inter-m-phenylene PGI2 methyl ester (213.9 mg, 0.509 mmol) in methanol (50 ml) was added 1N aqueous NaOH (2.5 ml, 2.55 mmol) and the reaction mixture was stirred under argon atmosphere at room temperature overnight. The solution was acidified to pH 4 with 1N hydrochloric acid and concentrated. The concentrate was mixed with water (10 ml) and extracted with ethyl acetate (20 m×3). The combined ethyl acetate layers were washed with water (10 ml), with brine (10 ml), dried over anhydrous sodium sulfate and concentrated to give quantitatively 16-phenoxy-15-epi-2,5,6,7,17,18,19,20-octanor-3,3,4,4-tetradehydro-4,8-inter-m-phenylene PGI2 (206.1 mg, 0.508 mmol) as a single product. The product was assigned the structure by the following data.

M.p.: 166.5°-167.5° C. (recrystallized from ethyl acetate/ethanol).

IR (KBr): 3500, 3340, 2970, 2920, 2880, 2210, 1685, 1595, 1580, 1490, 1465, 1435, 1330, 1290, 1260, 1230, 1200, 1170, 1150, 1125, 1085, 1035, 990, 970, 945, 900, 870, 845, 825, 780, 750, 735, 690 cm$^{-1}$.

NMR (400 MHz, CDCl3/DMSO-d6, δ): 2.04 (1H, ddd, J=5.1, 8.8, 13.7 Hz); 2.47 (1H, q, J=8.3 Hz); 2.56-2.65 (1H, m); 3.52 (1H, t, J=8.3 Hz); 3.93-4.04 (5H, m); 4.53 (1H, q, J=5.3 Hz); 5.23 (1H, m); 5.75 (1H, dd, J=5.3, 15.4 Hz); 5.89 (1H, dd, J=8.3, 15.4 Hz); 6.77 (1H, t, J=7.3 Hz); 6.92-6.99 (3H, m); 7.22-7.31 (4H, m).

MASS (EI, m/e): 362 (M+-CO2).

HR MASS: Calcd. (C23H22O4, M+-CO2): 362.1518. Found (M+-CO2): 362.1505.

EXAMPLE 166

16-Methyl-16-phenoxy-2,5,6,7,18,19,20-heptanor-3,3,4,4-tetradehydro-4,8-inter-m-phenylene PGI2 methyl ester 369 and its 15-epimer 370

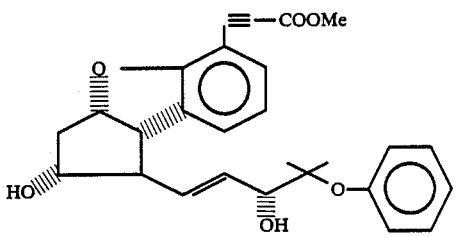

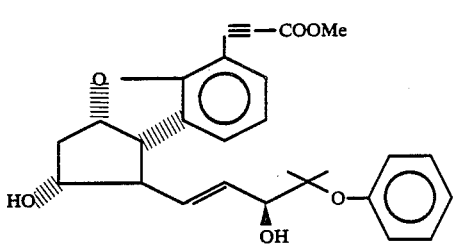

To a solution of 16-methyl-15-oxo-16-phenoxy-2,5,6,7,18,19,20-heptanor-3,3,4,4-tetradehydro-4,8-inter-m-phenylene PGI2 methyl ester, 11-acetate (1.1207 g, 2.30 mmol) in a mixture of 40 ml of methanol and 20 ml of THF was added cerium trichloride heptahydrate (856.9 mg, 2.30 mmol). Sodium borohydride (48.3 mg, 1.15 mmol) was added to the stirred mixture under ice-cooling and the resulting mixture was stirred for 5 min. This solution was mixed with a saturated aqueous solution of ammonium chloride (20 ml) and the mixture was filtered by celite. The resulting precipitate was washed with ethyl acetate (200 ml) and the filtrate was concentrated. The concentrate was extracted with ethyl acetate (18 ml×3). The combined ethyl acetate layers were washed with water (50 ml), with brine (50 ml), dried over anhydrous sodium sulfate (15 g) and concentrated to give an oily material (1.23 g).

After azeotropic distillation of the oily material with benzene (10 ml×2), the residue was dissolved in anhydrous methanol (30 ml). To this solution was added a solution of sodium methoxide in methanol (5.22N, 0.02 ml, 0.12 mmol). The reaction mixture was stirred under argon atmosphere for one hour at room temperature, mixed with acetic acid (0.1 ml) and concentrated. Water (15 ml) was added to the residue. Extraction with ethyl acetate (15 m×3) followed by washing with water (50 m) and with brine (50 ml), drying over anhydrous sodium sulfate (25 g) and concentration gave a crude crystal (1.0824 g). Column chromatography (silica gel, ethyl acetate/cyclohexane: 2/1) of the crude crystal first afforded less polar 16-methyl-16-phenoxy-15-epi-2,5,6,7,18,19,20-heptanor-3,3,4,4-tetradehydro-4,8-inter-m-phenylene PGI2 methyl ester (354.6 mg, 0.79 mmol, 34%), which was recrystallized from THF/cyclohexane (1/1) to give to colourless and needle-like crystal. The column chromatography gave then more polar 16-methyl-16-phenoxy-2,5,6,7,18,19,20-heptanor-3,3,4,4-tetradehydro-4,8-inter-m-phenylene PGI2 methyl ester (504.3 mg, 1.13 mmol, 49%), which was recrystallized from THF/cyclohexane (1/1) to give a colourless and needle-like crystal. The products were assigned the corresponding structures by the following data.

16-Methyl-16-phenoxy-2,5,6,7,18,19,20-heptanor-3,3,4,4-tetradehydro-4,8-inter-m-phenylene PGI₂ methyl ester M.p.: 171°–172° C.

IR (KBr): 3375, 2960, 2875, 2201, 1708, 1691, 1582, 1480, 1438, 1379, 1360, 1322, 1290, 1262, 1210, 1180, 1149, 1123, 1103, 1067, 1041, 1000, 963, 950, 938, 880, 863, 828, 780, 762, 736, 700, 622 cm⁻¹.

NMR (400 MHz, CDCl₃, δ): 1.24 (3H, s); 1.26 (3H, s); 1.45–1.77 (1H, broad s); 2.03–2.16 (1H, m); 2.47–2.55 (1H, m); 2.63–2.72 (1H, m); 2.91–3.12 (1H, broad s); 3.49–3.56 (1H, m); 3.83 (3H, s); 3.96–4.04 (1H, m); 4.20 (1H, d, J=6.34 Hz); 5.23–5.31 (1H, m); 5.69–5.77 (1H, m); 5.79–5.87 (1H, m); 6.81 (1H, t, J=7.32 Hz); 6.98 (2H, d, J=7.3 Hz); 7.10–7.18 (2H, m); 7.25–7.36 (3H, m).

MASS (EI, m/e): 417 (M⁺-CH₃O).

HR MASS: Calcd. (C₂₆H₂₅O₅, M⁺-CH₃O): 417.1699. Found (M⁺-CH₃O): 417.1677.

16-Methyl-16-phenoxy-15-epi-2,5,6,7,18,19,20-heptanor-3,3,4,4-tetradehydro-4,8-inter-m-phenylene PGI₂ methyl ester M.p.: 179°–180° C.

IR (KBr): 3375, 2960, 2851, 2201, 1702, 1582, 1481, 1464, 1439, 1379, 1352, 1330, 1293, 1250, 1202, 1179, 1123, 1100, 1070, 1043, 1037, 999, 974, 953, 937, 908, 877, 863, 823, 779, 764, 741, 701, 624, 611 cm⁻¹.

NMR (400 MHz, CDCl₃, δ): 1.24 (3H, s); 1.25 (3H, s); 1.52–1.79 (1H, broad s); 2.06–2.15 (1H, m); 2.51–2.56 (1H, m); 2.62–2.71 (1H, m); 2.88–2.95 (1H, broad s); 3.55 (1H, t, J=8.3 Hz); 3.83 (3H, s); 3.97–4.05 (1H, m); 4.20–4.23 (1H, m); 5.24–5.31 (1H, m); 5.74 (1H, dd, J=15.62, 5.86 Hz); 5.84 (1H, dd, J=15.62, 8.3 Hz); 6.81 (1H, t, J=7.33 Hz); 7.00 (2H, d, J=7.33 Hz); 7.11–7.15 (1H, m); 7.20–7.22 (1H, m); 7.28–7.32 (3H, m).

MASS (EI, m/e): 417 (M⁺-CH₃O).

HR MASS: Calcd. (C₂₆H₂₅O₅, M⁺-CH₃O): 417.1699. Found (M⁺-CH₃O): 417.1724.

EXAMPLE 167

16-Methyl-16-phenoxy-2,5,6,7,18,19,20-heptanor-3,3,4,4-tetradehydro-4,8-inter-m-phenylene PGI₂ 371

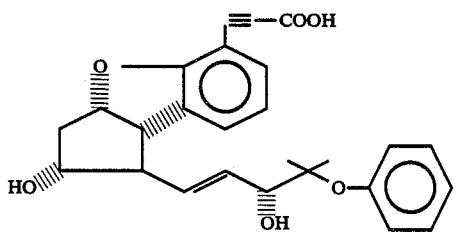

371

To a solution of 16-methyl-16-phenoxy-2,5,6,7,18,19,20-heptanor-3,3,4,4-tetradehydro-4,8-inter-m-phenylene PGI₂ methyl ester (116 mg, 0.26 mmol) in methanol (10 ml) was added 1N aqueous NaOH (0.78 ml) and the reaction mixture was stirred under argon atmosphere at room temperature overnight. The solution was mixed with 1N hydrochloric acid (0.85 ml) and water (15 ml) and the mixture was extracted with ethyl acetate (15 ml×3). The combined ethyl acetate layers were washed with water (50 ml), with brine (50 ml), dried over anhydrous sodium sulfate (20 g) and concentrated to give quantitatively 16-methyl-16-phenoxy-2,5,6,7,18,19,20-heptanor-3,3,4,4-tetradehydro-4,8-inter-m-phenylene PGI₂ (112.4 mg, 0.26 mmol) as a single product, which was recrystallized from THF/cyclohexane (1/1) to give a colourless and needle-like crystal. The product was assigned the structure by the following data.

M.p.: 176°–177° C.

IR (KBr): 3325 (3650–2200), 2960, 2865, 2201, 1672, 1583, 1481, 1438, 1408, 1379, 1362, 1295, 1264, 1224, 1203, 1152, 1123, 1094, 1064, 1033, 993, 970, 958, 910, 881, 869, 824, 783, 757, 739, 701, 668, 615 cm⁻¹.

NMR (400 MHz, CDCl₃, δ): 1.25 (3H, s); 1.27 (3H, s); 2.03–2.12 (1H, m); 2.49–2.52 (1H, m); 2.58–2.69 (1H, m); 3.50 (1H, t, J=8.3 Hz); 3.93–4.00 (1H, m); 4.19 (1H, d, J=5.86 Hz); 4.47–5.10 (3H, broad s); 5.21–5.28 (1H, m); 5.72–5.85 (2H, m); 6.79 (1H, t, J=7.32 Hz); 7.00 (2H, d, J=7.33 Hz); 7.08–7.17 (2H, m); 7.25–7.33 (3H, m).

MASS (EI, m/e): 390 (M⁺-CO₂).

HR MASS: Calcd. (C₂₅H₂₆O₄, M⁺-CO₂): 390.1831. Found (M⁺-CO₂): 390.1826.

EXAMPLE 168

16-Methyl-16-phenoxy-15-epi-2,5,6,7,18,19,20-heptanor-3,3,4,4-tetradehydro-4,8-inter-m-phenylene PGI₂ 372

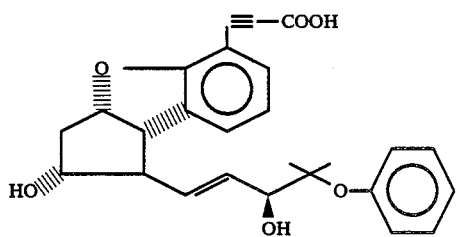

372

To a solution of 16-methyl-16-phenoxy-15-epi-2,5,6,7,18,19,20-heptanor-3,3,4,4-tetradehydro-4,8-inter-m-phenylene PGI₂ methyl ester (115.2 mg, 0.26 mmol) in methanol (10 ml) was added 1N aqueous NaOH (0.78 ml) and the reaction mixture was stirred under argon atmosphere at room temperature overnight. The solution was mixed with 1N hydrochloric acid (0.85 ml) and water (15 ml) and the mixture was extracted with ethyl acetate (15 ml×3). The combined ethyl acetate layers were washed with water (50 ml), with brine (50 ml), dried over anhydrous sodium sulfate (20 g) and concentrated to give quantitatively 16-methyl-16-phenoxy-15-epi-2,5,6,7,18,19,20-heptanor-3,3,4,4-tetradehydro-4,8-inter-m-phenylene PGI₂ (112.2 mg, 0.26 mmol) as a single product, which was recrystallized from THF/cyclohexane (1/1) to give a colourless and needle-like crystal. The product was assigned the structure by the following data.

M.p.: 156°–158° C.

IR (KRr): 3230 (3650–2300), 2960, 2920, 2200, 1680, 1585, 1482, 1438, 1360, 1254, 1197, 1154, 1131, 1079, 1038, 1019, 964, 940, 871, 843, 823, 781, 752, 734, 715, 695, 611 cm⁻¹.

NMR (400 MHz, CDCl₃, δ): 1.24 (3H, s); 1.26 (3H, s); 2.04–2.14 (1H, m); 2.51–2.56 (1H, m); 2.58–2.65 (1H, m); 3.54 (1H, t, J=8.3 Hz); 3.95–4.02 (1H, m); 4.20 (1H, d, J=5.86 Hz); 4.3–4.9 (3H, broad s); 5.18–5.32 (1H, m); 5.76 (1H, dd, J=15.62, 5.86 Hz); 5.85 (1H, dd, J=15.62, 8.30 Hz); 6.79 (1H, t, J=7.32 Hz); 6.99 (2H, d, J=7.32

Hz); 7.08–7.15 (1H, m); 7.18–7.23 (1H, m); 7.25–7.34 (3H, m).

MASS (EI, m/e): 390 (M+-CO₂).

HR MASS: Calcd. (C$_{25}$H$_{26}$O$_4$, M+-CO₂): 390.1831. Found (M+-CO₂): 390.1854.

EXAMPLE 169

3-Decarboxy-3-hydroxymethyl-2,5,6,7-tetranor-3,3,4,4-tetradehydro-4,8-inter-m-phenylene PGI₂ 373

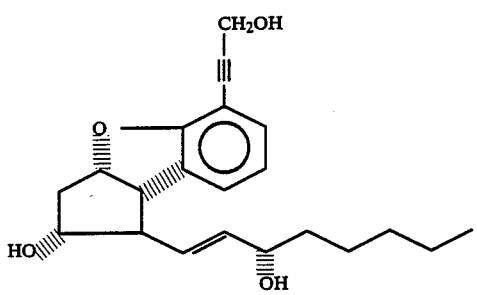

Anhydrous toluene (3 ml) was added to 2,5,6,7-tetranor-3,3,4,4-tetradehydro-4,8-inter-m-phenylene PGI₂ methyl ester (58 mg, 0.151 mmol) in a 25 ml flask filled with argon gas and the mixture was stirred to suspension. The suspension was cooled to −20° C. and mixed with a solution of diisobutylaluminum hydride in toluene (1.5N, 1.5 ml). The reaction mixture was stirred for 30 min. at −20° C. and then allowed to warm to 0° C. and stirred for 20 min. to become transparent. The solution was mixed with a saturated aqueous solution of ammonium chloride and the mixture was stirred for 10 min. to give a suspension. 1N hydrochloric acid was added to the suspension until it became transparent and the resulting mixture was extracted three times with ethyl acetate. The combined ethyl acetate layers were washed with brine until the washing became neutral and dried over anhydrous sodium sulfate. Evaporation of ethyl acetate in vacuo gave a yellow and oily material. Column chromatography (Merck, Lobar column B type, ethyl acetate) of the material gave 3-decarboxy-3-hydroxymethyl-2,5,6,7-tetranor-3,3,4,4-tetradehydro-4,8-inter-m-phenylene PGI₂ (52.7 mg, 0.148 mmol, 98%), which was recrystallized from n-hexane/ethyl acetate to afford a white crystal. The product was assigned the structure by the following data.

M.p.: 115°–116° C.

IR (KBr): 3420, 3370, 2960, 2930, 2860, 2240, 1570, 1478, 1423, 1370, 1355, 1330, 1315, 1280, 1270, 1200, 1170, 1143, 1090, 1073, 1060, 995, 979, 960, 910, 880, 865, 835, 785, 765, 735 cm⁻¹.

NMR (400 MHz, CDCl₃, δ): 0.89–0.93 (3H, m); 1.32–1.45 (6H, m); 1.49–1.59 (4H, m); 1.88 (1H, broad s); 2.03–2.10 (1H, m); 2.41–2.71 (1H, m); 3.05 (1H, broad s); 3.64 (1H, t, J=8.54 Hz); 3.92–3.98 (1H, m); 4.14 (1H, q, J=6.1 Hz); 4.52 (2H, s); 5.19–5.24 (1H, m); 5.58–5.68 (2H, m); 6.79 (1H, t, J=7.63 Hz); 7.06 (1H, d, J=7.32 Hz); 7.20–7.22 (1H, m).

MASS (EI, m/e): 356 (M+).

HR MASS: Calcd. (C$_{22}$H$_{28}$O$_4$, M+): 356.1987. Found (M+): 356.2013.

EXAMPLE 170

3-Decarboxy-3-hydroxymethyl-16-methyl-16-phenoxy-2,5,6,7,18,19,20-heptanor-3,3,4,4-tetradehydro-4,8-inter-m-phenylene PGI₂ 374

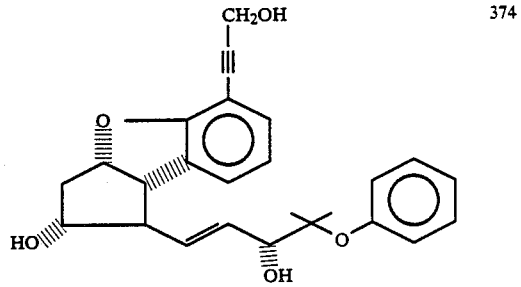

Anhydrous Toluene (3 ml) was added to 16-methyl-16-phenoxy-2,5,6,7,18,19,20-heptanor-3,3,4,4-tetradehydro-4,8-inter-m-phenylene PGI₂ methyl ester (54 mg, 0.120 mmol) in a 25 ml flask filled with argon gas and the mixture was stirred to give a suspension. The suspension was cooled to −22° C. and mixed with a solution of diisobutylaluminum hydride (1.5N, 0.48 ml) and the reaction mixture was stirred for 30 min. at −22° C. The reaction mixture was then allowed to warm to 0° C. and stirred for 20 min. to become transparent. The solution was mixed with a saturated aqueous solution of ammonium chloride and the mixture was stirred for 5 min. at room temperature to give a suspension. 1N hydrochloric acid was added to the suspension until it became transparent and the resulting mixture was extracted with ethyl acetate three times. The combined ethyl acetate layers were washed with brine until the washing became neutral. Evaporation of ethyl acetate in vacuo gave a yellow and oily material. Column chromatography (Merck, Lobar column B type, cyclohexane/ethyl acetate: 1/4) of the material gave 3-decarboxy-3-hydroxymethyl-16-methyl-16-phenoxy-2,5,6,7,18,19,20-heptanor-3,3,4,4-tetradehydro-4,8-inter-m-phenylene PGI₂ (45.1 mg, 0.108 mmol, 90%), which was recrystallized from n-hexane/ethyl acetate to afford a white crystal. The product was assigned the structure by the following data.

M.p.: 146°–147° C.

IR (KBr): 3360, 3070, 2998, 2980, 2945, 2915, 2230, 1592, 1488, 1479, 1442, 1400, 1382, 1365, 1350, 1330, 1325, 1310, 1298, 1270, 1257, 1238, 1220, 1203, 1185, 1163, 1135, 1120, 1095, 1082, 1077, 1050, 1025, 999, 962, 950, 942, 915, 890, 872, 860, 837, 815, 783, 760, 743, 710, 703 cm⁻¹.

NMR (400 MHz, CDCl₃, δ): 1.24 (3H, s); 1.26 (3H, s); 1.90 (1H, broad s); 2.05–2.13 (1H, m); 2.31 (1H, broad s); 2.47–2.53 (1H, m); 2.64–2.70 (1H, m); 3.06 (1H, broad s); 3.48–3.52 (1H, m); 3.96–4.01 (1H, m); 4.19–4.21 (1H, m); 4.52 (2H, s); 5.19–5.25 (1H, m); 5.69–5.86 (2H, m); 6.76–6.80 (1H, m); 6.98–7.00 (1H, m); 7.05–7.06 (2H, m); 7.11–7.31 (4H, m).

MASS (EI/ m/e): 420 (M+).

HR MASS: Calcd. (C$_{26}$H$_{28}$O$_5$, M+): 420.1936. Found (M+): 420.1914.

EXAMPLE 171

Gastric cytoprotection effect

Gastric cytoprotection effect was studied according to the method by A. Robert (Gastroenterology, 77(3), 443, (1979)). Thirty min. after oral administration of the compound according to the invention, 0.2N NaOH was orally applied to the animals.

One hour later, the animals were killed under anesthesia by chloroform. The stomach was removed and fixed in a solution of 5% formalin. After fixation, the stomach was cut along the greater curvature. A total length of the lesion appearing on the corpus of stomach was then measured and served as an ulcer index.

The dose of the compound which may reduce the sore to 50% of that of the control was designated as $ED_{50}$.

The gastric cytoprotection effects of the compounds according to the invention, which is thus represented by $ED_{50}$, are summarized in Table 1.

TABLE 1

| Gastric cytoprotection effect | |
|---|---|
| Compound | $ED_{50}$ (μg/kg) |
| 156 | 11.3 |
| 164 | 9.6 |
| 168 | 30.5 |
| 172 | 4.6 |
| 176 | 4.1 |
| 180 | 2.9 |
| 184 | 2.3 |
| 188 | 2.8 |
| 192 | 3.9 |
| 196 | 150 |
| 200 | 3.6 |
| 208 | 0.92 |
| 210 | 109 |
| 218 | 0.27 |
| 230 | 9.74 |
| 234 | 12.4 |
| 238 | 4.9 |
| 241 | 8.17 |
| 244 | 8.52 |
| 248 | 31.1 |
| 252 | 6.5 |
| 256 | 3.2 |
| 260 | 51.4 |
| 263 | 13.7 |
| 266 | 31.2 |
| 270 | 25.5 |
| 274 | 9.6 |
| 278 | 3.1 |
| 281 | 2.4 |
| 285 | 3.5 |
| 289 | 4.0 |
| 301 | 38.5 |
| 305 | 13.1 |
| 309 | 7.47 |
| 313 | 21.1 |
| 317 | 0.49 |
| 321 | 0.5 |
| 371 | 27.9 |

EXAMPLE 172

Inhibiting effect of gastric acid secretion

Under anesthesia by ether, the abdomen of the rat was incised in its median and a pylorus was ligated with silk thread according to Shay (Gastroenterology 5, 43 (1945)). Simultaneously, the compound was injected into a duodenum of the rat and then the incision was closed.

Five hours later, the median-incision of the abdomen was again performed and the esophargus was ligated and then the whole stomach was removed.

The stomach was cut along a greater curvature and the contents thereof was transferred into a graduated centrifuge tube. After centrifugation at 3,000 rpm for 10 min., a volume of a gastric juice was measured and a part of its supernatant was titrated to pH 7 with 0.1N NaOH using a pH-stat (Radio meter).

The mean dose of the compounds which may reduce the volume of gastric juice (ml) and acidity (mEq/ml) of a group of five animals to 50% of that of the controls were designated respectively as $ED_{50}$.

The obtained results were given in Table 2.

TABLE 2

| Inhibiting effect of gastric acid secretion | | |
|---|---|---|
| | $ED_{50}$ (mg/kg) | |
| Compound | Acidity | Volume of the gastric juice |
| 156 | 2.33 | 0.33 |
| 160 | 0.45 | 0.097 |
| 164 | 0.89 | 1.34 |
| 180 | 1.78 | 0.51 |
| 208 | 0.27 | 0.14 |
| 213 | 0.23 | 0.087 |
| 230 | 0.88 | 0.33 |
| 234 | 0.88 | 0.086 |
| 241 | 2.8 | 1.8 |
| 244 | >10 | 3.5 |
| 256 | 0.11 | 0.044 |
| 260 | 4.5 | 5.2 |
| 263 | 1.3 | 0.58 |
| 274 | 0.88 | 0.26 |
| 278 | 1.1 | 0.63 |
| 281 | 0.5 | 0.46 |
| 285 | 1.2 | 0.88 |
| 289 | 0.97 | 0.43 |
| 309 | 2.01 | 0.805 |
| 313 | 0.31 | 0.42 |
| 321 | 0.32 | 0.12 |
| 371 | 4.6 | >10 |

EXAMPLE 173

Inhibiting effect of gastric acid secretion

A male SD rat was incised in the abdomen under anesthesia by urethane and the lumen of a stomach was perfused with a physiolosical saline solution through a double-cannula inserted into a lumen of the stomach. A pH of a draining gastric acid was monitored using a pH-meter (M. Ghosh, H. Schild, Br. J. Pharmacol. 13, 54 (1958)). The secretion of gastric acid was stimulated by a continuous infusion of the pentagastrin at a rate of 0.05 μg/kg/min. When the pH of gastric acid became stable value of about 4, the compound was injected through a femoral vein. As an index of the inhibiting effect of gastric acid secretion by the compound was calculated from the area surrounded by the curve drawn by the time course of the pH of gastric acid, from the point increase by the injection of the compound and to the point it came back to baseline. The index thus obtained was compared to that of $PGE_2$ and a ratio therebetween was shown in Table 3, as a relative effect of the compound.

TABLE 3

| Inhibiting effect of gastric acid secretion | |
|---|---|
| Compound | Relative effect ($PGE_2$ = 1) |
| $PGE_2$ | 1 |
| 156 | 39 |
| 160 | 13 |
| 164 | 12 |
| 168 | 3.5 |
| 172 | 19 |
| 176 | 48 |
| 180 | 72 |
| 184 | 85 |
| 188 | 23 |
| 192 | 0.7 |
| 200 | 3.0 |

TABLE 3-continued

Inhibiting effect of gastric acid secretion

| Compound | Relative effect (PGE$_2$ = 1) |
|---|---|
| 208 | 45 |
| 210 | 13 |
| 213 | 41 |
| 230 | 1.4 |
| 234 | 4.1 |
| 238 | 11 |
| 241 | 2.1 |
| 244 | 3.9 |
| 248 | 13 |
| 252 | 13 |
| 256 | 7.8 |
| 260 | 13 |
| 263 | 42 |
| 266 | 7.2 |
| 270 | 16 |
| 274 | 12 |
| 278 | 6.9 |
| 281 | 10 |
| 285 | 4.1 |
| 289 | 17 |
| 293 | 4.8 |
| 297 | 75 |
| 301 | 16 |
| 305 | 99 |
| 309 | 33 |
| 313 | 53 |
| 317 | 62 |
| 321 | 41 |
| 371 | 8 |

EXAMPLE 174

Inhibiting effect of platelet aggregation

The blood taken from a human median cubital vein was centrifuged at 800 rpm for 10 min. and a supernatant thereof was used as a platelet-rich plasma (PRP). An aliquot of PRP thus obtained was put into a small tube, to which adenosine-2-phosphate (ADP) was added to induce platelet aggregation. The extent of aggregation was determined by detecting a change in turbidity of the aliquot by an apparatus for measuring platelet aggregation (Rika-Denki, Tokyo). The compound was added one minute before the addition of ADP. The concentration of the compound which may reduce the platelet aggregation, 50% of the control was designated as IC$_{50}$.

The results were summarized in Table 4.

TABLE 4

Inhibiting effect of platelet aggregation

| Compound | IC$_{50}$ (ng/ml) |
|---|---|
| 156 | 0.56 |
| 160 | 0.41 |
| 164 | 1.35 |
| 168 | 1.54 |
| 172 | 2.1 |
| 184 | 24 |
| 188 | 6.9 |
| 192 | 8 |
| 200 | 0.37 |
| 208 | 0.47 |
| 210 | 30 |
| 213 | 0.075 |
| 218 | 0.18 |
| 230 | 0.19 |
| 234 | 0.26 |
| 238 | 0.24 |
| 241 | 12 |
| 244 | 28 |
| 256 | 0.088 |
| 260 | 3.5 |
| 263 | 3.4 |
| 266 | 2.3 |

TABLE 4-continued

Inhibiting effect of platelet aggregation

| Compound | IC$_{50}$ (ng/ml) |
|---|---|
| 270 | 1.6 |
| 274 | 1.35 |
| 278 | 0.79 |
| 281 | 0.82 |
| 285 | 0.23 |
| 289 | 0.74 |
| 297 | 13 |
| 305 | 90 |
| 309 | 72 |
| 321 | 0.33 |

EXAMPLE 175

Hypotensive effect

A catheter was inserted to a carotid of the Wistar male rat under chloralose anesthesia. Another end of the catheter was connected to a polygraph with a pressure-transducer to detect a blood pressure of the carotid. The compound was injected via catheter connected to a femoral artery. The dose of the compound which may reduce the blood pressure in an amount of 25 mmHg was designated as ED$_{25}$.

The results were summarized in Table 5.

TABLE 5

Hypotensive effect

| Compound | ED$_{25}$ (μg/kg) |
|---|---|
| 156 | 0.46 |
| 160 | 0.23 |
| 168 | 0.49 |
| 172 | 0.72 |
| 176 | 0.69 |
| 180 | 0.69 |
| 184 | 0.5 |
| 188 | 1.5 |
| 192 | 0.59 |
| 200 | 0.16 |
| 208 | 0.074 |
| 210 | 0.89 |
| 213 | 0.023 |
| 218 | 0.045 |
| 230 | 0.094 |
| 234 | 0.34 |
| 238 | 0.14 |
| 241 | 0.083 |
| 244 | 0.47 |
| 248 | 11.0 |
| 252 | 5.6 |
| 256 | 0.1 |
| 260 | 0.98 |
| 263 | 0.23 |
| 266 | 0.32 |
| 270 | 0.12 |
| 274 | 0.053 |
| 278 | 0.11 |
| 281 | 0.14 |
| 285 | 0.055 |
| 289 | 0.084 |
| 293 | 46 |
| 297 | 0.34 |
| 301 | 0.36 |
| 305 | 0.55 |
| 309 | 0.3 |
| 313 | 2.1 |
| 317 | 1.3 |
| 321 | 0.22 |
| 371 | 2.4 |

EXAMPLE 176

Anti-hyperlipidemia effect

A group of five male Wistar rats (body weight: about 200 g) was fasted overnight. Hyperlipidemia was produced by injecting a saline solution of 6.25% Triton WR-1339 to the rat through the tail vein in an amount of 0.36 ml per 100 g of body weight. Three and seven hours after the intravenous injection of Triton, the drug was orally administered each at a dose of 0.3 mg/kg. Distilled water was administered to the control group in a similar manner. Twenty-four hours after the administration of Triton, the blood was taken and the total cholesterol (TC), total lipid (TG) and HDL cholesterol (HDL-C) in the plasma were determined. The results are shown in Table 6.

Administration of the drugs according to the present invention decreased significantly the levels of TC and TG. Further, HDL-C was either unchanged or rather increased; thus, valuable physiological effect was observed.

TABLE 6

| Item | Anti-hyperlipidemia effect | | |
|---|---|---|---|
| | TC(S.D.) | TG(S.D.) | HDL-C(S.D.) |
| Water (control) | 267(43) | 732(347) | 28(11) |
| 208 | 104(9.4)** | 132(35)** | 46(4)** |
| 321 | 109(14.5)** | 141(31)** | 50(6)** |
| 313 | 153(45)** | 205(101)* | 42(13) |
| 256 | 92(15)** | 116(32)* | 39(6) |
| 234 | 164(45)** | 363(226) | 34(12) |
| 317 | 168(35)** | 277(110)* | 39(12) |

S.D. Standard deviation
**$P < 0.05$
*$P < 0.1$

What is claimed is:

1. A 2,5,6,7-tetranor-4,8-inter-m-phenylene PGI$_2$ derivative represented by the formula:

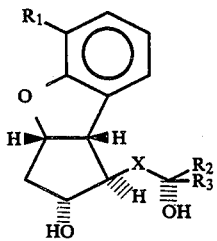

wherein
R$_1$ is
   (ii) —C≡C—COOR$_4$,
   (iii) —O—CH$_2$—CH$_2$—OH,
   (iv) —C≡C—CH$_2$—OH,
   (v)
   —O—CH$_2$—CON(R$_5$)(R$_6$),
   or
   (vi)
   —C≡C—CON(R$_5$)(R$_6$).

in which R$_4$ is hydrogen, a pharmacologically acceptable cation, or a pharmacologically acceptable ester residue, and R$_5$ and R$_6$ may be the same or different and are independently selected from the class consisting of hydrogen, normal alkyl having 1 to 12 carbon atoms, branched alkyl having 3 to 12 carbon atoms, cycloalkyl having 3 to 12 carbon atoms, cycloalkylalkylene having 4 to 13 carbon atoms, and phenyl;

X is
   (i) —CH$_2$—CH$_2$—, or
   (ii) —CH=CH—;

R$_2$ is hydrogen, methyl, ethyl or propyl group; and
R$_3$ is
   (i) a normal alkyl group having 1 to 12 carbon atoms or a branched alkyl group having 3 to 14 carbon atoms,
   (ii) —Z—Ar in which Z is a valence bond or a normal or branched alkylene group represented by the formula C$_t$H$_{2t}$ (t being an integer of 1 to 6), and Ar is a phenyl group unsubstituted or substituted by 1 to 4 substituents selected from the class consisting of alkyl, methoxy, chloro, bromo, fluoro, iodo, trifluoromethyl, nitro, cyano, and phenyl,
   (iii) —Z—R$_7$ in which Z is as defined above, and R$_7$ is a cycloalkyl group having 3 to 12 ring carbon atoms, said cycloalkyl group being optionally substituted by 1 to 4 normal alkyl substituents containing 1 to 4 carbon atoms,
   (iv) —C$_t$H$_{2t}$—C≡C—R$_8$ in which t is as defined above, and R$_8$ is a normal alkyl group having 1 to 6 carbon atoms, or
   (v) —C$_t$H$_{2t}$—O—R$_9$ in which t is as defined above, and R$_9$ is (1) a normal alkyl group having 1 to 6 carbon atoms or a branched alkyl group having 3 to 6 carbon atoms, (2) a cyclopentyl or cyclohexyl group unsubstituted or substituted by 1 to 4 normal alkyl substituents containing 1 to 4 carbon atoms, or (3) Ar as defined above.

* * * * *